US010766950B2

(12) United States Patent
Shoemaker

(10) Patent No.: US 10,766,950 B2
(45) Date of Patent: Sep. 8, 2020

(54) METHODS, COMPOSITIONS AND KITS FOR TREATING A SUBJECT USING A RECOMBINANT NEUTRALIZING BINDING PROTEIN

(71) Applicant: TUFTS UNIVERSITY, Boston, MA (US)

(72) Inventor: Charles B. Shoemaker, Boston, MA (US)

(73) Assignee: TUFTS UNIVERSITY, Boston, MA (US)

(*) Notice: Subject to any disclaimer, the term of this patent is extended or adjusted under 35 U.S.C. 154(b) by 0 days.

(21) Appl. No.: 16/237,877

(22) Filed: Jan. 2, 2019

(65) Prior Publication Data

US 2019/0225675 A1    Jul. 25, 2019

Related U.S. Application Data

(63) Continuation of application No. 15/191,739, filed on Jun. 24, 2016, now Pat. No. 10,202,441, which is a continuation of application No. PCT/US2014/072340, filed on Dec. 24, 2014.

(60) Provisional application No. 61/920,825, filed on Dec. 26, 2013.

(51) Int. Cl.
| C07K 16/12 | (2006.01) |
| C07K 16/18 | (2006.01) |
| C07K 16/16 | (2006.01) |
| A61K 39/00 | (2006.01) |

(52) U.S. Cl.
CPC ...... *C07K 16/1282* (2013.01); *C07K 16/1228* (2013.01); *C07K 16/1278* (2013.01); *C07K 16/16* (2013.01); *C07K 16/18* (2013.01); *A61K 2039/505* (2013.01); *A61K 2039/507* (2013.01); *C07K 2317/22* (2013.01); *C07K 2317/31* (2013.01); *C07K 2317/569* (2013.01); *C07K 2317/622* (2013.01); *C07K 2317/76* (2013.01); *C07K 2317/92* (2013.01); *C07K 2319/40* (2013.01)

(58) Field of Classification Search
None
See application file for complete search history.

(56) References Cited

U.S. PATENT DOCUMENTS

| 5,455,030 | A  | 10/1995 | Ladner et al. |
| 5,578,706 | A  | 11/1996 | Ghetie et al. |
| 5,840,526 | A  | 11/1998 | Casterman et al. |
| 6,015,695 | A  | 1/2000  | Casterman et al. |
| 7,345,161 | B2 | 3/2008  | Masuda et al. |
| 7,745,587 | B2 | 6/2010  | Devy et al. |
| 7,763,445 | B2 | 7/2010  | Moore et al. |
| 7,807,184 | B2 | 10/2010 | Vermeij |
| 7,867,724 | B2 | 1/2011  | Alexandru et al. |
| 7,879,333 | B2 | 2/2011  | Gerber |
| 8,131,480 | B2 | 3/2012  | Horowitz et al. |
| 8,216,865 | B2 | 7/2012  | Choi et al. |
| 8,349,326 | B2 | 1/2013  | Shoemaker et al. |
| 2005/0287129 | A1 | 12/2005 | Cicciarelli et al. |
| 2010/0092511 | A1 | 4/2010  | Waldor et al. |
| 2010/0278830 | A1 | 11/2010 | Shoemaker et al. |
| 2011/0010782 | A1 | 1/2011  | Horvitz et al. |
| 2011/0129474 | A1 | 6/2011  | Shoemaker et al. |
| 2013/0058962 | A1 | 3/2013  | Shoemaker et al. |
| 2017/0362310 | A1 | 12/2017 | Shoemaker |

FOREIGN PATENT DOCUMENTS

| WO | 2011068953 A2 | 6/2011 |
| WO | 2016094602 A1 | 6/2016 |

OTHER PUBLICATIONS

Vajdos et al. (J Mol Biol. Jul. 5, 2002;320(2):415-28.*
Brown et al. (J Immunol. May 1996;156(9):3285-91.*
Adelman, JP et al., "In Vitro Deletional Mutagenesis for Bacterial Production of the 20,000-dalton Form of Human Pituitary Growth Hormone", 1983, DNA 2:183-193.
Barbut et al., "Epidemiology of Recurrences or Reinfections of Clostridium Difficile-Associated Diarrea", 2000, J. Clin Microbiol, vol. 38, pp. 2386-2388.
Bartlett, "Antibiotic-Associated Diarrhea", 2002, N.Eng. J. Med., vol. 346, pp. 334-339.
Bilge A. et al., "Translocation of Ricin A-Chain into Proteoliposomes Reconstituted from Golgi and Endoplasmic Reticulum", 1995, Journal of Biological Chemistry 1995; 270(40): 23720-23725.
Borriello, SP, "Pathogenesis of Clostridium Difficile Infection", 1998, Antimicrob Chemother 41 Suppl C:13-19.
Brown, EM. et al., "Cloning and Characterization of an Extracellular Ca(2+) Sensing Receptor from Bovine Parathyroid", 1993, Nature, 366: 575-80.
Butterworth, AG., et al., "Ricin and Ricinus Communis Agglutinin Subunits are all Derived from a Single-Size Polypeptide Precursor", 1983 Eur. J. Biochem. 137, 57-65.
Chen, X et al., "A Mouse Model of Clostridiium Difficile-Associated Disease" 2008, Gastroenterol, vol. 135, pp. 1984-1992.
Cohen, J, "Naked DNA Points Way to Vaccines", Science 259: 1691-1692, 1993.
Cunnery RJ et al., "Clostridium Difficile Colitis Associated with Chronic Renal Failure", 1998, Nephrol Dial Transplant, 13:2842-2846.
Daeron, M, "FC Receptor Biology", 1997, Annu Rev Immunol 15: 203-234.

(Continued)

*Primary Examiner* — Brian Gangle
(74) *Attorney, Agent, or Firm* — Melissa Hunter-Ensor; Leslie Serunian; Greenberg Traurig, LLP

(57) ABSTRACT

Methods, compositions and kits are provided for treating a subject exposed to or at risk for exposure to a disease agent using a pharmaceutical composition including at least one recombinant binding protein or a source of expression of the binding protein, wherein the binding protein neutralizes a disease agent that is a toxin, for example a *Clostridium difficile* toxin, a Shiga toxin, a ricin toxin, or an anthrax toxin.

13 Claims, 83 Drawing Sheets

Specification includes a Sequence Listing.

(56) References Cited

OTHER PUBLICATIONS

Davies, KA et al., "Defective Fc-Dependent Processing of Immune Complexes in Patients with Systemic Lupus Erythematosus", 2002 Arthritis, Rheum 46: 1028-1038.
Dobson, G. et al., "Clostridium Difficile Colitis Causing Toxic Megacolon, Severe Sepsis and multiple Organ Dysfunction Syndrome", 2003, Intensive Care Medicine 29:1030.
Donnenberg, M, "Infections Due to *Escherichia coli* and Other Enteric Gram-Negative Bacilli", Chapter 138 in ACP Medicine Principles and Practice, 2007, pp. 1626-1633.
Eubanks, LM et al., "Identification of a Natural Product Antagonist Against the Botulinum Neurotoxin Light Chain Protease" 2010, ACS Med Chem Lett 1: 268-272.
Eubanks, LM et al., "An in Vitro and in Vivo Disconnect Uncovered through High-Throughput Identification of Botulinum Neurotoxin A Antagonist" 2007, Proc. Natl. Acad. Sci. USA 104: 2602-2607.
Feng, P *"Escherichia coli"* 2001, in Garcia (ed.) Guide to Foodborne Pathogens. John Wiley and Sons, Inc., pp. 143-162.
Fernie et al., "Active and Passive Immunization to Protect Against Antibiotic Associated Caecitis in Hamsters" 1983 Dev Biol Stand 53: 325-332.
Florin, I et al., "Internalization of Clostridium Difficile Cytotoxin into Cultered Human Lung Fibroblasts" 1983, Biochim Biophys Acta, 1983, vol. 763, pp. 383-392.
Florin, I et al., "Lysosomal Involvement in Cellular Intoxication with Clostridium Difficile Toxin B" 1986 Microb Pathog 1: 373-385.
Friedman, DI et al., "Bacteriophage lambda: Alive and Well and Still Doing It's Thing" 201, Curr Opin Microbiol 4(2): 201-7.
Gerding, DN et al., "Treatment of Clostridium Difficile Infection" 2008 Clin Infect Dis 46 Suppl 1:S32-42.
Giesemann, T et al., "Cholesterol-Dependent Pore Formation of Clostridium Difficile Toxin A" 2006, J Biol Chem, vol. 281, pp. 10808-10815.
Hamm, EE et al., "Identification of CLostridium Difficile Toxin B Cardiotoxicity Using a Zebrafish Embryo Model of Intoxication" 2006 Proc Natl Acad Sci USA 103: 14176-14181.
He et al., "Antibody-Enhance, Fc Gamma Receptor-Mediated Endocytosis of Clostridium Difficile Toxin A" 2009, Infect Immun, vol. 77, pp. 2294-2303.
Henriques, B et al., "Cellular Internalization of Clostridium Difficile Toxin A" 1987, Microb Pathog 2:455-463.
Higgins et al., "CLUSTAL: A Package for Performing Multiple Sequence Alignment on a Microcomputer" 1988, Gene, 73: 237 244.
Jacob, SS et al., "Clostridium Difficile and Acute Respiratory Distress Syndrome" 2004, Heart Lung 33: 265-268.
Jank, T. et al., "Structure and Mode of Action of Clostridial Glucosylating Toxins: the ABCD Model" 2008, Trends in Microbiology 16: 222-229.
Johansson, AG et al., "Liver Cell Uptake and Degradation of Soluble Immunoglobulin G Immune Complexes In Vivo and In Vitro in Rats" 1996, Hepatology 24: 169-175.
Johnson, S et al., "Fatal Pseudomembranous Colitis Associated with a Variant Clostridium Difficile Strain Not Detected by Toxin A Immunoassay" 2001, Annals of Internal Medicine 135: 434-438.
Just, I et al., "Glucosylation of Rho Proteins by Clostridium Difficile Toxin B" 1995, Nature 375: 500-503.
Kelly, CP et al., "Neutrophil Recruitment in Clostridium Difficile Toxin A Enteritis in the Rabbit" 1994 J Clin Invest 93: 1257-1265.
Kelly, CP et al., "Clostridium Difficile Infection" 1998, Annu Rev Med 49: 375-90.
Krautz-Peterson, G et al., "Intracellular Neutralization of Shiga Toxin 2 by an A Subunit-Specific Human Monoclonal Antibody" 2008, Infection and Immunity 76(5) 1931-1939.
Krehenbrink, M et al., "Artificial Binding Proteins (Affitins) as Probes for Conformational Changes in Secretin PuID", Journal of Molecular Biology, Nov. 28, 2008; 383(5): 1058-68.
Kuijper, EJ et al., "Clostridium Difficile: Changing Epidemiology and New Treatment Options" 2007, Curr Opin Infect Dis 20(4): 376-383.
Kyne, L et al., "Health Care Costs and Mortality Associated with Nosocomial Diarrhea Due to Clostridium Difficile", 2002 Clin Infect Dis 34: 346-353.
Ladin, BF et al., "Characterization of a eDNA Encoding Ricin E, a Hybrid ricin-Ricinus Communis Agglutinin Gene from the Castor Plant Ricinus Communis" 1987, Plant Molecular Biology 9: 287-295.
Libby, JM et al., "Effects of the Two Toxins of Clostridium Difficile in Antibiotic-Associated Cecitis in Hamsters" 1982, Infect Immun 36: 822-829.
Linskens, HF and Jackson, John F. (Eds) Plant Toxin Analysis 1992, XXVI, 389 p. 33 illus (23 pgs).
Loo, VG et al., "A Predominantly Clonal Multi-Institutional Outbreak of Clostridium Difficile-Associated Diarrhea with High Morbidity and Mortality" 2005, N Eng J Med, vol. 353, pp. 2442-2449.
Lord, JM et al., "Ricin, Structure, Mode of Action, and Some Current Applications", 1994 the FASEB Journal 8, 201-208.
Lovdal, Y et al., "Fc Receptor Mediated Endocytosis of Small Soluble Immunoglobulin G Immune Complexes in Kupffer and Endothelial Cells from Rat Liver" 2000J Cell Sci 113 (Pt 18): 3255-3266.
Lowy, I et al., "Treatment with Monoclonal Antibodies Against Clostridium Difficile Toxins" 2010, N Eng J Med, vol. 362, pp. 197-205.
Maass, DR et al., "Alpaca (*Lama pacos*) as a Convenient Source of Recombinant Camelid Heavy Chain Antibodies (VHHs)" 2007, Journal of Immunological Methods 324: 13-25.
Maass, DR et al., "Three Surface Antigens Dominate the Mucosal Antibody Response to Gastrointestinal L3-Stage Stongylid Nematodes in Field Immune Sheep" 2007 Int J Parasitol 37: 953-962.
McDonald, LC et al., "An Epidemic, Toxin Gene-Variant Strain of Clostridium Difficile" 2005, N Eng J Med, vol. 353, pp. 2433-2441.
Mead, PS et al., "Food-Related Illness and Death in the United States" 1999, Emerg Infect Dis, 5:607-625, 1999.
Mohamed, N et al., "A High-Affinity Monoclonal Antibody to Anthrax Protective Antigen Passively Protects Rabbits Before and After Aerosolized Bacillus Anthracis Spore Challenge" 2005 Infect Immun 73: 795-802.
Montfort, W et al., "The Three Dimensional Structure of Ricin at 2.8A" 1987 Journal of Biological Chemistry 262, 5398-403.
Morgenstern, B et al., "Dialign: Finding Local Similarities by Multiple Sequence Alignment", 1998, Bioinformatics 14:290-294.
Mukherjee, J et al., "Human Stx2-Specific Monoclonal Antibodies Prevent Systemic Complications of *Escherichia coli* O 157:H7 Infection", 2002, Infect Immun 70: 612-619.
Mukherjee, J et al., "A Novel Strategy for Development of Recombinant Antitoxin Therapeutics Tested in a Mouse Botulism Model" 2012, PLoS One 7(1):e29941.
Notredame, C et al., "SAGA: Sequence Alignment by Genetic Algorithm" 1996, Nuc. Acids Research 24:1515-1524.
Nowakowski, A et al., "Potent Neutralization of Botulinum Neurotoxin by Recombinant Oligoclonal Antibody" Proc Natl Acad Sci USA, 99: 11346-50 (2002).
Owens, RC et al., "Antimicrobial-Associated Risk Factors for Clostridium Difficile Infection" 2008, Clin Infect Dis, vol. 46, pp. S19-S31.
Pfeifer, G et al., "Cellular Uptake of Clostridium Difficile Toxin B. Translocation of the N-Terminal Catalytic Domain into the Cytosol of Eukaryotic Cells" 2003, J Biol Chem 278: 44535-44541.
Pothoulakis, C et al., "Microbes and Microbial Toxins: aradigms for Microbial-Mucosal Interactions II. The Integrated Response of the Intestine to Clostridium Difficile Toxins" 2001, AM J Physiol Gastrointest Liver Physiol, vol. 280, pp. G178-G183.
Qa'Dan M et al., "pH-Induced Conformational Changes in Clostridium Difficile Toxin B" 2000, Infect Immun 68: 2470-2474.
Reineke, J et al., "Autocatalytic Cleavage of Clostridium Difficile Toxin B" 2007, Nature, vol. 446 pp. 415-419.
Riegler, M et al., "Clostridium Difficile Toxin B is More Potent then Toxin A in Damaging Human Colonic Epithelium n Vitro" 1995, J Clin Invest 95: 2004-2011.

(56) References Cited

OTHER PUBLICATIONS

Roberge, JY et al., "A Strategy for a Convergent Synthesis of N-Linked Glycopeptides ona Solid Support" 1995, Science 269: 202-204.
Roberts, LM et al., "The Primary Sequence of Ricins Communis Agglutinin, Comparision with Ricin" 1985, Journal of Biological Chemistry 260, 15682-8.
Rupnik, M et al., "Characterization of the Cleavage Site and Function of Resulting Cleavage Fragments After Limited Proteolysis of Clostridium Difficile Toxin B (TcdB) by Host Cells" 2005 Microbiology 151: 199-208.
Sakurai T et al., "Liver Abscess Caused by Clostridium Difficile" 2001 J Infect Dis 33: 69-70.
Sandvig, K. et al., "Entry of Ricin and Shiga Toxin into Cells: Molecular Mechanisms and Medical Perspectives", 2000, EMBO J 19 (22): 5943-5950.
Savidge, TC et al., "Clostridium Difficile Toxin B is an Inflammatory Enterotoxin in Human Intestine" 2003, Gastroenterol, vol. 125, pp. 413-420.
Sehr, P et al., "Glucosylation and ADP Ribosylation of Rho Proteins: Effects of NucleotideBinding, GTPase Activity, and Effector Coupling" 1998, Biochemistry 37: 5296-5304.
Sepulveda, J et al., "Efficient Serum Clearance of Botulinum Neurotoxin Achieved Using a Pool of Small Antitoxin Binding Agents" 2009, Infect Immun 78:756-763.
Siemann, M et al., "Clostridium Difficile-Associated Diseases, the Clinical Courses of 18 Fatal Cases" 2000, Intensive Care Medicine 26:416-421.
Simpson, LL, "Identification of the Major Steps in Botulinum Toxin Action", 2004, Annu Rev. Pharmacol. Toxicol, 44: 167-193.
Skaper, SD et al., "A Procedure for Purifying Neuron-Like Cells in Cultures from Central Nervous Tissue with a Defined Medium" 1979, Dev. Neurosci 2: 233-237.
Spears, KJ et al., "A Comparison of Enteropathogenic and Enterohaemorrhagic *Escherichia coli* Pathogenesis" 2006, FEMS Microbiology Letter 187-202.
Tatusova, TA et al., "BLAST 2 Sequences, a New Tool for Comparing Protein and Nucleotide Sequences", 1999, FEMS Microbiology Letter 174: 247-250.
Thompson, JD et al., "Clustal W: Improving the Sensitivity of Progressive Multiple Sequence Alignment Through Sequence Weighting, Position-Specific Gap Penalties and Weight Matrix Choice" 1994, Nuc. Acids Research 22: 4673-4680.
Tonna, I et al., "Pathogenesis and Treatment of Clostridium Difficile Infection" 2005, Postgrad Med J, 81: 367-369.
Tremblay, Jm et al., "Camelid Single Domain Antibodies (VHHs) as Neuronal Cell Intrabody Binding Agents and Inhibitors of Clostridium Botulinum Neurotoxin (BoNT) Proteases" 2010 Toxicon, 56(6): 990-998.
Tremblay, JM et al., "A Single VHH-Based Toxin-Neutralizing Agent and an Effector Antibody Protect Mice Against Challenge with Shiga Toxins 1 and 2", 2013, 81, 12 pp. 4593-4594.
Tucker, KD et al., "Toxin A of Clostridium Difficile Binds to the Human Carbohydrate Antigens I, X, and Y" 1991, Infect Immun 59: 73-78.
Ulmer, JB et al., "Heterologous Protection Against Influenza by Injection of DNA Encoding a Viral Protein" 1993, Science 259: 1745-1749.
Von Eichel-Streiber, C et al., "Large Clostridial Cytotoxins—A Family of Glycosyltransferases Modifying a Small GTP-Binding Proteins" 1996, Trend Microbiol, vol. 4, pp. 375-382.
Voth, DE et al., "Clostridium Difficile Toxins: Mechanism of Action and Role in Disease" 2005, Clin Microbiol Rev, vol. 18, pp. 247-263.
Walker, K. 2010 Interscience Conference on Antimicrobial Agents and Chemotherapy—50th Annual Meeting—Research on Promising New Agents: Part 1. IDrugs 13: 743-745.
Zar, FA et al., "A Comparison of Vancomycin and Metronidazole for the Treatment of Clostridium Difficile-Associated Diarrhea, Stratified by Disease Severity" 2007 Clinical Infectious Diseases 45:302-307.
Babcock, GJ et al., "Human Monoclonal Antibodies Directed Against Toxins A and B Prevent Clostridium Difficile-Induced Mortality in Hamsters" 2006, Infect Immun 74(11): 6339-47.
International Search Report and Written Opinion of the International Searching Authority dated Jul. 30, 2015 in PCT/US14/72340 (14 pgs).

* cited by examiner

Anti-BoNT/A sheep scFv coding nucleotide sequences

>scFv#2
CAGGCTGTGCTGACTCAGCCGTCCTCCGTGTCCGGGTCCCCGGGCCNNANGG
TCTCCATCACCTGCTCTGGAAGCAGGAGTAACGTTGGCACATATGGTGTAGG
TTGGTTCCAACAGCTCCCAGGATCGGGCCTCAGAACCATCATCTATTATAATG
ACAAACGACCCTCAGGGGTCCCCGACCGATTCTCTGCCTCCAAATCGGGCAA
CACAGCCACCCTGATCATCAGCTCGCTCCAGGCTGAGGATGAGGCCGATTAT
TTCTGTGGAAGTGCCGACGGTAGTAGTTATGGTATTTTCGGCAGTGGGACCA
GACTGACCGTCCTGGGTCAGCCCGCGGCCGCTGGTGGAGGCGGTTCAGGCGG
AGGTGGCTCTGGCGGTGGCGGATCGGCGCGCCAGGTGGGGCTGCAGGAGTCG
GGACCCAGCCTGGTGAAGCCCTCACAGACCCTCTCCCTCACCTGCACGGTCTC
TGGATTCTCATTGTCCAACAGTGTTGTAGGCTGGGTCCGCCAGGCTCCAGGAA
AGGTGCCGGAGTGGCTTGGTAGTATAGACAGTGGTGGTTACACAGTCGCTGA
CCCGGCCCTGAAATCCCGACTCAGCATCACAAGGGACACTTCCAAGAGCCAA
GTCTCCCTGTCACTGAACAGCGTGACAACTGAGGACACGGCCGTGTACTACT
GTACAAGGGCTTATAGTATTACTTATTATGCGTATCCCCCCTATATCGACTAC
TGGGGCCCAGGACTCCTGGTCACCGTCTCCTCAACTAGTGGTGCGCCGGTGC
CGTATCCGGATCCGCTGGAACCGCGTGCCGCA (SEQ ID NO:1)

>scFv#3
CAGGCTGTGCTGACTCAGCCGTCCTCCGTGTCCAGGTCCCTGGGCCAGAGTGT
CTCCATCACCTGCTCTGGAAGCAGCAGCAACGTTGGATATGGTGATTATGTG
GGCTGGTTCCAACGGGTCCCAGGATCAGCCCCCAAACTCCTCATCTATGGTG
CAACCACTCGAGCCTCGGGGGTCCCCGACCGATTCTCCGGCTCCAGGTCTGG
CAACACAGCGACTCTGACCATCAGCTCGCTCCAGGCTGAGGACGAGGCCGAT
TATTACTGTTCATCTTACGACAGTAGTCACTATAGTATTTTCGGCAGTGGGAC
CAGCCTGACCGTCCTGGGTCAGCCCGCGGCCGCTGGTGGAGGCGGTTCAGGC
GGAGGTGGCTCTGGCGGTGGCGGATCGGCGCGCCAGGTGGAGCTGCAGGAG
TCGGGACCCAGCCTGGTGAAGCCCTCACAGACCCTCTCCCTCACCTGCACGG
TCTCTGGATTCTCATTAAGTAGCAATGCTGTAGGCTGGGTCCGCCAGGCTCCA
GGAAAGGCGCCGGAGTGGGTTGGTGGTATAGATATAGATGGAAGGCCGGTCT
ATAAACCAGGCCTTAAGTCCCGGCTCAGCATCACCAGGGACACCTCCAACGC
TCAAGTCTCCCTGTCACTGAGCAGCGTGACAACTGAGGACACGGCCGTGTAC
TTCTGTGCAAGTTATTATGGTGGTTATCTTTATAATTATGCCCCTGGGGCATAT
ATCGAGCACTTGAGCCCAGGACTCCTGATCACCGTCTCCTCAACTAGTGGTGC
GCCGGTGCCGTATCCGGATCCGCTGGAACCGCGTGCCGCA (SEQ ID NO:3)

FIG. 1A

\>scFv#7
TCCTATGAACTGACCCAGCCGCCTTCAATGTCGGTGGCCTTGGGACAGACGG
CCAAGGTCACCTGCCAGGGAGACAACTTAGAAAACTTTTATGTTCAGTGGCA
CCAGCAGAAGCCGGGCCAGGCCCCTGTGACGGTCATTTTTCAGGATAATAAG
AGGCCCTCGGGGATCCCTGACCGGTTCTCTGGCTCCAACTCGGGGAACACGG
CCACCCTGACCATCAGCGGGGCCCGGACCGAGGACGAGGCCGACTATTACTG
TCAGTCAGGCCACAGCAGTATCGGTGGTGTTTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCAGGTGCAGCTGCAGGAGTCGGGACC
CAGCCTGGTGAAGCCCTCACAGACCCTCTCCCTCACCTGCACGGTCTCTGGCT
TCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACG
GCCCTGAAGTCCCGGCTCAGCATCACCAGGGACACCTCCAAGAGGCAAGTCT
CCCTATCACTGAGCAGCGTGACGACTGAGGACACGGCCATGTACTTCTGTGC
AAGATCGGCATATAGTACTCTTTATGATTATGAGTATGCCGCTGATATCTACG
ACTGGGGCCAGGACTCCTGGTCACCGTCTCCTCAACTAGTGGTGCGCCGGT
GCCGTATCCGGATCCGCTGGAACCGCGTGCCGCA (SEQ ID NO:5)

\>scFv#8
TCCTATGAACTGACCCAGCCGCCTTCAGTGTCGGTGGTTTGGGGNCNGANGG
CCGAGATCACCTGCCAGGGAGACCTACTGGATAAAAAATATACAGCTTGGTA
CCAGCAGAAGCCGGGCCAGGCTCCTATGAAAATCATTAATAAAGACAGTGAG
CGGCCTTCAGGGATCCGGGACCGGTTCTCGGGCTCCAGCTCAGGCAAAACAG
CCACCCTAACCATCAACGGGGCCCGGCCTGAGGACGAGGCCGACTATTACTG
TTTATCAGGTGACAGCAATAATAATGGTGTCTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCAGGTGGAGCTGCAGGGGTCGGGAC
CCAGCCTGGTGAAGCCCTCGCAGACCCTCTCCCTCACCTGCACGGTCTCTGGA
TTCTCATGGCCCAACAATGCTGTGGATTGGGTCCGCCAGGCTCCAGGAAAGG
CGCCGGAGTGGCTTGGTGGTATTGCCGATAATGGAAGAACAAACTACAACAC
GGCCCTAAAAGCCCGGCTCAGCATCACTAGGGACACCGCCAAGAGCCATGTC
TCCCTATCGCTGAGCAGCGTGACAGCTGAGGATACGGCCGTTTACTATTGTAC
AGCGGGGGTTATGGTCATGCACGCCACTGACTACTGGGGCCCGGGACTCCTG
GTCACCGTCTCCTCAACTAGTGGTGCGCCGGTGCCGTATCCGGATCCGCTGGA
ACCGCGTGCCGCA (SEQ ID NO:7)

FIG. 1B

>scFv#21
CAGGCTGTGGTGACTCAGCCGTCCTCCGTGTCCGGGTCCCCGGGCCNNANAG
TCTCCATCACCTGCTCTGGAAGCAGCAGCAACGTTGGTAGATATGCTGTAGG
CTGGTTCCAACAGCTCCCAGGATCGGGCCTCAGAACCGTCATCTATTATAATA
GCAATCGACCCTCAGGGGTCCCCGACCGATTCTCTGGCTCCAAATCGGGCAA
CACAGCCACCCTGACCATCAGCTCGCTCCAGGCTGAGGATGAGGCCGATTAT
TTCTGTGGAAGTTATGACAGTAGTATCTATGGTGTTTTCGGCAGCGGGACCAG
GCTGACCGTCCTGGGTCAGCCCGCGGCCGCTGGTGGAGGCGGTTCAGGCGGA
GGTGGCTCTGGCGGTGGCGGATCGGCGCGCCAGGTGCAGCTGCAGGAGTCGG
GACCCAGCCTGGTGAGGCCCTCACAGACCCTCTCCCTCACCTGCACGATCTCT
GGATTCTCTTTAAGAGAGTATGGTGTAGGTTGGGTCCGCCAGGCTCCAGGAA
AGGCGTTGGAGTGGCTTGGGCGAATAGATGATTCTGGATACACATTACATAA
TCCTGCCCTTAAGTCCCGGCTCACCATAACTAGGGACATCTCCAAGAGCCAA
GTCTCCCTGTCACTGAGCAGCGTGACACTTGAGGACACGGCCGAATATTACT
GCGTATATGCTAGTCGTGGTACTGCTTGGTTGGGAGACATCGATGTCTGGGGC
CCAGGACTCCTGCTCACTGTCTCCTCAACTAGTGGTGCGCCGGTGCCGTATCC
GGATCCGCTGGAACCGCGTGCCGCA (SEQ ID NO:9)

>scFv#E
CAGGCTGTGCTGACTCAGCCGTCCTCCGTGTCCAGGTCCCTGGGCCNNANTGT
CTCGATCACCTGCTCTGGAGGCAGCAGCAACGTTGGACAAGGTGATTATGTG
GCCTGGTTCCAACAGGTCCCAGGATCAGCCCCCAAACTCCTCATCTATGATGC
GACGAATCGAGCCTCGGGGGTCCCCGACCGATTCGTCGGCTCCAGATATGGC
AACTCAGCGACTCTGATCATCACCTCGGTCCAGGCTGAGGACGAGGCCGATT
ATTATTGTGCATCTTATGACAGTAGTATGTATACGATTTTCGGCAGCGGGACC
AGCCTGACCGTCCTGGGTCAGCCCGCGGCCGCTGGTGGAGGCGGTTCAGGCG
GAGGTGGCTCTGGCGGTGGCGGATCGGCGCGCCAGGTGGAGCTGCAGGGGTC
GGGACCCAGCCAGGTGAAGCCCTCACAGACCCTCTCCCTCATCTGCACGATC
TCTGGATTCTCATTAACCAGCAATAATGTAGCCTGGGTCCGCCAGGCTCCAGG
AAAGGGACTGGAGTGGGTTGGTGTCATAAGTGATGGTGGAACTCCATACTAT
AACTCGGCCCTGAAATCCCGGCTCAGCATCACCAGGGACACCTCCAAGAGCC
AGGTCTCCCTGTCACTGAGCAGCGTGACAACTGAGGACACGGCCGTGTACTA
CTGTGCACGGACGTTGGATTATAGTCATATTTGGTTGTACTCCGCCGACCAAT
GGGGCCCAGGACTCCTGGTCACCGTCTCCTCAACTAGTGGTGCGCCGGTGCC
GTATCCGGATCCGCTGGAACCGCGTGCCGCA (SEQ ID NO:11)

FIG. 1C

Anti-BoNT/A sheep scFv amino acid sequences

>scFv#2
QAVLTQPSSVSGSPGXXVSITCSGSRSNVGTYGVGWFQQLPGSGLRTIIYYNDKR
PSGVPDRFSASKSGNTATLIISSLQAEDEADYFCGSADGSSYGIFGSGTRLTVLGQ
PAAAGGGGSGGGGSGGGGSARQVGLQESGPSLVKPSQTLSLTCTVSGFSLSNSV
VGWVRQAPGKVPEWLGSIDSGGYTVADPALKSRLSITRDTSKSQVSLSLNSVTTE
DTAVYYCTRAYSITYYAYPPYIDYWGPGLLVTVSSTSGAPVPYPDPLEPRAA
(SEQ ID NO:2)

>scFv#3
QAVLTQPSSVSRSLGQSVSITCSGSSSNVGYGDYVGWFQRVPGSAPKLLIYGATT
RASGVPDRFSGSRSGNTATLTISSLQAEDEADYYCSSYDSSHYSIFGSGTSLTVLG
QPAAAGGGGSGGGGSGGGGSARQVELQESGPSLVKPSQTLSLTCTVSGFSLSSN
AVGWVRQAPGKAPEWVGGIDIDGRPVYKPGLKSRLSITRDTSNAQVSLSLSSVTT
EDTAVYFCASYYGGYLYNYAPGAYIEHLSPGLLITVSSTSGAPVPYPDPLEPRAA
(SEQ ID NO:4)

>scFv#7
SYELTQPPSMSVALGQTAKVTCQGDNLENFYVQWHQQKPGQAPVTVIFQDNKR
PSGIPDRFSGSNSGNTATLTISGARTEDEADYYCQSGHSSIGGVFGSGTSLTVLGQ
PAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTE
DTAMYFCARSAYSTLYDYEYAADIYDWGPGLLVTVSSTSGAPVPYPDPLEPRAA
(SEQ ID NO:6)

>scFv#8
SYELTQPPSVSVVWGXXAEITCQGDLLDKKYTAWYQQKPGQAPMKIINKDSERP
SGIRDRFSGSSSGKTATLTINGARPEDEADYYCLSGDSNNNGVFGSGTSLTVLGQ
PAAAGGGGSGGGGSGGGGSARQVELQGSGPSLVKPSQTLSLTCTVSGFSWPNNA
VDWVRQAPGKAPEWLGGIADNGRTNYNTALKARLSITRDTAKSHVSLSLSSVTA
EDTAVYYCTAGVMVMHATDYWGPGLLVTVSSTSGAPVPYPDPLEPRAA
(SEQ ID NO:8)

>scFv#21
QAVVTQPSSVSGSPGXXVSITCSGSSSNVGRYAVGWFQQLPGSGLRTVIYYNSNR
PSGVPDRFSGSKSGNTATLTISSLQAEDEADYFCGSYDSSIYGVFGSGTRLTVLGQ
PAAAGGGGSGGGGSGGGGSARQVQLQESGPSLVRPSQTLSLTCTISGFSLREYGV
GWVRQAPGKALEWLGRIDDSGYTLHNPALKSRLTITRDISKSQVSLSLSSVTLED
TAEYYCVYASRGTAWLGDIDVWGPGLLLTVSSTSGAPVPYPDPLEPRAA
(SEQ ID NO:10)

FIG. 1D

>scFv#E
QAVLTQPSSVSRSLGXXVSITCSGGSSNVGQGDYVAWFQQVPGSAPKLLIYDAT
NRASGVPDRFVGSRYGNSATLIITSVQAEDEADYYCASYDSSMYTIFGSGTSLTV
LGQPAAAGGGGSGGGGSGGGGSARQVELQGSGPSQVKPSQTLSLICTISGFSLTS
NNVAWVRQAPGKGLEWVGVISDGGTPYYNSALKSRLSITRDTSKSQVSLSLSSV
TTEDTAVYYCARTLDYSHIWLYSADQWGPGLLVTVSSTSGAPVPYPDPLEPRAA
(SEQ ID NO:12)

FIG. 1E

Nucleotide sequence of scFv#7-2E is:

GGTGCGCCGGTGCCGTATCCGGATCCGCTCGAGCCGCGTGCCGGCTCCTATGAACTG
ACCCAGCCGCCTTCAATGTCGGTGGCCTTGGGACAGACGGCCAAGGTCACCTGCCAG
GGAGACAACTTAGAAAACTTTTATGTTCAGTGGCACCAGCAGAAGCCGGGCCAGGC
CCCTGTGACGGTCATTTTTCAGGATAATAAGAGGCCCTCGGGGATCCCTGACCGGTT
CTCTGGCTCCAACTCGGGGAACACGGCCACCCTGACCATCAGCGGGGCCCGGACCG
AGGACGAGGCCGACTATTACTGTCAGTCAGGCCACAGCAGTATCGGTGGTGTTTTCG
GCAGCGGGACCAGCCTGACCGTCCTGGGTCAGCCCGCGGCCGCTGGTGGAGGCGGT
TCAGGCGGAGGTGGCTCTGGCGGTGGCGGATCGGCGCGCCAGGTGCAGCTGCAGGA
GTCGGGACCCAGCCTGGTGAAGCCCTCACAGACCCTCTCCCTCACCTGCACGGTCTC
TGGCTTCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACGGCCCT
GAAGTCCCGGCTCAGCATCACCAGGGACACCTCCAAGAGGCAAGTCTCCCTATCACT
GAGCAGCGTGACGACTGAGGACACGGCCATGTACTTCTGTGCAAGATCGGCATATA
GTACTCTTTATGATTATGAGTATGCCGCTGATATCTACGACTGGGGCCCAGGACTCC
TGGTCACCGTCTCCTCAACTAGTGGTGCGCCGGTGCCGTATCCGGATCCGCTGGAAC
CGCGTGCCGCA (SEQ ID NO:13)

Amino acid sequence of scFv#7-2E is:

GAPVPYPDPLEPRAGSYELTQPPSMSVALGQTAKVTCQGDNLENFYVQWHQQKPGQAP
VTVIFQDNKRPSGIPDRFSGSNSGNTATLTISGARTEDEADYYCQSGHSSIGGVFGSGTSL
TVLGQPAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTEDTAM
YFCARSAYSTLYDYEYAADIYDWGPGLLVTVSSTSGAPVPYPDPLEPRAA
(SEQ ID NO:14)

FIG. 2

BoNT/A holotoxin binding VHHs:

JDA-D12
Nucleotide sequence:
CAGGTGCAGCTCGTGGAGTCAGGAGGAGGCTTGGTGCAGCCTGGGGGATCTCTGAGACTCTCGTGTGTAGTCTCTGGAAGTG
ACTTCAATATCCTATATCATGGGCTGGTACCGCCAGGTTCCAGGGAAGCCGCGAGTTGGTCGCAGATATTACTACTGAAGGA
AAAACAAACTATGGCGGCTCCGTAAAGGACGATTCACCATCTCCAGAGACAATGCCAAAAACACGGTTATCTGCAAATGTTC
GGCCTGAAACCTGAGACGCGGGTAATTATGTCTGTAACGCAGACTGAAGATGGTGCATGGACCGCGGGGGGACTACGGTA
TCGACTACTGGGGCAAAGGGACCCTGGTCACCGTCTCCTCAGAACCCAAGACACCAAAAACCACAA (SEQ ID NO:19)

amino acid sequence:
QVQLVESGGGLVQPGGSLRLSCVVSGSDFNTYIMGWYRQVPGKPRELVADITTEGKTNYGGSVKGRFTISRDNAKNTVYLQMFGLK
PEDAGNYVCNADWKMGAWTAGDYGIDYWGKGTLVTVSSEPKTPKPQ (SEQ ID NO:20)

JDQ-A5
Nucleotide sequence:
CAGGTGCAGCTCGTGGAGTCCGGTGGAGGCTTGGTGCAGCCTGGGGGGTCTCTGAGACTCTCCTGTGCAGCCTCTGCAGGCA
ATCTGGATTATTATGCCATAGGCTGGTTCCGCCAGGCCCCAGGGAAGGAGCGCGAGGGGTCTCATGTATTAGTAGTAGTGAT
GGTAGCACTGTCTATACAGATTCCGTGAAGGGCCGATTCACCATCTCCAGAGACAATACCAAGAACACGGTAGATCTGCAAATG
GACAATTTGAAACCTGAGGACACGGCCGTTTATTACTGTGCGACAGTCGTTAACTACTGCACAGCCGGTGGTCCATTCAC
GCGAGCCCGTATGAAATCTGGGGCCAGGGGACCCAGGTCACCGTCTCCTCAGCGCACCACCAGCAGCGAAGACCCCTCG
(SEQ ID NO:21)

amino acid sequence:
QVQLVESGGGLVQPGGSLRLSCAASAGNLDYYAIGWFRQAPGKEREGVSCISSSDGSTVYTDSVKGRFTISRDNTKNTVDLQMDNL
KPEDTAVYYCATVVNYYCTAGGSIHASPYEIWGQGTQVTVSSAHHSEDPS (SEQ ID NO:22)

FIG. 3A

JDQ-B5
Nucleotide sequence:

CAGGTGCAGCTCGTGGAGTCCGGCGGAGGCTTGGTGCACCCTGGGGGTCTCTGAGACTCTCTTGTGCACCCTCTGCCAGTC
TACCATCAACACCCTTCAACCCCTTCAACATATGGTGGGCTGGTACCGTCAGGCTCCAGGTAAACAGCGCGAAATGGTCGCA
AGTATTGGTCTACGAATAAACTATGCAGACTCCGTGAAGGGCCGATTCACCATCTCCAGAGACAACGCCAAGAACACGGTGGA
TCTGCAGATGGACAGCCTGCGACCTGAGGACTCAGCCACATACTACTGTCATATAGAATACACCCACTACTGGGGCAAAGGGA
CCCTGGTCACCGTCTCCTCGGAACCCAAGACACCAAAACCACAA (SEQ ID NO:23)

amino acid sequence:
QVQLVESGGGLVHPGGSLRLSCAPSASLPSTPFNPFNNMVGWYRQAPGKQREMVASIGLRINYADSVKGRFTISRDNAKNTVDLQM
DSLRPEDSATYYCHIEYTHYWGKGTLVTVSSEPKTPKPQ (SEQ ID NO:24)

JDQ-C2
Nucleotide sequence:

CAGGTGCAGCTCGTCGTGGAGTCTCTGGTGAGGCTTGGCGCAGCCTGGGGGTCTCTGAGACTCTCCTGTGAAGGCGTCTGGTTTTG
GGACATGGTTCAGGTTCGATGAGAACACCGTGAACTGGTACCGCCAGGCTCCGTGAACCTGAAAAGTCGCGACTTCGACGAGTTGGT
CGCTCGTTACCCAAAAAGTGGCATCGTAACCTATTTAGACTCCGTGAAGGGCCGATTCACGATCTCCAGAGACAACGCCAAAAA
AATGGCGTTTCTGCAAATGGACAACCTGAAACCTGAGGACCCGTCTATTATTGCAATGTCGGTGAATTTTGGGCCAGG
GGACCCAGGTCACGATCTCCTCAGAACCCAAGACACCAAAACCACAA (SEQ ID NO:25)

amino acid sequence:
QVQLVESGGGLAQPGGSLRLSCEEASGFGTWFRFDENTVNWYRQPPGKSREFDELVARYPKSGIVTYLDSVKGRFTISRDNAKKMAF
LQMDNLKPEDTAVYYCNVGEFWGQGTQVTISSEPKTPKPQ (SEQ ID NO:26)

FIG. 3A

JDQ-F12
Nucleotide sequence:
CAGGTGCAGCTCGTGGAGTCTGGGGGAGGCTTGGTGCAGCCTGGGGGGTCTCTGAGACTCTCCTGTGCAGCCTCTGGATTCA
CCCTAGGGTCGCGTTACATGAGCTGGGTCCGCCAGGCTCCAGGAGAGGGGTTCGAGTGGGTCTCAAGTATTGAACCCTCTGG
TACGCATGGGATGGAGACTCCGCGAAGGGACGATTCACCACTTCCAACAGGACACCCAAGAACACGCTTTATCTGCAAATGA
GCAACCTGAGAGACCCGAGGACACGGGTGTTTATTACTGTGCAACAGGGTATCGACAGGGATTCCGGGTGGCTCGTG
GGGCCAGGGGACCCAGGTCACCGTCTCCTCAGAACCCAAGACACCAAAACCACAA (SEQ ID NO:27)

amino acid sequence:
QVQLVESGGGLVQPGGSLRLSCAASGFTLGSRYMSWVRQAPGEGFEWVSSIEPSGTAWDGDSAKRFTTSRDDAKNTLYLQMSN
LQPEDTGVYYCATGYRTDTRIPGGSWGQTQVTVSSEPKTPKPQ (SEQ ID NO:28)

JDQ-G5
Nucleotide sequence:
CAGGTGCAGCTCGTGGAGTCTGGGGGAGGCTTGGTGCAGCCTGGGGGGTCTCTGAGACTCTCCTGTCAAGTCTCTGATTCA
CCTTCGGTGACTGGGTCATGAGCTGGGTCCGCCAGGCTCCGGGGAAGGAGCGGAATTCGTCGCAAGTATTACGGCTACTAG
TAGTCTAAAGTATTATGCAGAGACTCCAGAGACAATGTCAACAACAACACTGTTTCTGCAAATG
GATCGCCTGAAATCTGAGGACACGGCCGTTTATTACTGTCGGTCCCCCCAACTACTGGGGACCCAGGTCACCGTCTC
CGCCGAACCCAAGACACCAAAACCACAA (SEQ ID NO:29)

amino acid sequence:
QVQLVESGGGLVQPGGSLRLSCQVSGFTFGDWVMSWFRQAPGKEREFVASITATSSLKYYADSVKGRFTISRDNVNTLFLQMDRL
KSEDTAVYYCRSPNYWGQTQVTVSAEPKTPKPQ (SEQ ID NO:30)

JDQ-H7
Nucleotide sequence:
CAGGTGCAGCTCGTGGAGTCAGGTCAGGTGAGGCTTGGTGCAGCCTGGGGGGTCTCTGAGACTCTCCTGTGTAGTTTCTGAAGCG
ACATCAGTGGCATTGCGATGGCGATGGCTCCAGGGAAGCGCGCAGGAAGTGTCGCAGATATTTTTTCTGGCGG
TAGTACAGACTATGCAGGCTCCGTGAAGGGCCGATTCACCATCTCCAGAGACAACGCCAAGAAGACGAGCTATCTGCAAATGA
ACAAGTGAAACCTGAAAACCTGAGGACACGGCCGTGACTACTGGGGCCAGGGGACCCAGGT
CACCGTCTCCTCAGCGCACCACAGCGAAGACCCCCTCG (SEQ ID NO:31)

amino acid sequence:
QVQLVESGGGLVQVGGSLRLSCVVSGSDISGIAMGWYRQAPGKRREMVADIFSGGSTDYAGSVKGRFTISRDNAKKTSYLQMNNV
KPEDTGVYYCRLYGSGDYWGQGTQVTVSSAHHSEDPS (SEQ ID NO:32)

FIG. 3B

BoNT/B holotoxin binding VHHs:

JEQ-A5
Nucleotide sequence:

CAGGTGCAGCTCGTGGAGTCAGGCGGAGGCTTGGTGCAGCCTGGGGGGTCTCTGAAACTCTCCTGTGCAGCCTCTGGATTCA
CTTTGGGACACCATCGCGTTGGCTGTGTTCCGCCAGGCCCCAGGAAAGAAGCGTGAGGGGTCGCGTGTATTAGCGCCACTGG
TCTTAGCACACACTATTCAGACTCCGTGACTGAGACCGCCAGTGTTTATTACTGTGCAAGCAGAATTCTCCCTTAATTCGGTGCATGCGAATATGTGCCT
GAACAGCCTGAAACCTGAGGACGCCAGTGTTTATTACTGTGCAAGCAGAATTCTCCCTTAATTCGGTGCATGCGAATATGTGCCT
TTCAGAGCCTCAGTATGACAACTGGGGCCAGGGGACCCAGTCAGAATCTCCTCAGAACCCAAGACACCAAAACCACAA
(SEQ ID NO:33)

amino acid sequence:

QVQLVESGGGLVQPGGSLKLSCAASGFTLGHHRVGWFRQAPGKKREGVACISATGLSTHYSDSVTGRFTVSRDNLNNVAYLQLNSL
KPEDAGVYYCASRFSLNSVDANMCLSEPQYDNWGQGTQVRISSEPKTPKPQ (SEQ ID NO:34)

JEQ-H11
Nucleotide sequence:

CAGGTGCAGCTCGTGGAGAGCGGGTGAGGATTGGTGCAGGCCCGGGACCTCTCCTGCGCAGGCTCTGGACGC
TCCTTCAGCGCCGTCTGTCATGGGCTGTTCCGCCAGGCCCGGGAAGGAGCGAGAATTCGTAGCAGCACTTAGACAAATTAT
TGGTAGCACACACTATGCAGATCAGATCCGTGAAGGGCGATTCACCATCTCACAGCGGACCTCCGACTATGCTGAGCTTTCTACGACCGG
GAACAGCCTGAAACCTGACGACACTGGGGTCAGGGGACTCAGGTCACCGTCTCCTCAGCCACCACAGCGAAGACCCCCCTCG (SEQ ID NO:35)
GAGTATGACACTGGGGTCAGGGGACTCAGGTCACCGTCTCCTCAGCCACCACAGCGAAGACCCCCCTCG (SEQ ID NO:35)

amino acid sequence:

QVQLVESGGGLVQAGGSLRLSCAGSGRSFSAAVMGWFRQAPGKEREFVAALRQIIGSTHYADSVKGRFTISRDNAKNMLYLDMNSL
KPTDTAAYYCTAGPPTMLDVSTDREYDTWGQGTQVTVSSAHHSEDPS (SEQ ID NO:36)

FIG. 3C

JDQ-B5
Nucleotide sequence:

CAGGTGCAGCTCGTGGAGTCCGGCGGAGGCTTGGTGCACCCTGGGGGGTCTCTGAGACTCTCTTGTGCACCCTGCCAGTC
TACCATCAACACCCTTCAACATATGGTGGCTGGTACCGTCCAGTCCTGTGGCCCAGTAAACAGCGCGAAATGGTCGCA
AGTATTGGTCTACGAATAAACTATGCAGACTCCGTGAAGGGCCGATTCACCATCTCCAGAGACAACGCCAAGAACACGGTGGA
TCTGCAGATGGACAGCCTGCGACAGCCTGAGGACTGAGGACTCAGCCACATACTGTGTAATAGAATACACCCACTACTGGGGCAAAGGGA
CCCTGGTCACCGTCTCCTCGGAACCCAAGACACCAAAACCACAA (SEQ ID NO:23)

amino acid sequence:

QVQLVESGGGLVHPGGSLRLSCAPSASLPSTPFNPFNNMVGWYRQAPGKQREMVASIGLRINYADSVKGRFTISRDNAKNTVDLQM
DSLRPEDSATYYCHIEYTHYWGKGTLVTVSSEPKTPKQEPKTPKQ (SEQ ID NO:24)

JDQ-E9
Nucleotide sequence:

CAGGTGCAGCTCGTGGAGTCCGGAGGAGGCTTGGTGCACCTGGGGCTCTCTGAGACTCTCTTGTGTAGTCTCTGGATTCG
CCTACGAAATGCCCATGATGGGCTGGTACCGCCAGGCTCCAGGGAATCAGCGCGAGTTGGTCGCAACTATTGGTACAGGTGG
TAGGATGAACTATGCAGACTCCGTGAAGGGCCGATTCACCATCTCCAGAGACAACGCCAAGAACACGGTGTATCTGCAAATGA
ACAGCCTGAAACTGAAGACTGAGGACACAGCCGCCTATTACTGTAAAATCGAGTTTACAAATTACTGGGGCCAGGGGACCCAAGTCACC
GTCTCCTCAGAACCCAAGACACCAAAACCACAA (SEQ ID NO:37)

amino acid sequence:

QVQLVESGGGLVQPGGSLRLSCVVSGFAYEMPMMGWYRQAPGNQRELVATIGTGGRMNYADSVKGRFTISRDNAKNTVYLQMNS
LKPEDTAAYYCKIEFTNYWGQGTQVTVSSEPKTPKQ (SEQ ID NO:38)

JDQ-B2
Nucleotide sequence:

CAGGTGCAGCTCGTGGAGTCAGGTGGAGGCTTGGTGCAGCCGGGGGATCTCTGAGACTGCTCCTGTACAGTCTCTGGAAGCA
TCTTCGATCTACCTGGAATGAACTATCGCCAGCTCCGTATGCGCCAGCTCCAGCGCGAGTTGGTCGCAGATATTAGTAGTGATGGT
AGGAGGACAAACTATGCAGACTCCGTGAAGGGCCGATTCACCATGTCCAGAGACAATGCCAAGAAAACGGTGTATCTGCAAAT
GGACAGCCTGAAACCTGAAGACACGGCCGTCTATTACTGTAAGTGAAATTTACTCACCACTGGGCCAGGGGATCCAGGTCA
CCGTCTCCTCAGAACCCAAGACACCAAAACCACAA (SEQ ID NO:39)

amino acid sequence:

QVQLVESGGGLVQPGGSLRLSCTVSGSIFDLPGMNWYRQAPGAQRELVADISSDGRRTNYADSVKGRFTMSRDNAKKTVYLQMDS
LKPDDTAVYYCNVKFTHHWGQGIQVTVSSEPKTPKQ (SEQ ID NO:40)

FIG. 4A

JDQ-C5
Nucleotide sequence:

CAGGTGCAGCTCGTGGAGTCAGGCGGAGGCTTGGTGCAGCCGGGGGGATCTCTGAGGCTGTCCTGTACGGTCTCTGGAAGC
ATCTTCGGCCTACCTGGCATGAGCTGGTATCGCCAGGCTCCAGGGCGCCAGCCGAGTTGGTCGCAGATATTAGTAGTGATG
GTGGAGGACGCACTATGCAGATCCGTGAAGGGCCGCTTCACCATCTCCAGAGACAATGACAAGAAAACGGTGTATCTGCAG
ATGGACAGCCTGAAACCTGACGACACAGCCGTCTATTACTGTGTGAAATTTACTCACCACTGGGGCCAGGGGATCCAGGT
CACCGTCTCCTCAGAACCCAAGAACCCAAAACCACAA (SEQ ID NO:41)

amino acid sequence:

QVQLVESGGGLVQPGGSLRLSCTVSGSIFGLPGMSWYRQAPGAQRELVADISSDGGRTHYADSVKGRFTISRDNDKKTVYLQMDSL
KPDDTAVYYCNVKFTHHWGQGIQVTVSSEPKTPKPQ (SEQ ID NO:42)

JDQ-F9
Nucleotide sequence:

CAGGTGCAGCTCGTGGAGTCTGGGGGAGGCTTGGTGCAGGATGGGGGGTCTCTGAGGCTCTCCTGCACAACATCTGAAGTA
TCGACAGTTTCAATGCCATAGAGTGGTACCGCCAGGCTCCAGGGAAGCAGCGCGAATTGGTCGCAAGTATAAGTAGTGATGGT
CGTCGCACAAACTATGCAGATTCCGTGAAGGGCCGATTCACCATCTCCGGAGACAACGCCAAGAACACGGTGTATCTGCAAAT
GAACAGCCTGAAACCTGAGGACACAGCCGTGTATTACTGTCATAGACCTTTTACCCACCACTACTGGGCCAGGGGACCCAGGTCA
CCGTCTCCTCAGAACCCAAGACACCAAAACCACAA (SEQ ID NO:43)

amino acid sequence:

QVQLVESGGGLVQDGGSLRLSCTTSGSIDSFNAIEWYRQAPGKQRELVASISSDGRRTNYADSVKGRFTISGDNAKNTVYLQMNSLK
PEDTAVYYCHRPFTHYWGQGTQVTVSSEPKTPKPQ (SEQ ID NO:44)

Phylogenetic tree of JDQ-B5 competition group with random VHHs

BoNT/A binding VHHs binding the same epitope based on competition studies:
- 7-T3
- JDQ-F9 lh
- JDQ-B2 lh
- JDQ-C5 lh
- JDQ-B5 lh
- JDO-E9 lh Random VHHs from our publication Maass et al, JIM, 2007:
- 12-T3
- 6-T3
- 11-T3 VHH
- 8-T3 VHH
- 2-T3
- 3-T3
- 10-T3

Branch values: 23.3750, 8.3250, 2.9545, 3.0435, 9.6750, 13.9375, 11.0025, 22.5332, 21.8307, 25.1693, 28.1660, 19.2031, 17.5375, 19.6250, 3

Two VHHs were identified that bind to BoNT/A holotoxin, H7 and B5. Each was expressed in different formats fused to E-tag and, in some cases, fused to one another H7/E and B5/E, single-tagged VHH monomers H7/B5/E, single-tagged VHH heterodimer E/H7/B5/E, double-tagged VHH heterodimer

Fig. 6 anti E-tag mAb

Single-tagged heterodimer VHH potentially leads to decoration of toxin with two anti-tag mAbs E-tag BoNT single-tagged heterodimer

ATGAGCGATAAAATTATTCACCTGACTGACGACAGTTTGACACGGATGTACTCAAAGCGGACGGGGCGATCCTCGTCGATTTCTG
GGCAGAGTGGTGCGGTCCGTGCAAAATGATCGCCTGCCCGGATTCTGGATGAAATCGCTGACGAATATCAGGGCAAACTGACCGTTGCAA
AACTGAACATCGATCAAAACCCTGGCACTGCGCCGCCGAAATATGGCATCCGTGGTATCCGACTCTGCTGTTCAAAAACGGTGAA
GTGCGGCAACCAAAGTGGGTGCACTGTCTAAAGGTCAGTTGAAAGAGTTCCTCGACGCTAACCTGGCCGGTTCTGGTTCTGGCCA
TATGCACCATCATCATCATCATTCTTCTGGTCTGGTGCCACGGACACAAGGCCATGGCGATATCGGATCGAATTCGGATATCCCAGGTGCAGCTCGTG
AGCAGACATGGACAGCCCAGATCTGGGTACCGACGACGACAAGGCCATGGCGATATCGGATCGAATTCCCAGGTGCAGCTCGTG
GAGTCAGGTGGAGGCTTGGTGCAGGTTGGGGGGTCTCTGAGACTCTCCTGTGTAGTTTCTGGCGTTCTGGAAGCGACATCAGTGGCATTGCGAT
GGGCTGGTACCGCCAGGCTCCAGGAAGCGGGCTGGAGTGGGTAGTACAACGCCAGTAGTACAACGTGAAACCTGAGGACACCGGA
TGAAGGGCCGATTCACCATCTCCAGAGACAACGCCAAGAACGAGCTATCTGCAAATGAACAACGTGAAACCTGAGGACACCGGA
GTCTACTACTGTAGGCTGTACGGAGCGGTGACTACTGGGGCCAGGGAACCCAGGTCACCGTCTCCTCAGCGCACCACAGCGAAGA
CCCACTAGTGGTGCGCCCGGTGCCGTATCCGGATCCGCTGGAACCGCGTTAA (SEQ ID NO:45)

MSDKIIHLTDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDKAMAISDPNSQVQLV
ESGGGLVQVGGSLRLSCVVSGSDISGIAMGWYRQAPGK (cont.)

B5/E

ATGAGCGATAAAATTATTCACCTGACTGACGACAGTTTTGACACGGATGTACTCAAAGCGGACGGGGCGATCCTGCGATTTCTG
GGCAGAGTGGTGCGGTCCGTGCAAAATGATCGCCCGCCGCCGAAATCGCTGACGAATATCAGGGCAAACTGACCGTTGCAA
AACTGAACATCGATCAAAACCCTGGCACTGCCGCCGCCGAAATATGGCATCCGTGTATCCCGACTCTGCTGCTGTTCAAAAACGGTGAA
GTGGCGGCAACCAAAGTGGGTGCACTGTCTAAAGGTCAGTTGAAAGAGTTCCTGGACGCTAACCTGGCCGGTTCTGGTTCTGGCCA
TATGCACCATCATCATCATCATTCTTCTGGTCTGGTGCCACGCGATCGTCTGGTATGAAAGAAACCGCTGCTAAATTCGAACGCC
AGCACATGGACAGCCCAGATCTGGGTACCGACGACGACAAGGCCATGGCGATATCGGATCCGAATTCCAGGTGCAGCTCGTG
GAGTCCGCGCGAGGCTTGGTGCACCCTGGGGGGTCTCTCAGGCTCCAGGTCTCCAGGTAAACGCGAAATGTTCGAAGATCGAGTGGATCGACAACGTTGACGTGGATCTGCAGATGGACAGCCTGCGACCT
ATGCAGACTCCGTGAAGGGCCGATTCACCATCTCCAGAGACAACGCCAAGAACACGTTGACGTGGATCTGCAGATGGACAGCCTGCGACCT
GAGGACTCAGCCACATACTGTCATATAGAATACACCCACTACTGGGGCAAAGGGACCCTGGTCACCGTCTCCTCGGAACCCAA
GACACCAAAACCACAAACTAGTGGTGCGCCGGTCGCCCGTATCCGGATCCGCTGGAACCGCGTTAA (SEQ ID NO:47)

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDKAMAISDPNSQVQLV
ESGGGLVHPGGSLRLSCAPSASLPSTPFNPFNNMVGWYRQAPGKQREMVASIGLRINYADSVKGRFTISRDNAKNTVDLQMDSLRP
EDSATYYCHIEYTHYWGKGTLVTVSSEPKTPKPQTSGAPVPYPDPLEPR (SEQ ID NO:48)

ATGAGCGATAAAATTATTCACCTGACTGACGACAGTTTGACACGGATGTACTCAAAGCGGACGGGGCGATCCTCGTCGATTTCTG
GGCAGAGTGGTGCGGTCCGTGCAAAATGATCGCCGCCGCCGATTCTGATGAAATCGCTGACGAATATCGACACCGTTGCAA
AACTGAACATGCATCAAAACCCTGGCACTGCACTGCGCCGAAATATGGCATCCGTGTATCCGACTCGTCTGTTCAAAAACGGTGAA
GTGGCGGCAACCAAGTGGGTGCACTGTCTTCTGTGGTTCGATGCAGTTGAAGAGTTCCTGACACCTGGCCGTTCGGTTCTGGCCA
TATGCACCATCATCATCATGACGACAGCCCAGATCTGGTACCGACATCGGGTACCGACACTCTCCGTGTAGTTTCTGAAGAAACGGCCTAAATTCGAACGCC
AGCACATGGACAGCCAGCCAGATCTGGTACCGACATCGGGTACCGACTCTCCGTGTAGTTTCTGGAAGCGACATCAGTGGCATTGGCAGGCTGGTACCG
GGCTTGGTGCAGGTTGGGGCGCGCAAGGAAGCGGCGCAAGAGACAACGCGGTAGTACAGACTATGGCAGGCTCCGTGAAGGGCCGAT
CCAGGCTCCAGGGAAGCGGCGCAAGAGACAACGCGGTAGTACAGACTATGAAACCTGCACCGCCACCACAGCCAATCTACTGT
TCACCATCTCCAGAGACAACGCGGTGACTGGGGCCAGGGACCCCAGGTCACCGTCTCCTCAGCGCACACAGCGAAGACCCACTAGTGC
AGGCTGTACGGAGCGGTGACTGGGGCCAGGGACCGTTCAGGGAGGTGGCTTCAGAGCGGATCCTGTGCAGTCTACCATCAACACCCTTCAAC
GATCGCTGGTGGTGGGAGGCGGTTCAGGGGGGTCTCTGAGACTTCTGTGCACCGCAGTCTACCATCAACACCCTTCAAC
GAGGCTTGGTGTGCACCCTGGGGGGGTCTCAGGCTCCAGTAAACAGCGCAAGAACACGGTAGATCTGCAGATCTGCCAGATCTGCAGATCTGCAGATCTAGAGACCTGGAGATCTAGAGACCTCAGACTAT
AATATGGTGGGCTGGTACCGTCAGGCTCCAGATGAATACACCCACTACTGGGGCAAAGGAACCCTGGTCACCGTCTCCTCGAACCAAGACACCAAAA
CGTGAAGGGCCGATTCACCATCTGTCATATAGAATACACCCACTACTGGGGCAAAGGAACCCTGGTCACCGTCTCCTCGAACCAAGACACCAAAA
CCACCAACCGGCGCCCAGGGTGCGCCCGGGTGCGCCAGGGTGCGCCGGGAACCCGCGTTAA (SEQ ID NO:49)

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDKAMAAAQVQLVESGG
GLVQVGGSLRLSCVVSGSDISGIAMGWYRQAPGKRREMVADIFSGGSTDYAGSVKGRFTISRDNAKKTSYLQMNNVKPEDTGVYYC
RLYGSGDYWGQGTQVTVSSAHHSEDPTSAIAGGGSGGGGSLQGQLQLVEGGGLVHPGGSLRLSCAPSASLPSTPFNPFN
NMVGWYRQAPGKQREMVASIGLRINYADSVKGRFTISRDNAKNTVDLQMDSLRPEDSATYYCHIEYTHYWGKGTLVTVSSEPKTPK
PQPARQGAPVPYPDPLEPR (SEQ ID NO:50)

ATGAGCGATAAAATTATTCACCTGACTGACGACAGTTTTGACACGGATGTACTCAAAGCGGACGGGGCGATCCTCGTCGATTCTGGGCAGAGTGGT
GCGGTCCGTGCAAAATGATCGCCCCGATTCTGGATGAAATGCTGACGAATATCAGGGCAAACTGACCGTTGCAAAACTGAACATGATCAAAACCC
TGGCACTGCGCCCGAAATATGCAATGTTCCTGACGCTAACCTGGTATCCGGCCGGTTCTGGTTCTGGCCACGCACAGTGCAACCAAAGTGGTCACTGTCTAAA
GGTCAGTTGAAAGAGTTCCTGACGCTGCTCTAAATTCGAACGCCAGACACGAGACCCTTGGTAGTCCAGATCTGGTACCGGCGATTGCAGCTCTGGTGCACGACGAAGGCATGGCGAT
ATCGGATCCGAATTCTGGCGCACCTGTCCATACCCAGACTCTGGAACGCAGAGCGGCCGTCAGTGCAGCTCGTGGAGTCAGTGGAGGCTTG
GTGCAGTTGGGGTCTCTGAGACTCTTTTCTGGCGGTAGTACAGATACCGGCACATGCAGGCTCCGATTGCGATGGGCTGGTACCGCCAGGCTCCAGGAAGC
GGCGCGAAATGGTCGCAGATATTTTTCTGGCGGTAGTACAGACCTGGAAGGGGCCGATTTCCGTGAAGGGCCGATTACCATCTCCAGAGACAACGCCAAGAA
GACGAGCTATCTGCAAATGAACAGCTGAAACCTGAAGACACCGCAGTCTACTACTGTGCGGTCGTGTGAGGCGGTTCAGGCCGATATTGGCTCTGGGCTGGCGTT
CAGTCACCGTCTCCTCAGCGCCACCACAGCCGAAGACCCCACTAGTGCGATCCGGCCGAGCTTGGTGGCTGTACCGTCAGGCTTCTGAGACTCTCTGCCAGTCTACC
CCCTGCAGGTGCAGTCTGGAGTCGGCGAGTCCGGCGGGACTTGGTCGCGTCGAATATGGTGGGCTGTACCGTCAGGCTCCAGGTAACAGCGGCGAAATGGTCGCAGATGGCGCTCCAAGTATTGTCTACGAATA
ATCAACACCCCCTCAACCCCTTCAACATATGGCGGCCGATTCACCATTCCCAGAGACAACGCCAAGAACGCGTGGATCTGCAGATGACAGCCTGCGACCTGAGGACT
CAGCCACATACTACTGTGTCATATAGAATACACCCCACTGGGCAAGGGACCCTGTCACCGTCTCCCTGGAACCCAAGACACCAAACCACACC
GGGCGCCAGGTGCCGCCGGTCCGTATCCGGACCCGCTGGAACCGCGTTAA (SEQ ID NO:51)

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDKAMAISDPNSGAPVP
YPDPLEPRAAAQVQLVESGGGLVQVGGSLRLSCVVSGSDISGIAMGWYRQAPGKRREMVADIFSGGSTDYAGSVKGRFTISRDNAK
KTSYLQMNNVKPEDTGVYYCRLYCSGDYWGQGTQVTVSSAHSEDPTSAIAGGGSGGGGSGGGGSLQGQLQLVESGGGLVHPGGS
LRLSCAPSASLPSTPFNPFNNMVGWNYRQAPGKQREMVASIGLRINYADSVKGRFTISRDNAKNTVDLQMDSLRPEDSATYCHIEY
THYWGKGTLVTVSSEPKTPKPQPARQGAPVPYPDPLEPR (SEQ ID NO:52)

VHH sequences in italics
E-tag underlined

Thioredoxin:
MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLA (SEQ ID NO:53)

10 LD$_{50}$ at -1.5 hrs

FIG. 11B

10 LD$_{50}$ at -3 hrs

```
ciA-A5    SGGGLVQPGGSLRLSCAASA----GNLDYY--AIGWFRQAPGKEREGVSCISSS---DGSTVYTDSVKGRFTISRDNTKNTVDLQMDNLKPEDTAVYYCAT----VVNYYCTAGGSIHASPYEINGQGTQVTVSSAAHHSEDPS
ciA-B5    SGGGLVHPGGSLRLSCAPSASLPSTPNPNMWVGNYRQAPGKQREMVASIG-----LRINYADSVKGRFTISRDNAKNTVDLQMDSLRPEDSAIYYCH-------IEYTHY-------WGKGTLVTVSSEPKTPKPQ
ciA-C2    SGGGLAQPGGSLRLSCEASEFGTWFRFDEN--TVNWYRQPPGKSRREFDEIVARYPKSGLVTYIDSVKGRFTISRDNAKMAFLQMDNLKPEDTAVYYCNVG-----------EFWGQGTQVTISSEPKTPKPQ
ciA-D12   SGGGLVQPGGSLRLSCVVSG----SDFNTY--IMGNYIRQVPGKPRELVADITT---EGKTNYGGSVKGRFTISRDNAKNTVLQNFGLKPEDAGNYVCNADWKNGAWTAGDYG-------IDYWGKGTLVTVSSGPKTPKPQ
ciA-F12   SGGGLVQPGGSLRLSCAASG----FTILGSR--YMSNWRQAPGEGFEWVSSIEP---SGTAWDGDSAKGRFTISRDDAKNTLYLQNSNLQPEDTGVYYCATG-----YRIDTRIP------GGSWGQGTQVTVSSEPKTPKPQ
ciA-G5    SGGGLVQPGGSLRLSCQVSG----FTFGDW--VMSNWFRQAPGKEREFVASITAT--SSLKYADSVKGRFTISRDVANTLFLQNDRLKSEDTAVYYCRSP-------YRIDTRIP------NYWGQGTQVTVSAEPKTPKPQ
ciA-H7    SGGGLVQVGGSLRLSCVVSG----SDISGI--AMGNYRQAPGKRREMVADIFS---GGSTDYAGSVKGRFTISRDNAKKTSYLQMNNVKPEDTGVYYCR-------LVGSGDY-------WGQGTQVTVSSAAHHSEDPS ciB-A11   GGGGLVQPGGSALRLSCAASV----FGMDYY--YIGWVRQAPGKEREGVSCISN---IGRTHYADSVKGRFTISRDNAKNTVYLQMNSLKPEDTAVYYCAAP--LVGNYCPAS--YEYESWGQGTQVTVSSAAHHSEDPS
ciB-B5    SGGGLVQPGGSLRLSCAASG----QSLDNY--IIGWFRQAPGKEREGVSCIDRT--GTVTHYADSVKGRFTISTDNVKNTVYLEMNDLKPEDTATYFCAAERRNGVVSVCVIS--DYYPDSWGQGTQVTVSSAAHHSEDPS
ciB-B9    TGGGLVAGGSLRLSCTASG----RTSSFY--ALANFRQGPGKEREFVAAIGWI--DGSTRYTDSAKGRFTISRDAAKNTNYLQNMSLKPEDTAVYSCTARTQYGGSSADPKN------YGTWGQGTQVTVSAEPKTPKPQ
ciB-H11   TGGGLVAGGSLRLSCAGSG----RSFSAA--VMGNWFRQAPGKEREFVAALRQI--IGSTHYADSVKGRFTISRDNAKNMIYLDNSLKPTDTAAYYCTAGPPTMLDVSTDRE------YDTWGQGTQVTVSSAAHHSEDPS
```

FIG. 13A

```
ciA-D1    SGGGLVQPGGSLRLSCATSGFTLEYYAIGNFRQAPGKGREGVIACMNSSGGGTNYADSVKGRFTISRDNAKKNVLQMNSLKSEDTAVYYCVVDDFRCGSRMAALRSSWCQGTQVTVSSEPKTPKPQ
ciA-H5    SGGGLVQSGGSLRLSCAASVLTLEYYAIGNWFRQAPGKEREGISCTGSSGGSTVYIDSVKGRFTVVRDNAKNMVYLQMDSLQPEDTAVYYCAADDLRCGRGNSSYPRGSWCQGTQVTVSSEPKTPKPQ
ciA-H11   SGGGLVQPGGSLRLSCTASTLTLNYYAIGNWFRQAPGKEREGVSCTCSSGGSTVYIDSVKGRFTVVRDNAKNMVLQMDSLQPEDTAVYYCAADDLRCGRGWSSYPRGSWCQGTQVTVSSEPKTPKPQ
```

FIG. 13B

```
ciA-H7/ciA-B5 (2E)
MSDKIIHLTDDSPDTDVLKADGAILVDFWAEWCGPCKMIAPILDEIADEYQGKLTVAKLNIDQNPGTAPKYGIRGIPTLLLFKNGEVAATKVGALSKQLKEFLDANLAGSGSHMHHHHHSSGLVPRGSGMKETAAAKFE
RQHMDSPDLGTDDDAMAISDPNSGAPVPYDPLEPRAAAQVLVESGGLVQVGGSLRLSCVVSGSDISGIANGWVRQAPGKREMVADIFSGGSTDYAGSVKGRFTISRDNAKKTSYLQMNNVKPEDTGVYYCRLYSSG
DYWCQGTQVTVSSAHHSEDPTSAIAGGQSGGGSGGGSGGSLQQLQLVESGGSGGLVHPGGSLRLSCAPSASLPSTPNPNMWVGNYRQAPGKQREMVASIGLRINYADSVKGRFTISRDNAKNTVDLQMDSLRPEDSATYYC
HIEYTHYNGKGTLVTVSSEPKTPKPQPARQGAPVPYDPLEPR* ciA-F12/ciA-D12 (2E)
MSDKIIHLTDDSPDTDVLKADGAILVDFWAEWCGPCKMIAPILDEIADEYQGKLTVAKLNIDQNPGTAPKYGIRGIPTLLLFKNGEVAATKVGALSKQLKEFLDANLAGSGSHMHHHHHSSGLVPRGSGMKETAAAKFE
RQHMDSPDLGTDDDAMAISDPNSGAPVPYDPLEPRAAAQVLVESGGLVQPGGSLRLSCAASGFTLGSRYMSNWRQAPGEGFEWVSSIEPSGTAWDGDSAKGRFTISRDDAKNTLYLQMSNLQPEDTGVYYCATGYRI
DTRIPGGSWGQGTQVTVSSEPKTPKPQTSGGGSSGGGSSGGAPVQLVESGGSLRLSCVVSGSDFNTYIMGWYRQVPGKPRELVADITTEGKTNYGGSVKGRFTISRDNAKNTVDLQMFGLKPEDAGNVYC
NADWKMGAWTAGDYIGIDYWGKGTLVTVSSGPKTPKPQTSAAAGAPVPYDPLEPR*
```

1000 LD$_{50}$ 40 pm H7/B5(2E) + αE
13 pm H7/B5(2E) + αE
4.4 pm H7/B5(2E) + αE
1.5 pm H7/B5(2E) + αE
no agents Time (days)

FIG. 22

BoNT/A

FIG. 23A

BoNT/A

FIG. 23B

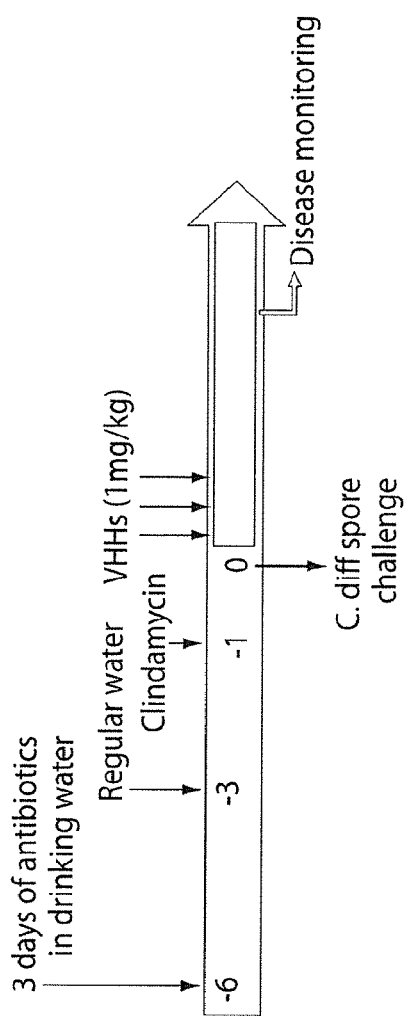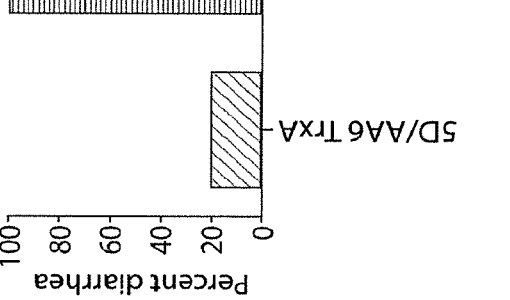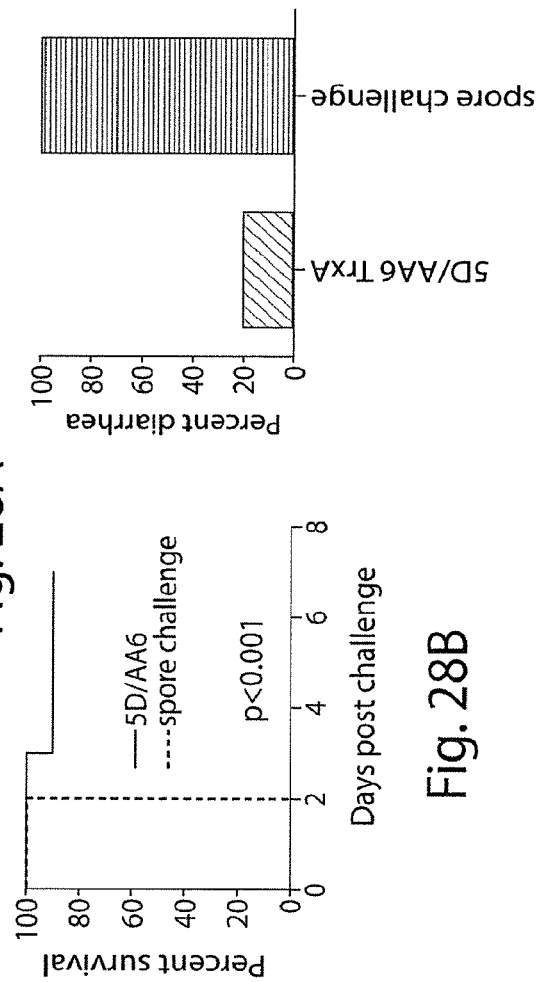
Fig. 28A
Fig. 28B
Fig. 28C

JET-H12
QVQLVETGGGLVQAGDPLRLSCVASGRTVSRYDKAWFRQAPGKEREFVAGISWNGDTKI
YADSVKGRFTISRENSRDTLDLQIDNLKPEDTAAYYCAVGIAGVQSMARMLGVRYWGQG
TQVTVSSEPKTPKPQ (SEQ ID NO: 96)

JFG-H6
QVQLVETGGGLVQPGGSLRLSCAASGFSLDPYVIGWFRQAPGKEREGVSCITSRAASRTSV
DSVNERFTISRDNAKNTVDLHINNLKPEDSGVYYCAAVPPAKLPLFSLCRSLPAKYDYWG
QGTQVTVSSAHHSEDPS (SEQ ID NO: 98)

JHD-B6
QVQLVESGGGLVQPGGSLRLSCAASGSSFSRYAMRWYRQAPGKQRELVANINSRGTSNY
ADSVKGRFTISRDNAKNTVYLQMNSLKPEDTAVYYCNAEWLGRSEPSWGQGTQVTVSSE
PKTPKPQ (SEQ ID NO: 100)

JHE-D9
QVQLVESGGGLVQPGGSLRLSCAASGFIFSLYTMRWHRQAPGKERELVATITSATGITNY
ADSVKGRFIISRDDAKKTGYLQMNSLKPEDTAVYYCNAVRTTVSRDYWGQGTQVTVSSE
PKTPKPQ (SEQ ID NO: 102)

JIJ-A12
QVQLVESGGGLVQPGGSLRLSCAASGIIFSIYTMGWYRQAPGKQRELVAAIPSGPSANATD
SVGGRFTITRDNAENTVYLQMNDLKPEDTAVYYCNARRGPGIKNYWGQGTQVTVSSEPK
TPKPQ (SEQ ID NO:104)

JIJ-B8
QVQLVESGGGLVQPGGSLSVSCAASGSIARPGAMAWYRQAPGKERELVASITPGGLTNY
ADSVTGRFTISRDNAKRTVYLQMNSLQPEDTAVYYCHARIIPLGLGSEYRDHWGQGTQVT
VSSAHHSEDPS (SEQ ID NO:106)

JIJ-C11
QVQLVETGGGLVQPGGSLGLSCVVASGRSINNYGMGWYRQAPGKQRELVAQISSGGTTNY
AGSVEGRFTISRDNVKKMVYLQMNSLKPEDTAVYYCNSLLRTFSWGQGTQVT
VSSAHHSEDPS (SEQ ID NO:108)

JIJ-D3
QVQLVETGGLVQPGGSLRLSCAASGLTFSSTAMAWFRQAPGKEREFVARISGAGITIYYSD
SVKDRFTISRNNVENTVYLQMNSLKTEDTAVYYCAARRNTYTSDYNIPARYPYWGQGTQ
VTVSSEPKTPKPQ (SEQ ID NO:110)

FIG. 29A (cont.)
JIJ-E9
QVQLVETGGLVQPGGSLRLSCAASRSTTATIYSMNWYRQAPGKQRELVAGMTSDGQTNY
ATSVKGRFTISRDNAKNTVYLLMNSLKLEDTAVYYCVKPWRLQGWDYWGQGTQVTV
SSEPKTPKPQ (SEQ ID NO:112)

JIJ-F11
QVQLVESGGGLVQPGGSLRLSCAAPESIVNSRTMAWYRQAPGKQRERVATITTAGSPNYA
DSVKGRFAISRDNAKNTVYLQMNSLKPEDTAVYYCNTLLSTLPYGQGTQVTVSSAHHSE
DPS (SEQ ID NO:114)

JIK-B8
QVQLVESGGGLVQPGGSLGLSCVVASERSINNYGMGWYRQAPGKQRELVAQISSGGTTN
YADSVEGRFTISRDNVKKMVHLQVNSLKPEDTAVYYCNSLLRTFSWGQGTQVTVSSEPK
TPKPQ (SEQ ID NO:116)

JIK-B10
QVQLVETGGGLVQPGGSLRLSCAASGFTFSSYRMSWYRQAAGKERDVVATITANGVPTG
YADSVMGRFTISRDNAKNTVYLEMNSLNPEDTAVYYCNAPRLHTSVGYWGQGTQVTVS
SEPKTPKPQ (SEQ ID NO:118)

JIK-B12
QVQLVESGGGLVQAGNSLRLSCTASGVIFSIYTMGWFRQAPGKEREFVAAIGVADGTALV
ADSVTGRFTISRDNAKNTVYLHMNSLKPEDTAVYSCAAYLSPRVQSPYITDSRYQLWGQG
TQVTVSSEPKTPKPQ (SEQ ID NO:120)

JIK-F4
TGGGLVQAGGSLRLSCAASGRYAMGWFRQAPGKEREFVATISRSGAIREYADSVKGRFTI
SRDGAENTVYLEMNSLKPDDTAIYVCAEGRGATFNPEYAYWGQGTQVTVSSAHHSEDPS
(SEQ ID NO:122)

JIV-F5
QVQLVESGGGLVQPGGSLRLSCAASGFTLDDYAIGWFRQVPGKEREGVACVKDGSTYYA
DSVKGRFTISRDNGAVYLQMNSLKPEDTAVYYCASRPCFLGVPLIDFGSWGQGTQVTVSS
EPKTPKPQ (SEQ ID NO:124)

JIV-F6
QVQLVESGGGLVQAGGSLRLSCATSGGTFSDYGMGWFRQAPGKEREFVAAIRRNGNGG
NGIEYADSVKGRFTISRDNAKNTVHLQMNSLTPEDTAVYYCAASISGYAYNTIERYNYWG
QGTQVTVSSEPKTPKPQ (SEQ ID NO:126)

FIG. 29A (cont.)

JIV-G12
QVQLVESGGGLVQAGGSLSLSCAASGGDFSRNAMAWFRQAPGKEREFVASINWTGSGTY
YLDSVKGRFTISRDNAKNALYLQMNNLKPEDTAVYYCARSTVFAEITGLAGYQSGSYDY
WGQGTQVTVSSEPKTPKPQ (SEQ ID NO:128)

JIY-A7
QVQLVETGGGTVQTGGSLRLSCSASGGSFSRNAMGWFRQAPGKEREFVAAINWSASSTY
YRDSVKGRFTVSRDNAKNTVYLHLNSLKLEDTAAYYCAGSSVYAEMPYADSVKATSYN
YWGQGTQVTVSSEPKTPKPQ (SEQ ID NO:130)

JIY-D9
QVQLVETGGGLVQAGGSLRLPCSFSGFPFDNYFVGWFRQAPGKEREGVSCISSSDGSTYY-
ADSVKGRFTISRDNAKNTVYLQMNSLKPEDTAVYYCGADFLTPHRCPALYDYWGQGTQVTV
SSAHHSEDPS (SEQ ID NO:132)

JIY-D10
QVQLVESGGGLVQPGGSLRLHCAASGSIASIYRTCWYRQGTGKQRELVAAITSGGNTYY
ADSVKGRFTISRDNAKNTIDLQMNSLKPEDTAVYYCNADEAGIGGFNDYWGQGTQ
VTVSSAHHSEDPS (SEQ ID NO:134)

JIY-E1
QVQLVESGGGLVQAGGSLRLSCAASGRTFSRSSMGWFRQAPGKEREFVASIVWADGTTL
YGDSVKGRFTVSRDNVKNMVYLQMNNLKPEDTALYYCADNKFVRGLVAVRAIDYDYW
GQGTQVTVSSEPKTPKPQ (SEQ ID NO:136)

JIY-E3
QVQLVESGGLVQAGGSLRLSCAASGRADIIYAMGWFRQAPGKEREFVAAVDWSGGSTY
YADSVKGRFTISRDNAKNSVYLQMNSLKPEDTAVYYCAARRSWYRDALSPSRVYEYDYW
GQGTQVTVSSEPKTPKPQ (SEQ ID NO:138)

JIY-E5
QVQLVETGGGLVQPGGSLTLSCAGSGGTLEHYAIGWFRQAPGKEHEWLVCNRGEYGSTV
YVDSVKGRFTASRDNAKNTVYLQLNSLKPDDTGIYYCVSGCYSWRGPWGQGTQVTVSS
AHHSEDPS (SEQ ID NO:140)

JIY-F10
QVQLVESGGGLVQPGGSLKLSCRASGSIVSIYAVGWYRQAPGKQRELLAAITTDGSTKYS
DSVKGRFTISRDNAKNTVYLQMNNLKPEDTAIYSCIGDAAGWGDQYYWGQGTQVTVSSE
PKTPKPQ (SEQ ID NO:142)

FIG. 29A (cont.)
JIY-G11
QVQLVESGGGLVQAGGSLRLSCAASGSIVNFETMGWYRQAPGKERELVATITNEGSSNY
ADSVKGRFTISGDNAKNTVSLQMNSLKPEDTAVYYCSATFGSRWPYAHSDHWGQGTQV
TVSSEPKTPKPQ (SEQ ID NO:144)

JIW-B1
QVQLVETGGALVHTGGSLRLSCEVSGSTFSSYGMAWYRQAPGEQRKWVAGIMPDGTPSY
VNSVKGRFTISRDNAKNSVYLHMNNLRPEDTAVYYCNQWPRTMPDANWGRGTQVTVSS
EPKTPKPQ (SEQ ID NO:146)

JIW-C12
QVQLVETGGSLRLTCVTSGSTFNNPAITWYRQPPGKQREWVASLRSGDGPVYRESVKGRF
TIFRDNATDALYLRMNSLKPEDTAVYHCNTASPASWLDWGQGTQVTVSSEPKTPKPQ
(SEQ ID NO:148)

JIW-D12
QVQLVETGGGLVQPGGSLRLSCATSGFPFSTERMSWVRQAPGKGLEWVSGITEGGETTLA
APSVKGRFNISRDNARNILYLQMNSLKPEDAAVYYCFRGVFFRTSFPPELARGQGTQVTVS
SEPKTPKPQ (SEQ ID NO:150)

JIW-G5
QVQLVESGGGLVQAGGSLRLSCAASGSAVSDSFSTYAISWHRQAPGKQREWIAGISNRGA
TSYRDSVKGRFTISRDNAKNTVYLQMNNLKPEDTGVYYCEPWPREGLGGGQGTQVTVSS
EPKTPKPQ (SEQ ID NO:152)

JIW-G10
QVQLVESGGGSVQTGGSLTLSCVVSGSTFSDYAVAWYRQVPGKSRAWVAGVSTTGSTSY
TDSVRGRFTISRDNHKKTVYLSMNSLKPEDTGIYYCNLWPFTNPPSWGQGTQVTVSSAHH
SEDPS (SEQ ID NO:154)

JIZ-B7
QVQLVESGGAVVQPGGSLRLSCATSGFTFSDDRMSWARQAPGKGLEWVSGISTASEGFA
TLYAPSVKGRFTISRDNAKHMLYLQMDTLKPEDTAVYYCLRGVFFRTNIPPEVLRGQGTQ
VTVSSAHHSEDPS (SEQ ID NO:156)

JIZ-B9
QVQLVETGGDLVQPGGSLRLSCAASGSSFSRAAVGWYRQAPGKEREWVARLASGDMTD
YTESVRGRFTISRDNAKHTVYLQMDNLKPEDTAVYYCKARIPPYYSIEYWGKGTRVTVSS
EPKTPKPQ (SEQ ID NO:158)

FIG. 29A (cont.)

JIZ-D8
QVQLVETGGGLVQAGGSLRLSCVVSSPLFNLYDMAWYRQAPGNQRELVAGILTDGRATY
SDSVKGRFTISRNNLTNTVFLQMSSLKPEDTAVYYCNRKNSIYWDSWGQGTQVTVSSEPK
TPKPQ (SEQ ID NO:160)

JIZ-G4
QVQLVESGGGLVQAGGSLRLSCVASGLTFSRYGMGWFRQAPGQERVVVSVISPDGGSAY
YADSVKGRFTISRDNAKNTVYLQMSTLRFEDTGVYYCTAGPRNGATTVLRPGDYDYWG
QGTQVTVSSEPKTPKPQ (SEQ ID NO:162)

FIG. 29A

JET-H12
CAGGTGCAGCTCGTGGAGACGGGGGGAGGATTGGTGCAGGCTGGGGACCCTCTGAGA
CTCTCCTGTGTAGCCTCTGGACGCACCGTCAGTCGCTATGACAAGGCCTGGTTCCGCC
AGGCTCCAGGGAAGGAGCGTGAGTTTGTAGCAGGAATTAGCTGGAACGGCGATACAA
AAATTTATGCAGACTCCGTGAAGGGCCGATTCACCATCTCCAGAGAGAACTCCAGGG
ATACACTGGATCTGCAAATTGACAACCTGAAACCTGAGGACACGGCCGCGTATTACTGTG
CGGTCGGAATTGCGGGTGTTCAGAGTATGGCGCGTATGCTCGGAGTGCGCTACTGG
GGCCAGGGGACCCAGGTCACCGTCTCCTCAGAACCCAAGACACCAAAACCACAA
(SEQ ID NO: 97)

JFG-H6
CAGGTGCAGCTCGTGGAGACGGGGGGAGGCTTGGTGCAGCCTGGGGGGTCTCTGAGA
CTCTCCTGTGCAGCCTCTGGTTTCAGTTTGGACCCTTATGTGATAGGATGGTTCCGGCA
GGCCCCAGGGAAGGAGCGTGAGGGGGTCTCATGTATTACGAGTAGGGCTGCTAGTCG
AACGTCTGTAGACTCCGTGAACGAGCGATTCACCATCTCCAGAGACAACGCCAAGAA
TACGGTCGATCTACACATCAATAACCTGAAACCTGAGGACTCGGGCGTTTATTACTGT
GCAGCGGTCCCCCCTGCCAAATTACCACTTTTCAGCCTATGTCGCTCCCTGCCAGCAA
AGTATGACTACTGGGGCCAGGGGACCCAGGTCACCGTCTCCTCAGCGCACCACAGCG
AAGACCCCTCG (SEQ ID NO: 99)

JHD-B6
CAGGTGCAGCTCGTGGAGTCGGGGGGAGGCTTGGTGCAGCCTGGGGGGTCTCTGAGA
CTCTCCTGTGCAGCCTCTGGAAGTAGCTTCAGTAGATATGCCATGCGCTGGTACCGCC
AGGCTCCAGGGAAGCAGCGCGAGTTGGTCGCAAACATTAATAGTCGTGGTACCTCAA
ACTATGCAGACTCCGTGAAGGGCCGATTCACCATCTCCAGAGACAACGCCAAGAACA
CGGTGTATCTGCAAATGAACAGCCTGAAACCTGAAGACACGGCCGTCTATTATTGTAA
TGCAGAGTGGTTGGGACGATCGGAGCCTTCCTGGGGCCAGGGGACCCAGGTCACCGT
CTCCTCGGAACCCAAGACACCAAAACCACAA (SEQ ID NO: 101)

JHE-D9
CAGGTGCAGCTCGTGGAGTCAGGAGGAGGCTTGGTGCAGCCTGGGGGGTCTCTGAGA
CTCTCCTGTGCAGCCTCTGGATTCATTTTCAGTCTTTATACCATGAGGTGGCACCGCCA
GGCTCCAGGGAAGGAGCGCGAGTTGGTCGCGACTATTACTAGTGCTACTGGTATTACA
AACTATGCAGACTCCGTGAAGGGCCGATTCATCATCTCCAGAGACGATGCCAAGAAG
ACGGGGTATCTGCAAATGAACAGCCTGAAACCTGAGGACACGGCCGTGTATTACTGT
AATGCAGTCCGCACTACCGTGTCACGAGACTACTGGGGCCAGGGGACCCAGGTCACC
GTCTCCTCAGAACCCAAGACACCAAAACCACAA (SEQ ID NO: 103)

JIJ-A12
CAGGTGCAGCTCGTGGAGTCTGGGGGAGGCTTGGTGCAGCCTGGGGGGTCTCTGAGA
CTCTCCTGTGCAGCCTCTGGAATCATCTTCAGTATCTATACCATGGGCTGGTACCGCCA
GGCTCCAGGGAAGCAGCGCGAATTGGTCGCAGCTATACCTAGTGGTCCTAGCGCAAA
CGCTACAGACTCCGTGGGGGCCGATTCACCATCACCAGAGACAACGCCGAGAACAC
GGTGTATCTGCAAATGAACGACCTGAAACCTGAGGACACGGCCGTCTATTACTGTAAT
GCTCGGCGGGGTCCGGGTATCAAAAACTACTGGGGCCAGGGGACCCAGGTCACCGTC
TCCTCAGAACCCAAGACACCAAAACCACAA (SEQ ID NO:105)

FIG. 29B (cont.)
JIJ-B8
CAGGTGCAGCTCGTGGAGTCCGGGGGCGGCTTGGTGCAGCCCGGGGGGTCTCTGAGT
GTCTCCTGTGCAGCCTCTGGAAGCATCGCAAGACCAGGTGCCATGGCCTGGTACCGCC
AGGCTCCAGGGAAGGAGCGCGAGTTGGTCGCGTCTATTACGCCTGGTGGTCTTACAAA
CTATGCGGACTCCGTGACGGGCCGATTCACCATTTCCAGAGACAACGCCAAGAGGAC
GGTGTATCTGCAGATGAACAGCCTCCAACCCGAGGACACGGCCGTCTATTACTGTCAT
GCACGAATAATTCCCCTAGGACTTGGGTCCGAATACAGGGACCACTGGGGCCAGGGG
ACTCAGGTCACCGTCTCCTCAGCGCACCACAGCGAAGACCCCTCG (SEQ ID NO: 107)

JIJ-C11
CAGGTGCAGCTCGTGGAGACGGGGGGAGGCTTGGTGCAGCCTGGGGGGTCTCTGGGA
CTCTCCTGTGTAGTCGCCTCTGGAAGAAGCATCAATAATTATGGCATGGGCTGGTACC
GCCAGGCTCCAGGGAAGCAGCGCGAGTTGGTCGCGCAAATTAGTAGTGGTGGTACCA
CAAATTATGCAGGCTCCGTAGAGGGCCGATTCACCATCTCCAGAGACAACGTCAAGA
AAATGGTGTATCTTCAAATGAACAGCCTGAAACCTGAGGACACGGCCGTCTATTACTG
TAATTCACTGCTCCGAACTTTTTCCTGGGGCCAGGGGACCCAGGTCACCGTCTCCTCG
GCGCACCACAGCGAAGACCCCTCG (SEQ ID NO: 109)

JIJ-D3
CAGGTGCAGCTCGTGGAGACCGGGGGGTTGGTGCAGCCTGGGGGCTCCCTGCGACT
CTCCTGTGCAGCCTCCGGACTCACCTTCAGTAGCACTGCCATGGCCTGGTTCCGCCAGG
CTCCAGGGAAGGAGCGTGAGTTTGTAGCACGTATTAGCGGGGCTGGTATTACGATCTA
CTATTCGGACTCCGTGAAGGACCGATTCACCATCTCCAGAAACAACGTCGAGAACAC
GGTGTATTTGCAAATGAACAGCCTGAAAACTGAGGACACGGCCGTTTACTACTGTGCA
GCAAGACGGAATACTTACACTAGCGACTATAACATACCCGCCCGGTATCCCTACTGGG
GCCAGGGGACCCAGGTCACCGTCTCCTCAGAACCCAAGACACCAAAACCACAA (SEQ
ID NO:111)

JIJ-E9
CAGGTGCAGCTCGTGGAGACGGGGGGCTTGGTGCAGCCTGGGGGGTCTCTGAGACT
CTCCTGTGCAGCCTCTAGAAGCACGACGGCCACAATTTATAGTATGAACTGGTACCGCC
AGGCTCCAGGGAAGCAGCGCGAGTTGGTCGCGGGTATGACTAGTGATGGTCAGACAA
ACTATGCAACCTCCGTGAAGGGCCGATTCACCATCTCCAGAGACAACGCCAAGAACA
CGGTATATTTGCTAATGAACAGCCTGAAACTTGAGGACACGGCCGTCTATTATTGTTA
TGTAAAACCATGGAGACTACAAGGTTGGGACTACTGGGGCCAGGGGACCCAGGTCAC
CGTCTCCTCAGAACCCAAGACACCAAAACCACAA (SEQ ID NO:113)

JIJ-F11
CAGGTGCAGCTCGTGGAGTCGGGCGGCGGCTTGGTGCAGCCTGGGGGGTCTCTGAGA
CTCTCCTGTGCAGCCCCTGAAAGCATCGTCAATAGCAGAACCATGGCCTGGTACCGCC
AGGCTCCAGGAAAGCAGCGCGAAGGGTCGCCACTATTACTACTGCTGGTAGCCCAA
ATTATGCAGACTCTGTGAAGGCCGATTCGCCATCTCCAGAGACAACGCCAAGAACA
CGGTATATCTGCAAATGAACAGCCTGAAACCTGAGGACACGGCCGTCTATTACTGCAA
TACACTTCTCAGCACCCTTCCCTATGGCCAGGGGACCCAGGTCACCGTCTCCTCGGCG
CACCACAGCGAAGACCCCTCG; (SEQ ID NO:115)

FIG. 29B (cont.)

JIK-B8
CAGGTGCAGCTCGTGGAGTCGGGCGGAGGCTTGGTGCAGCCTGGGGGGTCTCTGGGA
CTCTCCTGTGTAGTCGCCTCTGAAAGAAGCATCAATAATTATGGCATGGGCTGGTACC
GCCAGGCTCCAGGGAAGCAGCGCGAGTTGGTCGCGCAAATTAGTAGTGGTGGTACCA
CAAATTATGCAGACTCCGTAGAGGGCCGATTCACCATCTCCAGAGACAACGTCAAGA
AAATGGTGCATCTTCAAGTGAACAGCCTGAAACCTGAGGACACGGCCGTCTATTACTG
TAATTCGCTACTCCGAACTTTTTCCTGGGGCCAGGGGACCCAGGTCACCGTCTCCTCG
GAACCCAAGACACCAAAACCACAA (SEQ ID NO:117)

JIK-B10
CAGGTGCAGCTCGTGGAGACGGGAGGAGGCTTGGTGCAGCCTGGGGGGTCTCTGAGA
CTCTCCTGTGCAGCCTCTGGATTCACCTTCAGTAGTTATCGCATGAGCTGGTACCGGCA
GGCTGCAGGGAAGGAGCGCGACGTGGTCGCAACAATTACTGCTAATGGTGTTCCCAC
AGGCTATGCAGACTCCGTGATGGGCCGATTCACCATTTCCAGAGACAATGCCAAGAA
CACGGTGTATCTGGAAATGAACAGCCTGAATCCTGAGGACACGGCCGTGTATTACTGT
AACGCGCCCGTTTGCATACATCTGTAGGCTACTGGGGCCAGGGGACCCAGGTCACCG
TCTCCTCAGAACCCAAGACACCAAAACCACAA (SEQ ID NO:119)

JIK-B12
CAGGTGCAGCTCGTGGAGTCGGGAGGAGGATTGGTGCAGGCTGGGAACTCTCTGAGA
CTCTCCTGTACGGCCTCTGGTGTGATCTTCTCTATCTATACCATGGGCTGGTTCCGCCA
GGCTCCAGGGAAGGAGCGTGAGTTTGTAGCAGCGATAGGGGTGGCTGATGGTACCGC
ACTTGTGGCAGACTCCGTGACGGGCCGATTCACCATCTCCAGAGACAACGCCAAGAA
CACCGTTTATCTGCATATGAACAGCCTGAAGCCTGAGGACACGGCCGTCTATTCCTGT
GCAGCGTATCTTAGCCCCGTGTCCAATCCCCCTACATAACTGACTCCCGGTATCAAC
TCTGGGGCCAGGGGACCCAGGTCACCGTCTCCTCAGAACCCAAGACACCAAAACCAC
AA (SEQ ID NO: 121)

JIK-F4
CAGGTGCAGCTCGTGGAGACTGGGGGAGGATTGGTGCAGGCTGGGGGCTCTCTGAGG
CTCTCCTGTGCAGCCTCTGGACGCTATGCCATGGGCTGGTTCCGCCAGGCTCCAGGGA
AGGAGCGTGAATTTGTAGCGACTATTAGCCGGAGTGGTGCTATCAGAGAGTATGCAG
ACTCCGTGAAGGGCCGATTCACCATCTCCAGAGACGGCGCCGAGAACACGGTGTATC
TGGAAATGAACAGCCTGAAACCTGACGACACGGCCATTTATGTCTGTGCAGAAGGAC
GAGGGGCGACATTCAACCCCGAGTATGCTTACTGGGGCCAGGGGACCCAGGTCACCG
TCTCCTCAGCGCACCACAGCGAAGACCCCTCG (SEQ ID NO:123)

JIV-F5
CAGGTGCAGCTCGTGGAGTCGGGCGGAGGCTTGGTGCAGCCTGGGGGGTCTCTGAGA
CTCTCCTGTGCAGCCTCTGGATTCACTTTGGATGATTATGCCATAGGCTGGTTCCGCCA
GGTCCCAGGGAAGGAGCGTGAGGGGTCGCATGTGTTAAAGATGGTAGTACATACTA
TGCAGACTCCGTGAAGGGCCGATTCACCATCTCCAGAGACAACGGCGCGGTGTATCTG
CAAATGAACAGCCTGAAACCTGAGGACACAGCCGTTTATTACTGTGCATCCAGGCCCT
GCTTTTTGGGTGTACCACTTATTGACTTTGGTTCCTGGGGCCAGGGGACCCAGGTCAC
CGTCTCCTCGGAACCCAAGACACCAAAACCACAA (SEQ ID NO:125)

FIG. 29B (cont.)

JIV-F6
CAGGTGCAGCTCGTGGAGTCAGGGGGAGGATTGGTGCAGGCTGGGGGCTCTCTGAGA
CTCTCCTGCGCAACCTCTGGCGGCACCTTCAGTGACTATGGAATGGGCTGGTTCCGCC
AGGCTCCAGGGAAGGAGCGTGAGTTTGTAGCAGCTATTAGGCGGAATGGTAATGGCG
GTAATGGCATTGAATATGCAGACTCCGTGAAGGGCCGATTCACCATCTCCAGAGACA
ACGCCAAGAACACGGTGCATCTACAAATGAACAGCCTGACACCTGAGGACACGGCCG
TTTATTACTGTGCAGCGTCAATATCGGGATACGCTTATAACACAATTGAAAGATATAA
CTACTGGGGCCAGGGAACCCAGGTCACCGTCTCCTCAGGAACCCAAGACACCAAAAC
CACAA (SEQ ID NO:127)

JIV-G12
CAGGTGCAGCTCGTGGAGTCCGGCGGAGGATTGGTGCAGGCGGGGGGCTCTCTGAGT
CTCTCCTGTGCAGCCTCTGGAGGTGACTTCAGTAGGAATGCCATGGCCTGGTTCCGTC
AGGCTCCAGGGAAGGAGCGTGAATTTGTAGCATCTATTAACTGGACTGGTAGTGGCA
CATATTATCTAGACTCCGTGAAGGGCCGATTCACCATCTCCAGAGACAACGCCAAGAA
CGCCCTGTATCTGCAAATGAACAACCTGAAACCTGAGGACACGGCCGTTTATTACTGT
GCACGCTCCACGGTGTTTGCCGAAATTACAGGCTTAGCAGGCTACCAGTCGGGATCGT
ATGACTACTGGGGCCAGGGGACCCAGGTCACCGTCTCCTCAGAACCCAAGACACCAA
AACCACAA (SEQ ID NO:129)

JIY-A7
CAGGTGCAGCTCGTGGAGACCGGCGGAGGAACGGTGCANACTGGGGGCTCTCTGAGA
CTCTCCTGTTCAGCCTCTGGCGGCTCCTTCAGTAGGAATGCCATGGGCTGGTTCCGCCA
GGCTCCAGGGAAGGAGCGTGAATTTGTAGCAGCTATTAACTGGAGTGCCTCTAGTACT
TATTATAGAGACTCCGTGAAGGGACGATTCACCGTCTCCAGAGACAACGCCAAGAAC
ACGGTGTATCTGCATTTGAACAGCCTGAAACTTGAGGACACGGCCGCGTATTACTGTG
CTGGAAGCTCGGTGTATGCAGAAATGCCGTACGCCGACTCTGTCAAGGCAACTTCCTA
TAACTACTGGGGCCAGGGGACCCAGGTCACCGTCTCCTCAGAACCCAAGACACCAAA
ACCACAA (SEQ ID NO:131)

JIY-D9
CAGGTGCAGCTCGTGGAGACCGGGGGAGGCTTGGTGCAGGCTGGGGGGTCTCTGAGA
CTCCCCTGTTCATTCTCTGGATTCCCTTTCGATAATTATTTCGTAGGCTGGTTCCGCCA
GGCCCCAGGGAAGGAGCGTGAGGGGGTCTCATGTATTAGTAGTAGTGATGGTAGCACA
TACTATGCAGACTCCGTGAAGGGCCGGTTCACCATCTCCAGAGACAACGCCAAGAA
CACGGTGTATCTGCAAATGAACAGTCTGAAACCTGAGGATACGGCCGTTTATTACTGT
GGAGCAGATTTCCTCACCCCACATAGGTGTCCAGCCTTATATGACTACTGGGGCCAGG
GGACCCAGGTCACCGTCTCCTCAGCGCACCACAGCGAAGACCCCTCG
(SEQ ID NO:133)

FIG. 29B (cont.)

JIY-D10
CAGGTGCAGCTCGTGGAGTCTGGTGGAGGCTTGGTGCAGCCTGGGGGGTCTCTGAGA
CTCCACTGTGCAGCCTCTGGAAGCATCGCCAGTATCTATCGCACGTGCTGGTACCGCC
AGGGCACAGGGAAGCAGCGCGAGTTGGTCGCAGCCATTACTAGTGGTGGTAACACAT
ACTATGCGGACTCCGTTAAGGGCCGATTCACCATCTCCAGAGACAACGCCAAAAACA
CAATCGATCTGCAAATGAACAGCCTGAAACCTGAGGACACGGCCGTCTATTACTGTAA
TGCAGACGAGGCGGGGATCGGGGGATTTAATGACTACTGGGGCCAGGGGACCCAGGT
CACCGTCTCCTCAGCGCACCACAGCGAAGACCCCTCG (SEQ ID NO:135)

JIY-E1
CAGGTGCAGCTCGTGGAGTCGGGGGGAGGATTGGTGCAGGCTGGGGGCTCTCTGAGA
CTCTCCTGTGCAGCCTCTGGACGCACCTTCAGTCGCAGTTCCATGGGCTGGTTCCGCCA
GGCTCCAGGGAAGGAGCGTGAATTCGTTGCGTCCATTGTCTGGGCTGATGGTACGACG
TTGTATGGAGACTCCGTAAAGGGCCGATTCACCGTCTCCAGGGACAACGTCAAGAAC
ATGGTGTATCTACAAATGAACAACCTGAAACCTGAGGACACGGCCCTTTATTACTGTG
CGGACAATAAATTCGTCCGTGGATTAGTGGCTGTCCGTGCGATAGATTATGACTACTG
GGGCCAGGGGACCCAGGTCACCGTCTCGTCAGAACCCAAGACACCAAAACCACAA
(SEQ ID NO:137)

JIY-E3
CAGGTGCAGCTCGTGGAGTCGGGAGGATTGGTGCAGGCTGGAGGCTCTCTGAGACTC
TCCTGCGCAGCCTCTGGACGCGCCGACATAATCTATGCCATGGGCTGGTTCCGCCAGG
CTCCAGGGAAGGAGCGTGAGTTTGTAGCGGCAGTAGACTGGAGTGGTGGTAGCACAT
ACTATGCAGACTCCGTGAAGGGCCGATTCACCATCTCCAGAGACAACGCCAAGAACT
CGGTGTATCTGCAAATGAACAGCCTGAAACCTGAGGACACGGCCGTTTATTACTGTGC
AGCCCGAAGGAGCTGGTACCGAGACGCGCTATCCCCCTCCCGGGTGTATGAATATGA
CTACTGGGGCCAGGGGACCCAGGTCACCGTCTCCTCAGAACCCAAGACACCAAAACC
ACAA (SEQ ID NO:139)

JIY-E5
CAGGTGCAGCTCGTGGAGACGGGAGGAGGCTTGGTGCAGCCTGGGGGGTCTCTGACA
CTCTCCTGTGCAGGCTCCGGTGGCACTTTGGAACATTATGCTATAGGCTGGTTCCGCC
AGGCCCCTGGGAAAGAGCATGAGTGGCTCGTATGTAATAGAGGTGAATATGGGAGCA
CTGTCTATGTAGACTCCGTGAAGGGCCGATTCACCGCCTCCAGAGACAACGCCAAGA
ACACGGTGTATCTGCAATTGAACAGTCTGAAACCTGACGACACAGGCATTTATTACTG
TGTATCGGGATGTTACTCCTGGCGGGTCCCTGGGGCCAGGGGACCCAGGTCACCGTC
TCCTCGGCGCACCACAGCGAAGACCCCTCG (SEQ ID NO:141)

JIY-F10
CAGGTGCAGCTCGTGGAGTCTGGGGGAGGTTTGGTGCAGCCTGGGGGGTCTCTGAAA
CTCTCCTGTAGAGCCTCTGGAAGCATAGTCAGTATCTATGCCGTGGGCTGGTACCGCC
AGGCTCCAGGGAAGCAGCGCGAGTTGCTCGCGGCTATCACTACTGATGGTAGCACGA
AGTACTCAGACTCCGTGAAGGGCCGATTCACCATCTCCCGAGACAACGCCAAGAACA
CGGTATATCTGCAAATGAACAACCTCAAACCTGAGGACACGGCCATCTATTCCTGTAT
CGGGGACGCGGCGGGTTGGGGCGACCAATACTACTGGGGCCAGGGGACCCAGGTCAC
CGTCTCCTCAGAACCCAAGACACCAAAACCACAA (SEQ ID NO:143)

FIG. 29B (cont.)

JIY-G11
CAGGTGCAGCTCGTGGAGTCAGGCGGAGGCTTGGTGCAGGCTGGGGGGTCTCTGAGA
CTCTCCTGTGCAGCCTCTGGAAGCATCGTCAATTTCGAAACCATGGGCTGGTACCGCC
AGGCTCCAGGGAAGGAGCGCGAGTTGGTCGCAACTATTACTAATGAAGGTAGTTCAA
ACTATGCAGACTCCGTGAAGGGCCGATTCACCATCTCCGGAGACAACGCCAAGAACA
CGGTGTCCCTGCAAATGAACAGCCTGAAACCTGAGGACACGGCCGTCTACTACTGTTC
GGCGACGTTCGGCAGTAGGTGGCCGTACGCCCACAGTGATCACTGGGGCCAGGGGAC
CCAGGTCACCGTCTCCTCAGAACCCAAGACACCAAAACCACAA (SEQ ID NO:145)

JIW-B1
CAGGTGCAGCTCGTGGAGACGGGCGGAGCATTGGTGCACACTGGGGGTTCTCTGAGA
CTCTCCTGCGAAGTCTCCGGAAGCACCTTCAGTAGCTATGGCATGGCCTGGTACCGCC
AAGCTCCAGGCGAGCAGCGTAAGTGGGTCGCAGGTATTATGCCGGATGGTACTCCAA
GCTATGTAAACTCCGTGAAGGGCCGATTCACCATCTCCAGAGACAACGCCAAGAACT
CGGTGTATCTGCACATGAACAACCTGAGGCCTGAAGACACGGCCGTCTATTATTGCAA
CCAATGGCCGCGCACGATGCCTGACGCGAACTGGGGCCGGGGACCCAGGTCACCGT
CTCCTCAGAACCCAAGACACCAAAACCACAA (SEQ ID NO:147)

JIW-C12
CAGGTGCAGCTCGTGGAGACTGGGGGGTCTCTGAGGCTCACCTGTGTAACCTCTGGAA
GCACCTTCAATAATCCTGCCATAACCTGGTACCGCCAGCCTCCAGGGAAGCAGCGTGA
GTGGGTCGCAAGTCTTCGTAGTGGTGATGGTCCAGTATATAGGGAATCCGTGAAGGGC
CGATTCACCATTTTTAGAGACAACGCCACGGACGCGCTGTATCTGCGGATGAATAGCC
TGAAACCTGAGGACACGGCCGTCTATCACTGTAACACCGCCTCACCTGCTAGTTGGCT
GGACTGGGGCCAGGGGACCCAGGTCACTGTCTCCTCAGAACCCAAGACACCAAAACC
ACAA (SEQ ID NO:149)

JIW-D12
CAGGTGCAGCTCGTGGAGACGGGAGGAGGATTGGTGCAACCTGGGGGTTCTCTGAGA
CTCTCTTGTGCAACCTCTGGATTCCCCTTCAGTACGGAGCGTATGAGCTGGGTCCGCC
AGGCTCCAGGAAGGGGCTCGAGTGGGTCTCAGGTATTACTGAGGGTGGTGAAACCA
CTCTCGCGGCACCCTCCGTGAAGGGCCGATTCAACATCTCCAGAGACAACGCCAGGA
ATATCCTATATCTACAGATGAATTCCTTGAAACCTGAGGACGCGGCCGTTTACTATTG
TTTTAGAGGTGTTTTTTTAGAACGAGTTTTCCTCCCGAACTCGCGCGGGCCAGGGG
ACCCAGGTCACCGTCTCCTCAGAACCCAAGACACCAAAACCACAA (SEQ ID NO:151)

JIW-G5
CAGGTGCAGCTCGTGGAGTCGGGCGGAGGCTTGGTGCAGGCAGGGGGTCTTTGAGA
CTCTCCTGTGCAGCCTCTGGAAGCGCCGTCAGTGACAGCTTCAGTACCTATGCCATCT
CCTGGCACCGCCAGGCTCCAGGGAAGCAGCGTGAGTGGATCGCAGGTATTAGTAATC
GTGGTGCGACAAGCTATAGAGACTCCGTGAAGGGCCGATTCACCATCTCCAGAGACA
ACGCCAAGAACACGGTATATCTGCAAATGAACAACCTGAAACCTGAGGACACGGGCG
TCTATTATTGTGAGCCATGGCCACGCGAAGGACTTGGGGGGGCCAGGGGACTCAGG
TCACCGTCTCCTCAGAACCCAAGACACCAAAACCACAA (SEQ ID NO:153)

FIG. 29B (cont.)

JIW-G10
CAGGTGCAGCTCGTGGAGTCGGGGGGAGGCTCGGTGCANACTGGGGGGTCTCTGACA
CTCTCCTGTGTAGTCTCTGGAAGTACCTTCAGTGACTATGCGGTGGCCTGGTACCGCC
AGGTTCCAGGCAAATCGCGTGCGTGGGTCGCGGGTGTTAGTACTACTGGCTCGACATC
TTATACAGACTCCGTGAGGGGCCGGTTCACCATCTCCAGAGACAACCACAAGAAGAC
GGTGTATCTTTCAATGAACAGCCTGAAACCTGAGGACACGGGCATCTATTACTGCAAC
TTATGGCCGTTCACAAATCCTCCTTCCTGGGGCCAGGGAACCCAAGTCACCGTTTCCT
CGGCGCACCACAGCGAAGACCCCTCG (SEQ ID NO:155)

JIZ-B7
CAGGTGCAGCTCGTGGAGTCTGGAGGAGCCGTGGTGCAACCTGGGGGTTCTCTGAGA
CTCTCCTGTGCAACCTCTGGATTCACCTTCAGTGACGATCGTATGAGCTGGGCCCGCC
AGGCTCCAGGAAAGGGGCTCGAGTGGGTCTCAGGTATTAGTACTGCTAGTGAAGGTTT
TGCTACACTCTACGCACCCTCCGTGAAGGGCCGATTCACCATCTCCAGAGACAACGCC
AAGCATATGCTGTATCTGCAAATGGATACCTTGAAACCTGAGGACACGGCCGTGTATT
ACTGTTTAAGAGGGGTTTTTTTTAGAACGAACATTCCTCCCGAGGTACTGCGGGGCCA
GGGGACCCAGGTCACCGTCTCCTCAGCGCACCACAGCGAAGACCCCTCG (SEQ ID
NO:157)

JIZ-B9
CAGGTGCAGCTCGTGGAGACGGGGGGAGACTTGGTGCANCCTGGGGGGTCTCTGAGA
CTCTCCTGTGCAGCCTCTGGAAGCTCCTTCAGCCGCGCTGCCGTGGGCTGGTACCGTC
AGGCTCCAGGAAAGGAGCGTGAGTGGGTCGCACGTCTCGCGAGTGGTGATATGACGG
ACTATACCGAGTCCGTGAGGGGCCGATTCACTATCTCCAGAGACAACGCCAAGCACA
CGGTGTATCTGCAAATGGACAACCTGAAACCTGAGGACACGGCCGTCTACTATTGTAA
GGCCAGGATACCCCCTTATTACTCTATAGAGTACTGGGGCAAAGGGACCCGGGTCACC
GTCTCCTCANAACCCAAGACACCAAAACCACAA (SEQ ID NO:159)

JIZ-D8
CAGGTGCAGCTCGTGGAGACAGGTGGAGGCTTGGTGCAGGCTGGGGGGTCTCTGAGA
CTCTCCTGTGTAGTATCTAGTCCCCTGTTCAATCTTTACGACATGGCCTGGTATCGCCA
GGCTCCAGGGAATCAGCGTGAGTTGGTCGCAGGCATCTTGACTGATGGTCGCGCAAC
ATATTCAGACAGCGTGAAGGGCCGATTCACCATTTCCAGAAACAACCTGACGAACAC
GGTGTTTTTACAAATGAGCAGCCTGAAACCTGAGGACACGGCCGTCTATTATTGTAAT
AGAAAGAATAGTATCTACTGGGATTCCTGGGGCCAGGGGACCCAGGTCACCGTCTCCT
CGGAACCCAAGACACCAAAACCACAA (SEQ ID NO:161)

JIZ-G4
CAGGTGCAGCTCGTGGAGTCGGGGGGAGGATTGGTGCAGGCTGGGGGCTCTCTGAGA
CTCTCCTGCGTAGCCTCTGGACTCACCTTCAGTCGCTATGGCATGGGCTGGTTCCGCCA
GGCTCCAGGACAGGAGCGTGTAGTCGTATCAGTTATTAGTCCCGACGGTGGTAGCGCA
TACTACGCAGACTCCGTGAAGGGCCGATTCACCATCTCCAGAGACAACGCCAAGAAC
ACGGTGTATCTGCAAATGAGCACCCTGAGATTTGAGGACACGGGCGTTTATTATTGTA
CAGCAGGGCCCCGGAATGGAGCGACTACAGTCCTCCGGCCAGGGGATTATGACTACT
GGGGCCAGGGGACCCAGGTCACTGTCTCCTCAGAACCCAAGACACCAAAACCACAA
(SEQ ID NO:163)

FIG. 29B

```
                  CDR1                                            CDR2                                              CDR3
             ┌──────────┐                                      ┌──────┐                                          ┌──────┐
Stx1-A9   TGGGLAQAGDSLRLSCVEPGR--TLDMYAMGWIRQAPGEREFVASISGVGGSPRYADSVKGRFTISKDNTKSTIWLQMNSLKPEDTAVYYCAAG--------GDIYYGGSPQWRGQGTRVTVSS
Stx2-G9   SGGGLVQPGGSLRLSCAASGF--TLNSYKIGWFRQAPGKEREGVSCINSGGNLR----SVEGRFTISRDNTKNTVSLHMDSLKPEDTGVYHCAAAP----ALNVFSPCVLAPRYDYWGQGTQVTVSS
Stx2-H6   TGGGLVQPGGSLRLSCAASGF--SLDPYVIGWFRQAPGKEREGVSCITSRAASRITVDSWNERFTISRDNAKNTVDLHINNLKPEDSGVYTCAAVPPAKLPLFSLCRSLPAKYDYWGQGTQVTVSS
Stx2-A6   SGGGLVQPGGSLKLSCAASGR--TLADYTVWFRQAPGKEREGVSCISSSRGTPNVADSVKGRATVSRNNNKNTVYLQMNLKPDDTAIYYCAAIRPARLRAVRECLSSQAEVDYWGQGTQVTVSS
Stx2-D2   SGGGLVQPGGSLGLSCAMSGT--TQDYSAVGWFRQAPGKEREGVSCISRSGRRTNYADSVRGRFTISRDNAKDTVYLQMNLKPDDTAVYYCAARK---TDMSDPYYVGCNGMDYWGKGTLVTVSS
Stx2-B12  SGGGLVQPGGSLRLSCAASGF--TLDNYRIGWFRQAPGKEREGVSCIARTGDIRNVGDSVKGRFTISRDSIKYADSVRGRFTISRDNAKNTVYLQMNSLKPEDTAVYYCAAVR----TSSYSCDLRASYMDYWGKGTLVTVSS
Stx2-H12  TGGGLVQPGGSLRLSCAASGF--TLEGYHIGWFRQAPGNEREGTCSISSRGDSIKYADSVRGRFTISRDSIKYADSVRGRFTISRDNAKTTVLEMNSLKPEDTAVYYCAAVR----PVFSSSPCTLATRYNYWGQGTQVTVST
Stx-A3    SGGGLVQPGGSLRLSCAASGV--TLDNYHIGWFRQAPGKEREGASCISSSRGDTIKYADSVRGRFTISRGDDIKYADSVKGRFTISRDSAMSTVLQMNSLKPGDTADYPCAAVR----PVFSDSPCTLAFRYNYWGQSQVTVSS
Stx-H9    TGGGLVQPGGSLRLSCAASGF--TLDNYHIGWFRQAPGKEREGVSCIKEREGISCISSSRGDILKYADSVKGRFTISRDNAKRTVLQMNSLKPEDTAVYFCAAVR----PVFADSPCTLAFRYNYWGQGTQVTVSS
Stx-H3    TGGGLVQPGGSLRVSCAASGF--TLDNYHIGWFRQAPGKEREGVSCIEREGISCISSSRGDILKYADSVKGRFTISRDNAKRTVYLQMNSLKPEDTAVYYCAAVR----PVFDSPCTLATRYNYWGQGSQVTVSS
Stx-F1    TGGGLVQPGGSLRVSCAASGF--TLDNYHIGWFRQAPGKEREGVSCISRSGDILKYADSVKGRFTISRDNAKRTVYLQMNSLKPEDTAVYYCAAVR----PVPGSACTLATRYNYWGQGSQVTVSS
Stx-D4    SGGELVQPGGSLRLSCAASGF--TLDNVAIGWFRHAPGKEREGIACISGSGDNTKYADSVKGRFTIVLQMNAMKPEDTALYYCAAVR----PVRFSPCTLAPRYNDWGQGTQVTVSS
Stx-A4    SGGGLVQPGGSLRLSCAASGF--TLGSYHIGWFRQAPGKERETGTCSLSSRGDYTKYAEAVKGRFTISRDNTKSTVLQMNNLKPEDTGLYVCAAIR----PVLSDSHCTLAARYNYWGQGTQVTVSS
Stx-H5    TGGGLVRPGGSLRLSCAASEF--TLDNYHIGWFRQAPGKEREGVSCLSSSRTSTKYADSVKGRFTISEDNAKETVLQMNSLEPEDTAVYICAAIR----PVLSNSPCTLATRYNYWGQGTQVTVSS
Stx-H10   TGGGLVQPGGSLRLSCAGSAI--TLEYYAIGWFRQAPGKEREGISCLSSSGFNTNYADFVKGRFTISVKGRFTISRDNAKNTVYLQMSLKPEDTAVHCAAVR----PVFSDSPCTLATRYDNWGQGTQVTVSS
Stx-A5    SGGGLVQPGGSLRLSCAALEF--TLEDYAIAWFRQAPGKEREGVSCISKSG-VTKYTDSVKGRFTVARDNAKSTVLQMNNLRPEDTAVYNCAAVR----PVFVDSVCTLATRYTYWGEGTQVTVSS
Stx-G6    TGGGLVQPGGSLKLSCAASEF--TLDDYHIGWFRQAPGKEREGVSCINKRGDYINYKDSVKGRFTISRDGAKSTVFLQMNNIRPEDTAVYYCAAVN----PVFPDSRCTLATRYTHWGQGTQVTVSS
Stx2-A4   TGGGLVQPGGSLRLSCRASGD--TLDRYAIGWFRQAPGEREFVSCISIRGIPVDYADSVKGRFTISRDGAKTIVWLQMSLNPEDTGLYSCAAAS-------ACYRFNTWGQGTQVTVSS
Stx2-D10  TGG-LVQAGGSLRLSCAASGV--PFSDYTMAWFRQAPGKEREFVARITWRGGGPYYGNSGNGRFAISRDIAKSMVLHMDSLKPEDTAVYYCAASR-----LRPALASMASDYDYWGGTQYSVSS
Stx2-H3   SGGGLVQAGGSLRLSCAASGH--TSIGYTMAWFRQTPGKERESVAAINWMGSSTYYSDSVKGRFTISRDRAKOTLDLQMNSLKAEDTAVYYCAAG------GGSFTDPTRYAYWGQGTQVTVSS
Stx2-D4   SGGGLVQAGGSLRLSCAASGR--INGDYAMGWFRQAPGEEREFVAVNSWIGGSTYYTDSVKGRFLSRDNAKNTLSLQMNSLKPEDTAVYYCAAG------HYTDFPTYFKEYDYWGQGTQVTVSS
Stx2-B4   TGGGLVQAGDSLRLSCAPSVR--SFITYAMGWFRQAPGKEREFVGAISSIGLGTYYSDSVKGRFTISRDGAENTLYLQMNSLKPEDTARYYCAATT-----KRTTAWSTPPYQYNYWGQGTQVTVSS
Stx2-B7   SGGGLVQAGASLRLSCAASTSGLTFIRYAMGWFRQAPGKERDFVGAINWITSTTYYADSVKGRFTISRDNADNTLNLQMNNIQMNNJEPEDTAVYYCAATS-----RIPYTITTASAYDYWGQGTQVTVSS
Stx2-G1   SGGGLVQPGESLRLSCVASAS--TFFSTSLMGWVRQAPGKGLESVAEVRTTG-GTFYAKSVAGRFTISRDNAKNTLYLQMNSLKAEDTGVYYCTAG-------AGPIATRYRGQGTQVTVSS
Stx2-H12  TGGGLVQAGDPLRLSCVASGR--TVSRYDKAWFRQAPGKEREFVAGISWNGDTKIYADSVKGRFTISRENSRDTLDLQIDNLKPEDTAAYYCAVGI----AGVQSMARMLGVRYWGQGTQVTVSS
```

FIG. 38

The amino acid sequence of the full translation product expressed as VNA2-Tcd:

| | | |
|---|---|---|
| 1 | MSDKIIHLTD DSFDTDVLKA DGAILVDFWA EWCGPCKMIA PILDEIADEY | 50 |
| 51 | QGKLTVAKLN IDQNPGTAPK YGIRGIPTLL LFKNGEVAAT KVGALSKGQL | 100 |
| 101 | KEFLDANLAG SGSGHMHHHH HHSSGLVPRG SGMKETAAAK FERQHMDSPD | 150 |
| 151 | LGTDDDDKAMAISDPNSGAP VPYPDPLEPR AAAQVQLVES GGGLVQPGGS | 200 |
| 201 | LRLSCAASGF TLDYSSIGWF RQAPGKEREG VSCISSSGDS TKYADSVKGR | 250 |
| 251 | FTTSRDNAKN TVYLQMNSLK PDDTAVYYCA AFRATMCGVF PLSPYGKDDW | 300 |
| 301 | GKGTLVTVSS EPKTPKPQPT SAIAGGGGSG GGGSGGGGSA AAQLQLVESG | 350 |
| 351 | GGLVQPGGSL RLSCEASGFT LDYYGIGWFR QPPGKEREAV SYISASARTI | 400 |
| 401 | LYADSVKGRF TISRDNAKNA VYLQMNSLKR EDTAVYYCAR RRFSASSVNR | 450 |
| 451 | WLADDYDVWGRGTQVAVSSE PKTPKPQTSA LVGGGGSGGG GSGGGGSLQA | 500 |
| 501 | MAAAQVQLVESGGGLVQTGG SLRLSCASSG SIAGFETVTW SRQAPGKSLQ | 550 |
| 551 | WVASMTKTNNEIYSDSVKGR FIISRDNAKN TVYLQMNSLK PEDTGVYFCK | 600 |
| 601 | GPELRGQGIQ VTVSSEPKTP KPQAIAGGGG SGGGGSGGGG SLQGQVQLVE | 650 |
| 651 | SGGGLVQPGG SLRLSCAASG FTFSDYVMTW VRQAPGKGPE WIATINTDGS | 700 |
| 701 | TMRDDSTKGR FTISRDNAKN TLYLQMTSLK PEDTALYYCA RGRVISASAI | 750 |
| 751 | RGAVRGPGTQ VTVSSEPKTP KPQPARQGAP VPYPDPLEPR GGGSDICLPR | 800 |
| 801 | WGCLWED (SEQ ID NO: 170) | |

FIG. 41

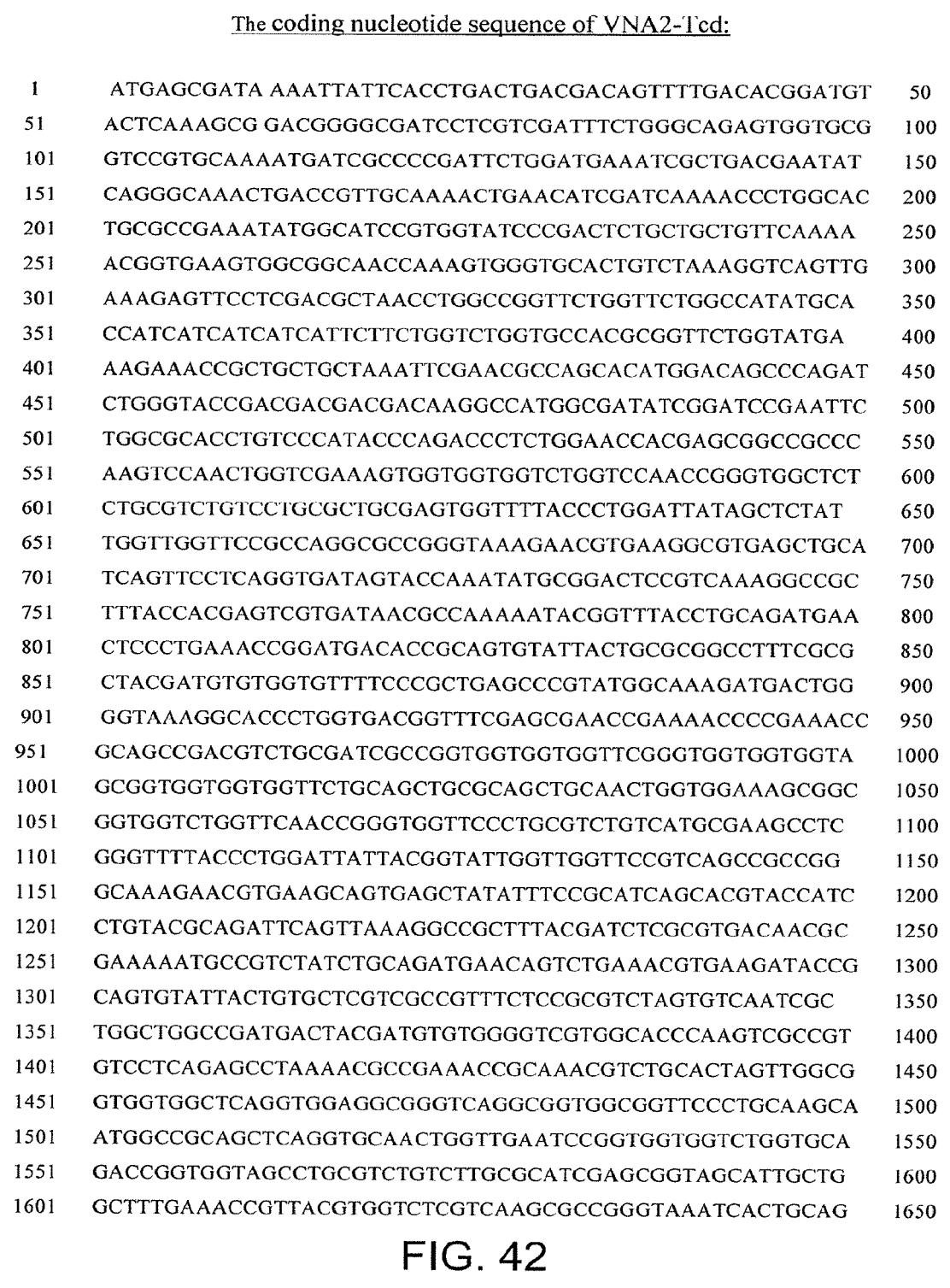

The coding nucleotide sequence of VNA2-Tcd:

| | | |
|---|---|---|
| 1 | ATGAGCGATA AAATTATTCACC (cont.)

| | | |
|---|---|---|
| 1651 | TGGGTCGCCTCGATGACCAAAACGAACAATGAAATCTATTCGGATAGCGT | 1700 |
| 1701 | TAAAGGCCGCTTTATTATCTCACGCGATAACGCGAAAAATACCGTGTATC | 1750 |
| 1751 | TGCAGATGAACTCGCTGAAACCGGAAGATACGGGTGTTTACTTCTGCAAA | 1800 |
| 1801 | GGCCCGGAACTGCGCGGTCAAGGCATTCAGGTTACCGTCTCTAGTGAGCC | 1850 |
| 1851 | TAAAACCCCGAAACCGCAAGCAATCGCAGGCGGCGGCGGCAGCGGCGGCG | 1900 |
| 1901 | GCGGCTCTGGTGGTGGTGGTTCCCTGCAGGGTCAAGTCCAGCTGGTGGAA | 1950 |
| 1951 | TCTGGCGGTGGTCTGGTGCAACCGGGTGGTAGTCTGCGTCTGTCCTGTGC | 2000 |
| 2001 | AGCCTCAGGCTTTACCTTCTCAGATTATGTTATGACGTGGGTCCGTCAGG | 2050 |
| 2051 | CACCGGGTAAAGGTCCGGAATGGATTGCTACCATCAATACGGACGGTAGC | 2100 |
| 2101 | ACCATGCGCGATGACTCTACCAAAGGCCGCTTCACGATTAGCCGTGATAA | 2150 |
| 2151 | TGCCAAAAATACCCTGTACCTGCAGATGACGTCTCTGAAACCGGAAGACA | 2200 |
| 2201 | CCGCGCTGTATTACTGTGCCCGCGGTCGTGTTATTTCTGCAAGTGCTATC | 2250 |
| 2251 | CGTGGCGCCGTCCGTGGTCCGGGCACCCAAGTCACCGTCTCCTCAGAACC | 2300 |
| 2301 | GAAAACGCCGAAACCGCAACCGGCGCGCCAGGGTGCGCCGGTGCCGTATC | 2350 |
| 2351 | CGGACCCGCTGGAACCGCGTTAA (SEQ ID NO: 169) | |

FIG. 42

The amino acid sequence of the full translation product of mammalian cell secreted VNA2-Tcd:

| | | |
|---|---|---|
| 1 | METDTLLLWVLLLWVPGSTGDAAQPARRARRTKLSGAPVPYPDPLEPRAA | 50 |
| 51 | AQVQLVESGGGLVQPGGSLRLSCAASGFTLDYSSIGWFRQAPGKEREGVS | 100 |
| 101 | CISSSGDSTKYADSVKGRFTTSRDNAKNTVYLQMNSLKPDDTAVYYCAAF | 150 |
| 151 | RATMCGVFPLSPYGKDDWGKGTLVTVSSEPKTPKPQPTSAIAGGGGSGGG | 200 |
| 201 | GSGGGGSAAAQLQLVESGGGLVQPGGSLRLSCEASGFTLDYYGIGWFRQP | 250 |
| 251 | PGKEREAVSYISASARTILYADSVKGRFTISRDNAKNAVYLQMNSLKRED | 300 |
| 301 | TAVYYCARRRFSASSVNRWLADDYDVWGRGTQVAVSSEPKTPKPQTSALV | 350 |
| 351 | GGGGSGGGGSGGGGSLQAMAAAQVQLVESGGGLVQTGGSLRLSCASSGSI | 400 |
| 401 | AGFETVTWSRQAPGKSLQWVASMTKTNNEIYSDSVKGRFIISRDNAKNTV | 450 |
| 451 | YLQMNSLKPEDTGVYFCKGPELRGQGIQVTVSSEPKTPKPQAIAGGGGSG | 500 |
| 501 | GGGSGGGGSLQGQVQLVESGGGLVQPGGSLRLSCAASGFTFSDYVMTWVR | 550 |
| 551 | QAPGKGPEWIATINTDGSTMRDDSTKGRFTISRDNAKNTLYLQMTSLKPE | 600 |
| 601 | DTALYYCARGRVISASAIRGAVRGPGTQVTVSSEPKTPKPQPARQGAPVP | 650 |
| 651 | YPDPLEPRGGGSDICLPRWGCLWED (SEQ ID NO: 167) | |

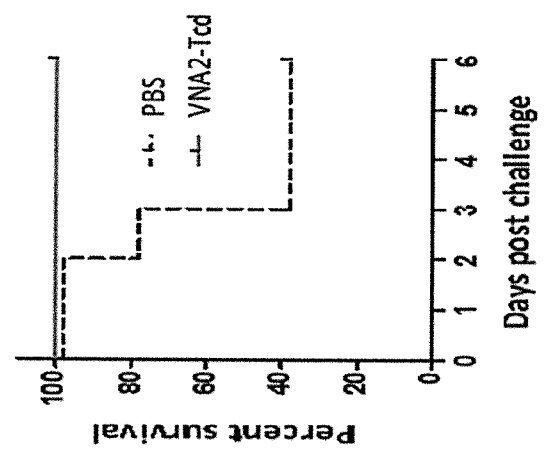
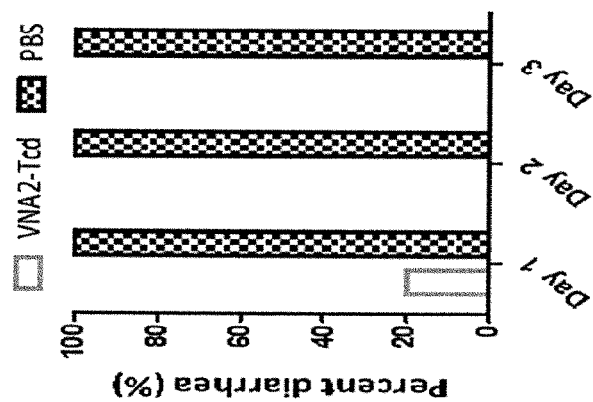
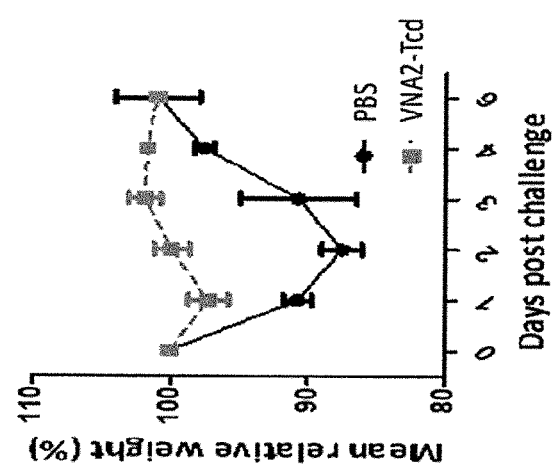

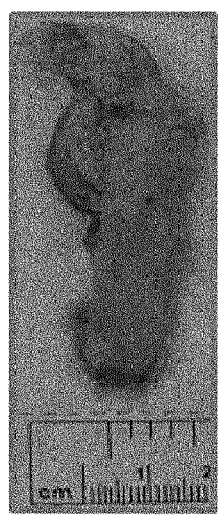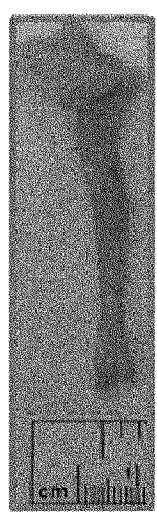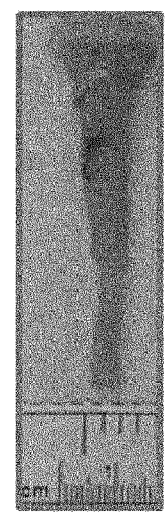
FIG. 48A  FIG. 48B

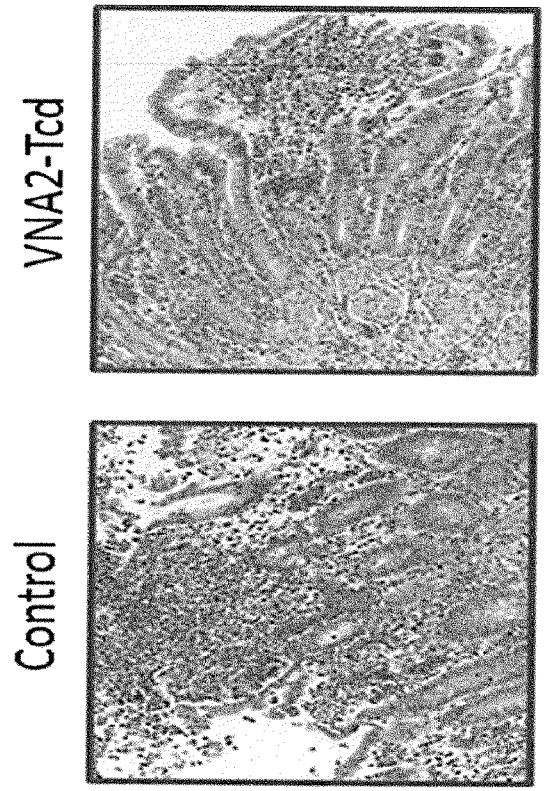
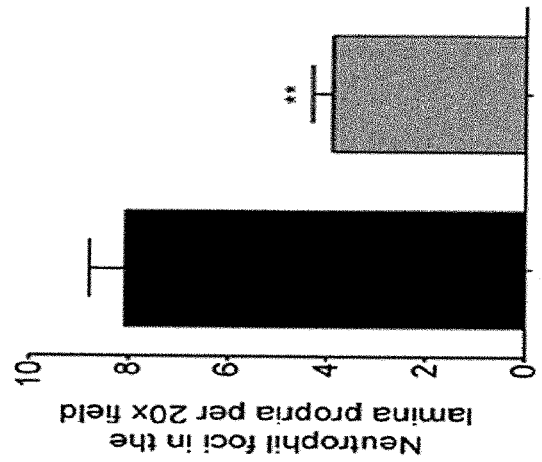

SEQUENCE LISTING

```
<160> NUMBER OF SEQ ID NOS: 174

<210> SEQ ID NO 1
<211> LENGTH: 816
<212> TYPE: DNA
<213> ORGANISM: Artificial Sequence
<220> FEATURE:
<223> OTHER INFORMATION: scFv#2 single chain antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 1
caggctgtgc tgactcagcc gtcctccgtg tccgggtccc cgggccnnan ggtctccatc      60
acctgctctg gaagcaggag taacgttggc acatatggtg taggttggtt ccaacagctc     120
ccaggatcgg gcctcagaac catcatctat tataatgaca aacgaccctc aggggtcccc     180
gaccgattct ctgcctccaa atcgggcaac acagccaccc tgatcatcag ctcgctccag     240
gctgaggatg aggccgatta tttctgtgga agtgccgacg gtagtagtta tggtattttc     300
```

```
ggcagtggga ccagactgac cgtcctgggt cagcccgcgg ccgctggtgg aggcggttca    360
ggcggaggtg gctctggcgg tggcggatcg gcgcgccagg tggggctgca ggagtcggga    420
cccagcctgg tgaagccctc acagaccctc tccctcacct gcacggtctc tggattctca    480
ttgtccaaca gtgttgtagg ctgggtccgc caggctccag aaaggtgcc ggagtggctt     540 ggtagtatag acagtggtgg ttacacagtc gctgacccgg ccctgaaatc ccgactcagc    600
atcacaaggg acacttccaa gagccaagtc tccctgtcac tgaacagcgt gacaactgag    660
gacacggccg tgtactactg tacaagggct tatagtatta cttattatgc gtatccccc     720 tatatcgact actggggccc aggactcctg gtcaccgtct cctcaactag tggtgcgccg    780
gtgccgtatc cggatccgct ggaaccgcgt gccgca                              816
```

<210> SEQ ID NO 2
<211> LENGTH: 272
<212> TYPE: PRT
<213> ORGANISM: Artificial Sequence
<220> FEATURE:
<223> OTHER INFORMATION: scFv#2 single chain antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 2

```
Gln Ala Val Leu Thr Gln Pro Ser Ser Val Ser Gly Ser Pro Gly Xaa
1               5                   10                  15

Xaa Val Ser Ile Thr Cys Ser Gly Ser Arg Ser Asn Val Gly Thr Tyr
            20                  25                  30

Gly Val Gly Trp Phe Gln Gln Leu Pro Gly Ser Gly Leu Arg Thr Ile
        35                  40                  45

Ile Tyr Tyr Asn Asp Lys Arg Pro Ser Gly Val Pro Asp Arg Phe Ser
    50                  55                  60

Ala Ser Lys Ser Gly Asn Thr Ala Thr Leu Ile Ile Ser Ser Leu Gln
65                  70                  75                  80

Ala Glu Asp Glu Ala Asp Tyr Phe Cys Gly Ala Asp Gly Ser Ser
                85                  90                  95

Tyr Gly Ile Phe Gly Ser Gly Thr Arg Leu Thr Val Leu Gly Gln Pro
            100                 105                 110

Ala Ala Ala Gly Gly Gly Ser Gly Gly Gly Ser Gly Gly Gly
        115                 120                 125

Gly Ser Ala Arg Gln Val Gly Leu Gln Glu Ser Gly Pro Ser Leu Val
    130                 135                 140

Lys Pro Ser Gln Thr Leu Ser Leu Thr Cys Thr Val Ser Gly Phe Ser
145                 150                 155                 160

Leu Ser Asn Ser Val Val Gly Trp Val Arg Gln Ala Pro Gly Lys Val
                165                 170                 175

Pro Glu Trp Leu Gly Ser Ile Asp Ser Gly Gly Tyr Thr Val Ala Asp
            180                 185                 190

Pro Ala Leu Lys Ser Arg Leu Ser Ile Thr Arg Asp Thr Ser Lys Ser
        195                 200                 205

Gln Val Ser Leu Ser Leu Asn Ser Val Thr Thr Glu Asp Thr Ala Val
    210                 215                 220

Tyr Tyr Cys Thr Arg Ala Tyr Ser Ile Thr Tyr Tyr Ala Tyr Pro Pro
225                 230                 235                 240

Tyr Ile Asp Tyr Trp Gly Pro Gly Leu Leu Val Thr Val Ser Ser Thr
                245                 250                 255
```

Ser Gly Ala Pro Val Pro Tyr Pro Asp Pro Leu Glu Pro Arg Ala Ala
        260                 265                 270

<210> SEQ ID NO 3
<211> LENGTH: 826
<212> TYPE: DNA
<213> ORGANISM: Artificial Sequence
<220> FEATURE:
<223> OTHER INFORMATION: scFv#3 Single Chain Antibody

<400> SEQUENCE: 3
caggctgtgc tgactcagcc gtcctccgtg tccaggtccc tgggccagag tgtctccatc     60
acctgctctg gaagcagcag caacgttgga tatggtgatt atgtgggctg gttccaacgg    120
gtcccaggat cagcccccaa actcctcatc tatggtgcaa ccactcgagc tcgggggtc     180
cccgaccgat tctccggctc caggtctggc aacacagcga ctctgaccat cagctcgctc    240
caggctgagg acgaggccga ttattactgt tcatcttacg acagtagtca ctatagtatt    300
ttcggcagtg ggaccagcct gaccgtcctg ggtcagcccg cggccgctgg tggaggcggt    360
tcaggcggag gtggctctgg cggtggcgga tcggcgcgcc aggtggagct gcaggagtcg    420
ggacccagcc tggtgaagcc ctcacagacc ctctccctca cctgcacggt ctctggattc    480
tcattaagta gcaatgctgt aggctgggtc cgccaggctc aggaaaggc gccggagtgg    540
gttggtggta tagatataga tggaaggccg gtctataaac caggcttaa gtcccggctc    600
agcatcacca gggacacctc caacgctcaa gtctccctgt cactgagcag cgtgacaact    660
gaggacacgg ccgtgtactt ctgtgcaagt tattatggtg ttatctttta taattatgcc    720
cctggggcat atatcgagca cttgagccca ggactcctga tcaccgtctc ctcaactagt    780
ggtgcgccgg tgccgtatcc ggatccgctg aaaccgcgt gccgca                    826

<210> SEQ ID NO 4
<211> LENGTH: 275
<212> TYPE: PRT
<213> ORGANISM: Artificial Sequence
<220> FEATURE:
<223> OTHER INFORMATION: scFv#3 single chain antibody

<400> SEQUENCE: 4

Gln Ala Val Leu Thr Gln Pro Ser Ser Val Ser Arg Ser Leu Gly Gln
1               5                   10                  15

Ser Val Ser Ile Thr Cys Ser Gly Ser Ser Ser Asn Val Gly Tyr Gly
            20                  25                  30

Asp Tyr Val Gly Trp Phe Gln Arg Val Pro Gly Ser Ala Pro Lys Leu
        35                  40                  45

Leu Ile Tyr Gly Ala Thr Thr Arg Ala Ser Gly Val Pro Asp Arg Phe
    50                  55                  60

Ser Gly Ser Arg Ser Gly Asn Thr Ala Thr Leu Thr Ile Ser Ser Leu
65                  70                  75                  80

Gln Ala Glu Asp Glu Ala Asp Tyr Tyr Cys Ser Ser Tyr Asp Ser Ser
                85                  90                  95

His Tyr Ser Ile Phe Gly Ser Gly Thr Ser Leu Thr Val Leu Gly Gln
            100                 105                 110

Pro Ala Ala Ala Gly Gly Gly Gly Ser Gly Gly Gly Gly Ser Gly Gly
        115                 120                 125

Gly Gly Ser Ala Arg Gln Val Glu Leu Gln Glu Ser Gly Pro Ser Leu
    130                 135                 140

```
Val Lys Pro Ser Gln Thr Leu Ser Leu Thr Cys Thr Val Ser Gly Phe
145                 150                 155                 160

Ser Leu Ser Ser Asn Ala Val Gly Trp Val Arg Gln Ala Pro Gly Lys
                165                 170                 175

Ala Pro Glu Trp Val Gly Gly Ile Asp Ile Asp Gly Arg Pro Val Tyr
            180                 185                 190

Lys Pro Gly Leu Lys Ser Arg Leu Ser Ile Thr Arg Asp Thr Ser Asn
        195                 200                 205

Ala Gln Val Ser Leu Ser Leu Ser Ser Val Thr Thr Glu Asp Thr Ala
    210                 215                 220

Val Tyr Phe Cys Ala Ser Tyr Tyr Gly Gly Tyr Leu Tyr Asn Tyr Ala
225                 230                 235                 240

Pro Gly Ala Tyr Ile Glu His Leu Ser Pro Gly Leu Leu Ile Thr Val
            245                 250                 255

Ser Ser Thr Ser Gly Ala Pro Val Pro Tyr Pro Asp Pro Leu Glu Pro
        260                 265                 270

Arg Ala Ala
    275
```

<210> SEQ ID NO 5
<211> LENGTH: 816
<212> TYPE: DNA
<213> ORGANISM: Artificial Sequence
<220> FEATURE:
<223> OTHER INFORMATION: scFv#7 Single Chain Antibody

<400> SEQUENCE: 5

```
tcctatgaac tgacccagcc gccttcaatg tcggtggcct tgggacagac ggccaaggtc    60
acctgccagg gagacaactt agaaaacttt tatgttcagt ggcaccagca gaagccgggc   120
caggcccctg tgacggtcat ttttcaggat aataagaggc cctcggggat ccctgaccgg   180
ttctctggct ccaactcggg gaacacggcc accctgacca tcagcggggc ccggaccgag   240
gacgaggccg actattactg tcagtcaggc cacagcagta tcggtggtgt tttcggcagc   300
gggaccagcc tgaccgtcct gggtcagccc gcggccgctg gtggaggcgg ttcaggcgga   360
ggtggctctg gcggtggcgg atcggcgcgc aggtgcagc tgcaggagtc gggacccagc   420
ctggtgaagc cctcacagac cctctccctc acctgcacgg tctctggctt ctcattaacg   480
ggaaattctg taacctgggt ccgccaggct ccaggaaacg tgccgagtg gcttggtggt   540
ataagccgcg gtggacgcac atactatgat acggccctga gtcccggct cagcatcacc   600
agggacacct ccaagaggca gtctcccta tcactgagca gcgtgacgac tgaggacacg   660
gccatgtact tctgtgcaag atcggcatat agtactcttt atgattatga gtatgccgct   720
gatatctacg actggggccc aggactcctg gtcaccgtct cctcaactag tggtgcgccg   780
gtgccgtatc cggatccgct ggaaccgcgt gccgca                              816
```

<210> SEQ ID NO 6
<211> LENGTH: 272
<212> TYPE: PRT
<213> ORGANISM: Artificial Sequence
<220> FEATURE:
<223> OTHER INFORMATION: scFv#7 Single Chain Antibody

<400> SEQUENCE: 6

```
Ser Tyr Glu Leu Thr Gln Pro Pro Ser Met Ser Val Ala Leu Gly Gln
1               5                   10                  15

Thr Ala Lys Val Thr Cys Gln Gly Asp Asn Leu Glu Asn Phe Tyr Val
```

20                  25                  30
Gln Trp His Gln Gln Lys Pro Gly Gln Ala Pro Val Thr Val Ile Phe
             35                  40                  45
Gln Asp Asn Lys Arg Pro Ser Gly Ile Pro Asp Arg Phe Ser Gly Ser
 50                  55                  60
Asn Ser Gly Asn Thr Ala Thr Leu Thr Ile Ser Gly Ala Arg Thr Glu
 65                  70                  75                  80
Asp Glu Ala Asp Tyr Tyr Cys Gln Ser Gly His Ser Ser Ile Gly Gly
                 85                  90                  95
Val Phe Gly Ser Gly Thr Ser Leu Thr Val Leu Gly Gln Pro Ala Ala
                100                 105                 110
Ala Gly Gly Gly Ser Gly Gly Gly Ser Gly Gly Gly Ser
            115                 120                 125
Ala Arg Gln Val Gln Leu Gln Glu Ser Gly Pro Ser Leu Val Lys Pro
             130                 135                 140
Ser Gln Thr Leu Ser Leu Thr Cys Thr Val Ser Gly Phe Ser Leu Thr
145                 150                 155                 160
Gly Asn Ser Val Thr Trp Val Arg Gln Ala Pro Gly Asn Val Pro Glu
                165                 170                 175
Trp Leu Gly Gly Ile Ser Arg Gly Gly Arg Thr Tyr Tyr Asp Thr Ala
                180                 185                 190
Leu Lys Ser Arg Leu Ser Ile Thr Arg Asp Thr Ser Lys Arg Gln Val
            195                 200                 205
Ser Leu Ser Leu Ser Ser Val Thr Thr Glu Asp Thr Ala Met Tyr Phe
210                 215                 220
Cys Ala Arg Ser Ala Tyr Ser Thr Leu Tyr Asp Tyr Glu Tyr Ala Ala
225                 230                 235                 240
Asp Ile Tyr Asp Trp Gly Pro Gly Leu Leu Val Thr Val Ser Ser Thr
                245                 250                 255
Ser Gly Ala Pro Val Pro Tyr Pro Asp Pro Leu Glu Pro Arg Ala Ala
            260                 265                 270

<210> SEQ ID NO 7
<211> LENGTH: 795
<212> TYPE: DNA
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 7
tcctatgaac tgacccagcc gccttcagtg tcggtggttt ggggncngan ggccgagatc    60
acctgccagg gagacctact ggataaaaaa tatacagctt ggtaccagca aaagccgggc   120
caggctccta tgaaaatcat taataaagac agtgagcggc cttcagggat ccgggaccgg   180
ttctcgggct ccagctcagg caaaacagcc accctaacca tcaacggggc ccggcctgag   240
gacgaggccg actattactg tttatcaggt gacagcaata ataatggtgt cttcggcagc   300

-continued

```
gggaccagcc tgaccgtcct gggtcagccc gcggccgctg gtggaggcgg ttcaggcgga      360
ggtggctctg gcggtggcgg atcggcgcgc caggtggagc tgcagggtc gggacccagc       420 ctggtgaagc cctcgcagac cctctcctc acctgcacgg tctctggatt ctcatggccc       480
aacaatgctg tggattgggt ccgccaggct ccaggaaagg cgccggagtg gcttggtggt      540
attgccgata atggaagaac aaactacaac acggccctaa agcccggct cagcatcact       600 agggacaccg ccaagagcca tgtctcccta tcgctgagca gcgtgacagc tgaggatacg      660
gccgtttact attgtacagc gggggttatg gtcatgcacg ccactgacta ctggggcccg      720
ggactcctgg tcaccgtctc ctcaactagt ggtgcgccgg tgccgtatcc ggatccgctg      780
gaaccgcgtg ccgca                                                       795
```

```
<210> SEQ ID NO 8
<211> LENGTH: 265
<212> TYPE: PRT
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 8

Ser Tyr Glu Leu Thr Gln Pro Pro Ser Val Ser Val Val Trp Gly Xaa
1               5                   10                  15

Xaa Ala Glu Ile Thr Cys Gln Gly Asp Leu Leu Asp Lys Lys Tyr Thr
            20                  25                  30

Ala Trp Tyr Gln Gln Lys Pro Gly Gln Ala Pro Met Lys Ile Ile Asn
        35                  40                  45

Lys Asp Ser Glu Arg Pro Ser Gly Ile Arg Asp Arg Phe Ser Gly Ser
    50                  55                  60

Ser Ser Gly Lys Thr Ala Thr Leu Thr Ile Asn Gly Ala Arg Pro Glu
65                  70                  75                  80

Asp Glu Ala Asp Tyr Tyr Cys Leu Ser Gly Asp Ser Asn Asn Asn Gly
                85                  90                  95

Val Phe Gly Ser Gly Thr Ser Leu Thr Val Leu Gly Gln Pro Ala Ala
            100                 105                 110

Ala Gly Gly Gly Ser Gly Gly Gly Ser Gly Gly Gly Ser
            115                 120                 125

Ala Arg Gln Val Glu Leu Gln Gly Ser Gly Pro Ser Leu Val Lys Pro
        130                 135                 140

Ser Gln Thr Leu Ser Leu Thr Cys Thr Val Ser Gly Phe Ser Trp Pro
145                 150                 155                 160

Asn Asn Ala Val Asp Trp Val Arg Gln Ala Pro Gly Lys Ala Pro Glu
                165                 170                 175

Trp Leu Gly Gly Ile Ala Asp Asn Gly Arg Thr Asn Tyr Asn Thr Ala
            180                 185                 190

Leu Lys Ala Arg Leu Ser Ile Thr Arg Asp Thr Ala Lys Ser His Val
        195                 200                 205

Ser Leu Ser Leu Ser Ser Val Thr Ala Glu Asp Thr Ala Val Tyr Tyr
    210                 215                 220

Cys Thr Ala Gly Val Met Val Met His Ala Thr Asp Tyr Trp Gly Pro
225                 230                 235                 240

Gly Leu Leu Val Thr Val Ser Ser Thr Ser Gly Ala Pro Val Pro Tyr
                245                 250                 255
```

Pro Asp Pro Leu Glu Pro Arg Ala Ala
            260                 265

<210> SEQ ID NO 9
<211> LENGTH: 810
<212> TYPE: DNA
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 9
caggctgtgg tgactcagcc gtcctccgtg tccgggtccc cgggccnnan agtctccatc      60
acctgctctg gaagcagcag caacgttggt agatatgctg taggctggtt ccaacagctc     120
ccaggatcgg gcctcagaac cgtcatctat tataatagca atcgaccctc aggggtcccc     180
gaccgattct ctggctccaa atcgggcaac acagccaccc tgaccatcag ctcgctccag     240
gctgaggatg aggccgatta tttctgtgga agttatgaca gtagtatcta tggtgttttc     300
ggcagcggga ccaggctgac cgtcctgggt cagcccgcgg ccgctggtgg aggcggttca     360
ggcggaggtg gctctggcgg tggcggatcg gcgcgccagg tgcagctgca ggagtcggga     420
cccagcctgg tgaggccctc acagaccctc tccctcacct gcacgatctc tggattctct     480
ttaagagagt atggtgtagg ttgggtccgc caggctccag gaaaggcgtt ggagtggctt     540
gggcgaatag atgattctgg atacacatta cataatcctg cccttaagtc ccggctcacc     600
ataactaggg acatctccaa gagccaagtc tccctgtcac tgagcagcgt gacacttgag     660
gacacggccg aatattactg cgtatatgct agtcgtggta ctgcttggtt gggagacatc     720
gatgtctggg gccaggact cctgctcact gtctcctcaa ctagtggtgc gccggtgccg     780
tatccggatc cgctggaacc gcgtgccgca                                     810

<210> SEQ ID NO 10
<211> LENGTH: 270
<212> TYPE: PRT
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 10

Gln Ala Val Val Thr Gln Pro Ser Ser Val Ser Gly Ser Pro Gly Xaa
1               5                   10                  15

Xaa Val Ser Ile Thr Cys Ser Gly Ser Ser Asn Val Gly Arg Tyr
            20                  25                  30

Ala Val Gly Trp Phe Gln Gln Leu Pro Gly Ser Gly Leu Arg Thr Val
            35                  40                  45

Ile Tyr Tyr Asn Ser Asn Arg Pro Ser Gly Val Pro Asp Arg Phe Ser
        50                  55                  60

Gly Ser Lys Ser Gly Asn Thr Ala Thr Leu Thr Ile Ser Ser Leu Gln
65                  70                  75                  80

```
Ala Glu Asp Glu Ala Asp Tyr Phe Cys Gly Ser Tyr Asp Ser Ser Ile
                85                  90                  95
Tyr Gly Val Phe Gly Ser Gly Thr Arg Leu Thr Val Leu Gly Gln Pro
            100                 105                 110
Ala Ala Ala Gly Gly Gly Gly Ser Gly Gly Gly Gly Ser Gly Gly Gly
            115                 120                 125
Gly Ser Ala Arg Gln Val Gln Leu Gln Glu Ser Gly Pro Ser Leu Val
130                 135                 140
Arg Pro Ser Gln Thr Leu Ser Leu Thr Cys Thr Ile Ser Gly Phe Ser
145                 150                 155                 160
Leu Arg Glu Tyr Gly Val Gly Trp Val Arg Gln Ala Pro Gly Lys Ala
                165                 170                 175
Leu Glu Trp Leu Gly Arg Ile Asp Asp Ser Gly Tyr Thr Leu His Asn
            180                 185                 190
Pro Ala Leu Lys Ser Arg Leu Thr Ile Thr Arg Asp Ile Ser Lys Ser
            195                 200                 205
Gln Val Ser Leu Ser Leu Ser Ser Val Thr Leu Glu Asp Thr Ala Glu
        210                 215                 220
Tyr Tyr Cys Val Tyr Ala Ser Arg Gly Thr Ala Trp Leu Gly Asp Ile
225                 230                 235                 240
Asp Val Trp Gly Pro Gly Leu Leu Leu Thr Val Ser Ser Thr Ser Gly
                245                 250                 255
Ala Pro Val Pro Tyr Pro Asp Pro Leu Glu Pro Arg Ala Ala
            260                 265                 270

<210> SEQ ID NO 11
<211> LENGTH: 816
<212> TYPE: DNA
<213> ORGANISM: Artificial Sequence
<220> FEATURE:
<223> OTHER INFORMATION: scFv#E Single Chain Antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 11
caggctgtgc tgactcagcc gtcctccgtg tccaggtccc tgggccnnan tgtctcgatc      60
acctgctctg gaggcagcag caacgttgga caaggtgatt atgtggcctg gttccaacag     120
gtcccaggat cagcccccaa actcctcatc tatgatgcga cgaatcgagc ctcgggggtc     180
cccgaccgat tcgtcggctc agatatggc aactcagcga ctctgatcat cacctcggtc      240
caggctgagg acgaggccga ttattattgt gcatcttatg acagtagtat gtatacgatt     300
ttcggcagcg ggaccagcct gaccgtcctg ggtcagcccg cggccgctgg tggaggcggt     360
tcaggcggag gtggctctgg cggtggcgga tcggcgcgcc aggtgagct gcaggggtcg      420
ggacccagcc aggtgaagcc ctcacagacc ctctcccta tctgcacgat ctctggattc      480
tcattaacca gcaataatgt agcctgggtc cgccaggctc aggaaaggg actgagtgg       540
gttggtgtca agtgatgg tggaactcca tactataact cggccctgaa atcccggctc       600
agcatcacca gggacacctc caagagccag gtccctgt cactgagcag cgtgacaact       660
gaggacacgg ccgtgtacta ctgtgcacgg acgttggatt atagtcatat ttggttgtac    720
tccgccgacc aatggggccc aggactcctg gtcaccgtct cctcaactag tggtgcgccg   780
```

```
gtgccgtatc cggatccgct ggaaccgcgt gccgca                                      816
```

<210> SEQ ID NO 12
<211> LENGTH: 272
<212> TYPE: PRT
<213> ORGANISM: Artificial Sequence
<220> FEATURE:
<223> OTHER INFORMATION: scFv#E Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 12

```
Gln Ala Val Leu Thr Gln Pro Ser Ser Val Ser Arg Ser Leu Gly Xaa
1               5                   10                  15

Xaa Val Ser Ile Thr Cys Ser Gly Gly Ser Ser Asn Val Gly Gln Gly
            20                  25                  30

Asp Tyr Val Ala Trp Phe Gln Gln Val Pro Gly Ser Ala Pro Lys Leu
        35                  40                  45

Leu Ile Tyr Asp Ala Thr Asn Arg Ala Ser Gly Val Pro Asp Arg Phe
    50                  55                  60

Val Gly Ser Arg Tyr Gly Asn Ser Ala Thr Leu Ile Ile Thr Ser Val
65                  70                  75                  80

Gln Ala Glu Asp Glu Ala Asp Tyr Tyr Cys Ala Ser Tyr Asp Ser Ser
                85                  90                  95

Met Tyr Thr Ile Phe Gly Ser Gly Thr Ser Leu Thr Val Leu Gly Gln
            100                 105                 110

Pro Ala Ala Ala Gly Gly Gly Ser Gly Gly Gly Ser Gly Gly
        115                 120                 125

Gly Gly Ser Ala Arg Gln Val Glu Leu Gln Gly Ser Gly Pro Ser Gln
    130                 135                 140

Val Lys Pro Ser Gln Thr Leu Ser Leu Ile Cys Thr Ile Ser Gly Phe
145                 150                 155                 160

Ser Leu Thr Ser Asn Asn Val Ala Trp Val Arg Gln Ala Pro Gly Lys
                165                 170                 175

Gly Leu Glu Trp Val Gly Val Ile Ser Asp Gly Gly Thr Pro Tyr Tyr
            180                 185                 190

Asn Ser Ala Leu Lys Ser Arg Leu Ser Ile Thr Arg Asp Thr Ser Lys
        195                 200                 205

Ser Gln Val Ser Leu Ser Leu Ser Ser Val Thr Thr Glu Asp Thr Ala
    210                 215                 220

Val Tyr Tyr Cys Ala Arg Thr Leu Asp Tyr Ser His Ile Trp Leu Tyr
225                 230                 235                 240

Ser Ala Asp Gln Trp Gly Pro Gly Leu Leu Val Thr Val Ser Ser Thr
                245                 250                 255

Ser Gly Ala Pro Val Pro Tyr Pro Asp Pro Leu Glu Pro Arg Ala Ala
            260                 265                 270
```

<210> SEQ ID NO 13
<211> LENGTH: 861
<212> TYPE: DNA
<213> ORGANISM: Artificial Sequence
<220> FEATURE:
<223> OTHER INFORMATION: scFv#7-2E Single Chain Antibody

<400> SEQUENCE: 13

```
ggtgcgccgg tgccgtatcc ggatccgctc gagccgcgtg ccggctccta tgaactgacc    60
```

-continued

```
cagccgcctt caatgtcggt ggccttggga cagacggcca aggtcacctg ccagggagac    120
aacttagaaa acttttatgt tcagtggcac cagcagaagc cgggccaggc ccctgtgacg    180
gtcatttttc aggataataa gaggccctcg gggatccctg accggttctc tggctccaac    240
tcggggaaca cggccaccct gaccatcagc ggggcccgga ccgaggacga ggccgactat    300
tactgtcagt caggccacag cagtatcggt ggtgttttcg gcagcgggac cagcctgacc    360
gtcctgggtc agcccgcggc cgctggtgga ggcggttcag gcggaggtgg ctctggcggt    420
ggcggatcgg cgcgccaggt gcagctgcag gagtcgggac ccagcctggt gaagccctca    480
cagaccctct ccctcacctg cacggtctct ggcttctcat taacgggaaa ttctgtaacc    540
tgggtccgcc aggctccagg aaacgtgccg gagtggcttg gtggtataag ccgcggtgga    600
cgcacatact atgatacggc cctgaagtcc cggctcagca tcaccaggga cacctccaag    660
aggcaagtct ccctatcact gagcagcgtg acgactgagg acacggccat gtacttctgt    720
gcaagatcgg catatagtac tctttatgat tatgagtatg ccgctgatat ctacgactgg    780
ggcccaggac tcctggtcac cgtctcctca actagtggtg cgccggtgcc gtatccggat    840
ccgctggaac gcgtgccgc a                                               861
```

<210> SEQ ID NO 14
<211> LENGTH: 287
<212> TYPE: PRT
<213> ORGANISM: Artificial Sequence
<220> FEATURE:
<223> OTHER INFORMATION: scFv#7-2E Single Chain Antibody

<400> SEQUENCE: 14

```
Gly Ala Pro Val Pro Tyr Pro Asp Pro Leu Glu Pro Arg Ala Gly Ser
1               5                   10                  15

Tyr Glu Leu Thr Gln Pro Pro Ser Met Ser Val Ala Leu Gly Gln Thr
            20                  25                  30

Ala Lys Val Thr Cys Gln Gly Asp Asn Leu Glu Asn Phe Tyr Val Gln
        35                  40                  45

Trp His Gln Gln Lys Pro Gly Gln Ala Pro Val Thr Val Ile Phe Gln
    50                  55                  60

Asp Asn Lys Arg Pro Ser Gly Ile Pro Asp Arg Phe Ser Gly Ser Asn
65                  70                  75                  80

Ser Gly Asn Thr Ala Thr Leu Thr Ile Ser Gly Ala Arg Thr Glu Asp
                85                  90                  95

Glu Ala Asp Tyr Tyr Cys Gln Ser Gly His Ser Ser Ile Gly Gly Val
            100                 105                 110

Phe Gly Ser Gly Thr Ser Leu Thr Val Leu Gly Gln Pro Ala Ala Ala
        115                 120                 125

Gly Gly Gly Gly Ser Gly Gly Gly Ser Gly Gly Gly Ser Ala
    130                 135                 140

Arg Gln Val Gln Leu Gln Glu Ser Gly Pro Ser Leu Val Lys Pro Ser
145                 150                 155                 160

Gln Thr Leu Ser Leu Thr Cys Thr Val Ser Gly Phe Ser Leu Thr Gly
                165                 170                 175

Asn Ser Val Thr Trp Val Arg Gln Ala Pro Gly Asn Val Pro Glu Trp
            180                 185                 190

Leu Gly Gly Ile Ser Arg Gly Gly Arg Thr Tyr Tyr Asp Thr Ala Leu
        195                 200                 205

Lys Ser Arg Leu Ser Ile Thr Arg Asp Thr Ser Lys Arg Gln Val Ser
```

Leu Ser Leu Ser Ser Val Thr Thr Glu Asp Thr Ala Met Tyr Phe Cys
225                 230                 235                 240

Ala Arg Ser Ala Tyr Ser Thr Leu Tyr Asp Tyr Glu Tyr Ala Ala Asp
            245                 250                 255

Ile Tyr Asp Trp Gly Pro Gly Leu Leu Val Thr Val Ser Ser Thr Ser
            260                 265                 270

Gly Ala Pro Val Pro Tyr Pro Asp Pro Leu Glu Pro Arg Ala Ala
        275                 280                 285

<210> SEQ ID NO 15
<211> LENGTH: 13
<212> TYPE: PRT
<213> ORGANISM: Artificial Sequence
<220> FEATURE:
<223> OTHER INFORMATION: Epitope Tag

<400> SEQUENCE: 15

Gly Ala Pro Val Pro Tyr Pro Asp Pro Leu Glu Pro Arg
1               5                   10

<210> SEQ ID NO 16
<211> LENGTH: 9
<212> TYPE: PRT
<213> ORGANISM: Artificial Sequence
<220> FEATURE:
<223> OTHER INFORMATION: VHH binding agents

<400> SEQUENCE: 16

Gln Val Gln Leu Val Glu Ser Gly Gly
1               5

<210> SEQ ID NO 17
<211> LENGTH: 8
<212> TYPE: PRT
<213> ORGANISM: Artificial Sequence
<220> FEATURE:
<223> OTHER INFORMATION: VHH binding agents

<400> SEQUENCE: 17

Ala His His Ser Glu Asp Pro Ser
1               5

<210> SEQ ID NO 18
<211> LENGTH: 8
<212> TYPE: PRT
<213> ORGANISM: Artificial Sequence
<220> FEATURE:
<223> OTHER INFORMATION: VHH binding agents

<400> SEQUENCE: 18

Glu Pro Lys Thr Pro Lys Pro Gln
1               5

<210> SEQ ID NO 19
<211> LENGTH: 396
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 19
caggtgcagc tcgtggagtc aggaggaggc ttggtgcagc ctggggggatc tctgagactc    60 tcgtgtgtag tctctggaag tgacttcaat acctatatca tgggctggta ccgccaggtt   120

```
ccagggaagc cgcgcgagtt ggtcgcagat attactactg aaggaaaaac aaactatggc      180
ggctccgtaa agggacgatt caccatctcc agagacaacg ccaaaaacac ggtgtatctg      240
caaatgttcg gcctgaaacc tgaggacgcg ggtaattatg tctgtaacgc agactggaag      300
atgggtgcat ggaccgcggg ggactacggt atcgactact ggggcaaagg gaccctggtc      360
accgtctcct cagaacccaa gacaccaaaa ccacaa                                396
```

```
<210> SEQ ID NO 20
<211> LENGTH: 132
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Val Val Ser Gly Ser Asp Phe Asn Thr Tyr
            20                  25                  30

Ile Met Gly Trp Tyr Arg Gln Val Pro Gly Lys Pro Arg Glu Leu Val
        35                  40                  45

Ala Asp Ile Thr Thr Glu Gly Lys Thr Asn Tyr Gly Gly Ser Val Lys
    50                  55                  60

Gly Arg Phe Thr Ile Ser Arg Asp Asn Ala Lys Asn Thr Val Tyr Leu
65                  70                  75                  80

Gln Met Phe Gly Leu Lys Pro Glu Asp Ala Gly Asn Tyr Val Cys Asn
                85                  90                  95

Ala Asp Trp Lys Met Gly Ala Trp Thr Ala Gly Asp Tyr Gly Ile Asp
            100                 105                 110

Tyr Trp Gly Lys Gly Thr Leu Val Thr Val Ser Ser Glu Pro Lys Thr
        115                 120                 125

Pro Lys Pro Gln
    130
```

```
<210> SEQ ID NO 21
<211> LENGTH: 408
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 21
caggtgcagc tcgtggagtc cggtggaggc ttggtgcagc tggggggtc tctgagactc       60 tcctgtgcag cctctgcagg caatctggat tattatgcca taggctggtt ccgccaggcc     120
ccagggaagg agcgcgaggg ggtctcatgt attagtagta gtgatggtag cactgtctat     180
acagactccg tgaagggccg attcaccatc tccagagaca taccaagaa cacggtagat     240 ctgcaaatgg acaatttgaa acctgaggac acggccgttt attactgtgc gacagtcgtt     300
aactactact gcacagccgg tgggtccatt cacgcgagcc cgtatgaaat ctggggccag     360
ggacccaggt caccgtctc ctcagcgcac cacagcgaag accctcg                    408
```

```
<210> SEQ ID NO 22
<211> LENGTH: 136
<212> TYPE: PRT
<213> ORGANISM: Artificial Sequence
<220> FEATURE:
<223> OTHER INFORMATION: VHH binding agents specific to BoNT/A holotoxin
```

<400> SEQUENCE: 22

Gln Val Gln Leu Val Glu Ser Gly Gly Gly Leu Val Gln Pro Gly Gly
1               5                   10                  15

Ser Leu Arg Leu Ser Cys Ala Ala Ser Ala Gly Asn Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Val Tyr Thr Asp Ser Val
    50                  55                  60

Lys Gly Arg Phe Thr Ile Ser Arg Asp Asn Thr Lys Asn Thr Val Asp
65                  70                  75                  80

Leu Gln Met Asp Asn Leu Lys Pro Glu Asp Thr Ala Val Tyr Tyr Cys
                85                  90                  95

Ala Thr Val Val Asn Tyr Tyr Cys Thr Ala Gly Gly Ser Ile His Ala
            100                 105                 110

Ser Pro Tyr Glu Ile Trp Gly Gln Gly Thr Gln Val Thr Val Ser Ser
        115                 120                 125

Ala His His Ser Glu Asp Pro Ser
    130                 135

<210> SEQ ID NO 23
<211> LENGTH: 375
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 23
caggtgcagc tcgtggagtc cggcggaggc ttggtgcacc ctgggggtc tctgagactc      60
tcttgtgcac cctctgccag tctaccatca cacccttca acccttcaa caatatggtg     120
ggctggtacc gtcaggctcc aggtaaacag cgcgaaatgg tcgcaagtat tggtctacga     180
ataaactatg cagactccgt gaagggccga ttcaccatct ccagagacaa cgccaagaac     240
acggtggatc tgcagatgga cagcctgcga cctgaggact cagccacata ctactgtcat     300
atagaataca cccactactg gggcaaaggg accctggtca ccgtctcctc ggaacccaag     360
acaccaaaac cacaa                                                     375

<210> SEQ ID NO 24
<211> LENGTH: 133
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 24

Gln Val Gln Leu Val Glu Ser Gly Gly Gly Leu Val His Pro Gly Gly
1               5                   10                  15

Ser Leu Arg Leu Ser Cys Ala Pro Ser Ala Ser Leu Pro Ser Thr Pro
            20                  25                  30

Phe Asn Pro Phe Asn Asn Met Val Gly Trp Tyr Arg Gln Ala Pro Gly
        35                  40                  45

Lys Gln Arg Glu Met Val Ala Ser Ile Gly Leu Arg Ile Asn Tyr Ala
    50                  55                  60

Asp Ser Val Lys Gly Arg Phe Thr Ile Ser Arg Asp Asn Ala Lys Asn
65                  70                  75                  80

```
Thr Val Asp Leu Gln Met Asp Ser Leu Arg Pro Glu Asp Ser Ala Thr
            85                  90                  95

Tyr Tyr Cys His Ile Glu Tyr Thr His Tyr Trp Gly Lys Gly Thr Leu
        100                 105                 110

Val Thr Val Ser Ser Glu Pro Lys Thr Pro Lys Pro Gln Glu Pro Lys
        115                 120                 125

Thr Pro Lys Pro Gln
        130

<210> SEQ ID NO 25
<211> LENGTH: 378
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 25
caggtgcagc tcgtggagtc tggtggaggc ttggcgcagc ctggggggtc tctgagactc      60
tcctgtgaag cgtctggttt tgggacatgg ttcaggttcg atgagaacac cgtgaactgg     120
taccgccagc ctccaggaaa gtcgcgcgag ttcgacgagt tggtcgctcg ttacccaaaa     180
agtggcatcg taacctattt agactccgtg aagggccgat tcacgatctc cagagacaac     240
gccaaaaaaa tggcgtttct gcaaatggac aacctgaaac tgaggacacg gccgtctat      300 tattgcaatg tcggtgaatt tggggccag gggacccagg tcacgatctc ctcagaaccc      360
aagacaccaa aaccacaa                                                   378

<210> SEQ ID NO 26
<211> LENGTH: 126
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 26

Gln Val Gln Leu Val Glu Ser Gly Gly Gly Leu Ala Gln Pro Gly Gly
1               5                   10                  15

Ser Leu Arg Leu Ser Cys Glu Ala Ser Gly Phe Gly Thr Trp Phe Arg
            20                  25                  30

Phe Asp Glu Asn Thr Val Asn Trp Tyr Arg Gln Pro Pro Gly Lys Ser
        35                  40                  45

Arg Glu Phe Asp Glu Leu Val Ala Arg Tyr Pro Lys Ser Gly Ile Val
    50                  55                  60

Thr Tyr Leu Asp Ser Val Lys Gly Arg Phe Thr Ile Ser Arg Asp Asn
65                  70                  75                  80

Ala Lys Lys Met Ala Phe Leu Gln Met Asp Asn Leu Lys Leu Glu Asp
            85                  90                  95

Thr Ala Val Tyr Tyr Cys Asn Val Gly Glu Phe Trp Gly Gln Gly Thr
        100                 105                 110

Gln Val Thr Ile Ser Ser Glu Pro Lys Thr Pro Lys Pro Gln
        115                 120                 125

<210> SEQ ID NO 27
<211> LENGTH: 384
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 27
```

```
caggtgcagc tcgtggagtc ggggggaggc ttggtgcagc ctgggggtc tctgagactc      60 tcctgtgcag cctctggatt caccctaggg tcgcgttaca tgagctgggt ccgccaggct    120
ccaggagagg ggttcgagtg ggtctcaagt attgaaccct ctggtaccgc atgggatgga    180
gactccgcga agggacgatt caccacttcc agagacgacg ccaagaacac gctttatctg    240
caaatgagca acctgcaacc cgaggacacg gtgtttatt actgtgcaac agggtatcgg    300
acggacacga ggattccggg tggctcgtgg ggccagggga cccaggtcac cgtctcctca    360
gaacccaaga caccaaaacc acaa                                            384
```

```
<210> SEQ ID NO 28
<211> LENGTH: 128
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 28
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ser Arg
            20                  25                  30

Tyr Met Ser Trp Val Arg Gln Ala Pro Gly Glu Gly Phe Glu Trp Val
        35                  40                  45

Ser Ser Ile Glu Pro Ser Gly Thr Ala Trp Asp Gly Asp Ser Ala Lys
    50                  55                  60

Gly Arg Phe Thr Thr Ser Arg Asp Asp Ala Lys Asn Thr Leu Tyr Leu
65                  70                  75                  80

Gln Met Ser Asn Leu Gln Pro Glu Asp Thr Gly Val Tyr Tyr Cys Ala
                85                  90                  95

Thr Gly Tyr Arg Thr Asp Thr Arg Ile Pro Gly Gly Ser Trp Gly Gln
            100                 105                 110

Gly Thr Gln Val Thr Val Ser Ser Glu Pro Lys Thr Pro Lys Pro Gln
        115                 120                 125

```
<210> SEQ ID NO 29
<211> LENGTH: 360
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 29
caggtgcagc tcgtggagtc tggaggaggc ttggtgcagc ctgggggtc tctgagactc      60 tcctgtcaag tctctggatt caccttcggt gactgggtca tgagctggtt ccgccaggct    120
ccggggaagg agcgcgaatt cgtcgcaagt attacggcta ctagtagtct aaagtattat    180
gcagactccg tgaagggccg attcaccatc tccagagaca atgtcaacaa cacactgttt    240
ctgcaaatgg atcgcctgaa atctgaggac acggccgttt attactgtcg gtcccccaac    300
tactggggcc aggggaccca ggtcaccgtc tccgccgaac ccaagacacc aaaaccacaa    360
```

```
<210> SEQ ID NO 30
<211> LENGTH: 120
<212> TYPE: PRT
<213> ORGANISM: Artificial Sequence
<220> FEATURE:
<223> OTHER INFORMATION: VHH binding agents specific to BoNT/A holotoxin
```

-continued

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Gln Val Ser Gly Phe Thr Phe Gly Asp Trp
            20                  25                  30

Val Met Ser Trp Phe Arg Gln Ala Pro Gly Lys Glu Arg Glu Phe Val
        35                  40                  45

Ala Ser Ile Thr Ala Thr Ser Ser Leu Lys Tyr Tyr Ala Asp Ser Val
    50                  55                  60

Lys Gly Arg Phe Thr Ile Ser Arg Asp Asn Val Asn Thr Leu Phe
65                  70                  75                  80

Leu Gln Met Asp Arg Leu Lys Ser Glu Asp Thr Ala Val Tyr Tyr Cys
                85                  90                  95

Arg Ser Pro Asn Tyr Trp Gly Gln Gly Thr Gln Val Thr Val Ser Ala
            100                 105                 110

Glu Pro Lys Thr Pro Lys Pro Gln
            115                 120

<210> SEQ ID NO 31
<211> LENGTH: 366
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 31
caggtgcagc tcgtggagtc aggtggaggc ttggtgcagg ttggggggtc tctgagactc        60
tcctgtgtag tttctggaag cgacatcagt ggcattgcga tgggctggta ccgccaggct       120
ccagggaagc ggcgcgaaat ggtcgcagat attttttctg gcggtagtac agactatgca       180
ggctccgtga agggccgatt caccatctcc agagacaacg ccaagaagac gagctatctg       240
caaatgaaca acgtgaaacc tgaggacacc ggagtctact actgtaggct gtacgggagc       300
ggtgactact ggggccaggg gacccaggtc accgtctcct cagcgcacca cagcgaagac       360
ccctcg                                                                  366

<210> SEQ ID NO 32
<211> LENGTH: 122
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 32

Gln Val Gln Leu Val Glu Ser Gly Gly Gly Leu Val Gln Val Gly Gly
1               5                   10                  15

Ser Leu Arg Leu Ser Cys Val Val Ser Gly Ser Asp Ile Ser Gly Ile
            20                  25                  30

Ala Met Gly Trp Tyr Arg Gln Ala Pro Gly Lys Arg Arg Glu Met Val
        35                  40                  45

Ala Asp Ile Phe Ser Gly Gly Ser Thr Asp Tyr Ala Gly Ser Val Lys
    50                  55                  60

Gly Arg Phe Thr Ile Ser Arg Asp Asn Ala Lys Lys Thr Ser Tyr Leu
65                  70                  75                  80

Gln Met Asn Asn Val Lys Pro Glu Asp Thr Gly Val Tyr Tyr Cys Arg
                85                  90                  95

Leu Tyr Gly Ser Gly Asp Tyr Trp Gly Gln Gly Thr Gln Val Thr Val

Ser Ser Ala His His Ser Glu Asp Pro Ser
          115                 120

<210> SEQ ID NO 33
<211> LENGTH: 411
<212> TYPE: DNA
<213> ORGANISM: Artificial Sequence
<220> FEATURE:
<223> OTHER INFORMATION: VHH binding agents specific to BoNT/B holotoxin

<400> SEQUENCE: 33

```
caggtgcagc tcgtggagtc aggcggaggc ttggtgcagc tgggggggtc tctgaaactc      60
tcctgtgcag cctctggatt cactttggga caccatcgcg ttggctggtt ccgccaggcc     120
ccaggaaaga gcgtgaggg ggtcgcgtgt attagcgcca ctggtcttag cacacactat     180
tcagactccg tgaccggccg atttaccgtc tccagagaca acctcaacaa cgtggcgtat     240
ctgcagctga acagcctgaa acctgaggac gcaggtgttt attactgtgc aagcagattc     300
tcccttaatt cggtcgatgc gaatatgtgc ctttcagagc ctcagtatga caactggggc     360
caggggaccc aggtcagaat ctcctcagaa cccaagacac caaaaccaca a             411
```

<210> SEQ ID NO 34
<211> LENGTH: 137
<212> TYPE: PRT
<213> ORGANISM: Artificial Sequence
<220> FEATURE:
<223> OTHER INFORMATION: VHH binding agents specific to BoNT/B holotoxin

<400> SEQUENCE: 34

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Leu Gly His His
            20                  25                  30

Arg Val Gly Trp Phe Arg Gln Ala Pro Gly Lys Arg Glu Gly Val
        35                  40                  45

Ala Cys Ile Ser Ala Thr Gly Leu Ser Thr His Tyr Ser Asp Ser Val
    50                  55                  60

Thr Gly Arg Phe Thr Val Ser Arg Asp Asn Leu Asn Asn Val Ala Tyr
65                  70                  75                  80

Leu Gln Leu Asn Ser Leu Lys Pro Glu Asp Ala Gly Val Tyr Tyr Cys
                85                  90                  95

Ala Ser Arg Phe Ser Leu Asn Ser Val Asp Ala Asn Met Cys Leu Ser
            100                 105                 110

Glu Pro Gln Tyr Asp Asn Trp Gly Gln Gly Thr Gln Val Arg Ile Ser
        115                 120                 125

Ser Glu Pro Lys Thr Pro Lys Pro Gln
    130                 135

<210> SEQ ID NO 35
<211> LENGTH: 399
<212> TYPE: DNA
<213> ORGANISM: Artificial Sequence
<220> FEATURE:
<223> OTHER INFORMATION: VHH binding agents specific to BoNT/B holotoxin

<400> SEQUENCE: 35

```
caggtgcagc tcgtggagac gggtggagga ttggtgcagg ccggggggctc tctgagactc      60
tcctgcgcag gctctggacg ctccttcagc gccgctgtca tgggctggtt ccgccaggcg     120
```

```
ccagggaagg agcgagaatt cgtagcagca cttagacaaa ttattggtag cacacactat      180
gcagactccg tgaagggccg attcaccatc tccagagaca cgccaagaa catgttgtat       240 ctcgacatga acagcctgaa acctacggac acggccgcgt attactgcac agcgggacct     300
ccgactatgc tggacgtttc taccgaccgg gagtatgaca cctggggtca ggggactcag     360
gtcaccgtct cctcagcgca ccacagcgaa gacccctcg                             399
```

```
<210> SEQ ID NO 36
<211> LENGTH: 133
<212> TYPE: PRT
<213> ORGANISM: Artificial Sequence
<220> FEATURE:
<223> OTHER INFORMATION: VHH binding agents specific to BoNT/B holotoxin

<400> SEQUENCE: 36
```

Gln Val Gln Leu Val Glu Ser Gly Gly Gly Leu Val Gln Ala Gly Gly
1               5                   10                  15

Ser Leu Arg Leu Ser Cys Ala Gly Ser Gly Arg Ser Phe Ser Ala Ala
            20                  25                  30

Val Met Gly Trp Phe Arg Gln Ala Pro Gly Lys Glu Arg Glu Phe Val
        35                  40                  45

Ala Ala Leu Arg Gln Ile Ile Gly Ser Thr His Tyr Ala Asp Ser Val
    50                  55                  60

Lys Gly Arg Phe Thr Ile Ser Arg Asp Asn Ala Lys Asn Met Leu Tyr
65                  70                  75                  80

Leu Asp Met Asn Ser Leu Lys Pro Thr Asp Thr Ala Ala Tyr Tyr Cys
                85                  90                  95

Thr Ala Gly Pro Pro Thr Met Leu Asp Val Ser Thr Asp Arg Glu Tyr
            100                 105                 110

Asp Thr Trp Gly Gln Gly Thr Gln Val Thr Val Ser Ser Ala His His
        115                 120                 125

Ser Glu Asp Pro Ser
    130

```
<210> SEQ ID NO 37
<211> LENGTH: 363
<212> TYPE: DNA
<213> ORGANISM: Artificial Sequence
<220> FEATURE:
<223> OTHER INFORMATION: VHH binding agent

<400> SEQUENCE: 37
caggtgcagc tcgtggagtc cggaggaggc ttggtgcgac tgggggggtc tctgagactc      60
tcttgtgtag tctctggatt cgcctacgaa atgcccatga tgggctggta ccgccaggct     120
ccagggaatc agcgcgagtt ggtcgcaact attggtacag gtggtaggat gaactatgca     180
gactccgtga agggccgatt caccatctcc agagacaacg ccaagaacac ggtgtatctg     240
caaatgaaca gcctgaaacc tgaggacaca gccgcctatt actgtaaaat cgagtttaca     300
aattactggg gccaggggac ccaagtcacc gtctcctcag aacccaagac accaaaacca     360
caa                                                                    363
```

```
<210> SEQ ID NO 38
<211> LENGTH: 121
<212> TYPE: PRT
<213> ORGANISM: Artificial Sequence
<220> FEATURE:
<223> OTHER INFORMATION: VHH binding agent
```

<400> SEQUENCE: 38

Gln Val Gln Leu Val Glu Ser Gly Gly Gly Leu Val Arg Pro Gly Gly
1               5                   10                  15

Ser Leu Arg Leu Ser Cys Val Val Ser Gly Phe Ala Tyr Glu Met Pro
            20                  25                  30

Met Met Gly Trp Tyr Arg Gln Ala Pro Gly Asn Gln Arg Glu Leu Val
        35                  40                  45

Ala Thr Ile Gly Thr Gly Arg Met Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ala Tyr Tyr Cys Lys
                85                  90                  95

Ile Glu Phe Thr Asn Tyr Trp Gly Gln Gly Thr Gln Val Thr Val Ser
            100                 105                 110

Ser Glu Pro Lys Thr Pro Lys Pro Gln
        115                 120

<210> SEQ ID NO 39
<211> LENGTH: 366
<212> TYPE: DNA
<213> ORGANISM: Artificial Sequence
<220> FEATURE:
<223> OTHER INFORMATION: VHH binding agent

<400> SEQUENCE: 39

```
caggtgcagc tcgtggagtc aggtggaggc ttggtgcagc cggggggatc tctgagactg      60
tcctgtacag tctctggaag catcttcgat ctacctggaa tgaactggta tcgccaggct     120
ccaggggcgc agcgcgagtt ggtcgcagat attagtagtg atggtaggag acaaactat      180
gcagactccg tgaagggccg attcaccatg tccagagaca atgccaagaa aacggtgtat     240
ctgcaaatgg acagcctgaa acctgacgac acggccgtct attactgtaa tgtgaaattt     300
actcaccact ggggccaggg gatccaggtc accgtctcct cagaacccaa gacaccaaaa     360
ccacaa                                                                366
```

<210> SEQ ID NO 40
<211> LENGTH: 122
<212> TYPE: PRT
<213> ORGANISM: Artificial Sequence
<220> FEATURE:
<223> OTHER INFORMATION: VHH binding agent

<400> SEQUENCE: 40

Gln Val Gln Leu Val Glu Ser Gly Gly Gly Leu Val Gln Pro Gly Gly
1               5                   10                  15

Ser Leu Arg Leu Ser Cys Thr Val Ser Gly Ser Ile Phe Asp Leu Pro
            20                  25                  30

Gly Met Asn Trp Tyr Arg Gln Ala Pro Gly Ala Gln Arg Glu Leu Val
        35                  40                  45

Ala Asp Ile Ser Ser Asp Gly Arg Arg Thr Asn Tyr Ala Asp Ser Val
    50                  55                  60

Lys Gly Arg Phe Thr Met Ser Arg Asp Asn Ala Lys Lys Thr Val Tyr
65                  70                  75                  80

Leu Gln Met Asp Ser Leu Lys Pro Asp Asp Thr Ala Val Tyr Tyr Cys
                85                  90                  95

```
Asn Val Lys Phe Thr His His Trp Gly Gln Gly Ile Gln Val Thr Val
            100                 105                 110
Ser Ser Glu Pro Lys Thr Pro Lys Pro Gln
        115                 120
```

<210> SEQ ID NO 41
<211> LENGTH: 366
<212> TYPE: DNA
<213> ORGANISM: Artificial Sequence
<220> FEATURE:
<223> OTHER INFORMATION: VHH binding agent

<400> SEQUENCE: 41

```
caggtgcagc tcgtggagtc aggcggaggc ttggtgcagc cggggggatc tctgaggctg      60
tcctgtacgg tctctggaag catcttcggc ctacctggca tgagctggta tcgccaggct     120
ccaggggcgc agcgcgagtt ggtcgcagat attagtagtg atggtgggag gacgcactat     180
gcagactccg tgaagggccg cttcaccatc tccagagaca tgacaagaa  aacggtgtat     240 ctgcagatgg acagcctgaa acctgacgac acggccgtct attactgtaa tgtgaaattt     300
actcaccact ggggccaggg gatccaggtc accgtctcct cagaacccaa gacaccaaaa     360
ccacaa                                                                366
```

<210> SEQ ID NO 42
<211> LENGTH: 122
<212> TYPE: PRT
<213> ORGANISM: Artificial Sequence
<220> FEATURE:
<223> OTHER INFORMATION: VHH binding agent

<400> SEQUENCE: 42

```
Gln Val Gln Leu Val Glu Ser Gly Gly Gly Leu Val Gln Pro Gly Gly
1               5                   10                  15
Ser Leu Arg Leu Ser Cys Thr Val Ser Gly Ser Ile Phe Gly Leu Pro
            20                  25                  30
Gly Met Ser Trp Tyr Arg Gln Ala Pro Gly Ala Gln Arg Glu Leu Val
        35                  40                  45
Ala Asp Ile Ser Ser Asp Gly Gly Arg Thr His Tyr Ala Asp Ser Val
    50                  55                  60
Lys Gly Arg Phe Thr Ile Ser Arg Asp Asn Asp Lys Lys Thr Val Tyr
65                  70                  75                  80
Leu Gln Met Asp Ser Leu Lys Pro Asp Asp Thr Ala Val Tyr Tyr Cys
                85                  90                  95
Asn Val Lys Phe Thr His His Trp Gly Gln Gly Ile Gln Val Thr Val
            100                 105                 110
Ser Ser Glu Pro Lys Thr Pro Lys Pro Gln
        115                 120
```

<210> SEQ ID NO 43
<211> LENGTH: 366
<212> TYPE: DNA
<213> ORGANISM: Artificial Sequence
<220> FEATURE:
<223> OTHER INFORMATION: VHH binding agent

<400> SEQUENCE: 43

```
caggtgcagc tcgtggagtc tgggggaggc ttggtgcagg atgggggtc  tctgaggctc      60 tcctgcacaa catctggaag tatcgacagt ttcaatgcca tagagtggta ccgccaggct     120
ccagggaagc agcgcgaatt ggtcgcaagt ataagtagtg atggtcgtcg cacaaactat     180
```

```
gcagactccg tgaagggccg attcaccatc tccggagaca acgccaagaa cacggtgtat    240
ctgcaaatga acagcctgaa acctgaggac acagccgtgt attactgtca tagacctttt    300
acccactact ggggccaggg gacccaggtc accgtctcct cagaacccaa gacaccaaaa    360
ccacaa                                                                366
```

<210> SEQ ID NO 44
<211> LENGTH: 122
<212> TYPE: PRT
<213> ORGANISM: Artificial Sequence
<220> FEATURE:
<223> OTHER INFORMATION: VHH binding agent

<400> SEQUENCE: 44

```
Gln Val Gln Leu Val Glu Ser Gly Gly Gly Leu Val Gln Asp Gly Gly
1               5                   10                  15

Ser Leu Arg Leu Ser Cys Thr Thr Ser Gly Ser Ile Asp Ser Phe Asn
            20                  25                  30

Ala Ile Glu Trp Tyr Arg Gln Ala Pro Gly Lys Gln Arg Glu Leu Val
        35                  40                  45

Ala Ser Ile Ser Ser Asp Gly Arg Arg Thr Asn Tyr Ala Asp Ser Val
    50                  55                  60

Lys Gly Arg Phe Thr Ile Ser Gly Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

His Arg Pro Phe Thr His Tyr Trp Gly Gln Gly Thr Gln Val Thr Val
            100                 105                 110

Ser Ser Glu Pro Lys Thr Pro Lys Pro Gln
        115                 120
```

<210> SEQ ID NO 45
<211> LENGTH: 912
<212> TYPE: DNA
<213> ORGANISM: Artificial Sequence
<220> FEATURE:
<223> OTHER INFORMATION: VHH binding agent with tag

<400> SEQUENCE: 45

```
atgagcgata aaattattca cctgactgac gacagttttg acacggatgt actcaaagcg    60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatatgca ccatcatcat    360
catcattctt ctggtctggt gccacgcggt tctggtatga agaaaaccgc tgctgctaaa    420
ttcgaacgcc agcacatgga cagcccagat ctgggtaccg acgacgacga caaggccatg    480
gcgatatcgg atccgaattc ccaggtgcag ctcgtggagt caggtggagg cttggtgcag    540 gttgggggt ctctgagact ctcctgtgta gtttctggaa gcgacatcag tggcattgcg    600
atgggctggt accgccaggc tccagggaag cggcgcgaaa tggtcgcaga tatttttct    660 ggcggtagta cagactatgc aggctccgtg aagggccgat tcaccatctc cagagacaac    720
gccaagaaga cgagctatct gcaaatgaac aacgtgaaac tgaggacac cggagtctac    780
```
tactgtaggc tgtacgggag cggtgactac tggggccagg ggacccaggt caccgtctcc    840
tcagcgcacc acagcgaaga ccccactagt ggtgcgccgg tgccgtatcc ggatccgctg    900
gaaccgcgtt aa    912

<210> SEQ ID NO 46
<211> LENGTH: 303
<212> TYPE: PRT
<213> ORGANISM: Artificial Sequence
<220> FEATURE:
<223> OTHER INFORMATION: VHH binding agent with tag

<400> SEQUENCE: 46

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
            115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Lys Ala Met
145                 150                 155                 160

Ala Ile Ser Asp Pro Asn Ser Gln Val Gln Leu Val Glu Ser Gly Gly
                165                 170                 175

Gly Leu Val Gln Val Gly Gly Ser Leu Arg Leu Ser Cys Val Val Ser
            180                 185                 190

Gly Ser Asp Ile Ser Gly Ile Ala Met Gly Trp Tyr Arg Gln Ala Pro
        195                 200                 205

Gly Lys Arg Arg Glu Met Val Ala Asp Ile Phe Ser Gly Gly Ser Thr
    210                 215                 220

Asp Tyr Ala Gly Ser Val Lys Gly Arg Phe Thr Ile Ser Arg Asp Asn
225                 230                 235                 240

Ala Lys Lys Thr Ser Tyr Leu Gln Met Asn Asn Val Lys Pro Glu Asp
                245                 250                 255

Thr Gly Val Tyr Tyr Cys Arg Leu Tyr Gly Ser Gly Asp Tyr Trp Gly
            260                 265                 270

Gln Gly Thr Gln Val Thr Val Ser Ser Ala His His Ser Glu Asp Pro
        275                 280                 285

Thr Ser Gly Ala Pro Val Pro Tyr Pro Asp Pro Leu Glu Pro Arg
    290                 295                 300

<210> SEQ ID NO 47
<211> LENGTH: 924
<212> TYPE: DNA
<213> ORGANISM: Artificial Sequence
<220> FEATURE:

<223> OTHER INFORMATION: VHH binding agent with tag

<400> SEQUENCE: 47

```
atgagcgata aaattattca cctgactgac gacagttttg cacggatgt actcaaagcg      60
gacggggcga tcctcgtcga tttctgggca gagtggtgcg gtccgtgcaa atgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatatgca ccatcatcat    360
catcattctt ctggtctggt gccacgcggt tctggtatga agaaaccgc tgctgctaaa    420
ttcgaacgcc agcacatgga cagcccagat ctgggtaccg acgacgacga caaggccatg    480
gcgatatcgg atccgaattc ccaggtgcag ctcgtggagt ccggcggagg cttggtgcac    540
cctgggggt ctctgagact ctcttgtgca ccctctgcca gtctaccatc aacacccttc    600
aaccccttca caatatggt gggctggtac cgtcaggctc caggtaaaca gcgcgaaatg    660
gtcgcaagta ttggtctacg aataaactat gcagactccg tgaagggccg attcaccatc    720
tccagagaca acgccaagaa cacggtggat ctgcagatgg acagcctgcg acctgaggac    780
tcagccacat actactgtca tatagaatac cccactact ggggcaaagg accctggtc    840
accgtctcct cggaacccaa gacaccaaaa ccacaaacta gtggtgcgcc ggtgccgtat    900
ccggatccgc tggaaccgcg ttaa                                          924
```

<210> SEQ ID NO 48
<211> LENGTH: 307
<212> TYPE: PRT
<213> ORGANISM: Artificial Sequence
<220> FEATURE:
<223> OTHER INFORMATION: VHH binding agent with tag

<400> SEQUENCE: 48

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Ala Ile Ser Asp Pro Asn Ser Gln Val Gln Leu Val Glu Ser Gly Gly
                165                 170                 175

| | | | | | | | | | | |
|---|---|---|---|---|---|---|---|---|---|---|
|Gly|Leu|Val|His|Pro|Gly|Gly|Ser|Leu|Arg|Leu|Ser|Cys|Ala|Pro|Ser|
| | | |180| | | |185| | | |190| | | | |
|Ala|Ser|Leu|Pro|Ser|Thr|Pro|Phe|Asn|Pro|Phe|Asn|Asn|Met|Val|Gly|
| | |195| | | |200| | | |205| | | | | |
|Trp|Tyr|Arg|Gln|Ala|Pro|Gly|Lys|Gln|Arg|Glu|Met|Val|Ala|Ser|Ile|
| |210| | | | |215| | | | |220| | | | |
|Gly|Leu|Arg|Ile|Asn|Tyr|Ala|Asp|Ser|Val|Lys|Gly|Arg|Phe|Thr|Ile|
|225| | | | |230| | | | |235| | | | |240|
|Ser|Arg|Asp|Asn|Ala|Lys|Asn|Thr|Val|Asp|Leu|Gln|Met|Asp|Ser|Leu|
| | | | |245| | | | |250| | | | |255| |
|Arg|Pro|Glu|Asp|Ser|Ala|Thr|Tyr|Tyr|Cys|His|Ile|Glu|Tyr|Thr|His|
| | | |260| | | | |265| | | | |270| | |
|Tyr|Trp|Gly|Lys|Gly|Thr|Leu|Val|Thr|Val|Ser|Ser|Glu|Pro|Lys|Thr|
| | |275| | | | |280| | | | |285| | | |
|Pro|Lys|Pro|Gln|Thr|Ser|Gly|Ala|Pro|Val|Pro|Tyr|Pro|Asp|Pro|Leu|
| |290| | | | |295| | | | |300| | | | |
|Glu|Pro|Arg| | | | | | | | | | | | | |
|305| | | | | | | | | | | | | | | |

```
<210> SEQ ID NO 49
<211> LENGTH: 1350
<212> TYPE: DNA
<213> ORGANISM: Artificial Sequence
<220> FEATURE:
<223> OTHER INFORMATION: VHH dimer binding agent with tag

<400> SEQUENCE: 49
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg ccatatgca  ccatcatcat   360 catcattctt ctggtctggt gccacgcggt tctggtatga agaaaccgc  tgctgctaaa   420 ttcgaacgcc agcacatgga cagcccagat ctgggtaccg acgacgacga caaggccatg   480
gcggccgctc aggtgcagct cgtggagtca ggtgaggct  tggtgcaggt tggggggtct   540
ctgagactct cctgtgtagt ttctggaagc gacatcagtg gcattgcgat gggctggtac   600
cgccaggctc agggaagcg  gcgcgaaatg gtcgcagata  ttttttctgg cggtagtaca   660
gactatgcag gctccgtgaa gggccgattc accatctcca gagacaacgc caagaagacg   720
agctatctgc aaatgaacaa cgtgaaacct gaggacaccg agtctacta  ctgtaggctg   780 tacgggagcg gtgactactg gggccagggg acccaggtca ccgtctcctc agcgcaccac   840
agcgaagacc ccactagtgc gatcgctggt ggaggcggtt caggcggagg tggctctggc   900
ggtggcggtt ccctgcaggg tcagttgcag ctcgtggagt ccggcggagg cttggtgcac   960 cctgggggt  ctctgagact ctcttgtgca ccctctgcca gtctaccatc aacacccttc  1020
aaccccttca caatatggt  gggctggtac cgtcaggctc aggtaaaca  gcgcgaaatg  1080 gtcgcaagta ttggtctacg aataaactat gcagactccg tgaagggccg attcaccatc  1140
tccagagaca cgccaagaa  cacggtggat ctgcagatgg acagcctgcg acctgaggac  1200
tcagccacat actactgtca tatagaatac acccactact ggggcaaagg gaccctggtc  1260
```

```
accgtctcct cggaacccaa gacaccaaaa ccacaaccgg cgcgccaggg tgcgccggtg    1320
ccgtatccgg acccgctgga accgcgttaa                                     1350
```

<210> SEQ ID NO 50
<211> LENGTH: 449
<212> TYPE: PRT
<213> ORGANISM: Artificial Sequence
<220> FEATURE:
<223> OTHER INFORMATION: VHH dimer binding agent with tag

<400> SEQUENCE: 50

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Lys Ala Met
145                 150                 155                 160

Ala Ala Ala Gln Val Gln Leu Val Glu Ser Gly Gly Gly Leu Val Gln
                165                 170                 175

Val Gly Gly Ser Leu Arg Leu Ser Cys Val Val Ser Gly Ser Asp Ile
            180                 185                 190

Ser Gly Ile Ala Met Gly Trp Tyr Arg Gln Ala Pro Gly Lys Arg Arg
        195                 200                 205

Glu Met Val Ala Asp Ile Phe Ser Gly Gly Ser Thr Asp Tyr Ala Gly
    210                 215                 220

Ser Val Lys Gly Arg Phe Thr Ile Ser Arg Asp Asn Ala Lys Lys Thr
225                 230                 235                 240

Ser Tyr Leu Gln Met Asn Asn Val Lys Pro Glu Asp Thr Gly Val Tyr
                245                 250                 255

Tyr Cys Arg Leu Tyr Gly Ser Gly Asp Tyr Trp Gly Gln Gly Thr Gln
            260                 265                 270

Val Thr Val Ser Ser Ala His His Ser Glu Asp Pro Thr Ser Ala Ile
        275                 280                 285

Ala Gly Gly Gly Gly Ser Gly Gly Gly Gly Ser Gly Gly Gly Gly Ser
    290                 295                 300

Leu Gln Gly Gln Leu Gln Leu Val Glu Ser Gly Gly Gly Leu Val His
305                 310                 315                 320

Pro Gly Gly Ser Leu Arg Leu Ser Cys Ala Pro Ser Ala Ser Leu Pro
                325                 330                 335

Ser Thr Pro Phe Asn Pro Phe Asn Asn Met Val Gly Trp Tyr Arg Gln
            340                 345                 350
```

```
Ala Pro Gly Lys Gln Arg Glu Met Val Ala Ser Ile Gly Leu Arg Ile
        355                 360                 365

Asn Tyr Ala Asp Ser Val Lys Gly Arg Phe Thr Ile Ser Arg Asp Asn
    370                 375                 380

Ala Lys Asn Thr Val Asp Leu Gln Met Asp Ser Leu Arg Pro Glu Asp
385                 390                 395                 400

Ser Ala Thr Tyr Tyr Cys His Ile Glu Tyr Thr His Tyr Trp Gly Lys
                405                 410                 415

Gly Thr Leu Val Thr Val Ser Ser Glu Pro Lys Thr Pro Lys Pro Gln
                420                 425                 430

Pro Ala Arg Gln Gly Ala Pro Val Pro Tyr Pro Asp Pro Leu Glu Pro
            435                 440                 445

Arg
```

<210> SEQ ID NO 51
<211> LENGTH: 1410
<212> TYPE: DNA
<213> ORGANISM: Artificial Sequence
<220> FEATURE:
<223> OTHER INFORMATION: VHH dimer binding agent with two tags

<400> SEQUENCE: 51

```
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg gccatatgca ccatcatcat     360
catcattctt ctggtctggt gccacgcggt tctggtatga agaaaccgc tgctgctaaa     420
ttcgaacgcc agcacatgga cagcccagat ctgggtaccg acgacgacga caaggccatg     480
gcgatatcgg atccgaattc tggcgcacct gtcccatacc cagaccctct ggaaccacga     540
gcggccgctc aggtgcagct cgtggagtca ggtgaggct tggtgcaggt tggggggtct     600
ctgagactct cctgtgtagt ttctggaagc gacatcagtg gcattgcgat gggctggtac     660
cgccaggctc cagggaagcg gcgcgaaatg gtcgcagata ttttttctgg cggtagtaca     720
gactatgcag gctccgtgaa gggccgattc accatctcca gagacaacgc caagaagacg     780
agctatctgc aaatgaacaa cgtgaaacct gaggacaccg agtctactat ctgtaggctg     840
tacgggagcg gtgactactg gggccagggg acccaggtca ccgtctcctc agcgcaccac     900
agcgaagacc ccactagtgc gatcgctggt ggaggcggtt caggcggagg tggctctggc     960
ggtggcggtt ccctgcaggg tcagttgcag ctcgtggagt ccggcggagg cttggtgcac    1020
cctggggggt ctctgagact ctcttgtgca ccctctgcca gtctaccatc aacacccttc    1080
aaccccttca caatatggt gggctggtac cgtcaggctc aggtaaaca gcgcgaaatg    1140
gtcgcaagta ttggtctacg aataaactat gcagactccg tgaagggccg attcaccatc    1200
tccagagaca cgccaagaa cacggtggat ctgcagatgg acagcctgcg acctgaggac    1260
tcagccacat actactgtca tatagaatac ccccactact ggggcaaagg gaccctggtc    1320
accgtctcct cggaacccaa gacaccaaaa ccacaaccgg cgcgccaggg tgcgccggtg    1380
ccgtatccgg acccgctgga accgcgttaa                                     1410
```

-continued

```
<210> SEQ ID NO 52
<211> LENGTH: 469
<212> TYPE: PRT
<213> ORGANISM: Artificial Sequence
<220> FEATURE:
<223> OTHER INFORMATION: VHH dimer binding agent with two tags

<400> SEQUENCE: 52
```

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
            115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Ala Gln Val Gln Leu Val Glu Ser Gly Gly
            180                 185                 190

Gly Leu Val Gln Val Gly Gly Ser Leu Arg Leu Ser Cys Val Val Ser
            195                 200                 205

Gly Ser Asp Ile Ser Gly Ile Ala Met Gly Trp Tyr Arg Gln Ala Pro
210                 215                 220

Gly Lys Arg Arg Glu Met Val Ala Asp Ile Phe Ser Gly Ser Thr
225                 230                 235                 240

Asp Tyr Ala Gly Ser Val Lys Gly Arg Phe Thr Ile Ser Arg Asp Asn
                245                 250                 255

Ala Lys Lys Thr Ser Tyr Leu Gln Met Asn Asn Val Lys Pro Glu Asp
            260                 265                 270

Thr Gly Val Tyr Tyr Cys Arg Leu Tyr Gly Ser Gly Asp Tyr Trp Gly
        275                 280                 285

Gln Gly Thr Gln Val Thr Val Ser Ser Ala His His Ser Glu Asp Pro
    290                 295                 300

Thr Ser Ala Ile Ala Gly Gly Gly Ser Gly Gly Gly Ser Gly
305                 310                 315                 320

Gly Gly Gly Ser Leu Gln Gly Gln Leu Gln Leu Val Glu Ser Gly Gly
                325                 330                 335

Gly Leu Val His Pro Gly Gly Ser Leu Arg Leu Ser Cys Ala Pro Ser
            340                 345                 350

Ala Ser Leu Pro Ser Thr Pro Phe Asn Pro Phe Asn Asn Met Val Gly
        355                 360                 365

```
Trp Tyr Arg Gln Ala Pro Gly Lys Gln Arg Glu Met Val Ala Ser Ile
    370                 375                 380
Gly Leu Arg Ile Asn Tyr Ala Asp Ser Val Lys Gly Arg Phe Thr Ile
385                 390                 395                 400
Ser Arg Asp Asn Ala Lys Asn Thr Val Asp Leu Gln Met Asp Ser Leu
                405                 410                 415
Arg Pro Glu Asp Ser Ala Thr Tyr Tyr Cys His Ile Glu Tyr Thr His
            420                 425                 430
Tyr Trp Gly Lys Gly Thr Leu Val Thr Val Ser Ser Glu Pro Lys Thr
        435                 440                 445
Pro Lys Pro Gln Pro Ala Arg Gln Gly Ala Pro Val Pro Tyr Pro Asp
    450                 455                 460
Pro Leu Glu Pro Arg
465
```

<210> SEQ ID NO 53
<211> LENGTH: 109
<212> TYPE: PRT
<213> ORGANISM: Clostridium botulinum

<400> SEQUENCE: 53

```
Met Ser Asp Lys Ile Ile His Leu Thr Asp Asp Ser Phe Asp Thr Asp
1               5                   10                  15
Val Leu Lys Ala Asp Gly Ala Ile Leu Val Asp Phe Trp Ala Glu Trp
            20                  25                  30
Cys Gly Pro Cys Lys Met Ile Ala Pro Ile Leu Asp Glu Ile Ala Asp
        35                  40                  45
Glu Tyr Gln Gly Lys Leu Thr Val Ala Lys Leu Asn Ile Asp Gln Asn
    50                  55                  60
Pro Gly Thr Ala Pro Lys Tyr Gly Ile Arg Gly Ile Pro Thr Leu Leu
65                  70                  75                  80
Leu Phe Lys Asn Gly Glu Val Ala Ala Thr Lys Val Gly Ala Leu Ser
                85                  90                  95
Lys Gly Gln Leu Lys Glu Phe Leu Asp Ala Asn Leu Ala
            100                 105
```

<210> SEQ ID NO 54
<211> LENGTH: 5
<212> TYPE: PRT
<213> ORGANISM: Artificial Sequence
<220> FEATURE:
<223> OTHER INFORMATION: The sequence has been designed and synthesized

<400> SEQUENCE: 54

```
Gly Gly Gly Gly Ser
1               5
```

<210> SEQ ID NO 55
<211> LENGTH: 15
<212> TYPE: PRT
<213> ORGANISM: Artificial Sequence
<220> FEATURE:
<223> OTHER INFORMATION: The sequence has been designed and synthesized

<400> SEQUENCE: 55

```
Gly Gly Gly Gly Ser Gly Gly Gly Gly Ser Gly Gly Gly Gly Ser
1               5                   10                  15
```

<210> SEQ ID NO 56
<211> LENGTH: 111

<212> TYPE: PRT
<213> ORGANISM: Artificial Sequence
<220> FEATURE:
<223> OTHER INFORMATION: The sequence has been designed and synthesized

<400> SEQUENCE: 56

Leu Val Gln Val Gly Gly Ser Leu Arg Leu Ser Cys Val Val Ser Gly
1               5                   10                  15

Ser Asp Ile Ser Gly Ile Ala Met Gly Trp Tyr Arg Gln Ala Pro Gly
            20                  25                  30

Lys Arg Arg Glu Met Val Ala Asp Ile Phe Ser Gly Gly Ser Thr Asp
        35                  40                  45

Tyr Ala Gly Ser Val Lys Gly Arg Phe Thr Ile Ser Arg Asp Asn Ala
    50                  55                  60

Lys Lys Thr Ser Tyr Leu Gln Met Asn Asn Val Lys Pro Glu Asp Thr
65                  70                  75                  80

Gly Val Tyr Tyr Cys Arg Leu Tyr Gly Ser Gly Asp Tyr Trp Gly Gln
                85                  90                  95

Gly Thr Gln Val Thr Val Ser Ser Ala His His Ser Glu Asp Pro
            100                 105                 110

<210> SEQ ID NO 57
<211> LENGTH: 115
<212> TYPE: PRT
<213> ORGANISM: Artificial Sequence
<220> FEATURE:
<223> OTHER INFORMATION: The sequence has been designed and synthesized

<400> SEQUENCE: 57

Leu Val His Pro Gly Gly Ser Leu Arg Leu Ser Cys Ala Pro Ser Ala
1               5                   10                  15

Ser Leu Pro Ser Thr Pro Phe Asn Pro Phe Asn Met Val Gly Trp
            20                  25                  30

Tyr Arg Gln Ala Pro Gly Lys Gln Arg Glu Met Val Ala Ser Ile Gly
        35                  40                  45

Leu Arg Ile Asn Tyr Ala Asp Ser Val Lys Gly Arg Phe Thr Ile Ser
    50                  55                  60

Arg Asp Asn Ala Lys Asn Thr Val Asp Leu Gln Met Asp Ser Leu Arg
65                  70                  75                  80

Pro Glu Asp Ser Ala Thr Tyr Tyr Cys His Ile Glu Tyr Thr His Tyr
                85                  90                  95

Trp Gly Lys Gly Thr Leu Val Thr Val Ser Ser Glu Pro Lys Thr Pro
            100                 105                 110

Lys Pro Gln
        115

<210> SEQ ID NO 58
<211> LENGTH: 269
<212> TYPE: PRT
<213> ORGANISM: Artificial Sequence
<220> FEATURE:
<223> OTHER INFORMATION: The sequence has been designed and synthesized

<400> SEQUENCE: 58

Gln Val Gln Leu Val Glu Ser Gly Gly Gly Leu Val Gln Val Gly Gly
1               5                   10                  15

Ser Leu Arg Leu Ser Cys Val Val Ser Gly Ser Asp Ile Ser Gly Ile
            20                  25                  30

Ala Met Gly Trp Tyr Arg Gln Ala Pro Gly Lys Arg Arg Glu Met Val

```
                35                  40                  45
Ala Asp Ile Phe Ser Gly Gly Ser Thr Asp Tyr Ala Gly Ser Val Lys
 50                  55                  60
Gly Arg Phe Thr Ile Ser Arg Asp Asn Ala Lys Lys Thr Ser Tyr Leu
 65                  70                  75                  80
Gln Met Asn Asn Val Lys Pro Glu Asp Thr Gly Val Tyr Tyr Cys Arg
                 85                  90                  95
Leu Tyr Gly Ser Gly Asp Tyr Trp Gly Gln Gly Thr Gln Val Thr Val
                100                 105                 110
Ser Ser Ala His His Ser Glu Asp Pro Thr Ser Ala Ile Ala Gly Gly
                115                 120                 125
Gly Gly Ser Gly Gly Gly Ser Gly Gly Gly Ser Leu Gln Gly
130                 135                 140
Gln Leu Gln Leu Val Glu Ser Gly Gly Gly Leu Val His Pro Gly Gly
145                 150                 155                 160
Ser Leu Arg Leu Ser Cys Ala Pro Ser Ala Ser Leu Pro Ser Thr Pro
                165                 170                 175
Phe Asn Pro Phe Asn Asn Met Val Gly Trp Tyr Arg Gln Ala Pro Gly
                180                 185                 190
Lys Gln Arg Glu Met Val Ala Ser Ile Gly Leu Arg Ile Asn Tyr Ala
                195                 200                 205
Asp Ser Val Lys Gly Arg Phe Thr Ile Ser Arg Asp Asn Ala Lys Asn
210                 215                 220
Thr Val Asp Leu Gln Met Asp Ser Leu Arg Pro Glu Asp Ser Ala Thr
225                 230                 235                 240
Tyr Tyr Cys His Ile Glu Tyr Thr His Tyr Trp Gly Lys Gly Thr Leu
                245                 250                 255
Val Thr Val Ser Ser Glu Pro Lys Thr Pro Lys Pro Gln
                260                 265

<210> SEQ ID NO 59
<211> LENGTH: 135
<212> TYPE: PRT
<213> ORGANISM: Artificial Sequence
<220> FEATURE:
<223> OTHER INFORMATION: The sequence has been designed and synthesized

<400> SEQUENCE: 59

Gln Val Gln Leu Val Glu Thr Gly Gly Leu Val Gln Pro Gly Gly Ser
 1                   5                  10                  15
Leu Arg Leu Ser Cys Ala Ala Ser Gly Phe Thr Leu Asp Tyr Ser Ser
                 20                  25                  30
Ile Gly Trp Phe Arg Gln Ala Pro Gly Lys Glu Arg Glu Gly Val Ser
                 35                  40                  45
Cys Ile Ser Ser Ser Gly Asp Ser Thr Lys Tyr Ala Asp Ser Val Lys
 50                  55                  60
Gly Arg Phe Thr Thr Ser Arg Asp Asn Ala Lys Asn Thr Val Tyr Leu
 65                  70                  75                  80
Gln Met Asn Ser Leu Lys Pro Asp Asp Thr Ala Val Tyr Tyr Cys Ala
                 85                  90                  95
Ala Phe Arg Ala Thr Met Cys Gly Val Phe Pro Leu Ser Pro Tyr Gly
                100                 105                 110
Lys Asp Asp Trp Gly Lys Gly Thr Leu Val Thr Val Ser Ser Glu Pro
                115                 120                 125
Lys Thr Pro Lys Pro Gln Pro
```

<210> SEQ ID NO 60
<211> LENGTH: 130
<212> TYPE: PRT
<213> ORGANISM: Artificial Sequence
<220> FEATURE:
<223> OTHER INFORMATION: The sequence has been designed and synthesized

<400> SEQUENCE: 60

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Glu Pro Lys Thr Pro Lys Pro
        115                 120                 125

Gln Pro
    130

<210> SEQ ID NO 61
<211> LENGTH: 137
<212> TYPE: PRT
<213> ORGANISM: Artificial Sequence
<220> FEATURE:
<223> OTHER INFORMATION: The sequence has been designed and synthesized

<400> SEQUENCE: 61

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Gly Ile Ser Ser Val Asp Gly Ser Thr Tyr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Gln Ser Pro Ile Pro Ile His Tyr Ser Arg Thr Tyr Ser
            100                 105                 110

Gly Pro Tyr Gly Met Asp Tyr Trp Gly Lys Gly Thr Leu Val Thr Val
        115                 120                 125

Ser Ser Ala His His Ser Glu Asp Pro
    130                 135

<210> SEQ ID NO 62
<211> LENGTH: 139

<212> TYPE: PRT
<213> ORGANISM: Artificial Sequence
<220> FEATURE:
<223> OTHER INFORMATION: The sequence has been designed and synthesized

<400> SEQUENCE: 62

```
Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Gly Ile Ser Phe Val Asp Gly Ser Thr Tyr Tyr Ala Asp Ser Val
    50                  55                  60

Lys Gly Arg Phe Ala Ile Ser Arg Gly Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Gln Ser Ser Ile Pro Met His Tyr Ser Ser Thr Tyr Ser
            100                 105                 110

Gly Pro Ser Gly Met Asp Tyr Trp Gly Lys Gly Thr Leu Val Thr Val
        115                 120                 125

Ser Ser Glu Pro Lys Thr Pro Lys Pro Gln Pro
    130                 135
```

<210> SEQ ID NO 63
<211> LENGTH: 136
<212> TYPE: PRT
<213> ORGANISM: Artificial Sequence
<220> FEATURE:
<223> OTHER INFORMATION: The sequence has been designed and synthesized

<400> SEQUENCE: 63

```
Gln Leu Gln Leu Val Glu Thr Gly Gly Gly Leu Val Gln Ala Gly Gly
1               5                   10                  15

Ser Leu Arg Leu Ser Cys Ala Ala Ser Gly Arg Thr Leu Ser Asn Tyr
            20                  25                  30

Pro Met Gly Trp Phe Arg Gln Ala Pro Gly Lys Glu Arg Glu Phe Val
        35                  40                  45

Ala Ala Ile Arg Arg Ile Ala Asp Gly Thr Tyr Tyr Ala Asp Ser Val
    50                  55                  60

Lys Gly Arg Phe Thr Ile Ser Arg Asp Asn Ala Trp Asn Thr Leu Tyr
65                  70                  75                  80

Leu Gln Met Asn Gly Leu Lys Pro Glu Asp Thr Ala Val Tyr Phe Cys
                85                  90                  95

Ala Thr Gly Pro Gly Ala Phe Pro Gly Met Val Val Thr Asn Pro Ser
            100                 105                 110

Ala Tyr Pro Tyr Trp Gly Gln Gly Thr Gln Val Thr Val Ser Ser Glu
        115                 120                 125

Pro Lys Thr Pro Lys Pro Gln Pro
    130                 135
```

<210> SEQ ID NO 64
<211> LENGTH: 139
<212> TYPE: PRT
<213> ORGANISM: Artificial Sequence
<220> FEATURE:
<223> OTHER INFORMATION: The sequence has been designed and synthesized

<400> SEQUENCE: 64

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Gly Ile Ser Ser Ser Asp Gly Ser Thr Tyr Tyr Ala Asp Ser Val
    50                  55                  60

Lys Gly Arg Phe Thr Ile Ser Arg Asp Asn Ala Thr Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Gln Ala Ala Ile Pro Met His Tyr Ser Ala Ser Tyr Ser
            100                 105                 110

Gly Pro Arg Gly Met Asp Tyr Trp Gly Lys Gly Thr Leu Val Thr Val
            115                 120                 125

Ser Ser Glu Pro Lys Thr Pro Lys Pro Gln Pro
            130                 135

<210> SEQ ID NO 65
<211> LENGTH: 135
<212> TYPE: PRT
<213> ORGANISM: Artificial Sequence
<220> FEATURE:
<223> OTHER INFORMATION: The sequence has been designed and synthesized

<400> SEQUENCE: 65

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Tyr Tyr
            20                  25                  30

Gly Ile Gly Trp Phe Arg Gln Ala Pro Gly Lys Glu Arg Gln Glu Val
        35                  40                  45

Ser Tyr Ile Ser Ala Ser Ala Lys Thr Lys Leu Tyr Ser Asp Ser Val
    50                  55                  60

Lys Gly Arg Phe Thr Ile Ser Arg Asp Asn Ala Lys Asn Ala Val Tyr
65                  70                  75                  80

Leu Glu Met Asn Ser Leu Lys Arg Glu Asp Thr Ala Val Tyr Tyr Cys
                85                  90                  95

Ala Arg Arg Arg Phe Asp Ala Ser Ala Ser Asn Arg Trp Leu Ala Ala
            100                 105                 110

Asp Tyr Asp Tyr Trp Gly Gln Gly Thr Gln Val Thr Val Ser Ser Glu
            115                 120                 125

Pro Lys Thr Pro Lys Pro Gln
        130                 135

<210> SEQ ID NO 66
<211> LENGTH: 123
<212> TYPE: PRT
<213> ORGANISM: Artificial Sequence
<220> FEATURE:
<223> OTHER INFORMATION: The sequence has been designed and synthesized

<400> SEQUENCE: 66

Gln Val Gln Leu Val Glu Ser Gly Gly Gly Leu Val Gln Ala Gly Gly
1               5                   10                  15

-continued

Ser Leu Arg Leu Ser Cys Val Ser Glu Arg Asn Pro Gly Ile Asn
           20                  25                  30

Ala Met Gly Trp Tyr Arg Gln Ala Pro Gly Ser Gln Arg Glu Leu Val
           35                  40                      45

Ala Ile Trp Gln Thr Gly Gly Ser Leu Asn Tyr Ala Asp Ser Val Lys
50                  55                      60

Gly Arg Phe Thr Ile Ser Arg Asp Asn Leu Lys Asn Thr Val Tyr Leu
65              70                  75                      80

Gln Met Asn Ser Leu Lys Pro Glu Asp Thr Ala Val Tyr Tyr Cys Tyr
                    85                  90                  95

Leu Lys Lys Trp Arg Asp Gln Tyr Trp Gly Gln Gly Thr Gln Val Thr
               100                 105                 110

Val Ser Ser Glu Pro Lys Thr Pro Lys Pro Gln
           115                 120

<210> SEQ ID NO 67
<211> LENGTH: 135
<212> TYPE: PRT
<213> ORGANISM: Artificial Sequence
<220> FEATURE:
<223> OTHER INFORMATION: The sequence has been designed and synthesized

<400> SEQUENCE: 67

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
           20                  25                  30

Gly Ile Gly Trp Phe Arg Gln Pro Pro Gly Lys Glu Arg Glu Ala Val
           35                  40                  45

Ser Tyr Ile Ser Ala Ser Ala Arg Thr Ile Leu Tyr Ala Asp Ser Val
50                  55                  60

Lys Gly Arg Phe Thr Ile Ser Arg Asp Asn Ala Lys Asn Ala Val Tyr
65              70                  75                      80

Leu Gln Met Asn Ser Leu Lys Arg Glu Asp Thr Ala Val Tyr Tyr Cys
                    85                  90                  95

Ala Arg Arg Phe Ser Ala Ser Val Asn Arg Trp Leu Ala Asp
               100                 105                 110

Asp Tyr Asp Val Trp Gly Arg Gly Thr Gln Val Ala Val Ser Ser Glu
           115                 120                 125

Pro Lys Thr Pro Lys Pro Gln
       130                 135

<210> SEQ ID NO 68
<211> LENGTH: 119
<212> TYPE: PRT
<213> ORGANISM: Artificial Sequence
<220> FEATURE:
<223> OTHER INFORMATION: The sequence has been designed and synthesized

<400> SEQUENCE: 68

Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
           20                  25                  30

Thr Val Thr Trp Ser Arg Gln Ala Pro Gly Lys Ser Leu Gln Trp Val
           35                  40                  45

Ala Ser Met Thr Lys Thr Asn Asn Glu Ile Tyr Ser Asp Ser Val Lys
50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser Glu
            100                 105                 110

Pro Lys Thr Pro Lys Pro Gln
        115

<210> SEQ ID NO 69
<211> LENGTH: 124
<212> TYPE: PRT
<213> ORGANISM: Artificial Sequence
<220> FEATURE:
<223> OTHER INFORMATION: The sequence has been designed and synthesized

<400> SEQUENCE: 69

Gln Val Gln Leu Val Glu Ser Gly Gly Gly Leu Val Glu Ala Gly Gly
1               5                   10                  15

Ser Leu Arg Leu Ser Cys Val Val Thr Gly Ser Ser Phe Ser Thr Ser
            20                  25                  30

Thr Met Ala Trp Tyr Arg Gln Pro Pro Gly Lys Gln Arg Glu Trp Val
        35                  40                  45

Ala Ser Phe Thr Ser Gly Gly Ala Ile Lys Tyr Thr Asp Ser Val Lys
    50                  55                  60

Gly Arg Phe Thr Met Ser Arg Asp Asn Ala Lys Lys Met Thr Tyr Leu
65                  70                  75                  80

Gln Met Glu Asn Leu Lys Pro Glu Asp Thr Ala Val Tyr Tyr Cys Ala
                85                  90                  95

Leu His Asn Ala Val Ser Ser Trp Gly Arg Gly Thr Gln Val
            100                 105                 110

Thr Val Ser Ser Glu Pro Lys Thr Pro Lys Pro Gln
        115                 120

<210> SEQ ID NO 70
<211> LENGTH: 123
<212> TYPE: PRT
<213> ORGANISM: Artificial Sequence
<220> FEATURE:
<223> OTHER INFORMATION: The sequence has been designed and synthesized

<400> SEQUENCE: 70

Val Gln Leu Val Glu Ser Gly Gly Gly Leu Val Gln Ala Gly Gly Ser
1               5                   10                  15

Leu Arg Leu Ser Cys Ala Ala Ser Gly Leu Met Phe Gly Ala Met Thr
            20                  25                  30

Met Gly Trp Tyr Arg Gln Ala Pro Gly Lys Glu Arg Glu Met Val Ala
        35                  40                  45

Tyr Ile Thr Ala Gly Gly Thr Glu Ser Tyr Ser Glu Ser Val Lys Gly
    50                  55                  60

Arg Phe Thr Ile Ser Arg Ile Asn Ala Asn Asn Met Val Tyr Leu Gln
65                  70                  75                  80

Met Thr Asn Leu Lys Val Glu Asp Thr Ala Val Tyr Tyr Cys Asn Ala
                85                  90                  95

His Asn Phe Trp Arg Thr Ser Arg Asn Trp Gly Gln Gly Thr Gln Val
            100                 105                 110

Thr Val Ser Ser Glu Pro Lys Thr Pro Lys Pro

<210> SEQ ID NO 71
<211> LENGTH: 131
<212> TYPE: PRT
<213> ORGANISM: Artificial Sequence
<220> FEATURE:
<223> OTHER INFORMATION: The sequence has been designed and synthesized

<400> SEQUENCE: 71

Val Gln Leu Val Glu Ser Gly Gly Leu Val Gln Ala Gly Asp Ser
1               5                   10                  15

Leu Thr Leu Ser Cys Ala Ala Ser Glu Ser Thr Phe Asn Thr Phe Ser
                20                  25                  30

Met Ala Trp Phe Arg Gln Ala Pro Gly Lys Glu Arg Glu Tyr Val Ala
            35                  40                  45

Ala Phe Ser Arg Ser Gly Gly Thr Thr Asn Tyr Ala Asp Ser Val Lys
        50                  55                  60

Gly Arg Ala Thr Ile Ser Thr Asp Asn Ala Lys Asn Thr Val Tyr Leu
65                  70                  75                  80

His Met Asn Ser Leu Lys Pro Glu Asp Thr Ala Val Tyr Phe Cys Ala
                85                  90                  95

Ala Asp Arg Pro Ala Gly Arg Ala Tyr Phe Gln Ser Arg Ser Tyr Asn
            100                 105                 110

Tyr Trp Gly Gln Gly Thr Gln Val Thr Val Ser Ser Ala His His Ser
        115                 120                 125

Glu Asp Pro
    130

<210> SEQ ID NO 72
<211> LENGTH: 125
<212> TYPE: PRT
<213> ORGANISM: Artificial Sequence
<220> FEATURE:
<223> OTHER INFORMATION: The sequence has been designed and synthesized

<400> SEQUENCE: 72

Val Gln Leu Val Glu Ser Gly Gly Gly Ser Val Gln Ile Gly Gly Ser
1               5                   10                  15

Leu Arg Leu Ser Cys Val Ala Ser Gly Phe Thr Phe Ser Lys Asn Ile
                20                  25                  30

Met Ser Trp Ala Arg Gln Ala Pro Gly Lys Gly Leu Glu Trp Val Ser
            35                  40                  45

Thr Ile Ser Ile Gly Gly Ala Ala Thr Ser Tyr Ala Asp Ser Val Lys
        50                  55                  60

Gly Arg Phe Thr Ile Ser Arg Asp Asn Ala Asn Asp Thr Leu Tyr Leu
65                  70                  75                  80

Gln Met Asn Asn Leu Lys Pro Glu Asp Thr Ala Val Tyr Tyr Cys Ser
                85                  90                  95

Arg Gly Pro Arg Thr Tyr Ile Asn Thr Ala Ser Arg Gly Gln Gly Thr
            100                 105                 110

Gln Val Thr Val Ser Ser Glu Pro Lys Thr Pro Lys Pro
        115                 120                 125

<210> SEQ ID NO 73
<211> LENGTH: 121
<212> TYPE: PRT
<213> ORGANISM: Artificial Sequence
<220> FEATURE:

```
<223> OTHER INFORMATION: The sequence has been designed and synthesized

<400> SEQUENCE: 73

Val Gln Leu Val Glu Ser Gly Gly Gly Leu Val Gln Ala Gly Gly Ser
1               5                   10                  15

Leu Arg Leu Ser Cys Val Gly Ser Gly Arg Asn Pro Gly Ile Asn Ala
            20                  25                  30

Met Gly Trp Tyr Arg Gln Ala Pro Gly Ser Gln Arg Glu Leu Val Ala
        35                  40                  45

Val Trp Gln Thr Gly Gly Ser Thr Asn Tyr Ala Asp Ser Val Lys Gly
    50                  55                  60

Arg Phe Thr Ile Ser Arg Asp Asn Leu Lys Asn Thr Val Tyr Leu Gln
65                  70                  75                  80

Met Asn Ser Leu Lys Pro Glu Asp Thr Ala Val Tyr Tyr Cys Tyr Leu
                85                  90                  95

Lys Lys Trp Arg Asp Glu Tyr Trp Gly Gln Gly Thr Gln Val Thr Val
                100                 105                 110

Ser Ser Ala His His Ser Glu Asp Pro
            115                 120

<210> SEQ ID NO 74
<211> LENGTH: 124
<212> TYPE: PRT
<213> ORGANISM: Artificial Sequence
<220> FEATURE:
<223> OTHER INFORMATION: The sequence has been designed and synthesized

<400> SEQUENCE: 74

Val Gln Leu Val Glu Ser Gly Gly Gly Leu Val Gln Ala Gly Glu Ser
1               5                   10                  15

Leu Arg Leu Ser Cys Val Val Ser Glu Ser Ile Phe Arg Ile Asn Thr
            20                  25                  30

Met Gly Trp Tyr Arg Gln Thr Pro Gly Lys Gln Arg Glu Val Val Ala
        35                  40                  45

Arg Ile Thr Leu Arg Asn Ser Thr Thr Tyr Ala Asp Ser Val Lys Gly
    50                  55                  60

Arg Phe Thr Ile Ser Arg Asp Asp Ala Lys Asn Thr Leu Tyr Leu Lys
65                  70                  75                  80

Met Asp Ser Leu Lys Pro Glu Asp Thr Ala Val Tyr Tyr Cys His Arg
                85                  90                  95

Tyr Pro Leu Ile Phe Arg Asn Ser Pro Tyr Trp Gly Gln Gly Thr Gln
                100                 105                 110

Val Thr Val Ser Ser Glu Pro Lys Thr Pro Lys Pro
            115                 120

<210> SEQ ID NO 75
<211> LENGTH: 122
<212> TYPE: PRT
<213> ORGANISM: Artificial Sequence
<220> FEATURE:
<223> OTHER INFORMATION: The sequence has been designed and synthesized

<400> SEQUENCE: 75

Val Gln Leu Val Glu Ser Gly Gly Gly Leu Val Gln Ala Gly Glu Ser
1               5                   10                  15

Leu Arg Leu Ser Cys Val Val Ser Glu Ser Ile Phe Arg Ile Asn Thr
            20                  25                  30

Met Gly Trp Tyr Arg Gln Thr Pro Gly Lys Gln Arg Glu Val Val Ala
```

```
            35                  40                  45
Arg Ile Thr Leu Arg Asn Ser Thr Thr Tyr Ala Asp Ser Val Lys Gly
        50                  55                  60

Arg Phe Thr Ile Ser Arg Asp Asp Ala Lys Asn Thr Leu Tyr Leu Lys
65                  70                  75                  80

Met Asp Ser Leu Lys Pro Glu Asp Thr Ala Val Tyr Tyr Cys His Arg
                85                  90                  95

Tyr Pro Leu Ile Phe Arg Asn Ser Pro Tyr Trp Gly Gln Gly Thr Gln
            100                 105                 110

Val Thr Val Ser Ser Glu Pro Lys Thr Pro
        115                 120

<210> SEQ ID NO 76
<211> LENGTH: 129
<212> TYPE: PRT
<213> ORGANISM: Artificial Sequence
<220> FEATURE:
<223> OTHER INFORMATION: The sequence has been designed and synthesized

<400> SEQUENCE: 76

Val Gln Leu Val Glu Ser Gly Gly Gly Leu Val Gln Ala Gly Gly Ser
1               5                   10                  15

Leu Arg Leu Ser Cys Ala Ala Pro Gly Leu Thr Phe Thr Ser Tyr Arg
            20                  25                  30

Met Gly Trp Phe Arg Gln Ala Pro Gly Lys Glu Arg Glu Tyr Val Ala
        35                  40                  45

Ala Ile Thr Gly Ala Gly Ala Thr Asn Tyr Ala Asp Ser Ala Lys Gly
        50                  55                  60

Arg Phe Thr Ile Ser Lys Asn Asn Thr Ala Ser Thr Val His Leu Gln
65                  70                  75                  80

Met Asn Ser Leu Lys Pro Glu Asp Thr Ala Val Tyr Tyr Cys Ala Ala
                85                  90                  95

Ser Asn Arg Ala Gly Gly Tyr Trp Arg Ala Ser Gln Tyr Asp Tyr Trp
            100                 105                 110

Gly Gln Gly Thr Gln Val Thr Val Ser Ser Ala His His Ser Glu Asp
        115                 120                 125

Pro

<210> SEQ ID NO 77
<211> LENGTH: 129
<212> TYPE: PRT
<213> ORGANISM: Artificial Sequence
<220> FEATURE:
<223> OTHER INFORMATION: The sequence has been designed and synthesized

<400> SEQUENCE: 77

Gln Val Gln Leu Val Glu Thr Gly Gly Gly Leu Ala Gln Ala Gly Asp
1               5                   10                  15

Ser Leu Arg Leu Ser Cys Val Glu Pro Gly Arg Thr Leu Asp Met Tyr
            20                  25                  30

Ala Met Gly Trp Ile Arg Gln Ala Pro Gly Glu Glu Arg Glu Phe Val
        35                  40                  45

Ala Ser Ile Ser Gly Val Gly Gly Ser Pro Arg Tyr Ala Asp Ser Val
        50                  55                  60

Lys Gly Arg Phe Thr Ile Ser Lys Asp Asn Thr Lys Ser Thr Ile Trp
65                  70                  75                  80

Leu Gln Met Asn Ser Leu Lys Pro Glu Asp Thr Ala Val Tyr Tyr Cys
```

```
                    85                  90                  95
Ala Ala Gly Gly Asp Ile Tyr Tyr Gly Gly Ser Pro Gln Trp Arg Gly
                100                 105                 110

Gln Gly Thr Arg Val Thr Val Ser Ser Glu Pro Lys Thr Pro Lys Pro
        115                 120                 125

Gln

<210> SEQ ID NO 78
<211> LENGTH: 132
<212> TYPE: PRT
<213> ORGANISM: Artificial Sequence
<220> FEATURE:
<223> OTHER INFORMATION: The sequence has been designed and synthesized

<400> SEQUENCE: 78

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Asn Gly Asp Tyr
            20                  25                  30

Ala Met Gly Trp Phe Arg Gln Ala Pro Gly Glu Glu Arg Glu Phe Val
        35                  40                  45

Ala Val Asn Ser Trp Ile Gly Gly Ser Thr Tyr Tyr Thr Asp Ser Val
    50                  55                  60

Lys Gly Arg Phe Thr Leu Ser Arg Asp Asn Ala Lys Asn Thr Leu Ser
65                  70                  75                  80

Leu Gln Met Asn Ser Leu Lys Pro Glu Asp Thr Ala Val Tyr Tyr Cys
                85                  90                  95

Ala Ala Gly His Tyr Thr Asp Phe Pro Thr Tyr Phe Lys Glu Tyr Asp
                100                 105                 110

Tyr Trp Gly Gln Gly Thr Gln Val Thr Val Ser Ser Glu Pro Lys Thr
            115                 120                 125

Pro Lys Pro Gln
        130

<210> SEQ ID NO 79
<211> LENGTH: 132
<212> TYPE: PRT
<213> ORGANISM: Artificial Sequence
<220> FEATURE:
<223> OTHER INFORMATION: The sequence has been designed and synthesized

<400> SEQUENCE: 79

Gln Val Gln Leu Val Glu Thr Gly Gly Gly Leu Val Gln Ala Gly Gly Ser
1               5                   10                  15

Leu Arg Leu Ser Cys Ala Ala Ser Gly Val Pro Phe Ser Asp Tyr Thr
            20                  25                  30

Met Ala Trp Phe Arg Gln Ala Pro Gly Lys Glu Arg Glu Val Val Ala
        35                  40                  45

Arg Ile Thr Trp Arg Gly Gly Pro Tyr Tyr Gly Asn Ser Gly Asn
    50                  55                  60

Gly Arg Phe Ala Ile Ser Arg Asp Ile Ala Lys Ser Met Val Tyr Leu
65                  70                  75                  80

His Met Asp Ser Leu Lys Pro Glu Asp Thr Ala Val Tyr Tyr Cys Ala
                85                  90                  95

Ala Ser Arg Leu Arg Pro Ala Leu Ala Ser Met Ala Ser Asp Tyr Asp
            100                 105                 110

Tyr Trp Gly Gln Gly Thr Gln Val Ser Val Ser Ser Glu Pro Lys Thr
```

Pro Lys Pro Gln
    130

<210> SEQ ID NO 80
<211> LENGTH: 124
<212> TYPE: PRT
<213> ORGANISM: Artificial Sequence
<220> FEATURE:
<223> OTHER INFORMATION: The sequence has been designed and synthesized

<400> SEQUENCE: 80

Gln Val Gln Leu Val Glu Ser Gly Gly Gly Leu Val Gln Pro Gly Glu
1               5                   10                  15

Ser Leu Arg Leu Ser Cys Val Ala Ser Ala Ser Thr Phe Ser Thr Ser
            20                  25                  30

Leu Met Gly Trp Val Arg Gln Ala Pro Gly Lys Gly Leu Glu Ser Val
        35                  40                  45

Ala Glu Val Arg Thr Thr Gly Thr Phe Tyr Ala Lys Ser Val Ala
    50                  55                  60

Gly Arg Phe Thr Ile Ser Arg Asp Asn Ala Lys Asn Thr Leu Tyr Leu
65                  70                  75                  80

Gln Met Asn Ser Leu Lys Ala Glu Asp Thr Gly Val Tyr Tyr Cys Thr
                85                  90                  95

Ala Gly Ala Gly Pro Ile Ala Thr Arg Tyr Arg Gly Gln Gly Thr Gln
            100                 105                 110

Val Thr Val Ser Ser Ala His His Ser Glu Asp Pro
        115                 120

<210> SEQ ID NO 81
<211> LENGTH: 137
<212> TYPE: PRT
<213> ORGANISM: Artificial Sequence
<220> FEATURE:
<223> OTHER INFORMATION: The sequence has been designed and synthesized

<400> SEQUENCE: 81

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Leu Ala Asp Tyr
            20                  25                  30

Val Thr Val Trp Phe Arg Gln Ala Pro Gly Lys Ser Arg Glu Gly Val
        35                  40                  45

Ser Cys Ile Ser Ser Ser Arg Gly Thr Pro Asn Tyr Ala Asp Ser Val
    50                  55                  60

Lys Gly Arg Ala Thr Val Ser Arg Asn Ala Asn Asn Thr Val Tyr
65                  70                  75                  80

Leu Gln Met Asn Gly Leu Lys Pro Asp Asp Thr Ala Ile Tyr Tyr Cys
                85                  90                  95

Ala Ala Ile Arg Pro Ala Arg Leu Arg Ala Tyr Arg Glu Cys Leu Ser
            100                 105                 110

Ser Gln Ala Glu Tyr Asp Tyr Trp Gly Gln Gly Thr Gln Val Thr Val
        115                 120                 125

Ser Ser Ala His His Ser Glu Asp Pro
    130                 135

<210> SEQ ID NO 82
<211> LENGTH: 134

```
<212> TYPE: PRT
<213> ORGANISM: Artificial Sequence
<220> FEATURE:
<223> OTHER INFORMATION: The sequence has been designed and synthesized

<400> SEQUENCE: 82

Gln Val Gln Leu Val Glu Ser Gly Gly Gly Leu Val Gln Pro Gly Gly
1               5                   10                  15

Ser Leu Gly Leu Ser Cys Ala Met Ser Gly Thr Thr Gln Asp Tyr Ser
                20                  25                  30

Ala Val Gly Trp Phe Arg Gln Ala Pro Gly Lys Glu Arg Glu Gly Val
            35                  40                  45

Ser Cys Ile Ser Arg Ser Gly Arg Arg Thr Asn Tyr Ala Asp Ser Val
        50                  55                  60

Arg Gly Arg Phe Thr Ile Ser Arg Asp Asn Ala Lys Asp Thr Val Tyr
65                  70                  75                  80

Leu Gln Met Asn Ser Leu Lys Pro Asp Asp Thr Ala Val Tyr Tyr Cys
                85                  90                  95

Ala Ala Arg Lys Thr Asp Met Ser Asp Pro Tyr Tyr Val Gly Cys Asn
            100                 105                 110

Gly Met Asp Tyr Trp Gly Lys Gly Thr Leu Val Thr Val Ser Ser Ala
        115                 120                 125

His His Ser Glu Asp Pro
    130

<210> SEQ ID NO 83
<211> LENGTH: 130
<212> TYPE: PRT
<213> ORGANISM: Artificial Sequence
<220> FEATURE:
<223> OTHER INFORMATION: The sequence has been designed and synthesized

<400> SEQUENCE: 83

Gln Val Gln Leu Val Glu Ser Gly Gly Gly Leu Val Gln Pro Gly Gly
1               5                   10                  15

Ser Leu Thr Leu Ser Cys Thr Ala Ser Gly Phe Thr Leu Asn Ser Tyr
                20                  25                  30

Lys Ile Gly Trp Phe Arg Gln Ala Pro Gly Lys Glu Arg Glu Gly Val
            35                  40                  45

Ser Cys Ile Asn Ser Gly Gly Asn Leu Arg Ser Val Glu Gly Arg Phe
        50                  55                  60

Thr Ile Ser Arg Asp Asn Thr Lys Asn Thr Val Ser Leu His Met Asp
65                  70                  75                  80

Ser Leu Lys Pro Glu Asp Thr Gly Val Tyr His Cys Ala Ala Ala Pro
                85                  90                  95

Ala Leu Asn Val Phe Ser Pro Cys Val Leu Ala Pro Arg Tyr Asp Tyr
            100                 105                 110

Trp Gly Gln Gly Thr Gln Val Thr Val Ser Ser Ala His His Ser Glu
        115                 120                 125

Asp Pro
    130

<210> SEQ ID NO 84
<211> LENGTH: 134
<212> TYPE: PRT
<213> ORGANISM: Artificial Sequence
<220> FEATURE:
<223> OTHER INFORMATION: The sequence has been designed and synthesized
```

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ser Tyr
            20                  25                  30

His Ile Gly Trp Phe Arg His Pro Pro Gly Lys Glu Arg Glu Gly Thr
        35                  40                  45

Ser Cys Leu Ser Ser Arg Gly Asp Tyr Thr Lys Tyr Ala Glu Ala Val
    50                  55                  60

Lys Gly Arg Phe Thr Ile Ser Arg Asp Asn Thr Lys Ser Thr Val Tyr
65                  70                  75                  80

Leu Gln Met Asn Asn Leu Lys Pro Glu Asp Thr Gly Ile Tyr Val Cys
                85                  90                  95

Ala Ala Ile Arg Pro Val Leu Ser Asp Ser His Cys Thr Leu Ala Ala
            100                 105                 110

Arg Tyr Asn Tyr Trp Gly Gln Gly Thr Gln Val Thr Val Ser Ser Ala
        115                 120                 125

His His Ser Glu Asp Pro
    130

<210> SEQ ID NO 85
<211> LENGTH: 133
<212> TYPE: PRT
<213> ORGANISM: Artificial Sequence
<220> FEATURE:
<223> OTHER INFORMATION: The sequence has been designed and synthesized

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Leu Glu Phe Thr Leu Glu Asp Tyr
            20                  25                  30

Ala Ile Ala Trp Phe Arg Gln Ala Pro Gly Lys Glu Arg Glu Gly Val
        35                  40                  45

Ser Cys Ile Ser Lys Ser Gly Val Thr Lys Tyr Thr Asp Ser Val Lys
    50                  55                  60

Gly Arg Phe Thr Val Ala Arg Asp Asn Ala Lys Ser Thr Val Ile Leu
65                  70                  75                  80

Gln Met Asn Asn Leu Arg Pro Glu Asp Thr Ala Val Tyr Asn Cys Ala
                85                  90                  95

Ala Val Arg Pro Val Phe Val Asp Ser Val Cys Thr Leu Ala Thr Arg
            100                 105                 110

Tyr Thr Tyr Trp Gly Glu Gly Thr Gln Val Thr Val Ser Ser Ala His
        115                 120                 125

His Ser Glu Asp Pro
    130

<210> SEQ ID NO 86
<211> LENGTH: 134
<212> TYPE: PRT
<213> ORGANISM: Artificial Sequence
<220> FEATURE:
<223> OTHER INFORMATION: The sequence has been designed and synthesized

<400> SEQUENCE: 86

Gln Val Gln Leu Val Glu Thr Gly Gly Gly Leu Val Gln Pro Gly Gly
1               5                   10                  15

```
Ser Leu Lys Leu Ser Cys Ala Ala Ser Glu Phe Thr Leu Asp Asp Tyr
            20                  25                  30

His Ile Gly Trp Phe Arg Gln Ala Pro Gly Lys Glu Arg Glu Gly Val
        35                  40                  45

Ser Cys Ile Asn Lys Arg Gly Asp Tyr Ile Asn Tyr Lys Asp Ser Val
50                  55                  60

Lys Gly Arg Phe Thr Ile Ser Arg Asp Gly Ala Lys Ser Thr Val Phe
65                  70                  75                  80

Leu Gln Met Asn Asn Leu Arg Pro Glu Asp Thr Ala Val Tyr Tyr Cys
                85                  90                  95

Ala Ala Val Asn Pro Val Phe Pro Asp Ser Arg Cys Thr Leu Ala Thr
            100                 105                 110

Arg Tyr Thr His Trp Gly Gln Gly Thr Gln Val Thr Val Ser Ser Ala
        115                 120                 125

His His Ser Glu Asp Pro
        130

<210> SEQ ID NO 87
<211> LENGTH: 453
<212> TYPE: PRT
<213> ORGANISM: Artificial Sequence
<220> FEATURE:
<223> OTHER INFORMATION: The sequence has been designed and synthesized

<400> SEQUENCE: 87

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Asp Lys Ala Met
145                 150                 155                 160

Ala Ile Ser Asp Pro Asn Ser Gln Val Gln Leu Val Glu Ser Gly Gly
            165                 170                 175

Gly Leu Val Gln Pro Gly Gly Ser Leu Arg Leu Ser Cys Glu Ala Ser
        180                 185                 190

Gly Phe Thr Leu Asp Tyr Tyr Gly Ile Gly Trp Phe Arg Gln Pro Pro
        195                 200                 205

Gly Lys Glu Arg Glu Ala Val Ser Tyr Ile Ser Ala Ser Ala Arg Thr
        210                 215                 220

Ile Leu Tyr Ala Asp Ser Val Lys Gly Arg Phe Thr Ile Ser Arg Asp
225                 230                 235                 240
```

```
Asn Ala Lys Asn Ala Val Tyr Leu Gln Met Asn Ser Leu Lys Arg Glu
            245                 250                 255

Asp Thr Ala Val Tyr Tyr Cys Ala Arg Arg Phe Ser Ala Ser Ser
        260                 265                 270

Val Asn Arg Trp Leu Ala Asp Asp Tyr Asp Val Trp Gly Arg Gly Thr
        275                 280                 285

Gln Val Ala Val Ser Ser Glu Pro Lys Thr Pro Lys Pro Gln Thr Ser
        290                 295                 300

Ala Ile Ala Gly Gly Gly Ser Gly Gly Gly Ser Gly Gly Gly
305                 310                 315                 320

Gly Ser Leu Gln Ala Met Ala Ala Ala Ser Gln Val Gln Leu Val Glu
            325                 330                 335

Ser Gly Gly Gly Leu Val Gln Thr Gly Gly Ser Leu Arg Leu Ser Cys
            340                 345                 350

Ala Ser Ser Gly Ser Ile Ala Gly Phe Glu Thr Val Thr Trp Ser Arg
            355                 360                 365

Gln Ala Pro Gly Lys Ser Leu Gln Trp Val Ala Ser Met Thr Lys Thr
            370                 375                 380

Asn Asn Glu Ile Tyr Ser Asp Ser Val Lys Gly Arg Phe Ile Ile Ser
385                 390                 395                 400

Arg Asp Asn Ala Lys Asn Thr Val Tyr Leu Gln Met Asn Ser Leu Lys
                405                 410                 415

Pro Glu Asp Thr Gly Val Tyr Phe Cys Lys Gly Pro Glu Leu Arg Gly
            420                 425                 430

Gln Gly Ile Gln Val Thr Val Ser Ser Glu Pro Lys Thr Pro Lys Pro
            435                 440                 445

Gln Pro Ala Arg Arg
        450

<210> SEQ ID NO 88
<211> LENGTH: 6
<212> TYPE: PRT
<213> ORGANISM: Artificial Sequence
<220> FEATURE:
<223> OTHER INFORMATION: The sequence has been designed and synthesized

<400> SEQUENCE: 88

Gln Leu Gln Leu Val Glu
1               5

<210> SEQ ID NO 89
<211> LENGTH: 6
<212> TYPE: PRT
<213> ORGANISM: Artificial Sequence
<220> FEATURE:
<223> OTHER INFORMATION: The sequence has been designed and synthesized

<400> SEQUENCE: 89

Gln Val Gln Leu Val Glu
1               5

<210> SEQ ID NO 90
<211> LENGTH: 22
<212> TYPE: DNA
<213> ORGANISM: Artificial Sequence
<220> FEATURE:
<223> OTHER INFORMATION: The sequence has been designed and synthesized

<400> SEQUENCE: 90
tttgtttatc caccgaacta ag                                         22
```

<210> SEQ ID NO 91
<211> LENGTH: 22
<212> TYPE: DNA
<213> ORGANISM: Artificial Sequence
<220> FEATURE:
<223> OTHER INFORMATION: The sequence has been designed and synthesized

<400> SEQUENCE: 91
tcttcagaaa gggatccacc ag                                              22

<210> SEQ ID NO 92
<211> LENGTH: 22
<212> TYPE: DNA
<213> ORGANISM: Artificial Sequence
<220> FEATURE:
<223> OTHER INFORMATION: The sequence has been designed and synthesized

<400> SEQUENCE: 92
tggtggatcc ctttctgaag ac                                              22

<210> SEQ ID NO 93
<211> LENGTH: 18
<212> TYPE: DNA
<213> ORGANISM: Artificial Sequence
<220> FEATURE:
<223> OTHER INFORMATION: The sequence has been designed and synthesized

<400> SEQUENCE: 93
actgctccag tttcccac                                                   18

<210> SEQ ID NO 94
<211> LENGTH: 43
<212> TYPE: PRT
<213> ORGANISM: Artificial Sequence
<220> FEATURE:
<223> OTHER INFORMATION: The sequence has been designed and synthesized

<400> SEQUENCE: 94

Thr Ser Pro Ser Thr Val Arg Leu Glu Ser Arg Val Arg Glu Leu Glu
1               5                   10                  15

Asp Arg Leu Glu Glu Leu Arg Asp Glu Leu Glu Arg Ala Glu Arg Arg
            20                  25                  30

Ala Asn Glu Met Ser Ile Gln Leu Asp Glu Cys
        35                  40

<210> SEQ ID NO 95
<211> LENGTH: 505
<212> TYPE: PRT
<213> ORGANISM: Artificial Sequence
<220> FEATURE:
<223> OTHER INFORMATION: The sequence has been designed and synthesized

<400> SEQUENCE: 95

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu

-continued

```
                65                  70                  75                  80
Leu Phe Lys Asn Gly Glu Ala Ala Thr Lys Val Gly Ala Leu Ser
                    85                  90                  95

Lys Gly Gln Leu Lys Glu Phe Leu Asp Ala Asn Leu Ala Gly Ser Gly
                    100                 105                 110

Ser Gly His Met His His His His His His Ser Ser Gly Leu Val Pro
                    115                 120                 125

Arg Gly Ser Gly Met Lys Glu Thr Ala Ala Ala Lys Phe Glu Arg Gln
                130                 135                 140

His Met Asp Ser Pro Asp Leu Gly Thr Asp Asp Asp Lys Ala Met
145                 150                 155                 160

Ala Ile Ser Asp Pro Asn Ser Gln Val Gln Leu Val Glu Thr Gly Gly
                        165                 170                 175

Leu Val Gln Pro Gly Gly Ser Leu Arg Leu Ser Cys Ala Ala Ser Gly
                    180                 185                 190

Phe Thr Leu Asp Tyr Ser Ser Ile Gly Trp Phe Arg Gln Ala Pro Gly
                    195                 200                 205

Lys Glu Arg Glu Gly Val Ser Cys Ile Ser Ser Ser Gly Asp Ser Thr
                210                 215                 220

Lys Tyr Ala Asp Ser Val Lys Gly Arg Phe Thr Thr Ser Arg Asp Asn
225                 230                 235                 240

Ala Lys Asn Thr Val Tyr Leu Gln Met Asn Ser Leu Lys Pro Asp Asp
                    245                 250                 255

Thr Ala Val Tyr Tyr Cys Ala Ala Phe Arg Ala Thr Met Cys Gly Val
                    260                 265                 270

Phe Pro Leu Ser Pro Tyr Gly Lys Asp Asp Trp Gly Lys Gly Thr Leu
                275                 280                 285

Val Thr Val Ser Ser Glu Pro Lys Thr Pro Lys Pro Gln Pro Thr Ser
                290                 295                 300

Ala Ile Ala Gly Gly Gly Ser Gly Gly Gly Ser Gly Gly Gly
305                 310                 315                 320

Gly Ser Leu Gln Ala Met Ala Ala Ala Gln Leu Gln Leu Val Glu Thr
                    325                 330                 335

Gly Gly Gly Leu Val Gln Pro Gly Gly Ser Leu Arg Leu Ser Cys Ala
                340                 345                 350

Ala Ser Gly Phe Thr Phe Ser Asp Tyr Val Met Thr Trp Val Arg Gln
                355                 360                 365

Ala Pro Gly Lys Gly Pro Glu Trp Ile Ala Thr Ile Asn Thr Asp Gly
                370                 375                 380

Ser Thr Met Arg Asp Asp Ser Thr Lys Gly Arg Phe Thr Ile Ser Arg
385                 390                 395                 400

Asp Asn Ala Lys Asn Thr Leu Tyr Leu Gln Met Thr Ser Leu Lys Pro
                    405                 410                 415

Glu Asp Thr Ala Leu Tyr Tyr Cys Ala Arg Gly Arg Val Ile Ser Ala
                420                 425                 430

Ser Ala Ile Arg Gly Ala Val Arg Gly Pro Gly Thr Gln Val Thr Val
                435                 440                 445

Ser Ser Glu Pro Lys Thr Pro Lys Pro Gln Pro Ala Arg Gln Thr Ser
                450                 455                 460

Pro Ser Thr Val Arg Leu Glu Ser Arg Val Arg Glu Leu Glu Asp Arg
465                 470                 475                 480

Leu Glu Glu Leu Arg Asp Glu Leu Glu Arg Ala Glu Arg Arg Ala Asn
                    485                 490                 495
```

```
Glu Met Ser Ile Gln Leu Asp Glu Cys
            500                 505
```

<210> SEQ ID NO 96
<211> LENGTH: 133
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 96

```
Gln Val Gln Leu Val Glu Thr Gly Gly Gly Leu Val Gln Ala Gly Asp
1               5                   10                  15

Pro Leu Arg Leu Ser Cys Val Ala Ser Gly Arg Thr Val Ser Arg Tyr
            20                  25                  30

Asp Lys Ala Trp Phe Arg Gln Ala Pro Gly Lys Glu Arg Glu Phe Val
        35                  40                  45

Ala Gly Ile Ser Trp Asn Gly Asp Thr Lys Ile Tyr Ala Asp Ser Val
    50                  55                  60

Lys Gly Arg Phe Thr Ile Ser Arg Glu Asn Ser Arg Asp Thr Leu Asp
65                  70                  75                  80

Leu Gln Ile Asp Asn Leu Lys Pro Glu Asp Thr Ala Ala Tyr Tyr Cys
                85                  90                  95

Ala Val Gly Ile Ala Gly Val Gln Ser Met Ala Arg Met Leu Gly Val
            100                 105                 110

Arg Tyr Trp Gly Gln Gly Thr Gln Val Thr Val Ser Ser Glu Pro Lys
        115                 120                 125

Thr Pro Lys Pro Gln
    130
```

<210> SEQ ID NO 97
<211> LENGTH: 399
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 97

```
caggtgcagc tcgtggagac ggggggagga ttggtgcagg ctggggaccc tctgagactc      60
tcctgtgtag cctctggacg caccgtcagt cgctatgaca aggcctggtt ccgccaggct     120
ccagggaagg agcgtgagtt tgtagcagga attagctgga acggcgatac aaaaatttat     180
gcagactccg tgaagggccg attcaccatc tccagagaga actccaggga tacactggat     240
ctgcaaattg acaacctgaa acctgaggac acggccgcgt attactgtgc ggtcggaatt     300
gcgggtgttc agagtatggc gcgtatgctc ggagtgcgct actggggcca gggacccag      360 gtcaccgtct cctcagaacc caagacacca aaaccacaa                            399
```

<210> SEQ ID NO 98
<211> LENGTH: 138
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 98

```
Gln Val Gln Leu Val Glu Thr Gly Gly Gly Leu Val Gln Pro Gly Gly
```

```
                1               5                   10                  15
Ser Leu Arg Leu Ser Cys Ala Ala Ser Gly Phe Ser Leu Asp Pro Tyr
            20                  25                  30

Val Ile Gly Trp Phe Arg Gln Ala Pro Gly Lys Glu Arg Glu Gly Val
            35                  40                  45

Ser Cys Ile Thr Ser Arg Ala Ala Ser Arg Thr Ser Val Asp Ser Val
            50                  55                  60

Asn Glu Arg Phe Thr Ile Ser Arg Asp Asn Ala Lys Asn Thr Val Asp
 65                 70                  75                  80

Leu His Ile Asn Asn Leu Lys Pro Glu Asp Ser Gly Val Tyr Tyr Cys
                85                  90                  95

Ala Ala Val Pro Pro Ala Lys Leu Pro Leu Phe Ser Leu Cys Arg Ser
            100                 105                 110

Leu Pro Ala Lys Tyr Asp Tyr Trp Gly Gln Gly Thr Gln Val Thr Val
            115                 120                 125

Ser Ser Ala His His Ser Glu Asp Pro Ser
            130                 135
```

<210> SEQ ID NO 99
<211> LENGTH: 414
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 99

```
caggtgcagc tcgtggagac gggggggaggc ttggtgcagc ctggggggtc tctgagactc      60
tcctgtgcag cctctggttt cagtttggac ccttatgtga taggatggtt ccggcaggcc     120
ccagggaagg agcgtgaggg ggtctcatgt attacgagta gggctgctag tcgaacgtct     180
gtagactccg tgaacgagcg attcaccatc tccagagaca cgccaagaa tacggtcgat      240 ctacacatca ataacctgaa acctgaggac tcgggcgttt attactgtgc agcggtcccc     300
cctgccaaat taccactttt cagcctatgt cgctccctgc cagcaaagta tgactactgg     360
ggccagggga cccaggtcac cgtctcctca gcgcaccaca gcgaagaccc ctcg           414
```

<210> SEQ ID NO 100
<211> LENGTH: 125
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 100

```
Gln Val Gln Leu Val Glu Ser Gly Gly Gly Leu Val Gln Pro Gly Gly
 1               5                   10                  15

Ser Leu Arg Leu Ser Cys Ala Ala Ser Gly Ser Ser Phe Ser Arg Tyr
            20                  25                  30

Ala Met Arg Trp Tyr Arg Gln Ala Pro Gly Lys Gln Arg Glu Leu Val
            35                  40                  45

Ala Asn Ile Asn Ser Arg Gly Thr Ser Asn Tyr Ala Asp Ser Val Lys
            50                  55                  60

Gly Arg Phe Thr Ile Ser Arg Asp Asn Ala Lys Asn Thr Val Tyr Leu
 65                 70                  75                  80

Gln Met Asn Ser Leu Lys Pro Glu Asp Thr Ala Val Tyr Tyr Cys Asn
                85                  90                  95
```

```
Ala Glu Trp Leu Gly Arg Ser Glu Pro Ser Trp Gly Gln Gly Thr Gln
            100                 105                 110

Val Thr Val Ser Ser Glu Pro Lys Thr Pro Lys Pro Gln
        115                 120                 125
```

<210> SEQ ID NO 101
<211> LENGTH: 375
<212> TYPE: DNA
<213> ORGANISM: Artificial Sequence
<220> FEATURE:
<223> OTHER INFORMATION: The sequence has been designed and synthesized. The antibody is a camelid (VHH)

<400> SEQUENCE: 101

```
caggtgcagc tcgtggagtc ggggggaggc ttggtgcagc ctgggggtc tctgagactc      60 tcctgtgcag cctctggaag tagcttcagt agatatgcca tgcgctggta ccgccaggct    120
ccagggaagc agcgcgagtt ggtcgcaaac attaatagtc gtggtacctc aaactatgca    180
gactccgtga agggccgatt caccatctcc agagacaacg ccaagaacac ggtgtatctg    240
caaatgaaca gcctgaaacc tgaagacacg gccgtctatt attgtaatgc agagtggttg    300
ggacgatcgg agccttcctg gggccagggg acccaggtca ccgtctcctc ggaacccaag    360
acaccaaaac cacaa                                                     375
```

<210> SEQ ID NO 102
<211> LENGTH: 126
<212> TYPE: PRT
<213> ORGANISM: Artificial Sequence
<220> FEATURE:
<223> OTHER INFORMATION: The sequence has been designed and synthesized. The antibody is a camelid (VHH)

<400> SEQUENCE: 102

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Leu Tyr
            20                  25                  30

Thr Met Arg Trp His Arg Gln Ala Pro Gly Lys Glu Arg Glu Leu Val
        35                  40                  45

Ala Thr Ile Thr Ser Ala Thr Gly Ile Thr Asn Tyr Ala Asp Ser Val
    50                  55                  60

Lys Gly Arg Phe Ile Ile Ser Arg Asp Asp Ala Lys Lys Thr Gly Tyr
65                  70                  75                  80

Leu Gln Met Asn Ser Leu Lys Pro Glu Asp Thr Ala Val Tyr Tyr Cys
                85                  90                  95

Asn Ala Val Arg Thr Thr Val Ser Arg Asp Tyr Trp Gly Gln Gly Thr
            100                 105                 110

Gln Val Thr Val Ser Ser Glu Pro Lys Thr Pro Lys Pro Gln
        115                 120                 125
```

<210> SEQ ID NO 103
<211> LENGTH: 378
<212> TYPE: DNA
<213> ORGANISM: Artificial Sequence
<220> FEATURE:
<223> OTHER INFORMATION: The sequence has been designed and synthesized. The antibody is a camelid (VHH)

<400> SEQUENCE: 103

```
caggtgcagc tcgtggagtc aggaggaggc ttggtgcagc ctgggggtc tctgagactc      60
```

```
tcctgtgcag cctctggatt cattttcagt ctttatacca tgaggtggca ccgccaggct    120
ccagggaagg agcgcgagtt ggtcgcgact attactagtg ctactggtat tacaaactat    180
gcagactccg tgaagggccg attcatcatc tccagagacg atgccaagaa gacggggtat    240
ctgcaaatga acagcctgaa acctgaggac acggccgtgt attactgtaa tgcagtccgc    300
actaccgtgt cacgagacta ctggggccag ggacccaggg tcaccgtctc ctcagaaccc    360
aagacaccaa aaccacaa                                                   378
```

<210> SEQ ID NO 104
<211> LENGTH: 125
<212> TYPE: PRT
<213> ORGANISM: Artificial Sequence
<220> FEATURE:
<223> OTHER INFORMATION: The sequence has been designed and synthesized. The antibody is a camelid (VHH)

<400> SEQUENCE: 104

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Ile Ile Phe Ser Ile Tyr
             20                  25                  30

Thr Met Gly Trp Tyr Arg Gln Ala Pro Gly Lys Gln Arg Glu Leu Val
         35                  40                  45

Ala Ala Ile Pro Ser Gly Pro Ser Ala Asn Ala Thr Asp Ser Val Gly
     50                  55                  60

Gly Arg Phe Thr Ile Thr Arg Asp Asn Ala Glu Asn Thr Val Tyr Leu
 65                  70                  75                  80

Gln Met Asn Asp Leu Lys Pro Glu Asp Thr Ala Val Tyr Tyr Cys Asn
                 85                  90                  95

Ala Arg Arg Gly Pro Gly Ile Lys Asn Tyr Trp Gly Gln Gly Thr Gln
            100                 105                 110

Val Thr Val Ser Ser Glu Pro Lys Thr Pro Lys Pro Gln
        115                 120                 125
```

<210> SEQ ID NO 105
<211> LENGTH: 375
<212> TYPE: DNA
<213> ORGANISM: Artificial Sequence
<220> FEATURE:
<223> OTHER INFORMATION: The sequence has been designed and synthesized. The antibody is a camelid (VHH)

<400> SEQUENCE: 105

```
caggtgcagc tcgtggagtc tgggggaggc ttggtgcagc ctggggggtc tctgagactc     60
tcctgtgcag cctctggaat catcttcagt atctatacca tgggctggta ccgccaggct    120
ccagggaagc agcgcgaatt ggtcgcagct ataccuagtg gtcctagcgc aaacgctaca    180
gactccgtgg gggccgatt caccatcacc agagacaacg ccgagaacac ggtgtatctg    240
caaatgaacg acctgaaacc tgaggacacg gccgtctatt actgtaatgc tcggcgggt    300 ccgggtatca aaaactactg gggccagggg acccaggtca ccgtctcctc agaacccaag    360
acaccaaaac cacaa                                                     375
```

<210> SEQ ID NO 106
<211> LENGTH: 130
<212> TYPE: PRT
<213> ORGANISM: Artificial Sequence
<220> FEATURE:

<223> OTHER INFORMATION: The sequence has been designed and synthesized.
The antibody is a camelid (VHH)

<400> SEQUENCE: 106

```
Gln Val Gln Leu Val Glu Ser Gly Gly Gly Leu Val Gln Pro Gly Gly
 1               5                  10                  15

Ser Leu Ser Val Ser Cys Ala Ala Ser Gly Ser Ile Ala Arg Pro Gly
             20                  25                  30

Ala Met Ala Trp Tyr Arg Gln Ala Pro Gly Lys Glu Arg Glu Leu Val
         35                  40                  45

Ala Ser Ile Thr Pro Gly Gly Leu Thr Asn Tyr Ala Asp Ser Val Thr
     50                  55                  60

Gly Arg Phe Thr Ile Ser Arg Asp Asn Ala Lys Arg Thr Val Tyr Leu
 65                  70                  75                  80

Gln Met Asn Ser Leu Gln Pro Glu Asp Thr Ala Val Tyr Tyr Cys His
                 85                  90                  95

Ala Arg Ile Ile Pro Leu Gly Leu Gly Ser Glu Tyr Arg Asp His Trp
            100                 105                 110

Gly Gln Gly Thr Gln Val Thr Val Ser Ser Ala His His Ser Glu Asp
        115                 120                 125

Pro Ser
    130
```

<210> SEQ ID NO 107
<211> LENGTH: 390
<212> TYPE: DNA
<213> ORGANISM: Artificial Sequence
<220> FEATURE:
<223> OTHER INFORMATION: The sequence has been designed and synthesized.
The antibody is a camelid (VHH)

<400> SEQUENCE: 107

```
caggtgcagc tcgtggagtc cggggggcggc ttggtgcagc cggggggtc tctgagtgtc      60
tcctgtgcag cctctggaag catcgcaaga ccaggtgcca tggcctggta ccgccaggct     120
ccagggaagg agcgcgagtt ggtcgcgtct attacgcctg gtggtcttac aaactatgcg     180
gactccgtga cgggccgatt caccatttcc agagacaacg ccaagaggac ggtgtatctg     240
cagatgaaca gcctccaacc cgaggacacg gccgtctatt actgtcatgc acgaataatt     300
cccctaggac ttgggtccga atacagggac cactggggcc aggggactca ggtcaccgtc     360
tcctcagcgc accacagcga agacccctcg                                     390
```

<210> SEQ ID NO 108
<211> LENGTH: 123
<212> TYPE: PRT
<213> ORGANISM: Artificial Sequence
<220> FEATURE:
<223> OTHER INFORMATION: The sequence has been designed and synthesized.
The antibody is a camelid (VHH)

<400> SEQUENCE: 108

```
Gln Val Gln Leu Val Glu Thr Gly Gly Gly Leu Val Gln Pro Gly Gly
 1               5                  10                  15

Ser Leu Gly Leu Ser Cys Val Val Ala Ser Gly Arg Ser Ile Asn Asn
             20                  25                  30

Tyr Gly Met Gly Trp Tyr Arg Gln Ala Pro Gly Lys Gln Arg Glu Leu
         35                  40                  45

Val Ala Gln Ile Ser Ser Gly Gly Thr Thr Asn Tyr Ala Gly Ser Val
     50                  55                  60
```

```
Glu Gly Arg Phe Thr Ile Ser Arg Asp Asn Val Lys Met Val Tyr
65                  70                  75                  80

Leu Gln Met Asn Ser Leu Lys Pro Glu Asp Thr Ala Val Tyr Tyr Cys
                85                  90                  95

Asn Ser Leu Leu Arg Thr Phe Ser Trp Gly Gln Gly Thr Gln Val Thr
            100                 105                 110

Val Ser Ser Ala His His Ser Glu Asp Pro Ser
        115                 120
```

<210> SEQ ID NO 109
<211> LENGTH: 369
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 109

```
caggtgcagc tcgtggagac ggggggaggc ttggtgcagc ctggggggtc tctgggactc      60
tcctgtgtag tcgcctctgg aagaagcatc aataattatg catgggctg gtaccgccag     120 gctccaggga agcagcgcga gttggtcgcg caaattagta gtggtggtac cacaaattat     180
gcaggctccg tagagggccg attcaccatc tccagagaca acgtcaagaa aatggtgtat     240
cttcaaatga acagcctgaa acctgaggac acggccgtct attactgtaa ttcactgctc     300 cgaactttt cctggggcca ggggacccag gtcaccgtct cctcggcgca ccacagcgaa     360
gaccctctcg                                                            369
```

<210> SEQ ID NO 110
<211> LENGTH: 133
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 110

```
Gln Val Gln Leu Val Glu Thr Gly Gly Leu Val Gln Pro Gly Gly Ser
1               5                   10                  15

Leu Arg Leu Ser Cys Ala Ala Ser Gly Leu Thr Phe Ser Ser Thr Ala
            20                  25                  30

Met Ala Trp Phe Arg Gln Ala Pro Gly Lys Glu Arg Glu Phe Val Ala
        35                  40                  45

Arg Ile Ser Gly Ala Gly Ile Thr Ile Tyr Tyr Ser Asp Ser Val Lys
50                  55                  60

Asp Arg Phe Thr Ile Ser Arg Asn Asn Val Glu Asn Thr Val Tyr Leu
65                  70                  75                  80

Gln Met Asn Ser Leu Lys Thr Glu Asp Thr Ala Val Tyr Tyr Cys Ala
                85                  90                  95

Ala Arg Arg Asn Thr Tyr Thr Ser Asp Tyr Asn Ile Pro Ala Arg Tyr
            100                 105                 110

Pro Tyr Trp Gly Gln Gly Thr Gln Val Thr Val Ser Ser Glu Pro Lys
        115                 120                 125

Thr Pro Lys Pro Gln
        130
```

<210> SEQ ID NO 111
<211> LENGTH: 399

<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 111

```
caggtgcagc tcgtggagac cgggggttg gtgcagcctg ggggctccct gcgactctcc      60
tgtgcagcct ccggactcac cttcagtagc actgccatgg cctggttccg ccaggctcca    120
gggaaggagc gtgagtttgt agcacgtatt agcggggctg gtattacgat ctactattcg    180
gactccgtga aggaccgatt caccatctcc agaaacaacg tcgagaacac ggtgtatttg    240
caaatgaaca gcctgaaaac tgaggacacg gccgtttact actgtgcagc aagacggaat    300
acttacacta gcgactataa catacccgcc cggtatccct actggggcca ggggacccag    360
gtcaccgtct cctcagaacc caagacacca aaaccacaa                           399
```

<210> SEQ ID NO 112
<211> LENGTH: 126
<212> TYPE: PRT
<213> ORGANISM: Artificial Sequence
<220> FEATURE:
<223> OTHER INFORMATION: The sequence has been designed and synthesized.
      The antibody is a
      camelid (VHH)

<400> SEQUENCE: 112

```
Gln Val Gln Leu Val Glu Thr Gly Gly Leu Val Gln Pro Gly Gly Ser
1               5                   10                  15
Leu Arg Leu Ser Cys Ala Ala Ser Arg Ser Thr Thr Ala Thr Ile Tyr
            20                  25                  30
Ser Met Asn Trp Tyr Arg Gln Ala Pro Gly Lys Gln Arg Glu Leu Val
        35                  40                  45
Ala Gly Met Thr Ser Asp Gly Gln Thr Asn Tyr Ala Thr Ser Val Lys
    50                  55                  60
Gly Arg Phe Thr Ile Ser Arg Asp Asn Ala Lys Asn Thr Val Tyr Leu
65                  70                  75                  80
Leu Met Asn Ser Leu Lys Leu Glu Asp Thr Ala Val Tyr Tyr Cys Tyr
                85                  90                  95
Val Lys Pro Trp Arg Leu Gln Gly Trp Asp Tyr Trp Gly Gln Gly Thr
            100                 105                 110
Gln Val Thr Val Ser Ser Glu Pro Lys Thr Pro Lys Pro Gln
        115                 120                 125
```

<210> SEQ ID NO 113
<211> LENGTH: 378
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 113

```
caggtgcagc tcgtggagac ggggggcttg gtgcagcctg ggggtctct gagactctcc     60
tgtgcagcct ctagaagcac gacggccaca atttatagta tgaactggta ccgccaggct   120
ccagggaagc agcgcgagtt ggtcgcgggt atgactagtg atggtcagac aaactatgca   180
acctccgtga aggccgatt caccatctcc agagacaacg ccaagaacac ggtatatttg    240
ctaatgaaca gcctgaaact tgaggacacg gccgtctatt attgttatgt aaaaccatgg   300
```

-continued

```
agactacaag gttgggacta ctggggccag gggacccagg tcaccgtctc ctcagaaccc      360
aagacaccaa aaccacaa                                                    378
```

<210> SEQ ID NO 114
<211> LENGTH: 122
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 114

```
Gln Val Gln Leu Val Glu Ser Gly Gly Gly Leu Val Gln Pro Gly Gly
1               5                   10                  15

Ser Leu Arg Leu Ser Cys Ala Ala Pro Glu Ser Ile Val Asn Ser Arg
            20                  25                  30

Thr Met Ala Trp Tyr Arg Gln Ala Pro Gly Lys Gln Arg Glu Arg Val
        35                  40                  45

Ala Thr Ile Thr Thr Ala Gly Ser Pro Asn Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Leu Leu Ser Thr Leu Pro Tyr Gly Gln Gly Thr Gln Val Thr Val
            100                 105                 110

Ser Ser Ala His His Ser Glu Asp Pro Ser
        115                 120
```

<210> SEQ ID NO 115
<211> LENGTH: 366
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 115

```
caggtgcagc tcgtggagtc gggcggcggc ttggtgcagc ctgggggtc tctgagactc       60 tcctgtgcag cccctgaaag catcgtcaat agcagaacca tggcctggta ccgccaggct     120
ccaggaaagc agcgcgaaag ggtcgccact attactactg ctggtagccc aaattatgca     180
gactctgtga aggccgatt cgccatctcc agagacaacg ccaagaacac ggtatatctg      240
caaatgaaca gcctgaaacc tgaggacacg gccgtctatt actgcaatac acttctcagc    300
acccttccct atggccaggg gacccaggtc accgtctcct cggcgcacca cagcgaagac    360
ccctcg                                                               366
```

<210> SEQ ID NO 116
<211> LENGTH: 123
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 116

```
Gln Val Gln Leu Val Glu Ser Gly Gly Gly Leu Val Gln Pro Gly Gly
1               5                   10                  15

Ser Leu Gly Leu Ser Cys Val Val Ala Ser Glu Arg Ser Ile Asn Asn
```

```
            20                  25                  30
Tyr Gly Met Gly Trp Tyr Arg Gln Ala Pro Gly Lys Gln Arg Glu Leu
        35                  40                  45

Val Ala Gln Ile Ser Ser Gly Gly Thr Thr Asn Tyr Ala Asp Ser Val
    50                  55                  60

Glu Gly Arg Phe Thr Ile Ser Arg Asp Asn Val Lys Lys Met Val His
65                  70                  75                  80

Leu Gln Val Asn Ser Leu Lys Pro Glu Asp Thr Ala Val Tyr Tyr Cys
                85                  90                  95

Asn Ser Leu Leu Arg Thr Phe Ser Trp Gly Gln Gly Thr Gln Val Thr
            100                 105                 110

Val Ser Ser Glu Pro Lys Thr Pro Lys Pro Gln
        115                 120
```

<210> SEQ ID NO 117
<211> LENGTH: 369
<212> TYPE: DNA
<213> ORGANISM: Artificial Sequence
<220> FEATURE:
<223> OTHER INFORMATION: The sequence has been designed and synthesized. The antibody is a camelid (VHH)

<400> SEQUENCE: 117

```
caggtgcagc tcgtggagtc gggcggaggc ttggtgcagc ctggggggtc tctgggactc      60
tcctgtgtag tcgcctctga aaagcatc aataattatg gcatgggctg gtaccgccag       120
gctccaggga agcagcgcga gttggtcgcg caaattagta gtggtggtac cacaaattat     180
gcagactccg tagagggccg attcaccatc tccagagaca acgtcaagaa aatggtgcat     240
cttcaagtga acagcctgaa acctgaggac acggccgtct attactgtaa ttcgctactc     300
cgaactttt cctggggcca ggggacccag gtcaccgtct cctcggaacc caagacacca     360
aaaccacaa                                                              369
```

<210> SEQ ID NO 118
<211> LENGTH: 126
<212> TYPE: PRT
<213> ORGANISM: Artificial Sequence
<220> FEATURE:
<223> OTHER INFORMATION: The sequence has been designed and synthesized. The antibody is a camelid (VHH)

<400> SEQUENCE: 118

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Tyr Arg Gln Ala Ala Gly Lys Glu Arg Asp Val Val
        35                  40                  45

Ala Thr Ile Thr Ala Asn Gly Val Pro Thr Gly Tyr Ala Asp Ser Val
    50                  55                  60

Met Gly Arg Phe Thr Ile Ser Arg Asp Asn Ala Lys Asn Thr Val Tyr
65                  70                  75                  80

Leu Glu Met Asn Ser Leu Asn Pro Glu Asp Thr Ala Val Tyr Tyr Cys
                85                  90                  95

Asn Ala Pro Arg Leu His Thr Ser Val Gly Tyr Trp Gly Gln Gly Thr
            100                 105                 110

Gln Val Thr Val Ser Ser Glu Pro Lys Thr Pro Lys Pro Gln
        115                 120                 125
```

<210> SEQ ID NO 119
<211> LENGTH: 378
<212> TYPE: DNA
<213> ORGANISM: Artificial Sequence
<220> FEATURE:
<223> OTHER INFORMATION: The sequence has been designed and synthesized.
The antibody is a camelid (VHH)

<400> SEQUENCE: 119

```
caggtgcagc tcgtggagac gggaggaggc ttggtgcagc ctgggggtc tctgagactc      60
tcctgtgcag cctctggatt caccttcagt agttatcgca tgagctggta ccggcaggct    120
gcagggaagg agcgcgacgt ggtcgcaaca attactgcta atggtgttcc cacaggctat    180
gcagactccg tgatgggccg attcaccatt tccagagaca tgccaagaa cacggtgtat     240
ctggaaatga acagcctgaa tcctgaggac acggccgtgt attactgtaa cgcgccccgt    300
ttgcatacat ctgtaggcta ctggggccag gggacccagg tcaccgtctc ctcagaaccc    360
aagacaccaa aaccacaa                                                  378
```

<210> SEQ ID NO 120
<211> LENGTH: 135
<212> TYPE: PRT
<213> ORGANISM: Artificial Sequence
<220> FEATURE:
<223> OTHER INFORMATION: The sequence has been designed and synthesized.
The antibody is a camelid (VHH)

<400> SEQUENCE: 120

```
Gln Val Gln Leu Val Glu Ser Gly Gly Gly Leu Val Gln Ala Gly Asn
1               5                   10                  15
Ser Leu Arg Leu Ser Cys Thr Ala Ser Gly Val Ile Phe Ser Ile Tyr
            20                  25                  30
Thr Met Gly Trp Phe Arg Gln Ala Pro Gly Lys Glu Arg Glu Phe Val
        35                  40                  45
Ala Ala Ile Gly Val Ala Asp Gly Thr Ala Leu Val Ala Asp Ser Val
    50                  55                  60
Thr Gly Arg Phe Thr Ile Ser Arg Asp Asn Ala Lys Asn Thr Val Tyr
65                  70                  75                  80
Leu His Met Asn Ser Leu Lys Pro Glu Asp Thr Ala Val Tyr Ser Cys
                85                  90                  95
Ala Ala Tyr Leu Ser Pro Arg Val Gln Ser Pro Tyr Ile Thr Asp Ser
            100                 105                 110
Arg Tyr Gln Leu Trp Gly Gln Gly Thr Gln Val Thr Val Ser Ser Glu
        115                 120                 125
Pro Lys Thr Pro Lys Pro Gln
    130                 135
```

<210> SEQ ID NO 121
<211> LENGTH: 405
<212> TYPE: DNA
<213> ORGANISM: Artificial Sequence
<220> FEATURE:
<223> OTHER INFORMATION: The sequence has been designed and synthesized.
The antibody is a camelid (VHH)

<400> SEQUENCE: 121

```
caggtgcagc tcgtggagtc gggaggagga ttggtgcagg ctgggaactc tctgagactc      60
tcctgtacgg cctctggtgt gatcttctct atctatacca tgggctggtt ccgccaggct    120
```

```
ccagggaagg agcgtgagtt tgtagcagcg atagggdtgg ctgatggtac cgcacttgtg    180
gcagactccg tgacgggccg attcaccatc tccagagaca acgccaagaa caccgtttat    240
ctgcatatga acagcctgaa gcctgaggac acggccgtct attcctgtgc agcgtatctt    300 agccccgtg tccaatcccc ctacataact gactcccggt atcaactctg gggccagggg    360
acccaggtca ccgtctcctc agaacccaag acaccaaaac cacaa                    405
```

<210> SEQ ID NO 122
<211> LENGTH: 119
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 122

Thr Gly Gly Gly Leu Val Gln Ala Gly Gly Ser Leu Arg Leu Ser Cys
1               5                   10                  15

Ala Ala Ser Gly Arg Tyr Ala Met Gly Trp Phe Arg Gln Ala Pro Gly
            20                  25                  30

Lys Glu Arg Glu Phe Val Ala Thr Ile Ser Arg Ser Gly Ala Ile Arg
        35                  40                  45

Glu Tyr Ala Asp Ser Val Lys Gly Arg Phe Thr Ile Ser Arg Asp Gly
    50                  55                  60

Ala Glu Asn Thr Val Tyr Leu Glu Met Asn Ser Leu Lys Pro Asp Asp
65                  70                  75                  80

Thr Ala Ile Tyr Val Cys Ala Glu Gly Arg Gly Ala Thr Phe Asn Pro
                85                  90                  95

Glu Tyr Ala Tyr Trp Gly Gln Gly Thr Gln Val Thr Val Ser Ser Ala
            100                 105                 110

His His Ser Glu Asp Pro Ser
        115

<210> SEQ ID NO 123
<211> LENGTH: 375
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 123

```
caggtgcagc tcgtggagac tgggggagga ttggtgcagg ctgggggctc tctgaggctc     60
tcctgtgcag cctctggacg ctatgccatg ggctggttcc gccaggctcc agggaaggag    120
cgtgaatttg tagcgactat tagccggagt ggtgctatca gagagtatgc agactccgtg    180
aagggccgat tcaccatctc cagagacggc gccgagaaca cggtgtatct ggaaatgaac    240
agcctgaaac ctgacgacac ggccatttat gtctgtgcag aaggacgagg ggcgacattc    300 aacccccgagt atgcttactg gggccagggg acccaggtca ccgtctcctc agcgcaccac    360
agcgaagacc cctcg                                                      375
```

<210> SEQ ID NO 124
<211> LENGTH: 127
<212> TYPE: PRT
<213> ORGANISM: Artificial Sequence
<220> FEATURE:
<223> OTHER INFORMATION: The sequence has been designed and synthesized.
      The antibody is a camelid (VHH)

-continued

<400> SEQUENCE: 124

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Val Pro Gly Lys Glu Arg Glu Gly Val
        35                  40                  45

Ala Cys Val Lys Asp Gly Ser Thr Tyr Tyr Ala Asp Ser Val Lys Gly
    50                  55                  60

Arg Phe Thr Ile Ser Arg Asp Asn Gly Ala Val Tyr Leu Gln Met Asn
65                  70                  75                  80

Ser Leu Lys Pro Glu Asp Thr Ala Val Tyr Tyr Cys Ala Ser Arg Pro
                85                  90                  95

Cys Phe Leu Gly Val Pro Leu Ile Asp Phe Gly Ser Trp Gly Gln Gly
            100                 105                 110

Thr Gln Val Thr Val Ser Ser Glu Pro Lys Thr Pro Lys Pro Gln
        115                 120                 125
```

<210> SEQ ID NO 125
<211> LENGTH: 381
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 125

```
caggtgcagc tcgtggagtc gggcggaggc ttggtgcagc ctgggggtc tctgagactc       60
tcctgtgcag cctctggatt cactttggat gattatgcca taggctggtt ccgccaggtc     120
ccagggaagg agcgtgaggg ggtcgcatgt gttaaagatg gtagtacata ctatgcagac     180
tccgtgaagg gccgattcac catctccaga gacaacggcg cggtgtatct gcaaatgaac     240
agcctgaaac tgaggacac agccgtttat tactgtgcat ccaggccctg cttttttggt     300
gtaccactta ttgactttgg ttcctggggc caggggaccc aggtcaccgt ctcctcggaa     360
cccaagacac caaaaccaca a                                              381
```

<210> SEQ ID NO 126
<211> LENGTH: 135
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 126

```
Gln Val Gln Leu Val Glu Ser Gly Gly Gly Leu Val Gln Ala Gly Gly
1               5                   10                  15

Ser Leu Arg Leu Ser Cys Ala Thr Ser Gly Gly Thr Phe Ser Asp Tyr
            20                  25                  30

Gly Met Gly Trp Phe Arg Gln Ala Pro Gly Lys Glu Arg Glu Phe Val
        35                  40                  45

Ala Ala Ile Arg Arg Asn Gly Asn Gly Gly Asn Gly Ile Glu Tyr Ala
    50                  55                  60

Asp Ser Val Lys Gly Arg Phe Thr Ile Ser Arg Asp Asn Ala Lys Asn
65                  70                  75                  80

Thr Val His Leu Gln Met Asn Ser Leu Thr Pro Glu Asp Thr Ala Val
                85                  90                  95
```

-continued

```
Tyr Tyr Cys Ala Ala Ser Ile Ser Gly Tyr Ala Tyr Asn Thr Ile Glu
            100                 105                 110

Arg Tyr Asn Tyr Trp Gly Gln Gly Thr Gln Val Thr Val Ser Ser Glu
        115                 120                 125

Pro Lys Thr Pro Lys Pro Gln
    130             135
```

<210> SEQ ID NO 127
<211> LENGTH: 406
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 127

```
caggtgcagc tcgtggagtc agggggagga ttggtgcagg ctgggggctc tctgagactc      60
tcctgcgcaa cctctggcgg caccttcagt gactatggaa tggctggtt ccgccaggct     120
ccagggaagg agcgtgagtt tgtagcagct attaggcgga atggtaatgg cggtaatggc    180
attgaatatg cagactccgt gaagggccga ttcaccatct ccagagacaa cgccaagaac    240
acggtgcatc tacaaatgaa cagcctgaca cctgaggaca cggccgttta ttactgtgca    300
gcgtcaatat cgggatacgc ttataacaca attgaaagat ataactactg gggccaggga    360
acccaggtca ccgtctcctc aggaacccaa gacaccaaaa ccacaa                   406
```

<210> SEQ ID NO 128
<211> LENGTH: 137
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 128

```
Gln Val Gln Leu Val Glu Ser Gly Gly Gly Leu Val Gln Ala Gly Gly
1               5                   10                  15

Ser Leu Ser Leu Ser Cys Ala Ala Ser Gly Gly Asp Phe Ser Arg Asn
            20                  25                  30

Ala Met Ala Trp Phe Arg Gln Ala Pro Gly Lys Glu Arg Glu Phe Val
        35                  40                  45

Ala Ser Ile Asn Trp Thr Gly Ser Gly Thr Tyr Tyr Leu Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Asn Leu Lys Pro Glu Asp Thr Ala Val Tyr Tyr Cys
                85                  90                  95

Ala Arg Ser Thr Val Phe Ala Glu Ile Thr Gly Leu Ala Gly Tyr Gln
            100                 105                 110

Ser Gly Ser Tyr Asp Tyr Trp Gly Gln Gly Thr Gln Val Thr Val Ser
        115                 120                 125

Ser Glu Pro Lys Thr Pro Lys Pro Gln
    130                 135
```

<210> SEQ ID NO 129
<211> LENGTH: 411
<212> TYPE: DNA
<213> ORGANISM: Artificial Sequence
<220> FEATURE:

<223> OTHER INFORMATION: The sequence has been designed and synthesized.
     The antibody is a camelid (VHH)

<400> SEQUENCE: 129

```
caggtgcagc tcgtggagtc cggcggagga ttggtgcagg cggggggctc tctgagtctc      60
tcctgtgcag cctctggagg tgacttcagt aggaatgcca tggcctggtt ccgtcaggct     120
ccagggaagg agcgtgaatt tgtagcatct attaactgga ctggtagtgg cacatattat     180
ctagactccg tgaagggccg attcaccatc tccagagaca cgccaagaa cgccctgtat      240 ctgcaaatga caacctgaa acctgaggac acggccgttt attactgtgc acgctccacg      300
gtgtttgccg aaattacagg cttagcaggc taccagtcgg gatcgtatga ctactggggc     360
caggggaccc aggtcaccgt ctcctcagaa cccaagacac caaaaccaca a              411
```

<210> SEQ ID NO 130
<211> LENGTH: 137
<212> TYPE: PRT
<213> ORGANISM: Artificial Sequence
<220> FEATURE:
<223> OTHER INFORMATION: The sequence has been designed and synthesized.
     The antibody is a camelid (VHH)

<400> SEQUENCE: 130

```
Gln Val Gln Leu Val Glu Thr Gly Gly Gly Thr Val Gln Thr Gly Gly
1               5                   10                  15

Ser Leu Arg Leu Ser Cys Ser Ala Ser Gly Gly Ser Phe Ser Arg Asn
            20                  25                  30

Ala Met Gly Trp Phe Arg Gln Ala Pro Gly Lys Glu Arg Glu Phe Val
        35                  40                  45

Ala Ala Ile Asn Trp Ser Ala Ser Ser Thr Tyr Tyr Arg Asp Ser Val
    50                  55                  60

Lys Gly Arg Phe Thr Val Ser Arg Asp Asn Ala Lys Asn Thr Val Tyr
65                  70                  75                  80

Leu His Leu Asn Ser Leu Lys Leu Glu Asp Thr Ala Ala Tyr Tyr Cys
                85                  90                  95

Ala Gly Ser Ser Val Tyr Ala Glu Met Pro Tyr Ala Asp Ser Val Lys
            100                 105                 110

Ala Thr Ser Tyr Asn Tyr Trp Gly Gln Gly Thr Gln Val Thr Val Ser
        115                 120                 125

Ser Glu Pro Lys Thr Pro Lys Pro Gln
    130                 135
```

<210> SEQ ID NO 131
<211> LENGTH: 411
<212> TYPE: DNA
<213> ORGANISM: Artificial Sequence
<220> FEATURE:
<223> OTHER INFORMATION: The sequence has been designed and synthesized.
     The antibody is a camelid (VHH)
<220> FEATURE:
<221> NAME/KEY: misc_feature
<222> LOCATION: (39)..(39)
<223> OTHER INFORMATION: n is a, c, g, or t

<400> SEQUENCE: 131

```
caggtgcagc tcgtggagac cggcggagga acggtgcana ctgggggctc tctgagactc      60
tcctgttcag cctctggcgg ctccttcagt aggaatgcca tgggctggtt ccgccaggct     120
ccagggaagg agcgtgaatt tgtagcagct attaactgga gtgcctctag tacttattat     180
agagactccg tgaagggacg attcaccgtc tccagagaca cgccaagaa cacggtgtat      240
```

```
ctgcatttga acagcctgaa acttgaggac acggccgcgt attactgtgc tggaagctcg    300
gtgtatgcag aaatgccgta cgccgactct gtcaaggcaa cttcctataa ctactggggc    360
caggggaccc aggtcaccgt ctcctcagaa cccaagacac caaaaccaca a             411
```

```
<210> SEQ ID NO 132
<211> LENGTH: 131
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 132
```

```
Gln Val Gln Leu Val Glu Thr Gly Gly Gly Leu Val Gln Ala Gly Gly
 1               5                  10                  15

Ser Leu Arg Leu Pro Cys Ser Phe Ser Gly Phe Pro Phe Asp Asn Tyr
            20                  25                  30

Phe Val Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Gly Ala Asp Phe Leu Thr Pro His Arg Cys Pro Ala Leu Tyr Asp Tyr
            100                 105                 110

Trp Gly Gln Gly Thr Gln Val Thr Val Ser Ser Ala His His Ser Glu
        115                 120                 125

Asp Pro Ser
    130
```

```
<210> SEQ ID NO 133
<211> LENGTH: 393
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 133
```

```
caggtgcagc tcgtggagac cggggggaggc ttggtgcagg ctgggggtc tctgagactc     60 ccctgttcat tctctggatt cccttttcgat aattatttcg taggctggtt ccgccaggcc   120
ccagggaagg agcgtgaggg ggtctcatgt attagtagta gtgatggtag cacatactat   180
gcagactccg tgaagggccg gttcaccatc tccagagaca acgccaagaa cacggtgtat   240
ctgcaaatga acagtctgaa acctgaggat acggccgttt attactgtgg agcagatttc   300
ctcaccccac ataggtgtcc agccttatat gactactggg gccaggggac ccaggtcacc   360
gtctcctcag cgcaccacag cgaagacccc tcg                                  393
```

```
<210> SEQ ID NO 134
<211> LENGTH: 127
<212> TYPE: PRT
<213> ORGANISM: Artificial Sequence
<220> FEATURE:
<223> OTHER INFORMATION: The sequence has been designed and synthesized.
      The antibody is a camelid (VHH)
```

<400> SEQUENCE: 134

Gln Val Gln Leu Val Glu Ser Gly Gly Gly Leu Val Gln Pro Gly Gly
1               5                   10                  15

Ser Leu Arg Leu His Cys Ala Ala Ser Gly Ser Ile Ala Ser Ile Tyr
            20                  25                  30

Arg Thr Cys Trp Tyr Arg Gln Gly Thr Gly Lys Gln Arg Glu Leu Val
        35                  40                  45

Ala Ala Ile Thr Ser Gly Gly Asn Thr Tyr Tyr Ala Asp Ser Val Lys
    50                  55                  60

Gly Arg Phe Thr Ile Ser Arg Asp Asn Ala Lys Asn Thr Ile Asp Leu
65                  70                  75                  80

Gln Met Asn Ser Leu Lys Pro Glu Asp Thr Ala Val Tyr Tyr Cys Asn
                85                  90                  95

Ala Asp Glu Ala Gly Ile Gly Gly Phe Asn Asp Tyr Trp Gly Gln Gly
            100                 105                 110

Thr Gln Val Thr Val Ser Ser Ala His His Ser Glu Asp Pro Ser
        115                 120                 125

<210> SEQ ID NO 135
<211> LENGTH: 381
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 135
caggtgcagc tcgtggagtc tggtggaggc ttggtgcagc tggggggtc tctgagactc       60 cactgtgcag cctctggaag catcgccagt atctatcgca cgtgctggta ccgccagggc      120
acagggaagc agcgcgagtt ggtcgcagcc attactagtg gtggtaacac atactatgcg      180
gactccgtta agggccgatt caccatctcc agagacaacg ccaaaaacac aatcgatctg      240
caaatgaaca gcctgaaacc tgaggacacg gccgtctatt actgtaatgc agacgaggcg      300
gggatcgggg gatttaatga ctactgggc caggggaccc aggtcaccgt ctcctcagcg      360
caccacagcg aagacccctc g                                               381

<210> SEQ ID NO 136
<211> LENGTH: 134
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 136

Gln Val Gln Leu Val Glu Ser Gly Gly Gly Leu Val Gln Ala Gly Gly
1               5                   10                  15

Ser Leu Arg Leu Ser Cys Ala Ser Gly Arg Thr Phe Ser Arg Ser
            20                  25                  30

Ser Met Gly Trp Phe Arg Gln Ala Pro Gly Lys Glu Arg Glu Phe Val
        35                  40                  45

Ala Ser Ile Val Trp Ala Asp Gly Thr Thr Leu Tyr Gly Asp Ser Val
    50                  55                  60

Lys Gly Arg Phe Thr Val Ser Arg Asp Asn Val Lys Asn Met Val Tyr
65                  70                  75                  80

Leu Gln Met Asn Asn Leu Lys Pro Glu Asp Thr Ala Leu Tyr Tyr Cys
                85                  90                  95

Ala Asp Asn Lys Phe Val Arg Gly Leu Val Ala Val Arg Ala Ile Asp
            100                 105                 110

Tyr Asp Tyr Trp Gly Gln Gly Thr Gln Val Thr Val Ser Ser Glu Pro
        115                 120                 125

Lys Thr Pro Lys Pro Gln
    130

<210> SEQ ID NO 137
<211> LENGTH: 402
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 137
caggtgcagc tcgtggagtc gggggggagga ttggtgcagg ctgggggctc tctgagactc     60
tcctgtgcag cctctggacg caccttcagt cgcagttcca tgggctggtt ccgccaggct    120
ccagggaagg agcgtgaatt cgttgcgtcc attgtctggg ctgatggtac gacgttgtat    180
ggagactccg taaagggccg attcaccgtc tccagggaca cgtcaagaa catggtgtat    240 ctacaaatga acaacctgaa acctgaggac acggcccttt attactgtgc ggacaataaa    300
ttcgtccgtg gattagtggc tgtccgtgcg atagattatg actactgggg ccaggggacc    360
caggtcaccg tctcgtcaga acccaagaca ccaaaaccac aa                       402

<210> SEQ ID NO 138
<211> LENGTH: 135
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 138

Gln Val Gln Leu Val Glu Ser Gly Gly Leu Val Gln Ala Gly Gly Ser
1               5                   10                  15

Leu Arg Leu Ser Cys Ala Ala Ser Gly Arg Ala Asp Ile Ile Tyr Ala
            20                  25                  30

Met Gly Trp Phe Arg Gln Ala Pro Gly Lys Glu Arg Glu Phe Val Ala
        35                  40                  45

Ala Val Asp Trp Ser Gly Gly Ser Thr Tyr Tyr Ala Asp Ser Val Lys
    50                  55                  60

Gly Arg Phe Thr Ile Ser Arg Asp Asn Ala Lys Asn Ser Val Tyr Leu
65                  70                  75                  80

Gln Met Asn Ser Leu Lys Pro Glu Asp Thr Ala Val Tyr Tyr Cys Ala
                85                  90                  95

Ala Arg Arg Ser Trp Tyr Arg Asp Ala Leu Ser Pro Ser Arg Val Tyr
            100                 105                 110

Glu Tyr Asp Tyr Trp Gly Gln Gly Thr Gln Val Thr Val Ser Ser Glu
        115                 120                 125

Pro Lys Thr Pro Lys Pro Gln
    130                 135

<210> SEQ ID NO 139
<211> LENGTH: 405
<212> TYPE: DNA
<213> ORGANISM: Artificial Sequence
<220> FEATURE:

<223> OTHER INFORMATION: The sequence has been designed and synthesized.
      The antibody is a camelid (VHH)

<400> SEQUENCE: 139

```
caggtgcagc tcgtggagtc gggaggattg gtgcaggctg gaggctctct gagactctcc    60
tgcgcagcct ctggacgcgc cgacataatc tatgccatgg gctggttccg ccaggctcca   120
gggaaggagc gtgagtttgt agcggcagta gactggagtg gtggtagcac atactatgca   180
gactccgtga agggccgatt caccatctcc agagacaacg ccaagaactc ggtgtatctg   240
caaatgaaca gcctgaaacc tgaggacacg gccgtttatt actgtgcagc ccgaaggagc   300
tggtaccgag acgcgctatc ccctcccgg gtgtatgaat atgactactg gggccagggg   360
acccaggtca ccgtctcctc agaacccaag acaccaaaac cacaa                    405
```

<210> SEQ ID NO 140
<211> LENGTH: 125
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 140

```
Gln Val Gln Leu Val Glu Thr Gly Gly Gly Leu Val Gln Pro Gly Gly
1               5                   10                  15
Ser Leu Thr Leu Ser Cys Ala Gly Ser Gly Gly Thr Leu Glu His Tyr
            20                  25                  30
Ala Ile Gly Trp Phe Arg Gln Ala Pro Gly Lys Glu His Glu Trp Leu
        35                  40                  45
Val Cys Asn Arg Gly Glu Tyr Gly Ser Thr Val Tyr Val Asp Ser Val
    50                  55                  60
Lys Gly Arg Phe Thr Ala Ser Arg Asp Asn Ala Lys Asn Thr Val Tyr
65                  70                  75                  80
Leu Gln Leu Asn Ser Leu Lys Pro Asp Asp Thr Gly Ile Tyr Tyr Cys
                85                  90                  95
Val Ser Gly Cys Tyr Ser Trp Arg Gly Pro Trp Gly Gln Gly Thr Gln
            100                 105                 110
Val Thr Val Ser Ser Ala His His Ser Glu Asp Pro Ser
        115                 120                 125
```

<210> SEQ ID NO 141
<211> LENGTH: 375
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 141

```
caggtgcagc tcgtggagac gggaggaggc ttggtgcagc tggggggtc tctgacactc     60
tcctgtgcag gctccggtgg cactttggaa cattatgcta taggctggtt ccgccaggcc   120
cctgggaaag agcatgagtg gctcgtatgt aatagaggtg aatatgggag cactgtctat   180
gtagactccg tgaagggccg attcaccgcc tccagagaca cgccaagaa cacggtgtat    240
ctgcaattga acagtctgaa acctgacgac acaggcattt attactgtgt atcgggatgt   300
tactcctggc ggggtccctg gggccagggg acccaggtca ccgtctcctc ggcgcaccac   360
agcgaagacc cctcg                                                     375
```

<210> SEQ ID NO 142
<211> LENGTH: 126
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 142

Gln Val Gln Leu Val Glu Ser Gly Gly Gly Leu Val Gln Pro Gly Gly
1               5                   10                  15

Ser Leu Lys Leu Ser Cys Arg Ala Ser Gly Ser Ile Val Ser Ile Tyr
            20                  25                  30

Ala Val Gly Trp Tyr Arg Gln Ala Pro Gly Lys Gln Arg Glu Leu Leu
        35                  40                  45

Ala Ala Ile Thr Thr Asp Gly Ser Thr Lys Tyr Ser Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Ile Tyr Ser Cys Ile
                85                  90                  95

Gly Asp Ala Ala Gly Trp Gly Asp Gln Tyr Tyr Trp Gly Gln Gly Thr
            100                 105                 110

Gln Val Thr Val Ser Ser Glu Pro Lys Thr Pro Lys Pro Gln
        115                 120                 125

<210> SEQ ID NO 143
<211> LENGTH: 378
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 143
caggtgcagc tcgtggagtc tgggggaggt ttggtgcagc ctggggggtc tctgaaactc      60
tcctgtagag cctctggaag catagtcagt atctatgccg tgggctggta ccgccaggct     120
ccagggaagc agcgcgagtt gctcgcggct atcactactg atggtagcac gaagtactca     180
gactccgtga agggccgatt caccatctcc cgagacaacg ccaagaacac ggtatatctg     240
caaatgaaca acctcaaacc tgaggacacg gccatctatt cctgtatcgg ggacgcggcg     300
ggttggggcg accaatacta ctggggccag gggacccagg tcaccgtctc ctcagaaccc     360
aagacaccaa aaccacaa                                                  378

<210> SEQ ID NO 144
<211> LENGTH: 129
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 144

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Val Asn Phe Glu
            20                  25                  30

Thr Met Gly Trp Tyr Arg Gln Ala Pro Gly Lys Glu Arg Glu Leu Val
        35                  40                  45

```
Ala Thr Ile Thr Asn Glu Gly Ser Ser Asn Tyr Ala Asp Ser Val Lys
        50                  55                  60

Gly Arg Phe Thr Ile Ser Gly Asp Asn Ala Lys Asn Thr Val Ser Leu
 65                  70                  75                  80

Gln Met Asn Ser Leu Lys Pro Glu Asp Thr Ala Val Tyr Tyr Cys Ser
                 85                  90                  95

Ala Thr Phe Gly Ser Arg Trp Pro Tyr Ala His Ser Asp His Trp Gly
            100                 105                 110

Gln Gly Thr Gln Val Thr Val Ser Ser Glu Pro Lys Thr Pro Lys Pro
        115                 120                 125

Gln
```

<210> SEQ ID NO 145
<211> LENGTH: 387
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 145

```
caggtgcagc tcgtggagtc aggcggaggc ttggtgcagg ctggggggtc tctgagactc    60
tcctgtgcag cctctggaag catcgtcaat ttcgaaacca tgggctggta ccgccaggct   120
ccagggaagg agcgcgagtt ggtcgcaact attactaatg aaggtagttc aaactatgca   180
gactccgtga agggccgatt caccatctcc ggagacaacg ccaagaacac ggtgtccctg   240
caaatgaaca gcctgaaacc tgaggacacg gccgtctact actgttcggc gacgttcggc   300
agtaggtggc cgtacgccca cagtgatcac tggggccagg ggacccaggt caccgtctcc   360
tcagaaccca agacaccaaa accacaa                                       387
```

<210> SEQ ID NO 146
<211> LENGTH: 125
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 146

```
Gln Val Gln Leu Val Glu Thr Gly Gly Ala Leu Val His Thr Gly Gly
 1               5                  10                  15

Ser Leu Arg Leu Ser Cys Glu Val Ser Gly Ser Thr Phe Ser Ser Tyr
             20                  25                  30

Gly Met Ala Trp Tyr Arg Gln Ala Pro Gly Glu Gln Arg Lys Trp Val
            35                  40                  45

Ala Gly Ile Met Pro Asp Gly Thr Pro Ser Tyr Val Asn Ser Val Lys
        50                  55                  60

Gly Arg Phe Thr Ile Ser Arg Asp Asn Ala Lys Asn Ser Val Tyr Leu
 65                  70                  75                  80

His Met Asn Asn Leu Arg Pro Glu Asp Thr Ala Val Tyr Tyr Cys Asn
                 85                  90                  95

Gln Trp Pro Arg Thr Met Pro Asp Ala Asn Trp Gly Arg Gly Thr Gln
            100                 105                 110

Val Thr Val Ser Ser Glu Pro Lys Thr Pro Lys Pro Gln
        115                 120                 125
```

```
<210> SEQ ID NO 147
<211> LENGTH: 375
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 147
caggtgcagc tcgtggagac gggcggagca ttggtgcaca ctgggggttc tctgagactc    60
tcctgcgaag tctccggaag caccttcagt agctatggca tggcctggta ccgccaagct   120
ccaggcgagc agcgtaagtg ggtcgcaggt attatgccgg atggtactcc aagctatgta   180
aactccgtga agggccgatt caccatctcc agagacaacg ccaagaactc ggtgtatctg   240
cacatgaaca acctgaggcc tgaagacacg gccgtctatt attgcaacca atggccgcgc   300
acgatgcctg acgcgaactg gggccggggg acccaggtca ccgtctcctc agaacccaag   360
acaccaaaac cacaa                                                    375

<210> SEQ ID NO 148
<211> LENGTH: 117
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 148

Gln Val Gln Leu Val Glu Thr Gly Gly Ser Leu Arg Leu Thr Cys Val
1               5                   10                  15

Thr Ser Gly Ser Thr Phe Asn Asn Pro Ala Ile Thr Trp Tyr Arg Gln
            20                  25                  30

Pro Pro Gly Lys Gln Arg Glu Trp Val Ala Ser Leu Arg Ser Gly Asp
        35                  40                  45

Gly Pro Val Tyr Arg Glu Ser Val Lys Gly Arg Phe Thr Ile Phe Arg
    50                  55                  60

Asp Asn Ala Thr Asp Ala Leu Tyr Leu Arg Met Asn Ser Leu Lys Pro
65                  70                  75                  80

Glu Asp Thr Ala Val Tyr His Cys Asn Thr Ala Ser Pro Ala Ser Trp
                85                  90                  95

Leu Asp Trp Gly Gln Gly Thr Gln Val Thr Val Ser Ser Glu Pro Lys
            100                 105                 110

Thr Pro Lys Pro Gln
        115

<210> SEQ ID NO 149
<211> LENGTH: 351
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 149
caggtgcagc tcgtggagac tgggggtct ctgaggctca cctgtgtaac ctctggaagc    60
accttcaata atcctgccat aacctggtac cgccagcctc agggaagca gcgtgagtgg   120 gtcgcaagtc ttcgtagtgg tgatggtcca gtataggg aatccgtgaa gggccgattc   180 accatttta gagacaacgc cacggacgcg ctgtatctgc ggatgaatag cctgaaacct   240
gaggacacgg ccgtctatca ctgtaacacc gcctcacctg ctagttggct ggactgggc   300
``` cagggggaccc aggtcactgt ctcctcagaa cccaagacac caaaaccaca a        351

<210> SEQ ID NO 150
<211> LENGTH: 130
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 150

Gln Val Gln Leu Val Glu Thr Gly Gly Gly Leu Val Gln Pro Gly Gly
1               5                   10                  15

Ser Leu Arg Leu Ser Cys Ala Thr Ser Gly Phe Pro Phe Ser Thr Glu
            20                  25                  30

Arg Met Ser Trp Val Arg Gln Ala Pro Gly Lys Gly Leu Glu Trp Val
        35                  40                  45

Ser Gly Ile Thr Glu Gly Gly Glu Thr Thr Leu Ala Ala Pro Ser Val
    50                  55                  60

Lys Gly Arg Phe Asn Ile Ser Arg Asp Asn Ala Arg Asn Ile Leu Tyr
65                  70                  75                  80

Leu Gln Met Asn Ser Leu Lys Pro Glu Asp Ala Ala Val Tyr Tyr Cys
                85                  90                  95

Phe Arg Gly Val Phe Phe Arg Thr Ser Phe Pro Pro Glu Leu Ala Arg
            100                 105                 110

Gly Gln Gly Thr Gln Val Thr Val Ser Ser Glu Pro Lys Thr Pro Lys
        115                 120                 125

Pro Gln
    130

<210> SEQ ID NO 151
<211> LENGTH: 390
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 151
caggtgcagc tcgtggagac gggaggagga ttggtgcaac tggggggttc tctgagactc     60
tcttgtgcaa cctctggatt cccccttcagt acggagcgta tgagctgggt ccgccaggct    120
ccaggaaagg ggctcgagtg gtctcaggt attactgagg gtggtgaaac cactctcgcg     180
gcaccctccg tgaagggccg attcaacatc tccagagaca cgccaggaa tatcctatat      240 ctacagatga attccttgaa acctgaggac gcggccgttt actattgttt tagaggtgtt      300 tttttttagaa cgagttttcc tcccgaactc gcgcggggcc aggggaccca ggtcaccgtc     360
tcctcagaac ccaagacacc aaaaccacaa                                     390

<210> SEQ ID NO 152
<211> LENGTH: 127
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 152

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ala Val Ser Asp Ser
            20                  25                  30

Phe Ser Thr Tyr Ala Ile Ser Trp His Arg Gln Ala Pro Gly Lys Gln
        35                  40                  45

Arg Glu Trp Ile Ala Gly Ile Ser Asn Arg Gly Ala Thr Ser Tyr Arg
50                  55                  60

Asp Ser Val Lys Gly Arg Phe Thr Ile Ser Arg Asp Asn Ala Lys Asn
65                  70                  75                  80

Thr Val Tyr Leu Gln Met Asn Asn Leu Lys Pro Glu Asp Thr Gly Val
                85                  90                  95

Tyr Tyr Cys Glu Pro Trp Pro Arg Glu Gly Leu Gly Gly Gly Gln Gly
            100                 105                 110

Thr Gln Val Thr Val Ser Ser Glu Pro Lys Thr Pro Lys Pro Gln
        115                 120                 125

<210> SEQ ID NO 153
<211> LENGTH: 381
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 153
caggtgcagc tcgtggagtc gggcggaggc ttggtgcagg cagggggtc tttgagactc        60 tcctgtgcag cctctggaag cgccgtcagt gacagcttca gtacctatgc catctcctgg      120
caccgccagg ctccagggaa gcagcgtgag tggatcgcag gtattagtaa tcgtggtgcg      180
acaagctata gagactccgt gaagggccga ttcaccatct ccagagacaa cgccaagaac      240
acggtatatc tgcaaatgaa caacctgaaa cctgaggaca cgggcgtcta ttattgtgag      300
ccatggccac gcgaaggact tggggggggc caggggactc aggtcaccgt ctcctcagaa      360
cccaagacac caaaaccaca a                                                381

<210> SEQ ID NO 154
<211> LENGTH: 124
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 154

Gln Val Gln Leu Val Glu Ser Gly Gly Gly Ser Val Gln Thr Gly Gly
1               5                   10                  15

Ser Leu Thr Leu Ser Cys Val Val Ser Gly Ser Thr Phe Ser Asp Tyr
            20                  25                  30

Ala Val Ala Trp Tyr Arg Gln Val Pro Gly Lys Ser Arg Ala Trp Val
        35                  40                  45

Ala Gly Val Ser Thr Thr Gly Ser Thr Ser Tyr Thr Asp Ser Val Arg
50                  55                  60

Gly Arg Phe Thr Ile Ser Arg Asp Asn His Lys Lys Thr Val Tyr Leu
65                  70                  75                  80

Ser Met Asn Ser Leu Lys Pro Glu Asp Thr Gly Ile Tyr Tyr Cys Asn
                85                  90                  95

Leu Trp Pro Phe Thr Asn Pro Pro Ser Trp Gly Gln Gly Thr Gln Val
            100                 105                 110

Thr Val Ser Ser Ala His His Ser Glu Asp Pro Ser
        115                 120

<210> SEQ ID NO 155
<211> LENGTH: 372
<212> TYPE: DNA
<213> ORGANISM: Artificial Sequence
<220> FEATURE:
<223> OTHER INFORMATION: The sequence has been designed and synthesized.
      The antibody is a camelid (VHH)
<220> FEATURE:
<221> NAME/KEY: misc_feature
<222> LOCATION: (39)..(39)
<223> OTHER INFORMATION: n is a, c, g, or t

<400> SEQUENCE: 155
caggtgcagc tcgtggagtc ggggggaggc tcggtgcana ctgggggtc tctgacactc      60 tcctgtgtag tctctggaag taccttcagt gactatgcgg tggcctggta ccgccaggtt     120
ccaggcaaat cgcgtgcgtg gtcgcgggt gttagtacta ctggctcgac atcttataca    180
gactccgtga ggggccggtt caccatctcc agagacaacc acaagaagac ggtgtatctt    240
tcaatgaaca gcctgaaacc tgaggacacg ggcatctatt actgcaactt atggccgttc    300
acaaatcctc cttcctgggg ccagggaacc caagtcaccg tttcctcggc gcaccacagc    360
gaagacccct cg                                                        372

<210> SEQ ID NO 156
<211> LENGTH: 132
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 156

Gln Val Gln Leu Val Glu Ser Gly Gly Ala Val Val Gln Pro Gly Gly
1               5                   10                  15

Ser Leu Arg Leu Ser Cys Ala Thr Ser Gly Phe Thr Phe Ser Asp Asp
            20                  25                  30

Arg Met Ser Trp Ala Arg Gln Ala Pro Gly Lys Gly Leu Glu Trp Val
        35                  40                  45

Ser Gly Ile Ser Thr Ala Ser Glu Gly Phe Ala Thr Leu Tyr Ala Pro
    50                  55                  60

Ser Val Lys Gly Arg Phe Thr Ile Ser Arg Asp Asn Ala Lys His Met
65                  70                  75                  80

Leu Tyr Leu Gln Met Asp Thr Leu Lys Pro Glu Asp Thr Ala Val Tyr
                85                  90                  95

Tyr Cys Leu Arg Gly Val Phe Phe Arg Thr Asn Ile Pro Pro Glu Val
            100                 105                 110

Leu Arg Gly Gln Gly Thr Gln Val Thr Val Ser Ser Ala His His Ser
        115                 120                 125

Glu Asp Pro Ser
    130

<210> SEQ ID NO 157
<211> LENGTH: 396
<212> TYPE: DNA
<213> ORGANISM: Artificial Sequence
<220> FEATURE:
<223> OTHER INFORMATION: The sequence has been designed and synthesized.
      The antibody is a camelid (VHH)

-continued

<400> SEQUENCE: 157

```
caggtgcagc tcgtggagtc tggaggagcc gtggtgcaac ctggggggtc tctgagactc    60
tcctgtgcaa cctctggatt caccttcagt gacgatcgta tgagctgggc ccgccaggct   120
ccaggaaagg ggctcgagtg gtctcaggt attagtactg ctagtgaagg ttttgctaca   180
ctctacgcac cctccgtgaa gggccgattc accatctcca gagacaacgc caagcatatg   240
ctgtatctgc aaatggatac cttgaaacct gaggacacgg ccgtgtatta ctgtttaaga   300
ggggtttttt ttagaacgaa cattcctccc gaggtactgc ggggccaggg gacccaggtc   360
accgtctcct cagcgcacca cagcgaagac ccctcg                            396
```

<210> SEQ ID NO 158
<211> LENGTH: 126
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 158

```
Gln Val Gln Leu Val Glu Thr Gly Gly Asp Leu Val Gln Pro Gly Gly
1               5                   10                  15

Ser Leu Arg Leu Ser Cys Ala Ala Ser Gly Ser Ser Phe Ser Arg Ala
            20                  25                  30

Ala Val Gly Trp Tyr Arg Gln Ala Pro Gly Lys Glu Arg Glu Trp Val
        35                  40                  45

Ala Arg Leu Ala Ser Gly Asp Met Thr Asp Tyr Thr Glu Ser Val Arg
    50                  55                  60

Gly Arg Phe Thr Ile Ser Arg Asp Asn Ala Lys His Thr Val Tyr Leu
65                  70                  75                  80

Gln Met Asp Asn Leu Lys Pro Glu Asp Thr Ala Val Tyr Tyr Cys Lys
                85                  90                  95

Ala Arg Ile Pro Pro Tyr Tyr Ser Ile Glu Tyr Trp Gly Lys Gly Thr
            100                 105                 110

Arg Val Thr Val Ser Ser Glu Pro Lys Thr Pro Lys Pro Gln
        115                 120                 125
```

<210> SEQ ID NO 159
<211> LENGTH: 378
<212> TYPE: DNA
<213> ORGANISM: Artificial Sequence
<220> FEATURE:
<223> OTHER INFORMATION: The sequence has been designed and synthesized.
      The antibody is a camelid (VHH)
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t

<400> SEQUENCE: 159

```
caggtgcagc tcgtggagac ggggggagac ttggtgcanc ctggggggtc tctgagactc    60
tcctgtgcag cctctggaag ctccttcagc cgcgctgccg tgggctggta ccgtcaggct   120
ccaggaaagg agcgtgagtg gtcgcacgt ctcgcgagtg gtgatatgac ggactatacc   180
gagtccgtga gggccgatt cactatctcc agagacaacg ccaagcacac ggtgtatctg   240
caaatggaca acctgaaacc tgaggacacg gccgtctact attgtaaggc caggataccc   300
```

```
ccttattact ctatagagta ctggggcaaa gggacccggg tcaccgtctc ctcanaaccc    360
aagacaccaa aaccacaa                                                  378
```

<210> SEQ ID NO 160
<211> LENGTH: 124
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 160

```
Gln Val Gln Leu Val Glu Thr Gly Gly Gly Leu Val Gln Ala Gly Gly
1               5                   10                  15

Ser Leu Arg Leu Ser Cys Val Val Ser Ser Pro Leu Phe Asn Leu Tyr
            20                  25                  30

Asp Met Ala Trp Tyr Arg Gln Ala Pro Gly Asn Gln Arg Glu Leu Val
        35                  40                  45

Ala Gly Ile Leu Thr Asp Gly Arg Ala Thr Tyr Ser Asp Ser Val Lys
    50                  55                  60

Gly Arg Phe Thr Ile Ser Arg Asn Asn Leu Thr Asn Thr Val Phe Leu
65                  70                  75                  80

Gln Met Ser Ser Leu Lys Pro Glu Asp Thr Ala Val Tyr Tyr Cys Asn
                85                  90                  95

Arg Lys Asn Ser Ile Tyr Trp Asp Ser Trp Gly Gln Gly Thr Gln Val
            100                 105                 110

Thr Val Ser Ser Glu Pro Lys Thr Pro Lys Pro Gln
        115                 120
```

<210> SEQ ID NO 161
<211> LENGTH: 372
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 161

```
caggtgcagc tcgtggagac aggtggaggc ttggtgcagg ctggggggtc tctgagactc    60
tcctgtgtag tatctagtcc cctgttcaat ctttacgaca tggcctggta tcgccaggct    120
ccagggaatc agcgtgagtt ggtcgcaggc atcttgactg atggtcgcgc aacatattca    180
gacagcgtga agggccgatt caccatttcc agaaacaacc tgacgaacac ggtgttttta    240
caaatgagca gcctgaaacc tgaggacacg gccgtctatt attgtaatag aaagaatagt    300
atctactggg attcctgggg ccaggggacc caggtcaccg tctcctcgga acccaagaca    360
ccaaaaccac aa                                                        372
```

<210> SEQ ID NO 162
<211> LENGTH: 134
<212> TYPE: PRT
<213> ORGANISM: Artificial Sequence
<220> FEATURE:
<223> OTHER INFORMATION: The sequence has been designed and synthesized.
      The antibody is a camelid (VHH)

<400> SEQUENCE: 162

```
Gln Val Gln Leu Val Glu Ser Gly Gly Gly Leu Val Gln Ala Gly Gly
1               5                   10                  15
```

Ser Leu Arg Leu Ser Cys Val Ala Ser Gly Leu Thr Phe Ser Arg Tyr
            20                  25                  30

Gly Met Gly Trp Phe Arg Gln Ala Pro Gly Gln Glu Arg Val Val Val
        35                  40                  45

Ser Val Ile Ser Pro Asp Gly Ser Ala Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Ser Thr Leu Arg Phe Glu Asp Thr Gly Val Tyr Tyr Cys
                85                  90                  95

Thr Ala Gly Pro Arg Asn Gly Ala Thr Thr Val Leu Arg Pro Gly Asp
                100                 105                 110

Tyr Asp Tyr Trp Gly Gln Gly Thr Gln Val Thr Val Ser Ser Glu Pro
            115                 120                 125

Lys Thr Pro Lys Pro Gln
            130

<210> SEQ ID NO 163
<211> LENGTH: 402
<212> TYPE: DNA
<213> ORGANISM: Artificial Sequence
<220> FEATURE:
<223> OTHER INFORMATION: The sequence has been designed and synthesized.
      The antibody is a camelid (VHH)

<400> SEQUENCE: 163
caggtgcagc tcgtggagtc ggggggagga ttggtgcagg ctggggggctc tctgagactc      60
tcctgcgtag cctctggact caccttcagt cgctatggca tgggctggtt ccgccaggct     120
ccaggacagg agcgtgtagt cgtatcagtt attagtcccg acgtggtag cgcatactac      180
gcagactccg tgaagggccg attcaccatc tccagagaca acgccaagaa cacggtgtat     240
ctgcaaatga gcaccctgag atttgaggac acgggcgttt attattgtac agcagggccc     300
cggaatggag cgactacagt cctccggcca ggggattatg actactgggg ccaggggacc     360
caggtcactg tctcctcaga acccaagaca ccaaaaccac aa                        402

<210> SEQ ID NO 164
<211> LENGTH: 135
<212> TYPE: PRT
<213> ORGANISM: Artificial Sequence
<220> FEATURE:
<223> OTHER INFORMATION: The amino acid was designed and synthesized

<400> SEQUENCE: 164

Gln Leu Gln Leu Val Glu Ser Gly Gly Gly Leu Val Gln Pro Gly Gly
 1                5                  10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
 50                  55                  60

Lys Gly Arg Phe Thr Ile Ser Arg Asp Asn Ala Lys Asn Ala Val Tyr
 65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
                100                 105                 110

Asp Tyr Asp Val Trp Gly Arg Gly Thr Gln Val Ala Val Ser Ser Glu
        115                 120                 125

Pro Lys Thr Pro Lys Pro Gln
    130                 135

<210> SEQ ID NO 165
<211> LENGTH: 119
<212> TYPE: PRT
<213> ORGANISM: Artificial Sequence
<220> FEATURE:
<223> OTHER INFORMATION: The amino acid sequence was designed and
      synthesized

<400> SEQUENCE: 165

Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser Glu
            100                 105                 110

Pro Lys Thr Pro Lys Pro Gln
        115

<210> SEQ ID NO 166
<211> LENGTH: 129
<212> TYPE: PRT
<213> ORGANISM: Artificial Sequence
<220> FEATURE:
<223> OTHER INFORMATION: The amino acid sequence was designed and
      synthesized

<400> SEQUENCE: 166

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Glu Pro Lys Thr Pro Lys Pro
        115                 120                 125

Gln

<210> SEQ ID NO 167
<211> LENGTH: 675
<212> TYPE: PRT
<213> ORGANISM: Artificial Sequence
<220> FEATURE:
<223> OTHER INFORMATION: The amino acid sequence was designed and synthesized

<400> SEQUENCE: 167

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ser Gly Ala Pro Val Pro Tyr Pro Asp Pro Leu Glu Pro Arg
        35                  40                  45

Ala Ala Ala Gln Val Gln Leu Val Glu Ser Gly Gly Gly Leu Val Gln
50                  55                  60

Pro Gly Gly Ser Leu Arg Leu Ser Cys Ala Ala Ser Gly Phe Thr Leu
65                  70                  75                  80

Asp Tyr Ser Ser Ile Gly Trp Phe Arg Gln Ala Pro Gly Lys Glu Arg
                85                  90                  95

Glu Gly Val Ser Cys Ile Ser Ser Gly Asp Ser Thr Lys Tyr Ala
            100                 105                 110

Asp Ser Val Lys Gly Arg Phe Thr Thr Ser Arg Asp Asn Ala Lys Asn
        115                 120                 125

Thr Val Tyr Leu Gln Met Asn Ser Leu Lys Pro Asp Asp Thr Ala Val
130                 135                 140

Tyr Tyr Cys Ala Ala Phe Arg Ala Thr Met Cys Gly Val Phe Pro Leu
145                 150                 155                 160

Ser Pro Tyr Gly Lys Asp Asp Trp Gly Lys Gly Thr Leu Val Thr Val
                165                 170                 175

Ser Ser Glu Pro Lys Thr Pro Lys Pro Gln Pro Thr Ser Ala Ile Ala
            180                 185                 190

Gly Gly Gly Gly Ser Gly Gly Gly Ser Gly Gly Gly Ser Ala
        195                 200                 205

Ala Ala Gln Leu Gln Leu Val Glu Ser Gly Gly Gly Leu Val Gln Pro
210                 215                 220

Gly Gly Ser Leu Arg Leu Ser Cys Glu Ala Ser Gly Phe Thr Leu Asp
225                 230                 235                 240

Tyr Tyr Gly Ile Gly Trp Phe Arg Gln Pro Gly Lys Glu Arg Glu
                245                 250                 255

Ala Val Ser Tyr Ile Ser Ala Ser Ala Arg Thr Ile Leu Tyr Ala Asp
            260                 265                 270

Ser Val Lys Gly Arg Phe Thr Ile Ser Arg Asp Asn Ala Lys Asn Ala
        275                 280                 285

Val Tyr Leu Gln Met Asn Ser Leu Lys Arg Glu Asp Thr Ala Val Tyr
290                 295                 300

Tyr Cys Ala Arg Arg Arg Phe Ser Ala Ser Ser Val Asn Arg Trp Leu
305                 310                 315                 320

Ala Asp Asp Tyr Asp Val Trp Gly Arg Gly Thr Gln Val Ala Val Ser
                325                 330                 335

Ser Glu Pro Lys Thr Pro Lys Pro Gln Thr Ser Ala Leu Val Gly Gly
            340                 345                 350

Gly Gly Ser Gly Gly Gly Gly Ser Gly Gly Gly Ser Leu Gln Ala
        355                 360                 365
```

```
Met Ala Ala Gln Val Gln Leu Val Glu Ser Gly Gly Leu Val
    370                 375                 380

Gln Thr Gly Gly Ser Leu Arg Leu Ser Cys Ala Ser Ser Gly Ser Ile
385                 390                 395                 400

Ala Gly Phe Glu Thr Val Thr Trp Ser Arg Gln Ala Pro Gly Lys Ser
                405                 410                 415

Leu Gln Trp Val Ala Ser Met Thr Lys Thr Asn Asn Glu Ile Tyr Ser
            420                 425                 430

Asp Ser Val Lys Gly Arg Phe Ile Ile Ser Arg Asp Asn Ala Lys Asn
        435                 440                 445

Thr Val Tyr Leu Gln Met Asn Ser Leu Lys Pro Glu Asp Thr Gly Val
    450                 455                 460

Tyr Phe Cys Lys Gly Pro Glu Leu Arg Gly Gln Gly Ile Gln Val Thr
465                 470                 475                 480

Val Ser Ser Glu Pro Lys Thr Pro Lys Pro Gln Ala Ile Ala Gly Gly
                485                 490                 495

Gly Gly Ser Gly Gly Gly Ser Gly Gly Gly Ser Leu Gln Gly
            500                 505                 510

Gln Val Gln Leu Val Glu Ser Gly Gly Leu Val Gln Pro Gly Gly
    515                 520                 525

Ser Leu Arg Leu Ser Cys Ala Ala Ser Gly Phe Thr Phe Ser Asp Tyr
    530                 535                 540

Val Met Thr Trp Val Arg Gln Ala Pro Gly Lys Gly Pro Glu Trp Ile
545                 550                 555                 560

Ala Thr Ile Asn Thr Asp Gly Ser Thr Met Arg Asp Asp Ser Thr Lys
                565                 570                 575

Gly Arg Phe Thr Ile Ser Arg Asp Asn Ala Lys Asn Thr Leu Tyr Leu
            580                 585                 590

Gln Met Thr Ser Leu Lys Pro Glu Asp Thr Ala Leu Tyr Tyr Cys Ala
        595                 600                 605

Arg Gly Arg Val Ile Ser Ala Ser Ala Ile Arg Gly Ala Val Arg Gly
    610                 615                 620

Pro Gly Thr Gln Val Thr Val Ser Ser Glu Pro Lys Thr Pro Lys Pro
625                 630                 635                 640

Gln Pro Ala Arg Gln Gly Ala Pro Val Pro Tyr Pro Asp Pro Leu Glu
                645                 650                 655

Pro Arg Gly Gly Gly Ser Asp Ile Cys Leu Pro Arg Trp Gly Cys Leu
            660                 665                 670

Trp Glu Asp
    675
```

<210> SEQ ID NO 168
<211> LENGTH: 13
<212> TYPE: PRT
<213> ORGANISM: Artificial Sequence
<220> FEATURE:
<223> OTHER INFORMATION: Epitope tag

<400> SEQUENCE: 168

```
Asp Ile Cys Leu Pro Arg Trp Gly Cys Leu Trp Glu Asp
1               5                   10
```

<210> SEQ ID NO 169
<211> LENGTH: 2373
<212> TYPE: DNA
<213> ORGANISM: Artificial Sequence
<220> FEATURE:
<223> OTHER INFORMATION: The nucleotide sequence was designed and
synthesized

<400> SEQUENCE: 169

```
atgagcgata aaattattca cctgactgac gacagttttg acacggatgt actcaaagcg      60
gacgggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg gccatatgca ccatcatcat     360
catcattctt ctggtctggt gccacgcggt tctggtatga agaaaccgc tgctgctaaa      420
ttcgaacgcc agcacatgga cagcccagat ctgggtaccg acgacgacga caaggccatg     480
gcgatatcgg atccgaattc tggcgcacct gtcccatacc agaccctct ggaaccacga      540
gcggccgccc aagtccaact ggtcgaaagt ggtggtggtc tggtccaacc gggtggctct     600
ctgcgtctgt cctgcgctgc gagtggtttt accctggatt atagctctat tggttggttc     660
cgccaggcgc gggtaaaga acgtgaaggc gtgagctgca tcagttcctc aggtgatagt      720
accaaatatg cggactccgt caaaggccgc tttaccacga gtcgtgataa cgccaaaaat     780
acggtttacc tgcagatgaa ctccctgaaa ccggatgaca ccgcagtgta ttactgcgcg     840
gcctttcgcg ctacgatgtg tggtgttttc ccgctgagcc gtatggcaa agatgactgg      900
ggtaaaggca ccctggtgac ggtttcgagc gaaccgaaaa ccccgaaacc gcagccgacg     960
tctgcgatcg ccggtggtgg tggttcgggt ggtggtggta gcggtggtgg tggttctgca    1020
gctgcgcagc tgcaactggt ggaaagcggc ggtggtctgg ttcaaccggg tggttccctg    1080
cgtctgtcat gcgaagcctc gggttttacc ctggattatt acggtattgg ttggttccgt    1140
cagccgccgg gcaaagaacg tgaagcagtg agctatattt ccgcatcagc acgtaccatc    1200
ctgtacgcag attcagttaa aggccgcttt acgatctcgc gtgacaacgc gaaaaatgcc    1260
gtctatctgc agatgaacag tctgaaacgt gaagataccg cagtgtatta ctgtgctcgt    1320
cgccgtttct ccgcgtctag tgtcaatcgc tggctggccg atgactacga tgtgtggggt    1380
cgtggcaccc aagtcgccgt gtcctcagag cctaaaacgc cgaaaccgca aacgtctgca    1440
ctagttggcg gtggtggctc aggtggaggc gggtcaggcg gtggcggttc cctgcaagca    1500
atggccgcag ctcaggtgca actggttgaa tccggtggtg gtctggtgca gccggtggt    1560
agcctgcgtc tgtcttgcgc atcgagcggt agcattgctg ctttgaaac cgttacgtgg    1620
tctcgtcaag cgccgggtaa atcactgcag tgggtcgcct cgatgaccaa acgaacaat    1680
gaaatctatt cggatagcgt taaaggccgc tttattatct cacgcgataa cgcgaaaaat    1740
accgtgtatc tgcagatgaa ctcgctgaaa ccggaagata cgggtgttta cttctgcaaa    1800
ggcccggaac tgcgcggtca aggcattcag gttaccgtct ctagtgagcc taaaaccccg    1860
aaaccgcaag caatcgcagg cggcggcggc agcggcggcg gcggctctgg tggtggtggt    1920
tccctgcagg gtcaagtcca gctggtggaa tctggcggtg gtctggtgca accgggtggt    1980
agtctgcgtc tgtcctgtgc agcctcaggc tttaccttct cagattatgt tatgacgtgg    2040
gtccgtcagg caccgggtaa aggtccggaa tggattgcta ccatcaatac ggacggtagc    2100
accatgcgcg atgactctac caaaggccgc ttcacgatta gccgtgataa tgccaaaaat    2160
accctgtacc tgcagatgac gtctctgaaa ccggaagaca ccgcgctgta ttactgtgcc    2220
```

```
cgcggtcgtg ttatttctgc aagtgctatc cgtggcgccg tccgtggtcc gggcacccaa    2280
gtcaccgtct cctcagaacc gaaaacgccg aaaccgcaac cggcgcgcca gggtgcgccg    2340
gtgccgtatc cggacccgct ggaaccgcgt taa                                 2373
```

<210> SEQ ID NO 170
<211> LENGTH: 807
<212> TYPE: PRT
<213> ORGANISM: Artificial Sequence
<220> FEATURE:
<223> OTHER INFORMATION: The amino acid was designed and synthesized

<400> SEQUENCE: 170

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Ala Gln Val Gln Leu Val Glu Ser Gly Gly
            180                 185                 190

Gly Leu Val Gln Pro Gly Gly Ser Leu Arg Leu Ser Cys Ala Ala Ser
        195                 200                 205

Gly Phe Thr Leu Asp Tyr Ser Ser Ile Gly Trp Phe Arg Gln Ala Pro
    210                 215                 220

Gly Lys Glu Arg Glu Gly Val Ser Cys Ile Ser Ser Ser Gly Asp Ser
225                 230                 235                 240

Thr Lys Tyr Ala Asp Ser Val Lys Gly Arg Phe Thr Thr Ser Arg Asp
                245                 250                 255

Asn Ala Lys Asn Thr Val Tyr Leu Gln Met Asn Ser Leu Lys Pro Asp
            260                 265                 270

Asp Thr Ala Val Tyr Tyr Cys Ala Ala Phe Arg Ala Thr Met Cys Gly
        275                 280                 285

Val Phe Pro Leu Ser Pro Tyr Gly Lys Asp Asp Trp Gly Lys Gly Thr
    290                 295                 300

Leu Val Thr Val Ser Ser Glu Pro Lys Thr Pro Lys Pro Gln Pro Thr
305                 310                 315                 320

Ser Ala Ile Ala Gly Gly Gly Gly Ser Gly Gly Gly Ser Gly Gly
                325                 330                 335
```

```
Gly Gly Ser Ala Ala Ala Gln Leu Gln Leu Val Glu Ser Gly Gly Gly
            340                 345                 350

Leu Val Gln Pro Gly Gly Ser Leu Arg Leu Ser Cys Glu Ala Ser Gly
            355                 360                 365

Phe Thr Leu Asp Tyr Tyr Gly Ile Gly Trp Phe Arg Gln Pro Pro Gly
            370                 375                 380

Lys Glu Arg Glu Ala Val Ser Tyr Ile Ser Ala Ser Ala Arg Thr Ile
385                 390                 395                 400

Leu Tyr Ala Asp Ser Val Lys Gly Arg Phe Thr Ile Ser Arg Asp Asn
            405                 410                 415

Ala Lys Asn Ala Val Tyr Leu Gln Met Asn Ser Leu Lys Arg Glu Asp
            420                 425                 430

Thr Ala Val Tyr Tyr Cys Ala Arg Arg Phe Ser Ala Ser Ser Val
            435                 440                 445

Asn Arg Trp Leu Ala Asp Asp Tyr Asp Val Trp Gly Arg Gly Thr Gln
            450                 455                 460

Val Ala Val Ser Ser Glu Pro Lys Thr Pro Lys Pro Gln Thr Ser Ala
465                 470                 475                 480

Leu Val Gly Gly Gly Ser Gly Gly Gly Ser Gly Gly Gly Gly
            485                 490                 495

Ser Leu Gln Ala Met Ala Ala Ala Gln Val Gln Leu Val Glu Ser Gly
            500                 505                 510

Gly Gly Leu Val Gln Thr Gly Gly Ser Leu Arg Leu Ser Cys Ala Ser
            515                 520                 525

Ser Gly Ser Ile Ala Gly Phe Glu Thr Val Thr Trp Ser Arg Gln Ala
            530                 535                 540

Pro Gly Lys Ser Leu Gln Trp Val Ala Ser Met Thr Lys Thr Asn Asn
545                 550                 555                 560

Glu Ile Tyr Ser Asp Ser Val Lys Gly Arg Phe Ile Ile Ser Arg Asp
            565                 570                 575

Asn Ala Lys Asn Thr Val Tyr Leu Gln Met Asn Ser Leu Lys Pro Glu
            580                 585                 590

Asp Thr Gly Val Tyr Phe Cys Lys Gly Pro Glu Leu Arg Gly Gln Gly
            595                 600                 605

Ile Gln Val Thr Val Ser Ser Glu Pro Lys Thr Pro Lys Pro Gln Ala
            610                 615                 620

Ile Ala Gly Gly Gly Ser Gly Gly Gly Gly Ser Gly Gly Gly Gly
625                 630                 635                 640

Ser Leu Gln Gly Gln Val Gln Leu Val Glu Ser Gly Gly Gly Leu Val
            645                 650                 655

Gln Pro Gly Gly Ser Leu Arg Leu Ser Cys Ala Ala Ser Gly Phe Thr
            660                 665                 670

Phe Ser Asp Tyr Val Met Thr Trp Val Arg Gln Ala Pro Gly Lys Gly
            675                 680                 685

Pro Glu Trp Ile Ala Thr Ile Asn Thr Asp Gly Ser Thr Met Arg Asp
            690                 695                 700

Asp Ser Thr Lys Gly Arg Phe Thr Ile Ser Arg Asp Asn Ala Lys Asn
705                 710                 715                 720

Thr Leu Tyr Leu Gln Met Thr Ser Leu Lys Pro Glu Asp Thr Ala Leu
            725                 730                 735

Tyr Tyr Cys Ala Arg Gly Arg Val Ile Ser Ala Ser Ala Ile Arg Gly
            740                 745                 750
```

```
Ala Val Arg Gly Pro Gly Thr Gln Val Thr Val Ser Ser Glu Pro Lys
            755                 760                 765

Thr Pro Lys Pro Gln Pro Ala Arg Gln Gly Ala Pro Val Pro Tyr Pro
    770                 775                 780

Asp Pro Leu Glu Pro Arg Gly Gly Ser Asp Ile Cys Leu Pro Arg
785                 790                 795                 800

Trp Gly Cys Leu Trp Glu Asp
                805
```

<210> SEQ ID NO 171
<211> LENGTH: 289
<212> TYPE: PRT
<213> ORGANISM: Artificial Sequence
<220> FEATURE:
<223> OTHER INFORMATION: The amino acid was designed and synthesized

<400> SEQUENCE: 171

```
Gln Gly Val Gln Ser Gln Leu Gln Leu Val Glu Ser Gly Gly Gly Leu
1               5                   10                  15

Val Gln Pro Gly Gly Ser Leu Arg Leu Ser Cys Ala Ala Ser Gly Phe
            20                  25                  30

Thr Leu Asp Tyr Ser Ser Ile Gly Trp Phe Arg Gln Ala Pro Gly Lys
        35                  40                  45

Glu Arg Glu Gly Val Ser Cys Ile Ser Ser Ser Gly Asp Ser Thr Lys
50                  55                  60

Tyr Ala Asp Ser Val Lys Gly Arg Phe Thr Thr Ser Arg Asp Asn Ala
65                  70                  75                  80

Lys Asn Thr Val Tyr Leu Gln Met Asn Ser Leu Lys Pro Asp Asp Thr
                85                  90                  95

Ala Val Tyr Tyr Cys Ala Ala Phe Arg Ala Thr Met Cys Gly Val Phe
            100                 105                 110

Pro Leu Ser Pro Tyr Gly Lys Asp Asp Trp Gly Lys Gly Thr Leu Val
        115                 120                 125

Thr Val Ser Ser Glu Pro Lys Thr Pro Lys Pro Gln Gly Gly Gly Gly
130                 135                 140

Ser Gly Gly Gly Gly Ser Gly Gly Gly Gly Ser Gln Val Gln Leu Ser
145                 150                 155                 160

Gln Val Gln Leu Val Glu Ser Gly Gly Gly Leu Val Gln Pro Gly Gly
                165                 170                 175

Ser Leu Arg Leu Ser Cys Ala Ala Ser Gly Phe Thr Phe Ser Asp Tyr
            180                 185                 190

Val Met Thr Trp Val Arg Gln Ala Pro Gly Lys Gly Pro Glu Trp Ile
        195                 200                 205

Ala Thr Ile Asn Thr Asp Gly Ser Thr Met Arg Asp Asp Ser Thr Lys
210                 215                 220

Gly Arg Phe Thr Ile Ser Arg Asp Asn Ala Lys Asn Thr Leu Tyr Leu
225                 230                 235                 240

Gln Met Thr Ser Leu Lys Pro Glu Asp Thr Ala Leu Tyr Tyr Cys Ala
                245                 250                 255

Arg Gly Arg Val Ile Ser Ala Ser Ala Ile Arg Gly Ala Val Arg Gly
            260                 265                 270

Pro Gly Thr Gln Val Thr Val Ser Ser Glu Pro Lys Thr Pro Lys Pro
        275                 280                 285

Gln
```

```
<210> SEQ ID NO 172
<211> LENGTH: 279
<212> TYPE: PRT
<213> ORGANISM: Artificial Sequence
<220> FEATURE:
<223> OTHER INFORMATION: The amino acid was designed and synthesized

<400> SEQUENCE: 172
```

Gln Gly Val Gln Ser Gln Leu Gln Leu Val Glu Ser Gly Gly Gly Leu
1               5                   10                  15

Val Gln Pro Gly Gly Ser Leu Arg Leu Ser Cys Glu Ala Ser Gly Phe
            20                  25                  30

Thr Leu Asp Tyr Tyr Gly Ile Gly Trp Phe Arg Gln Pro Pro Gly Lys
        35                  40                  45

Glu Arg Glu Ala Val Ser Tyr Ile Ser Ala Ser Ala Arg Thr Ile Leu
    50                  55                  60

Tyr Ala Asp Ser Val Lys Gly Arg Phe Thr Ile Ser Arg Asp Asn Ala
65                  70                  75                  80

Lys Asn Ala Val Tyr Leu Gln Met Asn Ser Leu Lys Arg Glu Asp Thr
                85                  90                  95

Ala Val Tyr Tyr Cys Ala Arg Arg Arg Phe Ser Ala Ser Ser Val Asn
            100                 105                 110

Arg Trp Leu Ala Asp Asp Tyr Asp Val Trp Gly Arg Gly Thr Gln Val
        115                 120                 125

Ala Val Ser Ser Glu Pro Lys Thr Pro Lys Pro Gln Gly Gly Gly Gly
    130                 135                 140

Ser Gly Gly Gly Ser Gly Gly Gly Ser Gln Gly Val Gln Ser
145                 150                 155                 160

Gln Val Gln Leu Val Glu Ser Gly Gly Gly Leu Val Gln Thr Gly Gly
                165                 170                 175

Ser Leu Arg Leu Ser Cys Ala Ser Ser Gly Ser Ile Ala Gly Phe Glu
            180                 185                 190

Thr Val Thr Trp Ser Arg Gln Ala Pro Gly Lys Ser Leu Gln Trp Val
        195                 200                 205

Ala Ser Met Thr Lys Thr Asn Asn Glu Ile Tyr Ser Asp Ser Val Lys
    210                 215                 220

Gly Arg Phe Ile Ile Ser Arg Asp Asn Ala Lys Asn Thr Val Tyr Leu
225                 230                 235                 240

Gln Met Asn Ser Leu Lys Pro Glu Asp Thr Gly Val Tyr Phe Cys Lys
                245                 250                 255

Gly Pro Glu Leu Arg Gly Gln Gly Ile Gln Val Thr Val Ser Ser Glu
            260                 265                 270

Pro Lys Thr Pro Lys Pro Gln
        275

```
<210> SEQ ID NO 173
<211> LENGTH: 583
<212> TYPE: PRT
<213> ORGANISM: Artificial Sequence
<220> FEATURE:
<223> OTHER INFORMATION: The amino acid was designed and synthesized

<400> SEQUENCE: 173
```

Gln Gly Val Gln Ser Gln Leu Gln Leu Val Glu Ser Gly Gly Gly Leu
1               5                   10                  15

Val Gln Pro Gly Gly Ser Leu Arg Leu Ser Cys Ala Ala Ser Gly Phe
            20                  25                  30

```
Thr Leu Asp Tyr Ser Ser Ile Gly Trp Phe Arg Gln Ala Pro Gly Lys
             35                  40                  45

Glu Arg Glu Gly Val Ser Cys Ile Ser Ser Gly Asp Ser Thr Lys
 50                  55                  60

Tyr Ala Asp Ser Val Lys Gly Arg Phe Thr Thr Ser Arg Asp Asn Ala
 65                  70                  75                  80

Lys Asn Thr Val Tyr Leu Gln Met Asn Ser Leu Lys Pro Asp Asp Thr
                 85                  90                  95

Ala Val Tyr Tyr Cys Ala Ala Phe Arg Ala Thr Met Cys Gly Val Phe
                100                 105                 110

Pro Leu Ser Pro Tyr Gly Lys Asp Asp Trp Gly Lys Gly Thr Leu Val
                115                 120                 125

Thr Val Ser Ser Glu Pro Lys Thr Pro Lys Pro Gln Gly Gly Gly
130                 135                 140

Ser Gly Gly Gly Gly Ser Gly Gly Gly Ser Gln Gly Val Gln Ser
145                 150                 155                 160

Gln Leu Gln Leu Val Glu Ser Gly Gly Leu Val Gln Pro Gly Gly
                165                 170                 175

Ser Leu Arg Leu Ser Cys Glu Ala Ser Gly Phe Thr Leu Asp Tyr Tyr
                180                 185                 190

Gly Ile Gly Trp Phe Arg Gln Pro Pro Gly Lys Glu Arg Glu Ala Val
                195                 200                 205

Ser Tyr Ile Ser Ala Ser Ala Arg Thr Ile Leu Tyr Ala Asp Ser Val
                210                 215                 220

Lys Gly Arg Phe Thr Ile Ser Arg Asp Asn Ala Lys Asn Ala Val Tyr
225                 230                 235                 240

Leu Gln Met Asn Ser Leu Lys Arg Glu Asp Thr Ala Val Tyr Tyr Cys
                245                 250                 255

Ala Arg Arg Arg Phe Ser Ala Ser Ser Val Asn Arg Trp Leu Ala Asp
                260                 265                 270

Asp Tyr Asp Val Trp Gly Arg Gly Thr Gln Val Ala Val Ser Ser Glu
                275                 280                 285

Pro Lys Thr Pro Lys Pro Gln Gly Gly Gly Ser Gly Gly Gly
                290                 295                 300

Ser Gly Gly Gly Gly Ser Gln Gly Val Gln Ser Gln Val Gln Leu Val
305                 310                 315                 320

Glu Ser Gly Gly Gly Leu Val Gln Thr Gly Gly Ser Leu Arg Leu Ser
                325                 330                 335

Cys Ala Ser Ser Gly Ser Ile Ala Gly Phe Glu Thr Val Thr Trp Ser
                340                 345                 350

Arg Gln Ala Pro Gly Lys Ser Leu Gln Trp Val Ala Ser Met Thr Lys
                355                 360                 365

Thr Asn Asn Glu Ile Tyr Ser Asp Ser Val Lys Gly Arg Phe Ile Ile
                370                 375                 380

Ser Arg Asp Asn Ala Lys Asn Thr Val Tyr Leu Gln Met Asn Ser Leu
385                 390                 395                 400

Lys Pro Glu Asp Thr Gly Val Tyr Phe Cys Lys Gly Pro Glu Leu Arg
                405                 410                 415

Gly Gln Gly Ile Gln Val Thr Val Ser Ser Glu Pro Lys Thr Pro Lys
                420                 425                 430

Pro Gln Gly Gly Gly Ser Gly Gly Gly Gly Ser Gly Gly Gly Gly
                435                 440                 445
```

-continued

```
Ser Gln Gly Val Gln Ser Gln Val Gln Leu Val Glu Ser Gly Gly Gly
    450                 455                 460

Leu Val Gln Pro Gly Gly Ser Leu Arg Leu Ser Cys Ala Ala Ser Gly
465                 470                 475                 480

Phe Thr Phe Ser Asp Tyr Val Met Thr Trp Val Arg Gln Ala Pro Gly
                485                 490                 495

Lys Gly Pro Glu Trp Ile Ala Thr Ile Asn Thr Asp Gly Ser Thr Met
                500                 505                 510

Arg Asp Asp Ser Thr Lys Gly Arg Phe Thr Ile Ser Arg Asp Asn Ala
                515                 520                 525

Lys Asn Thr Leu Tyr Leu Gln Met Thr Ser Leu Lys Pro Glu Asp Thr
                530                 535                 540

Ala Leu Tyr Tyr Cys Ala Arg Gly Arg Val Ile Ser Ala Ser Ala Ile
545                 550                 555                 560

Arg Gly Ala Val Arg Gly Pro Gly Thr Gln Val Thr Val Ser Ser Glu
                565                 570                 575

Pro Lys Thr Pro Lys Pro Gln
                580

<210> SEQ ID NO 174
<211> LENGTH: 135
<212> TYPE: PRT
<213> ORGANISM: Artificial Sequence
<220> FEATURE:
<223> OTHER INFORMATION: The amino acid sequence was designed and
      synthesized

<400> SEQUENCE: 174

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Ser
                20                  25                  30

Ser Ile Gly Trp Phe Arg Gln Ala Pro Gly Lys Glu Arg Glu Gly Val
            35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
                100                 105                 110

Gly Lys Asp Asp Trp Gly Lys Gly Thr Leu Val Thr Val Ser Ser Glu
            115                 120                 125

Pro Lys Thr Pro Lys Pro Gln
            130                 135
```

METHODS, COMPOSITIONS AND KITS FOR TREATING A SUBJECT USING A RECOMBINANT NEUTRALIZING BINDING PROTEIN

RELATED APPLICATIONS

This application is a continuation of application U.S. Ser. No. 15/191,739, filed Jun. 24, 2016, now U.S. Pat. No. 10,202,441, which is a continuation of International PCT Application No. PCT/US14/72340, filed Dec. 24, 2014, which claims priority to and benefit of U.S. provisional application 61/920,825, filed Dec. 26, 2013, the contents of each of which are incorporated by reference herein in their entireties. International PCT Application No. PCT/US14/72340 is related to prior U.S. utility application U.S. Ser. No. 13/566,524, filed Aug. 3, 2012, now U.S. Pat. No. 9,023,352, issued May 5, 2015, and to U.S. provisional application 61/809,685, filed Apr. 8, 2013, the entire contents of both of which are incorporated by reference herein.

STATEMENT REGARDING FEDERALLY SPONSORED RESEARCH OR DEVELOPMENT

This invention was made with government support under grant AI057159 awarded by the National Institutes of Health. The government has certain rights in the invention.

TECHNICAL FIELD

The present invention relates to, in part, compositions, methods, and kits using a recombinant neutralizing binding protein for treating a subject at risk for exposure or exposed to a disease agent.

BACKGROUND

*Clostridium difficile* infections cause serious disease with increasing incidence worldwide. The infections occur primarily in hospitals and longterm care facilities in patients receiving prolonged antibiotic treatments. The disease symptoms may result from production and release by *C. difficile* organisms of two toxins, TcdA and TcdB in the colon.

A need exists for generating high affinity binding agents that treat both routine incidents of disease and pandemics, and efforts to discover and produce these agents are underway. The production of antibodies and their storage is a costly and lengthy process. In fact, development of a single antibody therapeutic agent often requires years of clinical study. Yet multiple, different therapeutic antibodies are necessary for the effective treatment of patients exposed to a disease agent, an infection outbreak or a bio-terrorist assault. Developing and producing multiple antibodies that can bind to different targets (e.g. microbial pathogens, viral pathogens, toxins, and cancer cells) is often a difficult task because it involves separately producing, storing and transporting multiple antibodies for each pathogen or toxin. Production and stockpiling a sufficient amount of antibodies to protect large populations is a challenge and currently has not been achieved. The shelf life of antibodies is often relatively short (e.g., weeks or months), and accordingly freshly prepared batches of antibodies have to be produced to replace the expiring antibodies.

Accordingly, there is a need for a cost effective and efficient way to provide alternatives to current therapeutic agents. Further a need exists for alternative therapeutics that are easier to develop and produce, have a longer shelf life, and bind as a single agent to multiple targets on the same disease agent, as well as to different disease agents.

SUMMARY

An aspect of the invention provides a pharmaceutical composition for treating a subject exposed to at least one disease agent, such that the pharmaceutical composition includes at least one recombinant binding protein that neutralizes the one or more disease agents and treats the subject for exposure to the disease agent, such that the binding protein includes at least one disease agent binding domain amino acid sequence, for example, selected from the group of:

```
                                     (SEQ ID NO: 174)
QVQLVESGGGLVQPGGSLRLSCAASGFTLDYSSIGWFRQAPGKEREGV

SCISSSGDSTKYADSVKGRFTTSRDNAKNTVYLQMNSLKPDDTAVYYC

AAFRATMCGVFPLSPYGKDDWGKGTLVTVSSEPKTPKPQ;

(SEQ ID NO: 164)
QLQLVESGGGLVQPGGSLRLSCEASGFTLDYYGIGWFRQPPGKEREAV

SYISASARTILYADSVKGRFTISRDNAKNAVYLQMNSLKREDTAVYYC

ARRRFSASSVNRWLADDYDVWGRGTQVAVSSEPKTPKPQ;

(SEQ ID NO: 165)
QVQLVESGGGLVQTGGSLRLSCASSGSIAGFETVTWSRQAPGKSLQWV

ASMTKTNNEIYSDSVKGRFIISRDNAKNTVYLQMNSLKPEDTGVYFCK

GPELRGQGIQVTVSSEPKTPKPQ;
and
                                     (SEQ ID NO: 166)
QVQLVESGGGLVQPGGSLRLSCAASGFTFSDYVMTWVRQAPGKGPEWI

ATINTDGSTMRDDSTKGRFTISRDNAKNTLYLQMTSLKPEDTALYYCA

RGRVISASAIRGAVRGPGTQVTVSSEPKTPKPQ.
```

In certain embodiments of the pharmaceutical composition comprises SEQ ID NO:167

```
                                     (SEQ ID NO: 167)
METDTLLLWVLLLWVPGSTGDAAQPARRARRTKLSGAPVPYPDPLEPR

AAAQVQLVESGGGLVQPGGSLRLSCAASGFTLDYSSIGWFRQAPGKER

EGVSCISSSGDSTKYADSVKGRFTTSRDNAKNTVYLQMNSLKPDDTAV

YYCAAFRATMCGVFPLSPYGKDDWGKGTLVTVSSEPKTPKPQPTSAIA

GGGGSGGGGSGGGGSAAAQLQLVESGGGLVQPGGSLRLSCEASGFTLD

YYGIGWFRQPPGKEREAVSYISASARTILYADSVKGRFTISRDNAKNA

VYLQMNSLKREDTAVYYCARRRFSASSVNRWLADDYDVWGRGTQVAVS

SEPKTPKPQTSALVGGGGSGGGGSGGGGSLQAMAAAQVQLVESGGGLV

QTGGSLRLSCASSGSIAGFETVTWSRQAPGKSLQWVASMTKTNNEIYS

DSVKGRFIISRDNAKNTVYLQMNSLKPEDTGVYFCKGPELRGQGIQVT

VSSEPKTPKPQAIAGGGGSGGGGSGGGGSLQGQVQLVESGGGLVQPGG

SLRLSCAASGFTFSDYVMTWVRQAPGKGPEWIATINTDGSTMRDDSTK

GRFTISRDNAKNTLYLQMTSLKPEDTALYYCARGRVISASAIRGAVRG

PGTQVTVSSEPKTPKPQPARQGAPVPYPDPLEPRGGGSDICLPRWGCL

WED,
```
or variants thereof.

In some embodiments, the pharmaceutical composition comprises a dimer of one or more of a *C. difficile* A toxin-binding protein and a *C. difficile* B toxin-binding protein. In certain embodiments, the pharmaceutical composition comprises a dimer of AH3 and AA6 or 5D and E3. In certain embodiments, the pharmaceutical composition comprises the amino acids sequences of SEQ ID NOs: 171 and/or 172. In some embodiments, the pharmaceutical composition comprises a tetramer of one or more of a *C. difficile* A toxin-binding protein and a *C. difficile* B toxin-binding protein. In certain embodiments, the pharmaceutical composition comprises a tetramer of AH3, AA6, 5D, and E3. In certain embodiments, the pharmaceutical composition comprises the amino acids sequence of SEQ ID NO: 173. In various embodiments, the dimers or tetramers further comprise a linker of SEQ ID NO: 55.

In some embodiments, the present compositions, methods, and kits include the following sequence:

```
(SEQ ID NO: 171, dimer of AH3-AA6)
QGVQSQLQLVESGGGLVQPGGSLRLSCAASGFTLDYSSIGWFRQAPGK

EREGVSCISSSGDSTKYADSVKGRFTTSRDNAKNTVYLQMNSLKPDDT

AVYYCAAFRATMCGVFPLSPYGKDDWGKGTLVTVSSEPKTPKPQGGGG

SGGGGSGGGGSQGVQSQVQLVESGGGLVQPGGSLRLSCAASGFTFSDY

VMTWVRQAPGKGPEWIATINTDGSTMRDDSTKGRFTISRDNAKNTLYL

QMTSLKPEDTALYYCARGRVISASAIRGAVRGPGTQVTVSSEPKTPKP

Q.
```

In some embodiments, the present compositions, methods, and kits include the following sequence:

```
(SEQ ID NO: 172, dimer of 5D-E3)
QGVQSQLQLVESGGGLVQPGGSLRLSCEASGFTLDYYGIGWFRQPPGK

EREAVSYISASARTILYADSVKGRFTISRDNAKNAVYLQMNSLKREDT

AVYYCARRRFSASSVNRWLADDYDVWGRGTQVAVSSEPKTPKPQGGGG

SGGGGSGGGGSQGVQSQVQLVESGGGLVQTGGSLRLSCASSGSIAGFE

TVTWSRQAPGKSLQWVASMTKTNNEIYSDSVKGRFIISRDNAKNTVYL

QMNSLKPEDTGVYFCKGPELRGQGIQVTVSSEPKTPKPQ.
```

In some embodiments, the present compositions, methods, and kits include the following sequence:

```
(SEQ ID NO: 173, tetramer of AH3, 5D, E3, AA6)
QGVQSQLQLVESGGGLVQPGGSLRLSCAASGFTLDYSSIGWFRQAPGK

EREGVSCISSSGDSTKYADSVKGRFTTSRDNAKNTVYLQMNSLKPDDT

AVYYCAAFRATMCGVFPLSPYGKDDWGKGTLVTVSSEPKTPKPQGGGG

SGGGGSGGGGSQGVQSQLQLVESGGGLVQPGGSLRLSCEASGFTLDYY

GIGWFRQPPGKEREAVSYISASARTILYADSVKGRFTISRDNAKNAVY

LQMNSLKREDTAVYYCARRRFSASSVNRWLADDYDVWGRGTQVAVSSE

PKTPKPQGGGGSGGGGSGGGGSQGVQSQVQLVESGGGLVQTGGSLRLS

CASSGSIAGFETVTWSRQAPGKSLQWVASMTKTNNEIYSDSVKGRFII

SRDNAKNTVYLQMNSLKPEDTGVYFCKGPELRGQGIQVTVSSEPKTPK

PQGGGGSGGGGSGGGGSQGVQSQVQLVESGGGLVQPGGSLRLSCAASG

FTFSDYVMTWVRQAPGKGPEWIATINTDGSTMRDDSTKGRFTISRDNA

KNTLYLQMTSLKPEDTALYYCARGRVISASAIRGAVRGPGTQVTVSSE

PKTPKPQ.
```

In certain embodiments of the pharmaceutical composition, the binding protein includes at least one Vh domain corresponding to heavy chain-only camelid antibodies. For example, the recombinant binding protein includes at least three Vh disease agent-binding domains. In certain embodiments, the three disease agent binding domains include at least two of the amino acid sequences selected from the group of: SEQ ID NO: 174, SEQ ID NO: 164, SEQ ID NO: 165, SEQ ID NO: 166, SEQ ID NO: 167, SEQ ID NO: 171, SEQ ID NO: 172, and, SEQ ID NO: 173 or variants thereof. In certain embodiments, each of the disease agent binding domains is separated from another disease agent binding site by flexible spacer amino acid sequences. For example, the flexible spacer amino acid sequence includes amino acid sequence: GGGGSGGGGSGGGGS (SEQ ID NO: 55), or a variant thereof. In certain embodiments, the recombinant binding protein includes a plurality of disease agent binding domains that bind and neutralize toxin A of *Clostridium difficile* (TcdA). In certain embodiments, the recombinant binding protein includes a plurality of disease agent binding domains that bind and neutralize toxin B of *Clostridium difficile* (TcdB).

In some embodiments, the pharmaceutical composition comprises a dimer of one or more of a *C. difficile* A toxin-binding protein and a *C. difficile* B toxin-binding protein. In certain embodiments, the pharmaceutical composition comprises a dimer of AH3 and AA6 or 5D and E3. In certain embodiments, the pharmaceutical composition comprises the amino acids sequences of SEQ ID NOs: 171 and/or 172. In some embodiments, the pharmaceutical composition comprises a tetramer of one or more of a *C. difficile* A toxin-binding protein and a *C. difficile* B toxin-binding protein. In certain embodiments, the pharmaceutical composition comprises a tetramer of AH3, AA6, 5D, and E3. In certain embodiments, the pharmaceutical composition comprises the amino acids sequence of SEQ ID NO: 173. In certain embodiments, the pharmaceutical composition comprises the amino acids sequence of SEQ ID NO: 167. In various embodiments, the dimers or tetramers further comprise a linker of SEQ ID NO: 55.

In an embodiment of the pharmaceutical composition, the recombinant binding protein includes an epitope tag amino acid sequence. For example, the recombinant binding protein includes a plurality of copies of epitope tag SEQ 11) NO: 15, or a variant thereof. In an embodiment of the pharmaceutical composition, the recombinant binding protein carboxyl terminus includes an albumin binding domain amino acid sequence. For example, the albumin binding domain comprises amino acid sequence DICLPRWGCL-WED (SEQ ID NO: 168), or a variant thereof. In an embodiment of the pharmaceutical composition, the recombinant binding protein amino terminus includes an *E. coli* thioredoxin. In certain embodiments, the recombinant binding protein has a cleavage site between the *E. coli* thioredoxin protein amino acid sequence and an adjacent disease agent binding domain.

In certain embodiments of the pharmaceutical composition, the disease agent includes a first and second non-identical disease agent, and the binding protein binds and neutralizes the first and the second of disease agents. In certain embodiments of the pharmaceutical composition, the disease agent includes a *Clostridium difficile* toxin.

An aspect of the invention provides a pharmaceutical composition for treating a subject at risk for exposure to at least one disease agent, the pharmaceutical composition including: a source of expression of a recombinant disease agent binding protein for neutralizing the disease agent and treating the subject for exposure, wherein the source of expression comprises nucleotide sequence:

(SEQ ID NO: 169)
ATGAGCGATAAAATTATTCACCTGACTGACGACAGTTTTGACACGGATGT

ACTCAAAGCGGACGGGGCGATCCTCGTCGATTTCTGGGCAGAGTGGTGCG

GTCCGTGCAAAATGATCGCCCCGATTCTGGATGAAATCGCTGACGAATAT

CAGGGCAAACTGACCGTTGCAAAACTGAACATCGATCAAAACCCTGGCAC

TGCGCCGAAATATGGCATCCGTGGTATCCCGACTCTGCTGCTGTTCA, or a variant thereof.

An aspect of the invention provides a kit for treating a subject exposed to or at risk for exposure to a disease agent including: a unit dosage of a pharmaceutical composition for treating a subject at risk for exposure to at least one disease agent such that, the pharmaceutical composition includes: at least one recombinant binding protein that neutralizes the disease agent thereby treating the subject for exposure to the disease agent, wherein the binding protein comprises at least one amino acid sequence selected from the group of: SEQ ID NO: 174, SEQ ID NO: 164, SEQ ID NO: 165, SEQ ID NO: 166, and SEQ ID NO: 167, or variants thereof; a container; and instructions for use. In certain embodiments, the pharmaceutical composition includes a pharmaceutically acceptable excipient. In certain embodiments of the kit, the disease agent includes a *Clostridium difficile* toxin. In certain embodiments of the kit, the disease agent comprises a first and a second non-identical disease agent, and the binding protein binds and neutralizes the first and the second disease agent. In certain embodiments of the kit, the pharmaceutical composition includes a plurality of the disease agent binding domains that bind and neutralize toxin A of *Clostridium difficile* (TcdA). In certain embodiments of the kit, the pharmaceutical composition includes a plurality of the disease agent binding domains that bind and neutralize toxin B of *Clostridium difficile* (TcdB). In some embodiments, the kit comprises a dimer of one or more of a *C. difficile* A toxin-binding protein and a *C. difficile* B toxin-binding protein. In certain embodiments, the kit comprises a dimer of AH3 and AA6 or 5D and E3. In certain embodiments, the kit comprises the amino acids sequences of SEQ ID NOs: 171 and/or 172. In some embodiments, the kit comprises a tetramer of one or more of a *C. difficile* A toxin-binding protein and a *C. difficile* B toxin-binding protein. In certain embodiments, the kit comprises a tetramer of AH3, AA6, 5D, and E3. In certain embodiments, the kit comprises the amino acids sequence of SEQ ID NO: 173. In various embodiments, the dimers or tetramers further comprise a linker of SEQ ID NO: 55.

An aspect of this invention provides a method for treating a subject at risk for exposure to at least one disease agent, such that the method includes administering to the subject a source of expression of a recombinant disease agent binding protein, wherein the source of expression of the binding protein is a nucleotide sequence encoding the binding protein, the nucleotide sequence comprising SEQ ID NO: 169, or a variant thereof; and measuring neutralization of the disease agent or plurality of disease agents by the binding protein.

An aspect of the invention provides a pharmaceutical composition for treating a subject exposed to at least one disease agent, the pharmaceutical composition including: at least one recombinant binding protein that neutralizes the disease agent and treats the subject for exposure to the disease agent, such that the binding protein includes at least one disease agent binding domain amino acid sequence selected from the group of: SEQ ID NO: 174, SEQ ID NO: 164, SEQ ID NO: 165, SEQ ID NO: 166, and SEQ ID NO:167; and further includes amino acid sequence SEQ ID NO: 168, or variants thereof.

An aspect of the invention provides a pharmaceutical composition for treating a subject exposed to at least one disease agent, the pharmaceutical composition including at least one recombinant binding protein that neutralizes the disease agent and treats the subject for exposure to the disease agent, such that the binding protein includes at least one disease agent binding domain amino acid sequence selected from the group of: SEQ ID NO: 174, SEQ ID NO: 164, SEQ ID NO: 165, SEQ ID NO: 166, and SEQ ID NO:167; and further including amino acid sequence SEQ ID NO: 53, or variants thereof.

In some embodiments, there is provided a method of treating or preventing a *C. difficile* infection (CDI) or associated disease as described herein comprising administering to a patient in need thereof an effective amount of a pharmaceutical composition comprising at least one recombinant binding protein comprising at least one disease agent binding domain amino acid sequence selected from SEQ ID NO: 174, SEQ ID NO: 164, SEQ ID NO: 165, SEQ ID NO: 166 SEQ ID NO: 167, SEQ ID NO: 171, SEQ ID NO: 172, and SEQ ID NO: 173 or variants thereof. In some embodiments, the recombinant binding protein comprising at least one disease agent binding domain comprises a recombinant camelid heavy-chain-only antibody (VHH). In some embodiments, the patient in need of such treatment is receiving or will receive treatment with one or more antibiotics.

The sequence listing material in computer readable form ASCII text file (220 kilobytes) created 05/26/2016 entitled "34724171_SeqListing_ST25", containing sequence listings numbers 1-174, has been electronically filed herewith and is incorporated by reference herein in its entirety.

BRIEF DESCRIPTION OF THE DRAWINGS

FIG. 1 A-FIG. 1 E are nucleotide sequences of scFv #2 (SEQ ID NO: 1), scFv #3 (SEQ ID NO: 3), scFv #7 (SEQ ID NO: 5), scFv #8 (SEQ ID NO: 7), scFv #21 (SEQ ID NO: 9), scFv # E (SEQ ID NO: 11), and amino acid sequences of scFv #2 (SEQ ID NO: 2), scFv #3 (SEQ ID NO: 4), scFv #7 (SEQ ID NO: 6), scFv #8 (SEQ ID NO: 8), scFv #21 (SEQ ID NO: 10), scFv # E (SEQ ID NO: 12).

FIG. 2 is the nucleotide sequence of scFv #7-2E (SEQ ID NO: 13) and the amino acid sequence of scFv #7-2E (SEQ ID NO: 14).

FIG. 3 A-FIG. 3 C are the nucleotide sequences of BoNT/A holotoxin binding VHHs including JDA-D12 (SEQ ID NO: 19), JDQ-A5 (SEQ ID NO: 21), JDQ-B5 (SEQ ID NO: 23), JDQ-C2 (SEQ ID NO: 25), JDQ-F12 (SEQ ID NO: 27), JDQ-G5 (SEQ ID NO: 29), JDQ-H7 (SEQ ID NO: 31), and BoNT/B holotoxin binding VHHs including JEQ-A5 (SEQ ID NO: 33), JEQ-H11 (SEQ ID NO: 35). The figures also show the corresponding amino acid sequences of BoNT/A holotoxin binding VHHs including JDA-D12 (SEQ ID NO: 20), JDQ-A5 (SEQ ID NO: 22), JDQ-B5 (SEQ ID NO: 24), JDQ-C2 (SEQ ID NO: 26), JDQ-F12 (SEQ ID NO: 28), JDQ-G5 (SEQ ID NO: 30), JDQ-H7 (SEQ ID NO: 32), and BoNT/B holotoxin binding VHHs including JEQ-A5 (SEQ ID NO: 34), JEQ-H11 (SEQ ID NO: 36).

FIG. 4 A is a set of three nucleotide sequences of VHHs identified as BoNT/A binders that were experimentally shown to bind to the same epitope, and the set of three corresponding VHH amino acid sequences. The VHH sequences are DQ-B5 (SEQ ID NO: 23), JDO-E9 (SEQ ID NO: 37), and JDQ-B2 (SEQ ID NO: 39), and the corresponding VHH amino acid sequences are JDQ-B5 (SEQ ID NO: 24), JDO-E9 (SEQ ID NO: 38), and JDQ-B2 (SEQ ID NO: 40).

FIG. 4 B is a set of two nucleotide sequences of VHHs identified as BoNT/A binders that were experimentally shown to bind to the same epitope, and the set of two corresponding VHH amino acid sequences. The VHH sequences are JDQ-05 (SEQ ID NO: 41), and JDQ-F9 (SEQ ID NO: 43), and, the corresponding VHH amino acid sequences are JDQ-05 (SEQ ID NO: 42), and JDQ-F9 (SEQ ID NO: 44).

FIG. 5 is a schematic drawing of a phylogenetic tree comparing the homology between BoNT/A binding VHHs within the JDQ-B5 competition group (which compete for binding, thus bind the same epitope) in comparison to control alpaca VHHs.

FIG. 6 is a schematic drawing of binding agent VHHs that are produced in different formats including formats in which the binding agents are fused to one or more E-tags or as fusion proteins.

FIG. 7 is a drawing of a single-tagged heterodimeric binding protein (exemplary VHHs) binding to the disease agent, a toxin, and leading to decoration of the toxin with two anti-tag monoclonal antibodies (mAbs).

FIG. 8 is a drawing of a double-tagged binding protein (here shown are VHHs) a heterodimeric binding to the disease agent, toxin, and leading to decoration of the toxin with four anti-tag mAbs.

FIG. 9 A-FIG. 9 B are a set of Meyer-Kaplan survival plots that double-tagged heterodimer E/H7/B5/E and the anti-tag mAb completely protected subjects from 1,000-fold and 1,000-fold the median lethal dose of a Botulinum neurotoxin serotype A toxin.

FIG. 9 A is a Meyer-Kaplan survival plot showing percent (%) of mice surviving over a period of time (days) after receiving 1,000-fold the median lethal dose ($LD_{50}$) of a Botulinum neurotoxin serotype A (BoNT/A) and each of combinations of the following binding agents: H7 and B5 VHH heterodimer with a single epitopic tag (tag or E-tag) and an anti-E-tag mAb (H7/B5/E+anti-E mAb); H7 and B5 VHH monomers each with an E-tag and an anti-E-tag mAb (H7/E+B5/E+anti-E mAb); H7 and B5 VHH heterodimer with two E-tags and an anti-E-tag mAb (E/H7/B5/E+anti-E mAb) and a control (the toxin alone). The data show that administration of heterodimer E/H7/B5/E and anti-E mAb resulted in survival of subjects for seven days.

FIG. 9 B is a Meyer-Kaplan survival plot showing percent (%) of subjects surviving over a period of time (days) after receiving 10,000-fold the $LD_{50}$ of a Botulinum neurotoxin (BoNT) and H7 and B5 VHH heterodimer with two E-tags and an anti-E-tag mAb (E/H7/B5/E+anti-E mAb) and a control (the toxin alone). Remarkably, 100% of the mice survived a 10,000 $LD_{50}$ challenge of BoNT/A when administered the double-tagged heterodimer and the anti-tag mAb.

FIG. 10 A-FIG. 10 B are nucleotide sequences and amino acid sequences of recombinant BoNT/A holotoxin binding VHHs: thioredoxin/JDQ-H7(H7)/E-tag (SEQ ID NO: 45), thioredoxin/JDQ-B5(B5)/E-tag (SEQ ID NO: 47), thioredoxin/H7/flexible spacer (fs)/B5/E-tag (SEQ ID NO: 49), and thioredoxin/E-tag/H7/fs/B5/E-tag (SEQ ID NO: 51). The corresponding amino acid sequences of the VHHs including amino acid sequences for thioredoxin/H7/E-tag (SEQ ID NO: 46), thioredoxin/B5/E-tag (SEQ ID NO: 48), thioredoxin/H7/fs/B5/E-tag (SEQ ID NO: 50), thioredoxin/E-tag/H7/fs/B5/E-tag (SEQ ID NO: 52), and thioredoxin (SEQ ID NO: 53) are shown.

FIG. 11 A-FIG. 11 B are Meyer-Kaplan survival plots showing percent survival (% survival, ordinate) of subjects as a function of time in days (abscissa) following contact with BoNT/A and later time (1.5 hours or three hours later) administered VHH binding/neutralizing agents. Subjects (five per group) were intravenously exposed to 10 $LD_{50}$ (ten-fold $LD_{50}$) of BoNT/A, and then later administered either: a mixture of 1 μg ciA-H7 monomer (SEQ ID NO: 32) and 1 μg of ciA-B5 monomer (SEQ ID NO: 24); H7/B5 heterodimeric protein (SEQ ID NO: 58); a sheep antitoxin serum; or control (no binding agent). Data show that the H7/B5 heterodimer was effective as an antitoxin neutralizing agent and protected subjects from the lethal challenge of BoNT/A.

FIG. 11 A shows percent survival for subjects exposed to ten-fold $LD_{50}$ of BoNT/A then administered 1.5 hours later either a mixture of H7 and B5 monomers; H7/B5 heterodimer; a sheep serum antitoxin; or control toxin only (no agents).

FIG. 11 B shows percent survival for subjects exposed to ten-fold $LD_{50}$ of BoNT/A then administered three hours later either a mixture of H7 and B5 monomers; H7/B5 heterodimer; a sheep serum antitoxin; or control toxin only (no agents).

FIG. 12 A is a line graph showing that VHH monomers neutralized C. difficile toxin B (TcdAB) and protected cells from the toxin. The percent CT26 cells affected by TcdB (% affected; ordinate) is shown as a function of concentration (0.003 nM, 0.03 nM, 0.3 nM, 3 nM, 30 nM, 300 nM, or 3000 nM) of administered VHH monomers: 5D (circle), 2D (square), or E3 (light upward facing triangle). Control cells were administered toxin only (TcdB; dark downward facing triangle). Strength of neutralizing VHH activity was observed in the order 5D as strongest followed by E3 and 2D.

FIG. 12 B is a line graph showing percent of cells affected by TcdB (% affected; ordinate) as a function of concentration of administered mixture of 5D and E3 monomers, 5D/E3 heterodimer (VHH; abscissa), or a toxin only control. It was observed that the 5D/E3 VHH heterodimer (squares) was about ten-fold more potent as toxin neutralizing agent than the mixture of 5D monomer and E3 monomer (triangles).

FIG. 12 C is a Meyer-Kaplan survival plot of a C. difficile infection model showing percent mouse survival (ordinate) as a function of time (hours post challenge, abscissa) of subjects co-administered toxin and VHH neutralizing agents. Subjects were co-administered a lethal dose of TcdB with: a mixture of 10 μg of 5D monomers and E3 monomers (5 μg of each monomer per mouse; dashed line, blue); a mixture of 1 μg of 5D monomers and E3 monomers (500 ng of each monomer per mouse; thick solid line, blue), 5D/E3 heterodimer (250 ng per mouse; light solid line, red), or phosphate-buffered saline (PBS; thin solid line, black). Percent survival was calculated for each group of subjects.

FIG. 13 A-FIG. 13 C are amino acid sequences for VHH monomers and VHH heterodimers designed to specifically bind epitopes of botulism toxins serotype A (BoNT/A) and serotype B (BoNT/B). Each VHH was purified from E. coli as a thioredoxin fusion protein having a single carboxyl-terminal epitopic tag (tag or E-tag).

FIG. 13 A is a set of amino acid sequences of VHH monomers that specifically recognize and bind to epitopes on BoNT/A (ciA-A5, ciA-B5, ciA-D12, ciA-F12, ciA-G5, and ciA-H7) and epitopes of BoNT/B (ciB-A11, ciB-B5, ciB-B9, and ciB-H11). The sequences are aligned to show homology. Dashed regions of the amino acid sequences are spaces inserted to align the amino acid regions.

FIG. 13 B is a set of amino acid sequences of VHH monomers (ciA-D1, ciA-H5, and ciA-H11) that bind specifically to the same epitope of BoNT/B as ciA-H7.

FIG. 13 C shows amino acid sequences for double-tagged VHH heterodimers, ciA-H7/ciA-B5(2E) and ciA-F12/CiA-D12(2E), that specifically bind BoNT/A.

FIG. 14 A shows SDS-PAGE analysis of the tagged (E) VHH monomers ciA-D1, ciA-H4, ciA-H11, ciA-A5, ciA-C2, ciA-D12, ciA-F12, ciA-G5, and ciA-H7.

FIG. 14 B is a SDS-PAGE analysis of single- or double-tagged VHH heterodimers including: ciA-H7/ciA-B5 singly tagged on ciA-B5 (left channel); double tagged ciA-H7/ciA-B5 having a tag on both ciA/H7 and ciA-B5 (second channel from left), ciA-F12/ciA-D12 singly tagged on ciA-B5 (third channel from the left); double tagged ciA-F12/ciA-D12 having a tag on both ciA/F12 and ciA-D12 (fourth channel from left), double tagged ciA-A11/ciA-B5 having a tag on both ciA/A11 and ciA-B5 (right channel).

FIG. 15 are photographs of Western blots showing ability of VHH monomers to prevent BoNT/A from cleaving synaptosomal-associated protein 25 (SNAP25) in primary neurons in culture.

FIG. 16 A-FIG. 16 C is a set of drawings and Meyer-Kaplan survival plots showing that mouse subjects administered each of a set of mixtures of VHH monomers in combination with anti-tag clearing antibody were protected from BoNT/A.

FIG. 16 A (top) is a drawing of a BoNT/A bound to two different tagged binding protein monomers that are each specifically bound by an anti-tag antibody. FIG. 16 A (bottom) is a set of graphs showing percent of survival (% survival, ordinate) as a function of time (days, abscissa) of subjects co-administered 100-fold (FIG. 16 A bottom left graph) or 1,000-fold (FIG. 16 A bottom right graph) the $LD_{50}$ of a BoNT/A and combinations of VHH monomers (ciA-D12 and ciA-F12) with or without anti-tag clearing antibody (+αE and −αE respectively). The mixture of VHH monomer B5, VHH monomer H7 and anti-tag clearing antibody protected subjects from the 100-fold LD50 of toxin.

FIG. 16 B (top) is a drawing of a BoNT/A bound to three different monomeric tagged binding protein each specifically bound by an anti-tag antibody. FIG. 16 B (bottom) is a set of graphs showing percent survival on the ordinate as a function of time (days, abscissa) of subjects co-administered 1,000-fold BoNT/A $LD_{50}$ (FIG. 16 B bottom left graph) or 10,000-fold BoNT/A $LD_{50}$ (FIG. 16 bottom B right graph), and combinations of three VHH monomers with or without anti-tag clearing antibody (+αE and −αE respectively).

FIG. 16 C (top) is a drawing of a BoNT/A bound to four different tagged binding protein monomers that are each specifically bound by an anti-tag antibody. FIG. 16 C (bottom) is a set of graphs showing percent survival, ordinate, of subjects as a function of time (days, abscissa) of subjects co-administered 1,000-fold BoNT/A $LD_{50}$ (FIG. 16 C bottom left graph) or 10,000-fold BoNT/A $LD_{50}$ (FIG. 16 C bottom right graph), and a mixture of ciA-B5, ciA-H7, ciA-D12 and ciA-F12 VHH monomers with (+αE) or without (−αE) anti-tag clearing antibody.

FIG. 18 A is a table showing binding affinities (Kd) determined by surface plasmon resonance (SPR) analysis of each of VHH monomers ciA-H7, ciA-D1, ciA-H4, and ciA-H11. SPR analysis was used to determine the binding affinities to epitope A1 of BoNT/A for each VHH monomer. H7 has the greatest affinity and H11 the least affinity.

FIG. 18 B is a set of graphs showing percent survival on the ordinate of subjects as a function of time (days, abscissa) following co-administration of BoNT/A at 100-fold (FIG. 18 B left graph) or 1,000-fold (FIG. 18 B right graph) the $LD_{50}$, and a mixture of two VHH monomers (B5+C2) or a mixture of three VHH monomers with anti-tag clearing antibody: B5+C2+H11; B5+C2+H7; B5+C2+D1; or B5+C2+H2.

FIG. 19 A-FIG. 19 B are drawings and graphs showing that administering heterodimers composed of neutralizing VHH components resulted in greater antitoxin efficacy than heterodimers composed of non-neutralizing VHHs, and that presence of two or more E-tags within the VHH heterodimers further increased the antitoxin efficacy.

FIG. 19 A (top) is a drawing of a BoNT/A bound to two different tagged heterodimer binding proteins that are each specifically bound by an anti-tag antibody. FIG. 19 A (bottom) is a set of graphs showing percent survival on the ordinate of subjects as a function of time (days, abscissa) after co-administration of 1,000-fold (FIG. 19 A bottom left graph) or 10,000-fold (FIG. 19 A bottom right graph) the BoNT/A $LD_{50}$, and a VHH heterodimer composition with (+αE) or without (−αE) anti-tag clearing antibody. The tagged VHH heterodimer composition was either composed of neutralizing VHHs ciA-H7 and ciA-B5 (H7/B5), or of non-neutralizing VHHs ciA-D12 and ciA-F12 (D12/F12). Data show that subjects administered the heterodimer composition containing neutralizing VHHs ciA-B5 and ciA-H7 survived longer than subjects administered the heterodimer composition containing non-neutralizing VHHs ciA-D12 and ciA-F12. Subjects administered clearing anti-tag antibodies generally survived longer than subjects not administered clearing-tag antibodies.

FIG. 19 B (top) is a drawing of a BoNT/A bound to two different double-tagged heterodimer binding proteins that are each specifically bound by two anti-tag antibodies. FIG. 19 B (bottom) is a set of graphs showing percent survival, ordinate, of subjects as a function of time (days, abscissa) after co-administration of an amount of BoNT/A 1,000-fold (FIG. 19 B bottom left graph) or 10,000-fold (FIG. 19 B bottom right graph) the $LD_{50}$, and double tagged VHH heterodimers with (+αE) or without (−αE) anti-tag clearing antibody. Subjects administered neutralizing ciA-B5/ciA-H7 heterodimer survived longer than subjects administered non-neutralizing ciA-D12/ciA-F12 heterodimer. Data show that all subjects administered double-tagged ciA-B5/ciA-H7 heterodimers and anti-tag clearing antibody survived exposure to 1,000-fold (FIG. 19 B bottom left graph) or 10,000-fold the $LD_{50}$ of BoNT/A (FIG. 19 B bottom right graph).

FIG. 21 is a set of graphs showing percent survival, ordinate, of subjects treated with different amounts of anti-tag clearing antibody as a function of time (days, abscissa) after exposure to BoNT/A 100-fold (FIG. 21 left graph) or 1,000-fold (FIG. 21 right graph) the $LD_{50}$ and to double tagged ciA-D12/ciA-F12 heterodimer (20 picomoles). Anti-tag clearing antibody was administered at: 20 picomoles, 40 picomoles, 60 picomoles, 120 picomoles, or control (none). Control subjects received toxin only (no agents). Data show improved antitoxin efficacy in subjects co-administered amounts (40, 60 or 120 picomoles) increased anti-tag clearing antibody compared to 20 picomoles.

FIG. 22 is a graph showing percent survival, ordinate, of subjects treated with different doses of double tagged neutralizing ciA-B5/ciA-H7 heterodimers as a function of time (days, abscissa) for subjects co-administered 1,000-fold BoNT/A $LD_{50}$, and anti-tag clearing antibody. Heterodimer ciA-B5/ciA-H7 was administered in doses of: 1.5 picomoles, 4.4 picomoles, 13 picomoles, or 40 picomoles. Control subjects received toxin only (no agents). Data show complete survival after seven days of subjects receiving amounts of 13 picomoles or 40 picomoles double tagged neutralizing ciA-B5/ciA-H7 heterodimer, such that than 13 picomoles protected subjects fully from 1,000-fold BoNT/A $LD_{50}$, compared to 1.5 picomoles or 4.4 picomoles (no survival after one day).

FIG. 23 A-FIG. 23 B are graphs showing percent survival, ordinate, after subjects were exposed to ten-fold BoNT/A $LD_{50}$ and were administered double-tagged heterodimer and anti-tag clearing antibody of subjects as a function of time (days, abscissa). Administration of heterodimer after toxin exposure was observed to have protected subjects from symptoms and death caused by exposure to ten-fold BoNT/A $LD_{50}$.

FIG. 23 A is a set of graphs showing percent survival of subjects as a function administration of: double tagged ciA-D12/ciA-F12 heterodimer with anti-tag clearing antibody (+αE), double tagged ciA-D12/ciA-F12 heterodimer without anti-tag clearing antibody (−αE), a sheep serum antitoxin, or toxin only control (no agents). Prior to administration of heterodimer, subjects were exposed 1.5 hours (FIG. 23 A left graph) or three hours (FIG. 23 A right graph) to ten-fold BoNT/A $LD_{50}$. Data show 100% survival of subjects administered ciA-D12/ciA-F12 heterodimer and anti-tag antibody after 1.5 hours. Survival of subjects administered ciA-D12/ciA-F12 heterodimer was comparable to that in subjects administered sheep serum antitoxin.

FIG. 23 B is a set of graphs showing percent survival of subjects as a function administration of: double tagged ciA-B5 and ciA-H7 heterodimer with anti-tag clearing antibody (+αE), or with double tagged ciA-B5/ciA-H7 heterodimer without anti-tag clearing antibody (−αE), or with a sheep serum antitoxin, or toxin only control (no agents). Prior to treatment with heterodimer, subjects were exposed to ten-fold BoNT/A $LD_{50}$ either 1.5 hours (FIG. 23 B left graph) or three hours (FIG. 23 B right graph). Data show that subjects administered ciA-B5/ciA-H7 heterodimer with or without anti-E tag antibody survived longer than subjects administered sheep serum antitoxin. Survival of subjects administered ciA-B5/ciA-H7 heterodimer was greater than subjects administered sheep serum antitoxin.

FIG. 24 A is a graph showing survival on the ordinate as a function of time (days, abscissa) co-administration of 1,000-fold (FIG. 24 A left graph) or 10,000-fold (FIG. 24 A right graph) BoNT/B $LD_{50}$ and a combination of ciB-A11 and ciB-B5 heterodimer with (+αE) or without (−αE) anti-tag clearing antibody, or toxin only control (no agents). Data show that subjects administered ciA-A11/ciA-B5 heterodimer and anti-E-tag clearing antibody survived and were protected longer from BoNT/A than control subjects administered no agents and no anti-E tag antibody.

FIG. 24 B is a set of graphs showing subject survival (ordinate) as a function of time, abscissa, after administration of: double tagged ciB-A11 and ciB-B5 heterodimer and anti-tag clearing antibody (+αE), or double tagged ciB-A11 and ciB-B5 heterodimer without anti-tag clearing antibody (−αE), a sheep serum antitoxin, or toxin only control. Following 1.5 hours (FIG. 24 B left graph) or three hours (FIG. 24 B right graph) exposure to ten-fold BoNT/B $LD_{50}$, the subjects were administered the heterodimer. A greater percentage of subjects administered ciB-A11 and ciB-B5 heterodimer survived exposure to BoNT/B than subjects administered sheep serum antitoxin.

containing AH3 and AA6 using a dimerizer sequence oAgB (AH3/AA6/oAgB, stars; SEQ ID NO: 95). Control cells were treated with medium only. Percent cell rounding was analyzed using a phase contrast microscope. It was observed that the homodimer of the heterodimer containing AH3 and AA6 resulted in the strongest TcdA neutralization.

Figure 27:
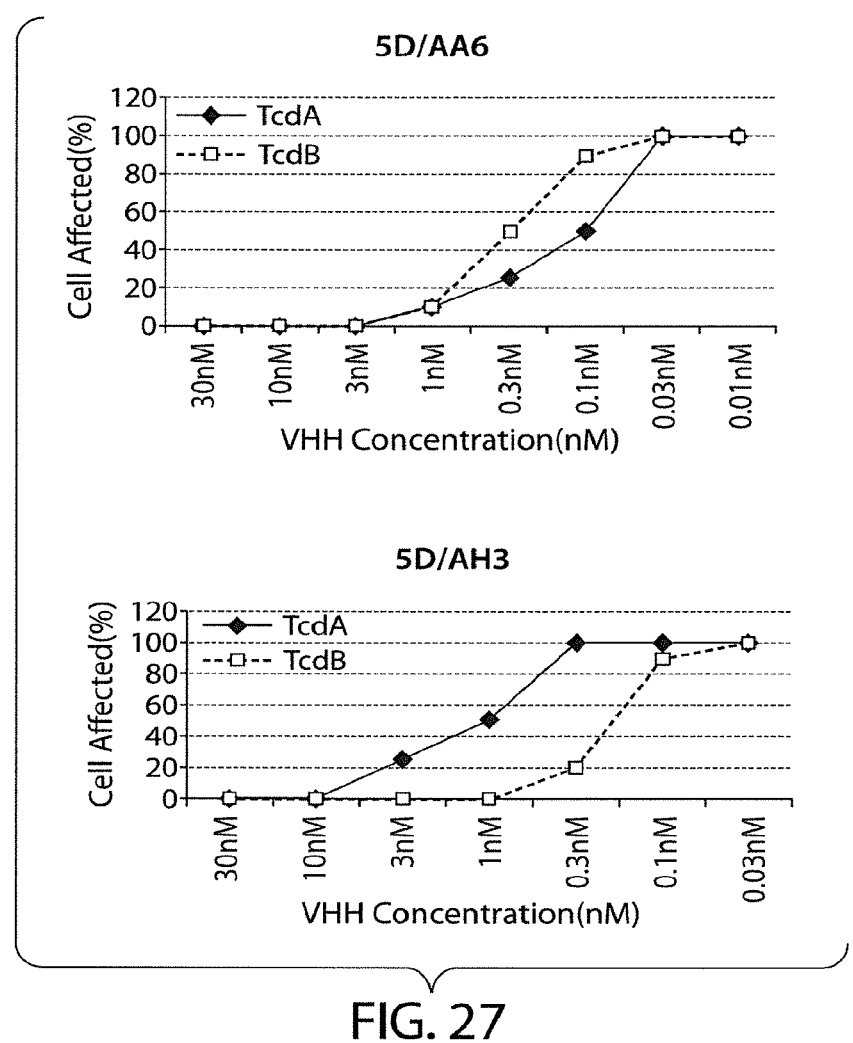

FIG. 27 is a set of line graphs showing percent affected CT26 cells exposed to toxin (ordinate) and then contacted with VHH heterodimer of 5D and AA6 (FIG. 27 top graph) or with heterodimer of 5D and AH3 (FIG. 27 bottom graph) as a function of concentration of VHH (abscissa: 0.01 nM, 0.03 nM, 0.1 nM, 0.3 nM, 1 nM, 3 nM, 10 nM, or 30 nM). CT26 cells were exposed overnight to TcdA (2 ng/mL; diamond) or TcdB (0.1 ng/mL; square), and then treated with either heterodimer 5D/AA6 (FIG. 27 top graph) or heterodimer 5D/AH3 (FIG. 27 bottom graph). Each heterodimer included a VHH monomer (5D) that neutralized TcdB, and a VHH monomer (AA6 or AH3) that neutralized TcdA. Data show that the treatment was effective to protect cells from both toxins.

FIG. 28 A-FIG. 28 C are a drawing, a line graph and a bar graph showing that a VHH heterodimer of 5D and AA6 protected mouse subjects from TcdA and TcdB in an oral *C. difficile* spore challenge model.

FIG. 28 A is a protocol for a clinically relevant murine *C. difficile* infection model. Administration of VHH is given after a spore challenge.

FIG. 28 B shows percent survival (ordinate) as a function of time following spore challenge (abscissa) for subjects administered 5D/AA6 heterodimer as described in FIG. 28 A. Data show that after the spore challenge, 90% of 5D/AA6 heterodimer contacted-subjects survived, and all control subjects not administered 5D/AA6 heterodimer or other agent died within two days.

FIG. 28 C showing percent diarrhea (ordinate) as a function of time following spore challenge (abscissa) for subjects administered 5D/AA6 heterodimer (5D/AA6 TrxA; left bar), or control PBS (right bar) as described in FIG. 28 A. Data show that 5D/AA6 heterodimer administered-subjects were five-fold less likely to display symptoms of diarrhea than control untreated subjects.

FIG. 29 A-FIG. 29 B are amino acid sequences and nucleotide sequences for VHHs that specifically bind either Shiga toxin, anthrax protective antigen, ricin A chain (RTA) antigen, or ricin B chain (RTB) antigen. The nucleotide SEQ ID NOs: 131, 155 and 159 shown in FIG. 29 B include the letter "N" in the nucleotide sequences in FIG. 29 B which indicates a position in the nucleotide sequence for which an adenine (A) residue or a guanine (G) residue may be inserted to encode the corresponding amino acid in FIG. 29 A.

FIG. 29 A shows a list of amino acid sequences of VHHs identified that bind each target as indicated:

Shiga toxin: JET-H12 (SEQ ID NO: 96) and JFG-H6 (SEQ ID NO: 98);

anthrax protective antigen: JHD-B6 (SEQ ID NO: 100), JHE-D9 (SEQ ID NO: 102), JIJ-A12 (SEQ ID NO: 104), JIJ-B8 (SEQ ID NO: 106), JIJ-C11 (SEQ ID NO: 108), JIJ-D3 (SEQ ID NO: 110), JIJ-E9 (SEQ ID NO: 112), JIJ-F11 (SEQ ID NO: 114), JIK-B8 (SEQ ID NO: 116), JIK-B10 (SEQ ID NO: 118), JIK-B12 (SEQ ID NO: 120), and JIK-F4 (SEQ ID NO: 122);

RTA: JIV-F5 (SEQ ID NO: 124), JIV-F6 (SEQ ID NO: 126), JIV-G12 (SEQ ID NO: 128), JIY-A7 (SEQ ID NO: 130), JIY-D9 (SEQ ID NO: 132), JIY-D10 (SEQ ID NO: 134), JIY-E1 (SEQ ID NO: 136), JIY-E3 (SEQ ID NO: 138), JIY-E5 (SEQ ID NO: 140), JIY-F10 (SEQ ID NO: 142), and JIY-G11 (SEQ ID NO: 144); and, RTB: JIW-B1 (SEQ ID NO: 146), JIW-C12 (SEQ ID NO: 148), JIW-D12 (SEQ ID NO: 150), JIW-G5 (SEQ ID NO: 152), JIW-G10 (SEQ ID NO: 154), JIZ-B7 (SEQ ID NO: 156), JIZ-B9 (SEQ ID NO: 158), JIZ-D8 (SEQ ID NO: 160), and JIZ-G4 (SEQ ID NO: 162).

FIG. 29 B shows a list of nucleotide sequences that encode the VHH amino acid sequences listed in FIG. 29 A. The nucleotide sequences encode VHHs that bind each target as indicated:

Shiga toxin: JET-H12 (SEQ ID NO: 97) and JFG-H6 (SEQ ID NO: 99);

anthrax protective antigen: JHD-B6 (SEQ ID NO: 101), JHE-D9 (SEQ ID NO: 103), JIJ-A12 (SEQ ID NO: 105), JIJ-B8 (SEQ ID NO: 107), JIJ-C11 (SEQ ID NO: 109), JIJ-D3 (SEQ ID NO: 111), JIJ-E9 (SEQ ID NO: 113), JIJ-F11 (SEQ ID NO: 115), JIK-B8 (SEQ ID NO: 117), JIK-B10 (SEQ ID NO: 119), JIK-B12 (SEQ ID NO: 121), and JIK-F4 (SEQ ID NO: 123);

RTA: JIV-F5 (SEQ ID NO: 125), JIV-F6 (SEQ ID NO: 127), JIV-G12 (SEQ ID NO: 129), JIY-A7 (SEQ ID NO: 131), JIY-D9 (SEQ ID NO: 133), JIY-D10 (SEQ ID NO: 135), JIY-E1 (SEQ ID NO: 137), JIY-E3 (SEQ ID NO: 139), JIY-E5 (SEQ ID NO: 141), JIY-F10 (SEQ ID NO: 143), and JIY-G11 (SEQ ID NO: 145); and, RTB: JIW-B1 (SEQ ID NO: 147), JIW-C12 (SEQ ID NO: 149), JIW-D12 (SEQ ID NO: 151), JIW-G5 (SEQ ID NO: 153), JIW-G10 (SEQ ID NO: 155), JIZ-B7 (SEQ ID NO: 157), JIZ-B9 (SEQ ID NO: 159), JIZ-D8 (SEQ ID NO: 161), and JIZ-G4 (SEQ ID NO: 163).

FIG. 30A-FIG. 30D are a set of line graphs showing VHH binding to Stx1 toxin as a function of input VHH concentration. Dilution ELISAs were performed by coating plates with 0.5 µg/ml of 4D3 mAb Stx1. The plates were blocked and then incubated with 0.3 µg/ml of Stx1. For standard ELISAs, plates were coated with 1.5 µg of Stx1. VHH agents to be tested were serially diluted, incubated for 1 hour at room temperature, washed and the bound VHH agent were detected with HRP-anti-E-tag. The bound VHH-HRP tagged agents were detected using the TMB kit by Sigma and values were plotted as a function of the input VHH concentration.

Figure 30A:
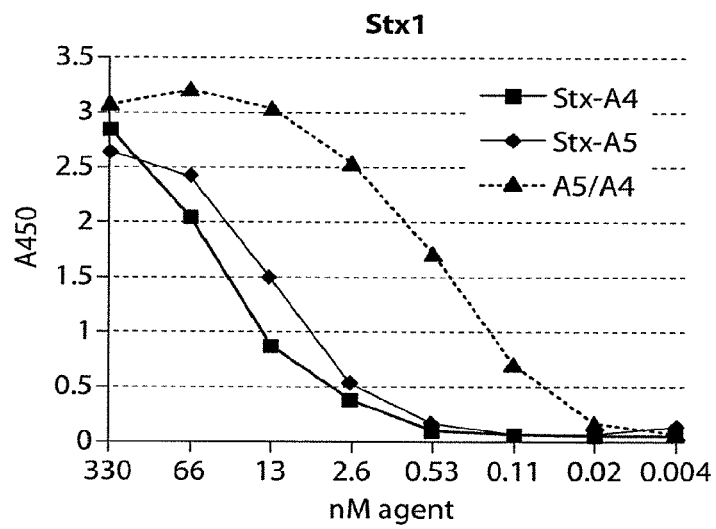

FIG. 30A is a line graph of Stx-A4 VHH, Stx-A5 VHH and heterodimer StxA4-A5 VHH binding to Stx1 toxin as a function of input VHH concentration. VHH heterodimer Stx A4-A5 is displayed by dotted line.

Figure 30B:
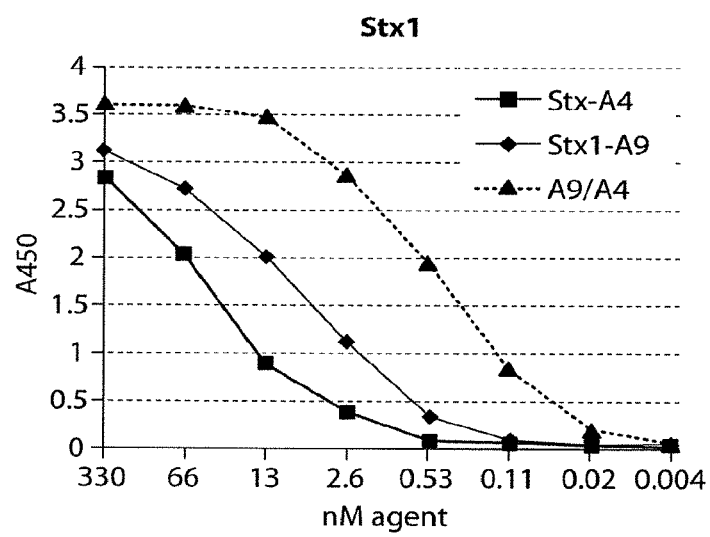

FIG. 30B is a line graph of Stx-A4 VHH, Stx1-A9 VHH and heterodimer StxA4-A9 VHH binding to Stx1 toxin as a function of input VHH concentration. VHH heterodimer Stx A4-A9 is displayed by dotted line.

Figure 30C:
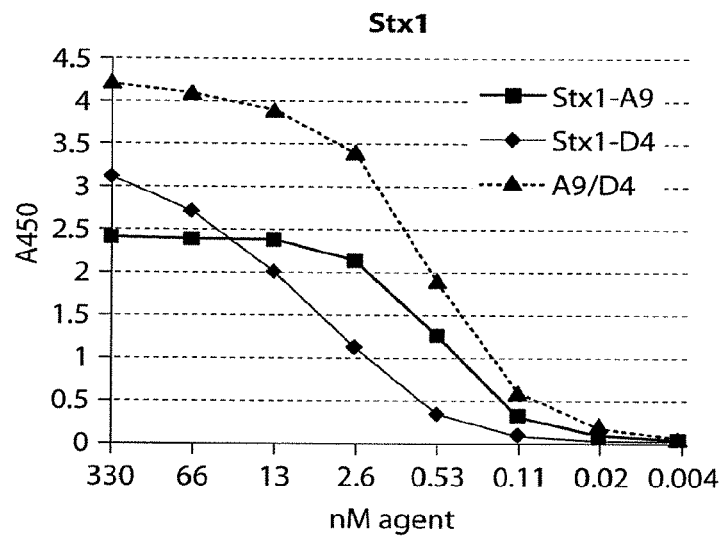

FIG. 30C is a line graph of Stx1-A9 VHH, Stx1-D4 VHH and heterodimer StxA9-D4 VHH binding to Stx1 toxin as a function of input VHH concentration. VHH heterodimer StxA9-D4 is displayed by dotted line.

Figure 30D:
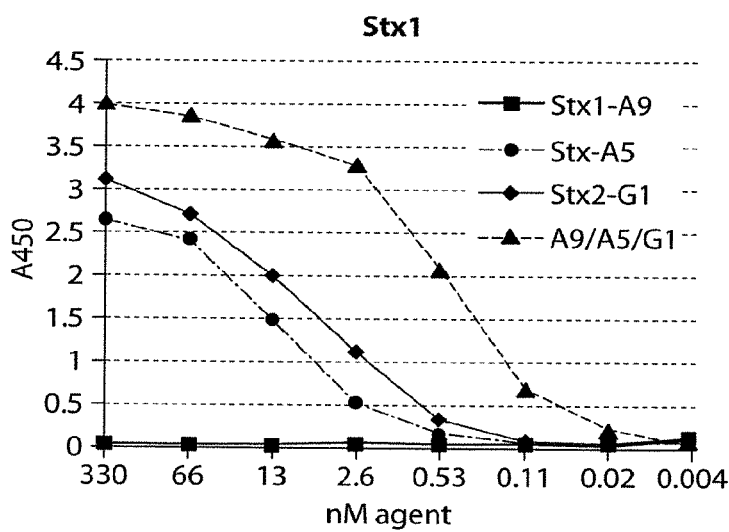

FIG. 30D is a line graph of Stx1-A9 VHH, Stx-A5 VHH, Stx2-G1 VHH and heterotrimer StxA9-A5-G1 VHH binding to Stx1 toxin as a function of input VHH concentration. VHH heterotrimer StxA9-A5-G1 is displayed by dashed line.

FIG. 31A-FIG. 31D are a set of line graphs showing VHH binding to Stx1 toxin as a function of input VHH concentration. Dilution ELISAs were performed by coating plates with 0.5 µg/ml of 3D1 mAb Stx2. The plates were blocked and then incubated with 0.3 µg/ml of Stx1. For standard ELISAs, plates were coated with 1.5 µg of Stx2. VHH agents to be tested were serially diluted, incubated for 1 hour at room temperature, washed and the bound VHH agent were detected with HRP-anti-E-tag. The bound VHH-HRP tagged agents were detected using the TMB kit by Sigma and values were plotted as a function of the input VHH concentration.

Figure 31A:
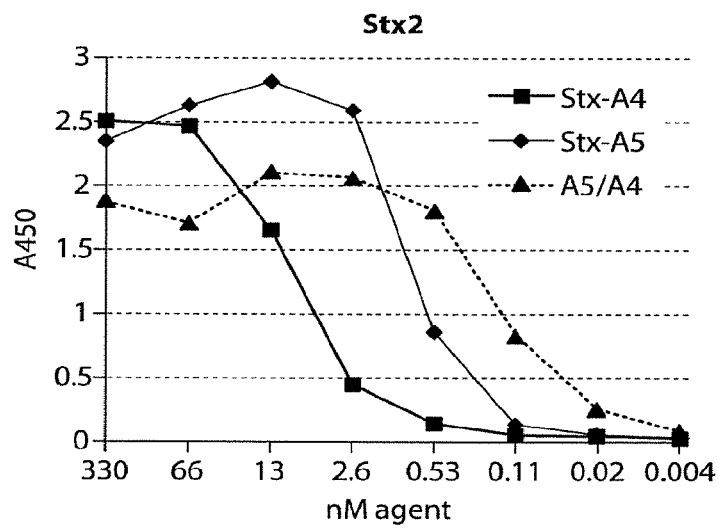

FIG. 31A is a line graph of Stx-A4 VHH, Stx-A5 VHH and heterodimer StxA4-A5 VHH binding to Stx2 toxin as a function of input VHH concentration. VHH heterodimer Stx A4-A5 is displayed by dotted line.

Figure 31B:
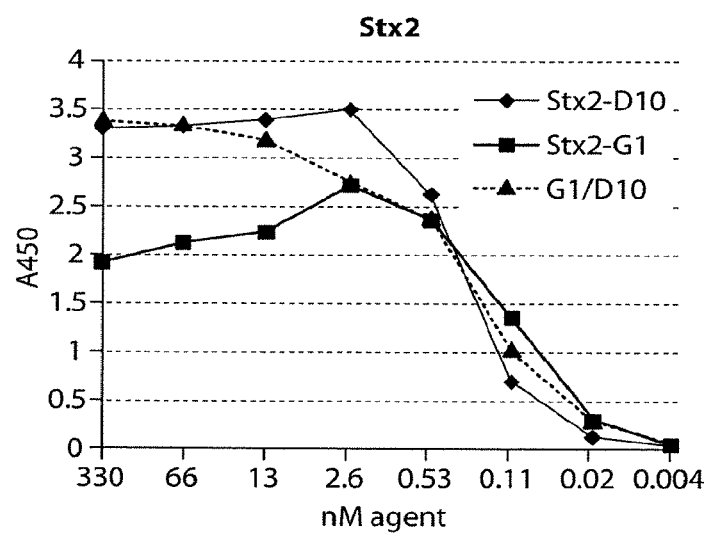

FIG. 31B is a line graph of Stx2-D10 VHH, Stx2-G1 VHH and heterodimer Stx G1-D10 VHH binding to Stx2 toxin as a function of input VHH concentration. VHH heterodimer Stx G1-D10 is displayed by dotted line.

Figure 31C:
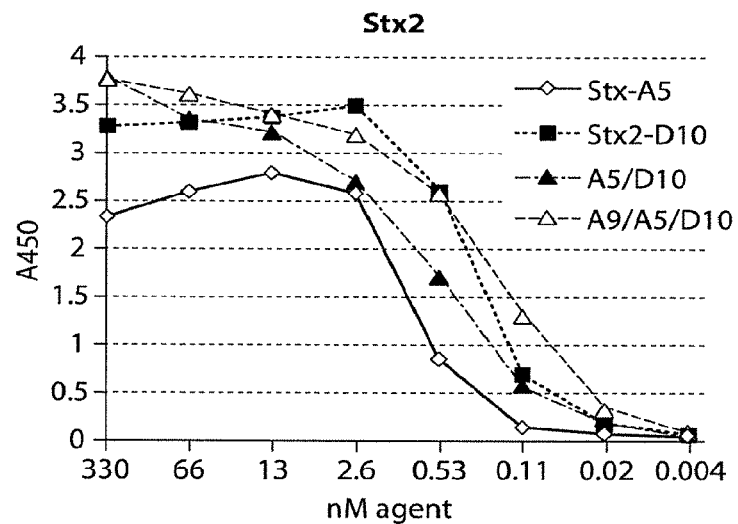

FIG. 31C is a line graph of Stx-A5 VHH, Stx2-D10 VHH, heterodimer Stx-A5-D10 VHH and heterotrimer Stx A9-A5-D10 VHH binding to Stx2 toxin as a function of input VHH concentration. VHH heterotrimer Stx A9-A5-D10 is displayed by dashed line.

Figure 31D:
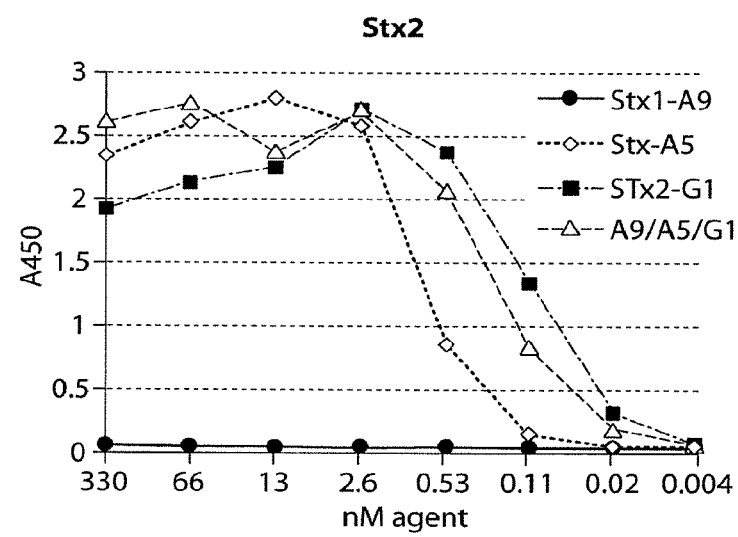

FIG. 31D is a line graph of Stx1-A9 VHH, Stx-A5VHH, Stx2-G1 VHH and heterotrimer StxA9-A5-G1 VHH binding to Stx2 toxin as a function of input VHH concentration. VHH heterotrimer StxA9-A5-G1 is displayed by dashed line.

Figure 32A:
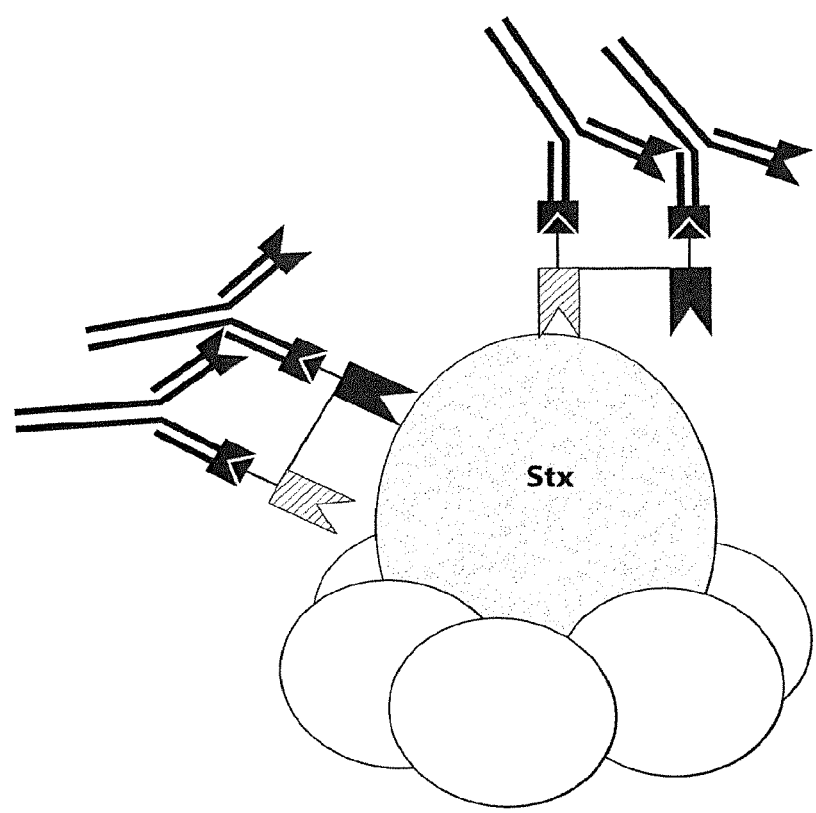
Figure 32B:
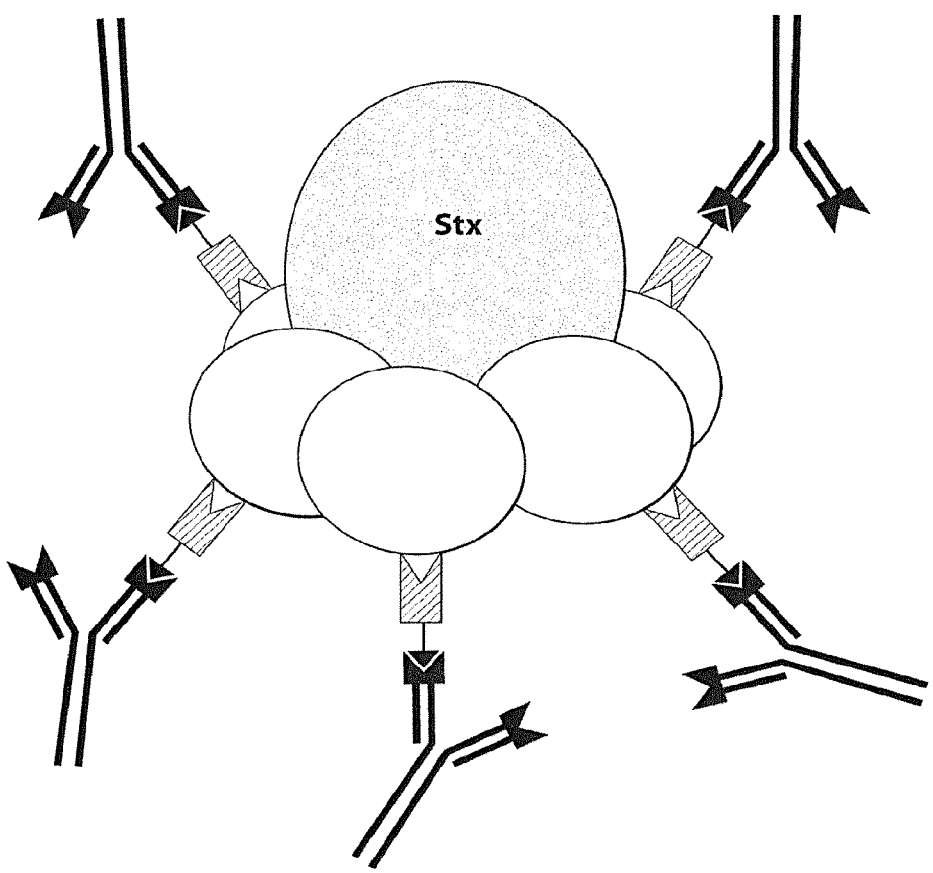

FIG. 32A-FIG. 32B are schematic drawings showing binding of multiple efAb molecules to Shiga toxin directed by a double-tagged VHH heterodimer targeting two epitopes (called a VNA), or to a single-tagged VHH-monomer which binds the pentameric B subunit.

FIG. 32A is a schematic drawing of a VHH-heterodimer VNA binding to a toxin, such as Shiga toxin (Stx), at two separate, non-overlapping epitopes. If the heterodimer contains two copies of an epitopic 'tag', then two molecules of the anti-tag efAb bind each bound heterodimer molecule leading to decoration of each toxin molecule by four efAb molecules.

FIG. 32B is a schematic drawing of a VHH-monomer binding to an epitope that is present at multiple sites on the toxin, such as the pentameric B-subunit of Stx, thereby binding at multiple sites on the toxin. If the VHH contains an epitopic tag, the efAb decorates each toxin molecule at five sites.

FIG. 33A-FIG. 33D are a set of line graphs of Stx 1 toxin neutralization in a cell based assay as a function of VHH agent concentration. A Stx1 dose (about 15 pmoles) that induced about 100% Vero cell and killed them after 48 hours was selected. A VHH monomer, VHH monomer pool or VHH heterodimer, as labeled, were pre-mixed with Stx1 in culture medium and applied to Vero cells. Toxin neutralization was assessed after 48 hours by cell staining at A590 as described in examples herein. The extent of cell staining was plotted as a function of the VHH-agent concentration employed.

Figure 33A:
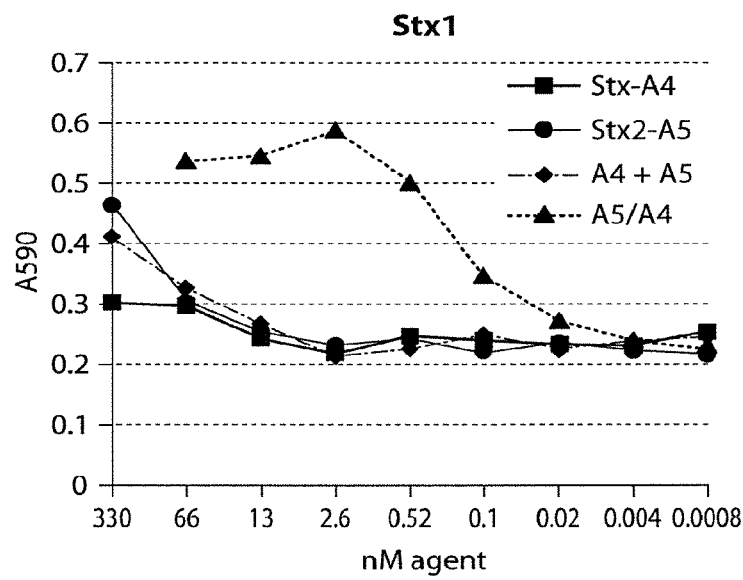

FIG. 33A is a line graph of Stx 1 toxin neutralization in a cell based assay by Stx-A4 VHH, Stx-A5 VHH, a monomer pool of Stx-A4 and Stx-A5 VHHs and heterodimer Stx-A4-A5 VHH as a function of VHH concentration. VHH heterodimer Stx-A4-A5 is displayed by dotted line.

Figure 33B:
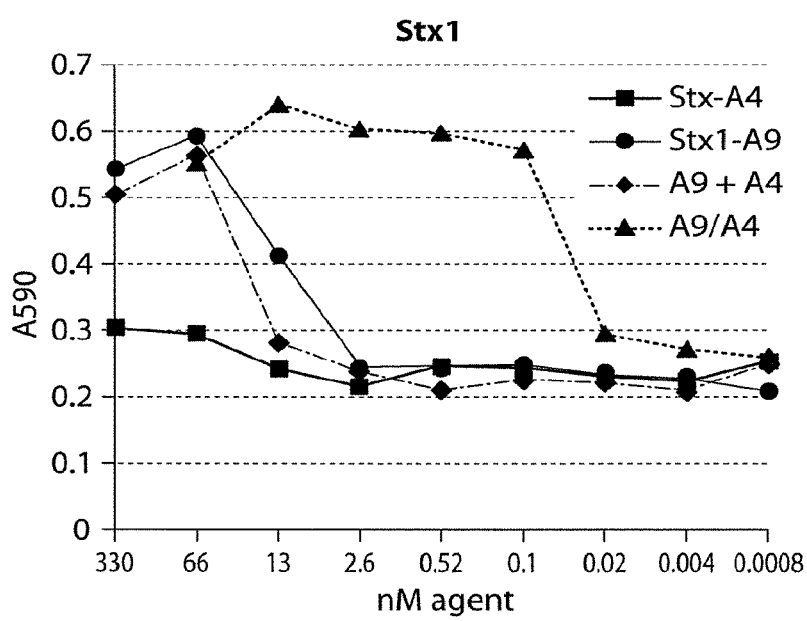

FIG. 33B is a line graph of Stx 1 toxin neutralization in a cell based assay by Stx-A4 VHH, Stx1-A9 VHH, a monomer pool of Stx-A4 and Stx1-A9 VHHs and heterodimer Stx1-A4-A9 VHH as a function of VHH concentration. VHH heterodimer Stx-A4-A9 is displayed by dotted line.

Figure 33C:
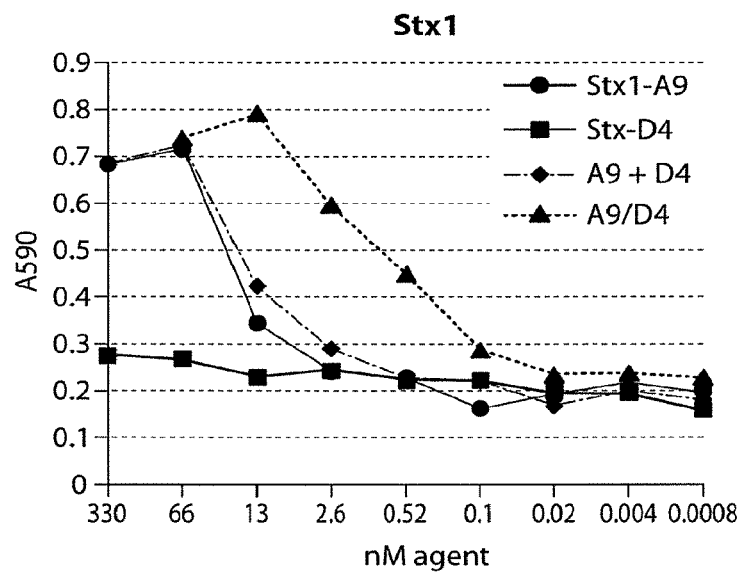

FIG. 33C is a line graph of Stx 1 toxin neutralization in a cell based assay by Stx1-A9 VHH, Stx-D4 VHH, a monomer pool of Stx1-A9 and Stx-D4 VHHs and heterodimer Stx1-A9-D4 VHH as a function of VHH concentration. VHH heterodimer Stx1-A9-D4 is displayed by dotted line.

Figure 33D:
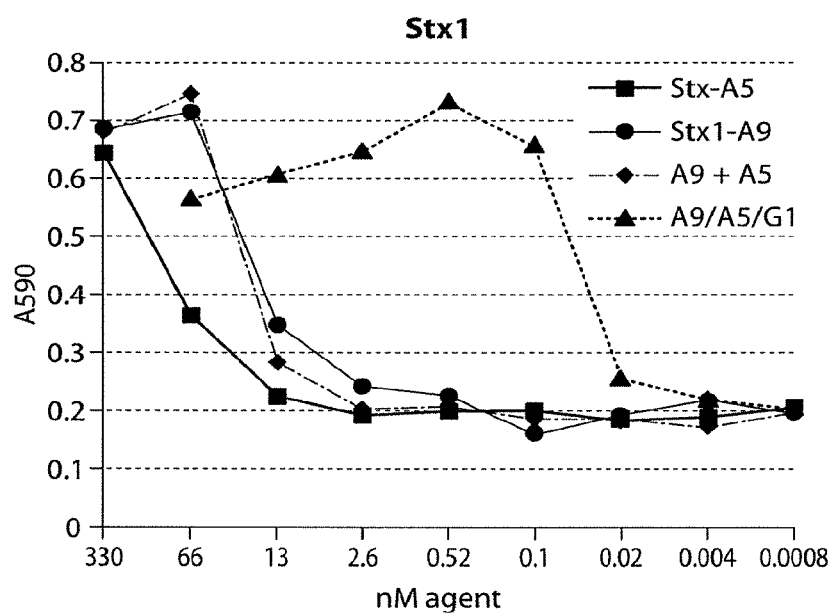

FIG. 33D is a line graph of Stx 1 toxin neutralization in a cell-based assay by Stx-A5 VHH, Stx1-A9 VHH, a monomer pool of Stx-A5 and Stx1-A5 VHHs and heterotrimer Stx1-A9-A5-G1 VHH as a function of VHH concentration. VHH heterotrimer Stx1-A9-A5-G1 is displayed by dashed line.

FIG. 34A-FIG. 34D are a set of line graphs of Stx 2 toxin neutralization in a cell based assay as a function of VHH agent concentration. A Stx2 dose (about 35 pmoles) that induced about 100% Vero cell and killed them after 48 hours was selected. A VHH monomer, VHH monomer pool or VHH heterodimer, as labeled, were pre-mixed with Stx2 in culture medium and applied to Vero cells. Toxin neutralization was assessed after 48 hours by cell staining at A590 as described in examples herein. The extent of cell staining was plotted as a function of the VHH-agent concentration employed.

Figure 34A:
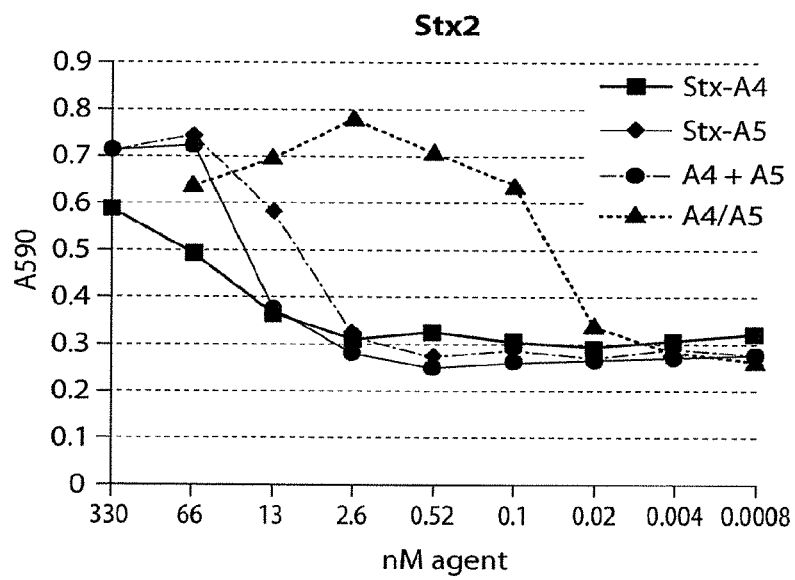

FIG. 34A is a line graph of Stx 2 toxin neutralization in a cell based assay by Stx-A4 VHH, Stx-A5 VHH, a monomer pool of Stx-A4 and Stx-A5 VHHs and heterodimer Stx-A4-A5 VHH as a function of VHH concentration. VHH heterodimer Stx-A4-A5 is displayed by dotted line.

Figure 34B:
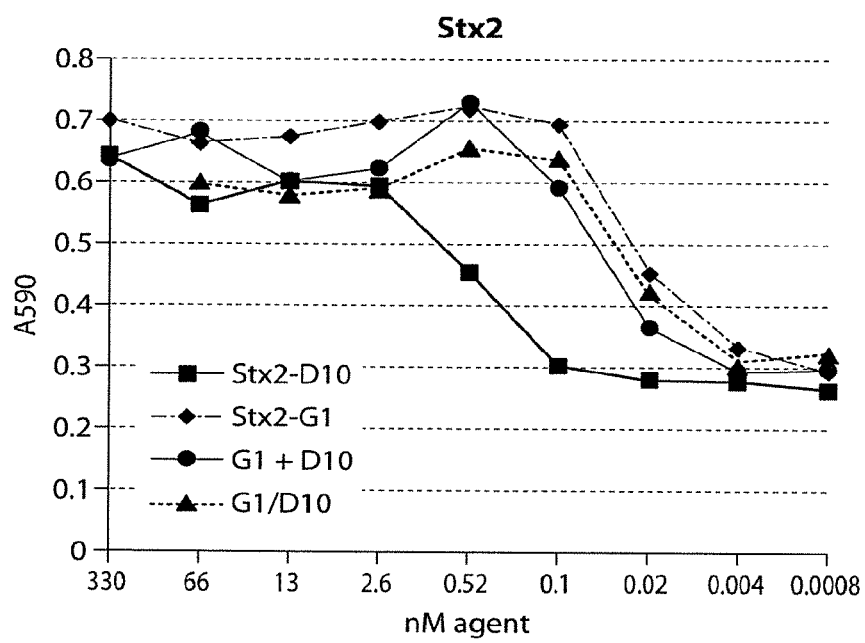

FIG. 34B is a line graph of Stx 2 toxin neutralization in a cell based assay by Stx2-D10 VHH, Stx2-G1 VHH, a monomer pool of Stx2-D10 and Stx2-G1VHHs and heterodimer Stx2-G1-D10 VHH as a function of VHH concentration. VHH heterodimer Stx2-G1-D10 is displayed by dotted line.

Figure 34C:
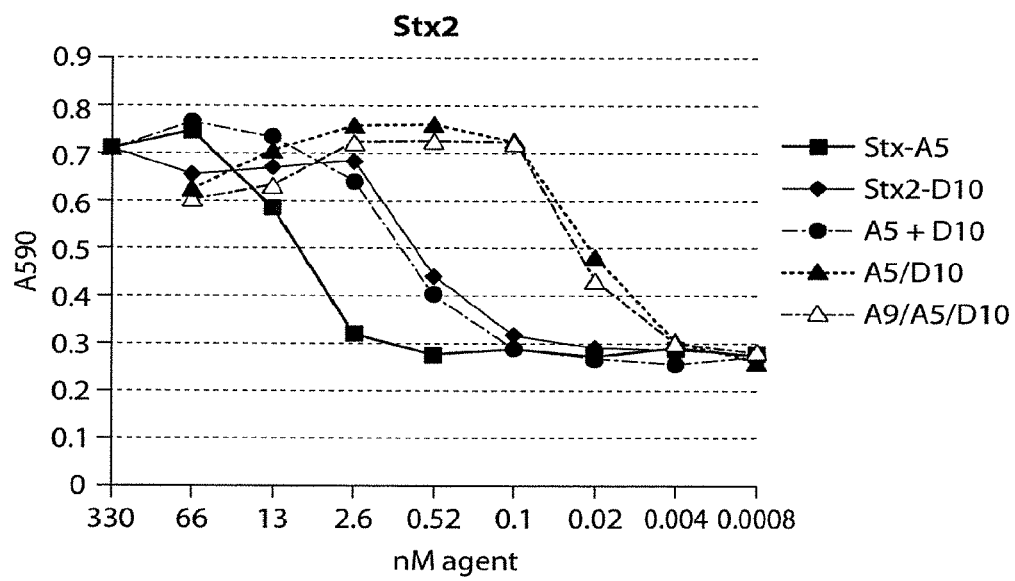

FIG. 34C is a line graph of Stx 2 toxin neutralization in a cell based assay by Stx-A5 VHH, Stx2-D10 VHH, a monomer pool of Stx-A5 and Stx2-D10 VHHs, heterodimer Stx-A5-D10 VHH and heterotrimer Stx-A9-A5-D10 as a function of VHH concentration. VHH heterodimer Stx1-A5-D10 is displayed by dotted line and VHH heterotrimer Stx-A9-A5-D10 is displayed by dashed line.

Figure 34D:
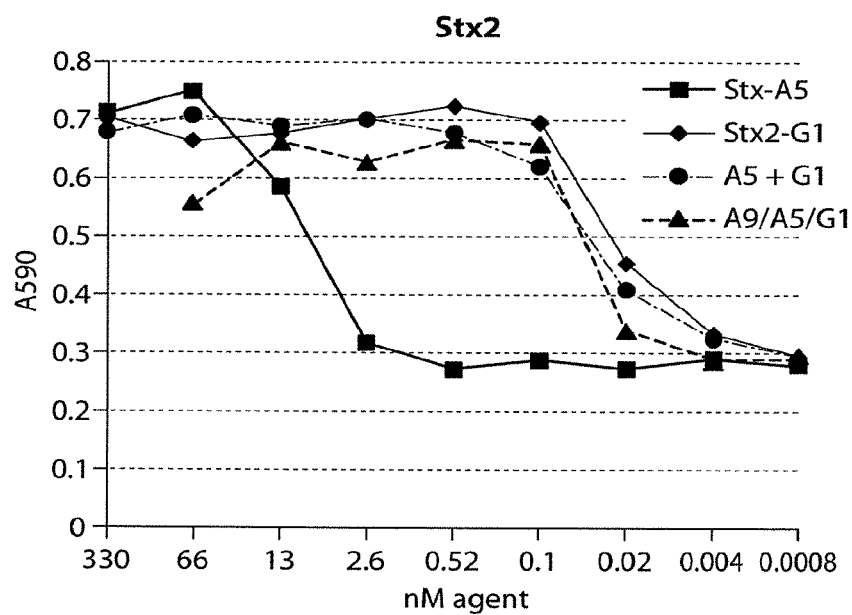

FIG. 34D is a line graph of Stx 2 toxin neutralization in a cell based assay by Stx-A5 VHH, Stx2-G1 VHH, a monomer pool of Stx-A5 and Stx2-G1 VHHs and heterotrimer Stx-A9-A5-G1 VHH as a function of VHH concentration. VHH heterotrimer Stx-A9-A5-G1 is displayed by dashed line.

FIG. 35A-FIG. 35D are a set of Meyer-Kaplan survival plots for percent survival of subjects as a function of time in days following contact with Stx1 toxin and later time administered VHH binding/neutralizing agents. Subjects, groups of five mice were injected with 20 pmoles of Stx1 premixed with 40 pmoles of the labeled VHH-based anti-toxin agent (or 640 pmoles of VHH-A9 where indicated) and monitored for illness and death for one week. The percent survival is plotted as a function of time. In some subjects, an 80 pmole dose of efAb was included in the treatment.

Figure 35A:
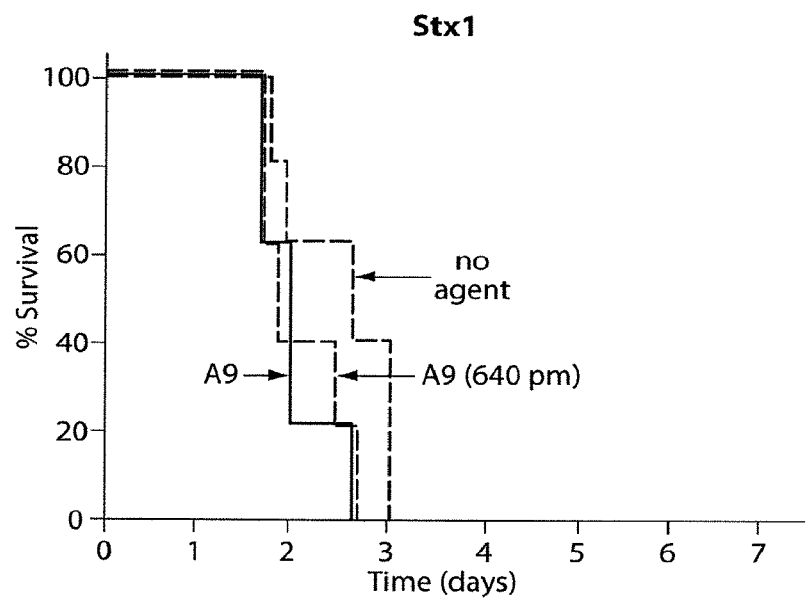

FIG. 35A is a Meyer-Kaplan survival plot for percent survival of subjects exposed to Stx1 toxin and then administered either Stx-A9 VHH, Stx-A9 (640 pm) VHH or no VHH agent.

Figure 35B:
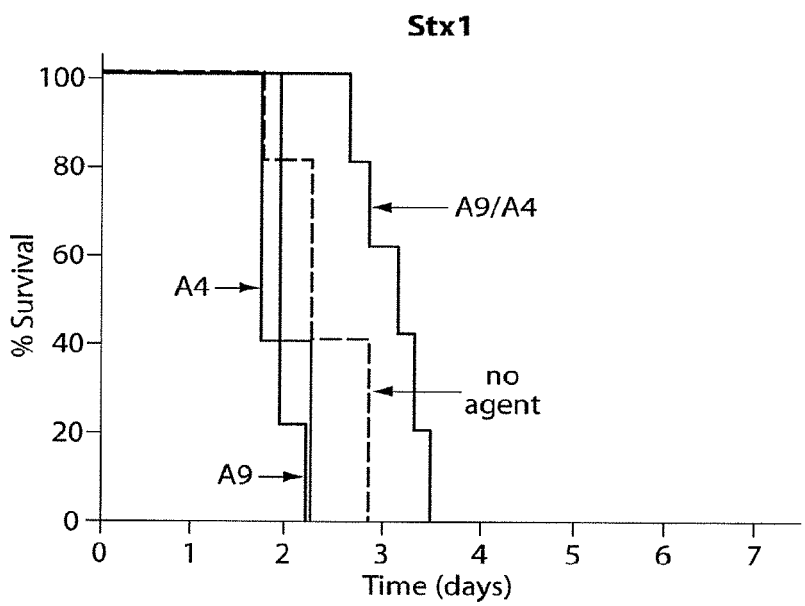

FIG. 35B is a Meyer-Kaplan survival plot for percent survival of subjects exposed to Stx1 toxin and then administered either Stx-A9 VHH, Stx-A4 VHH, Stx-A9-A4 heterodimer VHH or no VHH agent.

Figure 35C:
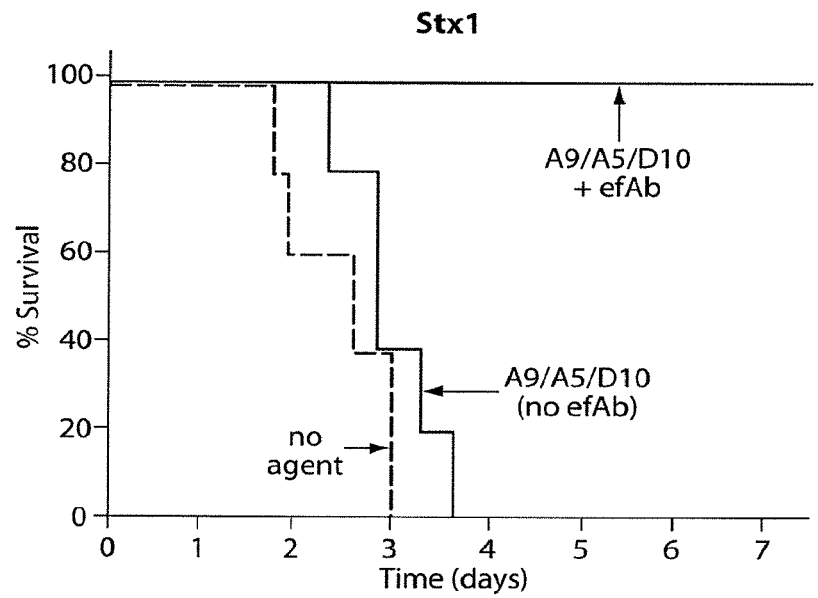

FIG. 35C is a Meyer-Kaplan survival plot for percent survival of subjects exposed to Stx1 toxin and then administered either heterotrimer Stx-A9-A5-D10 VHH without efAb, heterotrimer Stx-A9-A5-D10 VHH with efAb or no VHH agent.

Figure 35D:
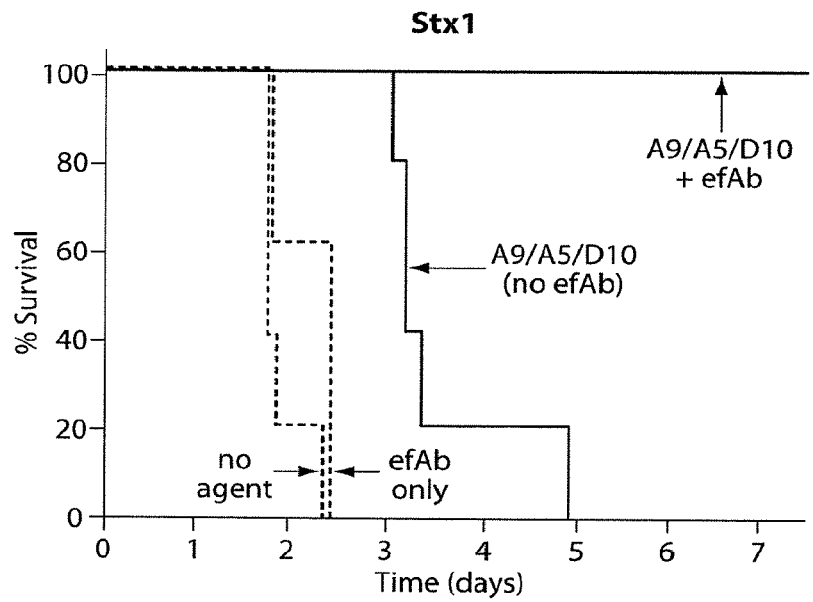

FIG. 35D is a Meyer-Kaplan survival plot for percent survival of subjects exposed to Stx1 toxin and then administered either heterotrimer Stx-A9-A5-G1 VHH with efAb or no VHH agent.

FIG. 36A-FIG. 36D are a set of Meyer-Kaplan survival plots for percent survival of subjects as a function of time in days following contact with Stx2 toxin and later time administered VHH binding/neutralizing agents. Subjects, groups of five mice were injected with 1 pmoles of Stx2 premixed with 40 pmoles of the labeled VHH-based antitoxin agent and monitored for illness and death for one week. The percent survival is plotted as a function of time. In some subjects, an 80 pmole dose of efAb was included in the treatment.

Figure 36A:
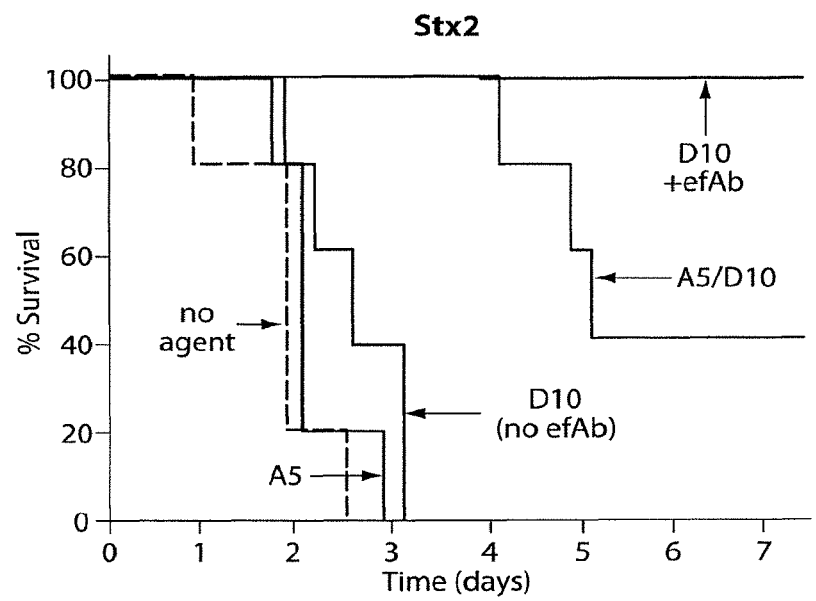

FIG. 36A is a Meyer-Kaplan survival plot for percent survival of subjects exposed to Stx2 toxin and then administered either Stx-A5 VHH, Stx-D10 VHH, Stx-D10 with efAb, heterodimer Stx-A5-D10 VHH, or no VHH agent.

Figure 36B:
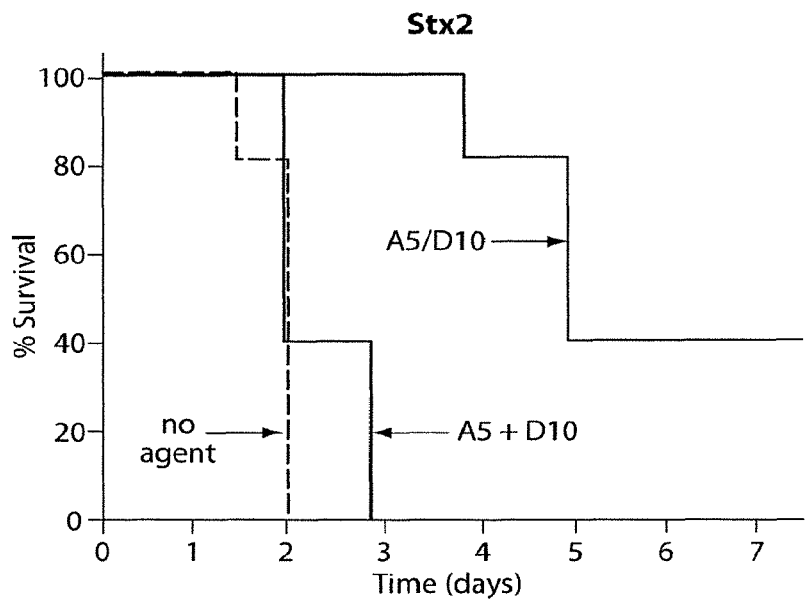

FIG. 36B is a Meyer-Kaplan survival plot for percent survival of subjects exposed to Stx2 toxin and then administered either a mixture of Stx-A5 VHH and Stx-D10, Stx-A5-D10 heterodimer VHH or no VHH agent.

Figure 36C:
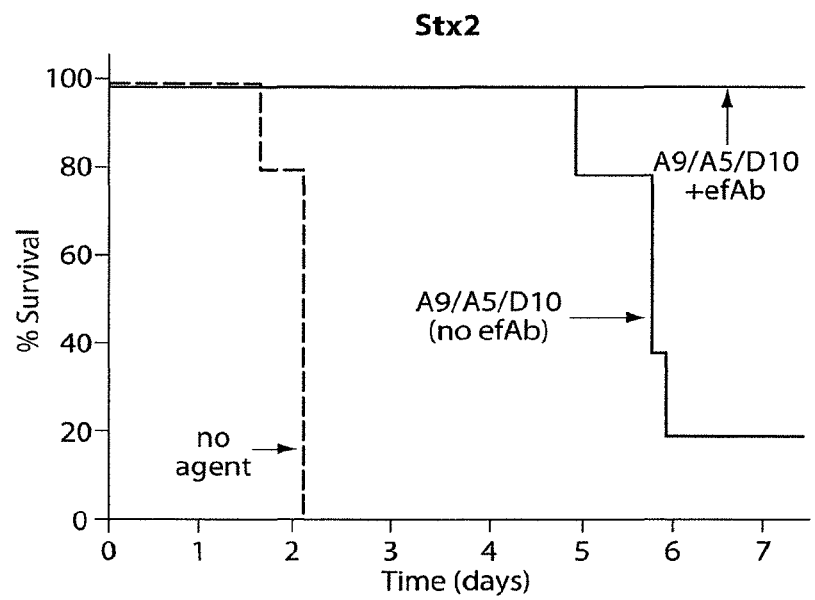

FIG. 36C is a Meyer-Kaplan survival plot for percent survival of subjects exposed to Stx2 toxin and then administered either heterotrimer Stx-A9-A5-D10 VHH without efAb, heterotrimer Stx-A9-A5-D10 VHH with efAb or no VHH agent.

Figure 36D:
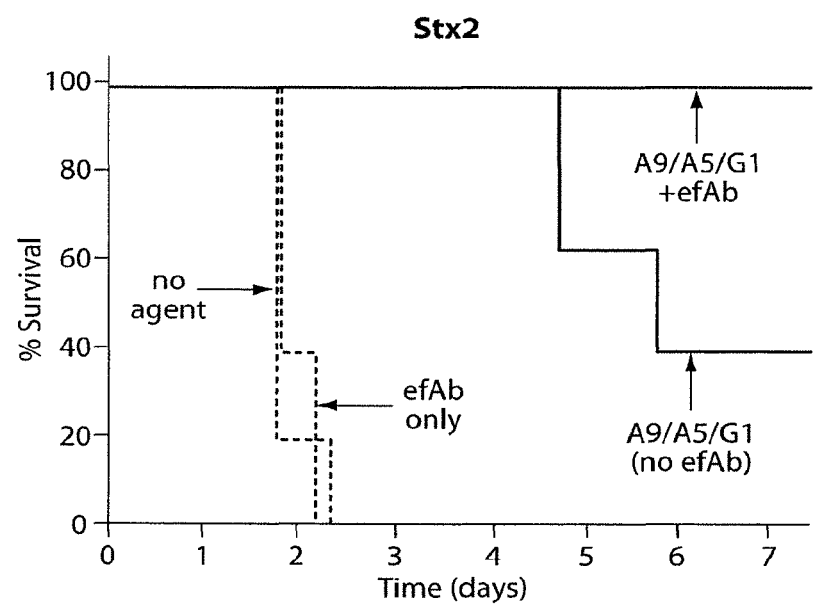

FIG. 36D is a Meyer-Kaplan survival plot for percent survival of subjects exposed to Stx2 toxin and then administered either heterotrimer Stx-A9-A5-G1 VHH with efAb, heterotrimer Stx-A9-A5-G1 VHH without efAb or no VHH agent.

Figure 37A:
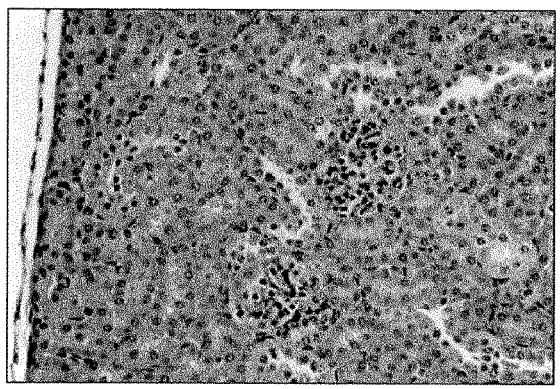
Figure 37B:
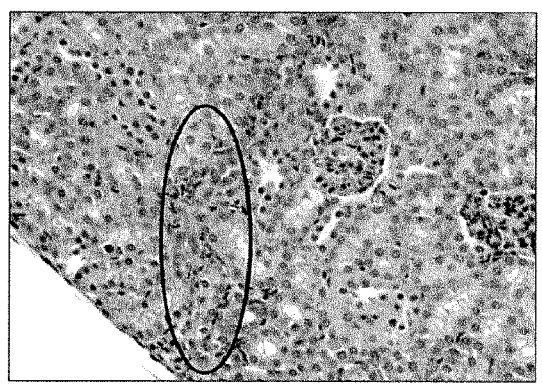
Figure 37C:
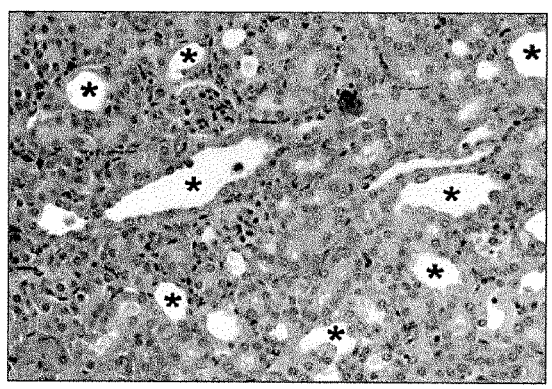
Figure 37D:
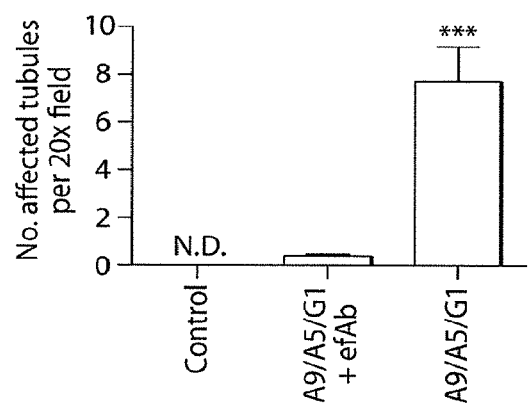

FIG. 37A-FIG. 37D are a set of micrographs and a bar graph showing that VNA plus efAb protect subjects from Stx2 induced renal damage. Formalin-fixed, paraffin embedded and hematoxylin and eosin stained 3 μm sections were examined by light microscopy from untreated age- and sex-matched controls (FIG. 37A), mice receiving the A9/A5/G1 VNA+efAb (FIG. 37B), and mice receiving only A9/A5/G1 VNA (FIG. 36C). The numbers of tubules with lesions such as epithelial apoptosis/necrosis, attenuation and restitution, hypertrophy, hyperplasia, luminal dilation, tubular atrophy/collapse, interstitial cell proliferation and early interstitial fibrosis were quantified in 6 random 20× fields per mouse totaling 114 measurements and plotted in a bar graph (FIG. 37D). Examples of lesions are highlighted by black oval in FIG. 37B and the asterisks in FIG. 37C. (N.D.=None Detected)

FIG. 38 is a listing of amino acid sequences of VHHs selected for binding to Stx1 or Stx2. Sequences shown begin within framework 1At the site of the primer binding employed in coding sequence DNA amplification from the immune alpaca cDNA and continue through the end of framework 4. The parentheses at the end indicate whether the VHH contains a long hinge (lh) or a short hinge (sh). The three-complementarity determining regions (CDRs) are indicated at the top.

Figure 39:
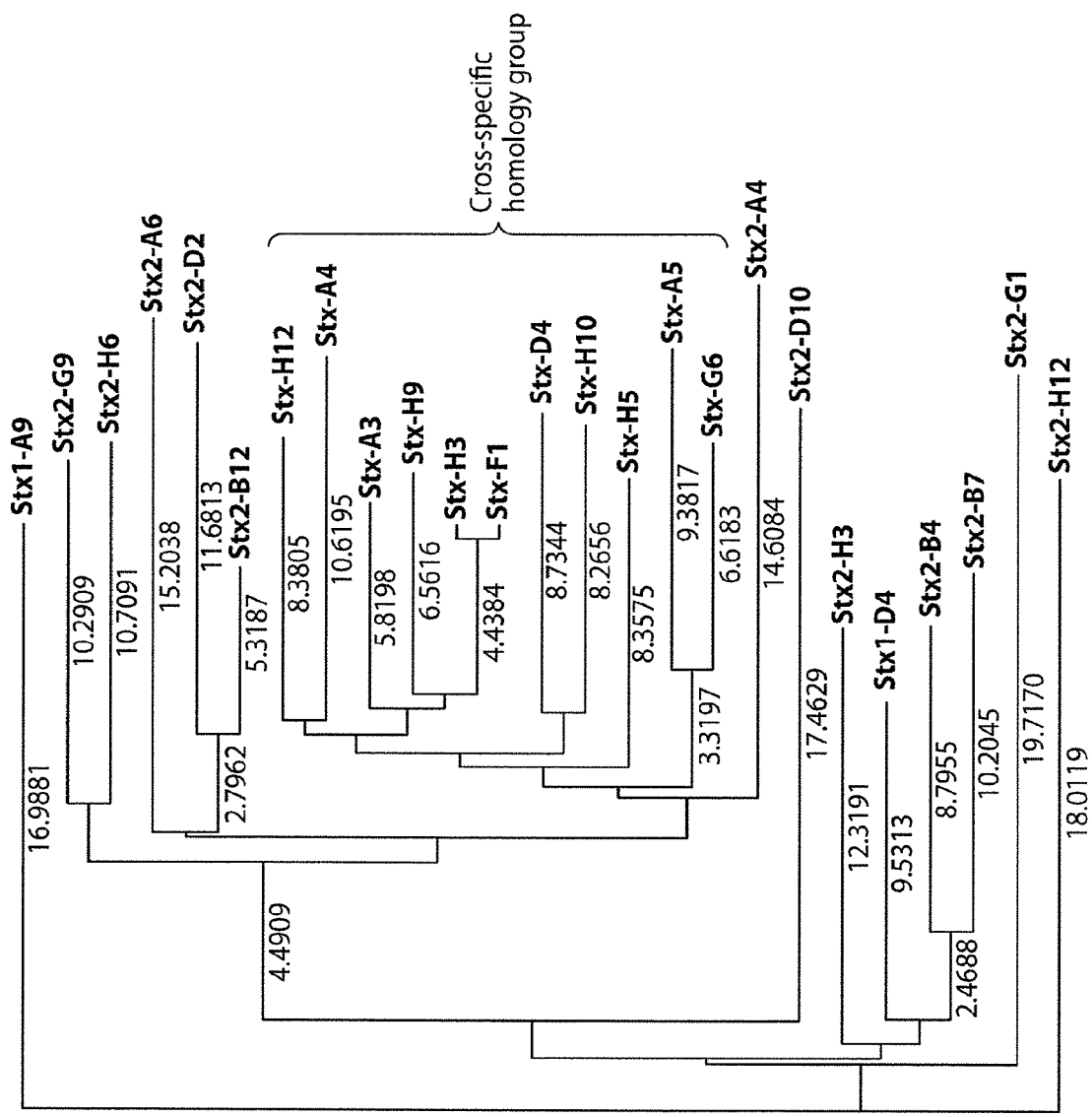

FIG. 39 is a dendrogram of VHHs selected for binding to Stx1 or Stx2. The VHH sequences shown in FIG. 38 were analyzed for homology to create a dendrogram. Longer branch lengths indicate less sequence homology. The central node labeled as the 'cross-specific homology group' indicate VHHs that recognize both Stx1 And Stx2 and possess significant homology in CDR3 (see FIG. 38).

Figure 40:
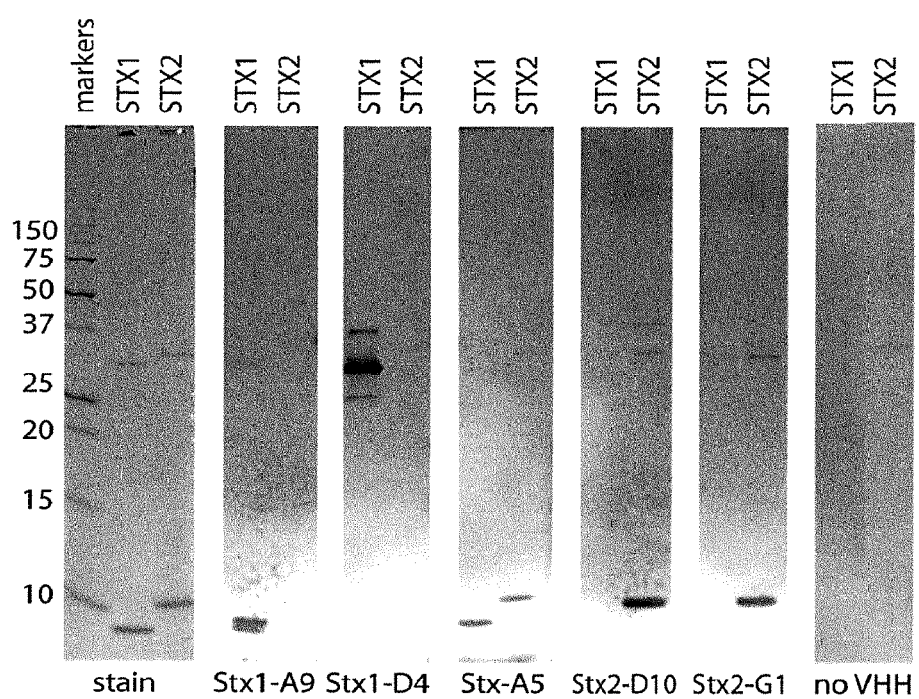
Figure 45A:
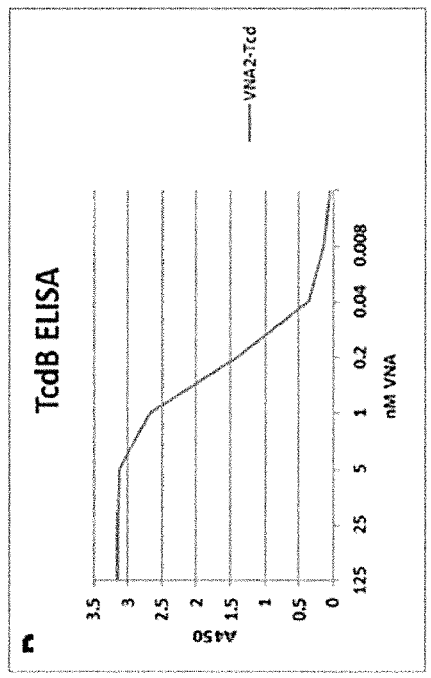
Figure 45B:
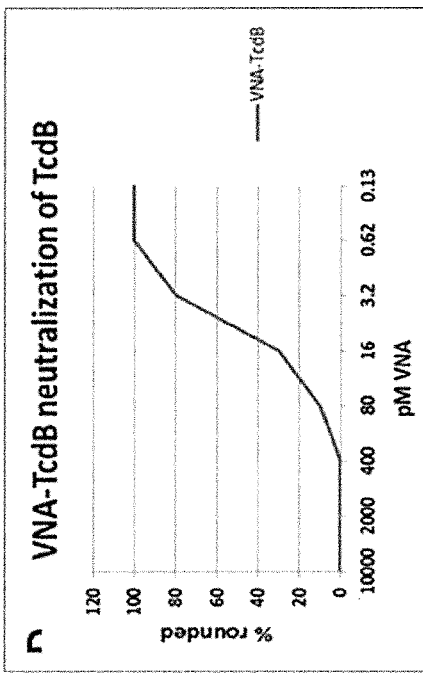
Figure 45C:
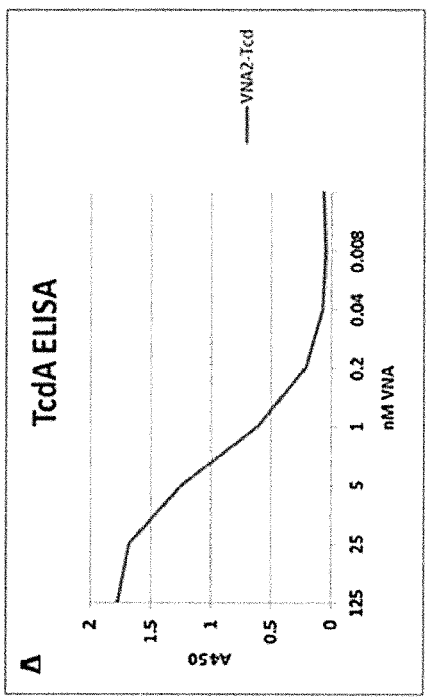
Figure 45D:
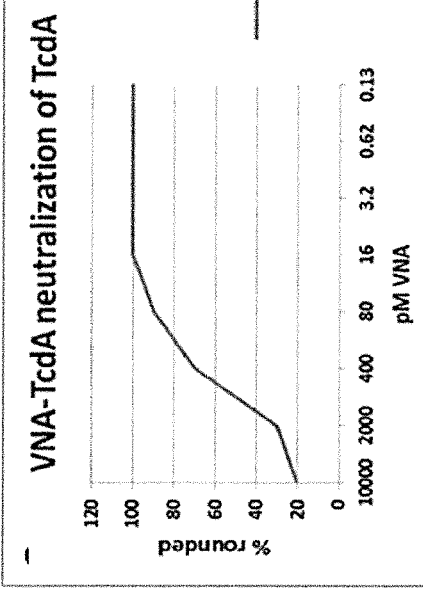

FIG. 40 is a photograph of Western blot for VHH binding to Stx1 And Stx2. Purified Stx1 and Stx2 were resolved by SDS-PAGE and the gel stained for protein (stain). Molecular weight markers are shown to the left. Similar lanes containing Stx1 And Stx2 were transferred to filters for Western blot. The blots were incubated with 10 μg/ml of the indicated VHHs or control. Bound VHH was visualized with HRP/anti-E-tag.

FIG. 41 is the amino acid sequence of the full translation product of the exemplary protein referred to herein as VNA2-Tcd (SEQ ID NO: 170). The underlined portions of the sequence show four recombinant VHH binding domains (see also SEQ ID NO: 174, SEQ ID NO: 164, SEQ ID NO: 165, SEQ ID NO: 166). The sequence from residue number 184 to reside number 318 is SEQ ID NO: 174. The sequence from residue number 343 to reside number 477 is SEQ ID NO: 164. The sequence from residue number 505 to reside number 623 is SEQ ID NO: 165. The sequence from residue number 645 to reside number 773 is SEQ ID NO: 166. Residue numbers 325-339, 483-497, and 627-641 include the flexible spacer amino acid sequence (GGGGS)$_3$ (SEQ ID NO: 55).

FIG. 42 is the coding nucleotide sequence of VNA2-Tcd (SEQ ID: 169).

FIG. 43 is the amino acid sequence of the full translation product of mammalian cell secreted VNA2-Tcd (SEQ ID NO: 167).

Figure 44:
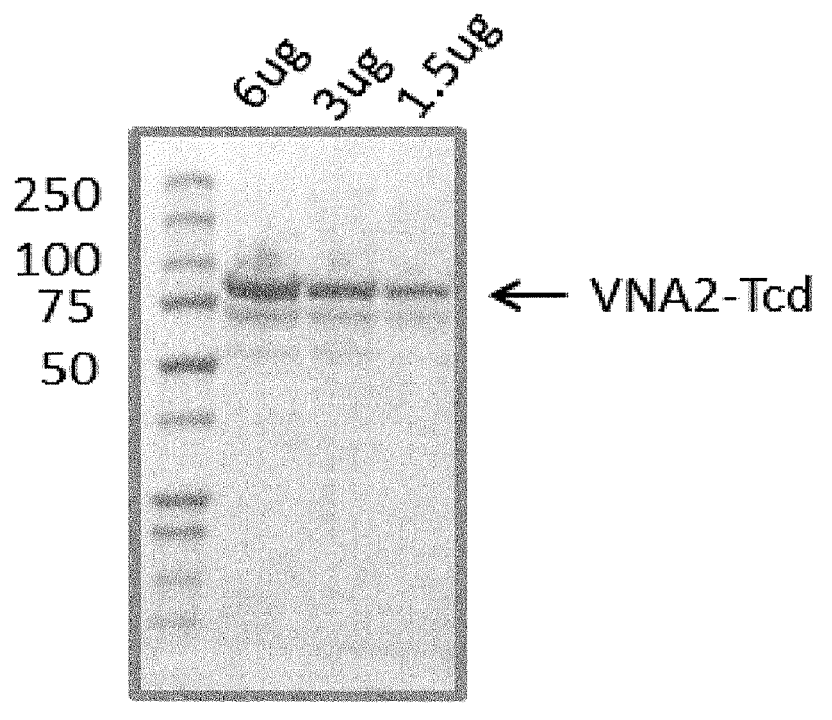

FIG. 44 is a photograph of an SDS-PAGE gel showing the purified VNA2-Tcd heterotetramer produced in *E. coli* and purified by Ni-affinity chromatography followed by gel filtration chromatography. A total of 6 ug, 3 ug, or 1.5 ug were loaded into the indicated lanes FIG. 45 A-FIG. 45 D are a set of line graphs showing neutralization of TcdA and TcdB by VNA-TcdA and VNA-TcdB respectively.

FIG. 45 A is a line graph showing that the VHH tetramer, VNA2-Tcd, binds *C. difficile* toxin A (TcdA) with high affinity. The ELISA assay was performed by coating the microtiter plates with TcdA and incubation with VNA2-Tcd at concentrations of 0.008 nM, 0.04 nM, 0.2 nM, 1 nM, 5 nM, 25 nM, or 125 nM, with visualization of binding using an HRP-conjugated detection antibody.

FIG. 45 B is a line graph showing that the VHH tetramer, VNA2-Tcd, binds *C. difficile* toxin B (TcdB) with high affinity. The ELISA assay was performed by coating the microtiter plates with TcdB and incubation with VNA2-Tcd at concentrations of 0.008 nM, 0.04 nM, 0.2 nM, 1 nM, 5 nM, 25 nM, or 125 nM, with visualization of binding using an HRP-conjugated detection antibody.

FIG. 45 C is a line graph showing that the VHH tetramer, VNA2-Tcd, neutralized *C. difficile* toxin A (TcdA) and protected cells from the toxin. The percent of CT26 cells affected by TcdA (% affected, ordinate) is shown as a function of concentration (from 0.13 pM, 0.62 pM, 3.2 pM, 16 pM, 80 pM, 400 pM, 2000 pM, and 10000 pM). Percent cell rounding was analyzed using a phase contrast microscope.

FIG. 45 D is a line graph showing that the VHH tetramer, VNA2-Tcd, neutralized *C. difficile* toxin B (TcdB) and protected cells from the toxin. The percent of CT26 cells affected by TcdB (% affected, ordinate) is shown as a function of concentration (from 0.13 pM, 0.62 pM, 3.2 pM, 16 pM, 80 pM, 400 pM, 2000 pM, and 10000 pM). Percent cell rounding was analyzed using a phase contrast microscope.

Figure 46:
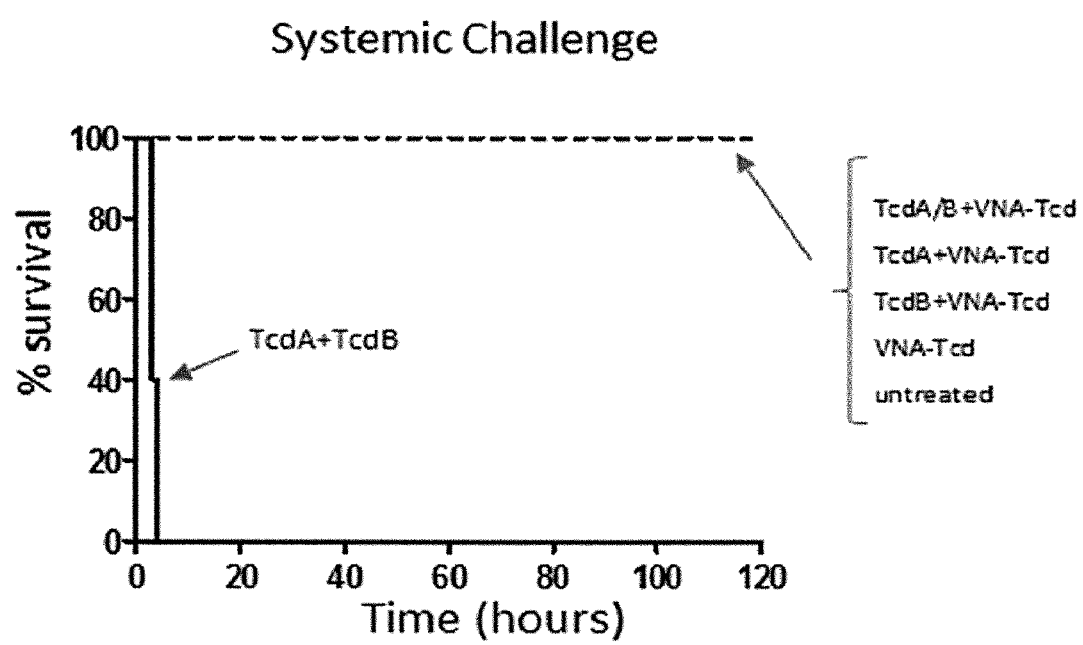

FIG. 46 is a Meyer-Kaplan survival plot showing percent survival (% survival, ordinate) of subjects as a function of time in days (abscissa) following contact with *C. difficile* toxin. Six-week-old female C57BL/6 mice were treated via IP injection with 50 ug/mouse of purified VNA2-Tcd one hour prior to IP challenge with 100 ng/mouse of *C. difficile* toxin A (TcdA) and 200 ng/mouse of *C. difficile* toxin B (TcdB). Control mice challenged with TcdA and TcdB all died or became moribund within 4 hours post challenge. Untreated, VNA2-Tcd alone, TcdA+VNA2-Tcd, TcdB+

VNA2-Tcd, and TcdA/B+VNA2-Tcd treated animals showed no signs of systemic effects and survived until study termination at 7 days post challenge.

FIG. 47A-FIG. 47 C are graphs showing neutralization of *C. difficile* infection by VNA-TcD.

FIG. 47 A is a line graph showing results of the *C. difficile* infection mouse study. Mice were treated with an antibiotic in the drinking water for 3 days, then received an IP injection of clindamycin. The next day, the animals were infected with $10^6$ *C. difficile* UK6 spores. Cohorts of animals were treated with 3 doses of VNA2-Tcd (2.5 mg/kg at 4, 24, and 48 hrs after infection) or PBS. PBS-treated control animals displayed rapid weight loss while the VNA2-Tcd-treated animals displayed little or no weight loss.

FIG. 47 B is a bar graph showing results of the *C. difficile* infection mouse study. Mice were treated with an antibiotic in the drinking water for 3 days, then received an IP injection of clindamycin. The next day, the animals were infected with $10^6$ *C. difficile* UK6 spores. Cohorts of animals were treated with 3 doses of VNA2-Tcd (2.5 mg/kg at 4, 24, and 48 hrs after infection) or PBS. All of the PBS-treated control animals displayed diarrhea for at least 3 days post infection, while only 20% of VNA2-Tcd-treated animals had diarrhea on Day 1 which resolved by Day 2.

FIG. 47 C is a Kaplan-Meier line graph showing results of the *C. difficile* infection mouse study. Mice were treated with an antibiotic in the drinking water for 3 days, then received an IP injection of clindamycin. The next day, the animals were infected with $10^6$ *C. difficile* UK6 spores. Cohorts of animals were treated with 3 doses of VNA2-Tcd (2.5 mg/kg at 4, 24, and 48 hrs after infection) or PBS. PBS-treated control animals rapidly became moribund and 60% of the animals were dead by Day 3. In contrast, 100% of the VNA2-Tcd-treated animals survived.

FIG. 48 A-FIG. 48 B are a set of photographs showing descending colons of *C. difficile*-infected control pigs.

FIG. 48 A is a photograph of the descending colon of a *C. difficile*-infected control pig treated with PBS. The colons displayed severe dilatation, mesocolonic edema, multifocal hemorrhages, and thickening of the intestinal wall.

FIG. 48 B is a photograph of the descending colon of a *C. difficile*-infected control pig treated with VNA2-Tcd. The colons show minimal or no dilatation, no intestinal wall thickening or hemorrhages.

FIG. 49 A-FIG. 49 C are photographs and bar graph showing neutrophil foci in the lamina of *C. difficile* infected piglets and histology sections of the intestinal lumen of *C. difficile* infected piglets.

FIG. 49 A is a bar graph that compares the amount of neutrophil foci in the lamina of *C. difficile* infected piglets treated with VNA2-Tcd or PBS (Control). The VNA2-Tcd treated animals had significantly fewer neutrophil foci than the control animals.

FIG. 49 B is a photograph of a histology section of the intestinal lumen of *C. difficile* infected piglets treated with PBS (Control). Mucosal ulceration, hemorrhage, and marked neutrophilic infiltration, eruption of neutrophils and sloughed mucosa is apparent.

FIG. 49 C is a photograph of a histology section of the intestinal lumen of *C. difficile* infected piglets treated with VNA2-Tcd. Mild mucosal erosion and mild neutrophilic infiltration is observed.

Figure 50:
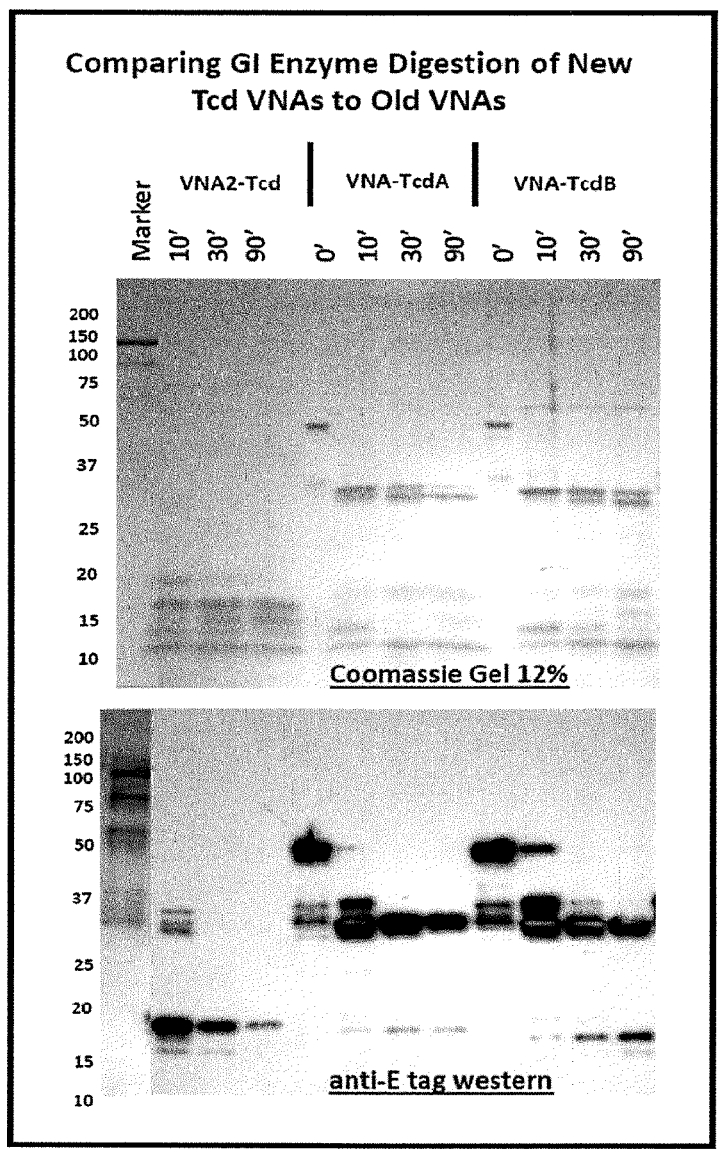

FIG. 50 is an SDS-PAGE gel. The top panel represents an SDS-PAGE gel in which protein is stained with Coomassie. The bottom panel is a Western blot of the same samples as in top panel, identifying proteins with an E-tag peptide, facilitating identification of the degradation products. The data shows that a heterotetrameric VNA (VNA2-Tcd) containing four VHHs is rapidly cleaved to the monomeric VHH components of the VNA. Two dimeric VNAs, VNA-TcdA and VNA-TcdB, that each contain two VHHs also present in VNA2-Tcd is more stable to GI enzyme digestion. The 50 kDa full-size protein is rapidly digested to a protein of ~30 KDa that contains the VHH heterodimers.

Figure 51A:
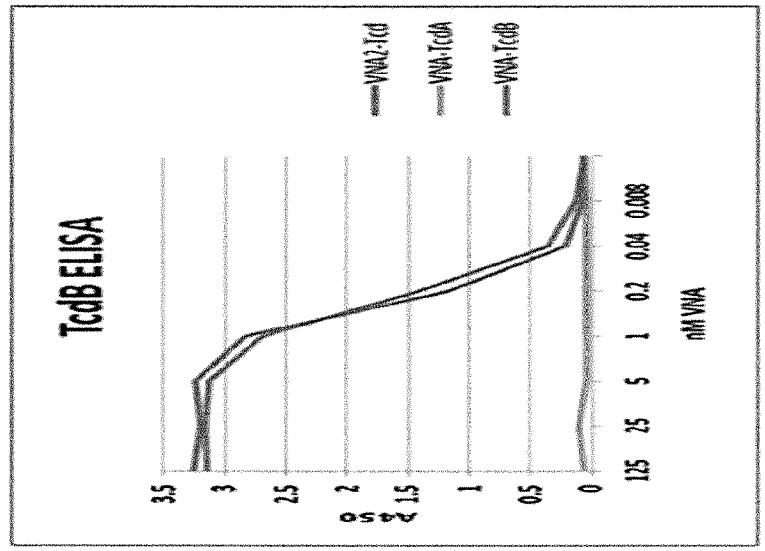
Figure 51B:
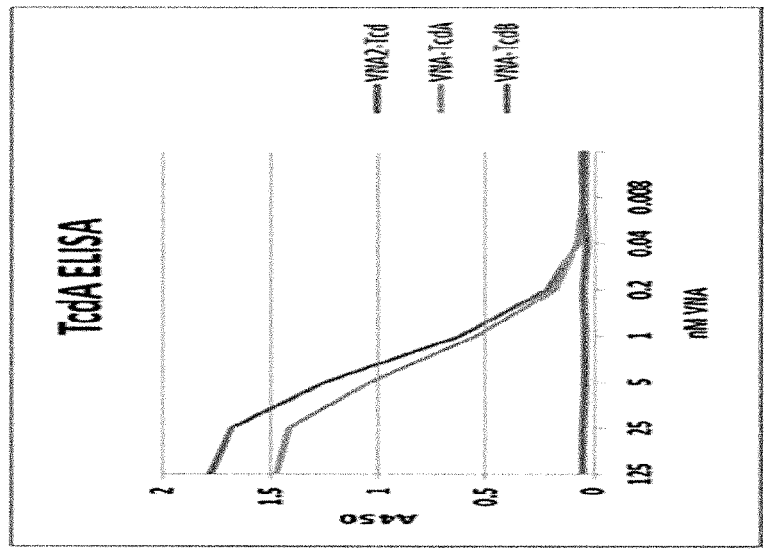

FIG. 51 A-FIG. 51 B are a set of line graphs showing affinity of VNA-TcdA and VNA-TcdB to *C. difficile* toxin A and toxin B respectively.

FIG. 51 A is a line graph showing that the VHH dimer, VNA-TcdA, lacking the protease-sensitive sites, binds *C. difficile* toxin A (TcdA) with the same affinity as the tetramer, VNA2-Tcd. VNA-TcdB did not show affinity for TcdA. The ELISA assay was performed by coating the microtiter plates with TcdA and incubation with VNA-TcdA, VNA-TcdB, or VNA2-Tcd at concentrations of 0.008 nM, 0.04 nM, 0.2 nM, 1 nM, 5 nM, 25 nM, or 125 nM, with visualization of binding using an HRP-conjugated detection antibody.

FIG. 51 B is a line graph showing that the VHH dimer, VNA-TcdB, lacking the protease-sensitive sites, binds *C. difficile* toxin B (TcdB) with the same affinity as the tetramer, VNA2-Tcd. VNA-TcdA did not show affinity for TcdB. The ELISA assay was performed by coating the microtiter plates with TcdA and incubation with VNA-TcdA, VNA-TcdB, or VNA2-Tcd at concentrations of 0.008 nM, 0.04 nM, 0.2 nM, 1 nM, 5 nM, 25 nM, or 125 nM, with visualization of binding using an HRP-conjugated detection antibody.

DETAILED DESCRIPTION

The presence of toxins in the circulation is the cause of a wide variety of human and animal illnesses. Antitoxins are therapeutic agents that prevent toxin infection or reduce further development of negative symptoms in patients that have been exposed to a toxin (a process referred to as "intoxication"). Typically, antitoxins are antisera obtained from large animals (e.g., sheep, horse, and pig) that were immunized with inactivated or non-functional toxin. More recently, antitoxin therapies have been developed using combinations of antitoxin monoclonal antibodies including yeast-displayed single-chain variable fragment antibodies generated from vaccinated humans or mice. See Nowakowski et al. 2002. Proc Natl Acad Sci USA 99: 11346-11350; Mukherjee et al. 2002. Infect Immun 70: 612-619; Mohamed et al. 2005 Infect Immun 73: 795-802; Walker, K. 2010 Interscience Conference on Antimicrobial Agents and Chemotherapy—50th Annual Meeting—Research on Promising New Agents: Part 1. Drugs 13: 743-745. Antisera and monoclonal antibodies can be difficult to produce economically at scale, usually requiring long development times and resulting in problematic quality control, shelf-life and safety issues. New therapeutic strategies to develop and prepare antitoxins are needed.

Antitoxins function through two key mechanisms neutralization of toxin function and clearance of the toxin from the body. Toxin neutralization occurs through biochemical processes including inhibition of enzymatic activity and prevention of binding to cellular receptors. Antibody mediated serum clearance occurs subsequent to the binding of multiple antibodies to the target antigen (Daeron M. 1997 Annu Rev Immunol 15: 203-234; Davies et al. 2002 Arthritis Rheum 46: 1028-1038; Johansson et al. 1996 Hepatology 24: 169-175; and Lovdal et al. 2000 J Cell Sci 113 (Pt 18): 3255-3266). Multimeric antibody decoration of the target is necessary to permit binding to low affinity Fc receptors (Davies et al. 2002 Arthritis Rheum 46: 1028-1038 and Lovdal et al. 2000 J Cell Sci 113 (Pt 18): 3255-3266). Without being limited by any particular theory or mechanism of action, it is here envisioned that an ideal antitoxin therapeutic would both promote toxin neutralization to immediately block further toxin activity and also accelerate toxin clearance to eliminate future pathology if neutralization becomes reversed.

Effective clearance of botulinum neurotoxin (BoNT), a National Institute of Allergy and Infectious Diseases (NIAID) Category A priority pathogen, is believed by some researchers to require three or more antibodies bound to the toxin. Nowakowski et al. 2002. (Proc Natl Acad Sci USA 99: 11346-11350) determined that effective protection of mice against high dose challenge of BoNT serotype A (BoNT/A) required co-administration of three antitoxin monoclonal antibodies, and that all three antibodies presumably promoted clearance. Data have shown that administration of a pool of three or more small binding agents, each produced with a common epitopic tag, reduced serum levels of a toxin when co-administered with an anti-tag monoclonal antibody (Shoemaker et al. U.S. published application 2010/0278830 A1 published Nov. 4, 2010 and Sepulveda et al. 2009 Infect Immun 78: 756-763, each of which is incorporated herein in its entirety). The tagged binding agents directed the binding of anti-tag monoclonal antibody to multiple sites on the toxin, thus indirectly decorating the toxin with antibody Fc domains and leading to its clearance through the liver.

Pools of scFv domain binding agents with specificity for BoNT/A and each containing a common epitopic tag (E-tag), had been shown to be effective for decorating the botulinum toxin with multiple anti-tag antibodies (Shoemaker et al. U.S. utility patent publication number 2010/0278830 published Nov. 4, 2010 and U.S. continuation-in-part patent publication number 2011/0129474 published Jun. 2, 2011, each of which is incorporated herein by reference in its entirety). Data showed that the administration of binding agents and clearance antibodies to subjects resulted in clearance via the liver with an efficacy in mouse assays equivalent to conventional polyclonal antitoxin sera. Ibid. and Sepulveda et al. 2009 Infect Immun 78: 756-763. The tagged scFvs toxin targeting agents and the anti-tag monoclonal antibodies were effective for treating subjects at risk for or having been contacted with a disease agent.

The use of small binding agents to direct the decoration of toxin with antibody permits new strategies for the development of agents with improved therapeutic and commercial properties. Examples herein show that a single recombinant heterodimeric binding protein/agent including two or more high-affinity BoNT binding agents (camelid heavy-chain-only Ab VH (VHH) domains) and two epitopic tags, co-administered with an anti-tag mAb, protected subjects from botulism caused negative symptoms and lethality. Further the binding protein resulted in antitoxin efficacy equivalent to and greater than conventional BoNT antitoxin serum in two different in vivo assays. Examples herein compare neutralizing or non-neutralizing binding agents administered with or without clearing antibody, and show the relative contributions of toxin neutralization and toxin clearance to antitoxin efficacy. Examples herein show that both toxin neutralization and toxin clearance contribute significantly to antitoxin efficacy in subjects. Toxin neutralization or toxin clearance using heterodimer binding protein antitoxins sufficiently protected subjects from BoNT lethality in a therapeutically relevant, post-intoxication assay. Methods in Examples herein optionally further include a clearing antibody for example a monoclonal anti-E-tag antibody.

It was observed in Examples herein that VHH binding agents that neutralized toxin function significantly improved the antitoxin efficacy and even obviated the need for clearing antibody in a clinically relevant post-intoxication BoNT/A assay. The methods, compositions and kits using the multimeric binding proteins described herein have widespread application in antitoxin development and other therapies in which neutralization and/or accelerated clearance of a target molecule benefits a patient. For example, the target molecule is an exogenous disease agent that infects or is at risk to infect a patient. Exogenous disease agent for example is a virus, a cancer cell, a fungus, a bacterium, a parasite and a product thereof such as a pathogenic molecule, a protein, a lipopolysaccharide, or a toxin. Alternatively, the molecule is an endogenous (body produced) molecule that is produced in the patient and that causes or produces harmful effects on the patient. For example, the molecule is a hormone or a protein that is associated with a disease or condition, e.g., inflammation, cancer, transplant rejection, kidney failure, or a defect in blood clotting such as hemophilia and thrombophilia. In various embodiments, the disease agent is a toxin of *C. difficile*.

*C. difficile* is a gram-positive, spore forming, anaerobic bacterium that is the leading cause of antibiotic-associated diarrhea, the severity of which ranges from mild diarrhea to life threatening pseudomembranous colitis (Bartlett J G. 200 2 N Engl J Med 346:334-9 and Feng et al. PCT/US10/58701 filed Dec. 2, 2010, each of which is incorporated by reference in its entirety). Pathogenic *C. difficile* strains excrete exotoxins A (TcdA) and B (TcdB) that have been intimately linked to its pathogenicity. Both TcdA and TcdB are enterotoxic, capable of inducing intestinal epithelial damage and increasing mucosal permeability, and hence are thought to be responsible for the pathogenesis of *C. difficile*-associated colitis (Kelly C P et al. 1998 Annu Rev Med 49:375-90). *C. difficile* has emerged as a leading cause of hospital-acquired enteric infections with rapidly escalating annual health care costs in the United States (Kyne L et al. 2002 Clin Infect Dis 34:346-353). The severity of *C. difficile*-associated infections ranges from mild diarrhea to life threatening pseudomembranous colitis (Bartlett J G et al. 2002 N Engl J Med 346:334-339; Borriello S P 1998 Antimicrob Chemother 41 Suppl C:13-19). Several hospital outbreaks of *C. difficile*-associated diarrhea (CDAD), with high morbidity and mortality in the past few years in North America, have been attributed to the widespread use of broad-spectrum antibiotics.

The emergence of more virulent *C. difficile* strains contributes also to the increased incidence and severity of the disease (Loo V G et al. 2005 N Engl J Med 353:2442-2449; McDonald L C et al. 2005 N Engl J Med 353:2433-2441). Antibiotic usage results in a reduction of commensal microflora in the gut, which permits *C. difficile* to proliferate more extensively, leading to the further production of toxins (Owens J R et al. 2008 Clinical Infectious Diseases 46(s1): S19-531). *C. difficile* infection (CDI) includes a range of symptoms varying from mild diarrhea to severe fulminate lethal disease (Kuijper E J et al. 2007 Curr Opin Infect Dis 20(4):376-383). Recent outbreaks of highly virulent *C. difficile* strains (McDonald L C et al. 2005 N Engl J Med 353(23):2433-2441; Loo V G et al. 2005 N Engl J Med 353(23):2442-2449) have increased the urgency to devote greater resources towards the understanding of the molecular, genetic, and biochemical basis for the pathogenesis, with a view to use such information to develop novel preventive and treatment modalities.

A cell-based immunocytotoxicity assay for detecting *C. difficile* toxins described in Feng et al. (PCT/US2009/003055 published Nov. 19, 2009 as WO 2009/139599) uses an anti-*C. difficile* toxin A (TcdA) monoclonal antibody, named A1H3, which substantially enhanced the activity of TcdA on Fc gamma receptor I (FcγRI)-expressing cells (He X, Sun X, Wang J, et al. Antibody-enhanced, Fc{gamma}R-mediated endocytosis of *C. difficile* toxin A. Infect Immun 2009). Feng et al. shows use of A1H3 enhancing antibody, in combination with an electronic sensing system to develop a real-time and ultrasensitive assay for the detection of biological activity of *C. difficile* toxins.

Toxin A (TcdA) and toxin B (TcdB) are the major virulence factors contributing to pathogenic *C. difficile* strains. These strains are enterotoxic, inducing intestinal epithelial cell damage, disrupting epithelium tight junctions leading to increased mucosal permeability (Pothoulakis C et al. 2001 Am J Physiol Gastrointest Liver Physiol 280:G178-183; Riegler M et al. 1995 J Clin Invest 95:2004-2011; Savidge T C et al. 2003 Gastroenterology 125:413-420). Moreover, these toxins induce production of immune mediators, leading to subsequent neutrophil infiltration and severe colitis (Kelly C P et al. 1994 J Clin Invest 93:1257-1265; Kelly C P et al. 1998 Annu Rev Med 49:375-390). TcdA and TcdB are structurally homologous, and contain a putative N-terminal glucosyltransferase and a cysteine proteinase domain, a transmembrane domain, and a C-terminal receptor binding domain (von Eichel-Streiber C et al. 1996 Trends Microbiol 4:375-382) (Dank T et al. 2008 Trends in microbiology 16:222-229; Voth D E et al. 2005 Clin Microbiol Rev 18:247-263).

Interaction between the toxin C-terminus and the host cell receptors initiates a receptor-mediated endocytosis (Florin I et al. 1983 Biochim Biophys Acta 763:383-392; Karlsson K A 1995 Curr Opin Struct Biol 5:622-635; Tucker K D et al. 1991 Infect Immun 59:73-78). Although the intracellular mode of action remains unclear, it has been proposed that the toxins undergo conformational change at low pH in the endosomal compartment, leading to membrane insertion and channel formation (Florin I et al. 1986 Microb Pathog 1:373-385; Giesemann T et al. 2006 J Biol Chem 281: 10808-10815; Henriques B et al. 1987 Microb Pathog 2:455-463; Qa'Dan M et al. 2000 Infect Immun 68:2470-2474). A host cofactor is then required to trigger a second structural change which is accompanied by an immediate autocatalytic cleavage and release of the glucosyltransferase domain into cytosol (Pfeifer G et al. 2003 J Biol Chem 278:44535-44541; Reineke J e al. 2007 Nature 446:415-419; Rupnik M et al. 2005 Microbiology 151:199-208). Once the glucosyltransferase domain reaches the cytosol, it inactivates proteins of the Rho/Rac family, leading to alterations of cytoskeleton and ultimately cell death (Just I et al. 1995 Nature 375:500-503; Sehr P et al. 1998 Biochemistry 37:5296-5304).

The clinical manifestation of CDI is highly variable, from asymptomatic carriage, to mild self-limiting diarrhea, to the more severe pseudomembranous colitis. The prevalence of systemic complication and death in CDI has become increasingly common (Siemann M et al. 2000 Intensive care medicine 26:416-421). In life-threatening cases of CDI, systemic complications are observed, including cardiopulmonary arrest (Johnson S et al. 2001 Annals of internal medicine 135:434-438), acute respiratory distress syndrome (Jacob S S et al. 2004 Heart Lung 33:265-268), multiple organ failure (Dobson G et al. 2003 Intensive care medicine 29:1030), renal failure (Cunney R J et al. 1998 Nephrol Dial Transplant 13:2842-2846), and liver damage (Sakurai T et al. 2001 J Infect Dis 33:69-70). The exact reason for these negative complications is unclear, and may be caused by entry of the toxin into the circulation and systemic dissemination (Hamm E E et al. 2006 Proc Natl Acad Sci USA 103:14176-14181).

Standard therapy depends on treatment with vancomycin or metronidazole, neither of which is fully effective (Zar et al. 2007 Clinical Infectious Diseases 45:302-307). Moreover, an estimated 15% to 35% of those infected with *C. difficile* relapse following treatment (Barbut et al. 2000 J Clin Microbiol 38: 2386-2388; Tonna et al: Postgrad Med J 81: 367). Unfortunately, the primary treatment option for recurrent CDI is still metronidazole or vancomycin. Other options, such as probiotics, toxin-absorbing polymer and anion-exchange resins, have limited efficacy (Gerding, D. N., Muto, C. A. & Owens, R. C., Jr. 2008 Clin Infect Dis 46 Suppl 1: S32-42). Therefore, immune-based therapies are a promising approach to control the disease. Antibodies specific for both of these toxins, and not against TcdA or TcdB alone, protect against toxigenic *C. difficile* infection in a hamster model (Libby et al, 1982 Infect Immun 36: 822-829; Fernie et al, 1983 Dev Biol Stand 53: 325; and Kim et al, 2006 Infection and immunity 74: 6339). Human serum antibodies specific for both TcdA and TcdB are associated also with protection against symptomatic disease and recurrence. Recent phase II clinical trial led by Merck demonstrated that the systemically administered human IgG monoclonal antibodies against TcdA and TcdB prevents disease relapse in CDI patients (Lowy et al, 2010 The New England journal of medicine 362: 197). However, the treatment involved the injection of a large quantity of two individual antibodies against each toxin.

Examples herein show, among others, a new approach to the development of antitoxins that employs a single recombinant protein to promote toxin decoration with multiple copies of a single monoclonal antibody leading to its neutralization and clearance from the body. The methods, compositions, and kits herein are useful for treating a great number of the most common pathogenic biological targets by accelerating neutralization and clearance from the subject or patient.

Examples herein show, among others, that camelid VHH binding domains, which have multiple commercial advantages over scFvs due in part to the ease and reduced cost of producing VHHs, were effective as toxin targeting agents both with and without being administered with clearing antibody. An important advantage of VHHs is the ability of medical professionals and scientists to express these binding agents as heterodimers in which each component VHH remains fully functional. The multimeric fusion proteins containing at least two VHH binding regions resulted in the component VHHs binding to different epitopes on the same toxin target. Without being limited by any particular theory or mechanism of action, it is believed that incorporation of two epitope tags on the heterodimers resulted in decoration of the toxin with two clearing antibodies at each epitope, and resulted in a total of four monoclonal clearing antibodies binding to the heterodimers on the toxin. In addition, with certain heterodimers the decoration promoted efficient toxin clearance. Either neutralization or clearance or both are important mechanisms of remediating toxin exposure. As each double-tagged heterodimeric binding agent was bound only to only two monoclonal antibodies, the heterodimeric agent itself may not be effectively cleared by low affinity Fc receptors unless actually bound to the toxin.

The ability of antitoxin antibodies to protect mammalian subjects from the symptoms of toxin exposure is influenced by several factors that are described herein. Examples herein used intoxication models and varied the dose of antitoxin agent and the timing of antitoxin administration relative to exposure to toxin in order to determine whether both the dose and the timing of the antitoxin are factors that influence antitoxin efficacy. In addition, examples herein analyzed the role that affinity of the antibody for the toxin has on the ability of the antibody to bind ($K_{on}$) and remain bound ($K_{off}$) to the toxin and exert its effect. Data show that the ability of the antibody monomer/heterodimer to inhibit the enzymatic activity of the toxin and/or prevent its entry into target cells (i.e. neutralization) is a major factor in effective antitoxin treatment of subjects. Specifically, data show that the greater the binding affinity of the binding protein to the target molecule, the greater the potential neutralization and clearance of the binding protein. Examples herein show also that the multimeric binding proteins promoted the clearance of the toxin from the serum and minimized further negative symptoms or lethality by the target molecule or disease agent. A portion of this work was published Jan. 6, 2012 in the Public Library of Science One and was entitled, "A Novel Strategy for Development of Recombinant Antitoxin Therapeutics Tested in a Mouse Botulism", authored by Jean Mukherjee, Jacqueline M. Tremblay, Clinton E. Leysath, Kwasi Ofori, Karen Baldwin, Xiaochuan Feng, Daniela Bedenice, Robert P. Webb, Patrick M. Wright, Leonard A. Smith, Saul Tzipori, and Charles B. Shoemaker (Mukherjee J. et al. 2012 PLoS One. 7(1):e29941), which is incorporated by reference herein in its entirety.

Methods for engineering and selecting proteins for binding to disease agents are shown for example in U.S. utility application Ser. No. 13/566,524 filed Aug. 3, 2012; U.S. publication number 2011/0129474 published Jun. 2, 2011 (U.S. application Ser. No. 12/889,511 filed Sep. 24, 2010), which is a continuation-in-part application of U.S. publication number 2010/0278830 published Nov. 4, 2010 (U.S. utility application Ser. No. 12/032,744 filed Feb. 18, 2008), each of which is incorporated by reference herein in its entirety.

An aspect of the invention provides a method for treating a subject at risk for exposure to or exposed to a disease agent, the method including: contacting the subject with at least one recombinant heteromultimeric neutralizing binding protein including two or multiple binding regions, such that the binding regions are not identical, and each binding region specifically binds a non-overlapping portion of the disease agent, such that the binding protein neutralizes the disease agent, thereby treating the subject for exposure to the disease agent.

In various embodiments of the method, the binding protein includes at least one tag. For example, the tag is a molecule or epitope that is attached or genetically fused to the binding protein and/or binding regions. The tag in various embodiments of the method induces endogeneous clearance of the disease agent from the body in vivo. For example the tag includes SEQ ID NO: 15, or a variant thereof. In a related embodiment, the tag includes an antibody epitope.

In certain embodiments of the method, the binding protein is selected from: a single-chain antibody (scFv); a recombinant camelid heavy-chain-only antibody (VHH); a shark heavy-chain-only antibody (VNAR); a microprotein; a darpin; an anticalin; an adnectin; an aptamer; a Sac7d derivative (affitins, e.g. NANOFITINS, see *Journal of Molecular Biology* 2008 Nov. 28; 383(5):1058-68, the contents of which are hereby incorporated by reference), a Fv; a Fab; a Fab'; and a F(ab')$_2$. In an embodiment, the binding protein is heterodimeric, for example the binding protein has greater potency than each individual monomer. In alternative embodiments, the heteromultimeric neutralizing binding protein is multimeric and the multimeric components are associated non-covalently or covalently.

The binding protein in certain embodiments of the method includes a linker that separates multimeric components of the binding regions. In various embodiments, the linker includes at least one selected from: a peptide, a protein, a sugar, or a nucleotide. For example, the linker includes amino acid sequence GGGGS (SEQ ID NO: 54), or a variant thereof, or includes amino acid sequence GGGGSGGGGSGGGGS (SEQ ID NO: 55), or a variant thereof or a portion thereof. In a related embodiment, the linker is a flexible linker located within subunits/domains of the binding protein, such that the linker does not negatively affect the function of the binding protein to the disease agent. For example, the linker includes amino acid sequences/residues including serine and glycine, and in various embodiments is at least about three to five amino acids long, or about five to eight amino acids long, or about eight to fifteen amino acids long.

In certain embodiments, the disease agent is a biological target or biological molecule. For example, the biological target or the biological molecule is naturally occurring within the subject, for example a molecule or compound synthesized by the subject. An example of a biological molecule synthesized by the subject is an IgE that is associated with an allergy or an auto antibody or an MHC protein (e.g., HLA class I antigens A and B and HLA class II antigen DR) associated with an autoimmune disease. For example the autoimmune disease is selected from: lupus erythematosus, Graves' disease, rheumatoid arthritis, Sjögren's syndrome, myasthenia gravis, and Hashimoto's thyroiditis.

The disease agent in various embodiments of the method includes a plurality of non-identical disease agents, for example two or more bacterial toxins, or a viral toxin and a fungal species. In various embodiments, the binding regions of the binding protein are specific to each non-identical disease agent and bind to and neutralize the plurality of disease agents.

In various embodiments of the method, the disease agent is at least one selected from: a virus, a cancer cell, a fungus, a bacterium, a parasite and a product thereof such as a pathogenic molecule, a protein, a lipopolysaccharide, and a toxin. In certain embodiments, the toxin includes a protein, a lipid, a lipopolysaccharide, and a small molecule toxin such as an aflatoxin or a dinoflagellate toxin. The toxin for example is a Botulinum neurotoxin comprising a serotype selected from: A, B, C, D, E, F, and G. In certain embodiments of the method, the toxin is a *Clostridium* exotoxin comprising toxin A (TcdA) and toxin B (TcdB).

In various embodiments of the method, the toxin is at least one selected from: staphylococcal α-hemolysin, staphylococcal leukocidin, aerolysin cytotoxic enterotoxin, a cholera toxin, *Bacillus cereus* hemolysis II toxin, a *Helicobacter pylori* vacuolating toxin, a *Bacillus anthracis* toxin, a cholera toxin, a *Escherichia coli* serotype O157:H7 toxin, a *Escherichia coli* serotype O104:H7 toxin, a lipopolysaccharide endotoxin, a Shiga toxin, a pertussis toxin, a *Clostridium perfringens* iota toxin, a *Clostridium spiroforme* toxin, a *Clostridium difficile* toxin A, a *Clostridium difficile* toxin B, a *Clostridium septicum* a toxin, and a *Clostridium botulinum* C2 toxin. In a related embodiment of the method, the disease agent is an infectious strain, for example a bacterial strain or a viral strain. In a related embodiment, the disease agent is a Gram-negative strain or a Gram positive strain.

The bacterium in various embodiments of the method is selected from the group consisting of: *B. anthracis, B. cereus, C. botulinum, C. difficile, C. perfringens, C. spiroforme*, and *V. cholera*, BI/NAP1/027 and the J strain.

In certain embodiments, the binding regions bind to different disease agents, such that the binding protein is specific for a plurality of disease agents, e.g., a *Clostridium* toxin and an *Escherichia* toxin. For example, the binding protein includes a chimeric fusion protein specific to at least two different disease agents described herein. In certain embodiments of the method, the binding protein is a humanized antibody derived from a non-human species for example a mouse, a rabbit, an alpaca, a llama, or horse.

In a related embodiment, the method further includes observing neutralizing of the disease agent by the binding protein and/or survival of the subject. In certain embodiments of the method, observing further includes measuring an amount of the disease agent or a disease agent product in a sample from the subject. In various embodiments, the sample is selected from: a cell, a fluid, and a tissue. For example, the fluid is at least one selected from: blood, serum, plasma, mucosal fluid, saliva, cerebrospinal fluid, semen, tears, and urine. In certain embodiments of the method, the cell or the tissue is at least one selected from: fecal; vascular; epithelial; endothelial; dermal; dental; connective; muscular; neuronal; facial; cranial; soft tissue including cartilage and collagen; brain; bone; bone marrow; joint tissue; and articular joints. For example, the method includes collecting the fluid, the cell, or the tissue from a biopsy. In certain embodiments, the method includes collecting the fluid, the cell, or the tissue from an ex vivo sample or aliquot. Alternatively, the method includes collecting from fluid, cell, or tissue that is in vivo or in situ.

The method further includes in a related embodiment observing a reduction or a remediation in at least one pathology symptom associated with the disease agent. In various embodiments, the method further includes prior to contacting the subject with the binding protein, observing and/or detecting in the subject an indicium of the exposure to the disease agent selected from: diarrhea, vomiting, breathing difficulty, fever, inflammation, bleeding, pain, numbness, loss of consciousness, tissue necrosis, or organ failure. For example, the subject is a transplant recipient or an immunosuppressed patient.

In a related embodiment, the method further includes contacting the subject with the binding protein at a period of time such as seconds, minutes, or hours after observing the indicium. Alternatively, the method further includes contacting the subject with the binding protein seconds, minutes, hours, or days prior to an event that is associated with the risk for the exposure. For example, the method includes contacting the subject prior to or after the subject's entering a potentially hazardous or dangerous environment such as biohazard facility, a combat zone, or a hazardous waste site.

The method in related embodiments includes contacting the subject with the binding protein by injecting a solution including the binding protein into the subject. In various embodiments, injecting involves at least one selected from: subcutaneous, intravenous, intramuscular, intraperitoneal, intradermal, intramedullary, transcutaneous, and intravitreal. In various embodiments of the method, contacting the subject with binding protein includes at least one technique selected from: topically, ocularly, nasally, bucally, orally, rectally, parenterally, intracisternally, intravaginally, or intraperitoneally. In a related embodiment, contacting the subject involves using an applicator, for example the applicator is a syringe, a needle, a sprayer, a sponge, a gel, a strip, a tape, a bandage, a tray, a string, or a device used to apply a solution to a cell or a tissue. In various embodiments, the pharmaceutical compositions (and/or additional therapeutic agents) are administered into the GI tract via, for example, oral delivery, nasogastral tube, intestinal intubation (e.g. an enteral tube or feeding tube such as, for example, a jejunal tube or gastro-jejunal tube, etc.), endoscopy, colonoscopy, or enema.

Some embodiments, provide a method of treating or preventing an antibiotic-induced adverse effect in the GI tract, comprising administering an effective amount of one or more pharmaceutical compositions described herein to a patient in need thereof (e.g. one receiving or likely to receive one or more antibiotic treatments, e.g. one or more of fluoroquinolones, cephalosporins, clindamycin and penicillins). In some embodiments, the antibiotic-induced adverse effect is associated with use of one or more of fluoroquinolones, cephalosporins, clindamycin and penicillins. Some embodiments, provide a method of maintaining a normal intestinal micrbiota, comprising administering an effective amount of one or more pharmaceutical compositions described herein to a patient in need thereof (e.g. one receiving or likely to receive one or more antibiotic treatments, e.g. one or more of fluoroquinolones, cephalosporins, clindamycin and penicillins). Some embodiments, provide a method of preventing an overgrowth of one or more pathogenic microorganisms in the GI tract of a patient, comprising administering an effective amount of one or more pharmaceutical compositions described herein to a patient in need thereof (e.g. one receiving or likely to receive one or more antibiotic treatments, e.g. one or more of fluoroquinolones, cephalosporins, clindamycin and penicillins). Some embodiments, provide a method of treating or preventing a *C. difficile* infection (CDI) or *C. difficile*-associated disease, comprising administering an effective amount of one or more pharmaceutical compositions described herein to a patient in need thereof (e.g. one receiving or likely to receive one or more antibiotic treatments, e.g. one or more of fluoroquinolones, cephalosporins, clindamycin and penicillins). In various embodiments, the CDI and/or *C. difficile* associated disease is treated in the context of initial onset or relapse. In various embodiments, the present compositions neutralize a *C. difficile* toxin (e.g toxin A and/or B).

In various embodiments, the CDI and/or *C. difficile* associated disease is one or more of antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon. In some embodiments, the present compositions and methods prevent or reduce dilatation, mesocolonic edema, multifocal hemorrhages, and thickening of the intestinal wall. In various embodiments, including treatment and/or prevention of, for example an antibiotic-induced adverse effect in the GI tract, a ceftriaxone-associated adverse effect, an overgrowth of one or more pathogenic microorganisms in the GI tract of a patient, a *C. difficile* infection (CDI) or *C. difficile*-associated disease and maintenance of a normal intestinal micrbiota, the pharmaceutical composition is any one of those described herein such as, by way of non-limiting example, pharmaceutical compositions comprising one or more recombinant binding protein comprising at least one disease agent binding domain amino acid sequence selected from SEQ ID NO: 174, SEQ ID NO: 164, SEQ ID NO: 165, SEQ ID NO: 166, SEQ ID NO: 167, SEQ ID NO: 171, SEQ ID NO: 172, and SEQ ID NO: 173, or variants thereof. In some embodiments, the recombinant binding protein comprising at least one disease agent binding domain comprises a recombinant camelid heavy-chain-only antibody (VHH).

In various embodiments, the present methods treat or prevent a nosocomial infection and/or a secondary emergent infection. In various embodiments, the patient is undergoing treatment or has recently undergone treatment with one or more primary antibiotic (e.g. one or more of fluoroquinolones, cephalosporins, clindamycin and penicillins). In various embodiments, the patient is undergoing treatment or has recently undergone treatment with one or more initial and/or adjunctive therapy. In various embodiments, the an initial and/or adjunctive therapy, selected from one or more of metronidazole, vancomycin, fidaxomicin, rifaximin, fecal bacteriotherapy, probiotic therapy, and antibody therapy, is administered to the patient.

In some embodiments, the present methods pertain to co-treatment (e.g. simultaneously or sequentially) with the pharmaceutical compositions of the present invention and/or any initial and/or adjunctive therapy. In another embodiment, the present methods pertain to treatment with a co-formulation of the pharmaceutical compositions of the present invention and any initial and/or adjunctive therapy. In other embodiments, the present methods pertain to treating a *C. difficile* infection (CDI) and/or a *C. difficile*-associated disease in a patient undergoing treatment with any additional agent described herein and/or any initial and/or adjunctive therapy described herein by administering a pharmaceutical composition of the present invention to the patient.

In various embodiments, a CDI and/or *C. difficile* associated disease is prevented by administration of the present pharmaceutical compositions to a patient that is at risk for CDI and/or *C. difficile* associated disease (e.g. is undergoing or will undergoing antibiotic treatment, including IV antibiotic treatment and/or has previously been afflicted with CDI and/or *C. difficile* associated disease). In various embodiments, the CDI and/or *C. difficile* associated disease is treated or prevented in the context of initial onset or relapse/recurrence (e.g. due to continued or restarted antibiotic therapy). For example, in a patient that has previously suffered from CDI, the present pharmaceutical compositions (and/or additional agents) may be administered upon the first symptoms of recurrence. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, CDI and/or *C. difficile* associated disease may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, CDI and/or *C. difficile* associated disease may also be diagnosed via enzyme immunoassays e.g. to detect the *C. difficile* toxin A or B antigen and/or glutamine dehydrogenase (GDH), which is produced by *C. difficile* organisms, polymerase chain reaction (e.g. to detect the *C. difficile* toxin A or B gene or a portion thereof (e.g. tcdA or tcdB), including the ILLUMIGENE LAMP assay), a cell cytotoxicity assay. For example, any one of the following tests may be used may be used: Meridian ImmunoCard Toxins A/B; Wampole Toxin A/B Quik Chek; Wampole *C. difficile* Quik Chek Complete; Remel Xpect *Clostridium difficile* Toxin A/B; Meridian Premier Toxins A/B; Wampole *C. difficile* Tox A/B II; Remel Prospect Toxin A/B EIA; Biomerieux Vidas *C. difficile* Toxin A&B; BD Geneohm *C. difficile*; Prodesse Progastro CD; and Cepheld Xpert *C. difficile* In various embodiments, the clinical sample is a patient stool sample. Also a flexible sigmoidoscopy "scope" test and/or an abdominal X-ray and/or a computerized tomography (CT) scan, which provides images of the colon, may be used in assessing a patient (e.g. looking for characteristic creamy white or yellow plaques adherent to the wall of the colon). Further, biopsies (e.g. of any region of the GI tract) may be used to assess a potential CDI and/or *C. difficile* associated disease patient.

Furthermore, the patients of the invention include, but are not limited to, patients that are at a particular risk for CDI and/or *C. difficile* associated disease, such as those which have been taking an antibiotic during the past 30 or so days and/or have an immune system that is weak (e.g. from a chronic illness) and/or are women and/or are elderly (e.g. over about 65 years old) and/or are elderly woman and/or undergo treatment with for heartburn or stomach acid disorders (e.g. with agents such as PREVACID, TAGAMET, PRILOSEC, or NEXIUM and related drugs) and/or have recently been in the hospital, including in an intensive care unit, or live in a nursing home. Accordingly, in some embodiments, the pharmaceutical composition of the present invention may be used to prophylactically prevent CDI and/or *C. difficile* associated disease.

In some embodiments, the methods and uses of the present invention relate to a patient is undergoing treatment or has recently undergone treatment with one or more primary antibiotic. A "primary antibiotic" refers to an antibiotic that is administered to a patient and which may result in CDI and/or *C. difficile* associated disease. These include the antibiotics that most often lead to CDI and/or *C. difficile* associated disease, such as, for example, fluoroquinolones, cephalosporins, clindamycin and penicillins.

In some embodiments, the methods and uses of the present invention include those in which an initial and/or adjunctive therapy is administered to a patient. Initial and/or adjunctive therapy indicates therapy that is used to treat CDI and/or *C. difficile* associated disease upon detection of such disease. In some embodiments, the initial and/or adjunctive therapy is one or more of metronidazole, vancomycin, fidaxomicin, rifaximin, fecal bacteriotherapy, probiotic therapy, a charcoal-based therapy, and antibody therapy, as described herein. In various embodiments, the methods and uses of the present invention include use of the inventive pharmaceutical composition as an adjuvant to any of these initial and/or adjunctive therapies (including co-administration or sequential administration). In various embodiments, the methods and uses of the present invention include use of the inventive pharmaceutical composition in a patient undergoing initial and/or adjunctive therapies.

In a related embodiment of the method, contacting the subject with the binding protein includes administering to the subject a source of expression of the binding protein. In various embodiments of the method, the source of expression of the binding protein is a nucleotide sequence encoding the binding protein, such that the source of the expression includes at least one selected from the group consisting of: a naked nucleic acid vector, bacterial vector, and a viral vector. For example, the bacterial vector is derived from at least one selected from the group consisting of: *E. coli, Bacillus* spp, *Clostridium* spp, *Lactobacillus* spp, and *Lactococcus* spp.

In a related embodiment of the method, contacting further includes administering the vector, for example the naked nucleic acid vector, the bacterial vector, or the viral vector.

In a related embodiment, the nucleotide acid sequence further includes an operably linked signal for promoting expression of the binding protein. For example, the signal includes a mammalian promoter or a non-viral promoter. In a related embodiment, the method involves engineering the binding protein or the source of expression of the binding protein (e.g., viral vector or bacterial vector) using a dimerizer sequence for example having an amino acid sequence including SEQ ID NO: 94 or a portion or homolog or variant thereof. For example, the dimerizer sequences forms a covalent bond or disulfide linkage between at least two amino acid sequences to form a homodimer, a heterodimer, or a multimer. The method in various embodiments includes, prior to contacting, engineering the binding protein using an agent that multimerizes at least one binding region or a multimer, e.g., a heterodimer, a heterotrimer, and a heterotetramer, to form the binding protein.

In a related embodiment of the method, the viral vector is derived from at least one selected from: an adenovirus, an adeno-associated virus, a herpesvirus, and a lentivirus. The method in various embodiments further includes contacting the subject with a gene delivery vehicle selected from at least one of: a liposome, a lipid/polycation (LPD), a peptide, a nanoparticle, a gold particle, and a polymer. For example, the gene delivery vehicle specifically targets a cell or tissue in the body by contacting or binding a receptor located on the cell or tissue.

An aspect of the invention provides a pharmaceutical composition for treating a subject at risk for exposure to or exposed to a disease agent, the pharmaceutical composition including: at least one recombinant heteromultimeric neutralizing binding protein including two or more binding regions, such that the binding regions are not identical, and each binding region specifically binds a non-overlapping portion of the disease agent, such that the binding protein neutralizes the disease agent, thereby treating the subject for exposure to the disease agent.

In a related embodiment, the composition is compounded with a pharmaceutically acceptable buffer or diluent. For example, the composition is compounded for parenteral administration such as intravenous, mucosal administration, topical administration, or oral administration.

In various embodiments, the subject is at least one selected from: a human, a dog, a cat, a goat, a cow, a pig, and a horse. For example, the human subject is a: sick child or adult, healthcare profession (e.g., doctor and nurse), aid worker, member of the military, or an immunosuppressed patient such as a transplant recipient. In some embodiments, the subject is a hospital patient at risk for a Hospital Acquired Infections (or Healthcare Acquired Infections, HAI). In some embodiments, the subject is one receiving or likely to receive one or more antibiotic treatments, e.g. one or more of fluoroquinolones, cephalosporins, clindamycin and penicillins. In certain embodiments, the pharmaceutical composition is formulated to protect the subject against the exposure, for example that exposure includes a picogram amount, nanogram amount, microgram amount, or gram amount of the disease agent or a plurality of disease agents.

The binding protein or binding regions in various embodiments of the composition is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Sac7d derivative (affitins, e.g. NANOFITINS), a Fv; a Fab; a Fab'; and a F(ab')$_2$. In various embodiments, the binding regions are of a different type, for example at least one binding region is a VHH and at least other binding region is a scFv, an Fab or any of the types described herein.

The composition in various embodiments further includes at least one agent selected from the group of: an antitoxin, an anti-inflammatory, an anti-tumor, an antiviral, an anti-bacterial, an anti-mycobacterial, an anti-fungal, an anti-proliferative, an anti-apoptotic, an anti-allergy, and an anti-immune suppressant.

In an embodiment, the composition further includes a labeled detectable marker selected from the group consisting of: detectable, fluorescent, colorimetric, enzymatic, radioactive, and the like. For example, the marker is detectable in a sample taken from the subject, the sample exemplified by a cell, a fluid or a tissue. In a related embodiment, the marker includes a peptide, a protein, a carbohydrate, and a polymer.

In an embodiment of the composition, the binding protein includes a linker that separates the binding regions. The linker in a related embodiment separates the binding regions and/or subunits of the multimeric protein. In certain embodiments, the binding protein includes a linker that covalently joins each binding region of the heterodimeric or the multimeric protein. In various embodiments, the linker includes at least one selected from the group of: a peptide, a protein, a sugar, or a nucleic acid. In a related embodiment, the linker includes amino acid sequence GGGGS (SEQ ID NO: 54) or a portion or variant thereof. In a related embodiment, the linker includes amino acid sequence GGGGSGGGGSGGGGS (SEQ ID NO: 55) or a portion or variant thereof or multiples thereof. The linker in various embodiments stabilizes the binding protein and does not prevent the respective binding of the binding regions to the disease agent or to a plurality of disease agents.

In various embodiments of the pharmaceutical composition, the binding protein and/or binding regions include at least one tag that is attached or genetically fused to the binding protein and/or binding regions. The tag for example is a peptide, sugar, or DNA molecule that does not inhibit or prevent binding of the binding protein and/or binding regions to the disease agent. In various embodiments, the tag is at least about: three to five amino acids long, five to eight amino acids long, eight to twelve amino acids long, twelve to fifteen amino acids long, or fifteen to twenty amino acids long. For example, the tag includes SEQ ID NO: 15, or a variant thereof.

In various embodiments, the disease agent for which the binding protein is specific is at least one selected from: a virus, a cancer cell, a fungus, a bacterium, a parasite and a product thereof such as a pathogenic molecule, a protein, a lipopolysaccharide, or a toxin. In related embodiments of the composition, the toxin includes a protein, a lipid, a lipopolysaccharide, and a small molecule toxin such as an aflatoxin or a dinoflagellate toxin. For example, the toxin is a Botulinum neurotoxin comprising a serotype selected from: A, B, C, D, E, F, and G. In various embodiments of the composition, the toxin is at least one selected from: staphylococcal α-hemolysin, staphylococcal leukocidin, aerolysin cytotoxic enterotoxin, a cholera toxin, *Bacillus cereus* hemolysis II toxin, a *Helicobacter pylori* vacuolating toxin, a *Bacillus anthracis* toxin, a cholera toxin, a *Escherichia coli* serotype O157:H7 toxin, a *Escherichia coli* serotype O104:H7 toxin, a lipopolysaccharide endotoxin, a Shiga toxin, a pertussis toxin, a *Clostridium perfringens* iota toxin, a *Clostridium spiroforme* toxin, a *Clostridium difficile* toxin A, a *Clostridium difficile* toxin B, a *Clostridium septicum* a toxin, and a *Clostridium botulinum* C2 toxin. In certain embodiments, the disease agent includes a plurality of non-identical disease agents such that the binding regions of the binding protein bind to and neutralize the plurality of disease agents.

In various embodiments of the composition, the bacterium for which the binding protein is specific is selected from: *B. anthracis, B. cereus, C. botulinum, C. difficile, C. perfringens, V. cholerae,* and *C. spiroforme*. In a related embodiment, the bacterium is a virulent bacterium or apathogenic bacterium.

The composition in various embodiments is compounded or formulated for a route of delivery selected from the group of: topical, ocular, nasal, bucal, oral, rectal, parenteral, intracisternal, invaginal, and intraperitoneal.

In various embodiments of the composition, the binding protein is specific for a toxin which is a *C. botulinum* toxin, and the binding regions of the binding protein includes a recombinant camelid heavy-chain-only antibody, and the composition includes an amino acid sequence selected from the group:

```
(VHH H7, SEQ ID NO: 56)
LVQVGGSLRLSCVVSGSDISGIAMGWYRQAPGKRREMVADIFSGGSTD
YAGSVKGRFTISRDNAKKTSYLQMNNVKPEDTGVYYCRLYGSGDYWGQ
GTQVTVSSAHHSEDP;

(VHH B5, SEQ ID NO: 57)
LVHPGGSLRLSCAPSASLPSTPFNPFNNMVGWYRQAPGKQREMVASIG
LRINYADSVKGRFTISRDNAKNTVDLQMDSLRPEDSATYYCHIEYTHY
WGKGTLVTVSSEPKTPKPQ;
and (H7/B5 heterodimer, SEQ ID NO: 58)
QVQLVESGGGLVQVGGSLRLSCVVSGSDISGIAMGWYRQAPGKRREMV
ADIFSGGSTDYAGSVKGRFTISRDNAKKTSYLQMNNVKPEDTGVYYCR
LYGSGDYWGQGTQVTVSSAHHSEDPTSAIAGGGGSGGGGSGGGGSLQG
QLQLVESGGGLVHPGGSLRLSCAPSASLPSTPFNPFNNMVGWYRQAPG
KQREMVASIGLRINYADSVKGRFTISRDNAKNTVDLQMDSLRPEDSAT
YYCHIEYTHYWGKGTLVTVSSEPKTPKPQ,
or variants thereof.
```

In a related embodiment of the composition, the binding protein is specific for a toxin which is a *C. difficile* toxin A, and the binding region of the binding protein includes a recombinant camelid heavy-chain-only antibody having an amino acid sequence selected from the group of:

```
(AH3, SEQ ID NO: 59)
QVQLVETGGLVQPGGSLRLSCAASGFTLDYSSIGWFRQAPGKEREGVS
CISSSGDSTKYADSVKGRFTTSRDNAKNTVYLQMNSLKPDDTAVYYCA
AFRATMCGVFPLSPYGKDDWGKGTLVTVSSEPKTPKPQP;

(AA6, SEQ ID NO: 60)
QLQLVETGGGLVQPGGSLRLSCAASGFTFSDYVMTWVRQAPGKGPEWI
ATINTDGSTMRDDSTKGRFTISRDNAKNTLYLQMTSLKPEDTALYYCA
RGRVISASAIRGAVRGPGTQVTVSSEPKTPKPQP;

(A3H, SEQ ID NO: 61)
QVQLVESGGGLVQPGGSLRLSCAASGFTLDYYAIGWFRQAPGKEREGV
SGISSVDGSTYYADSVRGRFTISRDNAKNTVYLQMNSLKPEDTAVYYC
AADQSPIPIHYSRTYSGPYGMDYWGKGTLVTVSSAHHSEDP;

(AC1, SEQ ID NO: 62)
QLQLVESGGGLVQPGGSLRLSCAASGFTLDYYAIGWFRQAPGKEREGV
SGISFVDGSTYYADSVKGRFAISRGNAKNTVYLQMNSLKPEDTAVYYC
AADQSSIPMHYSSTYSGPSGMDYWGKGTLVTVSSEPKTPKPQP;

(A11G, SEQ ID NO: 63)
QLQLVETGGGLVQAGGSLRLSCAASGRTLSNYPMGWFRQAPGKEREFV
AAIRRIADGTYYADSVKGRFTISRDNAWNTLYLQMNGLKPEDTAVYFC
ATGPGAFPGMVVTNPSAYPYWGQGTQVTVSSEPKTPKPQP;

(AE1, SEQ ID NO: 64)
QLQLVESGGGLVQPGGSLRLSCAASGFTLDYYAIGWFRQAPGKEREGV
SGISSSDGSTYYADSVKGRFTISRDNATNTVYLQMNSLKPEDTAVYYC
AADQAAIPMHYSASYSGPRGMDYWGKGTLVTVSSEPKTPKPQP;

(SEQ ID NO: 87)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGSGSGHMHHHHHHSSGLVPRGSGMKETAAAKFERQ
HMDSPDLGTDDDDKAMAISDPNSQVQLVESGGGLVQPGGSLRLSCEAS
GFTLDYYGIGWFRQPPGKEREAVSYISASARTILYADSVKGRFTISRD
NAKNAVYLQMNSLKREDTAVYYCARRRFSASSVNRWLADDYDVWGRGT
QVAVSSEPKTPKPQTSAIAGGGGSGGGGSGGGGSLQAMAAASQVQLVE
SGGGLVQTGGSLRLSCASSGSIAGFETVTWSRQAPGKSLQWVASMTKT
NNEIYSDSVKGRFIISRDNAKNTVYLQMNSLKPEDTGVYFCKGPELRG
QGIQVTVSSEPKTPKPQPARR;
and, (SEQ ID NO: 95)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGSGSGHMHHHHHHSSGLVPRGSGMKETAAAKFERQ
HMDSPDLGTDDDDKAMAISDPNSQVQLVETGGLVQPGGSLRLSCAASG
FTLDYSSIGWFRQAPGKEREGVSCISSSGDSTKYADSVKGRFTTSRDN
AKNTVYLQMNSLKPDDTAVYYCAAFRATMCGVFPLSPYGKDDWGKGTL
VTVSSEPKTPKPQPTSAIAGGGGSGGGGSGGGGSLQAMAAAQLQLVET
GGGLVQPGGSLRLSCAASGFTFSDYVMTWVRQAPGKGPEWIATINTDG
STMRDDSTKGRFTISRDNAKNTLYLQMTSLKPEDTALYYCARGRVISA
SAIRGAVRGPGTQVTVSSEPKTPKPQPARQTSPSTVRLESRVRELEDR
LEELRDELERAERRANEMSIQLDEC,
or variants thereof.
```

In certain embodiments of the composition, the binding protein is specific for a toxin which is a *C. difficile* toxin B, and the binding region of the binding protein includes a recombinant camelid heavy-chain-only antibody having an amino acid sequence selected from the group consisting of:

(2D, SEQ ID NO: 65)
QVQLVESGGGLVQPGGSLRLSCAASGFSLDYYGIGWFRQAPGKERQEV

SYISASAKTKLYSDSVKGRFTISRDNAKNAVYLEMNSLKREDTAVYYC

ARRRFDASASNRWLAADYDYWGQGTQVTVSSEPKTPKPQ;

(2Ds, SEQ ID NO: 66)
QVQLVESGGGLVQAGGSLRLSCVSSERNPGINAMGWYRQAPGSQRELV

AIWQTGGSLNYADSVKGRFTISRDNLKNTVYLQMNSLKPEDTAVYYCY

LKKWRDQYWGQGTQVTVSSEPKTPKPQ;

(5D, SEQ ID NO: 67)
QVQLVESGGGLVQPGGSLRLSCEASGFTLDYYGIGWFRQPPGKEREAV

SYISASARTILYADSVKGRFTISRDNAKNAVYLQMNSLKREDTAVYYC

ARRRFSASSVNRWLADDYDVWGRGTQVAVSSEPKTPKPQ;

(E3, SEQ ID NO: 68)
QVQLVESGGGLVQTGGSLRLSCASSGSIAGFETVTWSRQAPGKSLQWV

ASMTKTNNEIYSDSVKGRFIISRDNAKNTVYLQMNSLKPEDTGVYFCK

GPELRGQGIQVTVSSEPKTPKPQ;

(7F, SEQ ID NO: 69)
QVQLVESGGGLVEAGGSLRLSCVVTGSSFSTSTMAWYRQPPGKQREWV

ASFTSGGAIKYTDSVKGRFTMSRDNAKKMTYLQMENLKPEDTAVYYCA

LHNAVSGSSWGRGTQVTVSSEPKTPKPQ;

(5E, SEQ ID NO: 70)
VQLVESGGGLVQAGGSLRLSCAASGLMFGAMTMGWYRQAPGKEREMVA

YITAGGTESYSESVKGRFTISRINANNMVYLQMTNLKVEDTAVYYCNA

HNFWRTSRNWGQGTQVTVSSEPKTPKP;

(B12, SEQ ID NO: 71)
VQLVESGGGLVQAGDSLTLSCAASESTFNTFSMAWFRQAPGKEREYVA

AFSRSGGTTNYADSVKGRATISTDNAKNTVYLHMNSLKPEDTAVYFCA

ADRPAGRAYFQSRSYNYWGQGTQVTVSSAHHSEDP;

(A11, SEQ ID NO: 72)
VQLVESGGGSVQIGGSLRLSCVASGFTFSKNIMSWARQAPGKGLEWVS

TISIGGAATSYADSVKGRFTISRDNANDTLYLQMNNLKPEDTAVYYCS

RGPRTYINTASRGQGTQVTVSSEPKTPKP;

(AB8, SEQ ID NO: 73)
VQLVESGGGLVQAGGSLRLSCVGSGRNPGINAMGWYRQAPGSQRELVA

VWQTGGSTNYADSVKGRFTISRDNLKNTVYLQMNSLKPEDTAVYYCYL

KKWRDEYWGQGTQVTVSSAHHSEDP;

(C6, SEQ ID NO: 74)
VQLVESGGGLVQAGESLRLSCVVSESIFRINTMGWYRQTPGKQREVVA

RITLRNSTTYADSVKGRFTISRDDAKNTLYLKMDSLKPEDTAVYYCHR

YPLIFRNSPYWGQGTQVTVSSEPKTPKP;

(C12, SEQ ID NO: 75)
VQLVESGGGLVQAGESLRLSCVVSESIFRINTMGWYRQTPGKQREVVA

RITLRNSTTYADSVKGRFTISRDDAKNTLYLKMDSLKPEDTAVYYCHR

YPLIFRNSPYWGQGTQVTVSSEPKTP;

(A1, SEQ ID NO: 76)
VQLVESGGGLVQAGGSLRLSCAAPGLTFTSYRMGWFRQAPGKEREYVA

AITGAGATNYADSAKGRFTISKNNTASTVHLQMNSLKPEDTAVYYCAA

SNRAGGYWRASQYDYWGQGTQVTVSSAHHSEDP;

SEQ ID NO: 87;
and

SEQ ID NO: 95,
or variants thereof.

In some embodiments, the present compositions, methods and kits pertain to one or more multimers, e.g. dimeric, trimer or tetrameric constructs of binding proteins specific for a toxin which is a *C. difficile* toxin A and/or a *C. difficile* toxin B, and the binding region of the binding protein optionally including a recombinant camelid heavy-chain. In some embodiments, the multimers are linked via any of the linkers disclosed herein (e.g. GGGGS (SEQ ID NO: 54), or GGGGSGGGGSGGGGS (SEQ ID NO: 55), or a portion or variant thereof). In some embodiments, the present compositions, methods and kits pertain to one or more multimers, e.g. dimeric, trimer or tetrameric constructs of binding proteins specific for a toxin which is a *C. difficile* toxin A and/or a *C. difficile* toxin B, and the binding region of the binding protein optionally including a recombinant camelid heavy-chain that are substantially protease-resistant, e.g. are stable in the GI tract. In some embodiments, the constructs have a reduced amount or are substantially free of alanine residues that are susceptible to proteolysis. In some embodiments, the multimers are linked via any of the linkers disclosed herein (e.g. GGGGS (SEQ ID NO: 54), or GGGGSGGGGSGGGGS (SEQ ID NO: 55), or a portion or variant thereof).

In some embodiments, the binding proteins specific for a *C. difficile* toxin A include one or more of AH3, e.g. SEQ ID NO: 59, AA6, e.g. SEQ ID NO: 60, A3H, e.g. SEQ ID NO: 61, AC1, e.g. SEQ ID NO: 62, A11G, e.g. SEQ ID NO: 63, and AE1, e.g. SEQ ID NO: 64. In some embodiments, the binding proteins specific for a *C. difficile* toxin B include one or more of 2D, e.g. SEQ ID NO: 65, 2Ds, e.g. SEQ ID NO: 66, 5D, e.g. SEQ ID NO: 67, E3, e.g. SEQ ID NO: 68, 7F, e.g. SEQ ID NO: 69, 5E, e.g. SEQ ID NO: 70, B12, e.g. SEQ ID NO: 71, A11, e.g. SEQ ID NO: 72, AB8, e.g. SEQ ID NO: 73, C6, e.g. SEQ ID NO: 74, C12, e.g. SEQ ID NO: 75, and A1, e.g. SEQ ID NO: 76, or variants thereof.

In some embodiments, such multimers may include dimers. For example, the dimers may be homo- or heterodimers. Illustrative dimers are two binding proteins specific for a *C. difficile* toxin A, including by way of non-limitation, AH3, e.g. SEQ ID NO: 59/AH3, e.g. SEQ ID NO: 59; AA6, e.g. SEQ ID NO: 60/AH3, e.g. SEQ ID NO: 59; A3H, e.g. SEQ ID NO: 61/AH3, e.g. SEQ ID NO: 59; AC1, e.g. SEQ ID NO: 62/AH3, e.g. SEQ ID NO: 59; A11G, e.g. SEQ ID NO: 63/AH3, e.g. SEQ ID NO: 59; AE1, e.g. SEQ ID NO: 64/AH3, e.g. SEQ ID NO: 59; AH3, e.g. SEQ ID NO: 59/AA6, e.g. SEQ ID NO: 60; AA6, e.g. SEQ ID NO: 60, /AA6, e.g. SEQ ID NO: 60; A3H, e.g. SEQ ID NO: 61/AA6, e.g. SEQ ID NO: 60; AC1, e.g. SEQ ID NO: 62/AA6, e.g. SEQ ID NO: 60; A11G, e.g. SEQ ID NO: 63/AA6, e.g. SEQ ID NO: 60; AE1, e.g. SEQ ID NO: 64/AA6, e.g. SEQ ID NO: 60; AH3, e.g. SEQ ID NO: 59/A3H, e.g. SEQ ID NO: 61; AA6, e.g. SEQ ID NO: 60/A3H, e.g. SEQ ID NO: 61; A3H, e.g. SEQ ID NO: 61/A3H, e.g. SEQ ID NO: 61; AC1, e.g. SEQ ID NO: 62/A3H, e.g. SEQ ID NO: 61; A11G, e.g. SEQ ID NO: 63/A3H, e.g. SEQ ID NO: 61; AE1, e.g. SEQ ID NO: 64/A3H, e.g. SEQ ID NO: 61; AH3, e.g. SEQ ID NO: 59/AC1, e.g. SEQ ID NO: 62; AA6, e.g. SEQ ID NO: 60/AC1, e.g. SEQ ID NO: 62; A3H, e.g. SEQ ID NO: 61/AC1, e.g. SEQ ID NO: 62; AC1, e.g. SEQ ID NO: 62/AC1, e.g. SEQ ID NO: 62; A11G, e.g. SEQ ID NO: 63/AC1, e.g. SEQ ID NO: 62; AE1, e.g. SEQ ID NO: 64/AC1, e.g. SEQ ID NO: 62; AH3, e.g. SEQ ID NO: 59/A11G, e.g. SEQ ID NO: 63; AA6, e.g. SEQ ID NO: 60/A11G, e.g. SEQ ID NO: 63; A3H, e.g. SEQ ID NO: 61/A11G, e.g. SEQ ID NO: 63; AC1, e.g. SEQ ID NO: 62/A11G, e.g. SEQ ID NO: 63; A11G, e.g. SEQ ID NO: 63/A11G, e.g. SEQ ID NO: 63; AE1, e.g. SEQ ID NO: 64/A11G, e.g. SEQ ID NO: 63; AH3, e.g. SEQ ID NO: 59/AE1, e.g. SEQ ID NO: 64; AA6, e.g. SEQ ID NO: 60/AE1, e.g. SEQ ID NO: 64; A3H, e.g. SEQ ID NO: 61/AE1, e.g. SEQ ID NO: 64; AC1, e.g. SEQ ID NO: 62/AE1, e.g. SEQ ID NO: 64; A11G, e.g. SEQ ID NO: 63/AE1, e.g. SEQ ID NO: 64; and AE1, e.g. SEQ ID NO: 64/AE1, e.g. SEQ ID NO: 64, or variants thereof.

In some embodiments, such multimers may include dimers. For example, the dimers may be homo- or heterodimers. Illustrative dimers are two binding proteins specific for a *C. difficile* toxin B, including by way of non-limitation, 2D, e.g. SEQ ID NO: 65/2D, e.g. SEQ ID NO: 65, 2Ds, e.g. SEQ ID NO: 66/2D, e.g. SEQ ID NO: 65, 5D, e.g. SEQ ID NO: 67/2D, e.g. SEQ ID NO: 65, E3, e.g. SEQ ID NO: 68/2D, e.g. SEQ ID NO: 65, 7F, e.g. SEQ ID NO: 69/2D, e.g. SEQ ID NO: 65, 5E, e.g. SEQ ID NO: 70/2D, e.g. SEQ ID NO: 65, B12, e.g. SEQ ID NO: 71/2D, e.g. SEQ ID NO: 65, A11, e.g. SEQ ID NO: 72/2D, e.g. SEQ ID NO: 65, AB8, e.g. SEQ ID NO: 73/2D, e.g. SEQ ID NO: 65, C6, e.g. SEQ ID NO: 74/2D, e.g. SEQ ID NO: 65, C12, e.g. SEQ ID NO: 75/2D, e.g. SEQ ID NO: 65, A1, e.g. SEQ ID NO: 76/2D, e.g. SEQ ID NO: 65, 2D, e.g. SEQ ID NO: 65/2Ds, e.g. SEQ ID NO: 66, 2Ds, e.g. SEQ ID NO: 66/2Ds, e.g. SEQ ID NO: 66, 5D, e.g. SEQ ID NO: 67/2Ds, e.g. SEQ ID NO: 66, E3, e.g. SEQ ID NO: 68/2Ds, e.g. SEQ ID NO: 66, 7F, e.g. SEQ ID NO: 69/2Ds, e.g. SEQ ID NO: 66, 5E, e.g. SEQ ID NO: 70/2Ds, e.g. SEQ ID NO: 66, B12, e.g. SEQ ID NO: 71/2Ds, e.g. SEQ ID NO: 66, A11, e.g. SEQ ID NO: 72/2Ds, e.g. SEQ ID NO: 66, AB8, e.g. SEQ ID NO: 73/2Ds, e.g. SEQ ID NO: 66, C6, e.g. SEQ ID NO: 74/2Ds, e.g. SEQ ID NO: 66, C12, e.g. SEQ ID NO: 75/2Ds, e.g. SEQ ID NO: 66, A1, e.g. SEQ ID NO: 76/2Ds, e.g. SEQ ID NO: 66, 2D, e.g. SEQ ID NO: 65/5D, e.g. SEQ ID NO: 67, 2Ds, e.g. SEQ ID NO: 66/5D, e.g. SEQ ID NO: 67, 5D, e.g. SEQ ID NO: 67/5D, e.g. SEQ ID NO: 67, E3, e.g. SEQ ID NO: 68/5D, e.g. SEQ ID NO: 67, 7F, e.g. SEQ ID NO: 69/5D, e.g. SEQ ID NO: 67, 5E, e.g. SEQ ID NO: 70/5D, e.g. SEQ ID NO: 67, B12, e.g. SEQ ID NO: 71/5D, e.g. SEQ ID NO: 67, A11, e.g. SEQ ID NO: 72/5D, e.g. SEQ ID NO: 67, AB8, e.g. SEQ ID NO: 73/5D, e.g. SEQ ID NO: 67, C6, e.g. SEQ ID NO: 74/5D, e.g. SEQ ID NO: 67, C12, e.g. SEQ ID NO: 75/5D, e.g. SEQ ID NO: 67, A1, e.g. SEQ ID NO: 76/5D, e.g. SEQ ID NO: 67, 2D, e.g. SEQ ID NO: 65/E3, e.g. SEQ ID NO: 68, 2Ds, e.g. SEQ ID NO: 66/E3, e.g. SEQ ID NO: 68, 5D, e.g. SEQ ID NO: 67/E3, e.g. SEQ ID NO: 68, E3, e.g. SEQ ID NO: 68/E3, e.g. SEQ ID NO: 68, 7F, e.g. SEQ ID NO: 69/E3, e.g. SEQ ID NO: 68, 5E, e.g. SEQ ID NO: 70/E3, e.g. SEQ ID NO: 68, B12, e.g. SEQ ID NO: 71/E3, e.g. SEQ ID NO: 68, A11, e.g. SEQ ID NO: 72/E3, e.g. SEQ ID NO: 68, AB8, e.g. SEQ ID NO: 73/E3, e.g. SEQ ID NO: 68, C6, e.g. SEQ ID NO: 74/E3, e.g. SEQ ID NO: 68, C12, e.g. SEQ ID NO: 75/E3, e.g. SEQ ID NO: 68, A1, e.g. SEQ ID NO: 76/E3, e.g. SEQ ID NO: 68, 2D, e.g. SEQ ID NO: 65/7F, e.g. SEQ ID NO: 69, 2Ds, e.g. SEQ ID NO: 66/7F, e.g. SEQ ID NO: 69, 5D, e.g. SEQ ID NO: 67/7F, e.g. SEQ ID NO: 69, E3, e.g. SEQ ID NO: 68/7F, e.g. SEQ ID NO: 69, 7F, e.g. SEQ ID NO: 69/7F, e.g. SEQ ID NO: 69, 5E, e.g. SEQ ID NO: 70/7F, e.g. SEQ ID NO: 69, B12, e.g. SEQ ID NO: 71/7F, e.g. SEQ ID NO: 69, A11, e.g. SEQ ID NO: 72/7F, e.g. SEQ ID NO: 69, AB8, e.g. SEQ ID NO: 73/7F, e.g. SEQ ID NO: 69, C6, e.g. SEQ ID NO: 74/7F, e.g. SEQ ID NO: 69, C12, e.g. SEQ ID NO: 75/7F, e.g. SEQ ID NO: 69, A1, e.g. SEQ ID NO: 76/7F, e.g. SEQ ID NO: 69, 2D, e.g. SEQ ID NO: 65/5E, e.g. SEQ ID NO: 70, 2Ds, e.g. SEQ ID NO: 66/5E, e.g. SEQ ID NO: 70, 5D, e.g. SEQ ID NO: 67/5E, e.g. SEQ ID NO: 70, E3, e.g. SEQ ID NO: 68/5E, e.g. SEQ ID NO: 70, 7F, e.g. SEQ ID NO: 69/5E, e.g. SEQ ID NO: 70, 5E, e.g. SEQ ID NO: 70/5E, e.g. SEQ ID NO: 70, B12, e.g. SEQ ID NO: 71/5E, e.g. SEQ ID NO: 70, A11, e.g. SEQ ID NO: 72/5E, e.g. SEQ ID NO: 70, AB8, e.g. SEQ ID NO: 73/5E, e.g. SEQ ID NO: 70, C6, e.g. SEQ ID NO: 74/5E, e.g. SEQ ID NO: 70, C12, e.g. SEQ ID NO: 75/5E, e.g. SEQ ID NO: 70, A1, e.g. SEQ ID NO: 76/5E, e.g. SEQ ID NO: 70, 2D, e.g. SEQ ID NO: 65/B12, e.g. SEQ ID NO: 71, 2Ds, e.g. SEQ ID NO: 66/B12, e.g. SEQ ID NO: 71, 5D, e.g. SEQ ID NO: 67/B12, e.g. SEQ ID NO: 71, E3, e.g. SEQ ID NO: 68/B12, e.g. SEQ ID NO: 71, 7F, e.g. SEQ ID NO: 69/B12, e.g. SEQ ID NO: 71, 5E, e.g. SEQ ID NO: 70/B12, e.g. SEQ ID NO: 71, B12, e.g. SEQ ID NO: 71/B12, e.g. SEQ ID NO: 71, A11, e.g. SEQ ID NO: 72/B12, e.g. SEQ ID NO: 71, AB8, e.g. SEQ ID NO: 73/B12, e.g. SEQ ID NO: 71, C6, e.g. SEQ ID NO: 74/B12, e.g. SEQ ID NO: 71, C12, e.g. SEQ ID NO: 75/B12, e.g. SEQ ID NO: 71, A1, e.g. SEQ ID NO: 76/B12, e.g. SEQ ID NO: 71, 2D, e.g. SEQ ID NO: 65/A11, e.g. SEQ ID NO: 72, 2Ds, e.g. SEQ ID NO: 66/A11, e.g. SEQ ID NO: 72, 5D, e.g. SEQ ID NO: 67/A11, e.g. SEQ ID NO: 72, E3, e.g. SEQ ID NO: 68/A11, e.g. SEQ ID NO: 72, 7F, e.g. SEQ ID NO: 69/A11, e.g. SEQ ID NO: 72, 5E, e.g. SEQ ID NO: 70/A11, e.g. SEQ ID NO: 72, B12, e.g. SEQ ID NO: 71/A11, e.g. SEQ ID NO: 72, A11, e.g. SEQ ID NO: 72/A11, e.g. SEQ ID NO: 72, AB8, e.g. SEQ ID NO: 73/A11, e.g. SEQ ID NO: 72, C6, e.g. SEQ ID NO: 74/A11, e.g. SEQ ID NO: 72, C12, e.g. SEQ ID NO: 75/A11, e.g. SEQ ID NO: 72, A1, e.g. SEQ ID NO: 76/A11, e.g. SEQ ID NO: 72, 2D, e.g. SEQ ID NO: 65/AB8, e.g. SEQ ID NO: 73, 2Ds, e.g. SEQ ID NO: 66/AB8, e.g. SEQ ID NO: 73, 5D, e.g. SEQ ID NO: 67/AB8, e.g. SEQ ID NO: 73, E3, e.g. SEQ ID NO: 68/AB8, e.g. SEQ ID NO: 73, 7F, e.g. SEQ ID NO: 69/AB8, e.g. SEQ ID NO: 73, 5E, e.g. SEQ ID NO: 70/AB8, e.g. SEQ ID NO: 73, B12, e.g. SEQ ID NO: 71/AB8, e.g. SEQ ID NO: 73, A11, e.g. SEQ ID NO: 72/AB8, e.g. SEQ ID NO: 73, AB8, e.g. SEQ ID NO: 73/AB8, e.g. SEQ ID NO: 73, C6, e.g. SEQ ID NO: 74/AB8, e.g. SEQ ID NO: 73, C12, e.g. SEQ ID NO: 75/AB8, e.g. SEQ ID NO: 73, A1, e.g. SEQ ID NO: 76/AB8, e.g. SEQ ID NO: 73, 2D, e.g. SEQ ID NO: 65/C6, e.g. SEQ ID NO: 74, 2Ds, e.g. SEQ ID NO: 66/C6, e.g. SEQ ID NO: 74, 5D, e.g. SEQ ID NO: 67/C6, e.g. SEQ ID NO: 74, E3, e.g. SEQ ID NO: 68/C6, e.g. SEQ ID NO: 74, 7F, e.g. SEQ ID NO: 69/C6, e.g. SEQ ID NO: 74, 5E, e.g. SEQ ID NO: 70/C6, e.g. SEQ ID NO: 74, B12, e.g. SEQ ID NO: 71/C6, e.g. SEQ ID NO: 74, A11, e.g. SEQ ID NO: 72/C6, e.g. SEQ ID NO: 74, AB8, e.g. SEQ ID NO: 73/C6, e.g. SEQ ID NO: 74, C6, e.g. SEQ ID NO: 74/C6, e.g. SEQ ID NO: 74, C12, e.g. SEQ ID NO: 75/C6, e.g. SEQ ID NO: 74, A1, e.g. SEQ ID NO: 76/C6, e.g. SEQ ID NO: 74, 2D, e.g. SEQ ID NO: 65/C12, e.g. SEQ ID NO: 75, 2Ds, e.g. SEQ ID NO: 66/C12, e.g. SEQ ID NO: 75, 5D, e.g. SEQ ID NO: 67/C12, e.g. SEQ ID NO: 75, E3, e.g. SEQ ID NO: 68/C12, e.g. SEQ ID NO: 75, 7F, e.g. SEQ ID NO: 69/C12, e.g. SEQ ID NO: 75, 5E, e.g. SEQ ID NO: 70/C12, e.g. SEQ ID NO: 75, B12, e.g. SEQ ID NO: 71/C12, e.g. SEQ ID NO: 75, A11, e.g. SEQ ID NO: 72/C12, e.g. SEQ ID NO: 75, AB8, e.g. SEQ ID NO:

73/C12, e.g. SEQ ID NO: 75, C6, e.g. SEQ ID NO: 74/C12, e.g. SEQ ID NO: 75, C12, e.g. SEQ ID NO: 75/C12, e.g. SEQ ID NO: 75, A1, e.g. SEQ ID NO: 76/C12, e.g. SEQ ID NO: 75, 2D, e.g. SEQ ID NO: 65/A1, e.g. SEQ ID NO: 76, 2Ds, e.g. SEQ ID NO: 66/A1, e.g. SEQ ID NO: 76, 5D, e.g. SEQ ID NO: 67/A1, e.g. SEQ ID NO: 76, E3, e.g. SEQ ID NO: 68/A1, e.g. SEQ ID NO: 76, 7F, e.g. SEQ ID NO: 69/A1, e.g. SEQ ID NO: 76, 5E, e.g. SEQ ID NO: 70/A1, e.g. SEQ ID NO: 76, B12, e.g. SEQ ID NO: 71/A1, e.g. SEQ ID NO: 76, A11, e.g. SEQ ID NO: 72/A1, e.g. SEQ ID NO: 76, AB8, e.g. SEQ ID NO: 73/A1, e.g. SEQ ID NO: 76, C6, e.g. SEQ ID NO: 74/A1, e.g. SEQ ID NO: 76, C12, e.g. SEQ ID NO: 75/A1, e.g. SEQ ID NO: 76, and A1, e.g. SEQ ID NO: 76/A1, e.g. SEQ ID NO: 76, or variants thereof.

In some embodiments, such multimers may include dimers that are one binding protein specific for a *C. difficile* toxin A and one binding protein specific for a *C. difficile* toxin B. For example, the dimers may one monomer binding protein selected from AH3, e.g. SEQ ID NO: 59, AA6, e.g. SEQ ID NO: 60, A3H, e.g. SEQ ID NO: 61, AC1, e.g. SEQ ID NO: 62, A11G, e.g. SEQ ID NO: 63, and AE1, e.g. SEQ ID NO: 64 and monomer binding protein selected from 2D, e.g. SEQ ID NO: 65, 2Ds, e.g. SEQ ID NO: 66, 5D, e.g. SEQ ID NO: 67, E3, e.g. SEQ ID NO: 68, 7F, e.g. SEQ ID NO: 69, 5E, e.g. SEQ ID NO: 70, B12, e.g. SEQ ID NO: 71, A11, e.g. SEQ ID NO: 72, AB8, e.g. SEQ ID NO: 73, C6, e.g. SEQ ID NO: 74, C12, e.g. SEQ ID NO: 75, and A1, e.g. SEQ ID NO: 76, or variants thereof.

In some embodiments, such multimers may include tetramers having at least one monomer selected from one binding protein specific for a *C. difficile* toxin A and one binding protein specific for a *C. difficile* toxin B. Such tetramers may comprise one or two, or three, or four of any of AH3, e.g. SEQ ID NO: 59, AA6, e.g. SEQ ID NO: 60, A3H, e.g. SEQ ID NO: 61, AC1, e.g. SEQ ID NO: 62, A11G, e.g. SEQ ID NO: 63, and AE1, e.g. SEQ ID NO: 64, 2D, e.g. SEQ ID NO: 65, 2Ds, e.g. SEQ ID NO: 66, 5D, e.g. SEQ ID NO: 67, E3, e.g. SEQ ID NO: 68, 7F, e.g. SEQ ID NO: 69, 5E, e.g. SEQ ID NO: 70, B12, e.g. SEQ ID NO: 71, A11, e.g. SEQ ID NO: 72, AB8, e.g. SEQ ID NO: 73, C6, e.g. SEQ ID NO: 74, C12, e.g. SEQ ID NO: 75, and A1, e.g. SEQ ID NO: 76, or variants thereof.

In certain embodiments of the composition, the binding protein is specific for a toxin which is a Shiga toxin, and the binding region of the binding protein includes a recombinant camelid heavy-chain-only antibody having an amino acid sequence selected from the group:

```
                                  (JET-A9, SEQ ID NO: 77)
QVQLVETGGGLAQAGDSLRLSCVEPGRTLDMYAMGWIRQAPGEEREFVAS

ISGVGGSPRYADSVKGRFTISKDNTKSTIWLQMNSLKPEDTAVYYCAAGG

DIYYGGSPQWRGQGTRVTVSSEPKTPKPQ;

(JGG-D4, SEQ ID NO: 78)
QVQLVESGGGLVQAGGSLRLSCAASGRINGDYAMGWFRQAPGEEREFVAV

NSWIGGSTYYTDSVKGRFTLSRDNAKNTLSLQMNSLKPEDTAVYYCAAGH

YTDFPTYFKEYDYWGQGTQVTVSSEPKTPKPQ;

(JEN-D10, SEQ ID NO: 79)
QVQLVETGGLVQAGGSLRLSCAASGVPFSDYTMAWFRQAPGKEREVVARI

TWRGGGPYYGNSGNGRFAISRDIAKSMVYLHMDSLKPEDTAVYYCAASRL

RPALASMASDYDYWGQGTQVSVSSEPKTPKPQ;

(JGH-G1, SEQ ID NO: 80)
QVQLVESGGGLVQPGESLRLSCVASASTFSTSLMGWVRQAPGKGLESVAE

VRTTGGTFYAKSVAGRFTISRDNAKNTLYLQMNSLKAEDTGVYYCTAGAG

PIATRYRGQGTQVTVSSAHHSEDP;

(JEU-A6, SEQ ID NO: 81)
QVQLVESGGGLVQPGGSLKLSCAASGFTLADYVTVWFRQAPGKSREGVSC

ISSSRGTPNYADSVKGRATVSRNNANNTVYLQMNGLKPDDTAIYYCAAIR

PARLRAYRECLSSQAEYDYWGQGTQVTVSSAHHSEDP;

(JEU-D2, SEQ ID NO: 82)
QVQLVESGGGLVQPGGSLGLSCAMSGTTQDYSAVGWFRQAPGKEREGVSC

ISRSGRRTNYADSVRGRFTISRDNAKDTVYLQMNSLKPDDTAVYYCAARK

TDMSDPYYVGCNGMDYWGKGTLVTVSSAHHSEDP;

(JGH-G9, SEQ ID NO: 83)
QVQLVESGGGLVQPGGSLTLSCTASGFTLNSYKIGWFRQAPGKEREGVSC

INSGGNLRSVEGRFTISRDNTKNTVSLHMDSLKPEDTGVYHCAAAPALNV

FSPCVLAPRYDYWGQGTQVTVSSAHHSEDP;

(JFD-A4, SEQ ID NO: 84)
QVQLVESGGGLVQPGGSLRLSCAASGFTLGSYHIGWFREIPPGKEREGTS

CLSSRGDYTKYAEAVKGRFTISRDNTKSTVYLQMNNLKPEDTGIYVCAAI

RPVLSDSHCTLAARYNYWGQGTQVTVSSAHHSEDP;

(JFD-A5, SEQ ID NO: 85)
QVQLVESGGGLVQPGGSLRLSCAALEFTLEDYAIAWFRQAPGKEREGVSC

ISKSGVTKYTDSVKGRFTVARDNAKSTVILQMNNLRPEDTAVYNCAAVRP

VFVDSVCTLATRYTYWGEGTQVTVSSAHHSEDP;
and (JGG-G6, SEQ ID NO: 86)
QVQLVETGGGLVQPGGSLKLSCAASEFTLDDYHIGWFRQAPGKEREGVSC

INKRGDYINYKDSVKGRFTISRDGAKSTVFLQMNNLRPEDTAVYYCAAVN

PVFPDSRCTLATRYTHWGQGTQVTVSSAHHSEDP
``` of variants thereof.

In certain embodiments amino acid sequence SEQ ID NO: 77 or a variant thereof, QVQLVETGGGLAQAGDSL-RLSCVEPGRTLDMYAMGWIRQAPGEEREFVASIS-GVGGSP RYADSVKGRFTISKDNTKSTIWLQMNSLK-PEDTAVYYCAAGGDIYYGGSPQWRGQGT RVTVSSEPKTPKPQ (JET-A9) binds to Stx1 or a portion or homolog thereof.

In certain embodiments amino acid sequence SEQ ID NO: 78 or a variant thereof, QVQLVESGGGLVQAGGSL-RLSCAASGRINGDYAMGWFRQAPGEEREFVAVN-SWIGGSTYYTDSVKGRFTLSRDNAKNTLSLQ MNSLKPEDTAVYYCAAGHYTDFPTYFKEYDYW GQGTQVTVSSEPKTPKPQ (JGG-D4) binds to Stx1 or a portion or homolog thereof.

In certain embodiments amino acid sequence SEQ ID NO: 79 or a variant thereof, QVQLVETGGLVQAGGSL-RLSCAASGVPFSDYTMAWFRQAPGKEREVVARIT-WRGGGP YYGNSGNGRFAISRDIAKSMVYLHMD-SLKPEDTAVYYCAASRLRPALASMASDYDYW GQGTQVSVSSEPKTPKPQ (JEN-D10) binds to Stx2 or a portion or homolog thereof.

In certain embodiments amino acid sequence SEQ ID NO: 80 or a variant thereof, QVQLVESGGGLVQPGESL-RLSCVASASTFSTSLMGWVRQAPGKGLESVAEVRT-TGGTF YAKSVAGRFTISRDNAKNTLYLQMNSLKAE- DTGVYYCTAGAGPIATRYRGQGTQVTVS SAHHSEDP (JGH-G1) binds to Stx2 or a portion or homolog thereof.

In certain embodiments amino acid sequence SEQ ID NO: 81 or a variant thereof, QVQLVESGGGLVQPGG-SLKLSCAASGFTLADYVTVWFRQAPGKSREGVS-CISSSRGTPNYADSVKGRATVSRNNANNTVYLQMN GLKPDDTAIYYCAAIRPARLRAYRECLSSQAE YDY-WGQGTQVTVSSAHHSEDP (JEU-A6) binds to Stx2 or a portion or homolog thereof.

In certain embodiments amino acid sequence SEQ ID NO: 82, QVQLVESGGGLVQPGGSLGLSCAMSGT-TQDYSAVGWFRQAPGKEREGVSCISRSGRRT NYADSVRGRFTISRDNAKDTVYLQMNSLKPDD-TAVYYCAARKTDMSDPYYVGCNGM DYWGK-GTLVTVSSAHHSEDP (JEU-D2) binds to Stx2 or a portion or homolog thereof.

In certain embodiments amino acid sequence SEQ ID NO: 83 or a variant thereof, QVQLVESGGGLVQPGG-SLTLSCTASGFTLNSYKIGWFRQAPGKEREGVSCIN-SGGNLRS VEGRFTISRDNTKNTVSLHMDSLKPEDT-GVYHCAAAPALNVFSPCVLAPRYDYWGQGT QVTVSSAHHSEDP (JGH-G9) binds to Stx2 or a portion or homolog thereof.

In certain embodiments amino acid sequence SEQ ID NO: 84 or a variant thereof, QVQLVESGGGLVQPGGSL-RLSCAASGFTLGSYHIGWFRHPPGKEREGTSCLSS-RGDYTK YAEAVKGRFTISRDNTKSTVYLQMNNLK-PEDTGIYVCAAIRPVLSDSHCTLAARYNYW GQGTQVTVSSAHHSEDP (JFD-A4) binds to Stx1, Stx2, or both Stx1 and Stx2. In various embodiments SEQ ID NO: 84 binds to at least one of Stx1, Stx2, or a portion or homolog thereof.

In certain embodiments amino acid sequence SEQ ID NO: 85 or a variant thereof, QVQLVESGGGLVQPGGSL-RLSCAALEFTLEDYAIAWFRQAPGKEREGVSCISKS-GVTKY TDSVKGRFTVARDNAKSTVILQMNNLRPED-TAVYNCAAVRPVFVDSVCTLATRYTYW GEGTQVTVSSAHHSEDP (JFD-A5) binds to Stx1, Stx2, or both Stx1 and Stx2. In various embodiments SEQ ID NO: 85 binds to at least one of Stx1, Stx2, or a portion or homolog thereof.

In certain embodiments amino acid sequence SEQ ID NO: 86 or a variant thereof, QVQLVETGGGLVQPGG-SLKLSCAASEFTLDDYHIGWFRQAPGKEREG VSCINKRGDYINYKDSVKGRFTISRDGAKSTV-FLQMNNLRPEDTAVYYCAAVNPVFPDSRCTLA-TRYTH WGQGTQVTVSSAHHSEDP (JGG-G6) binds to Stx1, Stx2, or both Stx1 and Stx2. In various embodiments SEQ ID NO: 86 binds to at least one of Stx1, Stx2, or a portion or homolog thereof.

In various embodiments, the amino acid sequence of the composition further includes an amino acid analog, an amino acid derivative, or a conservative substitution of an amino acid residue. The binding protein in various embodiments includes an amino acid sequence that is substantially identical to the amino acid sequence of SEQ ID NOs: 56-87 and 95 or variants thereof. In related embodiments, substantially identical means that the amino acid sequence of the binding protein has at least about 50% identity, at least about 60% identity, at least about 65% identity, at least about 70% identity, at least about 75% identity, at least about 80% identity, at least about 85% identity, at least about 90% identity, at least about 95% identity, at least about 97% identity, at least about 98% identity, or at least about 99% identity to the amino acid sequence of SEQ ID NOs: 56-87 and 95. Alternatively, the binding protein is encoded by at least one nucleotide sequence or the protein includes amino acid sequence selected from the group of SEQ ID NOs: 1-87 and 95, and substantially identical to any of these sequences.

The composition in various embodiments further includes the binding protein or a source of expression of the binding protein selected from the group of: a purified binding protein preparation; a nucleic acid vector with a gene encoding the binding protein; a viral vector encoding the binding protein; and a naked nucleic acid encoding the binding protein which is expressed from the DNA. In related embodiments, the viral vector is derived from a genetically engineered genome of at least one virus selected from: an adenovirus, an adeno-associated virus, a herpes virus, and a lentivirus.

In a related embodiment of the composition, the binding protein is heterodimeric. In various embodiments, the heterodimeric binding protein includes a first binding region and a second binding region. For example the first binding region and the second binding region include VHHs, and the first binding region binds specifically to a *C. difficile* TcdA and the second binding region binds specifically to a *C. difficile* TcdB. In various embodiments, homo- or heterotetramers are also provided (e.g. four binding regions which bind specifically to a *C. difficile* TcdA, four binding regions which bind specifically to *C. difficile* TcdB, three binding regions which bind specifically to *C. difficile* TcdA and one binding region which binds specifically to *C. difficile* TcdB, three binding regions which bind specifically to *C. difficile* TcdB and one binding region which binds specifically to *C. difficile* TcdA, and two binding regions which bind specifically to *C. difficile* TcdA and two binding regions which binds specifically to *C. difficile* TcdB).

An aspect of the invention provides a kit for treating a subject exposed to or at risk for exposure to a disease agent including: a pharmaceutical composition for treating a subject at risk for exposure to or exposed to a disease agent, the pharmaceutical composition including: at least one recombinant heteromultimeric neutralizing binding protein comprising a plurality of binding regions, such that the binding regions are not identical, and each binding region specifically binds a non-overlapping portion of the disease agent, such that the binding protein neutralizes the disease agent, thereby treating the subject for exposure to the disease agent; a container; and, instructions for use. In various embodiments, the instructions for use include instructions for a method for treating a subject at risk for exposure to or exposed to a disease agent using the pharmaceutical composition.

In various embodiments of the kit, the binding protein is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a F(ab')$_2$.

In a related embodiment of the kit, the binding protein includes a linker. In various embodiments, the linker includes at least one selected from: a peptide, a protein, a sugar, or a nucleic acid. For example, the linker includes amino acid sequence GGGGS (SEQ ID NO: 54), or GGGGSGGGGSGGGGS (SEQ ID NO: 55), or a portion or variant thereof. Alternatively, the linker includes a single amino acid or a plurality of amino acids.

In related embodiments of the kit, the disease agent for which the binding protein and binding regions are specific is selected from: a virus, a cancer cell, a fungus, a bacterium, a parasite, and a product of one of those such as a pathogenic molecule, a protein, a lipopolysaccharide, or a toxin. In related embodiments, the toxin for which the binding protein is specific is a Botulinum neurotoxin including a serotype selected from: A, B, C, D, E, F, and G. In various embodiments of the kit, the toxin for which the binding protein is specific is at least one selected from the group of: staphylococcal α-hemolysin, staphylococcal leukocidin, aerolysin cytotoxic enterotoxin, a cholera toxin, a *Bacillus cereus* hemolysis II toxin, a *Helicobacter pylori* vacuolating toxin, a *Bacillus anthracisi* toxin, a cholera toxin, an *Escherichia coli* serotype O157:H7 toxin, an *Escherichia coli* serotype O104:H7 toxin, a lipopolysaccharide endotoxin, a Shiga toxin, a pertussis toxin, a *Clostridium perfringens* iota toxin, a *Clostridium spiroforme* toxin, a *Clostridium difficile* toxin A, a *Clostridium difficile* toxin B, a *Clostridium septicum* a toxin, and a *Clostridium botulinum* C2 toxin. In certain embodiments, the binding regions of the binding protein are specific to different classes of disease agents, e.g., each of the plurality of binding regions is different and is specific for an agent from bacteria, virus, fungus, cancer, and a pathogenic molecule. For example a binding region is specific for a virus and another binding region is specific for a bacterium.

In a related embodiment of the kit, the binding protein is specific for a toxin which is a *C. botulinum* toxin, and the binding region includes a recombinant camelid heavy-chain-only antibody, such that the pharmaceutical composition includes the binding protein that has an amino acid sequence selected from the group consisting of: SEQ ID NO: 56, SEQ ID NO: 57, SEQ ID NO: 58, or a portion or variant thereof.

In a related embodiment of the kit, the binding region of the binding protein is specific for a toxin which is a *C. botulinum* toxin A, such that the binding region of the binding protein includes a recombinant camelid heavy-chain-only antibody having an amino acid sequence selected from the group of: SEQ ID NO: 59, SEQ ID NO: 60, SEQ ID NO: 61, SEQ ID NO: 62, SEQ ID NO: 63, SEQ ID NO: 64, SEQ ID NO: 87, SEQ ID NO: 95, and a portion or variant thereof.

In a related embodiment of the kit, the toxin for which the binding protein is specific is a *C. difficile* toxin B, and the binding region of the binding protein includes a recombinant camelid heavy-chain-only antibody having an amino acid sequence selected from: SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 87, SEQ ID NO: 95, and a portion or variant thereof. In certain embodiments, the binding protein and/or binding regions are encoded by a nucleotide sequence or the binding protein and/or regions include an amino acid sequence selected from the group of SEQ ID NOs: 1-87 and 95, or are substantially identical to these sequences.

In a related embodiment, the binding protein is specific for a Shiga toxin, and the binding region of the binding protein includes a recombinant camelid heavy-chain-only antibody having an amino acid sequence selected from: SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, and SEQ ID NO: 86 or variants thereof.

An aspect of the invention provides a composition including at least one amino acid sequence selected from the group of: SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 94, SEQ ID NO: 95 or a portion or variant thereof. The composition in various embodiments includes an amino acid sequence that is substantially identical to the amino acid sequence of SEQ ID NOs: 59-86. In related embodiments, substantially identical means an amino acid sequence that has at least 60% identity, at least 65% identity, at least 70% identity, at least 75% identity, at least 80% identity, at least 85% identity, at least 90% identity, at least 95% identity, at least about 97% identity, at least about 98% identity, or at least 99% identity to an amino acid sequence of any of SEQ ID NOs: 56-87 and 95.

An aspect of the invention provides a method for treating a subject at risk for exposure to or exposed to a plurality of disease agents, the method including: contacting the subject with at least one recombinant heteromultimeric neutralizing binding protein including two or more binding regions, such that the binding protein neutralizes at least two (plurality) of disease agents, thereby treating the subject for exposure to the plurality of disease agents.

In a related embodiment of the method, the at least two of the binding regions are identical. Alternatively, the at least two binding regions include at least two non-identical binding regions. In related embodiments of the method, the binding protein is at least one selected from the group of: a heterodimer, a trimer, a tetramer, a pentamer, and a hexamer. In various embodiments, the tetramer includes a homodimer of a heterodimer, for example a heterodimer of AH3 and AA6 as is shown in SEQ ID NO: 95.

In various embodiments, the plurality from which the exemplary disease agents are selected from a virus, a cancer cell, a fungus, a bacterium, a parasite and a product thereof such as a pathogenic molecule, a protein, a lipopolysaccharide, or a toxin. For example the disease agents include toxins such as TcdA and TcdB.

In related embodiments of the method, the binding protein includes at least one selected from the group of SEQ ID NOs: 56-87 and 95 or a portion or a homologue or variant thereof.

In related embodiments of the method, the binding protein is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a F(ab')$_2$. In a related embodiment of the method, the binding protein includes a linker located between each of the multimeric components of the binding regions. In various embodiments, the linker is at least one selected from the group of: a peptide, a protein, a sugar, or a nucleic acid. For example, the linker comprises amino acid sequence GGGGS (SEQ ID NO: 54) or amino acid sequence GGGGSGGGGSGGGGS (SEQ ID NO: 55).

In a related embodiment, the method further includes prior to contacting, engineering the binding protein using a dimerization agent. In a related embodiment, the dimerization agent includes amino acid sequence

```
                                              (SEQ ID NO: 94)
TSPSTVRLESRVRELEDRLEELRDELERAERRANEMSIQLDEC, or a portion or variant thereof.
```

In various embodiments of the method, the plurality of disease agents is at least two selected from the group of: Staphylococcal α-hemolysin, Staphylococcal leukocidin, aerolysin cytotoxic enterotoxin, a cholera toxin, *Bacillus* cereus hemolysis II, and *Helicobacter pylori* vacuolating toxin, *Bacillus anthracis*, cholera toxin, *Escherichia coli* serotype O157:H7, *Escherichia coli* serotype O104:H7, lipopolysaccharide endotoxin, Shiga toxin, pertussis toxin, *Clostridium perfringens* iota toxin, *Clostridium spiroforme* toxin, *Clostridium difficile* toxin A, *Clostridium difficile* toxin B, *Clostridium septicum* a toxin, and *Clostridium botulinum* C2 toxin. In related embodiments of the method, the binding protein includes at least one selected from the group of: SEQ ID NOs: 56-87 and 95 or variants thereof.

Binding Agent

The binding agent or binding protein is in one embodiment, a molecule that binds to a portion of a target molecule, disease agent, or disease agent target. The binding protein treats the subject by any or all of several mechanisms, including promoting clearance, phagocytosis, neutralization, inhibition, and activation of the immune response. The term "binding agent" or "binding protein", includes in addition to full-length antibodies, molecules such as antibody fragments (e.g., single chain antibodies, and VHHs), microproteins (also referred to as cysteine knot proteins or knottins), darpins, anticalins, adnectins, peptide mimetic molecules, aptamers, synthetic molecules, and refers to any composition that binds to a target and/or disease agent and elicits an immune effector activity against the molecule target and/or disease agent. In certain embodiments, the binding protein is a recombinant multimeric neutralizing binding protein including two or more binding regions, such that the binding regions are not identical, and each and/or disease agent. Alternatively, the binding protein includes binding regions that bind specifically to different types of disease agents such as different types of pathogenic molecules such as bacteria, viruses, fungi, allergens, and toxins. For example, at least one binding region of the binding protein bind to a virus surface protein, and at least one different binding regions binds to a bacterial toxin.

The multimeric neutralizing binding protein herein in certain embodiments includes one or a plurality of epitopic tags. In certain embodiments, the binding protein includes a linker that covalently connects each binding region of the heterodimer. For example, the linker is a single amino acid or a sequence of a plurality of amino acids that does not affect or reduce the stability, orientation, binding, neutralization, and/or clearance characteristics of the binding regions and binding protein. In certain embodiments, each binding region is specific to a non-identical disease agent. For example, the binding protein in certain embodiments includes a binding region specific to a bacterium or bacterial toxin, and at least one other binding region is specific to a virus, fungus, allergen, or to a non-identical bacterium or bacterial toxin. For example, a multimeric binding protein in certain embodiments has binding regions specific to a TcdA and to a TcdA or to a Shiga toxin, or the respective binding regions are specific to each of a Botulinum toxin and a virus.

In certain embodiments, the binding protein neutralizes or inhibits the molecule target and/or disease agent for example by preventing the disease agent entry into cells. In certain embodiments, the binding protein upon being administered to the subject neutralizes the toxin and/or triggers an antibody mediated effector activity in the subject.

The binding protein is in certain embodiments a monomer (e.g., a single unit), or includes a covalently bound protein including a plurality of monomers such as for example a dimer, a trimer, a tetramer, a pentamer, an octamer, a 10-mer, a 15-mer, a 20-mer, or any multimer. In certain embodiments, the binding protein is a monomer and the binding protein has one binding region that binds to an epitope of the molecule target and/or disease agent. Alternatively, the binding protein in certain embodiments has two or more connected or joined monomers each with a binding region and each binding to an epitope of a disease agent or to a plurality of epitopes of disease agents. The multimeric binding protein in certain embodiments includes the same monomer. Alternatively, the multimeric binding protein includes monomers or binding regions or a combination thereof (i.e., heteromulteric). Accordingly, the multimers can be homogeneous such that each includes two or more monomers having a binding region that binds to the same site of a disease agent. Alternatively, the multimers are heterogeneous and include two or more monomers having a binding region that binds to two or more different sites of one or more disease agents. The heterogeneous multimers (heteromultimers) bind non-overlapping portions of the molecule target and/or disease agent. In various embodiments, the binding protein is a homodimer of a heterodimer or a heterotrimer. In a related embodiment, the heteromultimers bind a plurality of non-identical epitopes on a plurality of disease agents.

In certain embodiments the binding protein includes a single tag, multiple tags, for example each multimeric binding protein includes two or more tags on each component binding region (i.e., monomer). Alternatively, the heterodimer comprises no tag attached to the monomers and/or linker. In certain embodiments, presence of the tag on or operably fused to the binding protein and/or binding region synergistically induces clearance of the disease agent from the body. For example, the tag attached to the binding protein induces an immune response from a patient or subject contacted with a pharmaceutical composition containing the tagged-binding protein. In certain embodiments the tag includes a portion (e.g., conserved, unique, inactivated, and non-functional) of a pathogenic molecule. In certain embodiments, the tag is an adjuvant. See Gerber et al. U.S. Pat. No. 7,879,333 issued Feb. 1, 2011 which is incorporated by reference herein in its entirety. For example, the tag is a peptide, carbohydrate, polymer, or nucleic acid that is effective for enhancing neutralization and/or clearance of the disease agent or plurality of disease agents.

The multimeric binding protein in certain embodiments is a heterodimer having two tags, one tag attached to each monomer, or alternatively the heterodimer includes one tag on each monomer or one tag total on one of the two monomers. The term "heterodimer" includes a single protein having two different monomers are joined by a linker. Data herein shown that a heterodimers having two E-tags effectively protected animals exposed to hundreds-fold and/or thousands-fold the lethal dose of a single disease agent such as a *C. difficile* toxin A. Examples herein show that recombinant multimeric binding proteins, having two or more non-identical binding regions, administered to subjects either before or after contact with a disease agent resulted in comparable and better antitoxin efficacy than serum-based polyclonal antitoxins.

The binding agents/proteins described herein include binding agent/protein portions, regions, and fragments. For example, the binding protein is an antibody and, in certain embodiments the binding protein includes antibody fragments. The term "antibody fragment" refers to portion of an immunoglobulin having specificity to a molecule target and/or disease agent, or a molecule involved in the interaction or binding of the molecule target and/or disease agent. The term "antibody fragment" encompasses fragments from binding protein, for example both polyclonal and monoclonal antibodies including transgenically produced antibodies, single-chain antibodies (scFvs), recombinant Fabs, and recombinant heavy-chain-only antibodies (VHHs), e.g., from any organism producing VHH antibody such as a camelid, a shark, or a designed VHH.

VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains (CH2 and CH3). The cloned and isolated VHH domain is a stable polypeptide harboring the antigen-binding capacity of the original heavy-chain antibody. See Castorman et al. U.S. Pat. No. 5,840,526 issued Nov. 24, 1998; and Castorman et al. U.S. Pat. No. 6,015,695 issued Jan. 18, 2000, each of which is incorporated by reference herein in its entirety. VHHs are commercially available from Ablynx Inc. (Ghent, Belgium) under the trademark of NANOBODIES™.

Suitable methods of producing or isolating antibody fragments having the requisite binding specificity and affinity are described herein and include for example, methods which select recombinant antibody from a library, by PCR (See Ladner U.S. Pat. No. 5,455,030 issued Oct. 3, 1995 and Devy et al. U.S. Pat. No. 7,745,587 issued Jun. 29, 2010, each of which is incorporated by reference herein in its entirety).

Functional fragments of antibodies, including fragments of chimeric, humanized, primatized, veneered or single chain antibodies, can also be produced. Functional fragments or portions of the foregoing antibodies include those which are reactive with the disease agent. For example, antibody fragments capable of binding to the disease agent or portion thereof, including, but not limited to scFvs, Fabs, VHHs, Fv, Fab, Fab' and F(ab')2 are encompassed by the invention. Such fragments can be produced by enzymatic cleavage or by recombinant techniques. For instance, papain or pepsin cleavage are used generate Fab or $F(ab')_2$ fragments, respectively. Antibody fragments are produced in a variety of truncated forms using antibody genes in which one or more stop codons has been introduced upstream of the natural stop site. For example, a chimeric gene encoding a $F(ab')_2$ heavy chain peptide portion can be designed to include DNA sequences encoding the $CH_1$ peptide domain and hinge region of the heavy chain. Accordingly, the present invention encompasses a polynucleic acid that encodes the binding protein described herein (e.g., a binding fragment with a tag). Binding proteins in certain embodiments are made as part of a multimeric protein, the monomer or single binding region (e.g., antibody fragments, microproteins, darpins, anticalins, adnectins, peptide mimetic molecules, aptamers, synthetic molecules, etc) can be linked. Any combination of binding protein or binding region types can be linked. In an embodiment, the monomer or binding region of a multimeric binding protein can be linked covalently. In another embodiment, a monomer binding protein can be modified, for example, by attachment (directly or indirectly (e.g., via a linker or spacer)) to another monomer binding protein. A monomer in various embodiments is attached or genetically fused to another monomer e.g., by recombinant protein that is engineered to contain extra amino acid sequences that constitute the monomers. Thus, the DNA encoding one monomer is joined (in reading frame) with the DNA encoding the second monomer, and so on. Additional amino acids in certain embodiments are encoded between the monomers that produce an unstructured region separating the different monomers to better promote the independent folding of each monomer into its active conformation or shape. Commercially available techniques for fusing proteins are used in various embodiments to join the monomers into a multimeric binding protein of the present invention.

The term "antagonist" as used herein includes proteins or polypeptides that bind to the disease agent, inhibit function of the disease agent, and are included in certain embodiments to the binding region of the binding protein.

A binding protein includes any amino acid sequence that binds to the disease agent or target including molecules that have scaffolds. Examples of binding proteins having scaffolds are DARPins, Anticalins, and AdNectins. DARPins are derived from natural ankyrin repeat proteins and bind to proteins including e.g., human receptors, cytokines, kinases, human proteases, viruses and membrane proteins (Molecular Partners AG Zurich Switzerland). Anticalins are derived from lipocalins, and comprise a hypervariable loops supported by a conserved β-sheet framework, which acts as a binding protein. (Pieris AG, Germany). The scaffold for anticalins are lipocalins. AdNectins are derived from human fibronectin (e.g., the scaffold), and bind to targets of various medical conditions and are commercially available from Adnexus (Waltham, Mass.). See also Alexandru et al. U.S. Pat. No. 7,867,724 issued Jan. 11, 2011, which is incorporated by reference herein in its entirety. In certain embodiments, the binding protein having the scaffold is encoded by a nucleotide sequence or the binding protein includes an amino acid sequence that is substantially identical or homologous to the sequences described herein, for example SEQ ID NO: 1-87 and 95 or variants thereof. Recombinant multimeric binding proteins herein include amino acid sequences from a binding protein sequence having conservative sequence modifications. As used herein, the term "conservative sequence modifications" refers to amino acid modifications that do not significantly affect or alter the characteristics (e.g., neutralization, clearance, binding, stability, and orientation) of the binding protein, i.e., amino acid sequences of binding protein that present these side chains at the same relative positions will function in a manner similar to the binding protein. Such conservative modifications include amino acid substitutions, additions and deletions. Modification of the amino acid sequence of recombinant multimeric binding protein is achieved using any known technique in the art e.g., site-directed mutagenesis or PCR based mutagenesis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989. Conservative amino acid substitutions are modifications in which the amino acid residue is replaced with an amino acid residue having a similar side chain such as replacing a small amino acid with a different small amino acid, a hydrophilic amino acid with a different hydrophilic amino acid, etc.

Examples herein show that a molecule target and/or disease agent is bound by a binding protein, the molecule target and/or disease agent exemplified by a bacterial toxin released by the pathogen, for example a botulinum toxin. Botulinum toxin serotypes A to G are synthesized by organisms including *Clostridium botulinum, Clostridium baratii*, and *Clostridium butyricum*. Simpson, L. L 2004 Annu. Rev. Pharmacol. Toxicol. 44: 167-193. *C. botulinum* produces serotypes A to G, *C. baratii* produces serotype F, and *C. butyricum* produces serotype E only. The structures and substrates for each of the botulism toxin serotypes as well as the serotype specific cleavage sites have been determined, and the mechanism of toxin killing has been elucidated. The botulinum toxin acts preferentially on peripheral cholinergic nerve endings to block acetylcholine release, and causes disease (i.e., botulism) and can be used to treat disease (e.g., dystonia). Ibid., Abstract. The toxigenicity of botulinum toxin depends on penetration of the toxin through cellular and intracellular membranes. Thus, toxin that is ingested or inhaled binds to epithelial cells and is transported to the general vascular circulation. Toxin that reaches peripheral nerve endings binds to the cell surface then penetrates the plasma membrane by receptor-mediated endocytosis and the endosome membrane by pH-induced translocation. Ibid., Abstract. Internalized toxin acts in the cytosol as a metal-loendoprotease to cleave polypeptides that are essential for exocytosis.

Examples herein show binding proteins/agents that specifically bind each of a variety of distinct serotypes of a microbial neurotoxin that causes botulism, BoNT/A and BoNT/B. The amino acid sequence of the binding agents include scFvs and VHHs for example SEQ ID NOs: 2, 4, 6, 8, 10, 12, 14, 20, 22, 24, 26, 28, 30, 32, 34, 36, 38, 40, 42, 44, 46, 48, 50, 52 or combinations or portions or variants thereof. The corresponding nucleic acid sequences of binding agents are shown in SEQ ID NOs: 1, 3, 5, 7, 9, 11, 13, 19, 21, 23, 25, 27, 29, 31, 33, 35, 37, 39, 41, 43, 45, 47, 49, 51 or a combination or variant thereof. In various embodiments the amino acid sequence of the binding agents includes VHHs for example SEQ ID NO: 56-87 or 95 or combinations or portions or variants thereof. In certain embodiments, the binding agent includes a tag that was engineered as a portion of the binding agent, for example the tag has amino acid sequence of SEQ ID NO: 15, and is genetically fused to the carboxyl end of the binding agents. In certain embodiments, the tag enhances ability of the binding protein to neutralize and/or clear the disease agent from the subject. FIG. 5 shows a phylogenetic tree of JDQ-B5 (SEQ ID NO: 24), a VHH binding agent that specifically binds to BoNT/A and other VHHs that compete with JDQ-B5 for binding to BoNT/A. The length of the branches in the tree represents the relatedness of the sequences with the shorter branches indicating greater relatedness (i.e., homology) and the longer branches indicating less homology of the amino acid sequences.

The present invention provides a number of different binding proteins, each having binding regions with specificity and affinity to target different areas of one or more disease agents. In an embodiment, two or three binding proteins specific to different epitopes of a disease agent are used. In a disease having a number of disease agents involved in causing the disease or condition, such as botulism, multiple disease agents are targeted by the compositions and methods herein. In the case of botulism, since any one of at least seven neurotoxin serotypes are involved, a pool/mixture of binding proteins is prepared containing binding proteins for a plurality of known serotypes that cause the disease in humans. Botulism is often caused by exposure to a single BoNT serotype, and it is generally difficult to quickly determine which serotype is the cause. Thus, the standard of care in treating botulism includes administration of a number of antibodies to protect against most if not all of the serotypes that cause the disease in human. Hence, it is appropriate to protect subjects from botulism, to stockpile binding proteins that bind to several or preferably all known serotypes that cause botulism.

The present invention in various embodiments further encompasses compositions that are multimeric binding proteins having two or more monomers in which a monomer is exemplified by a VHH amino sequence herein. In various embodiments, the composition includes at least one selected from the group of SEQ ID NOs: 56-87 and 95 or variants thereof. Compositions further include nucleic acid sequences that encode the amino acids sequences herein, for example SEQ ID NO: 56-87 and 95 or variants thereof. In certain embodiments, the monomer or binding region includes at least one sequence described herein, for example SEQ ID NOs: 1-87 and 95 or variants thereof. An embodiment of a multimeric binding protein includes two or more of the VHH sequences herein expressed as a single protein. Any combination of two or more of the VHH sequences forms a multimeric binding protein of the present invention. In a particular embodiment, the present invention relates to a heterodimer, i.e., protein, in which any two different VHH sequences herein are expressed as a single protein, i.e., linked and expressed as a genetic fusion.

The binding protein in certain embodiments is a multimeric fusion protein engineered and produced using a multimerization agent to form a complex that effectively binds to and neutralizes a disease agent or plurality of disease agents (Shoemaker et al. U.S. publication number 20130058962 published Mar. 7, 2013, which is incorporated by reference herein in its entirety). In certain embodiments, the multimerization agent includes a dimerization sequence for example including an amino acid sequence shown in SEQ ID NO: 94. For example the dimerization agent complexes peptide fragments each containing at least: about five to 25 amino acids, about 25 to 50 amino acids, about 50 to 100 amino acids, about 100 to 150 amino acids, and about 150 amino acids to about 200 amino acids. Multimerization agents and methods of using the agents for forming multimeric binding proteins are shown herein in Example 21. See also Moore et al. U.S. Pat. No. 7,763,445 issued Jul. 24, 2012 and Carter et al. U.S. Pat. No. 8,216,865 issued Jul. 10, 2012, each of which is incorporated by reference herein in its entirety.

The disease agent target is any from different classes of pathogens, infectious agents or other unwanted material. A multi-target approach is within the scope of the methods and compositions herein, exemplified by a binding protein that binds to a viral disease agent, a bacterial disease agent, a parasite disease agent, a cancer cell, and a protein produced therefrom and any combination thereof. In various embodiments, a binding protein neutralizes a plurality of pathogens or unwanted material. Examples herein show a VHH heterodimer that binds to and neutralizes both TcdA and TcdB.

The disease agent, pathogen or infectious agent that is neutralized by the binding agent is any molecule, virus or bacterium that infects a mammal (e.g., human, horse, dog, goat, and cow) or a mammalian cell. In certain embodiments, the disease agent is a bacterium selected from *Actinobacillus, Bacillus, Borrelia, Brucella, Campylobacter, Chlamydia, Clostridium, Coxiella, Enterococcus, Escherichia, Francisella, Hemophilus, Legionella, Mycobacterium, Neisseria, Pasteurella, Pneumophila, Pseudomonas, Rickettsia, Salmonella, Shigella, Staphylococcus, Streptococcus, Treponema,* and *Yersinia*. Alternatively, the disease agent is a virus including for example human immunodeficiency virus, foot-and-mouth disease virus, avian influenza virus, and sheep pox virus.

The binding agent in various embodiments binds to and neutralizes an infectious agent and/or a disease agent associated with a pathology resulting from overexpression of a self protein in the subject such as an immunoglobulin, a leukocyte, a cytokine, and a growth factor. For example, the overexpression is of an inflammatory agent such as a tumor necrosis factor (e.g., TnFα) or an interleukin (IL) such as IL-1 beta, or IL-6. Alternatively, an infectious agent and/or a disease agent is associated with expression of a mutated or modified molecule such as a protein, a sugar, a glycoprotein, or expression of a cell carrying a nucleotide sequence encoding the disease agent.

The binding agent in various embodiments binds to a cancer cell and/or cancer marker. For example, the cancer cell includes a melanoma; a carcinoma (e.g., colon carcinoma); a pancreatic cancer; a sarcoma; a lymphoma; a leukemia; a brain tumor such as glioma; a lung cancer; an esophageal cancer; a mammary (breast) cancer; a bladder cancer; a prostate cancer; a head and neck cancer; an ovarian cancer; a kidney cancer; or a liver cancer.

The binding agents described herein are used in certain embodiments to treat symptoms of an autoimmune disease, a class of disorder which includes Hashimoto's thyroiditis; idiopathic myxedema, a severe hypothyroidism; multiple sclerosis, a demyelinating disease marked by patches or hardened tissue in the brain or the spinal cord; myasthenia gravis which is a disease having progressive weakness of muscles caused by autoimmune attack on acetylcholine receptors at neuromuscular junctions; Guillain-Barre syndrome, a polyneuritis; systemic lupus erythematosis; uveitis; autoimmune oophoritis; chronic immune thrombocytopenic purpura; colitis; diabetes; Grave's disease, which is a form of hypothyroidism; psoriasis; pemphigus vulgaris; and rheumatoid arthritis (RA).

It will be appreciated that in certain embodiments, the binding agent (e.g., peptide, protein, or portion or homolog thereof) of this invention can be obtained from a peptide synthesizer or any commercial supplier of custom peptides produced synthetically, e.g., by solid phase procedures. For example, peptide synthesis can be performed using various solid-phase techniques (Roberge et al. 995 Science 269:202) and automated synthesis may be achieved, for example, using the 431A peptide synthesizer (available from Applied Biosystems of Foster City, Calif.) in accordance with the instructions provided by the manufacturer. See also Horowitz et al. U.S. Pat. No. 8,131,480 issued Mar. 6, 2012.

Molecule Target and Disease Agent Target

A molecule target and/or disease agent target is any target which is biological (e.g., protein, sugar, carbohydrate, DNA, RNA) or chemical to which the binding protein binds, and is any target associated with a disease, defect or negative condition. The molecule target or disease agent target is any molecule capable of being bound, or whose activity is altered (e.g., neutralized, reduced or ceased), or that can be recognized by immune effectors and leads for example to clearance, opsonization, killing, and phagocytosis. For example, the disease agent target in certain embodiments is a portion of a pathogen or a molecule released or secreted by the pathogen (e.g. toxin). A pathogen is an agent that causes a disease or condition, and includes a virus, cancer cell, bacterium, parasite or pathogenic protein. The disease agent target includes a pathogenic protein that is derived from normal cells, such as prions. The pathogenic protein or other molecule that is disease agent target is either independent of the pathogen or is associated with or produced by the pathogen.

In certain embodiments, the disease agent is a molecule (e.g, peptide) that is naturally produced by a plant or bacterium that inactivates or disrupts normal function of cellular membranes, cellular compartments, or cellular organelles. For example, the disease agent disrupts function of ribosomes.

A virus is a microscopic particle that infects the cells of a biological organism and replicates in the host cell. In various embodiments, viral antigens including viral proteins, are targeted by the binding protein. Binding proteins bind to molecules or receptors on the virus, and are neutralized and/or cleared using the methods described herein. Examples of viruses that are neutralized and/or cleared by the binding protein herein include Influenza, Rhinovirus, Rubeola, Rubella, Herpes, Smallpox, Chickenpox, Human Papilloma, Rabies, and Human Immunodeficiency viruses.

A parasite is an organism that lives on or in a different organism. Parasites have or express molecules that are used as a target by the binding agent. Types of parasites include endoparasites (e.g., parasites that live inside the body of the host) and ectoparasites (e.g., parasites that live on the outside of the host's body). Examples of parasites that are treated by the methods, compositions, and kits herein are shown in Horvitz et al. U.S. patent publication 20110010782 published Jan. 13, 2011. Exemplary parasites include a protozoan (e.g., a plasmodium, a cryptosporidium, a microsporidium, and isospora), a tick, a louse and a parasitic worm.

Molecules on cancer cells also are targets of the binding agent. In related embodiments, the target is a protein on the cancer cell such as a cancer marker. Examples of proteins or receptors associated with cancer cells include CD33, HER2/neu, CA 125 (MUC16), prostate-specific antigen (PSA), and CD44.

The disease agent target in certain embodiments includes bacteria including Gram negative and Gram positive bacteria. Examples of pathogenic bacteria bound by the binding protein include *Clostridium, Staphylococcus, Neisseria, Streptococcus, Moraxella, Listeria*, any of the Enterobacteriaceae, *Escherichia coli, Corynebacterium, Klebsiella, Salmonella, Shigella, Proteus, Pseudomonas, Haemophilus, Bordetella, Legionella, Campylobacter, Helicobacter*, and *Bacteroides*. For example, the disease agent target is *Bacillus anthracis* (Decker, J. 2003 Deadly Diseases and Epidemics, Anthrax. Chelsea House Publishers. pages 1-112).

Enterohemorrhagic *Escherichia coli* (EHEC) is an emerging food- and water-borne pathogen that colonizes the distal ileum and colon and produces potent cytotoxins (Donnenberg, "Infections due to *Escherichia coli* and other enteric gram-negative bacilli," in ACP Medicine, WebMD Professional Publishing, Danbury Conn., Chapter 7, pp. 8-1 to 8-18, 2005). After ingestion of contaminated food, humans develop symptoms ranging from mild diarrhea to the severe, and at times life-threatening, hemolytic uremic syndrome (HUS). Currently, EHEC is the most common cause of pediatric renal failure in the United States (Mead et al, Emerg Infect Dis, 5:607-625, 1999). Several EHEC serotypes cause disease, but the O157 serotype is by far the most common cause of EHEC-related disease in North America, Europe and Japan (Feng, "*Escherichia coli*" in Garcia (ed.) Guide to Foodborne Pathogens. John Wiley and Sons, Inc., pp. 143-162, 2001). See also Waldor et al., U.S. patent publication number 2010/0092511 A1 published Apr. 15, 2012, which is incorporated by reference herein in its entirety.

Shiga toxins are a family of related toxins with two major groups, Stx1 and Stx2 (Friedman et al., 2001 Curr Opin Microbiol 4 (2): 201-7). The toxins are named for Kiyoshi Shiga, who first described the bacterial origin of dysentery caused by *Shigella dysenteriae*. The most common sources for Shiga toxin are the bacteria *S. dysenteriae* and the Shigatoxigenic group of *Escherichia coli* (STEC), which includes serotypes O157:H7, O104:H4, and other enterohemorrhagic *E. coli*, EHEC (Spears et al. 2006 FEMS Microbiology Letter 187-202; Sandvig et al. 2000 EMBO J 19

(22): 5943-5950; and Krautz-Peterson et al. 2008 Infection and Immunity 76(5) 1931-1939; and Vermeij U.S. Pat. No. 7,807,184 issued Oct. 5, 2010, each of which is incorporated by reference herein in its entirety. Symptoms associated with Shiga toxin-exposure caused infection by EHEC include watery stool followed by severe abdominal pain and bloody stool. Exposed persons develop complications leading to HUS, encephalopathy, and even death (Masuda et al., U.S. Pat. No. 7,345,161 issued Mar. 18, 2008).

Methods for ascertaining the target molecule or disease agent are described herein and depend on the type of molecule being inhibited. For example, in a case in which a class or group of bacteria are to be inhibited, conserved regions of bacteria are targeted, and binding agents that bind to these targets are constructed. Methods for targeting a conserved region or polymorphic region of a nucleotide sequence that encodes the target molecule, or the target molecule having an amino acid sequence are shown in Cicciarelli et al., U.S. patent publication number 2005/0287129 A1 published Dec. 29, 2005 which is incorporated by reference herein in its entirety. In other embodiments, if a specific disease agent such as a bacterium is to be inhibited, a non-conserved region of the disease agent is targeted with the binding agents. The binding of the agents are determined and/or measured for example using standard assays, for example an enzyme-linked immunosorbent assay (ELISA), western blot and radioimmunoassay.

A molecule target or a disease agent target includes pathogenic molecules including polypeptides or toxins to which the binding protein described herein binds, neutralizes and/or clears. The term "pathogenic protein" refers to a protein that can cause, directly or indirectly, a disease, or condition in an individual. A pathogenic protein is for example a protein or a toxin produced by a bacterium, a virus, or a cancer cell. A recombinant multimeric binding protein described herein binds non-overlapping areas of the disease agent target (e.g., a toxin produced by a bacterium) and protects the subject from the pathology of the disease agent target by neutralizing and/or clearing the target. The binding protein protects subjects from negative symptoms caused by exposure to the disease agent target, and the risk of negative symptoms caused by a potential exposure to the target.

Anti-tag antibody described herein is used in various embodiments to effect or facilitate effector functions. The anti-tag antibody includes for example an immunoglobulin such as IgA, IgD, IgE, IgG, and IgM, and subtypes thereof. In addition to monoclonal antibodies, polyclonal antibodies specific to the tag are used in the methods, compositions and kits described herein. Effector functions are performed for example immune molecules interaction with the Fc portion of the immunoglobulin. Depending on the type of immunoglobulin chosen, the effector functions results in clearance of the disease agent (e.g., excretion, degradation, lysis or phagocytosis).

Mammalian antibody types IgA, IgD, IgE, IgG, and IgM, and antibody subtypes are classified according to differences in their heavy chain constant domains. Each immunoglobulin class differs in its biological properties and characteristics. IgA is found for example in areas containing mucus (e.g. in the gut, respiratory tract, and urogenital tract) and prevents the colonization of mucosal areas by pathogens. IgD functions as a disease agent receptor on B cells. IgE binds to allergens and triggers histamine release from mast cells and also provides protection against helminths (worms). IgG, in four forms, provides the majority of antibody-based immunity against invading pathogens. IgM has a very high affinity for eliminating pathogens in the early stages of B cell mediated immunity, and is expressed on the surface of B cells and also in a secreted form.

Leukocytes such as mast cells and phagocytes have specific receptors on the cell surface for binding antibodies. These Fc receptors interact with the Fc region of classes of antibodies (e.g. IgA, IgG, IgE). The engagement of a particular antibody with the Fc receptor on a particular cell triggers the effector function of that cell. For example, phagocytes function to perform phagocytosis, and mast cells function to degranulate. Effector functions generally result in destruction of an invading microbe. In various embodiments, the type of immunoglobulin is chosen specifically for a type of desired effector function.

The present invention includes methods of administering one or more recombinant multimeric binding proteins to a subject (e.g., human, cow, horse, pig, mouse, dog, and cat). The binding protein is administered in certain embodiments as a monomer, or as a multimeric binding protein comprising a plurality of monomers having different binding regions. The methods and compositions herein involve administration of one or more multimeric binding agents that include monomers that each has a binding region that is specific to the disease agent. The binding agent for example includes one or more tags. The binding agent/protein binds to the target region on the disease protein. Administration of two or more binding proteins (e.g., monomer binding proteins or multimeric binding proteins), in various embodiments, increased the effectiveness of the antibody therapy, and reduced the severity of one or more negative symptoms of exposure of the disease protein target. The binding protein is administered in various embodiments as a single monomer, a mixture of multiple (e.g., two or more) monomers, a multimeric binding protein including a plurality of monomers that are same or different, a mixture of multiple (e.g., two or more) multimeric binding proteins comprising more than one monomer, or any combination thereof. Examples herein show that administration of a binding protein containing more than one copy of the tag resulted in increased protection against a disease agent target, e.g., botulinum toxin serotype A. A single anti-tag antibody type in certain embodiments binds to all binding proteins having a tag. In certain embodiments in which the binding proteins have multiple copies (e.g., two or more) of the same tag, the anti-tag antibody binds to each copy of the tag on the binding protein. The phrase, "antibody therapeutic proteins" or "antibody therapeutic preparation" refers to one or more compositions that include at least one binding protein and optionally at least one anti-tag antibody. The multimeric binding protein preparation in certain embodiments contains additional elements including carriers as described herein.

The administration of the one or more binding proteins and/or anti-tag antibody is performed in related embodiments simultaneously or sequentially in time. The binding protein in certain embodiments is administered before, after or at the same time as another binding protein or the anti-tag antibody, providing that the binding proteins and/or the anti-tag antibodies are administered close enough in time to have the desired effect (e.g., before the binding proteins have been cleared by the body). Thus, the term "co-administration" is used herein to mean that the binding proteins and another binding protein or the anti-tag antibody are administered at time points to achieve effective treatment of the disease, and reduction in the level of the pathogen (e.g., virus, bacteria, cancer cell, proteins associated therewith, or combination thereof) and symptoms associated with it. The methods of the present invention are not limited by the amount of time in between which the binding proteins and/or anti-tag antibody are administered; providing that the compositions are administered close enough in time to produce the desired effect. In certain embodiment, the binding proteins is administered only, alternatively the binding protein and/or anti-tag antibody are premixed and administered together. The binding proteins and/or anti-tag antibody are in certain embodiments co-administered with other medications or compositions suitable to treating the disease agent.

The binding protein in certain embodiments is administered prior to the potential risk of exposure to the disease target agent to protect the subjects from symptoms of the disease agent target. For example, the binding protein and/or clearing antibody is administered minutes, hours or days prior to the risk of exposure. Alternatively, the binding protein is administered contemporaneously to the risk of exposure to the disease agent target, or slightly after the risk of exposure. For example, the binding protein is administered to a subject at the moment the subjects contacts, enters or passes through an environment (e.g., room, hallway, building, and field) containing the risk of exposure to the disease agent.

The methods of the present invention include treating a bacterial disease, a parasitic infection, a viral disease, a cancer, small unwanted molecule, a protein or a toxin associated therewith. This is accomplished by administering the binding proteins and anti-tag antibodies described herein to the affected individual or individual at risk. Administration ameliorates or reduces the severity of one or more the symptoms of the disease or condition. The presence, absence or severity of symptoms is measured for example using tests and diagnostic procedures known in the art. Presence, absence and/or level of the disease agent are measured in certain embodiments using methods known in the art. Symptoms or levels of the disease agent can be measured at one or more time points (e.g., before, during and after treatment, or any combination thereof) during the course of treatment to determine if the treatment is effective. A decrease or no change in the level of the disease agent, or severity of symptoms associated therewith indicates that treatment is working, and an increase in the level of the disease agent, or severity of symptoms indicates that treatment is not working. Symptoms and levels of disease agents are measured in various embodiments using methods known in the art. Symptoms that are monitored in certain embodiments include fever, plain including headache, joint pain, muscular pain, difficulty breathing, lethargy, and impaired mobility, appetite and unresponsiveness. Toxin protection is assessed as increased survival and reduction or prevention of symptoms. Methods, compositions and kits using the binding protein decrease and alleviate the symptoms of the disease target agent and also improve survival from exposure to the agent.

The antibody therapeutic agents including one or more binding proteins or agents, and/or an anti-tag antibody are administered in various embodiments with one or more pharmaceutical carriers. The terms "pharmaceutically acceptable carrier" and a "carrier" refer to any generally acceptable excipient or drug delivery device that is relatively inert and non-toxic. The binding agents and anti-tag antibody are administered with or without a carrier. Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The binding agents and anti-tag antibody are administered systemically or locally (e.g., by injection or diffusion).

Suitable carriers (e.g., pharmaceutical carriers) include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The binding protein preparations are sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. The binding protein preparations in certain embodiments are combined where desired with other active substances, e.g., enzyme inhibitors, to reduce metabolic degradation. A carrier (e.g., a pharmaceutically acceptable carrier) is used optionally in certain embodiments to administer one or more binding agents and an anti-tag antibody.

The binding agents and anti-tag antibodies in certain embodiments are administered topically (as by powders, ointments, or drops), orally, rectally, mucosally, sublingually, parenterally, intracisternally, intravaginally, intraperitoneally, bucally, ocularly, or intranasally, depending on preventive or therapeutic objectives and the severity and nature of a exposure or risk of exposure to the disease agent target. The composition in various embodiments is administered in a single dose or in more than one dose over a period of time to confer the desired effect.

An effective amount of compositions of the present invention varies according to choice of the binding agent, the particular composition formulated, the mode of administration and the age, weight and condition of the patient, for example. As used herein, an effective amount of the binding agents and/or anti-tag antibody is an amount which is capable of reducing one or more symptoms of the disease or conditions caused by the molecule target or disease agent target. Dosages for a particular patient are determined by one of ordinary skill in the art using conventional considerations, (e.g. by means of an appropriate, conventional pharmacological protocol).

A composition in certain embodiments includes one or more nucleotide sequences described herein that encode the binding protein. In various embodiments, a nucleotide sequence is either present as a mixture or in the form of a DNA molecule a multimer. In various embodiments, the composition includes a plurality of nucleotide sequences each encoding the binding protein including a monomer or polypeptide, or any combination of molecules described herein, such that the binding protein is generated in situ. In such compositions, a nucleotide sequence is administered using any of a variety of delivery systems known to those of ordinary skill in the art, including nucleic acid expression systems, bacterial and viral expression systems. Appropriate nucleic acid expression systems contain appropriate nucleotide sequences operably linked for expression in the patient (such as a suitable promoter and terminating signal). Bacterial delivery systems involve administration of a bacterium (such as Bacillus-Calmette-Guerrin) that expresses the polypeptide on its cell surface. In an embodiment, the DNA can be introduced using a viral expression system (e.g., vaccinia or other pox virus, retrovirus, or adenovirus), which uses a non-pathogenic (defective), replication competent virus. Techniques for incorporating DNA into such expression systems are well known to those of ordinary skill in the art. The DNA can also be "naked," as described, for example, in Ulmer et al., Science 259:1745-1749, 1993 and reviewed by Cohen, Science 259:1691-1692, 1993. The uptake of naked DNA can be increased by coating the DNA onto biodegradable beads, which are efficiently transported into recipient cells.

Systems or kits of the present invention include in various embodiments one or more binding agents having a binding region and one or more tags, and an anti-tag antibody having an anti-tag region (e.g., an anti-tag antibody), as described herein.

The methods, compositions and kits described herein in certain embodiments include isolated polypeptide molecules that have been engineered or isolated to act as binding agents or binding proteins. A binding protein composition includes for example an amino acid sequence selected from SEQ ID NOs: 2, 4, 6, 8, 10, 12, 14, 20, 22, 24, 26, 28, 30, 32, 34, 36, 38, 40, 42, 44, 46, 48, 50, 52 or combinations thereof. In various embodiments, a binding protein composition includes a nucleotide sequence that encodes an amino acid sequence, for example the nucleotide sequence is selected from SEQ ID NOs: 1, 3, 5, 7, 9, 11, 13, 19, 21, 23, 25, 27, 29, 31, 33, 35, 37, 39, 41, 43, 45, 47, 49, 51 or combinations thereof. The bindings protein composition includes for example a tag, for example a tag having an amino acid sequence of SEQ ID NO:15.

As used herein, the term "polypeptide" encompasses amino acid chains of any length, including full length proteins (i.e., disease agents), in which the amino acid residues are linked by covalent peptide bonds. A polypeptide comprises a portion of the binding agent, the entire binding agent, or contains additional sequences. The polypeptides of the binding agents of the present invention referred to herein as "isolated" are polypeptides that are separated away and purified from other proteins and cellular material of their source of origin. The compositions and methods of the present invention also encompass variants of the above polypeptides and DNA molecules. A polypeptide "variant," as used herein, is a polypeptide that differs from the recited polypeptide by having one or more conservative substitutions and/or modifications, such that the functional ability of the binding agent to bind to the disease agent target is retained.

The present invention also encompasses proteins and polypeptides, variants thereof, or those having amino acid sequences analogous to the amino acid sequences of binding agents described herein. Such polypeptides are defined herein as analogs (e.g., homologues), or mutants or derivatives or variants. "Analogous" or "homologous" amino acid sequences refer to amino acid sequences with sufficient identity of any one of the amino acid sequences of the present invention so as to possess the biological activity (e.g., the ability to bind to the disease agent target). For example, an analog polypeptide can be produced with "silent" changes in the amino acid sequence wherein one, or more, amino acid residues differ from the amino acid residues of any one of the sequence, yet still possesses the function or biological activity of the polypeptide. The binding protein includes for example an amino acid having at least about 60% (e.g., 65%, 70%, 75%, 80%, 85%, 90% or 95%) identity or similarity with SEQ ID NOs: 2, 4, 6, 8, 10, 12, 14, 20, 22, 24, 26, 28, 30, 32, 34, 36, 38, 40, 42, 44, 46, 48, 50, 52, 56-87, 95 or combination thereof. Percent "identity" refers to the amount of identical nucleotides or amino acids between two nucleotides or amino acid sequences, respectfully. As used herein, "percent similarity" refers to the amount of similar amino acids between two amino acid sequences, i.e., having conservative amino acid changes compared to the original sequences, or to the amount of similar nucleotides between two nucleotide sequences.

In some embodiments, the invention pertains to one or more (e.g. about 1, or about 2, or about 3, or about 4, or about 5, or about 6, or about 7, or about 8, or about 9, or about 10, or about 15, or about 20) mutations to any of the sequences disclosed herein (e.g. as a variant or a portion or a homolog of such sequences). In various embodiments, a variant or portion or homolog has at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to any of the sequences disclosed herein (e.g. a variant of SEQ ID NO: 163 may include a sequence having at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 163). In various embodiments, one or more amino acid of any of the sequences disclosed herein is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine β-alanine, GABA and δ-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Referring to FIGS. 4 and 5, by comparing the B5 (SEQ ID NO: 24) polypeptide sequence to the other polypeptide sequences in the chart, the polypeptide sequence similarity is determined as follows: E-9 (SEQ ID NO: 38) is 74% similar, C5 (SEQ ID NO: 42) is 67% similar, B2 (SEQ ID NO: 40) is 68% similar, and F9 (SEQ ID NO: 44) is 73% similar. The BLAST was done using default parameters on the NCBI website. Since these VHHs have been shown to compete with B5, i.e., for binding to the target, the present invention includes those sequences having a sequence similarity of at least about 65%. In like manner, by comparing the B5 (SEQ ID NO: 23) nucleic acid sequence to the other nucleic acid sequences in the chart, the polypeptide sequence similarity is determined as follows: E-9 (SEQ ID NO: 37) is 81% identical, C5 (SEQ ID NO: 41) is 75% identical, B2 (SEQ ID NO: 39) is 86% identical, and F9 (SEQ ID NO: 43) is 80% identical. The present invention includes those nucleic acid sequences having a sequence identity of at least about 75%.

Homologous polypeptides are determined using methods known to those of skill in the art. Initial homology searches are performed at NCBI by comparison to sequences found in the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., Gene, 1998 73:237-244, e.g., using default parameters). In certain embodiments, the recombinant multimeric binding protein acid sequence is an amino acid sequence that is substantially identical to sequences described herein, for example any of SEQ ID NOs: 56-87 and 95. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60% identity, or at least 75%, 85%, 95%, 96%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., *Nuc. Acids Research* 22:4673, 1994, BL2SEQ by Tatusova and Madden, *FEMS Microbiol. Lett.* 174:247, 1999, SAGA by Notredame and Higgins, *Nuc. Acids Research* 24:1515, 1996, and DIALIGN by Morgenstern et al., *Bioinformatics* 14:290, 1998.

The methods, compositions and kits described herein in various embodiments include nucleotide sequence or an isolated nucleic acid molecule (encoding the binding protein) having a nucleotide sequence of SEQ ID NOs: 1, 3, 5, 7, 9, 11, 13, 19, 21, 23, 25, 27, 29, 31, 33, 35, 37, 39, 41, 43, 45, 47, 49, 51 or combinations thereof. See FIGS. 1, 3 and 4. As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, substitutions or additions. Such modifications are readily introduced using standard mutagenesis techniques, such as oligonucleotide-directed site-specific mutagenesis as taught, for example, by Adelman et al. (DNA 2:183, 1983). Nucleotide variants are naturally occurring allelic variants, or non-naturally occurring variants. Variant nucleotide sequences in various embodiments exhibit at least about 70%, more preferably at least about 80% and most preferably at least about 90% homology to the recited sequence. Such variant nucleotide sequences hybridize to the recited nucleotide sequence under stringent conditions. In one embodiment, "stringent conditions" refers to pre-washing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses isolated nucleic acid sequences that encode the binding agents and in particular, those which encode a polypeptide molecule having an amino acid sequence of SEQ ID NOs: 2, 4, 6, 8, 10, 12, 14, 20, 22, 24, 26, 28, 30, 32, 34, 36, 38, 40, 42, 44, 46, 48, 50, 52, 56-87, 95 or combinations thereof.

As used herein, an "isolated" nucleotide sequence is a sequence that is not flanked by nucleotide sequences which in nature flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. The nucleic acid sequences of the binding agents of the present invention include homologous nucleic acid sequences. "Analogous" or "homologous" nucleic acid sequences refer to nucleic acid sequences with sufficient identity of any one of the nucleic acid sequences described herein, such that once encoded into polypeptides, they possess the biological activity of any one of the binding agents described herein. In particular, the present invention is directed to nucleic acid molecules having at least about 70% (e.g., 75%, 80%, 85%, 90% or 95%) identity with SEQ ID NOs: 1, 3, 5, 7, 9, 11, 13, 19, 21, 23, 25, 27, 29, 31, 33, 35, 37, 39, 41, 43, 45, 47, 49, 51 or combinations thereof.

Also encompassed by the present invention are nucleic acid sequences, DNA or RNA, which are substantially complementary to the DNA sequences encoding the polypeptides of the present invention, and which specifically hybridize with their DNA sequences under conditions of stringency known to those of skill in the art. As defined herein, substantially complementary means that the nucleotide sequence of the nucleic acid need not reflect the exact sequence of the encoding original sequences, but must be sufficiently similar in sequence to permit hybridization with nucleic acid sequence under high stringency conditions. For example, non-complementary bases can be interspersed in a nucleotide sequence, or the sequences can be longer or shorter than the nucleic acid sequence, provided that the sequence has a sufficient number of bases complementary to the sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

The invention also provides vectors, plasmids or viruses containing one or more of the nucleic acid molecules having the sequence of SEQ ID NO:1, 3, 5, 7, 9, 11, 13, 19, 21, 23, 25, 27, 29, 31, 33, 35, 37, 39, 41, 43, 45, 47, 49, 51 or combinations thereof). Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

Any of a variety of expression vectors known to those of ordinary skill in the art can be employed to express recombinant polypeptides of this invention. Expression can be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast, insect cells, or a mammalian cell line such as COS or CHO. The DNA sequences expressed in this manner can encode any of the polypeptides described herein including variants thereof.

Uses of plasmids, vectors or viruses containing the nucleic acids of the present invention include generation of mRNA or protein in vitro or in vivo. In related embodiments, the methods, compositions and kits encompass host cells transformed with the plasmids, vectors or viruses described above. Nucleic acid molecules can be inserted into a construct which can, optionally, replicate and/or integrate into a recombinant host cell, by known methods. The host cell can be a eukaryote or prokaryote and includes, for example, yeast (such as *Pichia pastoris* or *Saccharomyces cerevisiae*), bacteria (such as *E. coli*, or *Bacillus subtilis*), animal cells or tissue, insect 519 cells (such as baculoviruses infected SF9 cells) or mammalian cells (somatic or embryonic cells, Human Embryonic Kidney (HEK) cells, Chinese hamster ovary cells, HeLa cells, human 293 cells and monkey COS-7 cells). Host cells suitable in the present invention also include a mammalian cell, a bacterial cell, a yeast cell, an insect cell, and a plant cell.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is maintained under suitable conditions for expression and recovery of the polypeptides of the present invention. In certain embodiments, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria-Bertani broth, Superbroth, Dulbecco's Modified Eagles Media (DMEM), RPMI-1640, M199 and Grace's insect media. The growth media can contain a buffer, the selection of which is not critical to the invention. The pH of the buffered Media can be selected and is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature is selected so that the host cell tolerates the process and is for example, between about 13-40° Celsius.

The invention having now been fully described, it is further illustrated by the following claims and by the examples, which are found, in part, in a paper published in the Public Library of Science (PLoS) One and entitled, "A Novel Strategy for Development of Recombinant Antitoxin Therapeutics Tested in a Mouse Botulism Model", co-authored by Jean Mukherjee, Jacqueline M. Tremblay, Clinton E. Leysath, Kwasi Ofori, Karen Baldwin, Xiaochuan Feng, Daniela Bedenice, Robert P. Webb, Patrick M. Wright, Leonard A. Smith, Saul Tzipori, and Charles B. Shoemaker (12 pages; Mukherjee J et al. 2012 PLoS ONE 7(1): e29941. doi:10.1371/journal.pone.0029941). This published paper is hereby incorporated by reference herein in its entirety.

Plants species have evolved chemical defenses against other organisms (Linskens, Hans F.; Jackson, John F. (Eds.) Plant Toxin Analysis 1992, XXVI, 389 p. 33 illus). Plants contain and secrete a variety of toxic compounds sometimes referred to as "secondary compounds" that affect the behavior and productivity of wild and domestic animals. Classes of toxic compounds include soluble phenolics, alkaloids, and terpenoids. Soluble phenolics include flavonoids, isoflavonoids, and hydrolysable and condensed tannins.

Exemplary plants toxin molecules that in certain embodiments are treated using the compositions, methods and kits described herein are: Akar saga (*Abrus precatorius*), Death-camas, Amianthium Angel's Trumpet (*Brugmansia*), Angel Wings (*Caladium*), Anticlea, Autumn crocus (*Colchicum autumnale*), Azalea (*Rhododendron*), Bittersweet nightshade (*Solanum dulcamara*), Black hellebore (*Helleborus niger*), Black locust (*Robinia pseudoacacia*), Black nightshade (*Solanum nigrum*), Bleeding heart (*Dicentra cucullaria*), Blind-your-eye mangrove (*Excoecaria agallocha*), Blister Bush (*Peucedanum galbanum*), Bloodroot (*Sanguinaria canadensis*), Blue-green algae (*Cyanobacteria*), Bobbins (*Arum maculatum*), Bracken (*Pteridium aquilinum*), Broom (*Cytisus scoparius*), calabar bean (*Physostigma venenosum*), castor bean, Christmas rose (*Helleborus niger*), Columbine (*Aquilegia*), Corn cockle (*Agrostemma githago*), corn lily (*veratrum*), cowbane (*Cicuta*), cows and bulls (*Arum maculatum*), crab's eye (*Abrus precatorius*), cuckoo-pint (*Arum maculatum*), daffodil (*Narcissus*), Darnel (*Lolium temulentum*), Deadly nightshade (*Atropa belladonna*), Devils and angels (*Arum maculatum*), False acacia (*Robinia pseudoacacia*), False hellebore (*Veratrum*), Foxglove (*Digitalis purpurea*), Frangipani (*Plumeria*), Doll's eyes (*Actaea pachypoda*), Dumbcane (*Dieffenbachia*), Dutchman's breeches (*Dicentra cucullaria*), Elder/Elderberry (*Sambucus*), Giant hogweed (*Heracleum mantegazzianum*), Giddee giddee, Gifblaar (*Dichapetalum cymosum*), Greater celandine (*Chelidonium majus*), Gympie gympie (*Dendrocnide moroides*), Heart of Jesus (*Caladium*), hemlock (*Conium maculatum*), hemlock water-dropwort (*Oenanthe crocata*), henbane (*Hyoscyamus niger*), Horse chestnut (*Aesculus hippocastanum*), Holly (*Ilex aquifolium*), Hyacinth (*Hyacin*-

*thus orientalis*), Indian licorice, Jack in the pulpit, Jamestown weed, jequirity, Jerusalem cherry, Jimson weed, John Crow bead, Jumbie bead, Lily of the Valley, Lords and Ladies, Madiera winter cherry, Mayapple, Meadow saffron, Milky mangrove, Monkshood, Moonseed, Passion flower, Plumeria, Poison hemlock, Poison ivy, Poison oak, Poison parsnip, Poison sumac, Poison ryegrass, Pokeweed, Precatory bean, Privet, ragwort, redoul, River poison tree, *Robinia pseudoacacia* (also known as black locust and false acacia), Rosary pea, Sosnowsky's Hogweed, Spindle tree, Starchroot, Stenanthium, Stinging tree, Stinkweed, Strychnine tree, Suicide tree (*Cerbera odollam*), thorn apple, Toxicoscordion, Wake robin, Water hemlock, White baneberry, White snakeroot, Wild arum, Winter cherry, Wolfsbane, Yellow Jessamine, Yew, and Zigadenus

*Abrus precatorius* is known commonly as jequirity, crab's eye, rosary pea, 'John Crow' bead, precatory bean, Indian licorice, akar saga, giddee giddee, jumbie bead, ruti, and weather plant. The attractive seeds (usually about the size of a ladybug, glossy red with one black dot) contain abrin, which is related to ricin, a very potent toxic substance to humans as a single seed can kill an adult human. Symptoms of poisoning include nausea, vomiting, convulsions, liver failure, and death, usually after several days. The seeds have been used as beads in jewelry, which is dangerous; inhaled dust is toxic and pinpricks can be fatal. The seeds are unfortunately attractive to children.

*Aconitum* species, commonly called aconite, wolfsbane and monkshood are poisonous even by casual skin contact should be avoided; symptoms include numbness, tingling, and cardiac irregularity. The toxin is an alkaloid called aconitine, which disables nerves, lowers blood pressure, and can stop the heart. It has been used as poison for bullets (by Germany in WWII), as a bait and arrow poison (ancient Greece), and to poison water supplies (reports from ancient Asia). If ingested, it usually causes burning, tingling, and numbness in the mouth, followed by vomiting and nervous excitement.

*Actaea pachypoda* known as doll's eyes or white baneberry are poisonous berries, and other parts of the plant are toxic. Consumption of the berries has a sedative effect on cardiac muscle tissue and can cause cardiac arrest.

Adam and Eve (*Arum maculatum*) is a common woodland plant species of the Araceae family. It is widespread across temperate northern Europe and is known by an abundance of common names including Wild arum, Lords and Ladies, Devils and Angels, Cows and Bulls, Cuckoo-Pint, Adam and Eve, Bobbins, Naked Boys, Starch-Root and Wake Robin, *Adenium obesum* (also known as sabi star, kudu or desertrose). The plant exudes a highly toxic sap which is used by the Meridian High and Hadza in Tanzania to coat arrow-tips for hunting.

*Aesculus hippocastanum* (horse-chestnut) produces a toxin causing nausea, muscle twitches, and sometimes paralysis. *Ageratina altissima* (white snakeroot) produces a toxin, causing nausea and vomiting. Milk from cattle that have eaten white snakeroot can sicken or kill humans. *Aquilegia* (columbine) seeds and roots that contain cardiogenic toxins causing both severe gastroenteritis and heart palpitations if consumed, and poisoning by this plant is often fatal. *Areca catechu* (betel nut palm and pinyang) a nut contains an alkaloid related to nicotine which is addictive, mildly intoxicating, and if swallowed causes nausea. Use is correlated with mouth cancer, asthma and heart disease. *Arum maculatum* (jack in the pulpit) bright red berries contain oxalates of saponins and causes skin, mouth and throat irritation, resulting in swelling, burning pain, breathing difficulties and stomach upset. *Atropa belladonna* (deadly nightshade, and belladonna) is one of the most toxic plants found in the Western hemisphere, producing tropane alkaloids including atropine, hyoscine (scopolamine), and hyoscyamine, which have anticholinergic properties. The consumption of two to five berries by children and ten to twenty berries by adults can be lethal. The symptoms of poisoning include dilated pupils, sensitivity to light, blurred vision, tachycardia, loss of balance, staggering, headache, rash, flushing, dry mouth and throat, slurred speech, urinary retention, constipation, confusion, hallucinations, delirium, and convulsions. Ingestion of a single leaf of the plant can be fatal to an adult, and casual contact with the leaves causes skin pustules. The berries pose the greatest danger to children because they look attractive and have a somewhat sweet taste. In 2009 a case of *A. belladonna* mistaken for blueberries, with six berries ingested by an adult woman, resulted in severe anticholinergic syndrome. *A. belladonna* is toxic also to many domestic animals, causing narcosis and paralysis. *Brugmansia* (angel's trumpet) contains the tropane alkaloids scopolamine and atropine, and can be fatal.

*Caladium* (commonly known as angel wings, elephant ear and heart of Jesus) produces symptoms such as generally irritation, pain, and swelling of tissues in subjects. If the mouth or tongue swell, breathing may be fatally blocked. *Cerbera odollam* (suicide tree) produces seeds that contain cerberin, a potent alkaloid toxin related to digoxin. The poison blocks the calcium ion channels in heart muscle, causing disruption of the heart beat which is typically fatal. *Chelidonium majus* also known as greater celandine is toxic in moderate doses as it contains a range of isoquinoline alkaloids. The main alkaloid present in the herb and root is coptisine, with berberine, chelidonine, sanguinarine and chelerythrine also present. Sanguinarine is particularly toxic with an $LD_{50}$ of only 18 mg per kg body weight. *Cicuta* (water hemlock, cowbane, wild carrot, snakeweed, poison parsnip, false parsley, children's bane and death-of-man) is extremely poisonous and contains the toxin cicutoxin, a central nervous system stimulant, resulting in seizures. *Colchicum autumnale* (autumn crocus and meadow saffron) bulbs contain colchicine, having poisoning symptoms that include burning in the mouth and throat, fever, vomiting, diarrhea, abdominal pain and kidney failure. There is no specific antidote for colchicine, although various treatments do exist. *Conium maculatum* (commonly known as hemlock, poison hemlock, spotted parsley, spotted cowbane, bad-man's oatmeal, poison snakeweed and beaver poison) contains the alkaloid coniine which causes stomach pains, vomiting, and progressive paralysis of the central nervous system. Consolida commonly known as larkspur is a poisonous plant that causes nausea, muscle twitches, paralysis and is often fatal.

*Convallaria majalis* (lily of the valley) is a poisonous woodland flowering plant that contains cardiac glycosides fatal in humans. *Coriaria myrtifolia* (redoul) contains the toxin coriamyrtin. Ingestion of this plant produces digestive, neurological and respiratory problems. The poisonous fruit resemble blackberries and are often mistakenly eaten by children and adults. Cyanobacteria, a phylum of bacteria, is commonly known as blue-green algae. Many different species, including *Anacystis cynea* and *Anabaena circinalis*, produce several different toxins known collectively as cyanotoxins. Cyanotoxins include neurotoxins, hepatotoxins, endotoxins and cytotoxins. *Cytisus scoparius* (commonly known as broom or common broom) contains toxic alkaloids that depress the heart and nervous system. The alkaloid sparteine is a class 1a antiarrhythmic agent and a sodium channel blocker. The berries of Daphne are either red or yellow and are poisonous, causing burns to mouth and digestive tract, followed by coma. *Datura* contains the alkaloids scopolamine and atropine. *Datura* has been used as a hallucinogenic drug by the native peoples of the Americas and others. Incorrect consumption of this plant can lead to death. *Datura stramonium* (jimson weed, thorn apple, stinkweed and Jamestown weed) causes abnormal thirst, vision distortions, delirium, incoherence, and coma.

Deathcamas, including *Amianthium, Anticlea, Stenanthium, Toxicoscordion* and *Zigadenus*, are poisonous in many cases due to the presence of alkaloids in the plants. Ingestion of the plant by grazing animals, such as sheep and cattle, often results in death.

*Delphinium* (also known as larkspur) contains the alkaloid delsoline. Young plants and seeds of *Delphinium* are poisonous, causing nausea, muscle twitches, and paralysis. *Dendrocnide moroides* (also known as stinging tree and gympie gympie) causes a painful sting when touched and in some cases of widespread contact may be fatal. The stinging may last for several days and is exacerbated by touching, rubbing, and cold. *Dicentra cucullaria* (also known as bleeding heart and Dutchman's breeches) has leaves and roots that are poisonous and cause convulsions and other nervous symptoms. *Dichapetalum cymosum* (also known as gifblaar) is a well known as a livestock poison in South Africa. The plant contains the metabolic poison fluoroacetic acid. *Dieffenbachia* (a houseplant dumbcane) causes intense burning, irritation, and immobility of the tongue, mouth, and throat. Swelling can be severe enough to block breathing, leading to death. *Digitalis purpurea* (foxglove) leaves, seeds, and flowers are poisonous, containing cardiac or other steroid glycosides. These cause irregular heartbeat, general digestive upset, and confusion. *Euonymus europaeus* (commonly known as spindle, European spindle or spindle tree). produces a poisonous fruit that contains amongst other substances, the alkaloids theobromine and caffeine, as well as an extremely bitter terpene. Poisoning by this plant is more common in young children, who are enticed by the brightly-coloured fruit of the plant. Ingestion of the fruit results in liver and kidney damage and even death.

*Excoecaria agallocha* (milky mangrove) has a milky sap that causes skin irritation and blistering. Eye contact with the sap can even cause temporary blindness. *Gelsemium sempervirens* commonly known as yellow jessamine is poisonous, causing nausea, vomiting and even death. *Hedera helix* (English ivy) contains leaves and berries that can be poisonous, causing stomach pains, labored breathing, possible coma. *Helleborus niger* (Christmas rose) contains protoanemonin or ranunculin, which has an acrid taste and can cause burning of the eyes, mouth and throat, oral ulceration, gastroenteritis and hematemesis. *Heracleum mantegazzianum* (giant hogweed) produces a sap that is phototoxic, causing phytophotodermatitis (severe skin inflammations) when affected skin is exposed to sunlight or to UV-rays. Presence of minute amounts of sap in the eyes can lead to temporary or even permanent blindness. *Hippomane mancinella* (manchineel) contains toxic phorbol esters typical of the Euphorbiaceae plant family. Contact with the milky white sap of the plant produces strong allergic dermatitis. The fruit is fatal if eaten. *Hyacinthus orientalis* (hyacinth) bulbs are poisonous, causing nausea, vomiting, gasping, convulsions, and possibly death. Even handling the bulbs can cause skin irritation.

*Hyoscyamus niger* (henbane) has seeds and foliage contain hyoscyamine, scopolamine and other tropane alkaloids that produces dilated pupils, hallucinations, increased heart rate, convulsions, vomiting, hypertension and ataxia. *Ilex aquifolium* (European holly) berries cause gastroenteritis, resulting in nausea, vomiting and diarrhea. *Jacobaea vulgaris* (ragwort) contains alkaloids, including jacobine, jaconine, jacozine, otosenine, retrorsine, seneciphylline, senecionine, and senkirkine. *Kalanchoe delagoensis* (mother of millions) contains bufadienolide cardiac glycosides which cause cardiac poisoning, particularly in grazing animals. *Kalmia latifolia* (mountain laurel) contains andromedotoxin and arbutin. The green parts of the plant, flowers, twigs, and pollen are all toxic, and symptoms of toxicity begin to appear about six hours following ingestion. Poisoning produces anorexia, repeated swallowing, profuse salivation, depression, uncoordination, vomiting, frequent defecation, watering of the eyes, irregular or difficulty breathing, weakness, cardiac distress, convulsions, coma, and eventually death. Laburnum produces seeds that are poisonous and are lethal if consumed in excess. The main toxin in the seeds is cytisine, a nicotinic receptor agonist. Symptoms of poisoning may include intense sleepiness, vomiting, excitement, staggering, convulsive movements, slight frothing at the mouth, unequally dilated pupils, coma and death. Ligustrum (privet) berries and leaves that are poisonous. The berries contain syringin, which causes digestive disturbances, nervous symptoms. Privet is one of several plants which are poisonous to horses. *Lolium temulentum* (poison ryegrass) produces seeds that contain the alkaloids temuline and loliine. The fungus ergot grow on the seed heads of rye grasses, as an additional source of toxicity.

Mango peel and sap contains urushiol, the chemical in poison ivy and poison sumac that can cause urushiol-induced contact dermatitis in susceptible people. Cross-reactions between mango contact allergens and urushiol have been observed. Those with a history of poison ivy or poison oak contact dermatitis may be most at risk for such an allergic reaction. *Narcissus* bulbs and stems are poisonous, and cause nausea, vomiting, diarrhea, headaches, vomiting, and blurred vision.

*Oenanthe crocata* (hemlock water dropwort) contains oenanthotoxin in the stems and especially the carbohydrate-rich roots that are poisonous. *Peucedanum galbanum* (commonly known as blister bush) is poisonous and contact to the body causes painful blistering that is intensified with exposure to sunlight. *Physostigma venenosum* (calabar bean) contains parasympathomimetic alkaloid physostigmine toxin, a reversible cholinesterase inhibitor. Symptoms of poisoning include copious saliva, nausea, vomiting, diarrhea, anorexia, dizziness, headache, stomach pain, sweating, dyspepsia and seizures. Phytolacca (pokeweed) leaves, berries and roots contain phytolaccatoxin and phytolaccigenin. Ingestion of poisonous parts of the plant cause severe stomach cramping, persistent diarrhoea, nausea, vomiting (sometimes bloody vomiting), slow and difficult breathing, weakness, spasms, hypertension, severe convulsions, and even death. *Podophyllum peltatum* (mayapple) contains the non-alkaloid toxin podophyllotoxin, which causes diarrhea, severe digestive upset. *Pteridium aquilinum* (commonly known as bracken) if ingested is carcinogenic to humans and animals such as mice, rats, horses and cattle. The carcinogenic compound in the pant is ptaquiloside (PTQ), which can leach from the plant into the water supply. *Pteridium aquilinum* (African sumac) is closely related to poison ivy. The tree contains low levels of a highly irritating oil with urushiol. Skin reactions to contacting the plan include blisters and rashes that be further spread by contacting clothing of an exposed subjects. The smoke of burning *Rhus lancia* can cause reactions in the lungs, and can be fatal. *Ricinus*

*communis* (castor oil plant) seeds contain ricin, an extremely toxic water-soluble protein, ricinine, an alkaloid, and an irritant oil.

Sambucus (commonly known as elder or elderberry) roots are poisonous and cause nausea and digestive upset. *Sanguinaria canadensis* (bloodroot) rhizome or stem contains morphine-like benzylisoquinoline alkaloids, and the toxin sanguinarine. Sanguinarine kills animal cells by blocking the action of Na+/K+-ATPase transmembrane proteins. *Solanum dulcamara* (bittersweet nightshade) contains solanine which causes fatigue, paralysis, convulsions, and diarrhea in subjects exposed to the plant. *Solanum nigrum* (black nightshade) contains the toxic glycoalkaloid solanine. Solanine poisoning is primarily displayed by gastrointestinal and neurological disorders. Symptoms include nausea, diarrhea, vomiting, stomach cramps, burning of the throat, cardiac dysrhythmia, headache and dizziness. *Taxus baccata* (yew) contains toxic taxanes. The plant seeds themselves are particularly toxic if chewed. *Toxicodendron* contain a highly irritating oil with urushiol. Species of toxicodendrons include *Toxicodendron radicans* (commonly known as poison ivy), *Toxicodendron diversilobum* (commonly known as poison-oak), and *Toxicodendron vernix* (commonly known as poison sumac. These plants cause skin reactions such as blisters and rashes. *Urtica ferox* (ongaonga) cause a painful sting that lasts several days. *Veratrum* (false hellebore and corn lily) contain a highly toxic steroidal alkaloids (e.g. veratridine) that activate sodium ion channels and cause rapid cardiac failure and death if ingested. Symptoms typically occur between 30 minutes and four hours after ingestion and include nausea and vomiting, abdominal pain, numbness, headache, sweating, muscle weakness, bradycardia, hypotension, cardiac arrhythmia, and seizures. *Xanthium* (commonly known as cocklebur) includes *X. strumarium*, a native of North America, that is poisonous to livestock, including horses, cattle, and sheep. The seedlings and seeds are the most toxic parts of the plants and produce unsteadiness and weakness, depression, nausea and vomiting, twisting of the neck muscles, rapid and weak pulse, difficulty breathing, and eventually death. *Zantedeschia* (Calla lily) contain calcium oxalate and other toxins that producing irritation and swelling of the mouth and throat, acute vomiting and diarrhea.

Endosperm of castor seeds contain two highly toxic proteins (Ghetie et al. U.S. Pat. No. 5,578,706 issued Nov. 26, 1996; and Lord et al., 1994 The FASEB Journal 8, 201-208, each of which is incorporated by reference herein in its entirety). *R. communis* agglutinin (RCA), a 120 kDa hemagglutinin lectin, and ricin, a 65 kDa cytotoxic lectin, are lethal to eukaryotic cells. Ricin has two polypeptide chains, A and B, which together are highly lethal to mammalian cells. Agglutinin protein has four polypeptides, linked by disulfide bonds (Butterworth et al., 1983 Eur. J. Biochem. 137, 57-65), two of which are similar to the A chain (ricin A chain; RTA) and two similar to the B chain of ricin (ricin B chain, RTB). The A and B chains of ricin, together. Ricin E is a variant of the ricin toxin, having an A chain similar to ricin and a B chain, which is a hybrid of the ricin and RCA and B chains (Ladin et al. 1987 Plant Molecular Biology 9: 287-295).

Ricin A chain (32 kDa) has a ribosome-inactivating activity (Lord et al., 1994 The FASEB Journal 8, 201-208), irreversibly altering the ribosomal RNA subunits involved in translation. The A chain specifically binds 28S ribosomal subunits; the A chain requires the B chain to enter the cells as a heterodimeric toxin.

Ricin's B chain is a lectin which specifically binds glycoproteins and glycolipids on the cell surface terminating in galactose or N-acetylgalactosamine (Lord et al., 1994 The FASEB Journal 8, 201-208). The B chain binds more strongly to complex galactosides than to simple sugars. The B chain has four disulfide bonds and has a galactose/N-acetylgalactosamine binding activity. The N-terminal and C-terminal halves of the B chain contain 41 homologous pairs of amino acids when the two disulfide bonds in each half are aligned, yielding a bilobal structure with two galactose binding sites. Subdomains formed by the four disulfide bonds represent a conserved peptide which is repeated four times (Roberts et al., 1985 Journal of Biological Chemistry 260, 15682-8.). Up to 108 ricin B chains bind to an individual cell by hydrogen bonds (Lord et al., 1994 The FASEB Journal 8, 201-208). The B chain attaches to the eukaryotic cell and the intact toxin enters the cell by receptor mediated endocytosis (Bilge et al., 1995 Journal of Biological Chemistry 1995; 270(40):23720-23725). The B chain protects the A chain from proteolytic activities of lysosomes and cathepsins. Mannose residues attached to ricin are bound by cellular mannose receptors and initiate endocytosis (Montfort et al., 1987 Journal of Biological Chemistry 262, 5398-403).

A portion of the various embodiments herein are described in Tremblay et al. Figures in Tremblay et al. show that VHH domains neutralize Stx1 and/or Stx2.

Tremblay et al. is a published paper that describes heavy-chain-only camelid antibodies (VHHs) that were found to neutralize Stx1 and/or Stx2 in cell-based assays. It was observed that VHHs are effective heterodimer toxin neutralizing agents. The VHHs containing two linked Stx1-neutralizing VHHs or two Stx2-neutralizing VHHs were observed to be much more effective at neutralizing Stx in cell-based assays and in vivo in mouse subjects than a mixture of the two component monomers, e.g., heterodimer A5/D10 was found to have greater neutralization ability than a mixture of VHH A5 and VHH D10.

Further, clearance of toxins was observed to have been promoted by the presence of anti-tag monoclonal antibody co-administered with a VHH-based toxin neutralizing agent, referred to herein as the "effector Ab". The effector Ab binds to a common epitopic tag which was engineered to be located on each of the two VHH heterodimer molecules that bind to the toxin. It was observed that co-administration of effector Ab (or a plurality of effector Abs) substantially improved the efficacy of Stx toxin neutralizing agents, and prevention of death and kidney damage in mice following challenge with Stx1 or Stx2. A single toxin neutralizing agent composed of a double-tagged VHH heterotrimer co-administered with effector Ab was observed to effectively prevent all symptoms of intoxication due to Stx1 and Stx2. The VHH heterotrimer was engineered to contain a Stx1-specific VHH, a Stx2-specific VHH, and a Stx1/Stx2 cross-specific VHH. Without being limited by any particular theory or mechanism of action, it is envisioned that availability of simple, defined, recombinant proteins as described herein and in Tremblay et al. results in cost-effective protection against diseases such as hemolytic uremic syndrome, opening up new therapeutic approaches to managing these diseases.

A portion of the various embodiments herein are described in David J. Vance, Jacqueline M. Tremblay, Nicholas J. Mantis, and Charles B. Shoemaker; "Stepwise Engineering of Heterodimeric Single Domain Camelid VHH Antibodies That Passively Protect Mice from Ricin Toxin"; *Journal of Biological Chemistry;* 288(51):365-

36547 (2013) (hereinafter Vance et al.) which is incorporated herein by reference in its entireties.

A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. Therefore, it is contemplated to cover the present embodiments of the invention and any and all modifications, variations, or equivalents that fall within the true spirit and scope of the basic underlying principles disclosed and claimed herein.

The following examples and claims are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference.

EXAMPLES

Example 1: Toxins and Reagents

Botulinum neurotoxin serotype A1 (BoNT/A) and serotype B (BoNT/B) were obtained from Metabiologics Inc. Each batch of toxin was calibrated to establish the $LD_{50}$ dose in mice and stored in aliquots at −80° C. until use. Purified recombinant BoNT serotype A1 and B holotoxins containing mutations rendering them catalytically inactive (ciBoNTA, ciBoNTB) obtained. Sheep anti-BoNT/A1 antiserum was produced by immunization of sheep with BoNT/A1 toxoid followed by BoNT/A1 holotoxin. Less than 1 µl of this sheep antitoxin serum protects mice from lethality when co-administered with 10,000-fold the $LD_{50}$ of BoNT/A1. Reagents for Western blotting were purchased from KPL (Gaithersburg, Md.).

C. difficile holotoxins TcdA and TcdB were generated by transformation of shuttle vectors pHis1522 (pHis-TcdA and pHis-TcdB respectively) into B. megaterium described in Yang et al. 2008 BMC Microbiolgoy 8:192. Point mutations were introduced into conserved amino acids that are responsible for binding to the substrate, uridine diphosphoglucose (UDP-Glucose), in order to generate GT-deficient holotoxins. To generate GT-mutant holotoxin A, a unique restriction enzyme (BamHI) site was designed and constructed between sequences encoding GT and CPD domains using overlapping PCR. The primer sets used were:

```
pHis-F
(5'-TTTGTTTATCCACCGAACTAAG-3'; SEQ ID NO: 90),

Barn-R
(5'-TCTTCAGAAAGGGATCCACCAG-3'; SEQ ID NO: 91),

Barn-F
(5'-TGGTGGATCCCTTTCTGAAGAC-3'; SEQ ID NO: 92),
and

Bpu-R
(5'-ACTGCTCCAGTTTCCCAC-3'; SEQ ID NO: 93).
```

The final PCR product was digested with BsrGI and Bpu10I, and was used to replace the corresponding sequence in pHis-TcdA. The resulting plasmid was designated pH-TxA-b. Sequences encoding triple mutations (W101A, D287N, and W519A) in the GT were synthesized by Geneart (Regensburg, Germany) and cloned into pH-TxA-b through BsrGI/BamHI digestion. To generate the mutant holotoxin B construct, the sequence between BsrGI and NheI containing two point mutations (W102A and D288N) was synthesized and inserted into pHis-TcdB at the same restriction enzyme sites, leading to a new plasmid pH-aTcdB. The mutant aTcdA and aTcdB were expressed and purified identical to the wild types in B. megaterium as described by Yang et al. 2008 BMC Microbiology 8:192. The purified aTcdA and aTcdB were used to immunize alpacas.

Example 2: Alpaca Immunization and VHH-Display Library Preparation

Purified, catalytically inactive mutant forms of full-length recombinant BoNT/A (ciBoNTA) and BoNT/B (ciBoNTB) proteins were obtained as described in Webb et al. 2009 Vaccine 27: 4490-4497. Alpacas (two animals per immunization type) were immunized with either ciBoNTA or with ciBoNTB. Additional alpacas were immunized with aTcdA or aTcdB. The immunization regimen employed 100 µg of protein in the primary immunization and 50 µg in three subsequent boosting immunizations at three weekly intervals in aluminum hydroxide gel adjuvant in combination with oligodeoxynucleotides containing unmethylated CpG dinucleotides (alum/CpG; Superfos Biosector; Copenhagen, Denmark) adjuvant. Five days following the final boost immunization, blood from each animal was obtained for lymphocyte preparation and VHH-display phage libraries were prepared from the immunized alpacas as previously described (Maass et al. 2007 Int J Parasitol 37: 953-962 and Tremblay et al. 2010 Toxicon. 56(6): 990-998). Independent clones (greater than $10^6$ total) were prepared from B cells of alpacas successfully immunized with each of the BoNT immunogens.

Example 3: Anti-BoNT VHH Identification and Preparation

The VHH-display phage libraries were panned for binding to ciBoNTA or ciBoNTB targets that were coated onto each well of a 12-well plate. Coating was performed by overnight incubation at 4° C. with one ml of a 5 µg/ml target solution in PBS, followed by washing with PBS and two hours incubation at 37° C. with blocking agent (4% non-fat dried milk powder in PBS). Panning, phage recovery and clone fingerprinting were performed as previously described (Ibid.). Based on phage ELISA signals, a total of 192 VHH clones were identified as strong candidate clones for binding to BoNT/A, and 142 VHH clones were identified as strong positives for binding to BoNT/B respectively. Of the strong positives, 62 unique DNA fingerprints were identified among the VHHs selected for binding to BoNT/A and 32 unique DNA fingerprints were identified for VHHs selected for binding to BoNT/B. DNA sequences of the VHH coding regions were obtained for each phage clone and compared for identifying homologies. Based on these data, twelve of the anti-BoNT/A VHHs and eleven anti-BoNT/B VHHs were identified as unlikely to have common B cell clonal origins and were selected for protein expression. Expression and purification of VHHs in E. coli as recombinant thioredoxin (Trx) fusion proteins containing hexahistidine was performed as previously described in Tremblay et al. 2010 Toxicon. 56(6): 990-998. For heterodimers, DNA encoding two different VHHs were joined in frame downstream of Trx and separated by DNA encoding a fifteen amino acid flexible spacer having the amino acid sequence (GGGGS)$_3$. VHHs were expressed with a carboxyl terminal E-tag epitope. Furthermore, a number of VHH expression constructions were engineered to contain a second copy of the E-tag by introducing the coding DNA in frame between the Trx and VHH domains. An example of a Trx fusion to a VHH heterodimer with two E-tags is ciA-H7/ciA-B5(2E) shown in FIG. 13 C.

Example 4: VHH Target Binding Competition Analysis

Phage displaying individual VHHs were prepared and titered by phage dilution ELISA for recognition of ciBoNTA or ciBoNTB using HRP/anti-M13 Ab for detection (Maass et al. 2007 Int J Parasitol 37: 953-962). A dilution was selected for each phage preparation that produced a signal near the top of the linear range of the ELISA signal. The selected phage dilution (100 µl) for each VHH-displayed phage preparation were added to 96 well plate that has been coated with ciBoNTA or ciBoNTB and then pre-incubated for 30 minutes with 100 µl of a 10 µg/ml solution containing a purified Trx/VHH fusion protein test agent or control in PBS. After an hour, the wells were washed and phage binding was detected. Test VHHs that reduced target binding of phage-displayed VHHs by less than two-fold compared to controls were considered to recognize distinct epitopes. Positive controls were prepared in which the Trx/VHH competitor contained the same VHH as displayed on phage and typically reduced the ELISA signal detected by greater than 95%.

Example 5: Characterization of VHH Binding Properties

VHHs were tested for binding to native or atoxic mutant BoNT holotoxins by standard ELISA using plates coated with 100 µl of 1 µg/ml protein. VHHs were also tested for recognition of BoNT subunits by ELISA using plates coated with 5 µg/ml purified recombinant BoNT light chain or 1 µg/ml BoNT heavy chain. See Tremblay et al. 2010 Toxicon. 56(6): 990-998. VHHs were also characterized for recognition of subunits by Western blotting on BoNT holotoxin following SDS-PAGE electrophoresis under reducing conditions. VHHs were detected with HRP-anti-E-tag mAb (GE Healthcare) by standard procedures.

Example 6: Kinetic Analysis by Surface Plasmon Resonance

Assays to assess the kinetic parameters of the VHHs were performed using a ProteOn XPR36 Protein Interaction Array System (Bio-Rad, Hercules, Calif.) after immobilization of ciBoNT/A by amine coupling chemistry using the manufacturer recommended protocol. Briefly, after activation of a GLH chip surface with a mixture of 0.4 M ethyl (dimethylaminopropyl) carbodiimide (EDC) and 0.1 M N-hydroxysulfosuccinimide (sulfo-NHS) injected for 300 s at 30 µL/min, ciBoNT/A was immobilized by passing a 60 µg/mL solution of the protein at pH 5 over the surface for 180 s at 25 µL/min. The surface was deactivated with a 30 µL/min injection of 1 M ethanolamine for 300 s. A concentration series for each VHH (between 2.5 nM and 1000 nM, optimized for each antibody fragment) was passed over the surface at 100 µL/min for 60 s, then dissociation was recorded for 600 s or 1200 s. The surface was then regenerated with a 36 s injection of 10 mM glycine, pH 2.0 at 50 µL/min. The running buffer used for these assays was 10 mM Hepes, pH 7.4, 150 mM NaCl, 0.005% Tween-20. Data was evaluated with ProteOn Manager software (version 2.1.2) using the Langmuir interaction model.

Example 7: BoNT Neutralization Assay Using Primary Neurons

Neuronal granule cells from the pooled cerebella of either 7-8 day old Sprague-Dawley rats or 5-7 day old CD-1 mice were harvested (Skaper et al 1979 Dev Neurosci 2: 233-237) and cultured in 24 well plates as described by Eubanks et al 2010 ACS Med Chem Lett 1: 268-272. After at least a week of culture the well volumes were adjusted to 0.5 ml containing various VHH dilutions or buffer controls followed immediately by addition of BoNT/A in 0.5 ml to a final 10 pM. After overnight at 37° C., cells were harvested and the extent of SNAP25 cleavage assessed by Western blot as previously described (Eubanks, L. M. et al. 2007 Proc. Natl. Acad. Sci. USA 104: 2602-2607).

Example 8: Mouse Toxin Lethality Assay

Female CD1 mice (Charles River) about 15-17 g each were received from three to five days prior to use. On the day each assay was initiated, mice were weighed and placed into groups in an effort to minimize inter-group weight variation. Appropriate dilutions of the VHH agents were prepared in PBS. BoNT holotoxins were separately prepared in PBS at the desired doses. Amounts (600 µl) of VHH agent and (600 µl) of the toxin were combined and incubated at room temperature for 30-60 minutes. An amount (200 µl) of each mixture was administered by intravenous injection at time point zero to groups of mice (five mice per group). Mice were monitored at least four times per day and assessed for symptoms of toxin exposure and lethality/survival. Moribund mice were euthanized. Time to onset of symptoms and time to death were established for each mouse.

Example 9: Mouse Toxin Lethality Assay with Agents Administered Post-Intoxication Groups of mice were prepared as described in the description of the mouse toxin lethality assay. Subjects were administered 10 LD$_{50}$ of BoNT/A by intraperitoneal injection. At indicated times post-intoxication, mice were administered 200 ul of material (e.g., VHH monomer or VHH heterodimer) in PBS by intravenous injection. Mice were monitored for symptoms of intoxication and death as described herein.

Example 10: Single-Chain Fvs (scFv) that Recognize and Bind BoNT/A

To improve therapies that involve multiple monoclonal antibodies (mAbs) by using small recombinant peptide, protein or polynucleotide agents that have the same binding specificity as the mAbs, each of the recombinant binding agents is produced containing the same epitopic tag. A single mAb that recognizes the epitopic tag is co-administered to patients with the binding agents. The different agents bind to the same targets as the multiple mAbs and the anti-tag mAb binds to these agents through the epitopic tag. This permits delivery of the same therapeutic effect that is achieved with multiple mAb therapy, but requires only a single mAb. If desired, mAbs of different isotypes, or polyclonal anti-tag antibodies, could be used therapeutically to deliver different immune effector activities.

A number of small recombinant protein agents were generated. They were called single-chain Fvs (scFvs) and were observed to recognize botulinum neurotoxin serotype A (BoNT/A). These scFvs are recombinant proteins that represent the antigen combining region of an immunoglobulin. Several anti-BoNT/A scFvs were produced and were purified. Each scFv contains the amino acid sequence (GAPVPYPDPLEPR; SEQ ID NO: 15) near the carboxyl terminus which is an epitopic tag referred to herein as "E-tag." An scFvs (scFv #2) was shown to neutralize BoNT/A in a cell-based toxin assay (IC50~7 nM). A second scFv (scFv #7) had little or no neutralization activity in the assay, and was found to bind to BoNT/A with high affinity (Kd~1 nM).

The scFvs were tested for their ability to protect mice from the botulinum toxin BoNT/A by intravenous administration of the agents and toxin. The two scFvs were administered individually or together, and were given to mouse subjects with and without anti-E-tag mAb by intravenous administration. Each subject was administered a dose of 10 $LD_{50}$ of BoNT/A (i.e., an amount of BoNT/A ten-fold the $LD_{50}$), five mice per group. The results are shown in Table 1.

TABLE 1 scFv administration with and without anti-tag antibody alleviates toxin morbidity

| Agents Administered (dose) | Survival Observations | |
|---|---|---|
| none | 0% | Death in less than a day |
| scFv#2 (20 µg) | 0% | Death delayed about a day |
| scFv#7 (20 µg) | 0% | Death delayed less than a day |
| scFv#2 (20 µg) + anti-E-tag mAb (25 µg) | 100% | Symptoms severe |
| scFv#7 (20 µg) + anti-E-tag mAb (25 µg) | 0% | Death delayed several days |
| scFv#2 (10 µg) + scFv#7 (10 µg) + anti-E-tag mAb (25 µg) | 100% | No symptoms |

The results shown in Table 1 clearly show that a BoNT/A neutralizing scFv (scFv #2) alone did not significantly protect mice from the toxin. Subjects survived (100%) following co-administration scFV #2 and mAb that recognizes an epitopic tag (E-tag) on the scFv. More importantly, co-administering two scFvs, each with E-tag, and anti-tag mAb dramatically improved the protective effect.

Subjects were administered 10 $LD_{50}$ and lower doses of the scFvs and the anti-E-tag mAb, and were analyzed for percent survival. Further, two additional non-neutralizing anti-BoNT/A scFvs (scFv #3 and scFv #21) were tested in combination with the neutralizing scFv #2. Whether the anti-E-tag mAb would function upon administration at a different site and time than the toxin was also tested.

The results in Table 2 confirm those data herein and further show that the mAb specific for the epitopic tag does not have to be pre-mixed with the scFv containing the epitopic tag to be effective. In fact, doses were administered at different sites and times. Combinations of two scFvs (each with E-tags) and the single anti-E-tag mAb, provided greater protection than with one scFv alone. This synergistic protective effect occurred using different scFvs and was observed at significantly lower doses of the scFvs or mAb than used in the data observed in Table 1.

TABLE 2

Anti-E-tag mAbs administered separately protected subjects from toxin

| Agents Administered (dose) | Survival Observations | |
|---|---|---|
| none | 0% | Death in about a day |
| scFv#2 (10 µg) | 0% | Death delayed about 2 days |
| scFv#2 (10 µg) + anti-E-tag mAb (10 µg) (mAb administered intraperitoneally) | 100% | Symptoms moderate |
| scFv#2 (10 µg) + anti-E-tag mAb (10 µg) | 100% | Symptoms mild |
| scFv#2 (10 µg) + anti-E-tag mAb (2 µg) | 100% | Symptoms mild |
| scFv#2 (2 µg) + anti-E-tag mAb (2 µg) | 100% | Symptoms moderate |
| scFv#2 (5 µg) + scFv#7 (3 µg) + anti-E-tag mAb (10 µg) | 100% | No symptoms |
| scFv#2 (1 µg) + scFv#7 (1 µg) + anti-E-tag mAb (10 µg) | 100% | No symptoms |
| scFv#2 (5 µg) + scFv#3 (4 µg) + anti-E-tag mAb (10 µg) | 100% | No symptoms |
| scFv#2 (5 µg) + scFv#21 (3 µg) + anti-E-tag mAb (10 µg) | 100% | No symptoms |

Examples herein tested whether combinations of three and four scFvs with anti-tag mAb protect subjects from an amount of BoNT/A 100-fold, 1000-fold, or 10,000-fold the $LD_{50}$, i.e., 100 $LD_{50}$ BoNT/A, 1000 $LD_{50}$ BoNT/A or 10,000 $LD_{50}$ BoNT/A.

The data shown in Table 3 demonstrate the excellent potency of a tagged binding agent as an antitoxin. Specifically, completely protection of subjects from even mild symptoms of intoxication by 1,000 $LD_{50}$ was observed using combinations of three or four scFvs with anti-E-tag mAb. Subjects were protected from lethality from a 10,000 $LD_{50}$ dose with a combination of four scFvs, although moderate symptoms were observed. The ability to protect mice receiving up to 10,000 $LD_{50}$ of BoNT/A is equivalent to the highest level of protection reported with pools of different anti-BoNT/A mAbs (Nowakowski et al, Proc Natl Acad Sci USA, 99:11346-50).

TABLE 3

Combinations of scFv protect from 100, 1000, and 10,000 fold $LD_{50}$ BoNT/A doses in presence of 10 µg of anti-E-tag mAb

| BoNT/A | Additional agents administered (dose) | Survival Observations | |
|---|---|---|---|
| 100 $LD_{50}$ | None | 0% | Death in less than a day |
| 100 $LD_{50}$ | scFv#2 (2 µg) + scFv#3 (2 µg) + scFv#21 (2 µg) | 100% | No symptoms |
| 1,000 $LD_{50}$ | None | 0% | Death in less than a day |
| 1,000 $LD_{50}$ | scFv#2 (2 µg) + scFv#3 (2 µg) + scFv#21 (2 µg) | 100% | No symptoms |
| 1,000 $LD_{50}$ | scFv#2 (2 µg) + scFv#3 (2 µg) + scFv#7 (2 µg) + scFv#21 (2 µg) | 100% | No symptoms |
| 10,000 $LD_{50}$ | None | 0% | Death in a few hours |
| 10,000 $LD_{50}$ | scFv#2 (2 µg) + scFv#3 (2 µg) + scFv#21 (2 µg) | 0% | Death delayed one day |
| 10,000 $LD_{50}$ | scFv#2 (2 µg) + scFv#3 (2 µg) + scFv#7 (2 µg) + scFv#21 (2 µg) | 100% | Moderate symptoms |

The next example tested efficacy of a binding agent containing two copies of the epitopic tag. The anti-BoNT/A binding agent, scFv #7, was engineered to contain another copy of the E-tag peptide. The E-tag peptide was present on the carboxyl terminus of each scFv. An altered version of scFv #7 (called scFv #7-2E) was engineered to be identical to scFv #7 and to have an additional copy of the E-tag peptide fused to the amino terminus.

TABLE 4

Protection from BoNT/A using scFvs having multiple tag sequences in presence of 10 μg of anti-E-tag mAb

| BoNT/A $LD_{50}$ | Additional agents administered (1 μg each) | Survival | Observations |
|---|---|---|---|
| 100 | None | 0% | Death in less than 6 hours |
| 100 | scFv#2 + scFv#3 + scFv#7 | 100% | No symptoms |
| 100 | scFv#2 + scFv#3 + scFv#7-2E | 100% | No symptoms |
| 1,000 | None | 0% | Death in less than 2 hours |
| 1,000 | scFv#2 + scFv#3 + scFv#7 | 0% | Death delayed 2 days |
| 1,000 | scFv#2 + scFv#3 + scFv#7-2E | 100% | No symptoms |
| 10,000 | None | 0% | Death in less than 2 hours |
| 10,000 | scFv#2 + scFv#3 + scFv#7 | 0% | Death delayed less than a day |
| 10,000 | scFv#2 + scFv#3 + scFv#7-2E | 20% | Death delayed many days |
| 10,000 | scFv#2 + scFv#3 + scFv #21 + scFv#7 | 0% | Death delayed 2 days |
| 10,000 | scFv#2 + scFv#3 + scFv #21 + scFv#7-2E | 100% | Moderate symptoms |

The results in Table 4 demonstrate that the binding agent with two epitope tags dramatically improved the in vivo antitoxin efficacy of the tagged binding agent. With a combination of three scFvs, including scFvs #2, scFvs #3 and scFvs #7 or scFvs #7-2E, clearly the use of scFvs #7-2E was substantially superior in protection of mice to the use of scFvs #7 with only one E-tag. The improvement by presence of two copies of tag was particularly evident in the groups of mice challenged with 1,000 $LD_{50}$. In these groups, the triple combination of scFv #2+scFv #3+scFv #7 was insufficient to allow survival of the mice. When scFv #7 was replaced with scFv #7-2E, all the mice survived without symptoms. Furthermore, use of a pool of scFv #2+scFv #3+scFv #7-2E permitted the survival of one of five mice challenged with 10,000 $LD_{50}$ and delayed the death of the other mice by several days. The equivalent pool with scFv #7 having only one E-tag only delayed death for one day in mice challenged with 10,000 $LD_{50}$. Finally, an identical combination of four scFvs (#2, #3, #21 and #7) in which the efficacy using scFv #7 was compared with scFv #7-2E. Administering only one μg of each scFv, the presence of scFv #7 did not result in survival of mice challenged with 10,000 $LD_{50}$, and the same combination the scFv #7-2E was protective. These data show that mice were effectively protected from high doses of toxin by administering a smaller number of high affinity binding agents, each containing two or more epitope tags together with an anti-tag mAb.

The method herein improves therapeutic agent flexibility, provides highly stable binding agents with long shelf life, substantially reduces the cost of production, and permits commercially feasible therapeutic applications that involve multiple target agents. Furthermore, the strategy herein will permit much more rapid development of new antitoxins. The binding agents are much more quickly developed to commercialization than mAbs. The single anti-tag mAb needed for co-administration is the same for therapies requiring different tagged binding agents and thus can be pre-selected for its commercial scale up properties and stockpiled in advance of the development of the binding agents.

An immediate application is in anti-toxin therapy, an area of high interest because of bioterrorist threats. For example, it is now thought that effective prevention of botulinum intoxication using toxin neutralizing mAbs will require administration of three different mAbs each targeting the same toxin. Since there are at least seven different botulinum toxins, this suggests that 21 different mAbs (or more) may need to be stockpiled for use in the event of a major botulism outbreak as might occur through bioterror. Monoclonal antibodies are very expensive to produce and have relatively short shelf lives. Methods and compositions herein would make it possible to produce 21 different recombinant binding agents, each having longer shelf-life and lower production costs, and then stockpile only a single mAb. It is possible that this approach could open up many other mAb therapeutic strategies that involve multiple binding targets, but which have not been pursued because of prohibitive development and production costs and poor product shelf life. Methods and compositions herein permit the use of mAbs of different antibody isotypes to be used with the same binding agents to provide greater therapeutic flexibility.

Example 11: BoNT/a VHHs Binding Agents

VHH binding agents were identified, produced and purified that were specific to each of botulinum neurotoxin serotype A (BoNT/A) and serotype B (BoNT/B). The VHHs made herein included nine amino acids at the amino coding end and which are associated with the forward PCR primer sequence. See FIG. 3 A-C for the sequences. These sequences derive from 'framework 1' and include minor variants of the original coding sequence. The most common amino acid sequence is QVQLVESGG (SEQ ID NO: 16) and which is the amino acid sequence used in assays shown in FIG. 3 A-C.

At the carboxyl coding end of the VHHs either amino sequence, AHHSEDPS (SEQ ID NO: 17), or the amino sequence, EPKTPKPQ (SEQ ID NO: 18) is located, present in the VHHs sequence as shown in FIG. 3 A-C, and these were observed to be interchangeable without loss of function. Identical clones were identified from alpacas that vary only in the hinge sequence and retain virtually the same target binding function. See also D. R. Maass et al. 2007 Journal of Immunological Methods 324:13-25.

As a result of the altered splicing, the amino acid sequence that joins the VH domain to the CH2 domain in heavy chain IgGs is called the "hinge" region, and is unique to this class of camelid antibodies (See D. R. Maass et al. 2007 Journal of Immunological Methods 324:13-25 which is incorporated by reference in its entirety). The two distinct hinge sequence types found in camels and llamas are referred to as the "short" hinge and the "long" hinge respectively. SEQ ID NO: 17 is a short hinge sequence derived from a camel, and SEQ ID NO: 18 is a long hinge sequence derived from a llama.

During screening for VHH binding agents, different coding sequences are identified that display significant homology among randomly identified clones. VHH sequences that are homologous are predicted to be related and thus to recognize the same epitope on the target to which they have been shown to bind. Examples herein experimentally demonstrate epitope recognition by methods for binding competition. These findings demonstrate that significant variation is permitted in VHH amino acid sequences without loss of target binding. An example of the extent of variation permitted is shown in FIG. 4 A-B. Each VHH identified in FIG. 4 A-B as a BoNT/A binder was experimentally observed to bind to the same epitope as JDQ-B5 based on binding competition assays.

FIG. 5 shows a phylogenetic tree that compares the homology among BoNT/A binding VHHs within the JDQ-B5 competition group to random alpaca VHHs. The homology comparison uses the unique amino acids that are present between the forward PCR primer sequences and the hinge region (above). The distance of the lines is a measure of homology; the shorter the distance separating two VHHs, the more homologous. Four VHHs that bind to the same epitope as JDQ-B5 cluster within a group that is distinct from the random VHHs as shown, strong evidence of relatatedness of these clones. The results show that substantial variation in the VHH sequence is tolerated without loss of the target binding capability.

The coding DNAs for two different VHH monomers were cloned in an *E. coli* expression vector in several different ways to produce different recombinant proteins. To produce single VHH monomers, the VHH coding DNA was inserted into the plasmid pET32b to fuse the VHH in frame with an amino terminal bacterial thioredoxin and a carboxyl terminal epitopic tag (E-tag GAPVPYPDPLEPR; SEQ ID NO: 15). Additional coding DNA deriving from the pET32b expression vector DNA was also present between the thioredoxin and VHH coding sequences, the DNA encoding six histidines (to facilitate purification) and an enterokinase cleavage site, DDDDK to permit enzymatic separation of thioredoxin from the VHH. The resulting expression vectors were used for expression of VHH monomers. VHH monomers JDQ-H7 (SEQ ID NO: 32, referred to as "H7") and JDQ-B5 (SEQ ID NO: 24, referred to as "B5") were expressed using this system (FIG. 6). A representation of the two monomer VHH proteins produced by these expression vectors, labeled H7/E and B5/E, is shown in FIG. 10 A.

Expression vectors were prepared in pET32b in which DNA encoding two iterations of the VHH monomer (e.g., SEQ ID NOs: 46 and 48) was present, and the monomers joined in frame to yield heterodimers. For these constructions, the two nucleic acid sequences encoding the VHHs were separated by a nucleotide sequence encoding a 15 amino acid linker, SEQ ID NO: 55, that provides a flexible spacer (fs) between the expressed VHH proteins to separate the domains and facilitate independent folding. The E-tag coding DNA followed the second VHH coding DNA (SEQ ID NO: 49) in frame to obtain a single-tagged VHH heterodimer H7B5/E (SEQ ID NO: 50), expression of which is shown in FIG. 10 B. A second copy of the E-tag coding DNA (e.g., SEQ ID NO: 51) was included upstream of the first VHH (at the amino coding end) for expression of a double-tagged VHH heterodimer E/H7/B5/E (SEQ ID NO: 52) shown in FIG. 10 B.

The thioredoxin fusion partner was included to improve expression and folding of the VHHs, and was observed as not necessary for VHH function. The activity of the VHH agents to protect mice from BoNT/A intoxication in mouse lethality assays was tested using VHH agents in which thioredoxin was cleaved (by enterokinase) from the VHH. It was observed that absence of thioredoxin caused no significant reduction in activity.

Figure 8:
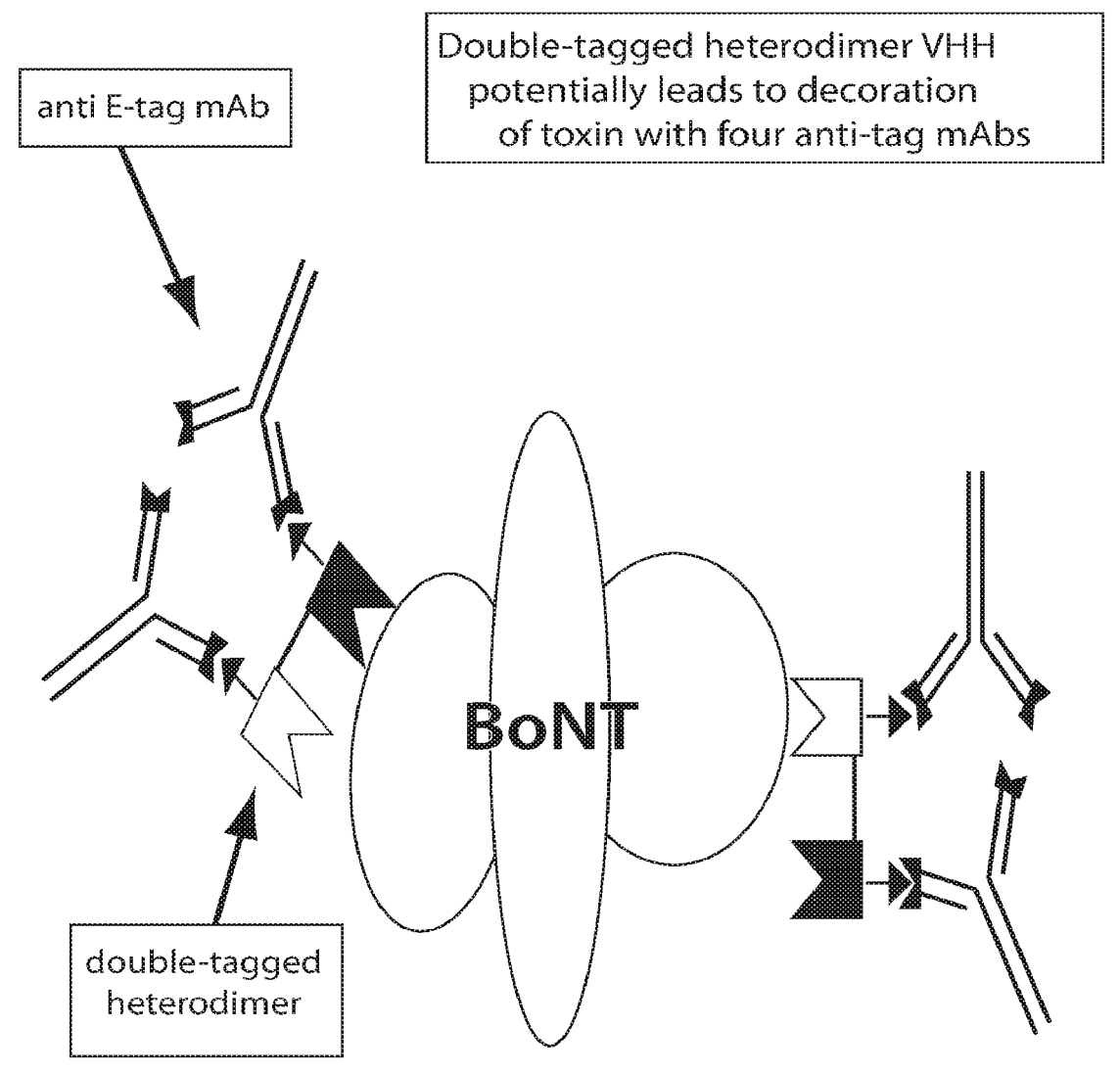

A single-tagged heterodimer VHH was predicted to lead to decoration of the BoNT toxin by the anti E-Tag mAb in a ratio of 1:1. Accordingly, a single-tagged heterodimer was expected to bind at two sites on the toxin and lead to decoration of the toxin with two anti E-tag antibodies (see FIG. 7). A double-tagged heterodimer provides for binding of the anti E-tag antibody in a ratio of 2:1 and thus should bind at two sites on the toxin and lead to decoration of the toxin with four anti-tag antibodies (see FIG. 8). These agents were tested for their ability to protect mice from BoNT/A toxin.

For these examples, the VHH agents and the toxin were pre-mixed and then intravenously administered to groups of five subjects (mice) per group. The subjects were monitored and the time to death was noted for those that succumbed to the toxin. In the results shown in FIG. 9 A, a pool of two VHH monomers, H7/E and B5/E (1 µg of each monomer per subject), in the presence of anti-E-tag mAb (Phadia, Sweden) (5 µg/mouse) delayed death only about one day in mice exposed to 1,000 $LD_{50}$ of BoNT/A. The single-tagged VHH heterodimer, H7/B5/E (2 µg/mouse) in the presence of anti-E-tag mAb (5 µg/mouse) delayed death by about a day and a half in mice exposed to 1,000 $LD_{50}$ of BoNT/A.

Figures 9A, 9B:
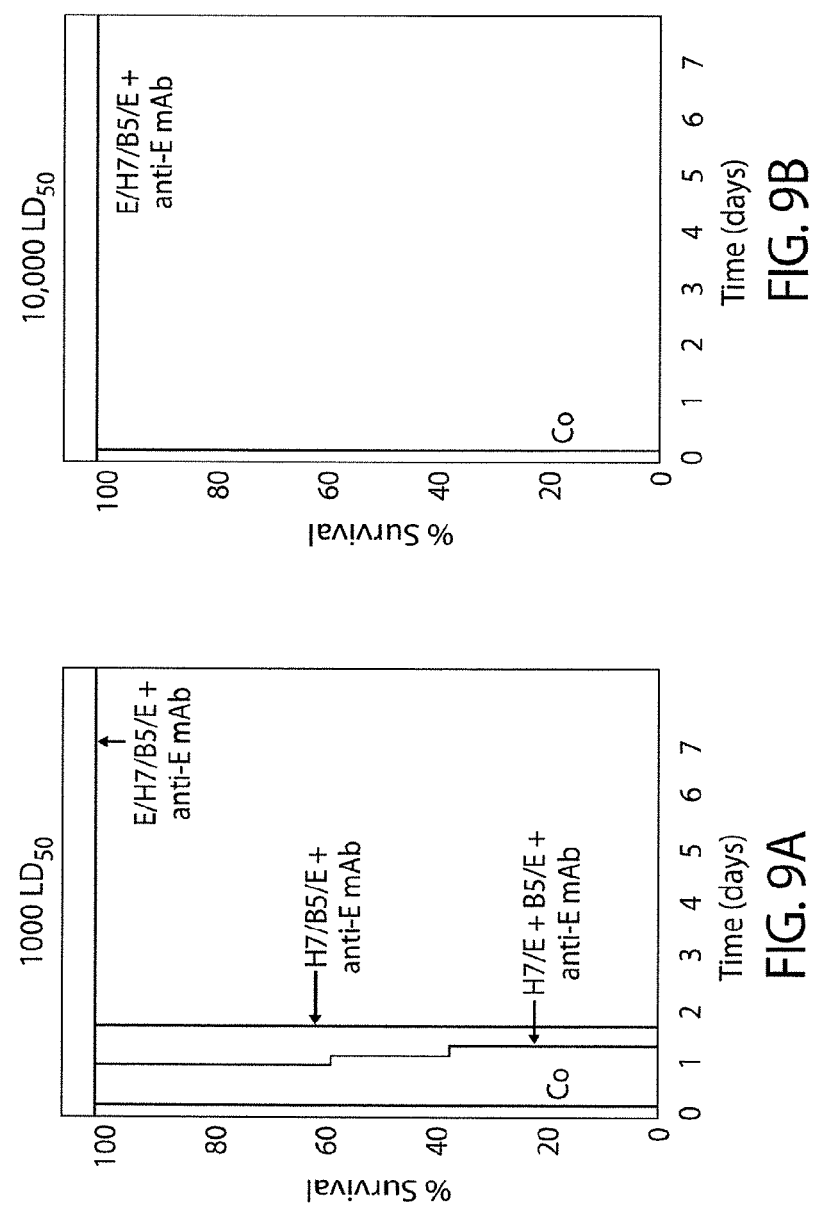

In contrast, it was observed that the double-tagged heterodimer, E/H7/B5/E (2 µg/mouse) administered with anti-E-tag mAb resulted in full survival of mice exposed to 1,000 $LD_{50}$ and even 10,000 $LD_{50}$ of BoNT/A (FIG. 9B). Mice given the double-tagged VHH heterodimer, E/H7/B5/E, in the absence of co-administered anti-E-tag mAb, did not survive a 1,000 $LD_{50}$ amount of BoNT/E, showing that the anti-tag mAb was necessary for full efficacy. The ability of the double-tagged VHH heterodimer, E/H7/B5/E, administered with anti-E-tag mAb to protect mice against 10,000 $LD_{50}$ demonstrates that this treatment achieved a level of efficacy similar to that obtained with a commercial polyclonal antitoxin sera.

In other examples, the BoNT/A-binding VHH heterodimer agents were tested for their ability to prevent death in subjects previously exposed to BoNT/A. In these examples, groups of five subjects were first exposed to 10 $LD_{50}$ BoNT/A. Then after 1.5 or three hours from exposure mice were treated either with the E/H7/B5/E heterodimer agent (2 µg/subject) administered with anti-E-tag mAb (5 µg/subject), or with a dose of potent polyclonal anti-BoNT/A sera that had been prepared in sheep. This sera had been previously shown to protect subjects against 10,000 $LD_{50}$ of BoNT/A when it was co-administered with the toxin (assays performed as in previous paragraph). All subjects were monitored and the time to death was determined for non-survivors. Control subjects (2 groups of five each) died within about a day. All subjects treated with polyclonal antisera 1.5 hour post-intoxication (five) survived, and four of five subjects treated three hours post-exposure both 1.5 hours and three hours post-intoxication survived. Five out of five subjects treated with the VHH heterodimer and anti-E-tag mAb both 1.5 hours and three hours post-exposure survived. Thus the VHH heterodimer and anti-E-tag treatment was at least as effective as conventional polyclonal antitoxins at protecting subjects from BoNT exposure in the more clinically relevant post-exposure challenge model.

Example. 12: Neutralization of Botulinum Neurotoxin Using VHH Binding Proteins

Examples herein show that scFv antitoxin compositions prevent development of disease symptoms in subjects exposed to a botulinum toxin. These antitoxin agents were antibodies that bound the toxin and neutralized the activity of the toxin and/or promoted rapid clearance from the body. Data show that effective neutralization was achieved using a mixture of two high-affinity toxin VHH binding agents, each of which strongly neutralized toxin in cell-based assays. Administration of a multimeric composition was much more effective at protecting subjects from toxin than a pool of two neutralizing monomer binding agents only.

Camelid heavy chain only Vh domain (VHH) binding agents with high affinity for Botulinum neurotoxin serotype A (BoNT/A) were produced including H7 (SEQ ID NO: 56), B5 (SEQ ID NO: 57). Methods of generating VHH binding agents are shown in Shoemaker et al. U.S. application Ser. No. 12/032,744 which is application 2010/0278830 A1 published Nov. 4, 2010, and Shoemaker et al. U.S. application Ser. No. 12/899,511 which is application 2011/0129474 A1 published Jun. 2, 2011, each of which is incorporated herein by reference in its entirety.

Figures 11A, 11B:
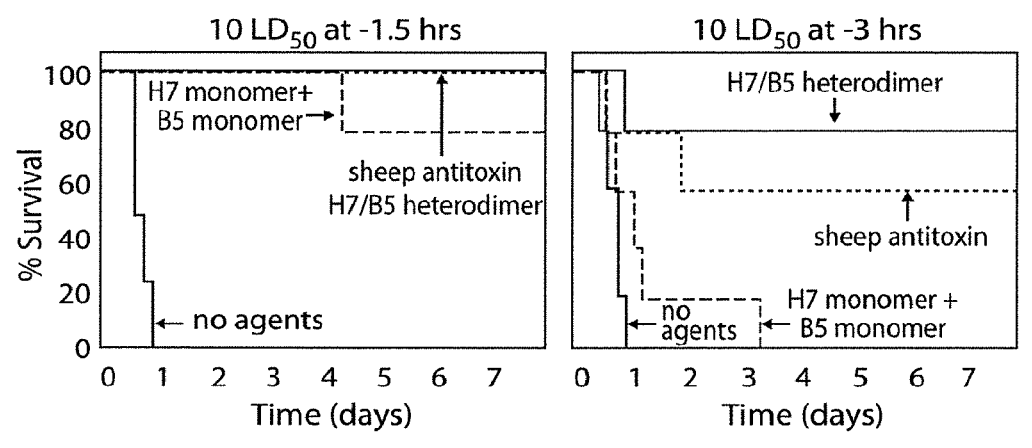

VHHs (H7, B5 and C2) displayed potent BoNT/A neutralization activity in assays of exposure or intoxication of primary neurons in culture. The H7 VHH and B5 VHH monomers were expressed in E. coli and a single heterodimeric polypeptide (H7/B5) was constructed and expressed with the H7 and B5 VHH domains/subunits separated by a fifteen amino acid flexible spacer having three repeats of amino acid sequence GGGGS (SEQ ID NO: 55). A combination of the H7 monomer binding agent and B5 monomer binding, and a H7/B5 single chain heterodimer binding agent were tested to determine ability to protect mouse subjects from death caused by BoNT/A. The subjects received ten-fold the lethal dose of BoNT/A that causes death in 50% of mice (10 $LD_{50}$), and either 1.5 hours or three hours later were administered either: 1 micrograms (µg) of H7 binding agent; a sheep antitoxin serum produced against BoNT/A; 1 of B5 monomer binding agent; or 2 µg of H7/B5 single chain heterodimer binding agent (FIG. 11 A-B). The amount of sheep antitoxin serum administered was equivalent to the amount of commercial antitoxin serum generally administered.

Data show that subjects administered a combination of monomeric H7 and B5 binding agents died within three days. Control subjects administered no therapeutic agent died within one day (FIG. 11 A-B). Subjects administered the sheep antitoxin serum survived at 80%. Most important, subjects administered H7/B5 single chain heterodimer binding agent survived additional days compared to the control subjects, with 80% of subjects administered H7/B5 heterodimer binding agent surviving for seven days.

Figure 12A:
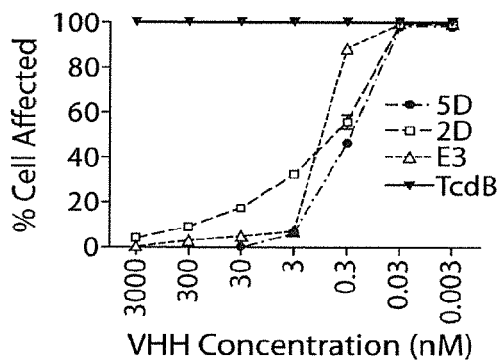
FIG. 12 A-FIG. 12 C are line graphs showing that VHH monomers and VHH heterodimers neutralized C. difficile toxin b (TcdB) and protected subjects from death caused by exposure to TcdB.
Figure 12B:
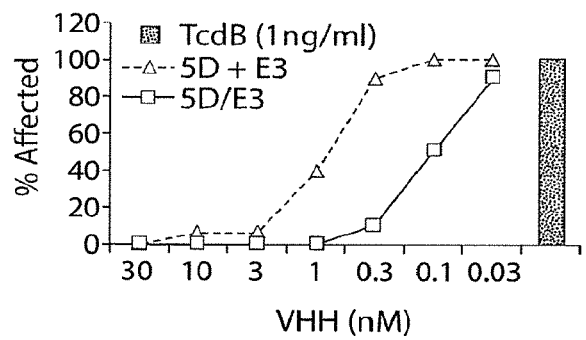
Figure 12C:
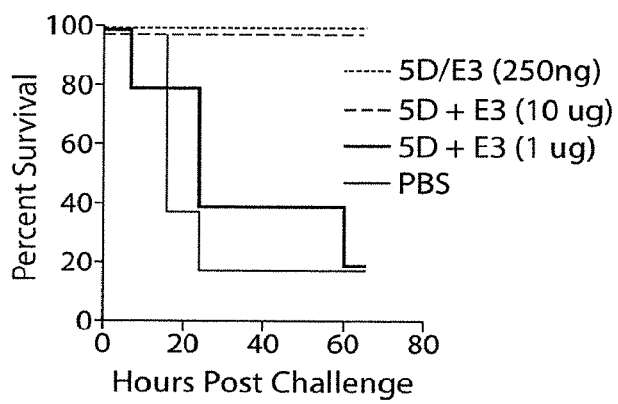

Example. 13: Neutralization of C. Difficile Toxins Using Heteromultimer Binding Agents A set of VHH binding agents that bind Clostridium difficile toxin B (TcdB) were obtained and shown in Examples herein to inhibit the ability of the toxin to intoxicate or infect cells (FIG. 12 A). Potent anti-TcdB neutralizing VHHs were selected, identified by codes names 5D and E3, and were expressed as separate monomers or as a heterodimer. A pool/mixture of VHH monomers, 5D and E3, was compared in for ability to prevent TcdB lethality to cells to the 5D/E3 heterodimer.

CT26 cells were exposed to TcdB (100 picograms/ml) in the presence of different concentrations (0.03 nM, 0.1 nM, 0.3 nM, 1 nM, 3 nM, 10 nM, or 30 nM) of: a mixture of 5D VHH monomer (SEQ ID NO: 67) and E3 VHH monomer (SEQ ID NO: 68), or a 5D/E3 heterodimer (SEQ ID NO: 87). Control cells were not administered neutralizing agents. Cell rounding caused by TcdB was monitored using a phase-contrast microscope.

Culture media from expressing cells were administered with either the mixture of 5D and E3 VHH monomers, or the 5D/E3 VHH heterodimer were found to be effective in protecting the cells from TcdB associated cell rounding. Control cells (100%) showed cell rounding and negative indicia of TcdB following toxin exposure.

It was observed that administering 0.1 nM 5D/E3 heterodimer to subjects prior to TcdB exposure resulted in 50% cell rounding (i.e., 50% TcdB infection; FIG. 12 B). The same level cell rounding protection (50%), was achieved with 1 nM of the mixture of 5D and E3 monomers. Thus, the 5D/E3 VHH heterodimer was observed to be about ten-fold more potent as a toxin neutralizing agent than a pool containing the same two VHHs as monomers (FIG. 12 B).

The improved antitoxin and protective potency 5D/E3 heterodimer was further analyzed using an in vivo toxin challenge mouse model. Subjects were co-administered a lethal dose of TcdB (1 ng/mL) with either a mixture of 500 nanograms (ng) of 5D monomer and 500 ng E3 VHH monomer; or with 250 ng of 5D/E3 VHH heterodimer; or with phosphate buffered saline, PBS. See FIG. 12 C. See Data show that each of the VHH binding agents was a more effective TcdB neutralizing agent for subjects than the PBS control. Survival was observed at 100% for subjects administered 5D/E3 VHH heterodimer (250 ng) and at about 40% for subjects administered a mixture of 5D and E3 VHH monomers. Control subjects receiving PBS survived at a rate of 20%.

Data show that subjects administered a mixture of 5D and E3 monomers survived for fewer days and were less protected from a lethal TcdB challenge than subjects administered the 5D/E3 heterodimer (FIG. 12 C). Most important the improved protection and neutralizing ability of the 5D/E3 heterodimers was observed even if the amount of heterodimer administered was 75% less than the amount of the mixture of 5D and E3 monomers. Further analysis was performed in Examples below to determine the relative factors for VHH monomers and heterodimers to effectively neutralize and clear disease agent targets from the body (FIG. 12 A-C).

Example 14: Identification and Characterization of Anti-BoNT VHHs

Serum clearance of Botulinum neurotoxin serotype A (BoNT/A) was dramatically accelerated by administering a pool of different epitopically-tagged single-chain Ig variable fragment (scFv) domain binding agents with an anti-tag monoclonal antibody (Shoemaker et al. U.S. Ser. No. 12/032,744 application 2010/0278830 A1 published Nov. 4, 2010; Shoemaker et al. U.S. Ser. No. 12/899,511 application 2011/0129474 A1 published Jun. 2, 2011; Sepulveda et al. 2009 Infect Immun 78: 756-763, and Tremblay et al. 2010 Toxicon. 56(6): 990-998, each of which is incorporated herein in its entirety).

To determine whether a more commercially and clinically acceptable binding agent than scFvs could be identified, a panel of camelid heavy-chain-only Vh (VHH) binding agents having high affinity for epitopes of BoNT/A holotoxin was produced. VHHs were obtained that bound to an epitope of a distinct BoNT serotype, BoNT/B holotoxin, and these VHHs were tested for antitoxin efficacy. Competition ELISAs were performed to identify the VHHs with the highest affinity for unique epitopes on BoNT/A and BoNT/B. VHHs specific for each of BoNT/A (FIG. 13 A) and for BoNT/B (FIG. 13 B) were identified.

The VHHs in FIG. 13 A-B include amino acid sequence QLQLVE (SEQ ID NO: 88) and QVQLVE (SEQ ID NO: 89) at the amino terminus region. The sequence was encoded by the PCR primer used to generate the VHH-display library (Maass et al. 2007 Int J Parasitol 37: 953-962). The eight amino acids shown at the carboxy-terminus end were encoded by the short hinge or long hinge PCR primers that were used to generate the VHH library.

The amino acid sequences for double-tagged VHH heterodimer antitoxins that specifically bind BoNT/A: ciA-H7/ciA-B5(2E) and ciA-F12/ciA-D12(2E) are shown in FIG. 13 C. Each heterodimer included two VHH monomers and two epitopic tags. The amino acid sequences of the tags within the amino acid sequences of the heterodimers are underlined (FIG. 13 C). The amino acid sequence preceding the first E-tag in each VHH protein contained the thioredoxin fusion partner and hexahistidine encoded by the pET32b expression vector. The VHH sequences were flanked by the two E-tag peptides and were separated by the unstructured spacer having amino acid sequence (GGGGS)$_3$, SEQ ID NO: 55.

Figure 14A:
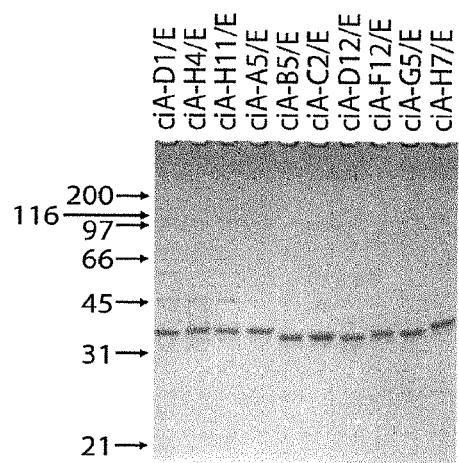
FIG. 14 A-FIG. 14 B are photographs of sodium dodecyl sulfate polyacrylamide gel electrophoresis (SDS-PAGE) analyses of VHH monomers and VHH heterodimers.
Figure 14B:
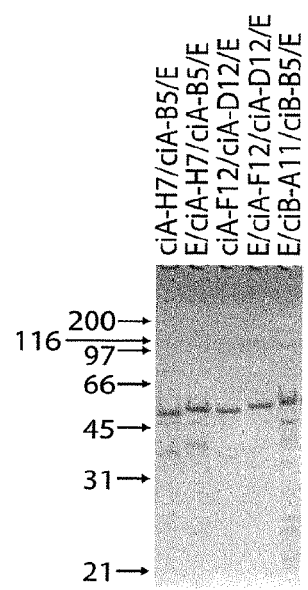

Each VHH was purified from *E. coli* as a thioredoxin fusion protein containing a single carboxyl-terminal epitopic tag (E-tag). Sodium dodecyl sulfate polyacrylamide gel electrophoresis (SDS-PAGE) analyses of VHH monomers and VHH heterodimers was performed (FIG. 14 A-B). The channels were loaded with one microgram (μg) of each VHH monomer or heterodimer. Molecular weight markers (12, 31, 45, 66, 97, 116 and 200 kilodaltons) are shown on the border of each gel. FIG. 14 A shows SDS-PAGE analysis of the tagged (E) VHH monomers: ciA-D1, ciA-H4, ciA-H11, ciA-A5, ciA-C2, ciA-D12, ciA-F12, ciA-G5, and ciA-H7. Dark bands were observed at approximately 35-38 kilodalton molecular weight for all single tagged VHH monomers. Channels loaded with ciA-D1, ciA-H4, ciA-H11, and ciA-B5 showed light bands at about 45-46 kilodaltons (kDa), and at about 59 kDa to about 62 kDa molecular weight. SDS-PAGE analysis was performed also on single- or double-tagged VHH heterodimers: ciA-H7/ciA-B5 singly tagged on ciA-B5; double tagged ciA-H7/ciA-B5 having a tag on both ciA/H7 and ciA-B5, ciA-F12/ciA-D12 singly tagged on ciA-B5; double tagged ciA-F12/ciA-D12 having a tag on both ciA/F12 and ciA-D12, double tagged ciA-A11/ciA-B5 having a tag on both ciA/A11 and ciA-B5 (FIG. 14 B). Strong dark bands at about 48 kDa to about 58 kDa molecular weight were observed for each heterodimer (FIG. 14 B).

The unique BoNT/A binding VHHs were further characterized and analyzed for ability to affinity target BoNT/A using surface plasmon resonance (SPR) in which a lower Kd indicates stronger binding/affinity between the VHH and the toxin target. Analysis was performed also to determine the ability of the BoNT/A binding VHHs to prevent intoxication of primary neurons in culture (FIG. 15 and Table 5).

Neuronal granule cells from pooled cerebella of seven day old to eight day old Sprague-Dawley rats or five day old to seven day old CD-1 mice were harvested as described by Skaper et al 1979 Dev Neurosci 2:233-237. The cells were then cultured in 24-well plates as described by Eubanks et al 2010 ACS Med Chem Lett 1: 268-272. After a week or more of culture, each culture well was adjusted to a volume of 0.5 ml with dilutions of VHHs (ciA-H7, ciA-B5, ciA-C2, ciA-D12, ciA-F12, ciA-A5 or ciA-G5) or a buffer control, and BoNT/A (ten picomoles) was added. After overnight incubation at 37° C., cells were harvested and the extent of synaptosomal-associated protein 25 (SNAP25) cleavage was determined by Western blot using commercially available rabbit anti-SNAP25 (Sigma-Aldrich Inc.). See FIG. 15. SNAP-25 is a membrane bound protein anchored to the cytosolic face of membranes by palmitoyl side chains within the molecule that is involved in the regulation of neurotransmitter release. Botulinum toxin serotypes including serotypes A, C and E function to cleave SNAP-25, resulting in paralysis and clinically developed botulism.

Figure 15:
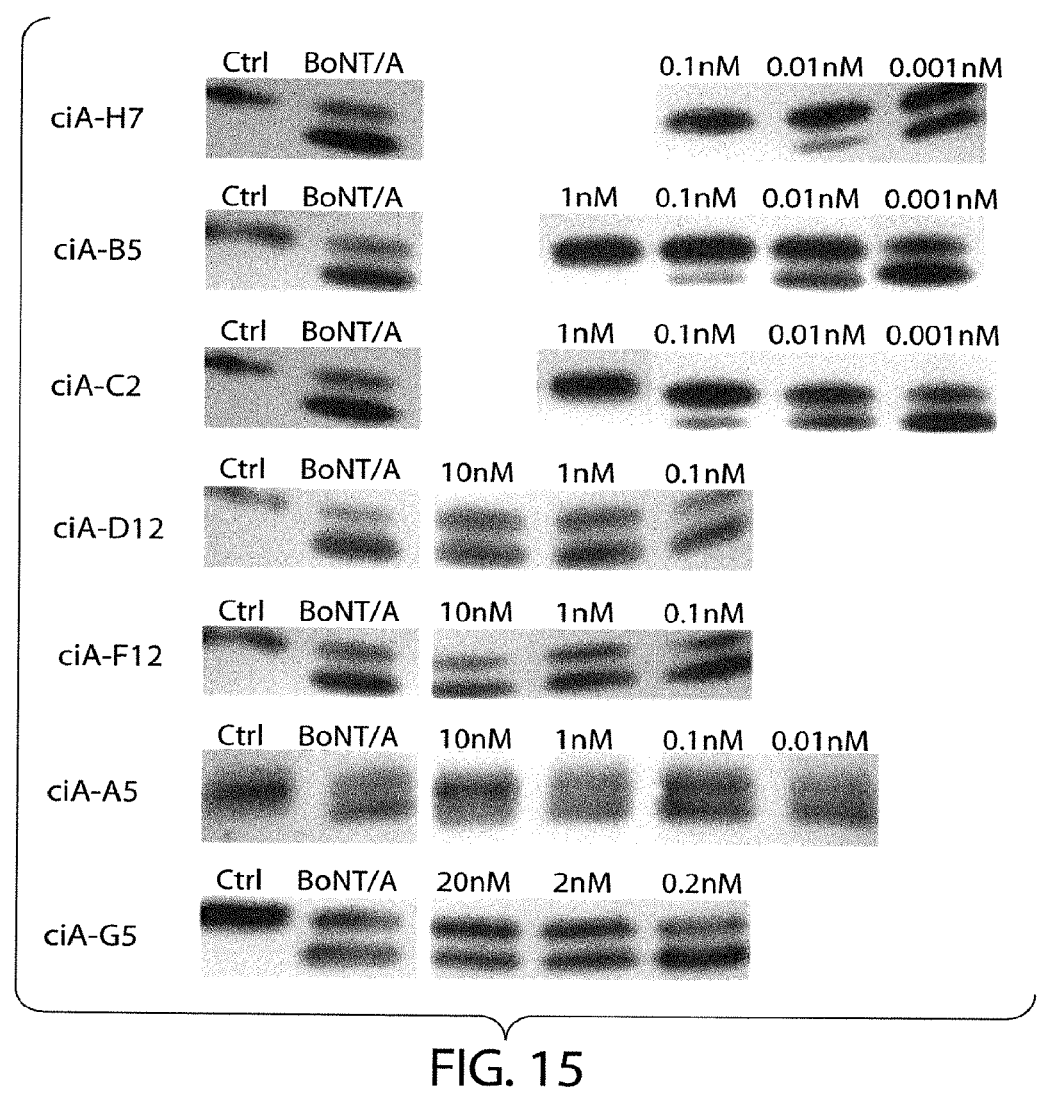

The upper band shown in the Western blot photographs is uncleaved SNAP25, and the lower band indicates cleaved SNAP25 (FIG. 15). SNAP25 cleavage (i.e., presence of a lower band) resulting from exposure to botulinum toxin was observed. VHHs were identified by the criterion that at concentrations of less than 0.1 nanomoles (nM) were observed to inhibit BoNT/A cleavage of SNAP25 (i.e., no lower band), are strong neutralizing agents. Weak neutralizing VHHs were identified as VHHs that required greater than 1 nM to inhibit BoNT/A cleavage of SNAP25. VHHs that required greater than 10 nM to prevent SNAP25 cleavage were identified as having no toxin neutralizing ability (FIG. 15).

It was observed that about equimolar amounts of ciA-B5, ciA-C2 and ciA-H7 VHHs prevented intoxication of neurons with 10 picomoles of BoNT/A. Two VHHs (ciA-D12 and ciA-F12) were observed to have no or negligible toxin neutralizing activity even at 1,000-fold excess VHH to toxin. Two VHHs (ciA-A5 and G5) displayed intermediate neutralizing activity compared to ciA-B5, ciA-C2 and ciA-H7, the strongly neutralizing VHHs, and ciA-D12 and ciA-F12, the non-neutralizing VHHs (FIG. 15 and Table 5).

Thus, ciA-B5, ciA-C2 and ciA-H7 were determined to be strong neutralizing VHHs. Other isolates including ciA-D12 and ciA-F12 were observed to be non-neutralizing VHHs that produced no detectable toxin neutralization.

Example 15: Protection from BoNT/a Lethality Using Monomeric Anti-BoNT/a VHHs

Epitopically tagged anti-BoNT/A VHH compositions were shown in the Example herein to prevent toxin induced lethality in the presence or absence of the clearing anti-tag mAb. Methods of testing VHHs are shown in Sepulveda et al. 2009 Infect Immun 78:756-763, and Tremblay et al. 2010 Toxicon. 56(6): 990-998. Pools/mixtures of two, three, four or six different anti-BoNT/A VHH monomers with or without anti-E-tag clearing antibody were co-administered to subjects with an amount (1000 LD$_{50}$ or 10,000 LD$_{50}$) of BoNT/A holotoxin. Subjects were then monitored for symptoms of toxin lethality and were observed for time to death.

Figure 16A:
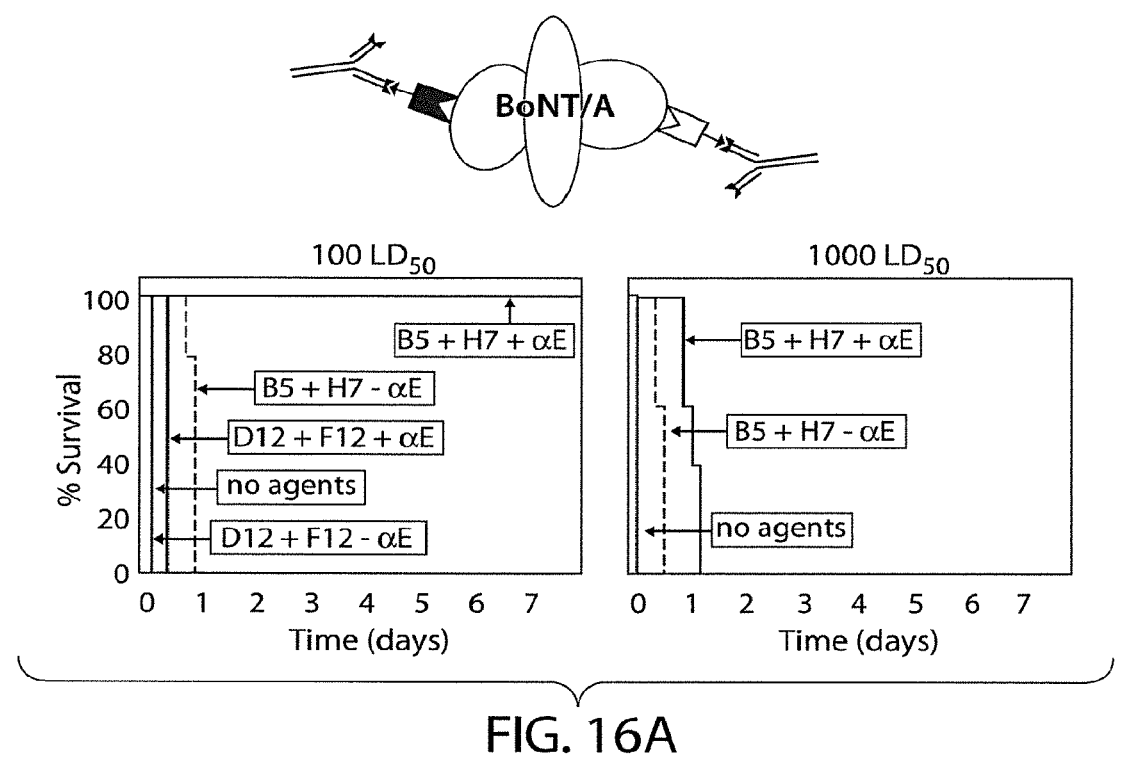
Figure 16B:
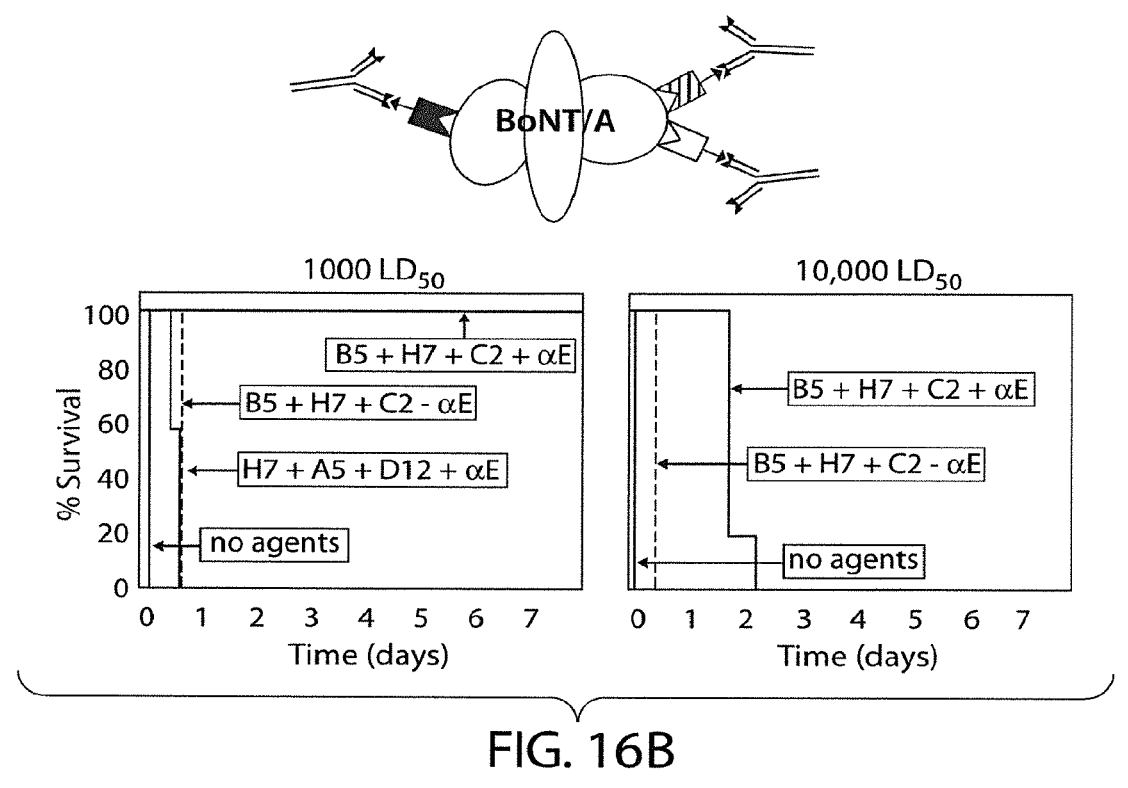
Figure 16C:
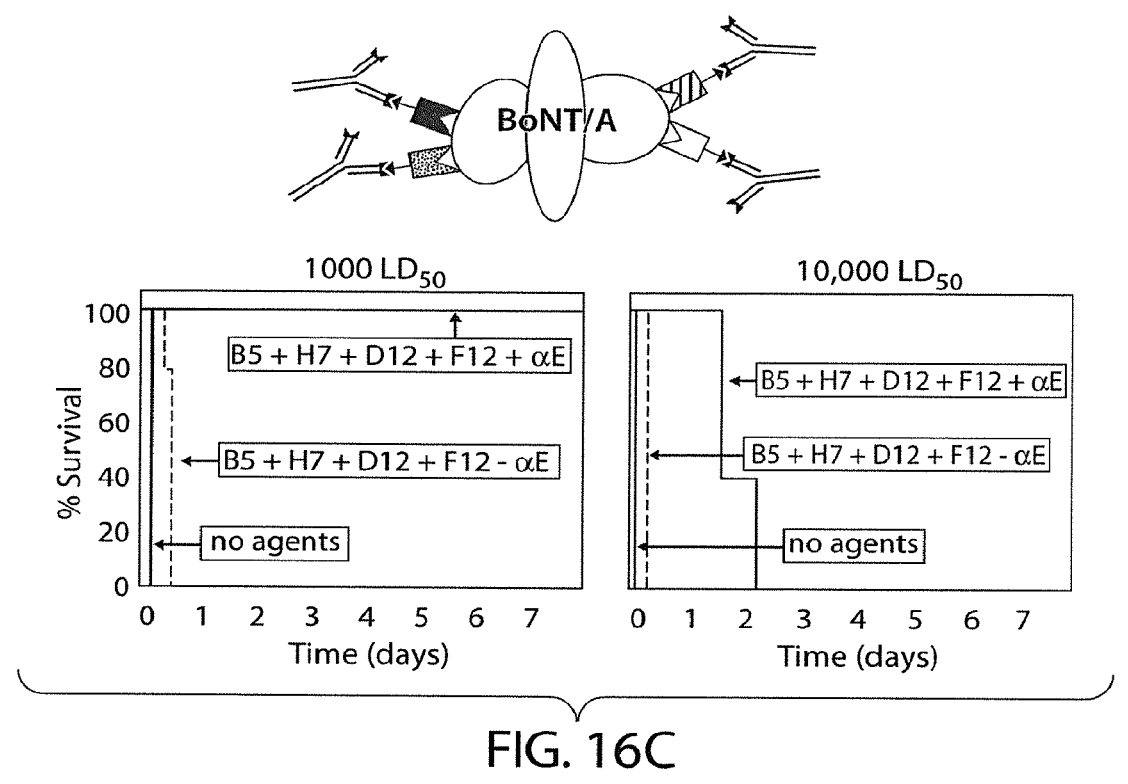

The subjects were co-administered BoNT/A with either a mixture of ciA-H7 and ciA-B5 monomers, or a mixture of ciA-D12 and ciA-F12 monomers (FIG. 16 A bottom graphs). Each mixture was administered with (+αE) or without (−αE) anti-E-tag clearing antibody that specifically bound the epitopic tags located on the VHHs. Control subjects were administered toxin only. Unless indicated otherwise, a dashed line in FIGS. 16-24 indicates that no anti-E-tag antibody was administered to the subjects. Each monomeric VHH was used at a total dose of two micrograms (μg) per mouse to ensure that the only the complexity and/or identity of the VHH mixtures was varied among groups and was the cause of observed antitoxin efficacy.

Results obtained show that subjects administered ciA-D12 and ciA-F12, two anti-BoNT/A VHH monomers previously determined not to neutralize BoNT/A in cell assays, did not survive toxin challenge for any greater time than did control subjects administered toxin only (FIG. 16 A bottom graphs). Administration of 5 μg amounts of anti-E-tag clearing antibody (αE) to subjects only slightly prolonged time before death. Data show that subjects administered neutralizing VHH monomers ciA-H7 and ciA-B5 with anti-E-tag clearing antibody were slightly protected against BoNT/A compared to subjects administered ciA-D12 and ciA-F12, and anti-E-tag clearing antibodies. Thus, the decoration of BoNT/A with two clearing antibodies provided little or no therapeutic benefit to the subjects.

Administration to subjects of a mixture of ciA-B5, and ciA-H7 monomers absent clearing antibody only delayed time to death. Data show that subjects challenged with 100-fold the $LD_{50}$ of BoNT/A (approximately 5 nanograms total) survived longer following administration of a mixture of neutralizing ciA-B5 and ciA-H7 compared to control subjects administered no VHHs. Most important, it was observed that co-administration of clearing antibody and the neutralizing VHHs resulted in 100% survival of subjects challenged with 100-fold the $LD_{50}$ of BoNT/A (FIG. 16 A bottom left graph). At a challenge of 1,000-fold the $LD_{50}$ of BoNT/A, death was delayed about one additional day for subjects co-administered a mixture of ciA-B5 and ciA-H7 and anti-E-tag clearing antibody compared to subjects administered VHHs alone or control subjects (FIG. 16 A bottom right graph). Thus, it was observed that administering a mixture of toxin neutralization VHH monomers with clearing antibody provided greater therapeutic benefit and protection against BoNT/A than administering VHHs absent the clearing antibody. Relative affinity of each VHH influences the therapeutic effect of the VHH, likewise for VHHs having similar sub-nanomolar affinities (See Table 5).

Whether mixtures of VHH monomers containing both neutralizing VHHs and non-neutralizing VHHs were effective antitoxin agents was further tested. Subjects were co-administered 1,000-fold or 10,000-fold BoNT/A $LD_{50}$ and one VHH monomer mixture of either a mixture of ciA-B5, ciA-H7, and ciA-C2; or a mixture of ciA-H7, ciA-A5 and ciA-D12 with (+αE) or without (−αE) an anti-E-tag clearing antibody preparation that specifically binds the epitopic tags located on the VHHs (FIG. 16 B bottom graphs). Control subjects were administered toxin only.

Administration of a mixture of ciA-B5, ciA-H7, ciA-C2 monomers, each capable of potent toxin neutralization, delayed death less than a day in mice exposed to 1000-fold the $LD_{50}$ of BoNT/A (FIG. 16 B bottom left graph). Subjects were completely protected (100% survival) at 1000-fold the $LD_{50}$ of BoNT/A following administration mixture of ciA-B5, ciA-H7, and ciA-C2 monomers and clearing antibody. Co-administration of 10,000-fold the $LD_{50}$ of BoNT/A (a total amount of 0.5 μg), a mixture of ciA-B5, ciA-H7, ciA-C2 monomers and clearing antibody delayed death more than two days in subjects (See FIG. 16 B bottom right graph) compared to control subjects.

It was observed that administration of a mixture of ciA-H7, ciA-A5, and ciA-D12 in which two VHH monomers (ciA-A5 and ciA-D12) in the mixture of monomers were weak toxin neutralizers, resulted in subjects surviving much less after exposure to an amount of BoNT/A 1,000-fold BoNT/A $LD_{50}$ (FIG. 16 B bottom left graph).

Thus, administration of the mixture of ciA-B5, ciA-H7, and ciA-C2 tagged monomers, each of which are strong neutralizing VHHs, to subjects provided greater protection against BoNT/A than the mixture of ciA-H7, ciA-A5 and ciA-D12, in which two of the three VHH monomers do not neutralize BoNT/A. Data show that 100% of subjects administered the mixture of ciA-B5, ciA-H7, and ciA-C2 with the anti-tag clearing antibody survived a dose of BoNT/A that was 1,000-fold the $LD_{50}$ of a BoNT/A (FIG. 16 B bottom left graph), and survived additional days following administration of 10,000-fold the $LD_{50}$ of a BoNT/A (FIG. 16 B bottom left graph).

TABLE 5

SPR binding data for VHH monomers and heterodimers

| Clone | protein | epitope[#] | neutralization[*] | SPR Kd (nM) | subunit[^] | Genbank |
|---|---|---|---|---|---|---|
| JDY-33 | ciA-H7 | A1 | strong | 0.06 +/− 0.07 | Lc | HQ700708 |
| JDT-2 | ciA-D1 | A1 | strong | 0.71 +/− 0.004 | Lc | |
| JEC-3 | ciA-H4 | A1 | not done | 1.54 +/− 0.06 | Lc | |
| JEC-11 | ciA-H1 | A1 | not done | 4.3 +/− 0.09 | Lc | |
| JDY-46 | ciA-C2 | A2 | strong | 2.7 +/− 3.1 | Lc | HQ700705 |
| JDY-9 | ciA-B5 | A3 | strong | 0.17 +/− 0.06 | Hc | HQ700704 |
| JED-27 | ciA-F12 | A4 | none | 0.24 +/− 0.03 | Lc | HQ700706 |
| JDU-26 | ciA-D12 | A5 | none | 0.21 +/− 0.1 | Lc | HQ700702 |
| JDY-2 | ciA-A5 | A6 | weak | 1.05 +/− 0.05 | none | HQ700703 |
| JDY-59 | ciA-G5 | A7 | weak | 0.32 +/− 0.03 | none | HQ700707 |
| JFA-10 | ciB-H11 | B1 | not done | 0.26 +/− 0.01 | none | |
| JFX-30 | ciB-A11 | B2 | not done | 0.84 +/− 0.68 | none | |
| JFV-48 | ciB-B5 | B3 | not done | 0.97 +/− 0.04 | none | |
| JFV-40 | ciA-B9 | B4 | not done | 23 +/− 5.6 | none | |
| JEZ-2 | ciA-H7/B5 | A1/A3 | strong | 0.014 +/− 0.007 | not done | |
| JFK-21 | ciA-F12/D12 | A4/A5 | not done | 0.097 +/− 0.038 | not done | |
| JGA-3 | ciB-A11/B5 | B2/B3 | not done | 5.3 +/− 1.5 | not done | |

Complete survival (100%) was observed for subjects administered a mixture of ciA-B5, ciA-H7, ciA-D12 and ciA-F12 tagged monomers and anti-tag clearing antibodies of the challenge with an amount of BoNT/A that was 1,000-fold the $LD_{50}$ (FIG. 16 C bottom left graph). Administering a pool of anti-BoNT/A VHHs (ciA-B5, ciA-H7, ciA-D12 and ciA-F12) in which only two VHHs (ciA-B5, ciA-H7) were strong toxin neutralizers only slightly delayed death in subjects exposed to 1000-fold the $LD_{50}$ of BoNT/A (FIG. 16 C bottom left graph). At 10,000-fold the $LD_{50}$ of a BoNT/A, subjects co-administered the mixture of four VHH tagged monomers and anti-tag clearing antibody survived additional days compared to control subjects (FIG. 16 C bottom left graph).

Figure 17:
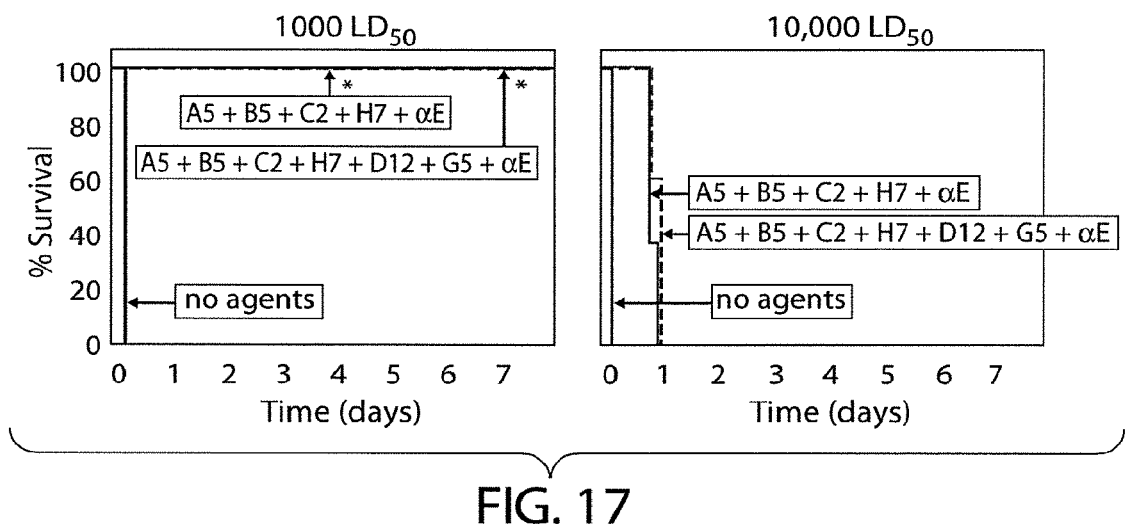
FIG. 17 are graphs showing percent survival, ordinate, of subjects as a function of time (days, abscissa) of subjects co-administered 1,000-fold BoNT/A $LD_{50}$ (FIG. 17 left graph) or 10,000-fold BoNT/A $LD_{50}$ (FIG. 17 right graph), and mixtures of VHH monomers and anti-tag clearing antibody (αE). Control subjects received toxin only. Unless indicated otherwise, an asterisk (*) in FIGS. 17-24 indicates that the subjects administered the VHH monomer or multimer displayed no symptoms of toxin exposure.

The antitoxin efficacy of a pool of four anti-BoNT/A VHHs tagged monomers (ciA-A5, ciA-B5, ciA-C2 and ciA-H7) was compared to a pool of six different VHH tagged monomers (ciA-A5, ciA-B5, ciA-C2, ciA-H7, ciA-D12, and ciA-G5). The pool of six VHH monomers contained the same VHHs as the pool of four VHHs and further included two VHHs (ciA-D12, and ciA-G5) that were weak neutralizers of BoNT/A (FIG. 17 and Table 5). The different pools of VHH monomers were each administered in the presence of clearing anti-tag antibody. It was observed that 100% of subjects administered either the pool of four VHH tagged monomers or the pool of six VHHs tagged monomers with anti-tag clearing antibody survived challenge with 1000-fold the $LD_{50}$ of BoNT/A (FIG. 17 left graph). Subjects challenged with 10,000-fold the $LD_{50}$ of BoNT/A survived longer following co-administration of either the pool of four VHH monomers or the pool of six VHH monomers with clearing anti-tag antibody, than control subjects administered only toxin (FIG. 17 right graph). These results show that decoration of BoNT/A with a greater number of VHH antibodies, four or more VHHs, greatly improved antitoxin efficacy. Administering a pool of four VHH monomers or a pool of six VHH monomers to the subjects provided additional antitoxin efficacy compared to administering three or fewer VHH monomers.

These data clearly show that toxin clearance was rendered much more effective under conditions in which BoNT is decorated by at least three VHH antibodies and at least about three clearing antibodies. It was observed also that mixtures of monomers having greater number or percentage of toxin neutralization VHHs greatly contributed to percent survival of subjects co-administered a vast excess of the lethal dose of BoNT/A.

Example 16: VHH Affinity and Antitoxin Efficacy

Toxin neutralization and clearance mechanisms were observed herein to depend on affinity of antitoxin binding to the toxin. Without being limited by a particular theory or mechanism of action, the kinetics of toxin binding ($K_{on}$) and release ($K_{off}$) by the antitoxin binding agents contribute to the antitoxin efficacy.

To determine the relationship of toxin affinity to antitoxin efficacy and the role of each, assays were performed for identification of multiple VHHs recognizing the same epitope. In the course of anti-BoNT/A VHH screening and based on competition ELISA analysis, several VHHs (ciA-D1, ciA-H4 and ciA-H11) were identified that recognized the same epitope as ciA-H7. SPR analysis showed that each VHH monomer recognized and bound the ciA-H7 epitope with a different affinity. The dissociation constant (Kd) identifies the strength of binding or affinity between a ligand and a receptor, between the VHH antibody and the toxin.

Figures 18A, 18B:
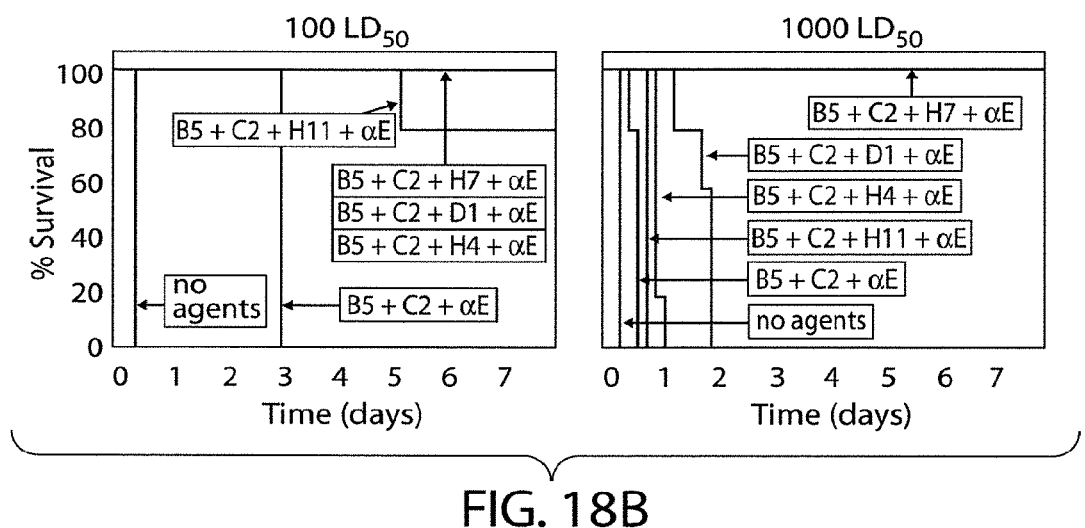
FIG. 18 A-FIG. 18 B are a table showing affinity binding data for VHHs and a set of line graphs showing improved protection of subjects from very large doses of BoNT/A following administration of each of sets of mixtures of VHH monomers with strong affinity for BoNT/A and clearing antibody.

The VHH Kd values for the VHHs having the stronger binding to BoNT/A were determined to be 0.06±0.07 nM for ciA-H7, 0.71±0.004 for ciA-D1, and the VHH Kd values for the VHHs having the weakest binding to BoNT/A were determined to be the 1.54±0.06 for ciA-H4, and 4.3±0.09 for ciA-H11 respectively (FIG. 18 A). These four VHHs were tested with anti-tag clearing antibody for their efficacy as antitoxin VHHs in combination with the two VHHs (ciA-B5, ciA-C2) that recognize distinct, non-overlapping epitopes of BoNT/A (FIG. 18 B left and right graphs).

Subjects (five mice per group) were co-administered BoNT/A and one of four mixtures containing three VHH monomers: ciA-H7, ciA-B5 and ciA-C2; ciA-D1, ciA-B5 and ciA-C2; ciA-H4, ciA-B5 and ciA-C2; or ciA-H11, ciA-B5 and ciA-C2. Each mixture included two strong neutralizing VHH monomers (ciA-B5 and ciA-C2), and one VHH of ciA-H7, ciA-D1, ciA-H4, or ciA-H11. Control subjects received toxin only.

Data show that 100% of subjects survived following co-administration of 100 BoNT/A $LD_{50}$ and VHH mixtures containing ciA-B5 and ciA-C2 and either ciA-H7, ciA-D1 or ciA-H4. Subjects administered the VHH mixture of ciA-B5, ciA-C2 and ciA-H11 survived the 100 $LD_{50}$ of BoNT/A at 80% (FIG. 18 B left graph). Among subjects challenged with 1,000-fold the $LD_{50}$ of a BoNT/A (FIG. 18 B right graph), the level of protection was a function of the relative binding affinity or Kd of the VHH to BoNT/A shown in FIG. 18 A. Specifically the greatest protection at 1,000-fold BoNT/A $LD_{50}$ was observed in subjects administered the VHH mixture containing ciA-B5, ciA-C2, and ciA-H7, which had the strongest BoNT/A affinity (i.e., lowest Kd value of 0.06±0.07; FIG. 18 A and FIG. 18 B right graph). The least extent of protection was observed in subjects administered the VHH mixture containing ciA-B5, ciA-C2, and ciA-H11 (weakest BoNT/A affinity and highest Kd value of 4.3±0.09; FIG. 18 A and FIG. 18 B right graph), the survival of which was comparable to control subjects not administered VHH monomers.

Correlating the Kd values with antitoxin-toxin binding and affinities, it was observed that the lower the Kd value the greater the respective toxin affinity and the greater the antitoxin efficacy of the VHH. VHH ciA-H7 was observed to have the lowest Kd and the strongest binding affinity to BoNT/A, and was determined to have greater antitoxin efficacy than other VHH compositions identified in FIG. 18 A. Thus, sub-nanomolar affinities or Kd values for the tagged toxin binding agents is an important factor in identifying the VHH with greatest antitoxin efficacy and most effective ability to protect subjects from toxin-associated infection and death.

Example 17: Antitoxin VHHs Heterodimers

By engineering and expressing two anti-BoNT/A VHHs as a heterodimer, a resulting multimeric binding protein molecule was obtained, and this composition was found to bind to two different sites on the toxin and yield an improved toxin affinity. Examples herein analyzed the role of epitopic tags on the heterodimer and the role of the amount of the tagging of the heterodimer compared to the clearing antibody with respect to increasing antitoxin efficacy of the heterodimer.

Figure 19A:
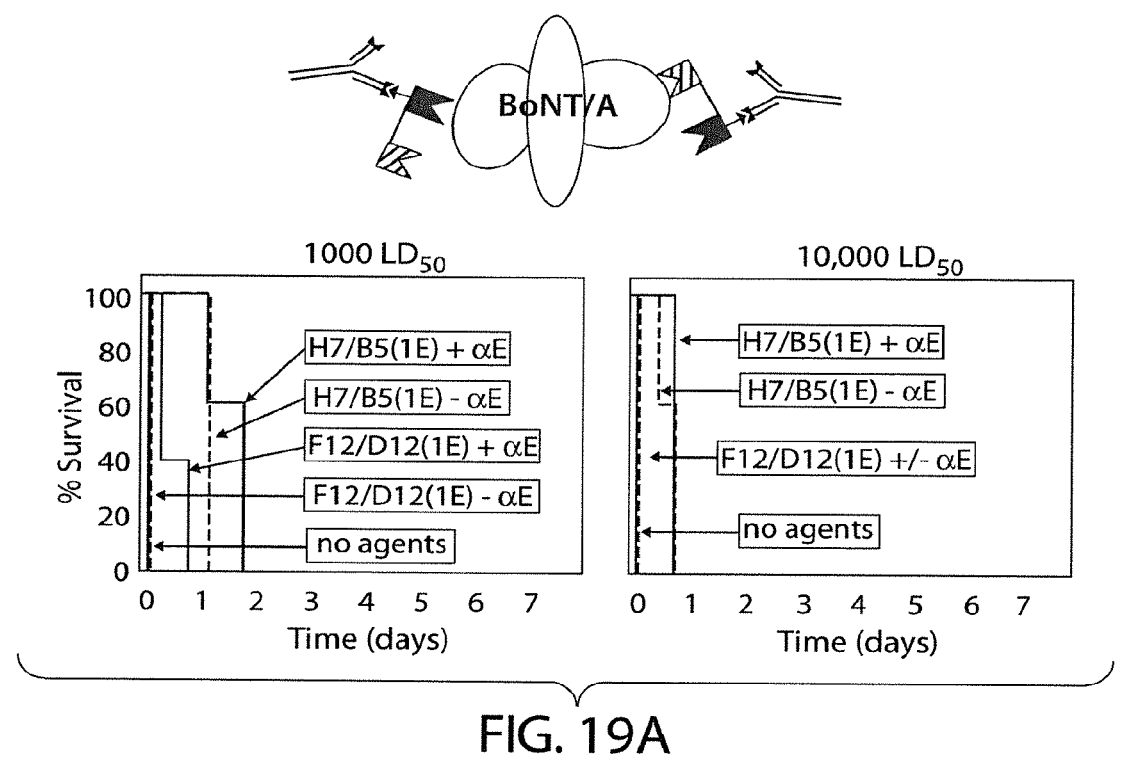
Figure 19B:
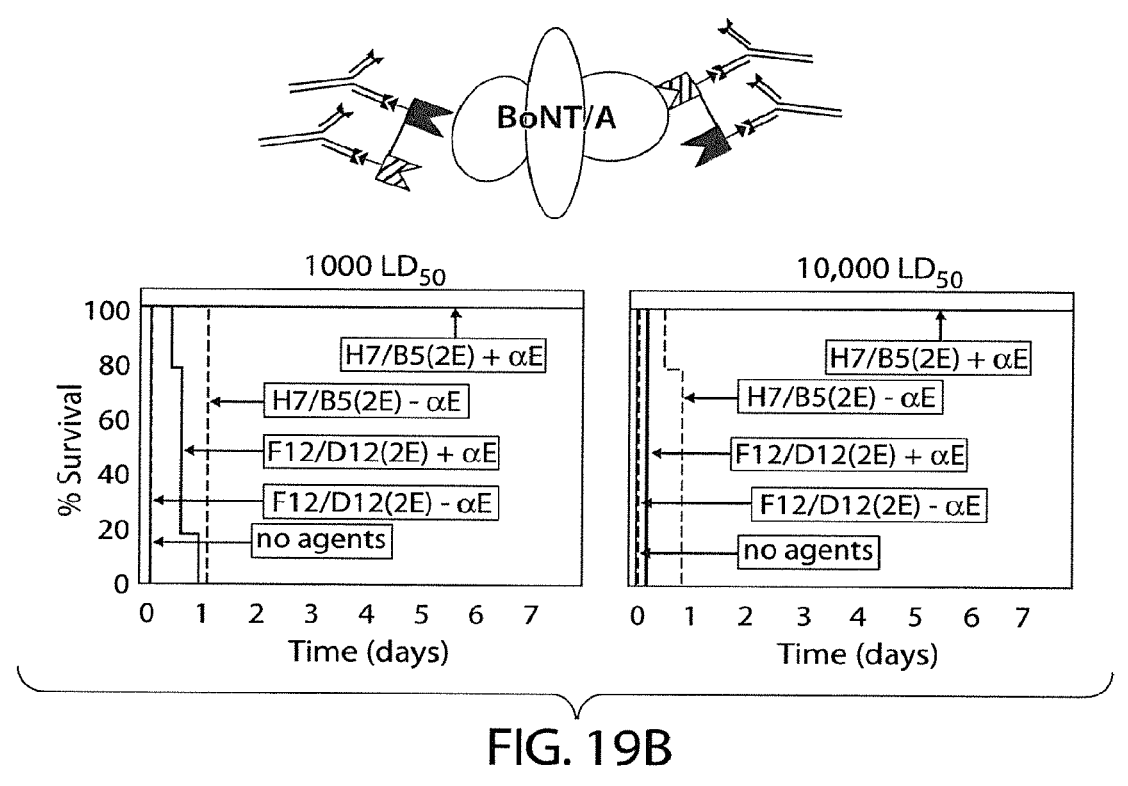

VHH heterodimers were engineered to contain an epitopic tag for decoration of BoNT/A with two anti-tag clearing antibodies (FIG. 19 A top drawing). Survival and protection of subjects was analyzed following challenge with each of 100-fold and 1000-fold the $LD_{50}$ of BoNT/A (FIG. 19 A bottom left and right graphs). Data show that administering heterodimer containing two strongly neutralizing VHHs, ciA-B5 and ciA-H7, resulted in greater antitoxin efficacy and longer survival of subjects than administering heterodimers containing two weak or non-neutralizing VHHs, ciA-D12 and ciA-F12 (FIG. 19 A bottom left and right graphs).

A second copy of the epitopic tag to the heterodimers compared to only one epitopic tag was observed to promote toxin decoration with four clearing antibodies and to yield greater clearing efficacy (FIG. 19 B top drawing). All (100%) of subjects survived a challenge with either 1000-fold or 10,000-fold the $LD_{50}$ of BoNT/A and co-administration of ciA-B5/ciA-H7 heterodimer having two epitopic tags and anti-tag clearing antibody (FIG. 19 B bottom graphs).

To further analyze whether two or more epitopic tags improved heterodimer antitoxin efficacy, two sets of anti-BoNT/A VHH heterodimers were constructed in which the two VHHs in the heterodimers were either non-neutralizing (ciA-D12/F12) or potent toxin neutralizing agents (ciA-B5/H7). The two different VHH heterodimers were engineered containing either one or two copies of the epitopic tag (E-tag) and were expressed. SPR analysis confirmed that the heterodimer affinities were in the range of 10 picomolar to 100 picomolar which was significantly greater than the affinities of the component monomers (FIG. 15 and Table 5).

The antitoxin efficacies of the single tagged heterodimers administered to mouse subjects after challenge with 1000-fold $LD_{50}$ of BoNT/A (FIG. 19 A bottom left graph) were observed to be similar to results obtained from administering a mixture of the two corresponding monomers only (FIG. 16 A bottom right graph). Administering the non-neutralizing single-tagged heterodimer, ciA-D12/F12(1E), resulted in no protection from challenge with 1000-fold $LD_{50}$ of BoNT/A in the absence of clearing antibody, and only slightly delayed death in the presence of clearing antibody 9 FIG. 19 A bottom left graph). The toxin neutralizing single-tagged heterodimer, ciA-B5/H7(1E), delayed death in mice exposed to 1000 $LD_{50}$ BoNT/A for one to two days in the absence of clearing antibody and efficacy was only slightly improved by the addition of clearing antibody (FIG. 19 A bottom left graph).

Improved antitoxin efficacy was observed in subjects administered a heteromultimeric agent having a second copy of the epitopic tag, with both non-neutralizing and neutralizing anti-BoNT/A VHH heterodimers in which the heterodimer agent was co-administered with clearing antibody. Without being limited by any particular theory or mechanism of action, it is here envisioned that component binding regions in a 'double-tagged heterodimer' bind at two sites on the toxin and each bound heterodimer decorates toxin with two clearing antibodies, resulting in decoration of the toxin with at least four clearing antibodies (FIG. 19 B top drawing) which Examples herein show had increased clearance. Administering non-neutralizing double-tagged heterodimer containing ciA-D12/F12(2E) resulted in virtually no antitoxin efficacy in subjects in the absence of clearing antibody at both 1000-fold and 10,000-fold the $LD_{50}$ of BoNT/A (FIG. 19 B bottom left and right graphs). In the presence of clearing antibody, ciA-D12/F12(2E) heterodimer fully protected subjects (100% survival) from 100-fold BoNT/A $LD_{50}$ and delayed death about a day in subjects receiving 1000-fold BoNT/A $LD_{50}$ compared to control subjects (FIG. 19 B bottom right graph and FIG. 20 left graph). Thus the presence of a second epitopic tag attached to the heterodimer dramatically improved the antitoxin efficacy.

Figure 20:
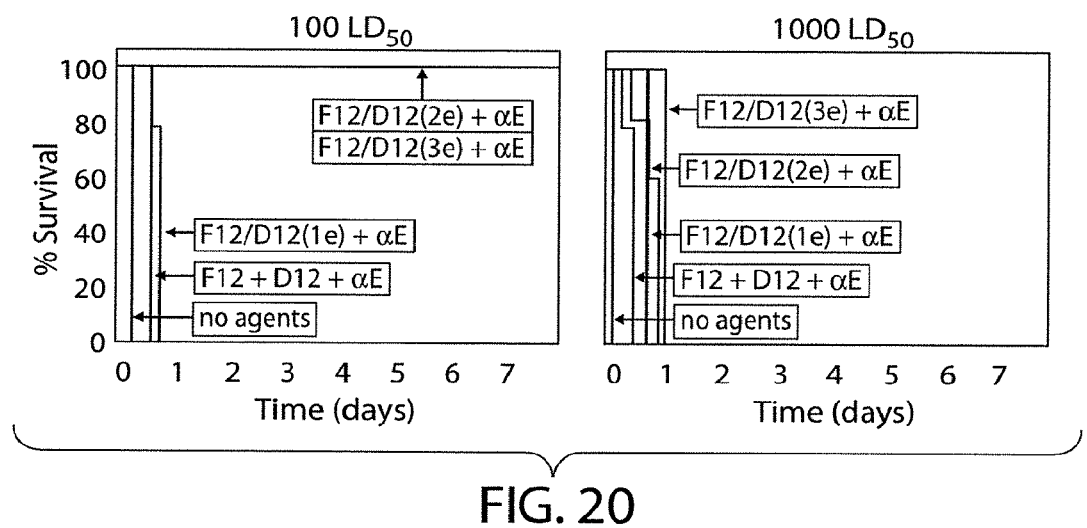
FIG. 20 is a set of graphs showing percent survival on the ordinate of subjects as a function of time (days, abscissa) after co-administration of 100-fold (FIG. 20 left graph) or 1,000-fold (FIG. 20 right graph) BoNT/A $LD_{50}$, and multi-tagged VHH heterodimers with anti-tag clearing antibody. The ciA-D12/ciA-F12 heterodimer protein contained either one tag (1e), two tags (2e), three tags (3e), or control no tag. Subjects (five mice per group) were administered 20 µg of the heterodimer composition or the mixture of ciA-D12 and ciA-F12 monomers (20 µg of each monomer). Control subjects were administered neither monomer nor heterodimer. Each subject received 60 picomoles of anti-E-tag clearing antibody. Data show that subjects administered ciA-D12/ciA-F12 heterodimers having either one tag or two tags survived (100% survival) the challenge of 100-fold the $LD_{50}$ of BoNT/A (FIG. 20 left graph). Subjects receiving 1,000-fold the $LD_{50}$ of BoNT/A and ciA-D12/ciA-F12 heterodimers with clearing antibody died within one day following challenge with independent of number of tags (FIG. 20 right graph).
Figure 21:
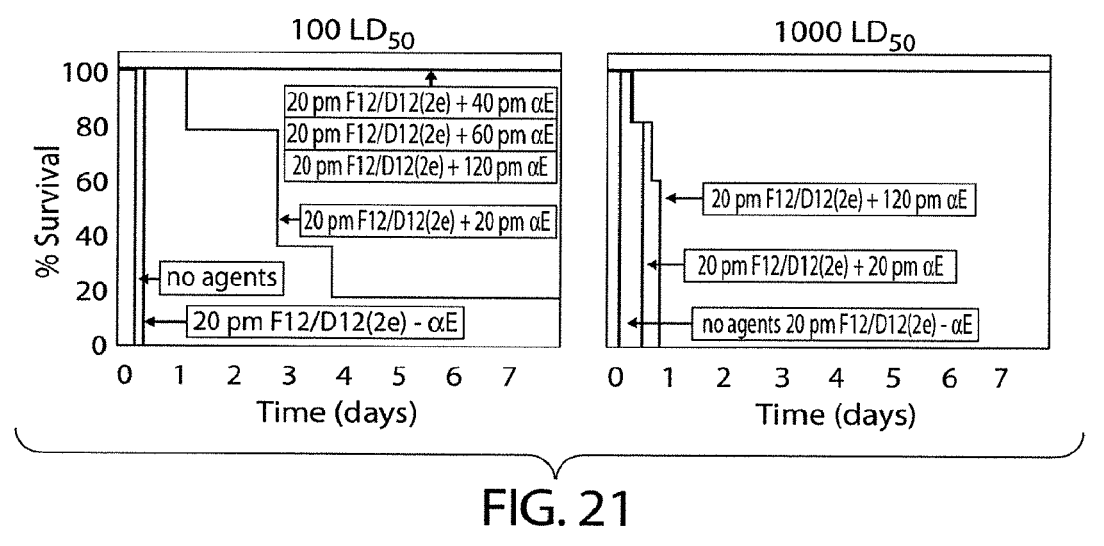

Non-neutralizing heterodimer, ciA-D12/F12, with either one, two or three epitopic tags was analyzed for antitoxin efficacy in the presence of clearing antibody (FIG. 20). The single-tagged heterodimer only slightly protected subjects from toxin challenge of 100-fold the $LD_{50}$ of BoNT/A. Subjects challenged with double-tagged heterodimers and triple-tagged heterodimers were fully protected from a challenge of 100-fold the $LD_{50}$ of BoNT/A (FIG. 20 left graph). Only little improvement in antitoxin efficacy was observed with the triple-tagged heterodimers compared to the double-tagged heterodimers, consistent with the observation that near maximal clearance was achieved by decorating the target with four clearing antibodies. A titration of the clearing antibody administered with the double-tagged ciA-D12/F12 heterodimer demonstrated that maximal antitoxin efficacy against both 100-fold and 1,000-fold the $LD_{50}$ of BoNT/A was achieved with the number of clearing antibody molecules (measured in picomoles) administered in an amount approximately equivalent to the number of epitopic tags (FIG. 21 left and right graphs).

An even more dramatic antitoxin effect was observed in cell culture intoxication assays using the double-tagged heterodimer, ciA-B5/H7(2E), in which both of the component anti-BoNT/A VHHs individually possess potent neutralizing activity (FIG. 15). In the absence of clearing antibody, the double-tagged ciA-B5/H7(2E) heterodimer produced the same antitoxin efficacy as the equivalent single-tagged heterodimer (compare FIG. 19 A bottom left and right graphs to FIG. 19 B bottom left and right graphs). In the presence of clearing antibody, the neutralizing double-tagged heterodimer at 40 picomoles (pmoles) was observed to be a highly potent antitoxin that fully protected cells from lethality when co-administered with 10,000-fold the $LD_{50}$ of BoNT/A, i.e., the total amount was about 3 pmoles.

A dose-response assay was performed in mouse subjects with double-tagged ciA-B5/H7(2E) heterodimer co-administered with 1000-fold the $LD_{50}$ of BoNT/A (FIG. 22). It was observed that both 40 pmoles and 13 pmoles of double-tagged ciA-B5/H7(2E) heterodimer completely protected the subjects against an exposure of 1000-fold the $LD_{50}$ of BoNT/A. A dose of 4 pmoles ciA-B5/H7(2E) heterodimer had the same protective efficacy for 1,000-fold the $LD_{50}$ of BoNT/A as a dose of 40 pmoles did with 10,000-fold the $LD_{50}$ of BoNT/A (FIG. 15 B and FIG. 22). These data show that co-administering about a fifteen-fold molar excess of the double-tagged heterodimer binding agent with the clearing antibody was sufficient to effectively neutralize and/or clear substantially all (greater than 99.99%) of the BoNT/A.

Figures 23A, 23B:
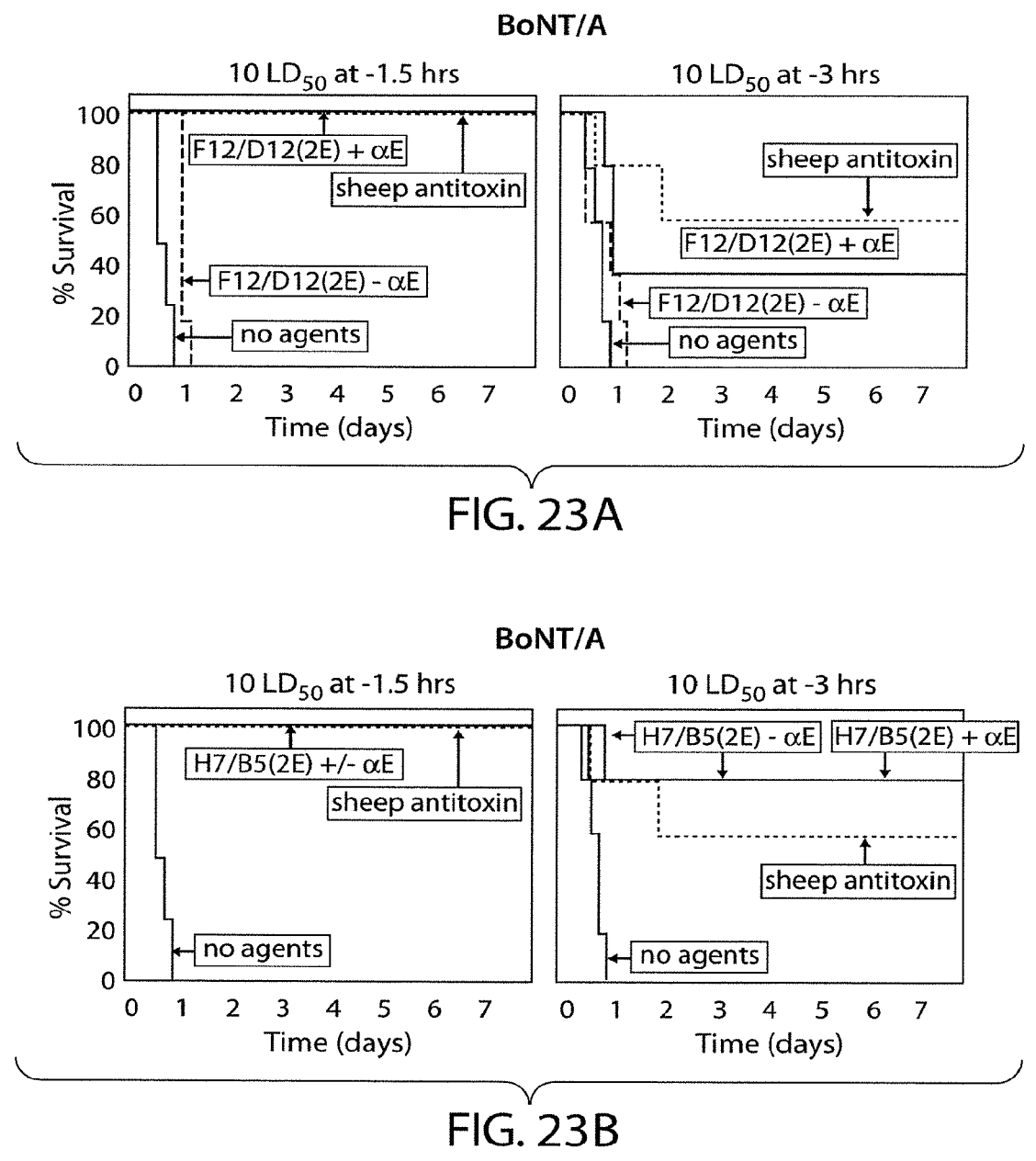

Example 18: Recombinant Antitoxin Efficacy in a Clinically Relevant Post-Intoxication Assay Assays in which varying doses of toxins are co-administered with antitoxin agents were observed to permit sensitive quantification of antitoxin efficacy. To more accurately reflect the typical clinical situation, antitoxin agents were tested in an assay of greater clinical relevance by intraperitoneally administering to mouse subjects ten-fold the $LD_{50}$ of BoNT/A, and at 1.5 hours and three hours afterwards, administering intravenously neutralizing heterodimer antitoxin agents with and without the anti-tag clearing antibody. Different sets of anti-BoNT/A VHH heterodimers were tested: a heterodimer containing non-neutralizing double-tagged ciA-D12/F12(2E), and a heterodimer containing neutralizing double-tagged ciA-H7/B5(2E) heterodimer (FIG. 23 A-B). A potent sheep anti-BoNT/A serum was used as a control in the assay at a dose demonstrated to protect 100% of mice from lethality given 10,000-fold the $LD_{50}$ of BoNT/A.

The non-neutralizing ciA-D12/F12(2E) heterodimer was observed to have little or no antitoxin efficacy in absence of clearing antibody following administration either 1.5 hours or three hours after BoNT/A challenge (FIG. 23 A left and right graphs). However, ciA-D12/F12(2E) heterodimer administered with clearing antibody displayed an efficacy nearly equivalent to the positive control sheep antiserum (FIG. 23 B left and right graphs). These results show that toxin clearance alone is sufficient to protect mice from a low dose BoNT challenge, even when administered several hours post-exposure to toxin.

Surprisingly the neutralizing ciA-H7/B5(2E) heterodimer was observed to be as highly effective as an antitoxin in this assay, in the presence or even absence of clearing antibody (FIG. 23 B). The double-tagged toxin neutralizing heterodimer administered 1.5 hours after toxin challenge with tenfold the $LD_{50}$ of BoNT/A resulted in an antitoxin efficacy equivalent to the sheep serum polyclonal antitoxin. It was observed that following challenge at 10 BoNT/A $LD_{50}$ for 1.5 hours, subjects administered ciA-H7/B5(2E) heterodimer absent anti-tag clearing fully survived (100% survival; FIG. 23 B left graph). The survival for subjects administered ciA-H7/B5(2E) heterodimer was comparable to subjects administered sheep antitoxin (FIG. 23 B left graph).

Data show that three hours after toxin challenge at tenfold the $LD_{50}$ of BoNT/A, the neutralizing ciA-H7/B5(2E) heterodimer resulted in greater subject survival (80%) than the sheep serum polyclonal antitoxin (60% survival; FIG. 23 B right graph). Most important, the survival of subjects using neutralizing ciA-H7/B5(2E) heterodimer was the same with or without clearing antibody (FIG. 23 B right graph).

These data clearly show that BoNT neutralization was sufficient for full antitoxin efficacy in a clinically relevant post-intoxication (post-exposure to toxin) assay with low dose toxin challenge. A single recombinant multimeric binding protein with potent toxin neutralization properties was as effective as antitoxin sera in a model of a typical clinical situation involving toxin exposure and subsequent treatment.

Example 19: Antitoxin Efficacy of a Double-Tagged Heterodimer Targeting Botulinum Toxin, BoNT/B Double-tagged VHH heterodimer antitoxins that specifically recognized and bound unique epitopes on BoNT/B holotoxin (FIG. 13 B) were identified and expressed. Two of the VHHs, ciB-A11 and ciA-B5, were observed to be the most effective antitoxins of those obtained from monomer pool assays, and were engineered and expressed as double-tagged heterodimer, ciB-A11/B5(2E).

Figure 24A:
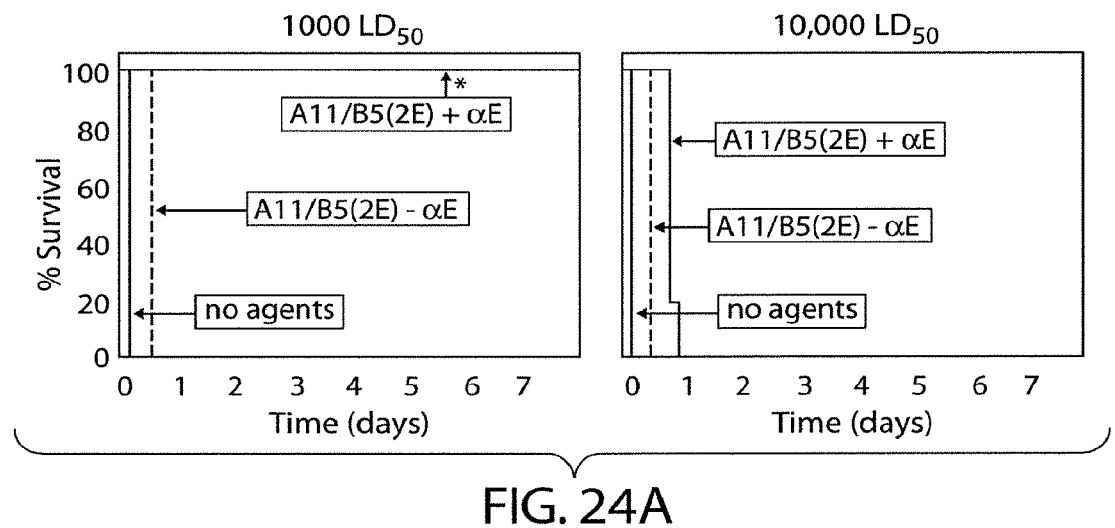
FIG. 24 A-FIG. 24 B are line graphs showing that subjects administered ciA-A11/ciA-B5 heterodimers with anti-tag clearing antibody were protected from BoNT/B exposure.
Figure 24B:
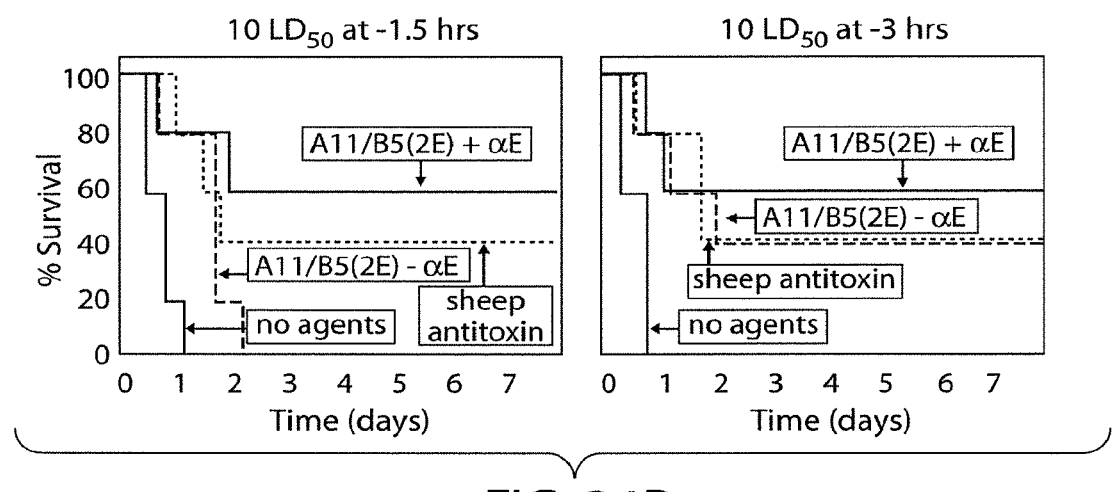

Subjects were exposed to either 1,000-fold (FIG. 24 A left graph) or 10,000-fold (FIG. 24 A right graph) BoNT/B $LD_{50}$, and were administered a ciB-A11 and ciB-B5 heterodimer with (+αE) or without (−αE) anti-tag clearing antibody. Control subject were exposed only to toxin (no heterodimer binding proteins). Data show that in the presence of clearing antibody the ciB-A11/B5(2E) heterodimer fully protected subjects challenged with 1000-fold the $LD_{50}$ of BoNT/B (FIG. 24 A left graph) and extended the life of subjects challenged with 10,000-fold the $LD_{50}$ of BoNT/B (FIG. 24 A right graph).

Analysis was performed to determine whether the ciB-A11 and ciA-B5 double tagged heterodimer was effective to treat subjects in a BoNT/B post-exposure in vivo model.

Subjects were intravenously exposed to 10 $LD_{50}$ of BoNT/A, and then administered 1.5 hours or three hours afterward either: ciB-A11 and ciA-B5 double tagged heterodimeric protein with or without clearing antibody, or a sheep antitoxin serum. Control subjects were only exposed to 10 $LD_{50}$ of BoNT/B (no heterodimeric binding protein was administered). See FIG. 24 B left and right graphs. Data show 60% of subjects administered ciB-A11/B5 double tagged heterodimer with anti-tag antibody survived 1.5 hours and three hours after BoNT/B exposure, and further that 20% more subjects survived with ciB-A11/B5 double tagged heterodimer with clearing antibody treatment than with sheep antitoxin at both time points (FIG. 24 B left and right graphs). It was observed that three hours after BoNT/B exposure subjects administered A11/B5 double tagged heterodimer binding protein only (without anti-tag antibody) survived as long as subjects administered sheep antitoxin (FIG. 24 B right graph).

Results from these clinically relevant post-intoxication assays herein showed that ciB-A11/B5 heterodimer with or without clearing antibody was as effective as sheep anti-BoNT/B serum in protecting subjects from death caused by BoNT/B holotoxin exposure.

Example 20: VHH Monomers Protect CT26 Cells from TcdA

Cells of murine colorectal cancer cell line CT26 were exposed to TcdA (2 ng/ml) for 24 hours and to a VHH monomer specific to TcdA (A3H, SEQ ID NO 61; A11G, SEQ ID NO:63; AC1, SEQ ID NO: 62; AE1, SEQ ID NO: 64; AH3, SEQ ID NO: A1; or AA6, SEQ ID NO: 60). Controls cells were exposed to TcdA (no VHH monomer was administered). The percentage of cell rounding was monitored using a phase contrast microscope. Control cells administered only TcdA showed extensive cell rounding and distorted cell morphology associated with TcdA toxin exposure.

Figure 25:
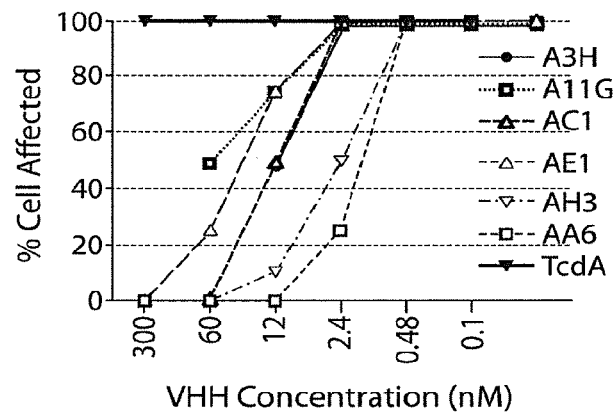
FIG. 25 is a line graph of percent of cells affected by *C. difficile* toxin A (TcdA) and protection of cells from the toxin by VHH monomers. The percent CT26 cells affected by TcdA (% affected; ordinate) is shown as a function of concentration (0.1 nM, 0.48 nM, 2.4 nM, 12 nM, 60 nM, or 300 nM) of each administered VHH monomer: A3H (circle), A11G (light square); AC1 (upward dark empty triangle), AE1 (upward light triangle), AH3 (downward triangle), or AA6 (dark empty square). Control cells were administered toxin only (TcdA; dark downward triangle). Strength of neutralizing VHH activity was observed in the following order: AA6 as strongest, then AH3, AC1, AE1, A11G, and A3H as weakest.

It was observed that each of the VHH monomers reduced the percentage of affected cells and protected the cells from TcdA exposure (FIG. 25). In order of greatest VHH monomer activity to the weakest VHH monomer activity, the greatest activity was observed for AA6, followed AH3, AC1, A3H, AE1, and A116 respectively. It was observed that VHH monomers AA6 and AH3 neutralized TcdA and protected 50% of cells from toxin cytotoxicity at VHH concentrations less than about 10 nM, and thus were considered to have strong TcdA neutralizing activity.

Example 21: Multimeric Binding Proteins Protect Cells from TcdA

CT26 cells were contacted to TcdA (2 ng/ml) and concentrations (0.1 nM, 0.48 nM, 2.4 nM, 12 nM, 60 nM, or 300 nM) of each of VHH monomers: A3H, A11G, AC1, AE1, AH3, or AA6. Control cells were administered toxin only. The strength of each neutralizing VHH activity was observed by analyzing protection of cells from the toxin by VHH monomers. Percentage of cell rounding (% cell affected) caused by TcdA was monitored using a phase contrast microscope (FIG. 25). Thus, the strongest VHH produced the greatest protection at the lowest concentration. The VHHs were identified in the following order of efficacy:

AA6 as the strongest therapeutic agent, followed by AH3, AC1, AE1, A11G, and then A3H as weakest therapeutic agent.

To determine whether VHH monomers or VHH multimers effectively neutralized TcdA, CT26 cells were exposed for 24 hours to TcdA (2 ng/ml) and different concentrations (0.03 ng/mL, 0.1 ng/mL, 1 ng/mL, 3 ng/mL, 10 ng/mL, 30 ng/mL, 100 ng/mL, 300 ng/mL, or 1000 ng/mL) of VHH monomers (AH3 or AA6), VHH heterodimer containing AH3 and AA6, or a homodimer of the heterodimer containing the heterodimer of AH3 and AA6 and fused to an artificial homodimerization domain called oAgB (Ah3/AA6/oAgB; SEQ ID NO: 95). The oAgB domain encodes a peptide having amino acid sequence TSPSTVRLESRVRELEDRLEELRDELERAERRANEMSIQLDEC (SEQ ID NO: 94) that binds to proteins having the same sequence to form homodimers. The cysteine (amino acid abbreviation Cys or C) at the carboxyl end of AgBc becomes oxidized forming a covalent disulfide linkage between the two protein molecules to stabilize the homodimer (dimerizing sequence). Thus, the AH3/AA6 heterodimer itself becomes a homodimer containing two copies of AH3/AA6 joined by the oAgBc dimerization domain (SEQ ID NO: 95). Control cells were exposed to toxin only and not to VHH agents. The percentage of cell rounding (% cell affected) was monitored using a phase contrast microscope (FIG. 26).

Figure 26:
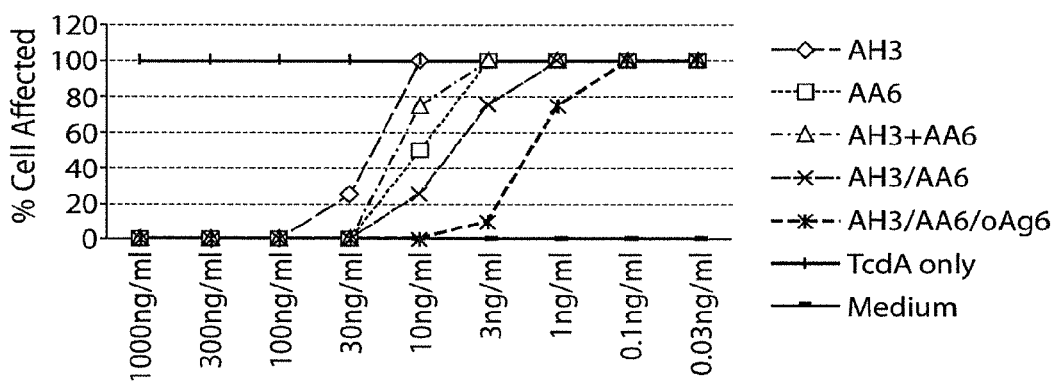
FIG. 26 is a line graph showing percent CT26 cells affected after 24 hours of TcdA exposure (ordinate) as a function of concentration administered (abscissa: 0.03 ng/mL, 0.1 ng/mL, 1 ng/mL, 3 ng/mL, 10 ng/mL, 30 ng/mL, 100 ng/mL, 300 ng/mL, or 1000 ng/mL), or toxin only control (TcdA; vertical line). Agents administered were: VHH monomer AH3 (AH3, diamond), VHH monomer AA6 (AA6, square), a mixture of VHH monomers AH3 and AA6 (AH3+AA6, triangle), VHH heterodimer of AH3 and AA6 (AH3/AA6, -x-); or a homodimer of heterodimer (tetramer)

Data show that control cells contacted with toxin only showed extensive toxin mediated-cell rounding, and that each of the VHH monomers, AH3/AA6 heterodimer and AH3/AA6/oAgB heterodimer/homodimer neutralized TcdA and protected the CT26 cells from the toxin (FIG. 26). The AH3/AA6/oAgB heterodimer/homodimer displayed greatest activity to neutralize and protect cells compared to the AH3/AA6 heterodimer, AH3 monomer, and AA6 monomer respectively. The AH3/AA6/oAgB heterodimer/homodimer displayed about three-fold stronger neutralizing activity for TcdA and protection of the cells than the AH3/AA6 heterodimer alone, and about ten-fold better activity and protection than the VHH monomers (AH3 and AA6 respectively).

Example 22: Heterodimer Binding Proteins Protect Cells from TcdA and TcdB

To determine activity of VHH heterodimers to neutralize both TcdA and TcdB, CT26 cells were exposed overnight to TcdA (2 ng/ml) or TcdB (0.1 ng/ml), and then treated with a heterodimer composition containing VHH 5D and VHH AA6 (FIG. 27 top graph) or with a heterodimer composition containing VHH 5D and VHH AH3 (FIG. 27 bottom graph). Each heterodimer was engineered to contain a VHH (5D) that strongly neutralized TcdB (FIG. 13) and to contain also a VHH (AA6 or AH3) that strongly neutralized TcdA (FIG. 25). The percentage of cell rounding (% cell affected) was monitored using a phase contrast microscope (FIG. 27 top and bottom graphs).

Data show that each of the 5D/AA6 heterodimer and the 5D/AH3 heterodimer neutralized both TcdA and TcdB (FIG. 27 top and bottom graphs). It was observed that 5D/AA6 heterodimer was about five-fold more effective in neutralizing TcdA than the 5D/AH3 heterodimer. Thus, the relative neutralization strength of each heterodimer (FIG. 27) corresponded to the relative neutralization strength of each corresponding AA6 monomer and AH3 monomer shown in FIGS. 25-26.

It was observed that the 5D/AA6 heterodimer was about three-fold or four-fold more effective to neutralize TcdB than the 5D/AH3 heterodimer. Using a concentration of about 0.2 nM of administered 5D/AA6 heterodimer, 50% of cells were protected, compared to about 1 nM of 5D/AH3 heterodimer required for this same level of protection. Without being limited by any particular theory or mechanism of action, it is here envisioned that the relative greater TcdA neutralization ability of the AA6 binding region compared to AH3 binding region resulted in a synergistically greater ability of the respective heterodimer to neutralize a separate toxin TcdB. The increased toxin neutralization for 5D/AA6 for TcdB is presumably caused by amino acid sequences in TcdA and TcdB that are similar and are neutralized effectively by the AA6 component of the heterodimer compared to the AH3 component of the heterodimer.

Example 23: 5D/AA6 Heterodimer Protected Subjects from *C. difficile* Infection

To further determine whether a single heterodimer could neutralize both TcdA and TcdB and protect mice from oral *C. difficile* spore challenge, a protocol for a clinically relevant mouse *C. difficile* infection model (Chen et al. 2008 Gastroenterology 135: 1984-1992) was performed as shown in FIG. 28. Groups of mice (ten mice/group) were treated to obtain a model of *C. difficile* associated diarrhea by treatment for three days with antibiotics in drinking water of the subjects, and then two days later by intraperitoneal administration of a single dose clindamycin before challenge with spores of a *C. difficile* strain expressing both TcdA and TcdB ($10^6$ spores/subject) on day zero (FIG. 28 A). To induce more severe and fulminant disease, steroid dexamethasone was supplied to the subjects in drinking water on day −6 (100 mg/mL) until day zero (Sun et al. 2001 Infection and Immunity 79: 2556-2864). Subjects were intraperitoneally injected with VHH heterodimer containing 5D and AA6 (1 mg/kg) three times (six hours, 16 hours, and 24 hours following inoculation/challenge). Control subjects were similarly treated by injection with PBS instead of the VHH heterodimer. Subjects were monitored hours and days following the VHH injection.

Data show that 100% of control subjects administered toxin died within two days of toxin challenge (FIG. 28 B) and suffered diarrhea (FIG. 28 C). Only 20% of subjects administered 5D/AA6 heterodimer developed diarrhea and 90% survived (FIGS. 28 B and C). Thus, 5D/AA6 heterodimer protected subjects from both TcdA and TcdB spore challenge in a clinically relevant mouse *C. difficile* infection model.

Example 24: Recombinant Multimeric Binding Proteins Neutralize a Plurality of Disease Agents Effectiveness of the antitoxin treatment using multimeric binding proteins are analyzed by determine ability of the binding proteins to bind to and neutralize a disease agent target.

Recombinant heteromultimeric neutralizing binding protein containing multiple binding regions with or without epitopic tags are produced. The binding regions are not identical and each binding region has affinity to specifically bind a non-overlapping portion of a disease agent: TcdA toxin, TcdB toxin, and a Shiga toxin. The genes encoding proteins are multimerized to form different heteromultimeric binding proteins using the oAgBc dimerization domain (SEQ ID NO: 94) shown in Example 21.

Subjects are exposed to a mixture of disease agents (TcdA toxin, TcdB toxin, Shiga toxin and a norovirus), and then are administered each of the heteromultimeric binding proteins, or a mixture of monoclonal antibodies specific for either TcdA, TcdB, Shiga Toxin 1, and the norovirus. Control subjects are administered the mixture of disease agents only (no multimeric binding proteins). Subjects are monitored for indicia of exposure to the pathogenic molecules such as diarrhea, fever, tachycardia, respiratory distress, and death.

Meyer-Kaplan plots quantifying survival of subjects are prepared and weeks later remaining subjects are sacrificed to analyze tissue and cell morphology. A surprising synergistic protective effect is observed for subjects administered the multimeric binding proteins with or without epitopic tags. Data show that subjects administered the multimeric binding proteins survive longer and have little or no indicia of exposure to the mixture of disease agents compared results for subjects administered monoclonal antibodies to each disease agent and for control subjects administered only disease agents. Subject administered heteromultimeric binding proteins specific for disease agents do not experience diarrhea, fever or other indicia of exposure to the disease agents. Tissues from subjects administered multimeric binding proteins show normal cell appearance without signs of cell rounding or cell lysis caused by either TcdA, TcdB, Shiga Toxin 1, and the norovirus. The multimeric binding proteins neutralize each of these disease agents. Control subjects have diarrhea, and tissues excised from the intestinal systems show indicia of colitis and extensive internal bleeding.

The multimeric binding protein specific for a mixture of bacterial toxins and a viral infectious agent neutralize each of the disease agents and protected the cells from the subjects from cytotoxicity and cell lysis.

Example 25: Materials and Methods

Purified, catalytically inactive mutant forms of full-length recombinant disease agent (shiga toxin, anthrax protective antigen, ricin A chain toxin, or ricin B chain) were obtained as described in Tremblay et al. pages 4593-4594. Shiga toxins were obtained from Phoenix Lab at Tufts Medical Center. Purified anti-Stx1 monoclonal antibody (mAb) 4D3, anti-Stx2 mAbs 3D1 and 5C12, and recombinant Stx1 B chain and recombinant Stx2 A and B chain were kindly provided by Dr. Abhineet Sheoran. Stx1 and Stx2 toxoids were prepared by formalin inactivation of the holotoxins and then dialyzed. Reagents for Western blotting were purchased from KPL Inc. (Gaithersburg, Md.). Antibodies used were anti-E-tag mAb (Phadia; Uppsala, Sweden); HRP-anti-E-tag mAb (Bethyl Laboratories Inc.; Montgomery, Tex.); HRP-anti-M13 Ab (GE Healthcare; Woburn, Mass.). Tremblay et al. pages 4593-4594 describe in detail the materials and methods used in examples herein.

Example 26: VHHs that Bind and Shiga Toxin

VHH binding agents were produced, purified and were screened to identify those that specifically bind to Shiga toxins. It was observed that one resulting VHHH, JET-H12, bound specifically to both Shiga-like toxin (Stx) 1 and Stx2. Another VHH, JFG-H6, was observed to bind specifically to Stx2 (See FIG. 29 A-B). The amino acid sequences and nucleotide sequences for JET-H12 and JFG-H6 were determined and are shown below:

JET-H12
(SEQ ID NO: 96)
QVQLVETGGGLVQAGDPLRLSCVASGRTVSRYDKAWFRQAPGKEREFVAG
ISWNGDTKIYADSVKGRFTISRENSRDTLDLQIDNLKPEDTAAYYCAVGI
AGVQSMARMLGVRYWGQGTQVTVSSEPKTPKPQ;

(SEQ ID NO: 97)
CAGGTGCAGCTCGTGGAGACGGGGGGAGGATTGGTGCAGGCTGGGGACCC
TCTGAGACTCTCCTGTGTAGCCTCTGGACGCACCGTCAGTCGCTATGACA
AGGCCTGGTTCCGCCAGGCTCCAGGGAAGGAGCGTGAGTTTGTAGCAGGA
ATTAGCTGGAACGGCGATACAAAAATTTATGCAGACTCCGTGAAGGGCCG
ATTCACCATCTCCAGAGAGAACTCCAGGGATACACTGGATCTGCAAATTG
ACAACCTGAAACCTGAGGACACGGCCGCGTATTACTGTGCGGTCGGAATT
GCGGGTGTTCAGAGTATGGCGCGTATGCTCGGAGTGCGCTACTGGGCCA
GGGGACCCAGGTCACCGTCTCCTCAGAACCCAAGACACCAAACCACAA;

JFG-H6
(SEQ ID NO: 98)
QVQLVETGGGLVQPGGSLRLSCAASGFSLDPYVIGWFRQAPGKEREGVSC
ITSRAASRTSVDSVNERFTISRDNAKNTVDLHINNLKPEDSGVYYCAAVP
PAKLPLFSLCRSLPAKYDYWGQGTQVTVSSAHHSEDPS;

(SEQ ID NO: 99)
CAGGTGCAGCTCGTGGAGACGGGGGGAGGCTTGGTGCAGCCTGGGGGGTC
TCTGAGACTCTCCTGTGCAGCCTCTGGTTTCAGTTTGGACCCTTATGTGA
TAGGATGGTTCCGGCAGGCCCCAGGGAAGGAGCGTGAGGGGGTCTCATGT
ATTACGAGTAGGGCTGCTAGTCGAACGTCTGTAGACTCCGTGAACGAGCG
ATTCACCATCTCCAGAGACAACGCCAAGAATACGGTCGATCTACACATCA
ATAACCTGAAACCTGAGGACTCGGCGTTTATTACTGTGCAGCGGTCCCC
CCTGCCAAATTACCACTTTTCAGCCTATGTCGCTCCCTGCCAGCAAAGTA
TGACTACTGGGGCCAGGGGACCCAGGTCACCGTCTCCTCAGCGCACCACA
GCGAAGACCCCTCG;

Example 27: VHHs that Bind Anthrax Protective Antigen

VHH binding agents were produced, purified and identified that are specific to anthrax protective antigen (PA) positive VHHs (See FIG. 29 A-B). It was observed that the following VHHs specifically bind anthrax PA: JHD-B6, JHE-D9, JIJ-A12, JIJ-B8, JIJ-C11, JIJ-D3, JIJ-F11, JIK-B8, JIK-B1, JIK-B12, and JIK-F4. The amino acid sequence and nucleotide sequence of each of these VHHs were determined and are shown below:

JHD-B6
(SEQ ID NO: 100)
QVQLVESGGGLVQPGGSLRLSCAASGSSFSRYAMRWYRQAPGKQRELVAN
INSRGTSNYADSVKGRFTISRDNAKNTVYLQMNSLKPEDTAVYYCNAEWL
GRSEPSWGQGTQVTVSSEPKTPKPQ;

(SEQ ID NO: 101)
CAGGTGCAGCTCGTGGAGTCGGGGGGAGGCTTGGTGCAGCCTGGGGGGTC
TCTGAGACTCTCCTGTGCAGCCTCTGGAAGTAGCTTCAGTAGATATGCCA

-continued
```
TGCGCTGGTACCGCCAGGCTCCAGGGAAGCAGCGCGAGTTGGTCGCAAAC

ATTAATAGTCGTGGTACCTCAAACTATGCAGACTCCGTGAAGGGCCGATT

CACCATCTCCAGAGACAACGCCAAGAACACGGTGTATCTGCAAATGAACA

GCCTGAAACCTGAAGCACGGCCGTCTATTATTGTAATGCAGAGTGGTTG

GGACGATCGGAGCCTTCCTGGGGCCAGGGGACCCAGGTCACCGTCTCCTC

GGAACCCAAGACACCAAAACCACAA;
```

JHE-D9

(SEQ ID NO: 102)
QVQLVESGGGLVQPGGSLRLSCAASGFIFSLYTMRWHRQAPGKERELVAT
ITSATGITNYADSVKGRFIISRDDAKKTGYLQMNSLKPEDTAVYYCNAVR
TTVSRDYWGQGTQVTVSSEPKTPKPQ;

(SEQ ID NO: 103)
```
CAGGTGCAGCTCGTGGAGTCAGGAGGAGGCTTGGTGCAGCCTGGGGGGTC

TCTGAGACTCTCCTGTGCAGCCTCTGGATTCATTTTCAGTCTTTATACCA

TGAGGTGGCACCGCCAGGCTCCAGGGAAGGAGCGCGAGTTGGTCGCGACT

ATTACTAGTGCTACTGGTATTACAAACTATGCAGACTCCGTGAAGGGCCG

ATTCATCATCTCCAGAGACGATGCCAAGAAGACGGGGTATCTGCAAATGA

ACAGCCTGAAACCTGAGGACACGGCCGTGTATTACTGTAATGCAGTCCGC

ACTACCGTGTCACGAGACTACTGGGGCCAGGGGACCCAGGTCACCGTCTC

CTCAGAACCCAAGACACCAAAACCACAA;
```

JIJ-A12

(SEQ ID NO: 104)
QVQLVESGGGLVQPGGSLRLSCAASGIIFSIYTMGWYRQAPGKERELVAA
IPSGPSANATDSVGGRFTITRDNAENTVYLQMNDLKPEDTAVYYCNARRG
PGIKNYWGQGTQVTVSSEPKTPKPQ;

(SEQ ID NO: 105)
```
CAGGTGCAGCTCGTGGAGTCTGGGGGAGGCTTGGTGCAGCCTGGGGGGTC

TCTGAGACTCTCCTGTGCAGCCTCTGGAATCATCTTCAGTATCTATACCA

TGGGCTGGTACCGCCAGGCTCCAGGGAAGCAGCGCGAATTGGTCGCAGCT

ATACCTAGTGGTCCTAGCGCAAACGCTACAGACTCCGTGGGGGCCGATT

CACCATCACCAGAGACAACGCCGAGAACACGGTGTATCTGCAAATGAACG

ACCTGAAACCTGAGGACACGGCCGTCTATTACTGTAATGCTCGGCGGGT

CCGGGTATCAAAAACTACTGGGGCCAGGGGACCCAGGTCACCGTCTCCTC

AGAACCCAAGACACCAAAACCACAA;
```

JIJ-B8

(SEQ ID NO: 106)
QVQLVESGGGLVQPGGSLSVSCAASGSIARPGAMAWYRQAPGKERELVAS
ITPGGLTNYADSVTGRFTISRDNAKRTVYLQMNSLQPEDTAVYYCHARII
PLGLGSEYRDHWGQGTQVTVSSAHHSEDPS;

(SEQ ID NO: 107)
```
CAGGTGCAGCTCGTGGAGTCCGGGGGCGGCTTGGTGCAGCCCGGGGGGTC

TCTGAGTGTCTCCTGTGCAGCCTCTGGAAGCATCGCAAGACCAGGTGCCA

TGGCCTGGTACCGCCAGGCTCCAGGGAAGGAGCGCGAGTTGGTCGCGTCT

ATTACGCCTGGTGGTCTTACAAACTATGCGGACTCCGTGACGGGCCGATT

CACCATTTCCAGAGACAACGCCAAGAGGACGGTGTATCTGCAGATGAACA

GCCTCCAACCCGAGGACACGGCCGTCTATTACTGTCATGCACGAATAATT

CCCCTAGGACTTGGGTCCGAATACAGGGACCACTGGGGCCAGGGGACTCA

GGTCACCGTCTCCTCAGCGCACCACAGCGAAGACCCCTCG;
```

JIJ-C11

(SEQ ID NO: 108)
QVQLVETGGGLVQPGGSLGLSCVVASGRSINNYGMGWYRQAPGKQRELVA
QISSGGTTNYAGSVEGRFTISRDNVKKMVYLQMNSLKPEDTAVYYCNSLL
RTFSWGQGTQVTVSSAHHSEDPS;

(SEQ ID NO: 109)
```
CAGGTGCAGCTCGTGGAGACGGGGGGAGGCTTGGTGCAGCCTGGGGGGTC

TCTGGGACTCTCCTGTGTAGTCGCCTCTGGAAGAAGCATCAATAATTATG

GCATGGGCTGGTACCGCCAGGCTCCAGGGAAGCAGCGCGAGTTGGTCGCG

CAAATTAGTAGTGGTGGTACCACAAATTATGCAGGCTCCGTAGAGGGCCG

ATTCACCATCTCCAGAGACAACGTCAAGAAAATGGTGTATCTTCAAATGA

ACAGCCTGAAACCTGAGGACACGGCCGTCTATTACTGTAATTCACTGCTC

CGAACTTTTTCCTGGGGCCAGGGGACCCAGGTCACCGTCTCCTCGGCGCA

CCACAGCGAAGACCCCTCG;
```

JIJ-D3

(SEQ ID NO: 110)
QVQLVETGGLVQPGGSLRLSCAASGLTFSSTAMAWFRQAPGKEREFVARI
SGAGITIYYSDSVKDRFTISRNNVENTVYLQMNSLKTEDTAVYYCAARRN
TYTSDYNIPARYPYWGQGTQVTVSSEPKTPKPQ;

(SEQ ID NO: 111)
```
CAGGTGCAGCTCGTGGAGACCGGGGGGTTGGTGCAGCCTGGGGGCTCCCT

GCGACTCTCCTGTGCAGCCTCCGGACTCACCTTCAGTAGCACTGCCATGG

CCTGGTTCCGCCAGGCTCCAGGGAAGGAGCGTGAGTTTGTAGCACGTATT

AGCGGGGCTGGTATTACGATCTACTATTCGGACTCCGTGAAGGACCGATT

CACCATCTCCAGAAACAACGTCGAGAACACGGTGTATTTGCAAATGAACA

GCCTGAAAACTGAGGACACGGCCGTTTACTACTGTGCAGCAAGACGGAAT

ACTTACACTAGCGACTATAACATACCCGCCCGGTATCCCTACTGGGGCCA

GGGGACCCAGGTCACCGTCTCCTCAGAACCCAAGACACCAAAACCACAA;
```

JIJ-E9

(SEQ ID NO: 112)
QVQLVETGGLVQPGGSLRLSCAASRSTTATIYSMNWYRQAPGKERELVAG
MTSDGQTNYATSVKGRFTISRDNAKNTVYLLMNSLKLEDTAVYYCYVKPW
RLQGWDYWGQGTQVTVSSEPKTPKPQ;

(SEQ ID NO: 113)
```
CAGGTGCAGCTCGTGGAGACGGGGGGCTTGGTGCAGCCTGGGGGGTCTCT

GAGACTCTCCTGTGCAGCCTCTAGAAGCACGACGGCCACAATTTATAGTA

TGAACTGGTACCGCCAGGCTCCAGGGAAGCAGCGCGAGTTGGTCGCGGGT

ATGACTAGTGATGGTCAGACAAACTATGCAACCTCCGTGAAGGGCCGATT

CACCATCTCCAGAGACAACGCCAAGAACACGGTATATTTGCTAATGAACA

GCCTGAAACTTGAGGACACGGCCGTCTATTATTGTTATGTAAAACCATGG

AGACTACAAGGTTGGGACTACTGGGGCCAGGGGACCCAGGTCACCGTCTC

CTCAGAACCCAAGACACCAAAACCACAA;
```

JIJ-F11

(SEQ ID NO: 114)
QVQLVESGGGLVQPGGSLRLSCAAPESIVNSRTMAWYRQAPGKQRERVAT
ITTAGSPNYADSVKGRFAISRDNAKNTVYLQMNSLKPEDTAVYYCNTLLS
TLPYGQGTQVTVSSAHHSEDPS;

(SEQ ID NO: 115)
CAGGTGCAGCTCGTGGAGTCGGGCGGCGGCTTGGTGCAGCCTGGGGGGTC
TCTGAGACTCTCCTGTGCAGCCCCTGAAAGCATCGTCAATAGCAGAACCA
TGGCCTGGTACCGCCAGGCTCCAGGAAAGCAGCGCGAAAGGGTCGCCACT
ATTACTACTGCTGGTAGCCCAAATTATGCAGACTCTGTGAAGGGCCGATT
CGCCATCTCCAGAGACAACGCCAAGAACACGGTATATCTGCAAATGAACA
GCCTGAAACCTGAGGACACGGCCGTCTATTACTGCAATACACTTCTCAGC
ACCCTTCCCTATGGCCAGGGGACCCAGGTCACCGTCTCCTCGGCGCACCA
CAGCGAAGACCCCTCG;

JIK-B8

(SEQ ID NO: 116)
QVQLVESGGGLVQPGGSLGLSCVVASERSINNYGMGWYRQAPGKQRELVA
QISSGGTTNYADSVEGRFTISRDNVKKMVHLQVNSLKPEDTAVYYCNSLL
RTFSWGQGTQVTVSSEPKTPKPQ;

(SEQ ID NO: 117)
CAGGTGCAGCTCGTGGAGTCGGGCGGAGGCTTGGTGCAGCCTGGGGGGTC
TCTGGGACTCTCCTGTGTAGTCGCCTCTGAAAGAAGCATCAATAATTATG
GCATGGGCTGGTACCGCCAGGCTCCAGGGAAGCAGCGCGAGTTGGTCGCG
CAAATTAGTAGTGGTGGTACCACAAATTATGCAGACTCCGTAGAGGGCCG
ATTCACCATCTCCAGAGACAACGTCAAGAAAATGGTGCATCTTCAAGTGA
ACAGCCTGAAACCTGAGGACACGGCCGTCTATTACTGTAATTCGCTACTC
CGAACTTTTTCCTGGGGCCAGGGGACCCAGGTCACCGTCTCCTCGGAACC
CAAGACACCAAAACCACAA;

JIK-B10

(SEQ ID NO: 118)
QVQLVETGGGLVQPGGSLRLSCAASGFTFSSYRMSWYRQAAGKERDVVAT
ITANGVPTGYADSVMGRFTISRDNAKNTVYLEMNSLNPEDTAVYYCNAPR
LHTSVGYWGQGTQVTVSSEPKTPKPQ;

(SEQ ID NO: 119)
CAGGTGCAGCTCGTGGAGACGGGAGGAGGCTTGGTGCAGCCTGGGGGGTC
TCTGAGACTCTCCTGTGCAGCCTCTGGATTCACCTTCAGTAGTTATCGCA
TGAGCTGGTACCGCCAGGCTGCAGGGAAGGAGCGCGACGTGGTCGCAACA
ATTACTGCTAATGGTGTTCCCACAGGCTATGCAGACTCCGTGATGGGCCG
ATTCACCATTTCCAGAGACAATGCCAAGAACACGGTGTATCTGGAAATGA
ACAGCCTGAATCCTGAGGACACGGCCGTGTATTACTGTAACGCGCCCCGT
TTGCATACATCTGTAGGCTACTGGGGCCAGGGGACCCAGGTCACCGTCTC
CTCAGAACCCAAGACACCAAAACCACAA;

JIK-B12

(SEQ ID NO: 120)
QVQLVESGGGLVQAGNSLRLSCTASGVIFSIYTMGWFRQAPGKEREFVAA
IGVADGTALVADSVTGRFTISRDNAKNTVYLHMNSLKPEDTAVYSCAAYL
SPRVQSPYITDSRYQLWGQGTQVTVSSEPKTPKPQ;

(SEQ ID NO: 121)
CAGGTGCAGCTCGTGGAGTCGGGAGGAGGATTGGTGCAGGCTGGGAACTC
TCTGAGACTCTCCTGTACGGCCTCTGGTGTGATCTTCTCTATCTATACCA
TGGGCTGGTTCCGCCAGGCTCCAGGGAAGGAGCGTGAGTTTGTAGCAGCG
ATAGGGGTGGCTGATGGTACCGCACTTGTGGCAGACTCCGTGACGGGCCG
ATTCACCATCTCCAGAGACAACGCCAAGAACACCGTTTATCTGCATATGA
ACAGCCTGAAGCCTGAGGACACGGCCGTCTATTCCTGTGCAGCGTATCTT
AGCCCCCGTGTCCAATCCCCCTACATAACTGACTCCCGGTATCAACTCTG
GGGCCAGGGGACCCAGGTCACCGTCTCCTCAGAACCCAAGACACCAAAAC
CACAA

JIK-F4

(SEQ ID NO: 122)
TGGGLVQAGGSLRLSCAASGRYAMGWFRQAPGKEREFVATISRSGAIREY
ADSVKGRFTISRDGAENTVYLEMNSLKPDDTAIYVCAEGRGATFNPEYAY
WGQGTQVTVSSAHHSEDPS;

(SEQ ID NO: 123)
CAGGTGCAGCTCGTGGAGACTGGGGGAGGATTGGTGCAGGCTGGGGGCTC
TCTGAGGCTCTCCTGTGCAGCCTCTGGACGCTATGCCATGGGCTGGTTCC
GCCAGGCTCCAGGGAAGGAGCGTGAATTTGTAGCGACTATTAGCCGGAGT
GGTGCTATCAGAGAGTATGCAGACTCCGTGAAGGGCCGATTCACCATCTC
CAGAGACGGCGCCGAGAACACGGTGTATCTGGAAATGAACAGCCTGAAAC
CTGACGACACGGCCATTTATGTCTGTGCAGAAGGACGAGGGGCGACATTC
AACCCCGAGTATGCTTACTGGGGCCAGGGGACCCAGGTCACCGTCTCCTC
AGCGCACCACAGCGAAGACCCCTCG;

Example 28: VHHs that Bind to Ricin Toxin A

VHH binding agents were produced, purified and identified that are specific to ricin toxin A chain (RTA; see FIG. 29 A-B). The following VHHs were determined to specifically bind RTA: JIV-F5, JIV-F6, JIV-G12, JIY-A7, JIY-D9, JIY-D10, JIY-E1, JIY-E3, JIY-E5, JIY-F10 and JIY-G11. The amino acid sequence and nucleotide sequence of each of these VHHs were determined and are shown below:

JIV-F5

(SEQ ID NO: 124)
QVQLVESGGGLVQPGGSLRLSCAASGFTLDDYAIGWFRQVPGKEREGVAC
VKDGSTYYADSVKGRFTISRDNGAVYLQMNSLKPEDTAVYYCASRPCFLG
VPLIDFGSWGQGTQVTVSSEPKTPKPQ;

(SEQ ID NO: 125)
CAGGTGCAGCTCGTGGAGTCGGGCGGAGGCTTGGTGCAGCCTGGGGGGTC
TCTGAGACTCTCCTGTGCAGCCTCTGGATTCACTTTGGATGATTATGCCA
TAGGCTGGTTCCGCCAGGTCCCAGGGAAGGAGCGTGAGGGGGTCGCATGT

```
GTTAAAGATGGTAGTACATACTATGCAGACTCCGTGAAGGGCCGATTCAC

CATCTCCAGAGACAACGGCGCGGTGTATCTGCAAATGAACAGCCTGAAAC

CTGAGGACACAGCCGTTTATTACTGTGCATCCAGGCCCTGCTTTTTGGGT

GTACCACTTATTGACTTTGGTTCCTGGGGCCAGGGGACCCAGGTCACCGT

CTCCTCGGAACCCAAGACACCAAAACCACAA;
```

JIV-F6

(SEQ ID NO: 126)
QVQLVESGGGLVQAGGSLRLSCATSGGTFSDYGMGWFRQAPGKEREFVAA

IRRNGNGGNGIEYADSVKGRFTISRDNAKNTVHLQMNSLTPEDTAVYYCA

ASISGYAYNTIERYNYWGQGTQVTVSSEPKTPKPQ;

(SEQ ID NO: 127)
```
CAGGTGCAGCTCGTGGAGTCAGGGGGAGGATTGGTGCAGGCTGGGGGCTC

TCTGAGACTCTCCTGCGCAACCTCTGGCGGCACCTTCAGTGACTATGGAA

TGGGCTGGTTCCGCCAGGCTCCAGGGAAGGAGCGTGAGTTTGTAGCAGCT

ATTAGGCGGAATGGTAATGGCGGTAATGGCATTGAATATGCAGACTCCGT

GAAGGGCCGATTCACCATCTCCAGAGACAACGCCAAGAACACGGTGCATC

TACAAATGAACAGCCTGACACCTGAGGACACGGCCGTTTATTACTGTGCA

GCGTCAATATCGGGATACGCTTATAACACAATTGAAAGATATAACTACTG

GGGCCAGGGAACCCAGGTCACCGTCTCCTCAGGAACCCAAGACACCAAAA

CCACAA;
```

JIV-G12

(SEQ ID NO: 128)
QVQLVESGGGLVQAGGSLSLSCAASGGDFSRNAMAWFRQAPGKEREFVAS

INWTGSGTYYLDSVKGRFTISRDNAKNALYLQMNNLKPEDTAVYYCARST

VFAEITGLAGYQSGSYDYWGQGTQVTVSSEPKTPKPQ;

(SEQ ID NO: 129)
```
CAGGTGCAGCTCGTGGAGTCCGGCGGAGGATTGGTGCAGGCGGGGGGCTC

TCTGAGTCTCTCCTGTGCAGCCTCTGGAGGTGACTTCAGTAGGAATGCCA

TGGCCTGGTTCCGTCAGGCTCCAGGGAAGGAGCGTGAATTTGTAGCATCT

ATTAACTGGACTGGTAGTGGCACATATTATCTAGACTCCGTGAAGGGCCG

ATTCACCATCTCCAGAGACAACGCCAAGAACGCCCTGTATCTGCAAATGA

ACAACCTGAAACCTGAGGACACGGCCGTTTATTACTGTGCACGCTCCACG

GTGTTTGCCGAAATTACAGGCTTAGCAGGCTACCAGTCGGGATCGTATGA

CTACTGGGGCCAGGGGACCCAGGTCACCGTCTCCTCAGAACCCAAGACAC

CAAAACCACAA;
```

JIY-A7

(SEQ ID NO: 130)
QVQLVETGGGTVQTGGSLRLSCSASGGSFSRNAMGWFRQAPGKEREFVAA

INWSASSTYYRDSVKGRFTVSRDNAKNTVYLHLNSLKLEDTAAYYCAGSS

VYAEMPYADSVKATSYNYWGQGTQVTVSSEPKTPKPQ;

(SEQ ID NO: 131)
```
CAGGTGCAGCTCGTGGAGACCGGCGGAGGAACGGTGCANACTGGGGGCTC

TCTGAGACTCTCCTGTTCAGCCTCTGGCGGCTCCTTCAGTAGGAATGCCA

TGGGCTGGTTCCGCCAGGCTCCAGGGAAGGAGCGTGAATTTGTAGCAGCT

ATTAACTGGAGTGCCTCTAGTACTTATTATAGAGACTCCGTGAAGGGACG

ATTCACCGTCTCCAGAGACAACGCCAAGAACACGGTGTATCTGCATTTGA

ACAGCCTGAAACTTGAGGACACGGCCGCGTATTACTGTGCTGGAAGCTCG

GTGTATGCAGAAATGCCGTACGCCGACTCTGTCAAGGCAACTTCCTATAA

CTACTGGGGCCAGGGGACCCAGGTCACCGTCTCCTCAGAACCCAAGACAC

CAAAACCACAA;
```

JIY-D9

(SEQ ID NO: 132)
QVQLVETGGGLVQAGGSLRLPCSFSGFPFDNYFVGWFRQAPGKEREGVSC

ISSSDGSTYYADSVKGRFTISRDNAKNTVYLQMNSLKPEDTAVYYCGADF

LTPHRCPALYDYWGQGTQVTVSSAHHSEDPS;

(SEQ ID NO: 133)
```
CAGGTGCAGCTCGTGGAGACCGGGGGAGGCTTGGTGCAGGCTGGGGGGTC

TCTGAGACTCCCCTGTTCATTCTCTGGATTCCCTTTCGATAATTATTTCG

TAGGCTGGTTCCGCCAGGCCCCAGGGAAGGAGCGTGAGGGGGTCTCATGT

ATTAGTAGTAGTGATGGTAGCACATACTATGCAGACTCCGTGAAGGGCCG

GTTCACCATCTCCAGAGACAACGCCAAGAACACGGTGTATCTGCAAATGA

ACAGTCTGAAACCTGAGGATACGGCCGTTTATTACTGTGGAGCAGATTTC

CTCACCCCACATAGGTGTCCAGCCTTATATGACTACTGGGGCCAGGGGAC

CCAGGTCACCGTCTCCTCAGCGCACCACAGCGAAGACCCCTCG;
```

JIY-D10

(SEQ ID NO: 134)
QVQLVESGGGLVQPGGSLRLHCAASGSIASIYRTCWYRQGTGKQRELVAA

ITSGGNTYYADSVKGRFTISRDNAKNTIDLQMNSLKPEDTAVYYCNADEA

GIGGFNDYWGQGTQVTVSSAHHSEDPS;

(SEQ ID NO: 135)
```
CAGGTGCAGCTCGTGGAGTCTGGTGGAGGCTTGGTGCAGCCTGGGGGGTC

TCTGAGACTCCACTGTGCAGCCTCTGGAAGCATCGCCAGTATCTATCGCA

CGTGCTGGTACCGCCAGGGCACAGGGAAGCAGCGCGAGTTGGTCGCAGCC

ATTACTAGTGGTGGTAACACATACTATGCGGACTCCGTTAAGGGCCGATT

CACCATCTCCAGAGACAACGCCAAAAACACAATCGATCTGCAAATGAACA

GCCTGAAACCTGAGGACACGGCCGTCTATTACTGTAATGCAGACGAGGCG

GGGATCGGGGGATTTAATGACTACTGGGGCCAGGGGACCCAGGTCACCGT

CTCCTCAGCGCACCACAGCGAAGACCCCTCG;
```

JIY-E1

(SEQ ID NO: 136)
QVQLVESGGGLVQAGGSLRLSCAASGRTFSRSSMGWFRQAPGKEREFVAS

IVWADGTTLYGDSVKGRFTVSRDNVKNMVYLQMNNLKPEDTALYYCADNK

FVRGLVAVRAIDYDYWGQGTQVTVSSEPKTPKPQ;

(SEQ ID NO: 137)
```
CAGGTGCAGCTCGTGGAGTCGGGGGGAGGATTGGTGCAGGCTGGGGGCTC

TCTGAGACTCTCCTGTGCAGCCTCTGGACGCACCTTCAGTCGCAGTTCCA

TGGGCTGGTTCCGCCAGGCTCCAGGGAAGGAGCGTGAATTCGTTGCGTCC

ATTGTCTGGGCTGATGGTACGACGTTGTATGGAGACTCCGTAAAGGGCCG

ATTCACCGTCTCCAGGGACAACGTCAAGAACATGGTGTATCTACAAATGA

ACAACCTGAAACCTGAGGACACGGCCCTTTATTACTGTGCGGACAATAAA
```

JIY-E3

(SEQ ID NO: 138)
QVQLVESGGLVQAGGSLRLSCAASGRADIIYAMGWFRQAPGKEREFVAAV
DWSGGSTYYADSVKGRFTISRDNAKNSVYLQMNSLKPEDTAVYYCAARRS
WYRDALSPSRVYEYDYWGQGTQVTVSSEPKTPKPQ;

(SEQ ID NO: 139)
CAGGTGCAGCTCGTGGAGTCGGGAGGATTGGTGCAGGCTGGAGGCTCTCT
GAGACTCTCCTGCGCAGCCTCTGGACGCGCCGACATAATCTATGCCATGG
GCTGGTTCCGCCAGGCTCCAGGGAAGGAGCGTGAGTTTGTAGCGGCAGTA
GACTGGAGTGGTGGTAGCACATACTATGCAGACTCCGTGAAGGGCCGATT
CACCATCTCCAGAGACAACGCCAAGAACTCGGTGTATCTGCAAATGAACA
GCCTGAAACCTGAGGACACGGCCGTTTATTACTGTGCAGCCCGAAGGAGC
TGGTACCGAGACGCGCTATCCCCCTCCCGGGTGTATGAATATGACTACTG
GGGCCAGGGGACCCAGGTCACCGTCTCCTCAGAACCCAAGACACCAAAAC
CACAA;

JIY-E5

(SEQ ID NO: 140)
QVQLVETGGGLVQPGGSLTLSCAGSGGTLEHYAIGWFRQAPGKEHEWLVC
NRGEYGSTVYVDSVKGRFTASRDNAKNTVYLQLNSLKPDDTGIYYCVSGC
YSWRGPWGQGTQVTVSSAHHSEDPS;

(SEQ ID NO: 141)
CAGGTGCAGCTCGTGGAGACGGGAGGAGGCTTGGTGCAGCCTGGGGGGTC
TCTGACACTCTCCTGTGCAGGCTCCGGTGGCACTTTGGAACATTATGCTA
TAGGCTGGTTCCGCCAGGCCCCTGGGAAAGAGCATGAGTGGCTCGTATGT
AATAGAGGTGAATATGGGAGCACTGTCTATGTAGACTCCGTGAAGGGCCG
ATTCACCGCCTCCAGAGACAACGCCAAGAACACGGTGTATCTGCAATTGA
ACAGTCTGAAACCTGACGACACAGGCATTTATTACTGTGTATCGGGATGT
TACTCCTGGCGGGTCCCTGGGGCCAGGGGACCCAGGTCACCGTCTCCTC
GGCGCACCACAGCGAAGACCCCTCG;

JIY-F10

(SEQ ID NO: 142)
QVQLVESGGGLVQPGGSLKLSCRASGSIVSIYAVGWYRQAPGKQRELLAA
ITTDGSTKYSDSVKGRFTISRDNAKNTVYLQMNNLKPEDTAIYSCIGDAA
GWGDQYYWGQGTQVTVSSEPKTPKPQ;

(SEQ ID NO: 143)
CAGGTGCAGCTCGTGGAGTCTGGGGGAGGTTTGGTGCAGCCTGGGGGGTC
TCTGAAACTCTCCTGTAGAGCCTCTGGAAGCATAGTCAGTATCTATGCCG
TGGGCTGGTACCGCCAGGCTCCAGGGAAGCAGCGCGAGTTGCTCGCGGCT
ATCACTACTGATGGTAGCACAAAGTACTCAGACTCCGTGAAGGGCCGATT
CACCATCTCCCGAGACAACGCCAAGAACACGGTATATCTGCAAATGAACA
ACCTCAAACCTGAGGACACGGCCATCTATTCCTGTATCGGGGACGCGGCG
GGTTGGGGCGACCAATACTACTGGGGCCAGGGGACCCAGGTCACCGTCTC
CTCAGAACCCAAGACACCAAAACCACAA;

JIY-G11

(SEQ ID NO: 144)
QVQLVESGGGLVQAGGSLRLSCAASGSIVNFETMGWYRQAPGKERELVAT
ITNEGSSNYADSVKGRFTISGDNAKNTVSLQMNSLKPEDTAVYYCSATFG
SRWPYAHSDHWGQGTQVTVSSEPKTPKPQ;

(SEQ ID NO: 145)
CAGGTGCAGCTCGTGGAGTCAGGCGGAGGCTTGGTGCAGGCTGGGGGGTC
TCTGAGACTCTCCTGTGCAGCCTCTGGAAGCATCGTCAATTTCGAAACCA
TGGGCTGGTACCGCCAGGCTCCAGGGAAGGAGCGCGAGTTGGTCGCAACT
ATTACTAATGAAGGTAGTTCAAACTATGCAGACTCCGTGAAGGGCCGATT
CACCATCTCCGGAGACAACGCCAAGAACACGGTGTCCCTGCAAATGAACA
GCCTGAAACCTGAGGACACGGCCGTCTACTACTGTTCGGCGACGTTCGGC
AGTAGGTGGCCGTACGCCCACAGTGATCACTGGGGCCAGGGGACCCAGGT
CACCGTCTCCTCAGAACCCAAGACACCAAAACCACAA;

Example 29: VHHs Specific for Ricin Toxin B

VHH binding agents were produced, purified and identified that are specific to ricin toxin B chain (See FIG. 29 A-B). VHHs that specifically bind RTB were determined and are: JIW-B1, JIW-C12, JIW-D12, JIW-G5, JIW-G10, JIZ-B7, JIZ-B9, JIZ-D8, and JIZ-G4. The amino acid sequence and nucleotide sequences of each of these VHHs were determined and are shown below:

JIW-B1

(SEQ ID NO: 146)
QVQLVETGGALVHTGGSLRLSCEVSGSTFSSYGMAWYRQAPGEQRKWVAG
IMPDGTPSYVNSVKGRFTISRDNAKNSVYLHMNNLRPEDTAVYYCNQWPR
TMPDANWGRGTQVTVSSEPKTPKPQ;

(SEQ ID NO: 147)
CAGGTGCAGCTCGTGGAGACGGGCGGAGCATTGGTGCACACTGGGGGTTC
TCTGAGACTCTCCTGCGAAGTCTCCGGAAGCACCTTCAGTAGCTATGGCA
TGGCCTGGTACCGCCAAGCTCCAGGCGAGCAGCGTAAGTGGGTCGCAGGT
ATTATGCCGGATGGTACTCCAAGCTATGTAAACTCCGTGAAGGGCCGATT
CACCATCTCCAGAGACAACGCCAAGAACTCGGTGTATCTGCACATGAACA
ACCTGAGGCCTGAAGACACGGCCGTCTATTATTGCAACCAATGGCCGCGC
ACGATGCCTGACGCGAACTGGGGCCGGGGGACCCAGGTCACCGTCTCCTC
AGAACCCAAGACACCAAAACCACAA;

JIW-C12

(SEQ ID NO: 148)
QVQLVETGGSLRLTCVTSGSTFNNPAITWYRQPPGKQREWVASLRSGDGP
VYRESVKGRFTIFRDNATDALYLRMNSLKPEDTAVYHCNTASPASWLDWG
QGTQVTVSSEPKTPKPQ;

(SEQ ID NO: 149)
CAGGTGCAGCTCGTGGAGACTGGGGGGTCTCTGAGGCTCACCTGTGTAAC
CTCTGGAAGCACCTTCAATAATCCTGCCATAACCTGGTACCGCCAGCCTC
CAGGGAAGCAGCGTGAGTGGGTCGCAAGTCTTCGTAGTGGTGATGGTCCA
GTATATAGGGAATCCGTGAAGGGCCGATTCACCATTTTTAGAGACAACGC
CACGGACGCGCTGTATCTGCGGATGAATAGCCTGAAACCTGAGGACACGG
CCGTCTATCACTGTAACACCGCCTCACCTGCTAGTTGGCTGGACTGGGGC
CAGGGGACCCAGGTCACTGTCTCCTCAGAACCCAAGACACCAAAACCACA
A;

JIW-D12
(SEQ ID NO: 150)
QVQLVETGGGLVQPGGSLRLSCATSGFPFSTERMSWVRQAPGKGLEWVSG
ITEGGETTLAAPSVKGRFNISRDNARNILYLQMNSLKPEDAAVYYCFRGV
FFRTSFPPELARGQGTQVTVSSEPKTPKPQ;

(SEQ ID NO: 151)
CAGGTGCAGCTCGTGGAGACGGGAGGAGGATTGGTGCAACCTGGGGGTTC
TCTGAGACTCTCTTGTGCAACCTCTGGATTCCCCTTCAGTACGGAGCGTA
TGAGCTGGGTCCGCCAGGCTCCAGGAAAGGGGCTCGAGTGGGTCTCAGGT
ATTACTGAGGGTGGTGAAACCACTCTCGCGGCACCCTCCGTGAAGGGCCG
ATTCAACATCTCCAGAGACAACGCCAGGAATATCCTATATCTACAGATGA
ATTCCTTGAAACCTGAGGACGCGGCCGTTTACTATTGTTTTAGAGGTGTT
TTTTTTTAGAACGAGTTTTCCTCCCGAACTCGCGCGGGGCCAGGGGACCCA
GGTCACCGTCTCCTCAGAACCCAAGACACCAAAACCACAA;

JIW-G5
(SEQ ID NO: 152)
QVQLVESGGGLVQAGGSLRLSCAASGSAVSDSFSTYAISWHRQAPGKQRE
WIAGISNRGATSYRDSVKGRFTISRDNAKNTVYLQMNNLKPEDTGVYYCE
PWPREGLGGGQGTQVTVSSEPKTPKPQ;

(SEQ ID NO: 153)
CAGGTGCAGCTCGTGGAGTCGGGCGGAGGCTTGGTGCAGGCAGGGGGGTC
TTTGAGACTCTCCTGTGCAGCCTCTGGAAGCGCCGTCAGTGACAGCTTCA
GTACCTATGCCATCTCCTGGCACCGCCAGGCTCCAGGGAAGCAGCGTGAG
TGGATCGCAGGTATTAGTAATCGTGGTGCGACAAGCTATAGAGACTCCGT
GAAGGGCCGATTCACCATCTCCAGAGACAACGCCAAGAACACGGTATATC
TGCAAATGAACAACCTGAAACCTGAGGACACGGGCGTCTATTATTGTGAG
CCATGGCCACGCGAAGGACTTGGGGGGGGCCAGGGGACTCAGGTCACCGT
CTCCTCAGAACCCAAGACACCAAAACCACAA;

JIW-G10
(SEQ ID NO: 154)
QVQLVESGGGSVQTGGSLTLSCVVSGSTFSDYAVAWYRQVPGKSRAWVAG
VSTTGSTSYTDSVRGRFTISRDNHKKTVYLSMNSLKPEDTGIYYCNLWPF
TNPPSWGQGTQVTVSSAHHSEDPS;

(SEQ ID NO: 155)
CAGGTGCAGCTCGTGGAGTCGGGGGGAGGCTCGGTGCANACTGGGGGGTC
TCTGACACTCTCCTGTGTAGTCTCTGGAAGTACCTTCAGTGACTATGCGG
TGGCCTGGTACCGCCAGGTTCCAGGCAAATCGCGTGCGTGGGTCGCGGGT
GTTAGTACTACTGGCTCGACATCTTATACAGACTCCGTGAGGGGCCGGTT
CACCATCTCCAGAGACAACCACAAGAAGACGGTGTATCTTTCAATGAACA
GCCTGAAACCTGAGGACACGGGCATCTATTACTGCAACTTATGGCCGTTC
ACAAATCCTCCTTCCTGGGGCCAGGGAACCCAAGTCACCGTTTCCTCGGC
GCACCACAGCGAAGACCCCTCG;

JIZ-B7
(SEQ ID NO: 156)
QVQLVESGGAVVQPGGSLRLSCATSGFTFSDDRMSWARQAPGKGLEWVSG
ISTASEGFATLYAPSVKGRFTISRDNAKHMLYLQMDTLKPEDTAVYYCLR
GVFFRTNIPPEVLRGQGTQVTVSSAHHSEDPS;

(SEQ ID NO: 157)
CAGGTGCAGCTCGTGGAGTCTGGAGGAGCCGTGGTGCAACCTGGGGGTTC
TCTGAGACTCTCCTGTGCAACCTCTGGATTCACCTTCAGTGACGATCGTA
TGAGCTGGGCCCGCCAGGCTCCAGGAAAGGGGCTCGAGTGGGTCTCAGGT
ATTAGTACTGCTAGTGAAGGTTTTGCTACACTCTACGCACCCTCCGTGAA
GGGCCGATTCACCATCTCCAGAGACAACGCCAAGCATATGCTGTATCTGC
AAATGGATACCTTGAAACCTGAGGACACGGCCGTGTATTACTGTTTAAGA
GGGGGTTTTTTTAGAACGAACATTCCTCCCGAGGTACTGCGGGGCCAGGG
GACCCAGGTCACCGTCTCCTCAGCGCACCACAGCGAAGACCCCTCG;

JIZ-B9
(SEQ ID NO: 158)
QVQLVETGGDLVQPGGSLRLSCAASGSSFSRAAVGWYRQAPGKEREWVAR
LASGDMTDYTESVRGRFTISRDNAKHTVYLQMDNLKPEDTAVYYCKARIP
PYYSIEYWGKGTRVTVSSEPKTPKPQ;

(SEQ ID NO: 159)
CAGGTGCAGCTCGTGGAGACGGGGGGAGACTTGGTGCANCCTGGGGGGTC
TCTGAGACTCTCCTGTGCAGCCTCTGGAAGCTCCTTCAGCCGCGCTGCCG
TGGGCTGGTACCGTCAGGCTCCAGGAAAGGAGCGTGAGTGGGTCGCACGT
CTCGCGAGTGGTGATATGACGGACTATACCGAGTCCGTGAGGGGCCGATT
CACTATCTCCAGAGACAACGCCAAGCACACGGTATATCTGCAAATGGACA
ACCTGAAACCTGAGGACACGGCCGTCTACTATTGTAAGGCCAGGATACCC
CCTTATTACTCTATAGAGTACTGGGGCAAAGGGACCCGGGTCACCGTCTC
CTCANAACCCAAGACACCAAAACCACAA;

JIZ-D8
(SEQ ID NO: 160)
QVQLVETGGGLVQAGGSLRLSCVVSSPLFNLYDMAWYRQAPGNQRELVAG
ILTDGRATYSDSVKGRFTISRNNLTNTVFLQMSSLKPEDTAVYYCNRKNS
IYWDSWGQGTQVTVSSEPKTPKPQ;

(SEQ ID NO: 161)
CAGGTGCAGCTCGTGGAGACAGGTGGAGGCTTGGTGCAGGCTGGGGGGTC
TCTGAGACTCTCCTGTGTAGTATCTAGTCCCCTGTTCAATCTTTACGACA
TGGCCTGGTATCGCCAGGCTCCAGGGAATCAGCGTGAGTTGGTCGCAGGC
ATCTTGACTGATGGTCGCGCAACATATTCAGACAGCGTGAAGGGCCGATT
CACCATTTCCAGAAACAACCTGACGAACACGGTGTTTTTACAAATGAGCA
GCCTGAAACCTGAGGACACGGCCGTCTATTATTGTAATAGAAAGAATAGT

-continued
ATCTACTGGGATTCCTGGGGCCAGGGGACCCAGGTCACCGTCTCCTCGGA

ACCCAAGACACCAAAACCACAA;

JIZ-G4
(SEQ ID NO: 162)
QVQLVESGGGLVQAGGSLRLSCVASGLTFSRYGMGWFRQAPGQERVVVSV

ISPDGGSAYYADSVKGRFTISRDNAKNTVYLQMSTLRFEDTGVYYCTAGP

RNGATTVLRPGDYDYWGQGTQVTVSSEPKTPKPQ;
and (SEQ ID NO: 163)
CAGGTGCAGCTCGTGGAGTCGGGGGGAGGATTGGTGCAGGCTGGGGCTC

TCTGAGACTCTCCTGCGTAGCCTCTGGACTCACCTTCAGTCGCTATGGCA

TGGGCTGGTTCCGCCAGGCTCCAGGACAGGAGCGTGTAGTCGTATCAGTT

ATTAGTCCCGACGGTGGTAGCGCATACTACGCAGACTCCGTGAAGGGCCG

ATTCACCATCTCCAGAGACAACGCCAAGAACACGGTGTATCTGCAAATGA

GCACCCTGAGATTTGAGGACACGGGCGTTTATTATTGTACAGCAGGGCCC

CGGAATGGAGCGACTACAGTCCTCCGGCCAGGGGATTATGACTACTGGGG

CCAGGGGACCCAGGTCACTGTCTCCTCAGAACCCAAGACACCAAAACCAC

AA

Example 30: VHH Binding Proteins Bind to Neutralized Toxin-Disease Agents

Effectiveness of the antitoxin treatment using VHH binding proteins composed of SEQ ID NOs:96-163 were analyzed to determine ability of the binding proteins to bind to and neutralize a toxin disease agent target (see Tremblay et al. and FIGS. 29 A and B). Data show that the VHH effectively bound to and neutralized Stx 1, Stx2, anthrax toxins, RTA, and RTB.

Example 31: Recombinant Multimeric Binding Proteins Neutralize a Plurality of Disease Agents Recombinant heteromultimeric neutralizing binding proteins containing multiple binding regions composed of any of SEQ ID NOs: 96-163 are produced. At least two of the binding regions are not identical and each binding region has affinity to specifically bind a non-overlapping portion of a disease agent associated with toxin proteins produced by bacteria or plants such as a Shiga toxin, a ricin toxin (e.g., RTA and RTB), and anthrax toxin.

Subjects are exposed to one or more of Shiga toxin, ricin toxin A chain, and ricin toxin B chain, and then are administered each of the heteromultimeric binding proteins. Control subjects are administered the one or more disease agents only (no multimeric binding proteins). Subjects are monitored for indicia of exposure to the pathogenic molecules such as diarrhea, fever, tachycardia, respiratory distress, and death.

Subject administered heteromultimeric binding proteins specific for disease agents are observed to have little or no indicia of exposure to the one or more disease agents. In vitro analysis of cell, blood and tissue samples from the subjects show that the multimeric binding proteins neutralize each of these disease agents in the samples. Control subjects show indicia of being exposed to the disease agents (e.g., diarrhea, internal bleeding, and cell lysis). Thus, the recombinant heteromultimeric neutralizing binding proteins are found to be effective inhibitors of the toxin disease agents.

Example 32: VHHs that Bind and Neutralize Plant Toxins

Methods as described in Examples herein using phage libraries are used to produce and identify VHHs that specifically bind and neutralize plant toxins. The VHHs specifically neutralize each of the following plant toxins: Akar saga (*Abrus precatorius*), Deathcamas, Amianthium Angel's Trumpet (*Brugmansia*), Angel Wings (*Caladium*), Anticlea, Autumn crocus (*Colchicum autumnale*), Azalea (*Rhododendron*), Bittersweet nightshade (*Solanum dulcamara*), Black hellebore (*Helleborus niger*), Black locust (*Robinia pseudoacacia*), Black nightshade (*Solanum nigrum*), Bleeding heart (*Dicentra cucullaria*), Blind-your-eye mangrove (*Excoecaria agallocha*), Blister Bush (*Peucedanum galbanum*), Bloodroot (*Sanguinaria canadensis*), Blue-green algae (*Cyanobacteria*), Bobbins (*Arum maculatum*), Bracken (*Pteridium aquilinum*), Broom (*Cytisus scoparius*), calabar bean (*Physostigma venenosum*), castor bean, Christmas rose (*Helleborus niger*), Columbine (*Aquilegia*), Corn cockle (*Agrostemma githago*), corn lily (*veratrum*), cowbane (*Cicuta*), cows and bulls (*Arum maculatum*), crab's eye (*Abrus precatorius*), cuckoo-pint (*Arum maculatum*), daffodil (*Narcissus*), Darnel (*Lolium temulentum*), Deadly nightshade (*Atropa belladonna*), Devils and angels (*Arum maculatum*), False acacia (*Robinia pseudoacacia*), False hellebore (*Veratrum*), Foxglove (*Digitalis purpurea*), Frangipani (*Plumeria*), Doll's eyes (*Actaea pachypoda*), Dumbcane (*Dieffenbachia*), Dutchman's breeches (*Dicentra cucullaria*), Elder/Elderberry (*Sambucus*), Giant hogweed (*Heracleum mantegazzianum*), Giddee giddee, Gifblaar (*Dichapetalum cymosum*), Greater celandine (*Chelidonium majus*), Gympie gympie (*Dendrocnide moroides*), Heart of Jesus (*Caladium*), hemlock (*Conium maculatum*), hemlock water-dropwort (*Oenanthe crocata*), henbane (*Hyoscyamus niger*), Horse chestnut (*Aesculus hippocastanum*), Holly (*Ilex aquifolium*), Hyacinth (*Hyacinthus orientalis*), Indian licorice, Jack in the pulpit, Jamestown weed, jequirity, Jerusalem cherry, Jimson weed, John Crow bead, Jumbie bead, Lily of the Valley, Lords and Ladies, Madiera winter cherry, Mayapple, Meadow saffron, Milky mangrove, Monkshood, Moonseed, Passion flower, *Plumeria*, Poison hemlock, Poison ivy, Poison oak, Poison parsnip, Poison sumac, Poison ryegrass, Pokeweed, Precatory bean, Privet, ragwort, redoul, River poison tree, *Robinia pseudoacacia* (also known as black locust and false acacia), Rosary pea, Sosnowsky's Hogweed, Spindle tree, Starch-root, Stenanthium, Stinging tree, Stinkweed, Strychnine tree, Suicide tree (*Cerbera odollam*), thorn apple, Toxicoscordion, Wake robin, Water hemlock, White baneberry, White snakeroot, Wild *arum*, Winter cherry, Wolfsbane, Yellow Jessamine, Yew, and Zigadenus.

Example 33: Immunoassay Using VHHs to Detect Toxin

Immunoassay are performed using VHH camelids to detect toxin in samples. Each of toxin-specific VHHs SEQ ID NO: 96, SEQ ID NO: 98, SEQ ID NO:100, SEQ ID NO:102, SEQ ID NO:104, SEQ ID NO:106, SEQ ID NO:108, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, and SEQ ID NO:162 are separately incubated in buffer in wells of a plastic microtiter plate. The VHH camelids are incubated for sufficient time and under conditions such that the VHHs are adsorbed to the surface of the well. Control cells are incubated with buffer only.

A panel of diluted aliquots of a sample containing either a Shiga toxin, a B. anthracis toxin, a ricin A chain toxin, or a ricin B chain toxin are incubated in duplicate in the VHH-coated wells and control wells, such that the VHH in the VHH-coated wells specifically bind to the toxin, thereby retaining the toxin in the well. Wells are washed to remove toxin that is not specifically bound to the VHH camelids.

A polyclonal antibody with enzymes or dye molecules attached to the polyclonal antibody is contacted to the wells, thereby forming an toxin antigen 'sandwich' between the VHH camelids and the polyclonal antibody. The enzymes or dye molecules attached to the polyclonal antibodies generate a color signal proportional to the amount of target toxin present in the sample added to the wells of the plate. It is observed that the toxin-specific VHHs specifically bound the respective toxin, such that SEQ ID NO: 96 and SEQ ID NO: 98 specifically bind the Shiga toxin, and SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, and SEQ ID NO: 122 specifically bind the anthrax toxin, and SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, and SEQ ID NO: 144 specifically bind the ricin A chain toxin, and wherein SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, and SEQ ID NO: 162 specifically bind the ricin B chain toxin.

Example 34: Immunofluorescence Staining Using the Toxin-Specific VHHs

Subconfluent test cells on coverslips are treated with toxin (either a Shiga toxin, a B. anthracis toxin, a ricin A chain toxin, or a ricin B chain toxin) alone or toxin in the presence of the toxin-specific VHHs (specific VHHs SEQ ID NO: 96, SEQ ID NO: 98, SEQ ID NO:100, SEQ ID NO:102, SEQ ID NO:104, SEQ ID NO:106, SEQ ID NO:108, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, and SEQ ID NO:162). The cells are fixed with paraformaldehyde, followed by permeabilization in a permeabilizing buffer. For immunocomplex or toxin staining, cells are incubated with fluorochrome-conjugated anti-VHH, or polyclonal rabbit anti-toxin serum (prepared herein by methods known to one of skill in the art of antibody production), followed by fluorochrome-conjugated anti-rabbit-IgG. Cells are counterstained with 4', 6-diamidino-2-phenylindole (DAPI) and imaged using a confocal microscope. Surface binding of toxin-specific VHHs to cells is examined by flow cytometry.

Data from the immunofluorescence staining that the toxin-specific VHHs specifically bind the respective toxin, and the toxin-specific VHHs are effective for detecting the toxin, such that SEQ ID NO: 96 and SEQ ID NO: 98 specifically bind the Shiga toxin, and SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, and SEQ ID NO: 122 specifically bind the anthrax toxin, and SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, and SEQ ID NO: 144 specifically bind the ricin A chain toxin, and wherein SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, and SEQ ID NO: 162 specifically bind the ricin B chain toxin.

Test cells are incubated with toxin alone, toxin/toxin-specific VHH, or toxin/non-specific VHH, followed by phycoerythrin-conjugated anti-VHH staining. Cells are subsequently analyzed by cell sorting using a FACS Calibur flow cytometer. Data show that the VHHs effectively detect the location and relative abundance of specific Shiga toxin proteins, anthrax proteins, and ricin toxin proteins.

Example 35: Construction and Expression of a Heterotetramer of Four VHHs, Two Neutralizing VHHs that Target TcdA and Two VHHs that Target TcdB An embodiment of the invention herein provides small binding agents that neutralize one of the C. difficile toxins have been identified. The binding agents are Vh domains prepared from heavy chain-only antibodies of Camelid animals such as alpacas, also called VHHs. U.S. patent application Ser. No. 13/566,524 filed Aug. 3, 2012 and U.S. provision patent application No. 61/809,685 filed Apr. 8, 2013, which are hereby incorporated by reference in their entirety, describe proteins that have two linked pathogen neutralizing VHHs that recognize distinct, non-overlapping epitopes on the target, and those proteins have enhanced substantially enhance neutralization potency compared to each VHH separately. Example 24 herein envisions linking neutralizing VHHs into a heteromultimer to target more than one pathogen, thereby permitting the neutralization of multiple pathogens by a single biomolecule. The present example describes construction and expression of a heterotetramer of four VHHs, two neutralizing VHHs that target TcdA and two VHHs that target TcdB and was demonstrated to be active. This molecule, a VHH-based neutralizing agent (VNA) which targets both C. difficile Tcd toxins, is referred to as 'VNA2-Tcd'.

The amino acid sequence of VNA2-Tcd protein is shown below (SEQ ID NO: 170). The protein contains two copies of an epitopic tag, E-tag (GAPVPYPDPLEPR; SEQ ID NO: 15) that flanks the four linked recombinant VHH binding domain proteins and permits binding an anti-E-tag mAb to the target to promote antibody effector activities (see U.S. Pat. No. 8,349,326 issued Jan. 8, 2013). The epitopic tag is optional and this sequence is merely exemplary and not further limiting. The sequence further includes an optional 13 amino acid albumin binding domain (DICLPRWGCL-WED; SEQ ID NO: 168) at the carboxyl terminus to improve serum persistence of the VNA. See, Nguyen et al, 2006, Protein Engineering, Design and Selection, 19:291. The VNA2-Tcd contains also an optional amino terminal *E. coli* thioredoxin protein to improve protein folding and levels of soluble expression. The sequence was derived from the expression vector, pET32b. A thrombin and enterokinase cleavage site was introduced between the thioredoxin and the functional VNA to permit separation of the two domains following expression of the product. The vector was designed to separate the VHH proteins (underlined) by a flexible spacer to promote independent folding of each of the distinct VHH proteins.

Several amino acid modifications were made to the VHH protein sequences as originally obtained and described in U.S. patent application Ser. No. 13/566,524 filed Aug. 3, 2012 and U.S. provision patent application No. 61/809,685 filed Apr. 8, 2013 to improve the framework region near the amino ends and improve protein folding and function (the amino terminal coding region is typically modified during the VHH cloning process, and the changes can be deleterious). Codons were optimized for improved expression in *E. coli* cells and regions of high DNA sequence homology were modified to reduce the homology and thus reduce the likelihood of DNA recombination. SEQ ID NO: 169 shows the coding DNA for the expressed VNA2-Tcd.

The VNA2-Tcd protein was expressed in *E. coli* and was purified using Ni-affinity chromatography followed by gel filtration chromatography (FIG. 44). Excellent purity and yields of soluble protein were observed. The purified VNA2-Tcd protein was demonstrated to be functional and bound to both *C. difficile* toxins, TcdA and TcdB, with high affinity in ELISAs and displayed sub-nM $IC_{50}$ neutralization potencies specific for both TcdA and TcdB in cell-based assays (FIG. 45). To test for in vivo efficacy, a *C. difficile* toxin systemic mouse challenge study was performed. Six week old female C57BL/6 mice were treated, via intraperitoneal (IP) injection, with 50 ug/mouse of purified VNA2-Tcd one hour prior to IP challenge with 100 ng/mouse of *C. difficile* toxin A (TcdA) and 200 ng/mouse of *C. difficile* toxin B (TcdB). Control mice challenged with TcdA and TcdB all died or became moribund within 4 hours post challenge. Untreated, VNA2-Tcd alone, TcdA+VNA2-Tcd, TcdB+VNA2-Tcd, and TcdA+TcdB+VNA2-Tcd treated animals showed no signs of systemic effects and survived until study termination at 7 days post challenge (FIG. 46). These data demonstrate that VNA2-Tcd protein prevented lethality from intoxication by both TcdA and TcdB toxins. VNA2-Tcd protein was demonstrated to be efficacious in a mouse model of *C. difficile* infection (CDI) (FIG. 47). Mice were treated with an antibiotic cocktail delivered in their drinking water for 3 days and then treated with a single IP injection of clindamycin one day prior to infection. Mice were infected with $10^6$ *C. difficile* UK6 spores alone or UK6 spores plus 3 doses of VNA2-Tcd protein (2.5 mg/kg at 4, 24 and 48 hours after infection). Animals that received only the UK6 spores lost weight, had diarrhea, and 60% were moribund by Day 3. In contrast, animals that received treatment with VNA2-Tcd protein displayed minimal or no weight loss, did not have diarrhea after Day 1, and 100% of the animals survived for the duration of the study. These data demonstrate the efficacy of VNA2-Tcd protein delivery as a therapy for CDI. The efficacy of VNA2-Tcd was evaluated in a large animal model of CDI, the gnotobiotic pig model. For this study, gnotobiotic piglets were derived via Cesarean section and maintained in sterile isolators for the duration of the experiment. Cohorts of 6, 5 day old piglets were orally inoculated with $10^6$ *C. difficile* UK6 spores only (control group), or were administered VNA2-Tcd (1 mg/pig, IP) 4 hours prior to oral inoculation with spores (treated group). After the initial dose, the treated group received 2 doses of VNA2-Tcd (1 mg/pig) each day for the duration of the experiment. Three out of six control pigs were moribund with signs of weakness, lethargy, severe diarrhea and severe edematous rectal prolapse (Table 6). All pigs in the control and treated groups developed diarrhea within 48 hrs of inoculation with spores, however none of the VNA2-Tcd treated pigs became moribund, or developed rectal prolapse, and diarrhea was only mild to moderate in this group (Table 6). All control piglets had signs of extra-intestinal lesions including pleural effusion and ascites (Table 6). In contrast, no VNA2-Tcd piglets showed any signs of ascites or pleural effusion (Table 6).

TABLE 6

Clinical outcome in VNA2-Tcd-treated and untreated *C. difficile*-infected piglets

| Clinical symptoms | Treatment | |
|---|---|---|
| | UK6 spores only | VNA2-Tcd + UK6 spores |
| Diarrhea[a] | 100 | 100 |
| Mild diarrhea[a] | 0 | 16 |
| Mild/Moderate diarrhea[a] | 0 | 66 |
| Moderate diarrhea[a] | 66 | 16 |
| Severe diarrhea[a] | 33 | 0 |
| Rectal prolapse | 83 | 0 |
| Ascites | 100 | 0 |
| Pleural effusion | 50 | 0 |
| Edema | 100 | 100 |
| Systemic Disease[b] | 83 | 0 |
| Fatal disease[c] | 50 | 0 |

[a]Severity of gastrointestinal disease was determined by clinical signs and histopathologic lesions, ranging from mild to severe
[b]Systemic disease indicates that piglets developed systemic signs such as lethargy, weakness, anorexia, or dyspnea
[c]Fatal disease indicates that piglets were euthanized due to the severity of the disease Additional gastrointestinal lesions in the severely affected piglets include profound thickening of the wall of the colon and rectum, which was minimal or absent in treated piglets (FIG. 48). Histopathologic analysis showed edema and lesions in both the control and treated groups with primary differences seen in levels of mesocolonic edema and neutrophil infiltration in the distal colon (FIG. 49). Control pigs had statistically significantly more neutrophil foci in the lamina propria of the distal colon compared to treated pigs. Control pigs had severe microvilli degradation and neutrophil infiltration, while treated pigs had reduced microvilli degradation compared to controls and less neutrophil infiltration (FIG. 49). These data demonstrate the efficacy of VNA2-Tcd protein for the treatment of CDI in a large animal model of the disease.

VNA2-Tcd coding DNA was inserted into a mammalian expression vector. The protein was observed secreted in the conditioned medium of the cells, and the product was observed to have retained full biological activities.

The amino acid sequence of the full translation product expressed as VNA2-Tcd:

(SEQ ID NO: 170)
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDKAMAISDPNSGAPVPYPDPLEPRAAAQVQLVESGGGLVQPGGS

-continued

LRLSCAASGFTLDYSSIGWFRQAPGKEREGVSCISSSGDSTKYADSVKGR

FTTSRDNAKNTVYLQMNSLKPDDTAVYYCAAFRATMCGVFPLSPYGKDDW

GKGTLVTVSSEPKTPKPQPTSAIAGGGGSGGGGSGGGGSAAAQLQLVESG

GGLVQPGGSLRLSCEASGFTLDYYGIGWFRQPPGKEREAVSYISASARTI

LYADSVKGRFTISRDNAKNAVYLQMNSLKREDTAVYYCARRRFSASSVNR

WLADDYDVWGRGTQVAVSSEPKTPKPQTSALVGGGGSGGGGSGGGGSLQA

MAAAQVQLVESGGGLVQTGGSLRLSCASSGSIAGFETVTWSRQAPGKSLQ

WVASMTKTNNEIYSDSVKGRFIISRDNAKNTVYLQMNSLKPEDTGVYFCK

GPELRGQGIQVTVSSEPKTPKPQAIAGGGGSGGGGSGGGGSLQGQVQLVE

SGGGLVQPGGSLRLSCAASGFTFSDYVMTWVRQAPGKGPEWIATINTDGS

TMRDDSTKGRFTISRDNAKNTLYLQMTSLKPEDTALYYCARGRVISASAI

RGAVRGPGTQVTVSSEPKTPKPQPARQGAPVPYPDPLEPRGGGSDICLPR

WGCLWED

The coding sequence of VNA2-Tcd:

(SEQ ID NO: 169)
ATGAGCGATAAAATTATTCACCTGACTGACGACAGTTTTGACACGGATGT

ACTCAAAGCGGACGGGGCGATCCTCGTCGATTTCTGGGCAGAGTGGTGCG

GTCCGTGCAAAATGATCGCCCCGATTCTGGATGAAATCGCTGACGAATAT

CAGGGCAAACTGACCGTTGCAAAACTGAACATCGATCAAAACCCTGGCAC

TGCGCCGAAATATGGCATCCGTGGTATCCCGACTCTGCTGCTGTTCAAAA

ACGGTGAAGTGGCGGCAACCAAAGTGGGTGCACTGTCTAAAGGTCAGTTG

AAAGAGTTCCTCGACGCTAACCTGGCCGGTTCTGGTTCTGGCCATATGCA

CCATCATCATCATCATTCTTCTGGTCTGGTGCCACGCGGTTCTGGTATGA

AAGAAACCGCTGCTGCTAAATTCGAACGCCAGCACATGGACAGCCCAGAT

CTGGGTACCGACGACGACGACAAGGCCATGGCGATATCGGATCCGAATTC

TGGCGCACCTGTCCCATACCCAGACCCTCTGGAACCACGAGCGGCCGCCC

AAGTCCAACTGGTCGAAAGTGGTGGTGGTCTGGTCCAACCGGGTGGCTCT

CTGCGTCTGTCCTGCGCTGCGAGTGGTTTTACCCTGGATTATAGCTCTAT

TGGTTGGTTCCGCCAGGCGCCGGGTAAAGAACGTGAAGGCGTGAGCTGCA

TCAGTTCCTCAGGTGATAGTACCAAATATGCGGACTCCGTCAAAGGCCGC

TTTACCACGAGTCGTGATAACGCCAAAAATACGGTTTACCTGCAGATGAA

CTCCCTGAAACCGGATGACACCGCAGTGTATTACTGCGCGGCCTTTCGCG

CTACGATGTGTGGTGTTTTCCCGCTGAGCCCGTATGGCAAAGATGACTGG

GGTAAAGGCACCCTGGTGACGGTTTCGAGCGAACCGAAAACCCCGAAACC

GCAGCCGACGTCTGCGATCGCCGGTGGTGGTGGTTCGGGTGGTGGTGGTA

GCGGTGGTGGTGGTTCTGCAGCTGCGCAGCTGCAACTGGTGGAAAGCGGC

GGTGGTCTGGTTCAACCGGGTGGTTCCCTGCGTCTGTCATGCGAAGCCTC

GGGTTTTACCCTGGATTATTACGGTATTGGTTGGTTCCGTCAGCCGCCGG

GCAAAGAACGTGAAGCAGTGAGCTATATTTCCGCATCAGCACGTACCATC

CTGTACGCAGATTCAGTTAAAGGCCGCTTTACGATCTCGCGTGACAACGC

-continued

GAAAAATGCCGTCTATCTGCAGATGAACAGTCTGAAACGTGAAGATACCG

CAGTGTATTACTGTGCTCGTCGCCGTTTCTCCGCGTCTAGTGTCAATCGC

TGGCTGGCCGATGACTACGATGTGTGGGGTCGTGGCACCCAAGTCGCCGT

GTCCTCAGAGCCTAAAACGCCGAAACCGCAAACGTCTGCACTAGTTGGCG

GTGGTGGCTCAGGTGGAGGCGGGTCAGGCGGTGGCGGTTCCCTGCAAGCA

ATGGCCGCAGCTCAGGTGCAACTGGTTGAATCCGGTGGTGGTCTGGTGCA

GACCGGTGGTAGCCTGCGTCTGTCTTGCGCATCGAGCGGTAGCATTGCTG

GCTTTGAAACCGTTACGTGGTCTCGTCAAGCGCCGGGTAAATCACTGCAG

TGGGTCGCCTCGATGACCAAAACGAACAATGAAATCTATTCGGATAGCGT

TAAAGGCCGCTTTATTATCTCACGCGATAACGCGAAAAATACCGTGTATC

TGCAGATGAACTCGCTGAAACCGGAAGATACGGGTGTTTACTTCTGCAAA

GGCCCGGAACTGCGCGGTCAAGGCATTCAGGTTACCGTCTCTAGTGAGCC

TAAAACCCCGAAACCGCAAGCAATCGCAGGCGGCGGCGGCAGCGGCGGCG

GCGGCTCTGGTGGTGGTGGTTCCCTGCAGGGTCAAGTCCAGCTGGTGGAA

TCTGGCGGTGGTCTGGTGCAACCGGGTGGTAGTCTGCGTCTGTCCTGTGC

AGCCTCAGGCTTTACCTTCTCAGATTATGTTATGACGTGGGTCCGTCAGG

CACCGGGTAAAGGTCCGGAATGGATTGCTACCATCAATACGGACGGTAGC

ACCATGCGCGATGACTCTACCAAAGGCCGCTTCACGATTAGCCGTGATAA

TGCCAAAAATACCCTGTACCTGCAGATGACGTCTCTGAAACCGGAAGACA

CCGCGCTGTATTACTGTGCCCGCGGTCGTGTTATTTCTGCAAGTGCTATC

CGTGGCGCCGTCCGTGGTCCGGGCACCCAAGTCACCGTCTCCTCAGAACC

GAAAACGCCGAAACCGCAACCGGCGCGCCAGGGTGCGCCGGTGCCGTATC

CGGACCCGCTGGAACCGCGTTAA.

The amino acid sequence of the full translation product of mammalian cell secreted VNA2-Tcd:

(SEQ ID NO: 167)
METDTLLLWVLLLWVPGSTGDAAQPARRARRTKLSGAPVPYPDPLEPRAA
AQVQLVESGGGLVQPGGSLRLSCAASGFTLDYSSIGWFRQAPGKEREGVS
CISSSGDSTKYADSVKGRFTTSRDNAKNTVYLQMNSLKPDDTAVYYCAAF
RATMCGVFPLSPYGKDDWGKGTLVTVSSEPKTPKPQPTSAIAGGGGSGGG
GSGGGGSAAAQLQLVESGGGLVQPGGSLRLSCEASGFTLDYYGIGWFRQP
PGKEREAVSYISASARTILYADSVKGRFTISRDNAKNAVYLQMNSLKRED
TAVYYCARRRFSASSVNRWLADDYDVWGRGTQVAVSSEPKTPKPQTSALV
GGGGSGGGGSGGGGSLQAMAAAQVQLVESGGGLVQTGGSLRLSCASSGSI
AGFETVTWSRQAPGKSLQWVASMTKTNNEIYSDSVKGRFIISRDNAKNTV
YLQMNSLKPEDTGVYFCKGPELRGQGIQVTVSSEPKTPKPQAIAGGGGSG
GGGSGGGGSLQGQVQLVESGGGLVQPGGSLRLSCAASGFTFSDYVMTWVR
QAPGKGPEWIATINTDGSTIVIRDDSTKGRFTISRDNAKNTLYLQMTSLK
PEDTALYYCARGRVISASAIRGAVRGPGTQVTVSSEPKTPKPQPARQGAP
VPYPDPLEPRGGGSDICLPRWGCLWED.

Example 36: Dimer and Tetramer Constructs for *C. difficile*

In this example, the structure of the VNA multimers was modified to enhance resistance to GI proteases and improve therapeutic efficacy.

Potent, camelid *C. difficile* toxin binding single chain antibodies, VHHs, were developed to neutralize *C. difficile* toxins. To develop an orally-deliverable protein therapy for the treatment of *C. difficile* infection (CDI), the *C. difficile* toxin-binding protein therapeutic should persist within the GI tract for sufficient time to neutralize the toxin. However, the GI track of mammals contains an abundance of protease enzymes used in food digestion that can degrade and inactivate orally delivered therapeutic proteins. The *C. difficile* toxin-binding proteins (VHHs) display unexpected potent neutralizing activity when joined together in one molecule to form heterodimers and heterotetramers. Initial studies using GI tract extracts from pigs demonstrated that the *C. difficile* toxin-binding proteins, when delivered in heterodimeric and heterotetrameric forms, were rapidly digested into monomers.

To determine the sites of cleavage in the heterodimeric and heterotetrameric *C. difficile* binding proteins, proteins were exposed to extracts of the porcine GI tract for different amounts of time, the products resolved by SDS-PAGE, purified, and subjected to amino-terminal sequence analyses. Sequencing revealed that the VHH functional domains were resistant to cleavage, while the sites sensitive to cleavage were within the unstructured region(s) flanking the flexible spacer ((GGGGS)$_3$) that connect the VHH domains together. This was an unexpected finding as the cleavage sites identified in this study do not represent those of known proteases, and were not predicted by proteomic analyses. Here, the identified sites contain one or more alanine residues, especially several adjacent alanines.

Without wishing to be bound by theory, to test the hypothesis that modification of the amino acid sequence flanking the flexible spacer ((GGGGS)$_3$) would reduce proteolytic cleavage of the heteromeric proteins in the GI tract, new proteins were designed and produced, VNA-TcdA (toxin A binding heterodimer, AH3+AA6; Seq ID NO: 171) and VNA-TcdB (toxin B-binding heterodimer, 5D+E3, Seq ID NO: 172), where alanine residues were not included within the regions flanking the flexible spacer ((GGGGS)$_3$) linking the VHH domains. The new dimer VNAs were compared directly to the heterotetrameric VNA, VNA2-Tcd, that contains the original, protease-sensitive regions (Seq ID NO: 167). VNA2-Tcd contains the same four VHHs present in the new dimer VNAs, VNA-TcdA (AH3+AA6) and VNA-TcdB (5D+E3), joined into a heterotetramer (AH3+ 5D+E3+AA6). FIG. 50 shows that new dimers were highly resistant to cleavage by proteases present in the pig GI tract, while the tetramer was rapidly cleaved to VHH monomers. These data demonstrate, among others, that the VNA multimers contained unexpected protease-sensitive sites and that modification of the sequence to remove these sites resulted in resistance to digestion by GI tract proteases.

Example 37: Removal of Protease-Sensitive Sites Did not Affect *C. difficile* Toxin Binding Activity of Dimeric VNAs The *C. difficile* toxin A-binding VHH dimer, VNA-TcdA, and toxin B-binding VHH dimer, VNA-TcdB, both containing the protease-resistant region connecting the VHH monomers, were compared directly to the tetramer, VNA2-Tcd, that contains the protease-sensitive spacer regions connecting the VHH monomers, in an ELISA (FIG. 51). The tetramer and dimers showed similar affinities to the *C. difficile* toxins A (TcdA) or toxin B (TcdB). Therefore, the sequence modification of the dimers had no effect on toxin binding activities. Therefore, removal of the protease-sensitive sites resulted in multimers with increased resistance to GI proteases (FIG. 50) without loss of functional activity. Such improved protease-resistant multimers are anticipated to achieve greater persistence in the GI tract, improve the efficiency of *C. difficile* toxin neutralization, and result in improved therapy for *C. difficile* infection.

---

What is claimed is:

1. An isolated recombinant binding protein comprising an amino acid sequence selected from SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122, which specifically binds to Anthrax protective antigen (PA) toxin.

2. A composition comprising at least one recombinant binding protein that specifically binds to Anthrax protective antigen (PA) toxin, wherein the at least one binding protein comprises an amino acid sequence selected from SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122.

3. A composition comprising at least one recombinant binding protein that specifically binds to Anthrax protective antigen (PA) toxin, wherein the at least one binding protein is encoded by a polynucleotide sequence comprising a nucleotide sequence selected from SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, or SEQ ID NO: 123.

4. The composition of claim 2, further comprising a pharmaceutically acceptable carrier, excipient, or vehicle.

5. A multimeric binding protein comprising at least two recombinant camelid heavy-chain-only antibody monomers (VHHs) which specifically bind Anthrax protective antigen (PA) toxin and which comprise an amino acid sequence selected from SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, or SEQ ID NO: 122; wherein the at least two VHHs are separated by spacers.

6. The multimeric binding protein of claim 5, comprising two VHHs which bind Anthrax PA toxin.

7. The multimeric binding protein of claim 5, further comprising one or more epitope tags to which an anti-epitope tag antibody specifically binds.

8. The multimeric binding protein of claim 5, wherein the spacer comprises a peptide having an amino acid sequence selected from GGGGS (SEQ ID NO: 54), GGGGSGGGGSGGGGS (SEQ ID NO: 55), or a combination thereof.

9. The multimeric binding protein of claim 7, wherein the one or more epitope tags comprises the amino acid sequence Gly Ala Pro Val Pro Tyr Pro Asp Pro Leu Glu Pro Arg of SEQ ID NO: 15.

10. A pharmaceutical composition comprising the multimeric binding protein of claim 5 and a pharmaceutically acceptable carrier, excipient, or vehicle.

11. A method of targeting and binding to Anthrax protective antigen (PA) toxin, said method comprising contacting said PA toxin with the composition of claim 4 in an amount effective to target and bind to said Anthrax PA toxin.

12. The method according to claim 11, wherein the Anthrax PA toxin is targeted and bound in vitro or in vivo.

13. A method of treating or preventing intoxication of a subject by Anthrax protective antigen (PA) toxin, said method comprising: administering to a subject in need thereof the composition of claim 4, in an amount effective for the binding protein to bind to and neutralize Anthrax PA toxin in the subject after intoxication or prior to the subject's having symptoms of intoxication.

* * * * *